United States Patent
Bräuer et al.

(10) Patent No.: US 10,172,814 B2
(45) Date of Patent: Jan. 8, 2019

(54) SUBSTITUTED PYRIDYL-CYCLOALKYL-CARBOXYLIC ACIDS, COMPOSITIONS CONTAINING THEM AND MEDICAL USES THEREOF

(71) Applicant: BAYER PHARMA AKTIENGESELLSCHAFT, Berlin (DE)

(72) Inventors: Nico Bräuer, Falkensee (DE); Jens Nagel, Daxweiler (DE); Horst Irlbacher, Berlin (DE); Andrea Rotgeri, Berlin (DE); Wolfgang Schwede, Glienicke (DE); Henrik Dahllöf, Uppsala (SE); Marcus Koppitz, Berlin (DE); Michaele Peters, Berlin (DE); Anne-Marie Godinho-Coelho, Bargfeld-Stegen (DE)

(73) Assignee: BAYER PHARMA AKTIENGESELLSCHAFT, Berlin (DE)

( * ) Notice: Subject to any disclaimer, the term of this patent is extended or adjusted under 35 U.S.C. 154(b) by 0 days.

(21) Appl. No.: 15/537,280

(22) PCT Filed: Dec. 16, 2015

(86) PCT No.: PCT/EP2015/080041
§ 371 (c)(1),
(2) Date: Jun. 16, 2017

(87) PCT Pub. No.: WO2016/097013
PCT Pub. Date: Jun. 23, 2016

(65) Prior Publication Data
US 2017/0354620 A1 Dec. 14, 2017

(30) Foreign Application Priority Data

Dec. 18, 2014 (EP) .................... 14199006

(51) Int. Cl.
| | |
|---|---|
| *A61K 31/167* | (2006.01) |
| *C07D 213/56* | (2006.01) |
| *C07D 213/84* | (2006.01) |
| *C07D 405/12* | (2006.01) |
| *C07D 213/61* | (2006.01) |
| *C07D 213/64* | (2006.01) |
| *C07D 213/65* | (2006.01) |
| *A61K 31/44* | (2006.01) |

(52) U.S. Cl.
CPC ............ *A61K 31/167* (2013.01); *A61K 31/44* (2013.01); *C07D 213/56* (2013.01); *C07D 213/61* (2013.01); *C07D 213/64* (2013.01); *C07D 213/65* (2013.01); *C07D 213/84* (2013.01); *C07D 405/12* (2013.01)

(58) Field of Classification Search
CPC .............. A61K 31/167; C07D 213/56
See application file for complete search history.

(56) References Cited

U.S. PATENT DOCUMENTS

| | | |
|---|---|---|
| 7,005,440 B1 | 2/2006 | Jayyosi et al. |
| 2011/0034450 A1 | 2/2011 | Hahn et al. |

FOREIGN PATENT DOCUMENTS

| | | |
|---|---|---|
| WO | 2002/081428 | 10/2002 |
| WO | 2004/099170 | 11/2004 |
| WO | 2005/049573 | 6/2005 |
| WO | 2005/086661 | 9/2005 |
| WO | 2011/051165 | 5/2011 |
| WO | 2012/076466 | 6/2012 |
| WO | 2012/139888 | 10/2012 |

OTHER PUBLICATIONS

International Search Report for PCT/EP2015/080041, six pages, dated Feb. 24, 2016.
Written Opinion of the ISA for PCT/EP2015/080041, eight pages, dated Feb. 24, 2016.
Aquino et al. "Development of a second generation of inhibitors of microsomal prostaglandin E synthase 1 expression bearing the γ-hydroxybutenolide scaffold" *Bioorganic & Medicinal Chemistry*, vol. 16, No. 19, pp. 9056-9064 (Oct. 2008).
Finettia et al. "Pharmacological inhibition of microsomal prostaglandin E synthase-1 suppresses epidermal growth factor receptor-mediated tumor growth and angiogenesis" *Plos One*, vol. 7, No. 7, pp. e40576, 12 pages (Jul. 2012).
Korotkova & Jakobsson "Characterization of microsomal prostaglandin E synthase 1 inhibitors" *Basic & Clinical Pharmacology & Toxicology*, vol. 114, No. 1, pp. 64-69 (Jan. 2014).

(Continued)

*Primary Examiner* — Golam M Shameem
(74) *Attorney, Agent, or Firm* — Nixon & Vanderhye P.C.

(57) ABSTRACT

The present invention relates to substituted Pyridyl-cycloalkyl-carboxylic acids of general formula (I), to pharmaceutical compositions and combinations comprising said compounds and to the use of said compounds for manufacturing a pharmaceutical composition for the treatment or prophylaxis of a disease, in particular in mammals, such as diseases associated with pains, or for the treatment or prophylaxis of pain syndromes (acute and chronic), inflammatory-induced pain, pelvic pain, cancer-associated pain, endometriosis-associated pain as well as endometriosis and adenomyosis as such, cancer as such, and proliferative diseases as such like endometriosis.

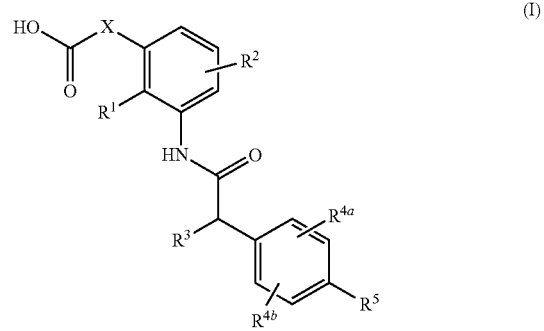

(I)

21 Claims, 3 Drawing Sheets

(56) References Cited

OTHER PUBLICATIONS

Figure 1:
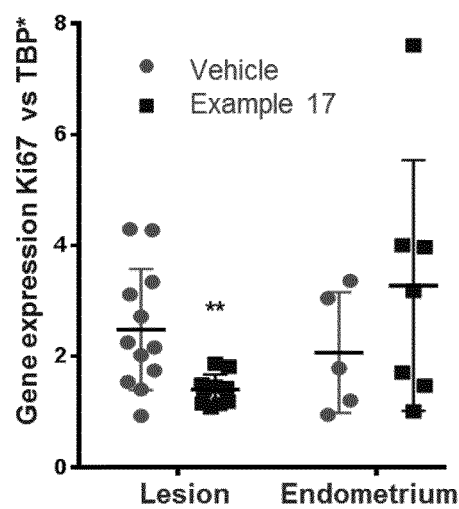
Figure 1:
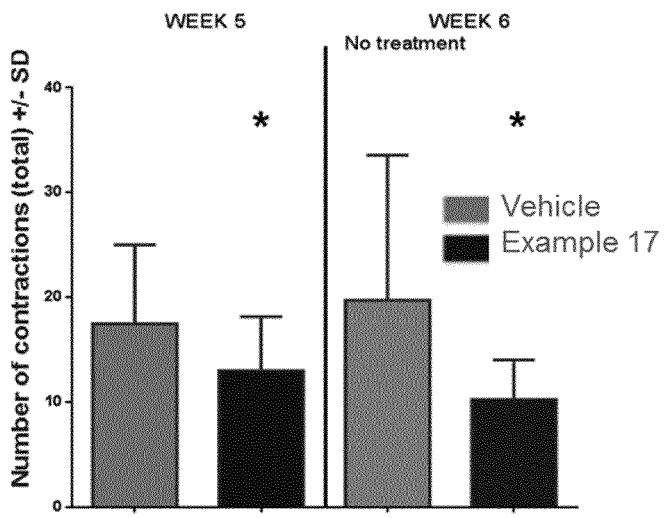

Mbalaviele et al. "Distinction of microsomal prostaglandin E synthase-1 (mPGES-1) inhibition from cyclooxygenase-2 inhibition in cells using a novel, selective mPGES-1 inhibitor" *Biochemical Pharmacology*, vol. 79, No. 10, pp. 1445-1454 (May 2010).

Xu et al. "MF63 [2-(6-chloro-1H-phenanthro[9,10-d]imidazol-2-yl)-isophthalonitrile], a selective microsomal prostaglandin E synthase-1 inhibitor, relieves pyresis and pain in preclinical models of inflammation" *Journal of Pharmacology and Experimental Therapeutics*, vol. 326, No. 3, pp. 754-763 (Sep. 2008).

Aquino et al. "Development of a second generation of inhibitors of microsomal prostaglandin E synthase 1 expression bearing the γ-hydroxybutenolide scaffold" Bioorg. Med. Chem. 16:9056-9064 (2008).

Berge et al. "Pharmaceutical salts" J. Pharm. Sci. 66:1-19 (1977).

Cross & Klyne "Rules for the nomenclature of organic chemistry section E: Stereochemistry" Pure Appl. Chem. 45:11-30 (1976).

Elander et al. "IL-1β and LPS induce anorexia by distinct mechanisms differentially dependent on microsomal prostaglandin E synthase-1" Am. J. Physiol. Regul. Integr. Comp. Physiol. 292:R258-R267 (2007).

Fahmi "mPGES-1 as a novel target for arthritis" Curr. Opin. Rheumatol. 16:623-627 (2004).

Finetti et al. "Pharmacological inhibition of microsomal prostaglandin E synthase-1 suppresses epidermal growth factor receptor-mediated tumor growth and angiogenesis" Plos One 7:e40576, 12 pages (2012).

Howe et al. "Genetic deletion of microsomal prostaglandin E synthase-1 suppresses mouse mammary tumor growth and angiogenesis" Prostaglandins Lipid Mediat. 106:99-105 (2013).

Iyer et al. "Prostaglandin $E_2$ synthase inhibition as a therapeutic target" Expert Opin. Therap. Targets 13:849-865 (2009).

Jakobsson et al. "Common structural features of MAPEG—A widespread superfamily of membrane associated proteins with highly divergent functions in eicosanoid and glutathione metabolism" Protein Sci. 8:689-692 (1999).

Kamei et al. "Reduced pain hypersensitivity and inflammation in mice lacking microsomal prostaglandin E synthase-1" J. Biol. Chem. 279:33684-33695 (2004).

King "The use of animal models in diabetes research" Br. J. Pharmacol. 166:877-894 (2012).

Kojima et al. "Defective generation of a humoral immune response is associated with a reduced incidence and severity of collagen-induced arthritis in microsomal prostaglandin E synthase-1 null mice" J. Immunol. 180:8361-8368 (2008).

Kömhoff et al. "Induction of microsomal prostaglandin E2 synthase in the macula densa in children with hypokalemic salt-losing tubulopathies" Pediatric Res. 55:261-266 (2004).

Korotkova & Jakobsson "Characterization of microsomal prostaglandin E synthase" Basic Clin. Pharmacol. Toxicol. 114:64-69 (2014).

Lecci et al. "Pharmacological evaluation of the role of cyclooxygenase isoenzymes on the micturition reflex following experimental cystitis in rats" Br. J. Pharmacol. 130:331-338 (2000).

Lousse et al. "Peritoneal endometriosis is an inflammatory disease" Front. Biosci. 4:23-40 (2012).

Mbalaviele et al. "Distinction of microsomal prostaglandin E synthase-1 (mPGES-1) inhibition from cyclooxygenase-2 inhibition in cells using a novel, selective mPGES-1 inhibitor" Biochem. Pharmacol. 79:1445-1454 (2010).

Misra et al. "COX-2 signaling and cancer: New players in old arena" Curr. Drug Targets 15:347-359 (2014).

Murakami et al. "Prostaglandin E synthase" Prostaglandins Lipid Mediat. 68:383-399 (2002).

Nakanishi et al. "Genetic deletion of mPGES-1 suppresses intestinal tumorigenesis" Cancer Res. 68:3251-3259 (2008).

Park et al. "Prostaglandin E2 synthesis and secretion: The role of PGE2 synthases" Clin. Immunol. 119:229-240 (2006).

Pecchi et al. "mPGES-1 knock-out mice are resistant to cancer-induced anorexia despite the absence of central mPGES-1 up-regulation in wild-type anorexic mice" J. Neuroimmunol. 199:104-114 (2008).

Pecchi et al. "Involvement of central microsomal prostaglandin E synthase-1 in IL-1-β induced anorexia" Physiol. Genomics 25:485-492 (2006).

Polyak et al. "A model for p53-induced apoptosis" Nature 389:300-305 (1997).

Rakhila et al. "Identification of multiple and distinct defects in prostaglandin biosynthetic pathways in eutopic and ectopic endometrium of women with endometriosis" Fertil. Steril. 100:1650-1659 (2013).

Sampey et al. "Microsomal prostaglandin E synthase-1: the inducible synthase for prostaglandin $E_2$" Arthritis Res. Therap. 7:114-117 (2005).

Samuelsson et al. "Membrane prostaglandin E synthase-1: A novel therapeutic target" Pharmacol. Rev. 59:207-224 (2007).

Seyberth et al. "Bartter- and Gitelman-like syndromes: Salt-losing tubulopathies with loop or DCT defects" Pediatr. Nephrol. 26:1789-1802 (2011).

Solheim et al. "Non-steroidal anti-inflammatory treatment in cancer cachexia: A systematic literature review" Acta Oncologica 52:6-17 (2013).

Tian et al. "Celecoxib ameliorates non-alcoholic steatohepatitis in type 2 diabetic rats via suppression of the non-canonical Wnt signaling pathway expression" Plos One 9:e83819, eight pages. (2014).

Trebino et al. "Impaired inflammatory and pain responses in mice lacking an inducible prostaglandin E synthase" Proc. Natl. Aca. Sci. USA 100:9044-9049 (2003).

Wang & Dubois "The role of COX-2 in intestinal inflammation and colorectal cancer" Oncogene 29:781-788 (2010).

Wang & Dubois "Eicosanoids and cancer" Nature Rev. 10:181-193 (2010).

Xu et al. "MF63 [2-(6-chloro-1H-phenanthro[9,1 O-d]imidazol-2-yl)isophthalonitrile], a selective microsomal prostaglandin E synthase-1 inhibitor, relieves pyresis and pain in preclinical models of inflammation" J. Pharmacol. Exper. Therap. 326:754-763 (2008).

Yamamoto et al. "Involvement of substance P in the development of cisplatin-induced acute and delayed pica in rats" Br. J. Pharmacol. 171:2888-2899 (2014).

Yoshimatsu et al. "Inducible prostaglandin E synthase is overexpressed in non-small cell lung cancer" Clin. Cancer Res. 7:2669-2674 (2001).

Yoshimatsu et al. "Inducible microsomal prostaglandin E synthase is overexpressed in colorectal adenomas and cancer" Clin. Cancer Res. 7:3971-3976 (2001).

A)

B)

SUBSTITUTED PYRIDYL-CYCLOALKYL-CARBOXYLIC ACIDS, COMPOSITIONS CONTAINING THEM AND MEDICAL USES THEREOF

This application is the U.S. national phase of International Application No. PCT/EP2015/080041, filed 16 Dec. 2015, which designated the U.S. and claims priority to Application No. EP 14199006.9, filed 18 Dec 2014; the entire contents of each of which are hereby incorporated by reference.

The present invention relates to substituted Pyridyl-cycloalkyl-carboxylic acids of general formula (I) as described and defined herein, to pharmaceutical compositions and combinations comprising said compounds and to the use of said compounds for manufacturing a pharmaceutical composition for the treatment or prophylaxis of a disease, in particular in mammals, such as but not limited to diseases associated with pains, or for the treatment or prophylaxis of pain syndromes (acute and chronic), inflammatory-induced pain, pelvic pain, cancer-associated pain, endometriosis-associated pain as well as endometriosis as such, cancer as such, and proliferative diseases as such like endometriosis.

BACKGROUND OF THE INVENTION

The present invention relates to chemical compounds that inhibit PTGES (also known as prostaglandin E synthase 1). Prostaglandin E synthase 1 is an enzyme that in humans is encoded by the PTGES gene (Polyak K, Xia Y, Zweier J L, Kinzler K W, Vogelstein B: Nature 389 (6648): 300-5; Jakobsson P J, Morgenstern R, Mancini J, Ford-Hutchinson A, Persson B: Protein Sci 8 (3): 689-92). PTGES is also known as mPGES-1 (microsomal prostaglandin E synthase 1) or PIG12, PP102, PP1294, MGST-IV, MGST1L1, TP53I12, MGST1-L1.

PTGES is a member of the Membrane Associated Proteins in Eicosanoid and Glutathione metabolism (MAPEG) family of glutathione transferases, which also includes FLAP and LTC4 synthases (Murakami M, Nakatani Y, Tanioka T, Kudo I, Prostaglandins Other Lipid Mediat. 2002, 68-69: 383-99.; Park J Y, Pillinger M H, Abramson S B, Clin. Immunol. 2006, 119 (3): 229-40).

PTGES is an inducible enzyme that is strongly up-regulated in response to pro-inflammatory stimuli leading to strong and selective production of PGE2 in inflammatory conditions including arthritis, osteoarthritis and endometriosis (Sampey A V et al., Arthritis Res Ther. 2005; 7(3):114-7; Fahmi H., Curr Opin Rheumatol. 2004 16(5):623-7; Rakhila H. et al., Fertil Steril. 2013, 100(6):1650-9). PGE2 produced by PTGES is considered as a critically important and strong pro-inflammatory mediator of inflammation, pain, angiogenesis, fever, bone metabolism, cancer and atherosclerosis. PTGES is an inducible enzyme for the selective production of pro-inflammatory PGE2 from PGH2. PTGES represents, therefore, an attractive target to achieve more specific inhibition of PGE2 production while preserving production of other prostaglandins (Iyer J P et al., Expert Opin Ther Targets. 2009 July; 13(7):849-65).

LPS (lipopolysaccharide) induced peritoneal PGE production in murine macrophages is markedly reduced in murine knockouts of PTGES (Trebino et al., PNAS 2003, 100:9044-49). Genetic deletion or pharmacological inhibition of PTGES has been demonstrated to reduce inflammation and pain behavior in experimental animal models of pain (Trebino et al., PNAS 2003, 100:9044-49; Kamei et al., Journal of Biological Chemistry 2004, 279:33684-95; Kojima et al., Journal of Immunology 2008, 180:8361-6; Xu et al., Journal of Pharmacology and Experimental Therapeutics 2008, 326:754-63).

Non-steroidal anti-inflammatory drugs (NSAIDs) and Cyclooxgenase (COX2) inhibitors reduce pain and inflammation by inhibition of one or both isoforms of the COX enzymes leading to reduced formation of PGE2 and other prostaglandins. COX1 is a constitutively expressed enzyme in many cells whereas COX2 is induced by pro-inflammatory mediators e.g. cytokines in response to inflammation or tissue injury. COX enzymes metabolize arachidonic acid to the unstable intermediate prostaglandin H2 (PGH2). PGH2 is further transformed to other physiological active prostaglandins including PGI2, PGD2, thromboxane A2, PGF2α and PGE2. In particular PGE2 has a role in pain, inflammation and fever responses (Samuelsson et al., Pharmacol Rev. 2007, 59(3):207-24; Iyer et al., Expert Opin Ther Targets 2009, 13(7):849-65).

Endometriosis is an inflammatory disease (Lousse J C, Van Langendonckt A, Defrere S, Ramos R G, Colette S, Donnez J. Front Biosci 2012, 4:23-40) and key PGE2 enzymes including COX2 and PTGES are up-regulated in human endometriotic lesions compared to the endometrium (Rakhila H. et al., Fertil Steril. 2013, 100(6):1650-9). Increased PGE2 levels are expected to contribute inflammatory pain symptoms in endometriosis patients.

Several lines of evidence also support a role of PTGES produced PGE2 in oncology and cancer diseases (Samuelsson et al., Pharmacological Reviews 2007, 59:207-224). High levels of PGE2 have been detected in various tumors, including colorectal cancer (Wang and DuBois, 2010 Oncogene 29: 781-788). PGE2 is involved in tumor progression by inducing proliferation, angiogenesis, invasion and metastasis in several solid tumors (Wang and DuBois, Nat Rev Cancer 2010, 10: 181-193). There are strong evidence provided in studies that PGE2 plays a key role in tumor promotion. Genetic deletion of PTGES in mice suppresses intestinal tumourogenesis (Nakanishi et. al., Cancer Research 2008, 68(9), 3251-9) and suppresses tumor growth (Howe et al., Prostaglandins Other Lipid Mediators 2013, 106:99-105). PTGES is overexpressed in several cancer diseases in man such as in colorectal cancer (Yoshimatsu K et al., Clin Cancer Res. 2001, 7(12):3971-6; Yoshimatsu K et al., Clin Cancer Res. 2001, 7(9):2669-74), indicating a role in cancer diseases (Misra S, Sharma K, Curr Drug Targets. 2014, 15(3):347-59). Several lines of evidence also indicate that PGE2 is involved in cancer cachexia. It has been shown that IL-1beta induces anorexia by mechanism dependent on PTGES (Pecchi E et al., Physiol Genomics. 2006, 16; 25(3):485-92; Elander et al., American Journal of Physiology 2007, 292, 258-267). NSAIDs were partially effective in reversing chemotherapeutic induced anorexia in rats (Yamamoto et al., Br J Pharmacol. 2014, 171(11): 2888-2899) and a trend for a benefit of NSAID treatment in cancer cachexia patients has been shown (Solheim et al., Acta Oncol. 2013 52(1):6-17). PTGES knock-out mice exhibit resistance to tumor-induced anorexia and maintain their body mass (Pecchi E et al., J Neuroimmunol. 2008, 199, 104-114).

Hyperprostaglandin E syndrome or antenatal Bartter and classic Bartter syndrome belong to the heterogeneous group of hypokalemic salt-losing tubulopathies. PTGES expression is increased in patients with Bartter syndrome and Hyperprostaglandin E Syndrome with a selective increase of renal PGE2 level (Kömhoff et al., Pediatric Research 2004, 55, 261-266). Current therapeutic approach includes salt and water supplementation and Prostaglandin E2-synthase inhibition (Seyberth et al., Pediatr Nephrol. 2011, 26(10):1789-1802).

Reduction of PGE2 formation by inhibition of cycloxygenase-2 (COX2) has been shown to be beneficial for non-alcoholic steatohepatitis (NASH) in type 2 diabetes mellitus rats [Tian et al., PLoS One 2014, 3; 9(1)].

In order to avoid side effects associated with COX inhibition, a selective inhibition of the transformation of PGH2 to the pro-inflammatory PGE2 is expected to reduce pain and inflammatory responses while sparing the production of other physiological important arachidonic acid metabolites such as PGI2.

PGH2 is transformed to PGE2 by prostaglandin E synthases, including the two microsomal prostaglandin E synthases (PTGES and PTGES-2), and the cytosolic prostaglandin E synthase (PTGES-3).

Since PTGES functions as an inducible enzyme downstream of COX2, selective inhibition of PTGES is not expected to inhibit levels of e.g. PGI2 and thromboxane A2 and to maintain residual PGE2 levels produced by the two other prostaglandin E synthases PTGES-2 and PTGES-3. Accordingly, PTGES inhibition has the potential to relieve pain and inflammation while limiting any unwanted gastrointestinal or cardiovascular side effects.

Substituted Pyridyl-cycloalkyl-carboxylic acids have been disclosed in prior art for the treatment or prophylaxis of different diseases:

WO2005086661 discloses compounds, pharmaceutical compositions and methods useful for treating or preventing a condition or disorder such as type II diabetes, obesity, hyperglycemia, glucose intolerance, insulin resistance, hyperinsulinemia, hypercholesterolemia, hypertension, hyperlipoproteinemia, hyperlipidemia, hyper-triglylceridemia, dyslipidemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycemia, cancer or edema were described. WO2005086661 does not disclose cycloalkyl substituted linker L2.

WO2005049573 discloses compounds of Formula (I)

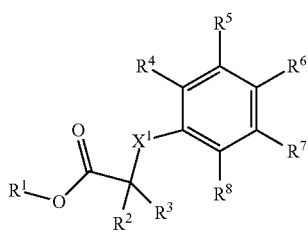

wherein one of $R^5$, $R^6$ and $R^7$ is (Formula II)

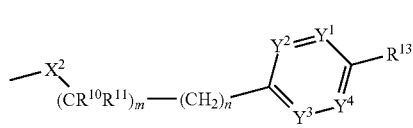

The invention further relates to pharmaceutical compositions containing such compounds, to a process for their preparation and to their use for the treatment and/or prevention of diseases which are modulated by PPAR-delta and/or PPAR-alpha agonists. At least one or two of $Y^1$-$Y^4$ has/have to be nitrogen. A Phenyl ring has not been claimed as inner aromatic ring.

WO2002081428 describes benzene compounds represented by the following general formula (I),

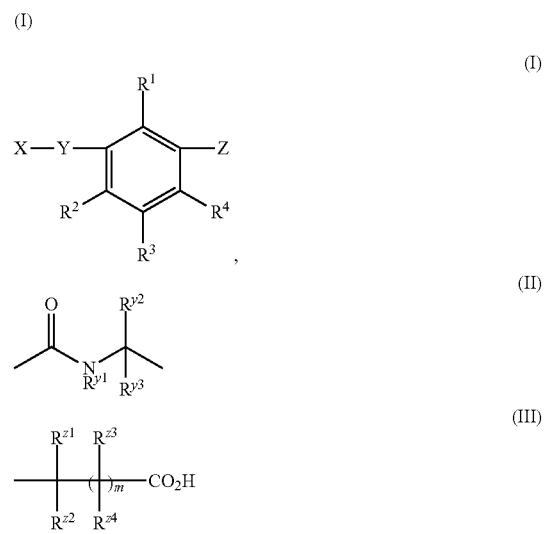

which is useful as an insulin-resistant ameliorant. In the formula (I), X represents optionally substituted aryl or heteroaryl; Y represents a group represented by the general formula (II) (wherein $R^{y1}$, $R^{y2}$, and $R^{y3}$ each represents hydrogen, etc.), etc.; Z represents a group represented by the general formula (III) (wherein m is 0 to 2 and $R^{z1}$, $R^{z2}$, $R^{z3}$, and $R^{z4}$ each represents hydrogen, etc.); and $R^1$, $R^2$, $R^3$, and $R^4$ each represents hydrogen, etc. Substituted pyridyl is not claimed for substituent X.

WO2011051165 discloses substituted 3-Phenylpropionic acids of formula (I)

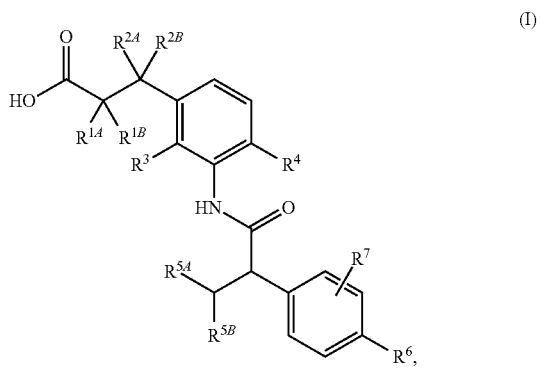

and use thereof for the treatment and/or prophylaxis of cardiovascular diseases. In formula (I), $R^6$ represents hydrogen, fluorine, chlorine, bromine, ($C_1$-$C_4$)-Alkyl, ($C_2$-$C_4$)-Alkenyl, cyclopropyl or cyclobutyl. Substituted pyridyl is not claimed for substituent $R^6$.

WO2012076466 describes substituted 1-benzylcycloalkylcarboxylic acid derivatives of formula (I),

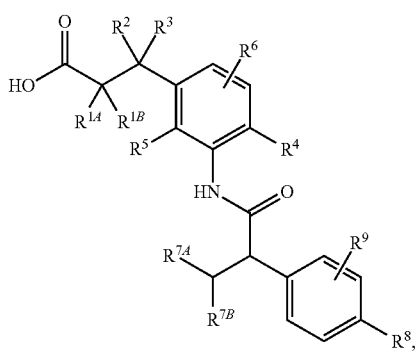

(I)

process for preparation thereof, the use thereof for treatment and/or prevention of disorders and the use thereof for production of medicaments for treatment and/or prevention of disorders, especially for treatment and/or prevention of cardiovascular disorders.

In the formula $R^8$ represents fluorine, chlorine, bromine, nitro, cyano, trifluor-methoxy, acetyl, 2-cyanovinyl, $(C_1$-$C_4)$-alkyl, $(C_2$-$C_4)$-alkenyl, cyclopropyl or cyclobutyl, but not substituted pyridyl.

WO2012139888 discloses 3-phenylpropionic acid derivatives of the following formula,

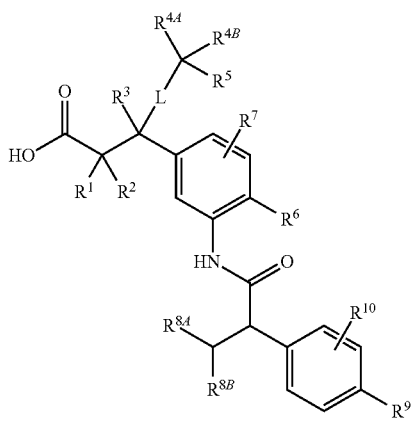

(I)

carrying a branched or cyclic alkyl substituent at the 3-position, methods for the production thereof, the use thereof for treating and/or preventing illnesses, and the use thereof for producing pharmaceuticals for treating and/or preventing illnesses, in particular for treating and/or preventing cardiovascular diseases. $R^9$ represents fluorine, chlorine, bromine, cyano, $(C_1$-$C_4)$-alkyl, $(C_2$-$C_4)$-alkenyl, cyclopropyl or cyclobutyl, but not substituted pyridyl.

WO2005086661 provides compounds useful, for example, for modulating insulin levels in a subject and that have the general formula Q-$L^1$-P-$L^2$-M-X-$L^3$-A wherein the definitions of the variables Q, $L^1$, P, $L^2$, M, X, $L^3$ and A are provided. The present invention also provides compositions and methods for use of the compounds, for instance, for treatment of type II diabetes. $L^2$ does not represent cycloalkyl.

$$Q\text{-}L^1\text{-}P\text{-}L^2\text{-}M\text{-}X\text{-}L^3\text{-}A \qquad\qquad I$$

WO2004099170 discloses compounds and pharmaceutically acceptable salts of formula (I):

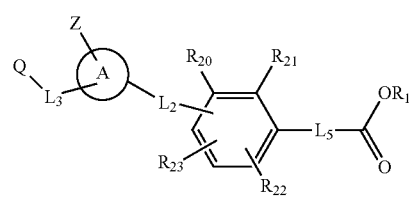

(I)

which are useful in the treatment of metabolic disorders related to insulin resistance, leptin resistance, or hyperglycemia. Compounds of the invention include inhibitors of Protein tyrosine phosphatases, in particular Protein tyrosine phosphatase-IB (PTP-1B), that are useful in the treatment of diabetes and other PTP mediated diseases, such as cancer, neurodegenerative diseases and the like. Pharmaceutical compositions comprising compounds of the invention and methods of treating the aforementioned conditions using such compounds have also been described.

$L^2$ does not represent cycloalkyl.

U.S. Pat. No. 7,005,440 discloses the use of triaryl acid derivatives of formula (I)

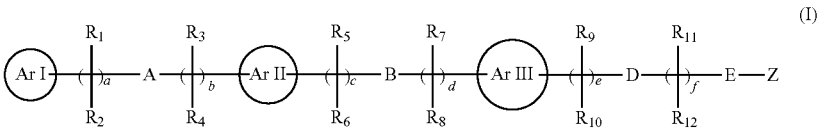

(I)

and their pharmaceutical compositions as PPAR ligand receptor binders. These PPAR ligand receptor binders were described as useful agonists or antagonists of the PPAR receptor.

Pyridyl-cycloalkyl-carboxylic acids were generically covered by general formula (I). However, those compounds are neither specifically described nor exemplified. Additionally, U.S. Pat. No. 7,005,440 does not contain any statement about the usefulness of the said triaryl acid derivatives as PTGES inhibitors.

So, the state of the art described above does not describe the specific substituted Pyridyl-cycloalkyl-carboxylic acids of general formula (I) of the present invention as defined herein or a tautomer, an N-oxide, a hydrate, a solvate, or a salt thereof, or a mixture of same, as described and defined herein, and as hereinafter referred to as "compounds of the present invention", or their pharmacological activity.

It has now been found, and this constitutes the basis of the present invention, that said compounds of the present invention have surprising and advantageous properties.

In particular, said compounds of the present invention have surprisingly been found to effectively inhibit PTGES and may therefore be used for the treatment or prophylaxis of following diseases:

genitourinary, gastrointestinal, respiratory, proliferative and pain-related diseases, conditions and disorders;
gynecological diseases including primary and secondary dysmenorrhea, dyspareunia, endometriosis, and adenomyosis; endometriosis-associated pain; endometriosis-associated symptoms, wherein said symptoms are in particular dysmenorrhea, dyspareunia, dysuria, or dyschezia; endometriosis-associated proliferation; pelvic hypersensitivity;
urinary tract disease states associated with the bladder outlet obstruction; urinary incontinence conditions such as reduced bladder capacity, increased frequency of micturition, urge incontinence, stress incontinence, or bladder hyperreactivity; benign prostatic hypertrophy; prostatic hyperplasia; prostatitis; detrusor hyperreflexia; overactive urinary bladder and symptoms related to overactive urinary bladder wherein said symptoms are in particular increased urinary frequency, nocturia, urinary urgency or urge incontinence; pelvic hypersensitivity; urethritis; prostatitis; prostatodynia; cystitis, in particular Interstitial cystitis; idiopathic bladder hypersensitivity; kidney disease as hyperprostaglandin E syndrome, classic Bartter syndrome;
cancer, cancer-related pain and cancer cachexia;
Epilepsy, partial and generalized seizures;
respiratory disorders including asthma, chronic obstructive pulmonary disease, pulmonary fibrosis, bronchospasm;
gastrointestinal disorders including irritable bowel syndrome (IBS), inflammatory bowel disease (IBD), biliary colic and other biliary disorders, renal colic, diarrhea-dominant IBS; gastroesophageal reflux, gastrointestinal distension, Crohn's disease and the like;
fatty liver disorders, in particular NASH (Non-Alcoholic Steato-Hepatitis); fibrotic diseases including lung fibrosis, heart fibrosis, kidney fibrosis and fibrosis of other organs; metabolic syndrome including, for example, insulin resistance, hypertension, refractory hypertension, dyslipoproteinaemia and obesity, diabetes mellitus, in particular Diabetes type II, myocardial infarction; atherosclerosis; lipid disorders;
neurodegenerative disorders such as Alzheimer's disease, Multiple Sclerosis, Parkinson's disease, Brain ischemia and traumatic brain injury;
pruritus;
Impaired wound healing and disease of the skeleton like degeneration of the joints, ankylosing spondylitis.

Additionally, the compounds of the present invention are potent human PTGES inhibitors, interfering with inflammatory induced PGE2 levels.

SUMMARY OF THE INVENTION

The present invention covers compounds of general formula (I):

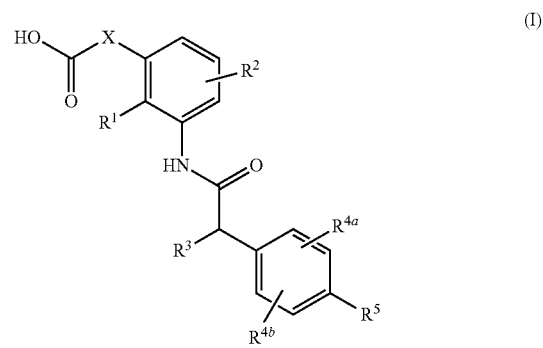

in which:

$R^1$ represents halogen, $C_1$-$C_4$-alkyl or O—($C_1$-$C_4$-alkyl), wherein $C_1$-$C_4$-alkyl and O—($C_1$-$C_4$-alkyl) are optionally substituted with 1-5 halogen atoms which are the same or different;

$R^2$ represents hydrogen, halogen, $C_1$-$C_4$-alkyl or O—($C_1$-$C_4$-alkyl), wherein $C_1$-$C_4$-alkyl and O—($C_1$-$C_4$-alkyl) are optionally substituted with 1-5 halogen atoms which are the same or different;

X is —$C_2H_4$—, —$CH_2$—Y—, —$CH_2$—$CR^6R^7$—, —$CR^6R^7$—$CH_2$— or 1,2-cyclopropylidene;

$R^3$ is $C_3$-$C_6$-cycloalkyl, which is optionally substituted with one or more substituents which are the same or different and selected from halogen or $C_1$-$C_4$-alkyl;

$R^{4a}$ and $R^{4b}$ represent hydrogen, halogen, $C_1$-$C_4$-alkyl, —O—($C_1$-$C_4$-alkyl), ($CH_2$)$_n$—OH, wherein $C_1$-$C_4$-alkyl is optionally substituted with one or more substituents which are the same or different and selected from halogen, or $C_1$-$C_4$-alkyl;

$R^5$ is pyridine, which is substituted with one or two substituents which are the same or different and selected from the group consisting of halogen, $C_1$-$C_4$-alkyl, —O—($C_1$-$C_4$-alkyl), OH, CN, —$CH_2$—OH, —$CH_2$—O—($C_1$-$C_4$-alkyl), $C_3$-$C_6$-cycloalkyl, —O—($C_3$-$C_6$-cycloalkyl), 3- to 7-membered-heterocycloalkyl-, and —O-(3- to 7-membered-heterocycloalkyl), and
wherein said $C_1$-$C_4$-alkyl and —O—($C_1$-$C_4$-alkyl) are optionally substituted with 1-5 halogen atoms which are the same or different;

$R^6$ and $R^7$ are different and selected from the group consisting of hydrogen, halogen, $C_1$-$C_4$-alkyl and $C_3$-$C_6$-cycloalkyl;

$R^8$ represents hydrogen or $C_1$-$C_4$-alkyl;

Y represents O or $NR^8$;

n 0, 1 or 2;

or a tautomer, an isomer, enantiomer, diastereomer, racemate, an N-oxide, a hydrate, a solvate, or a salt thereof, or a mixture of same.

The present invention further relates to pharmaceutical compositions and combinations comprising said compounds, to the use of said compounds for manufacturing a pharmaceutical composition for the treatment or prophylaxis of a disease.

DETAILED DESCRIPTION OF THE INVENTION

The terms as mentioned in the present text have preferably the following meanings:

The term "halogen atom", "halo-" or "Hal-" is to be understood as meaning a fluorine, chlorine, bromine or iodine atom, preferably a fluorine or a chlorine atom.

The term "alkyl" is to be understood as meaning a linear or branched, saturated, monovalent hydrocarbon group with the number of carbon atoms as specified and having as a rule, 1, 2, 3 or 4 carbon atoms for all alkyl substituents, e.g. a methyl, ethyl, n-propyl, butyl, iso-propyl, iso-butyl, sec-butyl or tert-butyl, or an isomer thereof. Particularly, said group has 1 or 2 carbon atoms ("$C_1$-$C_2$-alkyl"), e.g. a methyl or ethyl.

The term "alkoxy" is to be understood as meaning a linear or branched, saturated, monovalent, hydrocarbon group of formula —O-alkyl, in which the term "alkyl" is defined as meaning a linear or branched, saturated, monovalent hydrocarbon group with the number of carbon atoms as specified and having as a rule, 1 to 4, preferably 1 to 2 for all alkyl substituents, especially preferably 1 carbon atoms. Particularly, said group has 1, 2, 3 or 4 carbon atoms ("$C_1$-$C_4$-alkoxy"), e.g. a methoxy, ethoxy, n-propoxy, n-butoxy, iso-propoxy, iso-butoxy, sec-butoxy, or tert-butoxy group, more particularly 1, 2 or 3 carbon atoms ("—O—$C_1$-$C_3$-alkyl"), e.g. methoxy, ethoxy, n-propoxy- or iso-propoxy group, and even more particularly 1 or 2 carbon atoms ("—O—$C_1$-$C_2$-alkyl"), e.g. a methoxy or ethoxy group.

The term "—O—($C_1$-$C_4$-alkyl) optionally substituted with 1-5 halogen atoms" is to be understood as meaning a linear or branched, saturated, monovalent hydrocarbon group in which the term "$C_1$-$C_3$-alkoxy" is defined supra, and in which one or more hydrogen atoms is replaced by a halogen atom, which are the same or different, i.e. one halogen atom being independent from another. In particular, halogen is fluorine or chlorine.

The term "$C_1$-$C_4$-alkyl, optionally substituted with 1-5 halogen atoms", or in analogy "—O—($C_1$-$C_4$-alkyl), optionally substituted with 1-5 halogen atoms", is to be understood as meaning a linear or branched, saturated, monovalent hydrocarbon group in which the term "$C_1$-$C_4$-alkyl" is defined supra, and in which one or more hydrogen atoms is/are replaced by a halogen atom, which are the same or different, i.e. one halogen atom being independent from another. In particular, halogen is fluorine or chlorine.

In particular, said "$C_1$-$C_4$-alkyl, optionally substituted with 1-5 halogen atoms" is a $C_1$-$C_4$-alkyl group optionally substituted with 1-5 fluorine atoms, for example, —$CH_2CH_2CH_2CF_3$, —$CH_2CH_2CF_3$, —$CF_3$, —$CHF_2$, —$CH_2F$, —$CF_2CF_3$, —$CH_2CHF_2$, or —$CH_2CF_3$. Particularly, said "—O—($C_1$-$C_4$-alkyl), optionally substituted with 1-5 halogen atoms" is optionally substituted with 1 to 5 fluorine atoms, for example, —$OCF_3$, —$OCHF_2$, —$OCH_2F$, —$OCF_2CF_3$, —$OCH_2CHF_2$, —$OCH_2CF_3$, —$OCH_2CH_2CF_3$, —$OCH_2CF_2CF_3$, or —O—$CH_2CH_2CH_2CF_3$. In particular, said "—O—($C_1$-$C_4$-alkyl)" group optionally substituted with 1-5 fluorine atoms is —$OCF_3$.

In case of $R^5$ represents pyridine, which is substituted with one or two substituents which are the same or different and selected from the group consisting of halogen, $C_1$-$C_4$-alkyl, —O—($C_1$-$C_4$-alkyl), OH, CN, —$CH_2$—OH, —$CH_2$—O—($C_1$-$C_4$-alkyl), $C_3$-$C_6$-cycloalkyl, —O—($C_3$-$C_6$-cycloalkyl), 3- to 7-membered-heterocycloalkyl-, and —O-(3- to 7-membered-heterocycloalkyl), and wherein said $C_1$-$C_4$-alkyl and —O—($C_1$-$C_4$-alkyl) are optionally substituted with 1-5 halogen atoms which are the same or different, halogen is preferably fluorine. For example, in case of $R^5$ $CF_3$ is preferred.

In case of $R^{4a}$ and $R^{4b}$ in formula (I), said "$C_1$-$C_4$-alkyl" is, unless indicated otherwise, optionally substituted with one or more substituents which are the same or different and selected from halogen or $C_1$-$C_4$-alkyl.

The term "$C_3$-$C_6$-cycloalkyl" is to be understood as meaning a saturated, monovalent, monocyclic hydrocarbon ring which contains 3, 4, 5 or 6 carbon atoms. Said $C_3$-$C_6$-cycloalkyl group is for example a cyclopropyl, cyclobutyl, cyclopentyl or cyclohexyl ring.

In case of "$C_3$-$C_6$-cycloalkyl" stands for $R^3$, said ring particularly contains 4 or 5 carbon atoms, i.e. cyclobutyl or cyclopentyl.

If said "$C_3$-$C_6$-cycloalkyl" stands for $R^6$ or $R^7$, said ring particularly contains 3 carbon atoms, i.e. cyclopropyl.

In case of $R^3$ in formula (I), said "$C_3$-$C_6$-cycloalkyl" is, unless indicated otherwise, optionally substituted with one or more substituents which are the same or different and selected from halogen or $C_1$-$C_4$-alkyl.

The term "heterocycloalkyl" is to be understood as meaning a saturated, monovalent, monocyclic hydrocarbon ring with the number of ring atoms as specified in which one, two or three ring atoms of the hydrocarbon ring is/are replaced by one, two or three heteroatoms or heteroatom-containing groups independently selected from O, S, S(=O), S(=O)$_2$, or N.

"3- to 7-membered heterocycloalkyl" is to be understood as meaning a saturated, monovalent, monocyclic "heterocycloalkyl" ring as defined supra which contains 3, 4, 5, 6 or 7 ring atoms.

Particularly, said 3- to 7-membered heterocycloalkyl can contain 2, 3, 4, 5, or 6 carbon atoms, and one or more of the above-mentioned heteroatoms or heteroatom-containing groups provided that the total number of ring atoms does not greater than 7 (a "3- to 7-membered heterocycloalkyl"), more particularly said heterocycloalkyl can contain 4 or 5 carbon atoms, and one or more of the above-mentioned heteroatom-containing groups provided that the total number of ring atoms does not greater than 6 (a "5- to 6-membered heterocycloalkyl").

Particularly, without being limited thereto, said heterocycloalkyl can be a 4-membered ring, such as an azetidinyl, oxetanyl, or a 5-membered ring, such as tetrahydrofuranyl, dioxolinyl, pyrrolidinyl, imidazolidinyl, pyrazolidinyl, or a 6-membered ring, such as tetrahydropyranyl, piperidinyl, morpholinyl, dithianyl, thiomorpholinyl, piperazinyl, or trithianyl, or a 7-membered ring, such as a diazepanyl ring, for example.

The term "heterospirocycloalkyl" is to be understood as meaning a saturated, monovalent bicyclic hydrocarbon radical in which the two rings share one common ring carbon atom, and wherein said bicyclic hydrocarbon radical contains 2, 3, 4, 5, 6, 7, 8 or 9 carbon atoms, and one or more heteroatom-containing groups selected from C(=O), O, S, S(=O), S(=O)$_2$, NR$^a$, in which R$^a$ represents a hydrogen atom or a $C_1$-$C_6$-alkyl- or $C_3$-$C_7$-cycloalkyl; it being possible for said heterospirocycloalkyl to be attached to the rest of the molecule via any one of the carbon atoms or, if present, the nitrogen atom. Said heterospirocycloalkyl is, for example, azaspiro-[2.3]hexyl-, azaspiro[3.3]heptyl-, oxaazaspiro[3.3]heptyl-, thiaazaspiro[3.3]heptyl-, oxaspiro[3.3]heptyl-, oxazaspiro[5.3]nonyl-, oxazaspiro[4.3]octyl-, oxazaspiro-[5.5]undecyl-, diazaspiro[3.3]heptyl-, thiazaspiro[3.3]heptyl-, thiazaspiro[4.3]-octyl-, or azaspiro[5.5]decyl-.

The term "heterobicycloalkyl" is to be understood as meaning a saturated, monovalent bicyclic hydrocarbon radical in which the two rings share two immediately adjacent ring atoms, and wherein said bicyclic hydrocarbon radical contains 2, 3, 4, 5, 6, 7, 8 or 9 carbon atoms, and one or more heteroatom-containing groups selected from C(=O), O, S, S(=O), S(=O)$_2$, NR$^a$, in which R$^a$ represents a hydrogen atom or C$_1$-C$_6$-alkyl or C$_3$-C$_7$-cycloalkyl; it being possible for said heterobicycloalkyl to be attached to the rest of the molecule via any one of the carbon atoms or, if present, the nitrogen atom. Said heterobicyo-alkyl is, for example, azabicyclo[3.3.0]octyl-, azabicyclo[4.3.0]nonyl-, diazabicyclo[4.3.0]nonyl-, oxazabicyclo[4.3.0]nonyl-, thiazabicyclo[4.3.0]nonyl-, or azabicyclo[4.4.0]decyl-.

The term "bridged heterocycloalkyl" is to be understood as meaning a saturated, monovalent bicyclic hydrocarbon radical in which the two rings share two common ring atoms which are not immediately adjacent, and wherein said bicyclic hydrocarbon radical contains 2, 3, 4, 5, 6, 7, 8 or 9 carbon atoms, and one or more heteroatom-containing groups selected from C(=O), O, S, S(=O), S(=O)$_2$, NR$^a$, in which R$^a$ represents a hydrogen atom, or a C$_1$-C$_6$-alkyl- or C$_3$-C$_7$-cycloalkyl-group; it being possible for said bridged heterocycloalkyl-group to be attached to the rest of the molecule via any one of the carbon atoms or, if present, the nitrogen atom. Said bridged heterocycloalkyl-group is, for example, azabicyclo[2.2.1]heptyl-, oxazabicyclo[2.2.1]heptyl-, thiazabicyclo[2.2.1]heptyl-, diazabicyclo[2.2.1]heptyl-, azabicyclo[2.2.2]octyl-, diazabicyclo[2.2.2]octyl-, oxazabicyclo[2.2.2]octyl-, thiazabicyclo[2.2.2]octyl-, azabicyclo[3.2.1]octyl-, diazabicyclo[3.2.1]octyl-, oxazabicyclo[3.2.1]octyl-, thiazabicyclo[3.2.1]octyl-, azabicyclo[3.3.1]nonyl-, diazabicyclo[3.3.1]nonyl-, oxazabicyclo[3.3.1]nonyl-, thiazabicyclo[3.3.1]nonyl-, azabicyclo[4.2.1]nonyl-, diazabicyclo[4.2.1]nonyl-, oxazabicyclo[4.2.1]nonyl, thiazabicyclo[4.2.1]nonyl-, azabicyclo[3.3.2]decyl-, diazabicyclo[3.3.2]decyl-, oxazabicyclo[3.3.2]decyl-, thiazabicyclo[3.3.2]decyl-, or azabicyclo[4.2.2]decyl-.

The term "C$_1$-C$_4$", as used throughout this text, e.g. in the context of the definition of "C$_1$-C$_4$-alkyl" or "—O(C$_1$-C$_4$-alkyl)" is to be understood as meaning an alkyl group having a finite number of carbon atoms of 1 to 4, i.e. 1, 2, 3 or 4 carbon atoms. It is to be understood further that said term "C$_1$-C$_4$" is to be interpreted as any sub-range comprised therein, e.g. C$_1$-C$_4$, C$_2$-C$_4$, C$_3$-C$_4$, C$_1$-C$_2$, C$_1$-C$_3$, C$_2$-C$_3$; particularly C$_1$-C$_2$, C$_1$-C$_3$, C$_1$-C$_4$; more particularly C$_1$-C$_2$.

Further, as used herein, the term "C$_3$-C$_6$", as used throughout this text, e.g. in the context of the definition of "C$_3$-C$_6$-cycloalkyl", is to be understood as meaning a cycloalkyl group having a finite number of carbon atoms of 3 to 6, i.e. 3, 4, 5 or 6 carbon atoms. It is to be understood further that said term "C$_3$-C$_6$" is to be interpreted as any sub-range comprised therein, e.g. C$_3$-C$_6$, C$_4$-C$_5$, C$_3$-C$_5$, C$_3$-C$_4$, C$_4$-C$_6$; particularly C$_4$-C$_5$.

The term "substituted" means that one or more hydrogens on the designated atom is/are replaced with a selection from the indicated group, provided that the designated atom's normal valency under the existing circumstances is not exceeded, and that the substitution results in a stable compound. Combinations of substituents and/or variables are permissible only if such combinations result in stable compounds.

The term "optionally substituted" means that the number of substituents can be zero. Unless otherwise indicated, optionally substituted groups may be substituted with as many optional substituents as can be accommodated by replacing a hydrogen atom with a non-hydrogen substituent on any available carbon or nitrogen atom. Commonly, the number of optional substituents (when present) ranges from 1 to 3.

As used herein, the term "one or more", e.g. in the definition of the substituents of the compounds of the general formulae of the present invention, is understood as meaning "one, two, three, four or five, particularly one, two, three or four, more particularly one, two or three, even more particularly one or two".

The invention also includes all suitable isotopic variations of a compound of the invention. An isotopic variation of a compound of the invention is defined as one in which at least one atom is replaced by an atom having the same atomic number but an atomic mass different from the atomic mass usually or predominantly found in nature. Examples of isotopes that can be incorporated into a compound of the invention include isotopes of hydrogen, carbon, nitrogen, oxygen, phosphorus, sulphur, fluorine, chlorine, bromine and iodine, such as $^2$H (deuterium), $^3$H (tritium), $^{11}$C, $^{13}$C, $^{14}$C, $^{15}$N, $^{17}$O, $^{18}$O, $^{32}$P, $^{33}$P, $^{33}$S, $^{34}$S, $^{35}$S, $^{36}$S, $^{18}$F, $^{36}$Cl, $^{82}$Br, $^{123}$I, $^{124}$I, $^{129}$I and $^{131}$I, respectively. Certain isotopic variations of a compound of the invention, for example, those in which one or more radioactive isotopes such as $^3$H or $^{14}$C are incorporated, are useful in drug and/or substrate tissue distribution studies. Tritiated and carbon-14, i.e., $^{14}$C, isotopes are particularly preferred for their ease of preparation and detectability. Further, substitution with isotopes such as deuterium may afford certain therapeutic advantages resulting from greater metabolic stability, for example, increased in vivo half-life or reduced dosage requirements and hence may be preferred in some circumstances. Isotopic variations of a compound of the invention can generally be prepared by conventional procedures known by a person skilled in the art such as by the illustrative methods or by the preparations described in the examples hereafter using appropriate isotopic variations of suitable reagents.

Optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, ditoluoyltartaric and camphorsulfonic acid. Mixtures of diastereoisomers can be separated into their individual diastereomers on the basis of their physical and/or chemical differences by methods known in the art, for example, by chromatography or fractional crystallisation. The optically active bases or acids are then liberated from the separated diastereomeric salts. A different process for separation of optical isomers involves the use of chiral chromatography (e.g., chiral HPLC columns), with or without conventional derivatisation, optimally chosen to maximise the separation of the enantiomers. Suitable chiral HPLC columns are manufactured by Daicel, e.g., Chiracel OD and Chiracel OJ among many others, all routinely selectable. Enzymatic separations, with or without derivatisation, are also useful. The optically active compounds of this invention can likewise be obtained by chiral syntheses utilizing optically active starting materials.

In order to limit different types of isomers from each other reference is made to IUPAC Rules Section E (Pure Appl Chem 45, 11-30, 1976).

The present invention includes in case a second stereogenic center is present, diastereomers of the compounds of the present invention as single stereoisomers, or as any mixture of said stereoisomers, in any ratio. Isolation of a single stereoisomer, e.g. a single diastereomer, of a compound of the present invention may be achieved by any suitable state of the art method, such as chromatography, especially chiral chromatography, for example.

The present invention includes all possible tautomers of the compounds of the present invention as single tautomers, or as any mixture of said tautomers, in any ratio.

Further, the compounds of the present invention can exist as N-oxides, which are defined that at least one nitrogen of the compounds of the present invention is oxidized. The present invention includes all such possible N-oxides.

The present invention also relates to useful forms of the compounds as disclosed herein, such as metabolites, hydrates, solvates, prodrugs, salts, in particular pharmaceutically acceptable salts, and co-precipitates.

Where the plural form of the word compounds, salts, polymorphs, hydrates, solvates and the like, is used herein, this is taken to mean also a single compound, salt, polymorph, isomer, hydrate, solvate or the like.

By "stable compound' or "stable structure" is meant a compound that is sufficiently robust to survive isolation to a useful degree of purity from a reaction mixture, and formulation into an efficacious therapeutic agent.

The compounds of the present invention can exist as a hydrate, or as a solvate, wherein the compounds of the present invention contain polar solvents, in particular water, methanol or ethanol for example as structural element of the crystal lattice of the compounds. The amount of polar solvents, in particular water, may exist in a stoichiometric or non-stoichiometric ratio. In the case of stoichiometric solvates, e.g. a hydrate, hemi-, (semi-), mono-, sesqui-, di-, tri-, tetra-, penta- etc. solvates or hydrates, respectively, are possible. The present invention includes all such hydrates or solvates.

Further, the compounds of the present invention can exist in free form, e.g. as a free base, or as a free acid, or as a zwitterion, or can exist in the form of a salt. Said salt may be any salt, either an organic or inorganic addition salt, particularly any pharmaceutically acceptable organic or inorganic addition salt, customarily used in pharmacy.

The term "pharmaceutically acceptable salt" refers to a relatively non-toxic, inorganic or organic acid addition salt of a compound of the present invention. For example, see S. M. Berge, et al. "Pharmaceutical Salts," J. Pharm. Sci. 1977, 66, 1-19. A suitable pharmaceutically acceptable salt of the compounds of the present invention may be, for example, an acid-addition salt of a compound of the present invention bearing a nitrogen atom, in a chain or in a ring, for example, which is sufficiently basic, such as an acid-addition salt with an inorganic acid, such as hydrochloric, hydrobromic, hydroiodic, sulfuric, bisulfuric, phosphoric, or nitric acid, for example, or with an organic acid, such as formic, acetic, acetoacetic, pyruvic, trifluoroacetic, propionic, butyric, hexanoic, heptanoic, undecanoic, Lauric, benzoic, salicylic, 2-(4-hydroxybenzoyl)-benzoic, camphoric, cinnamic, cyclopentanepropionic, digluconic, 3-hydroxy-2-naphthoic, nicotinic, pamoic, pectinic, persulfuric, 3-phenylpropionic, picric, pivalic, 2-hydroxyethanesulfonic, itaconic, sulfamic, trifluoromethanesulfonic, dodecylsulfuric, ethansulfonic, benzenesulfonic, para-toluenesulfonic, methansulfonic, 2-naphthalenesulfonic, naphthalinedisulfonic, camphorsulfonic acid, citric, tartaric, stearic, lactic, oxalic, malonic, succinic, malic, adipic, alginic, maleic, fumaric, D-gluconic, mandelic, ascorbic, glucoheptanoic, glycerophosphoric, aspartic, sulfosalicylic, hemisulfuric, or thiocyanic acid, for example.

Further, another suitably pharmaceutically acceptable salt of a compound of the present invention which is sufficiently acidic, is an alkali metal salt, for example a sodium or potassium salt, an alkaline earth metal salt, for example a calcium or magnesium salt, an ammonium salt or a salt with an organic base which affords a physiologically acceptable cation, for example a salt with N-methyl-glucamine, dimethyl-glucamine, ethyl-glucamine, lysine, dicyclohexylamine, 1,6-hexadiamine, ethanolamine, glucosamine, sarcosine, serinol, tris-hydroxy-methyl-aminomethane, aminopropandiol, sovak-base, 1-amino-2,3,4-butantriol. Additionally, basic nitrogen containing groups may be quaternised with such agents as lower alkyl halides such as methyl, ethyl, propyl, and butyl chlorides, bromides and iodides; dialkyl sulfates like dimethyl, diethyl, and dibutyl sulfate; and diamyl sulfates, long chain halides such as decyl, lauryl, myristyl and strearyl chlorides, bromides and iodides, aralkyl halides like benzyl, and phenethyl bromides and others.

Those skilled in the art will further recognize that acid addition salts of the claimed compounds may be prepared by reaction of the compounds with the appropriate inorganic or organic acid via any of a number of known methods. Alternatively, alkali and alkaline earth metal salts of acidic compounds of the invention are prepared by reacting the compounds of the invention with the appropriate base via a variety of known methods.

The present invention includes all possible salts of the compounds of the present invention as single salts, or as any mixture of said salts, in any ratio.

As used herein, the term "in vivo hydrolysable ester" is understood as meaning an in vivo hydrolysable ester of a compound of the present invention containing a carboxy or hydroxy group, for example, a pharmaceutically acceptable ester which is hydrolyzed in the human or animal body to produce the parent acid or alcohol. Suitable pharmaceutically acceptable esters for said carboxy group include for example alkyl, cycloalkyl and optionally substituted phenylalkyl, in particular benzyl esters, $C_1$-$C_6$-alkoxymethyl esters, e.g. methoxymethyl, $C_1$-$C_6$-alkanoyloxymethyl esters, e.g. pivaloyloxymethyl, phthalidyl esters, $C_3$-$C_8$-cycloalkoxy-carbonyloxy-$C_1$-$C_6$-alkyl esters, e.g. 1-cyclohexylcarbonyloxyethyl; 1,3-dioxolen-2-carbonyloxymethyl esters, e.g. 5-methyl-1,3-dioxolen-2-carbonyloxymethyl; and $C_1$-$C_6$-alkoxycarbonyloxyethyl esters, e.g. 1-methoxycarbonyloxy-ethyl, and may be formed at any carboxy group in the compounds of this invention. An in vivo hydrolysable ester of a compound of the present invention containing a hydroxy group includes inorganic esters such as phosphate esters and [alpha]-acyloxyalkyl ethers and related compounds which as a result of the in vivo hydrolysis of the ester breakdown to give the parent hydroxy group. Examples of [alpha]-acyloxyalkyl ethers include acetoxymethoxy and 2,2-dimethylpropionyloxy-methoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl. The present invention covers all such esters.

Furthermore, the present invention includes all possible crystalline forms, or polymorphs, of the compounds of the present invention, either as single polymorphs or as a mixture of more than one polymorph in any ratio.

In accordance with a first aspect, the present invention covers compounds of general formula (I):

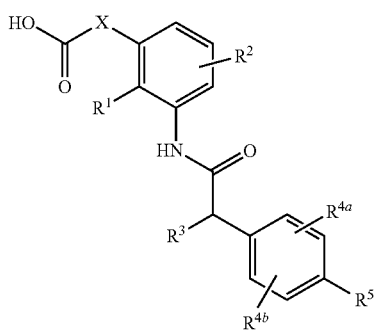

in which:
$R^1$ represents an optionally substituted $C_1$-$C_4$-alkyl; and
$R^2$ to $R^8$ have the same meaning as defined above;
or a tautomer, an isomer, enantiomer, diastereomer, racemate, an N-oxide, a hydrate, a solvate, or a salt thereof, or a mixture of same.

In another embodiment of the above-mentioned aspects, the invention relates to compounds of formula (I), wherein
$R^2$ represents hydrogen or halogen; and
$R^1$ and $R^3$ to $R^8$ have the same meaning as defined above;
or a tautomer, an isomer, enantiomer, diastereomer, racemate, an N-oxide, a hydrate, a solvate, or a salt thereof, or a mixture of same.

In another embodiment of the above-mentioned aspects, the invention relates to compounds of formula (I), according to any of the above-mentioned embodiments, wherein
$R^3$ represents unsubstituted $C_3$-$C_6$-Cycloalkyl; and
$R^1$, $R^2$, $R^4$ to $R^8$ have the same meaning as defined above;
or a tautomer, an isomer, enantiomer, diastereomer, racemate, an N-oxide, a hydrate, a solvate, or a salt thereof, or a mixture of same.

In yet another embodiment of the above-mentioned aspects, the invention relates to compounds of formula (I), according to any of the above-mentioned embodiments, wherein
n as defined for the two substituents $R^{4a}$ and $R^{4b}$ is 1; and
$R^1$ to $R^8$ have the same meaning as defined above;
or a tautomer, an isomer, enantiomer, diastereomer, racemate, an N-oxide, a hydrate, a solvate, or a salt thereof, or a mixture of same.

In yet another embodiment of the above-mentioned aspects, the invention relates to compounds of formula (I), according to any of the above-mentioned embodiments, wherein
$R^{4a}$ and $R^{4b}$ represent hydrogen, halogen or $C_1$-$C_4$-alkyl; and
$R^1$ to $R^3$ and $R^5$ to $R^8$ have the same meaning as defined above;
or a tautomer, an isomer, enantiomer, diastereomer, racemate, an N-oxide, a hydrate, a solvate, or a salt thereof, or a mixture of same.

In yet another embodiment of the above-mentioned aspects, the invention relates to compounds of formula (I), according to any of the above-mentioned embodiments, wherein
$R^{4a}$ is in ortho position in relation to $R^5$; and
$R^1$ to $R^3$, $R^5$ to $R^8$ have the same meaning as defined above;
or a tautomer, an isomer, enantiomer, diastereomer, racemate, an N-oxide, a hydrate, a solvate, or a salt thereof, or a mixture of same.

In yet another embodiment of the above-mentioned aspects, the invention relates to compounds of formula (I), according to any of the above-mentioned embodiments, wherein
$R^{4a}$ is in ortho position in relation to $R^5$; and
$R^{4b}$ is in meta position in relation to $R^5$; and
$R^1$ to $R^3$ and $R^5$ to $R^8$ have the same meaning as defined above;
or a tautomer, an isomer, enantiomer, diastereomer, racemate, an N-oxide, a hydrate, a solvate, or a salt thereof, or a mixture of same.

In yet another embodiment of the above-mentioned aspects, the invention relates to compounds of formula (I), according to any of the above-mentioned embodiments, wherein
$R^5$ represents pyridine-3-yl, which is substituted with one or two substituents which are the same or different and selected from the group consisting of halogen, $C_1$-$C_4$-alkyl, —O—($C_1$-$C_4$-alkyl), $C_3$-$C_6$-cycloalkyl, and —O—($C_3$-$C_6$-cycloalkyl); and
wherein said $C_1$-$C_4$-alkyl and —O—($C_1$-$C_4$-alkyl) are optionally substituted with 1-5 halogen atoms which are the same or different; and
$R^1$ to $R^3$, $R^{4a}$ and $R^{4b}$ as well as $R^6$ to $R^8$ have the same meaning as defined above;
or a tautomer, an isomer, enantiomer, diastereomer, racemate, an N-oxide, a hydrate, a solvate, or a salt thereof, or a mixture of same.

In yet another embodiment of the above-mentioned aspects, the invention relates to compounds of formula (I), according to any of the above-mentioned embodiments, wherein
$R^5$ represents pyridine-3-yl, which is substituted with a halogen or $C_1$-$C_4$-alkyl wherein said $C_1$-$C_4$-alkyl is optionally substituted with 1-5 halogen atoms which are the same or different; and
$R^1$ to $R^3$, $R^{4a}$ and $R^{4b}$ as well as $R^6$ to $R^8$ have the same meaning as defined above;
or a tautomer, an isomer, enantiomer, diastereomer, racemate, an N-oxide, a hydrate, a solvate, or a salt thereof, or a mixture of same.

In yet another embodiment of the above-mentioned aspects, the invention relates to compounds of formula (I), according to any of the above-mentioned embodiments, wherein
$R^5$ represents pyridine-3-yl, which is substituted with a halogen and additionally substituted with $C_1$-$C_4$-alkyl; and
wherein said $C_1$-$C_4$-alkyl is optionally substituted with 1-5 fluorine atoms; and
$R^1$ to $R^3$, $R^{4a}$ and $R^{4b}$ as well as $R^6$ to $R^8$ have the same meaning as defined above;
or a tautomer, an isomer, enantiomer, diastereomer, racemate, an N-oxide, a hydrate, a solvate, or a salt thereof, or a mixture of same.

In yet another embodiment of the above-mentioned aspects, the invention relates to compounds of formula (I), according to any of the above-mentioned embodiments, wherein
$R^1$ represents unsubstituted $C_1$-$C_4$-Alkyl; and
$R^2$ represents hydrogen; and
$R^3$ to $R^8$ have the same meaning as defined above;

or a tautomer, an isomer, enantiomer, diastereomer, racemate, an N-oxide, a hydrate, a solvate, or a salt thereof, or a mixture of same.

In yet another embodiment of the above-mentioned aspects, the invention relates to compounds of formula (I), according to any of the above-mentioned embodiments, wherein $R^1$ represents unsubstituted $C_1$-$C_4$-Alkyl; and
$R^2$ represents hydrogen; and
$R^3$ represents unsubstituted $C_3$-$C_6$-Cycloalkyl; and
$R^{4a}$ and $R^{4b}$ as well as $R^5$ to $R^8$ have the same meaning as defined above;

or a tautomer, an isomer, enantiomer, diastereomer, racemate, an N-oxide, a hydrate, a solvate, or a salt thereof, or a mixture of same.

In yet another embodiment of the above-mentioned aspects, the invention relates to compounds of formula (I), according to any of the above-mentioned embodiments, wherein $R^1$ represents unsubstituted $C_1$-$C_4$-Alkyl; and
$R^2$ represents hydrogen; and
$R^3$ represents unsubstituted $C_3$-$C_6$-Cycloalkyl; and
$R^{4a}$ and $R^{4b}$ both represents hydrogen; and
$R^5$ to $R^8$ have the same meaning as defined above;

or a tautomer, an isomer, enantiomer, diastereomer, racemate, an N-oxide, a hydrate, a solvate, or a salt thereof, or a mixture of same.

In yet another embodiment of the above-mentioned aspects, the invention relates to compounds of formula (I), according to any of the above-mentioned embodiments, wherein $R^1$ represents unsubstituted $C_1$-$C_4$-Alkyl, preferably methyl; and
$R^2$ represents hydrogen; and
$R^3$ represents unsubstituted $C_3$-$C_6$-Cycloalkyl, preferably cyclopentyl; and
$R^{4a}$ and $R^{4b}$ both represent hydrogen; and
$R^5$ represents pyridine-3-yl, which is substituted with one halogen, preferably chlorine; and
$R^6$ to $R^8$ have the same meaning as defined above;

or a tautomer, an isomer, enantiomer, diastereomer, racemate, an N-oxide, a hydrate, a solvate, or a salt thereof, or a mixture of same.

In yet another embodiment of the above-mentioned aspects, the invention relates to compounds of formula (I), according to any of the above-mentioned embodiments, wherein $R^1$ represents unsubstituted $C_1$-$C_4$-Alkyl, preferably methyl; and
$R^2$ represents hydrogen; and
$R^3$ represents unsubstituted $C_3$-$C_6$-Cycloalkyl, preferably cyclopentyl; and
$R^{4a}$ represents halogen, preferably fluorine or chlorine; or $C_1$-$C_4$-alkyl, preferably methyl; and
$R^{4b}$ represents hydrogen, $C_1$-$C_4$-alkyl, preferably methyl; or halogen, preferably fluorine; and
$R^5$ represents pyridine-3-yl, which is substituted with one halogen, preferably chlorine; or and $C_1$-$C_4$-alkyl which is optionally substituted with 1-5 halogen atoms which are the same or different;
$R^6$ to $R^8$ have the same meaning as defined above;

or a tautomer, an isomer, enantiomer, diastereomer, racemate, an N-oxide, a hydrate, a solvate, or a salt thereof, or a mixture of same.

In yet another embodiment of the above-mentioned aspects, the invention relates to compounds of formula (I), according to any of the above-mentioned embodiments, wherein $R^1$ represents unsubstituted $C_1$-$C_4$-Alkyl, preferably methyl; and
$R^2$ represents hydrogen; and
$R^3$ represents unsubstituted $C_3$-$C_6$-Cycloalkyl, preferably cyclopentyl; and
$R^{4a}$ represents halogen, preferably fluorine or chlorine; and
$R^{4b}$ represents hydrogen or $C_1$-$C_4$-alkyl, preferably methyl; and
$R^5$ represents pyridine-3-yl, which is substituted with one halogen, preferably chlorine; and
$R^6$ to $R^8$ have the same meaning as defined above;

or a tautomer, an isomer, enantiomer, diastereomer, racemate, an N-oxide, a hydrate, a solvate, or a salt thereof, or a mixture of same.

In yet another embodiment of the above-mentioned aspects, the invention relates to compounds of formula (I), according to any of the above-mentioned embodiments, wherein $R^1$ represents unsubstituted $C_1$-$C_4$-Alkyl, preferably methyl; and
$R^2$ represents hydrogen; and
$R^3$ represents unsubstituted $C_3$-$C_6$-Cycloalkyl, preferably cyclopentyl; and
$R^{4a}$ represents halogen, preferably fluorine; and
$R^{4b}$ represents halogen, preferably fluorine; and
$R^5$ represents pyridine-3-yl, which is substituted with one halogen, preferably chlorine; and
$R^6$ to $R^8$ have the same meaning as defined above;

or a tautomer, an isomer, enantiomer, diastereomer, racemate, an N-oxide, a hydrate, a solvate, or a salt thereof, or a mixture of same.

In yet another preferred embodiment, the invention relates to compounds of formula (I), as defined in any one of the embodiments, namely the following:

1) (R/S) 3-{3-[(Cyclopentyl{4-[5-(trifluormethyl)pyridin-3-yl]phenyl}-acetyl)amino]-2-methylphenyl}propanoic acid (Example 1)
2) (−) 3-{3-[(Cyclopentyl{4-[5-(trifluormethyl)pyridin-3-yl]phenyl}-acetyl)amino]-2-methylphenyl}propanoic acid (Example 2)
3) (+) 3-{3-[(Cyclopentyl{4-[5-(trifluormethyl)pyridin-3-yl]phenyl}-acetyl)amino]-2-methylphenyl}propanoic acid (Example 3)
4) (R/S) 3-{3-[(Cyclopentyl{4-[6-(trifluormethyl)pyridin-3-yl]phenyl}-acetyl)amino]-2-methylphenyl}propanoic acid (Example 4)
5) (−) 3-{3-[(Cyclopentyl{4-[6-(trifluormethyl)pyridin-3-yl]phenyl}-acetyl)amino]-2-methylphenyl}propanoic acid (Example 5)
6) (R/S) 3-[3-({Cyclopentyl[4-(5-fluoropyridin-3-yl)phenyl]acetyl}amino)-2-methylphenyl]propanoic acid (Example 6)
7) (R/S) 3-[3-({[4-(6-Cyanpyridin-3-yl)phenyl](cyclopentyl)acetyl}amino)-2-methylphenyl]propanoic acid (Example 7)
8) (R/S) 3-[3-({Cyclopentyl[4-(5-ethoxypyridin-3-yl)phenyl]acetyl}amino)-2-methylphenyl]propanoic acid (Example 8)
9) (R/S) 3-{3-[(Cyclopentyl{4-[5-(2-hydroxypropan-2-yl)pyridin-3-yl]-phenyl}acetyl)amino]-2-methylphenyl}propanoic acid (Example 9)

10) (R/S) 3-{3-[(Cyclopentyl{4-[5-(methoxymethyl)pyridin-3-yl]phenyl}-acetyl)amino]-2-methylphenyl}propanoic acid (Example 10)
11) (R/S) 3-[3-({Cyclopentyl[4-(5-methoxypyridin-3-yl)phenyl]acetyl}-amino)-2-methylphenyl]propanoic acid (Example 11)
12) (R/S) 3-[3-({Cyclopentyl[4-(4-methylpyridin-3-yl)phenyl]acetyl}amino)-2-methylphenyl]propanoic acid (Example 12)
13) (R/S) 3-[3-({Cyclopentyl[4-(5-ethylpyridin-3-yl)phenyl]acetyl}amino)-2-methylphenyl]propanoic acid (Example 13)
14) 3-[3-({Cyclopentyl[4-(5-cyclopropylpyridin-3-yl)phenyl]acetyl}amino)-2-methylphenyl]propanoic acid (Example 14)
15) (R/S) 3-{3-[(Cyclopentyl{4-[5-(tetrahydro-2H-pyran-4-yloxy)pyridin-3-yl]phenyl}acetyl)amino]-2-methylphenyl}propanoic acid (Example 15)
16) (R/S) 3-[3-({[4-(5-Chloropyridin-3-yl)phenyl](cyclopentyl)acetyl}amino)-2-methylphenyl]propanoic acid (Example 16)
17) (−) (R) 3-[3-({[4-(5-Chloropyridin-3-yl)phenyl](cyclopentyl)acetyl}amino)-2-methylphenyl]propanoic acid (Example 17)
18) (R/S) 3-[3-({Cyclopentyl[4-(6-methoxypyridin-3-yl)phenyl]acetyl}-amino)-2-methylphenyl]propanoic acid (Example 18)
19) (R/S) 3-[3-({Cyclopentyl[4-(6-fluoropyridin-3-yl)-phenyl]acetyl}amino)-2-methylphenyl]propanoic acid (Example 19)
20) (R/S) 3-[3-({Cyclopentyl[4-(2-methoxypyridin-3-yl)phenyl]acetyl}-amino)-2-methylphenyl]propanoic acid (Example 20)
21) (R/S) 3-[3-({Cyclopentyl[4-(5-methylpyridin-3-yl)phenyl]acetyl}amino)-2-methylphenyl]propanoic acid (Example 21)
22) (R/S) 3-[3-({Cyclopentyl[4-(6-methylpyridin-3-yl)phenyl]acetyl}amino)-2-methylphenyl]propanoic acid (Example 22)
23) (R/S) 3-[3-({cyclopentyl[4-(2-fluoropyridin-3-yl)phenyl]acetyl}amino)-2-methyl-phenyl]propanoic acid (Example 23)
24) (R/S) 3-[3-({[4-(5-Chloro-6-methylpyridin-3-yl)phenyl](cyclopentyl)-acetyl}amino)-2-methylphenyl]propanoic acid (Example 24)
25) (+) (S) 3-[3-({[4-(5-Chloro-6-methylpyridin-3-yl)phenyl](cyclopentyl)-acetyl}amino)-2-methylphenyl]propanoic acid (Example 25)
26) (−) (R) 3-[3-({[4-(5-Chloro-6-methylpyridin-3-yl)phenyl](cyclopentyl)-acetyl}amino)-2-methylphenyl]propanoic acid (Example 26)
27) (R/S) 3-[3-({Cyclopentyl[4-(5,6-dimethylpyridin-3-yl)phenyl]acetyl}-amino)-2-methylphenyl]propanoic acid (Example 27)
28) (R/S) 3-{3-[(Cyclopentyl{4-[5-(difluoromethoxy)pyridin-3-yl]phenyl}-acetyl)amino]-2-methylphenyl}propanoic acid (Example 28)
29) (R/S) 3-{3-[(Cyclopentyl{4-[5-(difluoromethyl)pyridin-3-yl]phenyl}-acetyl)amino]-2-methylphenyl}propanoic acid (Example 29)
30) (R/S) 3-{3-[(Cyclopentyl{4-[5-(fluoromethyl)pyridin-3-yl]phenyl}-acetyl)amino]-2-methylphenyl}propanoic acid (Example 30)
31) (R/S) 3-[3-({[4-(5-Chlorpyridin-3-yl)phenyl](cyclopropyl)acetyl}amino)-2-methylphenyl]propanoic acid (Example 31)
32) 3-{3-[(Cyclopropyl{4-[5-(trifluormethyl)pyridin-3-yl]phenyl}acetyl)-amino]-2-methylphenyl}propanoic acid (Example 32)
33) (R/S) {3-[(cyclopentyl{4-[5-(trifluoromethyl)pyridin-3-yl]phenyl}acetyl)amino]-2-methylphenoxy}acetic acid (Example 33)
34) (−) {3-[(cyclopentyl{4-[5-(trifluoromethyl)pyridin-3-yl]phenyl}acetyl)amino]-2-methylphenoxy}acetic acid (Example 34)
35) (+) {3-[(cyclopentyl{4-[5-(trifluoromethyl)pyridin-3-yl]phenyl}acetyl)amino]-2-methylphenoxy}acetic acid (Example 35)
36) (R/S) [3-({[4-(5-chloropyridin-3-yl)phenyl](cyclopentyl)acetyl}amino)-2-methylphenoxy]acetic acid (Example 36)
37) (−)[3-({[4-(5-chloropyridin-3-yl)phenyl](cyclopentyl)acetyl}amino)-2-methylphenoxy]acetic acid (Example 37)
38) (R/S) 3-[3-({[4-(5-Chloropyridin-3-yl)phenyl](cyclopentyl)acetyl}-amino)-6-methoxy-2-methylphenyl]propanoic acid (Example 38)
39) (−) 3-[3-({[4-(5-Chloropyridin-3-yl)phenyl](cyclopentyl)acetyl}amino)-6-methoxy-2-methylphenyl]propanoic acid (Example 39)
40) (R/S) 3-{3-[(Cyclopentyl{4-[5-(trifluoromethyl)pyridin-3-yl]phenyl}-acetyl)amino]-6-methoxy-2-methylphenyl}propanoic acid (Example 40)
41) (R/S) 3-{3-[(Cyclopentyl{3-methyl-4-[5-(trifluoromethyl)pyridin-3-yl]phenyl}acetyl)amino]-2-methylphenyl}propanoic acid (Example 41)
42) (R/S) 3-[3-({[4-(5-Chloropyridin-3-yl)-3-methylphenyl](cyclopentyl)-acetyl}amino)-2-methylphenyl]propanoic acid (Example 42)
43) (R/S) 3-[3-({[4-(5-Chloropyridin-3-yl)-3-fluorophenyl](cyclopentyl)-acetyl}amino)-2-methylphenyl]propanoic acid (Example 43)
44) (−) 3-[3-({[4-(5-Chloropyridin-3-yl)-3-fluorophenyl](cyclopentyl)-acetyl}amino)-2-methylphenyl]propanoic acid (Example 44)
45) (+) 3-[3-({[4-(5-Chloropyridin-3-yl)-3-fluorophenyl](cyclopentyl)acetyl}-amino)-acetyl}amino)-2-methyl-phenyl]propanoic acid (Example 45)
46) (R/S) 3-[3-({Cyclopentyl[4-(5-ethoxypyridin-3-yl)-3-fluoro-phenyl]-acetyl}amino)-2-methylphenyl]propanoic acid (Example 46)
47) (R/S) 3-{3-[(Cyclopentyl{3-fluoro-4-[5-(trifluoromethyl)pyridin-3-yl]-phenyl}acetyl)amino]-2-methylphenyl}propanoic acid (Example 47)
48) (−) 3-{3-[(Cyclopentyl{3-fluoro-4-[5-(trifluoromethyl)pyridin-3-yl]-phenyl}acetyl)amino]-2-methylphenyl}propanoic acid (Example 48)
49) (+) 3-{3-[(Cyclopentyl{3-fluoro-4-[5-(trifluoromethyl)pyridin-3-yl]-phenyl}acetyl)amino]-2-methylphenyl}propanoic acid (Example 49)
50) (R/S) 3-{3-[(cyclopentyl{4-[5-(difluoromethyl)pyridin-3-yl]-3-fluoro-phenyl}acetyl)amino]-2-methylphenyl}propanoic acid (Example 50)
51) (R/S) 3-[3-({[4-(5-Chloropyridin-3-yl)-2-fluorophenyl](cyclopentyl)-acetyl}amino)-2-methylphenyl]propanoic acid (Example 51)
52) (R/S) 3-[3-({Cyclopentyl[4-(5-ethoxypyridin-3-yl)-2-fluorophenyl]-acetyl}amino)-2-methylphenyl]propanoic acid (Example 52)
53) (R/S) 3-{3-[(Cyclopentyl{2-fluoro-4-[5-(trifluoromethyl)pyridin-3-yl]-phenyl}acetyl)amino]-2-methylphenyl}propanoic acid (Example 53)

54) (R/S) 3-{3-[(Cyclobutyl{4-[5-(trifluoromethyl)pyridin-3-yl]phenyl}-acetyl)amino]-2-methylphenyl}propanoic acid (Example 54)
55) (−) 3-{3-[(Cyclobutyl{4-[5-(trifluoromethyl)pyridin-3-yl]phenyl}acetyl)-amino]-2-methylphenyl}propanoic acid (Example 55)
56) (+) 3-{3-[(Cyclobutyl{4-[5-(trifluoromethyl)pyridin-3-yl]phenyl}acetyl)-amino]-2-methylphenyl}propanoic acid (Example 56)
57) (R/S) 3-[3-({[4-(5-Chloropyridin-3-yl)phenyl](cyclobutyl)acetyl}amino)-2-methylphenyl]propanoic acid (Example 57)
58) (R/S) 3-[3-({Cyclobutyl[4-(5-ethoxypyridin-3-yl)phenyl]acetyl}amino)-2-methylphenyl]propanoic acid (Example 58)
59) (R/S) 3-[3-({Cyclobutyl[4-(5,6-dimethylpyridin-3-yl)phenyl]acetyl}-amino)-2-methylphenyl]propanoic acid (Example 59)
60) (R/S) 3-[3-({Cyclobutyl[4-(5-fluoropyridin-3-yl)phenyl]acetyl}amino)-2-methylphenyl]propanoic acid (Example 60)
61) (R/S) 3-[3-({[4-(5-chloro-6-methylpyridin-3-yl)phenyl](cyclobutyl)-acetyl}amino)-2-methylphenyl]propanoic acid (Example 61)
62) (R/S) 3-[3-({[4-(5-Fluoro-6-methylpyridin-3-yl)phenyl](cyclobutyl)-acetyl}amino)-2-methylphenyl]propanoic acid (Example 62)
63) (R/S) 3-{3-[(Cyclobutyl{4-[5-(difluoromethoxy)pyridin-3-yl]phenyl}-acetyl)amino]-2-methylphenyl}propanoic acid (Example 63)
64) (R/S) 3-[3-({Cyclobutyl[4-(5-methylpyridin-3-yl)phenyl]acetyl}amino)-2-methylphenyl]propanoic acid (Example 64)
65) (R/S) 3-[3-({[4-(5-Chloropyridin-3-yl)phenyl](cyclohexyl)acetyl}amino)-2-methylphenyl]propanoic acid (Example 65)
66) (R/S) 3-{3-[(Cyclohexyl{4-[5-(trifluoromethyl)pyridin-3-yl]phenyl}-acetyl)amino]-2-methylphenyl}propanoic acid (Example 66)
67) (R/S) 3-[3-({Cyclohexyl[4-(5-ethoxypyridin-3-yl)phenyl]acetyl}amino)-2-methylphenyl]propanoic acid (Example 67)
68) (2R/S)-3-(3-{[(2R/S)-2-Cyclopentyl-2-{4-[5-(trifluoromethyl)pyridin-3-yl]phenyl}acetyl]amino}-2-methylphenyl)-2-methylpropanoic acid (Example 68)
69) (2R)-3-(3-{[(2R)-2-cyclopentyl-2-{4-[5-(trifluoromethyl)pyridin-3-yl]phenyl}acetyl]amino}-2-methylphenyl)-2-methylpropanoic acid (Example 69)
70) (2S)-3-(3-{[(2S)-2-cyclopentyl-2-{4-[5-(trifluoromethyl)pyridin-3-yl]phenyl}acetyl]amino}-2-methylphenyl)-2-methylpropanoic acid (Example 70)
71) (2R)-3-(3-{[(2S)-2-cyclopentyl-2-{4-[5-(trifluoromethyl)pyridin-3-yl]phenyl}acetyl]amino}-2-methylphenyl)-2-methylpropanoic acid (Example 71)
72) (2S)-3-(3-{[(2R)-2-cyclopentyl-2-{4-[5-(trifluoromethyl)pyridin-3-yl]phenyl}acetyl]amino}-2-methylphenyl)-2-methylpropanoic acid (Example 72)
73) (2R/S)-3-[3-({(2R/S)-2-[4-(5-Chloropyridin-3-yl)phenyl]-2-cyclopentylacetyl}amino)-2-methylphenyl]-2-methylpropanoic acid (Example 73)
74) (2R)-3-[3-({(2R)-2-[4-(5-chloropyridin-3-yl)phenyl]-2-cyclopentylacetyl}-amino)-2-methylphenyl]-2-methylpropanoic acid (Example 74)
75) (2S)-3-[3-({(2S)-2-[4-(5-chloropyridin-3-yl)phenyl]-2-cyclopentylacetyl}-amino)-2-methylphenyl]-2-methylpropanoic acid (Example 75)
76) (2R)-3-[3-({(2S)-2-[4-(5-chloropyridin-3-yl)phenyl]-2-cyclopentylacetyl}-amino)-2-methylphenyl]-2-methylpropanoic acid (Example 76)
77) (2S)-3-[3-({(2R)-2-[4-(5-chloropyridin-3-yl)phenyl]-2-cyclopentylacetyl}-amino)-2-methylphenyl]-2-methylpropanoic acid (Example 77)
78) (2R/2S)-3-[3-({(2R/2S)-2-Cyclopentyl-2-[4-(5,6-dimethylpyridin-3-yl)-phenyl]acetyl}amino)-2-methylphenyl]-2-methylpropanoic acid (Example 78)
79) (2R/2S)-3-[3-({(2R/2S)-2-Cyclopentyl-2-[4-(6-methylpyridin-3-yl)-phenyl]acetyl}amino)-2-methylphenyl]-2-methylpropanoic acid (Example 79)
80) (2R/2S)-3-(3-{[(2R/2S)-2-Cyclopentyl-2-{4-[5-(difluoromethoxy)pyridin-3-yl]phenyl}acetyl]amino}-2-methylphenyl)-2-methylpropanoic acid (Example 80)
81) (2R/2S)-3-[3-({(2R/2S)-2-Cyclopentyl-2-[4-(5-methylpyridin-3-yl)-phenyl]acetyl}amino)-2-methylphenyl]-2-methylpropanoic acid (Example 81)
82) (2R/2S)-3-[3-({(2R/2S)-2-Cyclopentyl-2-[4-(5-fluoro-6-methylpyridin-3-yl)phenyl]acetyl}amino)-2-methylphenyl]-2-methylpropanoic acid (Example 82)
83) (2R)-3-[3-({(2R)-2-[4-(5-chloro-6-methylpyridin-3-yl)phenyl]-2-cyclopentylacetyl}amino)-2-methylphenyl]-2-methylpropanoic acid (Example 83)
84) (2S)-3-[3-({(2R)-2-[4-(5-chloro-6-methylpyridin-3-yl)phenyl]-2-cyclopentylacetyl}amino)-2-methylphenyl]-2-methylpropanoic acid (Example 84)
85) (3R/S)-3-[3-({(2R/S)-2-[4-(5-Chloropyridin-3-yl)phenyl]-2-cyclopentylacetyl}amino)-2-methylphenyl]butanoic acid (Example 85)
86) (3R)-3-[3-({(2R)-2-[4-(5-chloropyridin-3-yl)phenyl]-2-cyclopentylacetyl}amino)-2-methylphenyl]butanoic acid (Example 86)
87) (3S)-3-[3-({(2S)-2-[4-(5-chloropyridin-3-yl)phenyl]-2-cyclopentylacetyl}amino)-2-methylphenyl]butanoic acid (Example 87)
88) (3R)-3-[3-({(2S)-2-[4-(5-chloropyridin-3-yl)phenyl]-2-cyclopentylacetyl}amino)-2-methylphenyl]butanoic acid (Example 88)
89) (3S)-3-[3-({(2R)-2-[4-(5-chloropyridin-3-yl)phenyl]-2-cyclopentylacetyl}amino)-2-methylphenyl]butanoic acid (Example 89)
90) (3R/S)-3-[3-({(2R/S)-2-Cyclopentyl-2-[4-(5-ethoxypyridin-3-yl)phenyl]-acetyl}amino)-2-methylphenyl]butanoic acid (Example 90)
91) (3R/S)-3-(3-{[(2R/S)-2-Cyclopentyl-2-{4-[5-(trifluoromethyl)pyridin-3-yl]phenyl}acetyl]amino}-2-methylphenyl)butanoic acid (Example 91)
92) (3R/S)-3-[3-({(2R/S)-2-Cyclopentyl-2-[4-(5-ethylpyridin-3-yl)phenyl]-acetyl}amino)-2-methylphenyl]butanoic acid (Example 92)
93) (3R/S)-3-[3-({(2R/S)-2-Cyclopentyl-2-[4-(5,6-dimethylpyridin-3-yl)-phenyl]acetyl}amino)-2-methylphenyl]butanoic acid (Example 93)
94) (3R/S)-3-[3-({(2R/S)-2-Cyclopentyl-2-[4-(5-methylpyridin-3-yl)phenyl]-acetyl}amino)-2-methylphenyl]butanoic acid (Example 94)
95) (3R/S)-3-[3-({(2R/S)-2-Cyclopentyl-2-[4-(5-fluoropyridin-3-yl)phenyl]-acetyl}amino)-2-methylphenyl]butanoic acid (Example 95)
96) (3R/S)-3-[3-({(2R/S)-2-[4-(5-Fluoro-6-methylpyridin-3-yl)phenyl]-2-cyclopentylacetyl}amino)-2-methylphenyl]butanoic acid (Example 96)
97) (3R/S)-3-[3-({(2R/S)-2-[4-(5-Chloro-6-methylpyridin-3-yl)phenyl]-2-cyclopentylacetyl}amino)-2-methylphenyl]butanoic acid (Example 97)

98) (3R/S)-3-(3-{[(2R/S)-2-Cyclopentyl-2-{4-[5-(difluoromethyl)pyridin-3-yl]phenyl}acetyl]amino}-2-methylphenyl)butanoic acid (Example 98)
99) (3R/S)-3-[3-({(2R/S)-2-[4-(5-Chloropyridin-3-yl)phenyl]-2-cyclopentylacetyl}amino)-2-methylphenyl]pentanoic acid (Example 99)
100) (3R)-3-[3-({(2R)-2-[4-(5-chloropyridin-3-yl)phenyl]-2-cyclopentylacetyl}amino)-2-methylphenyl]pentanoic acid (Example 100)
101) (3S)-3-[3-({(2S)-2-[4-(5-chloropyridin-3-yl)phenyl]-2-cyclopentylacetyl}amino)-2-methylphenyl]pentanoic acid (Example 101)
102) (3R)-3-[3-({(2S)-2-[4-(5-chloropyridin-3-yl)phenyl]-2-cyclopentylacetyl}amino)-2-methylphenyl]pentanoic acid (Example 102)
103) (3S)-3-[3-({(2R)-2-[4-(5-chloropyridin-3-yl)phenyl]-2-cyclopentylacetyl}amino)-2-methylphenyl]pentanoic acid (Example 103)
104) (3R/S)-3-[3-({(2RS)-2-Cyclopentyl-2-[4-(5-methylpyridin-3-yl)phenyl]-acetyl}amino)-2-methylphenyl]pentanoic acid (Example 104)
105) (3R/S)-3-[3-({(2R/S)-2-Cyclopentyl-2-[4-(5-ethylpyridin-3-yl)phenyl]-acetyl}amino)-2-methylphenyl]pentanoic acid (Example 105)
106) 3-[3-({[4-(5-Fluoropyridin-3-yl)phenyl](cyclopentyl)acetyl}amino)-2-methylphenyl]pentanoic acid (Example 106)
107) (3R/S)-3-[3-({(2R/S)-2-Cyclopentyl-2-[4-(5-ethoxypyridin-3-yl)phenyl]-acetyl}amino)-2-methylphenyl]pentanoic acid (Example 107)
108) (3R/S)-3-[3-({(2R/S)-2-[4-(5-chloro-6-methylpyridin-3-yl)phenyl]-2-cyclopentylacetyl}amino)-2-methylphenyl]-3-cyclopropylpropanoic acid (Example 108)
109) (3R/S)-3-(3-{[(2R/S)-2-cyclopentyl-2-{4-[5-(trifluoromethyl)pyridin-3-yl]phenyl}acetyl]amino}-2-methylphenyl)-3-cyclopropylpropanoic acid (Example 109)
110) (3R/S)-3-[3-({(2R/S)-2-[4-(5-chloropyridin-3-yl)phenyl]-2-cyclopentylacetyl}amino)-2-methylphenyl]-3-cyclopropylpropanoic acid (Example 110)
111) (3R/S)-3-[3-({(2R/S)-2-cyclopentyl-2-[4-(5-ethoxypyridin-3-yl)phenyl]-acetyl}amino)-2-methylphenyl]-3-cyclopropylpropanoic acid (Example 111)
112) (3R/S)-3-[3-({(2R/S)-2-cyclopentyl-2-[4-(5-fluoropyridin-3-yl)phenyl]-acetyl}amino)-2-methylphenyl]-3-cyclopropylpropanoic acid (Example 112)
113) (3R/S)-3-[3-({(2R/S)-2-cyclopentyl-2-[4-(5-methylpyridin-3-yl)phenyl]-acetyl}amino)-2-methylphenyl]-3-cyclopropylpropanoic acid (Example 113)
114) (3R/S)-3-[3-({(2R/S)-2-cyclopentyl-2-[4-(5-ethylpyridin-3-yl)phenyl]-acetyl}amino)-2-methylphenyl]-3-cyclopropylpropanoic acid (Example 114)
115) (3R/S)-3-(3-{[(2R/S)-2-Cyclopentyl-2-{3-fluoro-4-[5-(trifluoromethyl)-pyridin-3-yl]phenyl}acetyl]amino}-2-methylphenyl)butanoic acid (Example 115)
116) (3R)-3-(3-{[(2R)-2-cyclopentyl-2-{3-fluoro-4-[5-(trifluoromethyl)-pyridin-3-yl]phenyl}acetyl]amino}-2-methylphenyl)butanoic acid (Example 116)
117) (3S)-3-(3-{[(2S)-2-cyclopentyl-2-{3-fluoro-4-[5-(trifluoromethyl)-pyridin-3-yl]phenyl}acetyl)acetyl]amino}-2-methylphenyl)butanoic acid (Example 117)
118) (3R)-3-(3-{[(2S)-2-cyclopentyl-2-{3-fluoro-4-[5-(trifluoromethyl)-pyridin-3-yl]phenyl}acetyl]amino}-2-methylphenyl)butanoic acid (Example 118)
119) (3S)-3-(3-{[(2R)-2-cyclopentyl-2-{3-fluoro-4-[5-(trifluoromethyl)-pyridin-3-yl]phenyl}acetyl]amino}-2-methylphenyl)butanoic acid (Example 119)
120) (3R/S)-3-[3-({(2R/S)-2-[4-(5-Chloro-6-methylpyridin-3-yl)-3-fluoro-phenyl]-2-cyclopentylacetyl}amino)-2-methylphenyl]butanoic acid (Example 120)
121) (3R)-3-[3-({(2R)-2-[4-(5-chloro-6-methylpyridin-3-yl)-3-fluorophenyl]-2-cyclopentylacetyl}amino)-2-methylphenyl]butanoic acid (Example 121)
122) (3S)-3-[3-({(2S)-2-[4-(5-chloro-6-methylpyridin-3-yl)-3-fluorophenyl]-2-cyclopentylacetyl}amino)-2-methylphenyl]butanoic acid (Example 122)
123) (3R)-3-[3-({(2S)-2-[4-(5-chloro-6-methylpyridin-3-yl)-3-fluorophenyl]-2-cyclopentylacetyl}amino)-2-methylphenyl]butanoic acid (Example 123)
124) (3S)-3-[3-({(2R)-2-[4-(5-chloro-6-methylpyridin-3-yl)-3-fluorophenyl]-2-cyclopentylacetyl}amino)-2-methylphenyl]butanoic acid (Example 124)
125) (3R/S)-3-[3-({(2R/S)-2-[4-(5-Chloropyridin-3-yl)-3-fluorophenyl]-2-cyclopentylacetyl}amino)-2-methylphenyl]butanoic acid (Example 125)
126) (3R)-3-[3-({(2R)-2-[4-(5-chloropyridin-3-yl)-3-fluorophenyl]-2-cyclopentylacetyl}amino)-2-methylphenyl]butanoic acid (Example 126)
127) (3S)-3-[3-({(2S)-2-[4-(5-chloropyridin-3-yl)-3-fluorophenyl]-2-cyclopentylacetyl}amino)-2-methylphenyl]butanoic acid (Example 127)
128) (3R)-3-[3-({(2S)-2-[4-(5-chloropyridin-3-yl)-3-fluorophenyl]-2-cyclopentylacetyl}amino)-2-methylphenyl]butanoic acid (Example 128)
129) (3S)-3-[3-({(2R)-2-[4-(5-chloropyridin-3-yl)-3-fluorophenyl]-2-cyclopentylacetyl}amino)-2-methylphenyl]butanoic acid (Example 129)
130) (3R/S)-3-(3-{[(2R/S)-2-Cyclobutyl-2-{4-[5-(trifluoromethyl)pyridin-3-yl]phenyl}acetyl]amino}-2-methylphenyl)butanoic acid (Example 130)
131) (3R)-3-(3-{[(2R)-2-cyclobutyl-2-{4-[5-(trifluoromethyl)pyridin-3-yl]phenyl}acetyl]amino}-2-methylphenyl)butanoic acid (Example 131)
132) (3S)-3-(3-{[(2S)-2-cyclobutyl-2-{4-[5-(trifluoromethyl)pyridin-3-yl]phenyl}acetyl]amino}-2-methylphenyl)butanoic acid (Example 132)
133) (3R)-3-(3-{[(2S)-2-cyclobutyl-2-{4-[5-(trifluoromethyl)pyridin-3-yl]phenyl}acetyl]amino}-2-methylphenyl)butanoic acid (Example 133)
134) (3S)-3-(3-{[(2R)-2-cyclobutyl-2-{4-[5-(trifluoromethyl)pyridin-3-yl]phenyl}acetyl]amino}-2-methylphenyl)butanoic acid (Example 134)
135) (3R/S)-3-[3-({(2R/S)-2-[4-(5-Chloropyridin-3-yl)phenyl]-2-cyclobutyl-acetyl}amino)-2-methylphenyl]butanoic acid (Example 135)
136) (3R)-3-[3-({(2R)-2-[4-(5-chloropyridin-3-yl)phenyl]-2-cyclobutylacetyl}amino)-2-methylphenyl]butanoic acid (Example 136)
137) (3S)-3-[3-({(2S)-2-[4-(5-chloropyridin-3-yl)phenyl]-2-cyclobutylacetyl}amino)-2-methylphenyl]butanoic acid (Example 137)
138) (3R)-3-[3-({(2S)-2-[4-(5-chloropyridin-3-yl)phenyl]-2-cyclobutylacetyl}amino)-2-methylphenyl]butanoic acid (Example 138)
139) (3S)-3-[3-({(2R)-2-[4-(5-chloropyridin-3-yl)phenyl]-2-cyclobutylacetyl}amino)-2-methylphenyl]butanoic acid (Example 139)
140) (3R/S)-3-[3-({(2R/S)-2-[4-(5-Chloro-6-methylpyridin-3-yl)phenyl]-2-c (Example 140)
141) (3R)-3-[3-({(2R)-2-[4-(5-chloro-6-methylpyridin-3-yl)phenyl]-2-cyclobutylacetyl}amino)-2-methylphenyl]butanoic acid (Example 141)

142) (3S)-3-[3-({(2S)-2-[4-(5-chloro-6-methylpyridin-3-yl)phenyl]-2-cyclobutylacetyl}amino)-2-methylphenyl]butanoic acid (Example 142)
143) (3R)-3-[3-({(2S)-2-[4-(5-chloro-6-methylpyridin-3-yl)phenyl]-2-cyclobutylacetyl}amino)-2-methylphenyl]butanoic acid (Example 143)
144) (3S)-3-[3-({(2R)-2-[4-(5-chloro-6-methylpyridin-3-yl)phenyl]-2-cyclobutylacetyl}amino)-2-methylphenyl]butanoic acid (Example 144)
145) (3R/S)-3-(3-{[(2R/S)-2-Cyclobutyl-2-{3-fluoro-4-[5-(trifluoromethyl)-pyridin-3-yl]phenyl}acetyl]amino}-2-methylphenyl)butanoic acid (Example 145)
146) 3-{3-[(Cyclobutyl{3-fluoro-4-[5-(trifluoromethyl)pyridin-3-yl]phenyl}-acetyl)amino]-2-methylphenyl}butanoic acid (Example 146)
147) (3R)-3-(3-{[(2R)-2-cyclobutyl-2-{3-fluoro-4-[5-(trifluoromethyl)pyridin-3-yl]phenyl}acetyl]amino}-2-methylphenyl)butanoic acid (Example 147)
148) (3S)-3-(3-{[(2R)-2-cyclobutyl-2-{3-fluoro-4-[5-(trifluoromethyl)pyridin-3-yl]phenyl}acetyl]amino}-2-methylphenyl)butanoic acid (Example 148)
149) ((3R/S)-3-[3-({(2R/S)-2-[4-(5-Chloropyridin-3-yl)-3-fluorophenyl]-2-cyclobutylacetyl}amino)-2-methylphenyl]butanoic acid (Example 149)
150) (3R)-3-[3-({(2R)-2-[4-(5-chloropyridin-3-yl)-3-fluorophenyl]-2-cyclobutylacetyl}amino)-2-methylphenyl]butanoic acid (Example 150)
151) (3S)-3-[3-({(2S)-2-[4-(5-chloropyridin-3-yl)-3-fluorophenyl]-2-cyclobutylacetyl}amino)-2-methylphenyl]butanoic acid (Example 151)
152) (3R)-3-[3-({(2S)-2-[4-(5-chloropyridin-3-yl)-3-fluorophenyl]-2-cyclobutylacetyl}amino)-2-methylphenyl]butanoic acid (Example 152)
153) (3S)-3-[3-({(2R)-2-[4-(5-chloropyridin-3-yl)-3-fluorophenyl]-2-cyclobutylacetyl}amino)-2-methylphenyl]butanoic acid (Example 153)
154) 2-[3-({2-[4-(5-chloro-6-methylpyridin-3-yl)phenyl]-2-cyclopentylacetyl}(Example 154)
155) 2-[3-({2-cyclopentyl-2-[4-(5-ethoxypyridin-3-yl)phenyl]acetyl}amino)-2-methylphenyl]cyclopropanecarboxylic acid (Example 155)
156) 2-(3-{[2-cyclopentyl-2-{4-[5-(trifluoromethyl)pyridin-3-yl]phenyl}-acetyl]amino}-2-methylphenyl)cyclopropanecarboxylic acid (Example 156)
157) 2-(3-{[2-cyclopentyl-2-{4-[5-chloropyridin-3-yl]phenyl}acetyl]amino}-2-methylphenyl)cyclopropanecarboxylic acid (Example 157)
158) (R/S) 3-(3-{[{2-chloro-4-[5-(trifluoromethyl)pyridin-3-yl]phenyl}-(cyclopentyl)acetyl]amino}-2-methylphenyl)propanoic acid (Example 161)
159) (R/S) 3-{3-[(cyclopentyl{4-[5-(trifluoromethyl)pyridin-3-yl]phenyl}-acetyl)amino]-5-fluoro-2-methylphenyl}propanoic acid (Example 167)
160) (R/S) 3-[3-({[4-(5-chloropyridin-3-yl)phenyl](cyclopentyl)acetyl}-amino)-5-fluoro-2-methylphenyl]propanoic acid (Example 168)
161) (R/S) 3-[3-({[4-(5-chloro-6-methylpyridin-3-yl)phenyl](cyclopentyl)-acetyl}amino)-5-fluoro-2-methylphenyl]propanoic acid (Example 169)
162) (R/S) 3-[3-({[4-(5-ethoxypyridin-3-yl)phenyl](cyclopentyl)-acetyl}-amino)-5-fluoro-2-methylphenyl]propanoic acid (Example 170)
163) (R/S) N-{3-[(cyclopentyl{4-[5-(trifluoromethyl)pyridin-3-yl]phenyl}-acetyl)amino]-2-methylphenyl}glycine (Example 171)
164) (R/S) 3-[3-({[2-chloro-4-(5-chloropyridin-3-yl)-5-methylphenyl]-(cyclopentyl)acetyl}amino)-2-methylphenyl]propanoic acid (Example 172)
165) (R/S) 3-(3-{[{2-chloro-5-methyl-4-[5-(trifluoromethyl)pyridin-3-yl]-phenyl}-(cyclopentyl)acetyl]amino}-2-methylphenyl)propanoic acid (Example 173)
166) (R/S) 3-[3-({[2-chloro-4-(5-chloro-6-methylpyridin-3-yl)-5-methyl-phenyl]-(cyclopentyl)acetyl}amino)-2-methylphenyl]propanoic acid (Example 174)
167) (R/S) 3-(3-{[(2R)-2-{3-chloro-4-[5-(trifluoromethyl)pyridin-3-yl]-phenyl}-2-cyclopentylacetyl]amino}-2-methylphenyl)propanoic acid (Example 175)
168) (R/S) 3-[3-({[3-chloro-4-(5-chloro-6-methylpyridin-3-yl)phenyl]-(cyclopentyl)acetyl}amino)-2-methylphenyl]propanoic acid (Example 176)
169) (R/S) 3-[3-({[3-chloro-4-(5-chloropyridin-3-yl)phenyl](cyclopentyl)-acetyl}amino)-2-methylphenyl]propanoic acid (Example 177)
170) (R/S) 3-[3-({[4-(5-chloropyridin-3-yl)-2,5-difluorophenyl](cyclopentyl)-acetyl}amino)-2-methylphenyl]propanoic acid (Example 178)
171) (R/S) 3-{3-[(cyclopentyl{2,5-difluoro-4-[5-(trifluoromethyl)pyridin-3-yl]phenyl}acetyl)amino]-2-methylphenyl}propanoic acid (Example 179)
172) (R/S) 3-[3-({[4-(5-chloro-6-methylpyridin-3-yl)-2,5-difluorophenyl]-(cyclopentyl)acetyl}amino)-2-methylphenyl]propanoic acid (Example 180)
173) (R/S) 3-[3-({[4-(5-chloropyridin-3-yl)-2-fluoro-5-methylphenyl]-(cyclopentyl)acetyl}amino)-2-methylphenyl]propanoic acid (Example 181)
174) (R/S) 3-[3-({[4-(5-chloro-6-methylpyridin-3-yl)-2-fluoro-5-methyl-phenyl]-(cyclopentyl)acetyl}amino)-2-methylphenyl]propanoic acid (Example 182)
175) (R/S) 3-{3-[(cyclopentyl{2-fluoro-5-methyl-4-[5-(trifluoromethyl)-pyridin-3-yl]phenyl}acetyl)amino]-2-methylphenyl}propanoic acid (Example 183)
176) 3-[3-({(2R)-2-[4-(5-chloro-6-methylpyridin-3-yl)phenyl]-2-cyclopentylacetyl}amino)-6-fluoro-2-methylphenyl]propanoic acid (Example 184)
177) 3-[3-({(2R)-2-[4-(5-chloropyridin-3-yl)phenyl]-2-cyclopentylacetyl}-amino)-6-fluoro-2-methylphenyl]propanoic acid (Example 185)
178) N-[3-({(2R)-2-[4-(5-chloropyridin-3-yl)phenyl]-2-cyclopentylacetyl}-amino)-2-methylphenyl]-N-methylglycine (Example 186)
179) N-[3-({(2R)-2-[4-(5-chloro-6-methylpyridin-3-yl)phenyl]-2-cyclopentylacetyl}amino)-2-methylphenyl]-N-methylglycine (Example 187)
180) N-(3-{[(2R)-2-cyclopentyl-2-{3-fluoro-4-[5-(trifluoromethyl)pyridin-3-yl]phenyl}acetyl]amino}-2-methylphenyl)-N-methylglycine (Example 188)
181) 3-(3-{[(2R)-2-cyclopentyl-2-{4-[5-(2-methylpropyl)pyridin-3-yl]phenyl}-acetyl]amino}-2-methylphenyl)propanoic acid (Example 189)
182) 3-(3-{[(2R)-2-cyclopentyl-2-{4-[5-(propan-2-yloxy)pyridin-3-yl]phenyl}-acetyl]amino}-2-methylphenyl)propanoic acid (Example 190)
183) 3-(3-{[(2R)-2-cyclopentyl-2-{4-[5-(2,2,2-trifluoroethyl)pyridin-3-yl]-phenyl}acetyl]amino}-2-methylphenyl)propanoic acid (Example 191)
184) 3-(3-{[(2R)-2-cyclopentyl-2-{4-[6-methyl-5-(trifluoromethyl)pyridin-3-yl]phenyl}acetyl]amino}-2-methylphenyl)propanoic acid (Example 192)
185) 3-[3-({(2R)-2-[4-(5-chloropyridin-3-yl)phenyl]-2-cyclopentylacetyl}-amino)-2-methylphenyl]-3-hydroxypropanoic acid (Example 193)

186) 3-[3-({cyclopentyl[3-fluoro-4-(5-isobutylpyridin-3-yl)phenyl]acetyl}-amino)-2-methylphenyl]pentanoic acid (Example 194)

187) 3-[3-({cyclopentyl[4-(5-ethylpyridin-3-yl)-3-fluorophenyl]acetyl}-amino)-2-methylphenyl]pentanoic acid (Example 195)

188) (−) 3-{3-[(cyclopentyl{3-fluoro-4-[5-(2,2,2-trifluoroethyl)pyridin-3-yl]-phenyl}acetyl)amino]-2-methylphenyl}propanoic acid (Example 196)

189) (−) 3-{3-[(cyclopentyl{3-fluoro-4-[6-methyl-5-(trifluoromethyl)pyridin-3-yl]phenyl}acetyl)amino]-2-methylphenyl}propanoic acid (Example 197)

190) (−) 3-[3-({cyclopentyl[3-fluoro-4-(5-isobutyl-6-methylpyridin-3-yl)-phenyl]acetyl}amino)-2-methylphenyl]propanoic acid (Example 198)

191) (−) 3-[3-({cyclopentyl[3-fluoro-4-(5-isopropoxypyridin-3-yl)phenyl]-acetyl}amino)-2-methylphenyl]propanoic acid (Example 199)

192) 3-(3-{[(2R)-2-cyclopentyl-2-{4-[5-(2,2,2-trifluoroethyl)pyridin-3-yl]-phenyl}acetyl]amino}-2-methylphenyl)pentanoic acid (Example 200)

193) 3-(3-{[(2R)-2-cyclopentyl-2-{4-[6-methyl-5-(trifluoromethyl)pyridin-3-yl]phenyl}acetyl]amino}-2-methylphenyl)pentanoic acid (Example 201)

194) 3-[3-({(2R)-2-cyclopentyl-2-[4-(5-isobutylpyridin-3-yl)phenyl]acetyl}-amino)-2-methylphenyl]pentanoic acid (Example 202)

195) 3-[3-({(2R)-2-cyclopentyl-2-[4-(5-isopropoxypyridin-3-yl)phenyl]-acetyl}amino)-2-methylphenyl]pentanoic acid (Example 203)

196) 3-[3-({(2R)-2-cyclopentyl-2-[4-(5-ethylpyridin-3-yl)phenyl]acetyl}-amino)-2-methylphenyl]pentanoic acid (Example 204)

197) 3-{3-[(cyclobutyl{3-fluoro-4-[5-(2,2,2-trifluoroethyl)pyridin-3-yl]-phenyl}acetyl)amino]-2-methylphenyl}propanoic acid (Example 205)

198) (−) 3-{3-[(cyclobutyl{3-fluoro-4-[6-methyl-5-(trifluoromethyl)pyridin-3-yl]phenyl}acetyl)amino]-2-methylphenyl}propanoic acid (Example 206)

199) 3-[3-({cyclobutyl[3-fluoro-4-(5-isobutylpyridin-3-yl)phenyl]acetyl}-amino)-2-methylphenyl]propanoic acid (Example 207)

200) (−) 3-{3-[(cyclobutyl{3-fluoro-4-[5-(trifluoromethyl)pyridin-3-yl]phenyl}acetyl)amino]-2-methylphenyl}propanoic acid (Example 208)

201) (−) 3-[3-({cyclobutyl[3-fluoro-4-(5-isopropoxypyridin-3-yl)phenyl]-acetyl}amino)-2-methylphenyl]propanoic acid (Example 209)

202) (−) 3-[3-({cyclobutyl[4-(5-ethylpyridin-3-yl)-3-fluorophenyl]acetyl}-amino)-2-methylphenyl]propanoic acid (Example 210)

203) (R/S) 3-[3-({cyclopentyl[4-(5-fluoro-6-methylpyridin-3-yl)phenyl]-acetyl}amino)-2-methylphenyl]propanoic acid (Example 211)

204) 3-[3-({[4-(5-chloropyridin-3-yl)phenyl](cyclopentyl)acetyl}amino)-2-methoxyphenyl]propanoic acid (Example 212)

205) 3-{3-[(cyclopentyl{4-[5-(trifluoromethyl)pyridin-3-yl]phenyl}acetyl)-amino]-2-methoxyphenyl}propanoic acid (Example 213)

206) 3-[3-({(2R)-2-[4-(5-chloropyridin-3-yl)phenyl]-2-cyclopentylacetyl}-amino)-2-(trifluoromethyl)phenyl]propanoic acid (Example 214)

207) 3-[3-{[(2R)-2-cyclopentyl-2-{4-[5-(trifluoromethyl)pyridin-3-yl]phenyl}-acetyl]amino}-2-(trifluoromethyl)phenyl]propanoic acid (Example 215)

It is to be understood that the present invention relates also to any combination of the preferred embodiments described above.

It is to be understood that the present invention relates to any sub-combination within any embodiment or aspect of the present invention of compounds of general formula (I), supra.

More particularly still, the present invention covers compounds of general formula (I) which are disclosed in the Examples section of this text, infra.

In accordance with another aspect, the present invention covers methods of preparing compounds of the present invention, said methods comprising the steps as described in the Experimental Section herein.

Synthesis of Compounds of General Formula (I) of the Present Invention

General synthesis of the compounds of general formula (I) of the present invention The following paragraphs outline several synthetic approaches suitable to prepare compounds of formula (I), and intermediates useful for their synthesis.

In addition to the routes described below, also other routes may be used to synthesize the target compounds, in accordance with common general knowledge of a person skilled in the art of organic synthesis. The order of transformations exemplified in the following schemes is therefore not intended to be limiting, and suitable synthesis steps from various schemes can be combined to form additional synthesis sequences. In addition, interconversion of any of the substituents, in particular $R^1$, $R^2$, and $R^4$, as well as substituents attached to $R^3$ or $R^5$, can be achieved before and/or after the exemplified transformations. These modifications can be such as the introduction of protective groups, cleavage of protective groups, reduction or oxidation of functional groups, halogenation, metallation, metal catalyzed coupling reactions, exemplified by but not limited to Suzuki, Sonogashira and Ullmann coupling, ester saponification, amide coupling reactions, and/or substitution or other reactions known to a person skilled in the art. These transformations include those which introduce a functionality allowing for further interconversion of substituents. Appropriate protective groups and their introduction and cleavage are well-known to a person skilled in the art (see for example T. W. Greene and P. G. M. Wuts in Protective Groups in Organic Synthesis, 3rd edition, Wiley 1999). Specific examples are described in the subsequent paragraphs. Further, it is possible that two or more successive steps may be performed without work-up being performed between said steps, e.g. a "one-pot" reaction, as it is well-known to a person skilled in the art.

Compounds of the general formula (I) can be assembled from aniline derivatives of formula (II), in which $R^1$, $R^2$ and X are as defined in formula (I), and in which RE represents a $C_1$-$C_6$-alkyl or a benzyl group or other groups suitable for esterification, and from substituted phenylacetic acid derivatives of formula (III), in which $R^3$ and $R^4$ are as defined in formula (I), and in which LG represents a leaving group as defined supra, preferably bromo, or iodo, by means of carboxamide (or peptide) coupling reaction well known to the person skilled in the art, according to Scheme 1. Said coupling reaction can be performed by reaction of compounds of the formulae (II) and (III) in the presence of a suitable coupling reagent, such as HATU (0-(7-azabenzotriazol-1-yl)-N,N,N',N'-tetramethyluronium hexafluorophosphate), TBTU (O-(benzotriazol-1-yl)-N,N, N',N'-tetramethyluronium tetrafluoroborate), PyBOP (benzotriazol-1-yl-oxytripyrrolidinophosphonium hexafluorophosphate), or EDC (1-(3-dimethylaminopropyl)-3-ethylcarbodiimide hydrochloride) in combination with HOBt (1-hydroxy-1H-benzotriazole hydrate), in the presence of a base such as an aliphatic or aromatic tertiary amine, preferably a tertiary aliphatic amine of the formula N(C1-C4-alkyl)3, in an appropriate solvent, to give carboxamide derivatives of formula (IV).

Preferred herein is the performance of said carboxamide coupling reaction using HATU (0-(7-azabenzotriazol-1-yl)-N, N, N',N'-tetramethyluronium hexafluorophosphate) as a coupling agent, in the presence of N,N-diisopropylethylamine as a base, and in N,N-dimethylformamide as a solvent, within a temperature range from 0° C. to 50° C.

The preparation of carboxamides of formula (IV) from aniline derivatives of formula (II), in which $R^1$, $R^2$ and X are as defined in formula (I), and in which RE represents a $C_1$-$C_6$-alkyl or a benzyl group, and from substituted phenylacetic acid derivatives of formula (III), in which $R^3$ and $R^4$ are as defined in formula (I), and in which LG represents a leaving group as defined supra, preferably bromo, or iodo, can furthermore be accomplished, as well known to the person skilled in the art, by converting said substituted phenylacetic acid derivatives of formula (III) into the corresponding acyl halides, e.g. by reacting with a halogenating agent such as thionyl chloride, oxalyl chloride, or phosphoroxy chloride, and subsequent aminolysis using said aniline derivatives of formula (II).

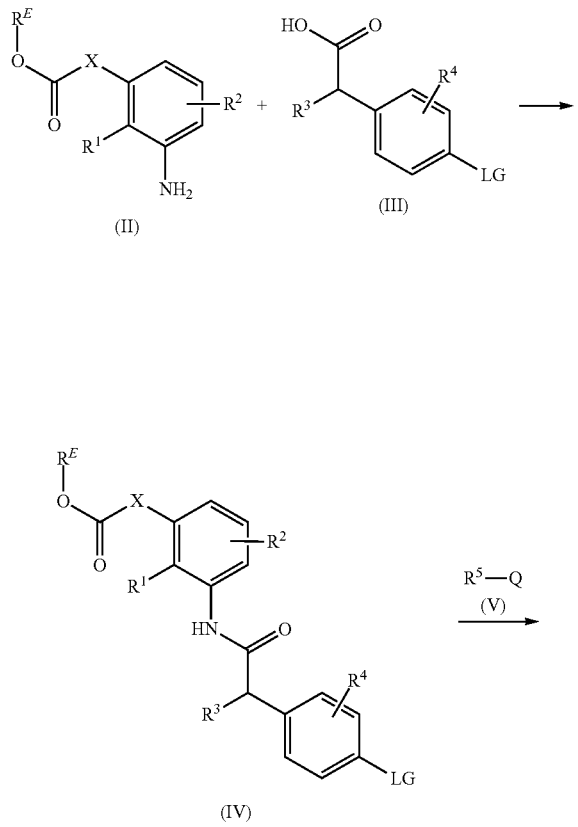

Scheme 1: Preparation of compounds of the general formula (I) from aniline derivatives of formula (II) and substituted phenylacetic acid derivatives of formula (III)

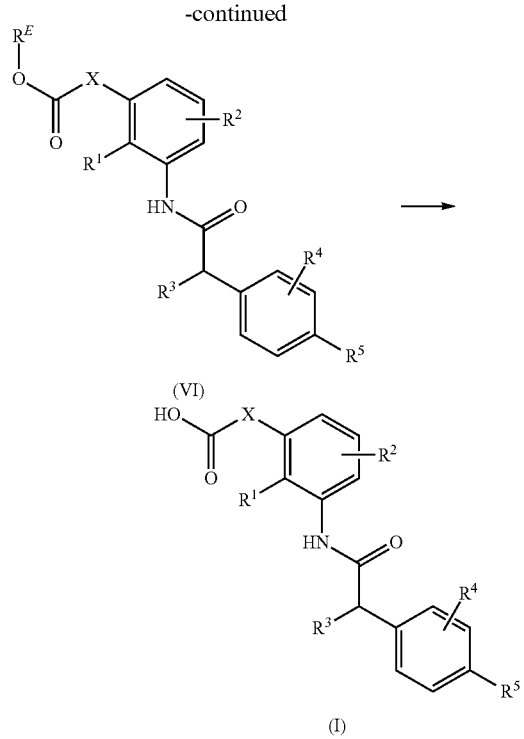

Said carboxamides of formula (IV) can subsequently be subjected to a palladium catalyzed Suzuki coupling with organoboron compounds of formula (V), in which $R^5$ is as defined in formula (I), and in which Q represents a group —$BF_3$— M+, wherein M+ stands for a cation of an alkali metal, preferably sodium or potassium, or in which Q represents a group —$B(OR)_2$, which may be a boronic acid (R=—H) or an ester of said boronic acid, e.g. its isopropyl ester (R=—CH(CH$_3$)$_2$), or, preferably, an ester derived from pinacol in which the boronic acid intermediate forms a 4,4,5,5-tetramethyl-1,3,2-dioxaborolane (R—R= —C(CH$_3$)$_2$—C(CH$_3$)$_2$—), to give intermediates of formula (VI).

The coupling reaction is catalyzed by palladium catalysts, e.g. by Pd(0) catalysts like tetrakis(triphenylphosphine)palladium(0) [Pd(PPh$_3$)$_4$], tris(dibenzylidene-acetone)di-palladium(0) [Pd$_2$(dba)$_3$], or by Pd(II) catalysts like dichlorobis-(triphenylphosphine)-palladium(II) [Pd(PPh3)2Cl2], palladium(II) acetate and triphenylphosphine or by 1,1'-bis(diphenylphosphino)ferrocenedichloro-palladium(II).

The reaction is preferably carried out in a mixture of solvents like 1,2-dimethoxyethane, dioxane, DMF, THF, or isopropanol, optionally mixed with water and in the presence of a base like potassium carbonate, sodium bicarbonate or potassium phosphate (for a review article see: D. G. Hall, Boronic Acids, 2005 WILEY-VCH Verlag GmbH & Co. KGaA, Weinheim, ISBN 3-527-30991-8 and references cited therein). Organoboron compounds of formula (V) are readily commercially available in substantial structural diversity.

The reaction is performed at temperatures ranging from room temperature (=20° C.) to the boiling point of the respective solvent. Further on, the reaction can be performed at temperatures above the boiling point using pressure tubes and a microwave oven. The reaction is preferably completed after 1 to 36 hours of reaction time.

Intermediates of formula (VI) can be converted into compounds of the general formula (I) by cleavage of the ester group —C(═O)O—RE, using methods well known to the person skilled in the art, preferably by basic hydrolysis using an alkali hydroxide, preferably sodium hydroxide or potassium hydroxide, in an aqueous aliphatic alcohol of the formula $C_1$-$C_3$-alkyl-OH, or by acidic hydrolysis e.g. of tert-butyl esters using a strong acid such as trifluoroacetic acid or hydrochloric acid in a halogenated lower aliphatic hydrocarbon, preferably dichloromethane or chloroform, or in a cyclic ether, preferably 1,4-dioxane, as a solvent.

Scheme 2 outlines an alternative approach to intermediates of the formula (VI), in which substituted phenylacetic acid derivatives of formula (III), in which $R^3$ and $R^4$ are as defined for the compounds of the general formula (I), and in which LG represents a leaving group as defined supra, preferably bromo, or iodo, are reacted with organoboron compounds of formula (V), in which $R^5$ is as defined for the compounds of the general formula (I), and in which Q represents a group —$BF_3$— M+, wherein M+ stands for a cation of an alkali metal, preferably sodium or potassium, or in which Q represents a group —$B(ORB)_2$, which may be a boronic acid (RB═—H) or an ester of said boronic acid, e.g. its isopropyl ester (RB═—CH(CH$_3$)$_2$), or, preferably, an ester derived from pinacol in which the boronic acid ester forms a 4,4,5,5-tetramethyl-1,3,2-dioxaborolane (RB—RB═—C(CH$_3$)$_2$—C(CH$_3$)$_2$—) ring, in a Suzuki coupling as described supra, to give carboxylic acid derivatives of formula (VII). Alternatively, an ester protected version of intermediate (III) can be converted to an ester protected intermediate (VII), which can be converted to intermediate (VII) by ester deprotection with methods known to persons skilled in the art.

Said carboxylic acid derivatives of formula (VII) are subsequently reacted with aniline derivatives of formula (II), in which $R^1$, $R^2$ and X are as defined for the compounds of the general formula (I), and in which RE represents a $C_1$-$C_6$-alkyl or a benzyl group, in a carboxamide (or peptide) coupling reaction as outlined in Scheme 1, to give intermediates of the general formula (VI).

Scheme 2: Alternative preparation of intermediates of formula (VI) from substituted phenylacetic acid derivatives of formula (III)

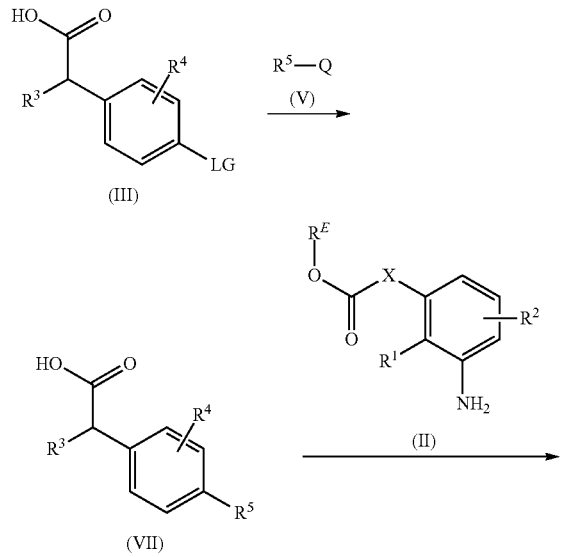

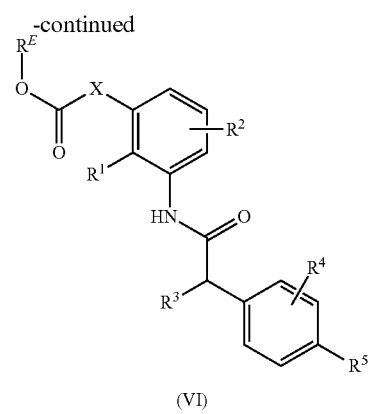

(VI)

Aniline derivatives of formula (II), if not commercially available, can be prepared using a variety of methods well known to the person skilled in the art, e.g. as outlined in Scheme 3, starting from precursors of formula (VIII), in which $R^1$ and $R^2$ are as defined in formula (I), and Y represents a functional group suitable for the elaboration of the —X—C(═O)O—RE moiety present in the aniline derivatives of formula (II), wherein X is as defined in formula (I), and in which RE represents a $C_1$-$C_6$-alkyl or a benzyl group or other groups suitable for esterification, said functional group Y being selected from bromo, iodo, —C(═O)H, —C(═O)CH$_3$, —OH, —CH$_2$OH, —CH$_2$C(═O)OH. Said precursors are subsequently converted into nitrobenzene derivatives of the formula (IX), in which X' represents a group X as defined in formula (I), or an unsaturated analogue thereof like ethylene, 1-methyl ethylene, 2-methyl ethylene, 1-ethyl ethylene, 2-ethyl ethylene, by reactions well known to the person skilled in the art exemplified by but not limited to:

Heck olefination, by reacting a precursor of formula (VIII), in which Y represents bromo or iodo, with an acrylic acid ester of the formula H$_2$C═C(═O)O—RE in the presence of a palladium catalyst such as palladium(II)acetate (see protocol of the preparation of intermediate 1b in the Experimental section below).

Horner-Wadsworth-Emmons olefination, by reacting a precursor of formula (VIII), in which Y represents —C(═O)H or —C(═O)CH$_3$, with phosphonic acid ester such as (C$_1$-C$_3$-alkoxy)2-P(═O)-L-C(═O)O—RE, in which L represents a linker suitable for the formation of an X' group as defined for the formula (IX), e.g. —C(CH$_3$)(H)—, in the presence of a base such as sodium hydride or n-butyllithium (see e.g. protocols of the preparations of intermediates 72a and 75a in the Experimental section below). Alkylation of a hydroxy or carboxy group, by reacting a precursor of formula (VIII), in which Y represents —OH, —CH$_2$OH, —CH$_2$C(═O)OH, with a halide of the formula RE-LG, in which LG represents a leaving group as defined supra, and in which RE stands for a $C_1$-$C_6$-alkyl or a benzyl group, in the presence of a suitable base, by methods known to the person skilled in the art (see e.g. protocols of the preparations of intermediates 39a, 43a and 49a in the Experimental section below. Said nitrobenzene derivatives of formula (IX) are then reduced to the anilines of formula (II) by methods known to the person skilled in the art, said methods encompassing the use of palladium catalyzed hydrogenation, using elemental hydrogen or alternative hydrogen sources such as ammonium formiate, or using tin (II) chloride e.g. in ethanol as a solvent, or zinc dust or powdered iron in the presence of acetic acid. Intermediates containing double bonds are reduced to their saturated products by methods known to the person skilled in the art, e. g. by the use of palladium catalyzed hydrogenation.

Scheme 3: Preparation of aniline derivatives of formula (II) from precursors of formula (VIII)

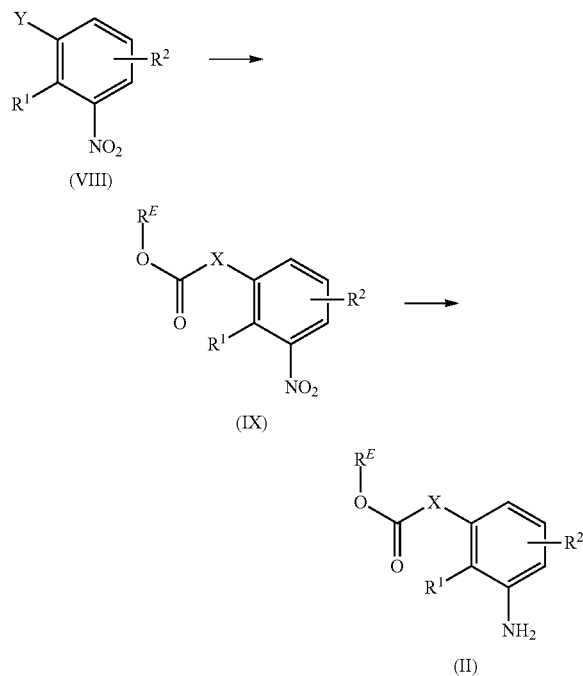

Substituted phenylacetic acid derivatives of formula (III) are well known to the person skilled in the art and can be prepared according to Scheme 4, e.g. by reacting alkyl phenylacetates of formula (X), in which $R^4$ is as defined in formula (I), and in which LG represents a leaving group as defined supra, preferably bromo or iodo, and in which RP stands for a $C_1$-$C_3$-alkyl group, with a compound of formula (XI), in which $R^3$ is as defined in formula (I), and in which LG represents a leaving group as defined supra, preferably bromo or iodo, to give esters of formula (XII) which are subsequently hydrolyzed using methods well known to the person skilled in the art, preferably by basic hydrolysis using an alkali hydroxide, preferably sodium hydroxide or potassium hydroxide, in an aqueous aliphatic alcohol of the formula $C_1$-$C_3$-alkyl-OH, to give substituted phenylacetic acid derivatives of formula (III).

Scheme 4: Preparation of substituted phenylacetic acid derivatives of formula (III) from alkyl phenylacetates of formula (X)

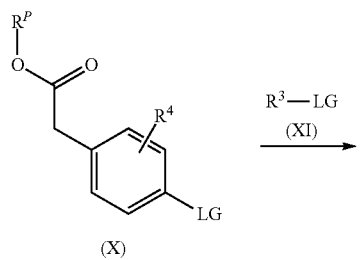

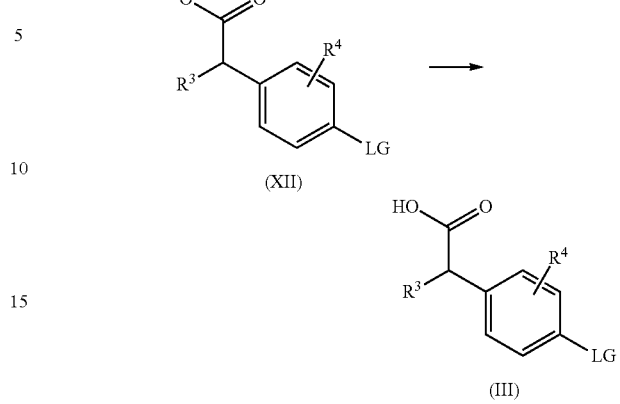

Alternatively, and as shown in Scheme 5, said substituted phenylacetic acid derivatives of formula (III) can also be prepared from ketones of formula (XIII), in which $R^3$ and $R^4$ are as defined in formula (I), and in which LG represents a leaving group as defined supra, preferably bromo or iodo, by Wittig olefination e.g. using a phosphonium salt of formula (XIV), in which Hal- represents a chloride, bromide or iodide anion, and Ph stands for phenyl, in the presence of a base such as potassium bis-(trimethylsilyl)amide, to give an enol ether of formula (XV) which is subsequently subjected to acidic hydrolysis e.g. using hydrochloric acid in tetrahydrofuran, to give aldehydes of formula (XVI). Said aldehydes of formula (XVI) can be oxidized to give phenylacetic acid derivatives of formula (III), e.g. by using sodium chlorite as oxidant in the presence of 2-methyl-2-butene and aqueous sodium dihydrogen phosphate.

Scheme 5: Preparation of substituted phenylacetic acid derivatives of formula (III) from ketones of formula (XIII)

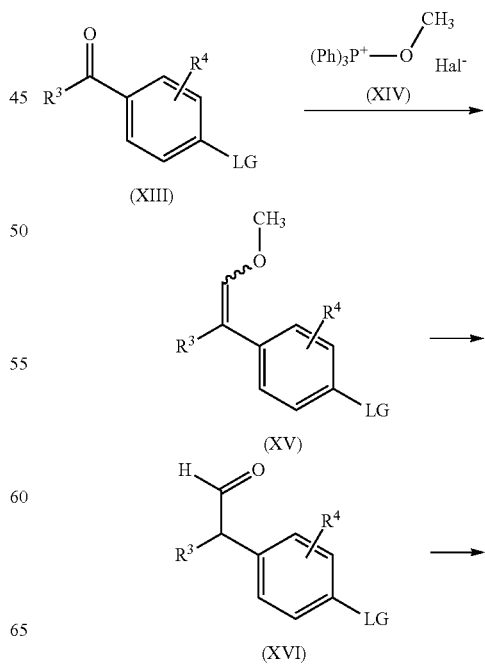

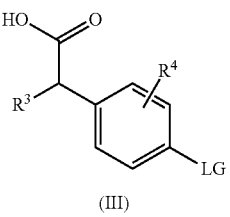

(III)

Compounds of general formula (I) are chiral and contain at least one stereocenter at the carbon bearing the $R^3$ group. Separation of those enantiomers is possible by chiral chromatography. Stereoisomers of chiral intermediates (IV), (VI) and (VII) can also be separated by chiral chromatography. Enantiomers of chiral intermediates of formula (III) can be separated by diastereomeric salt separation using a chiral base, for example 2-phenethylamine.

The starting material required for the performance of the synthetic sequences outlined in Schemes 3, 4 and 5, namely compounds of formulae (VIII), (X), (XI), (XIII) and (XIV), are well known to the person skilled in the art and are readily commercially available.

A. EXPERIMENTAL SECTION

The example testing experiments described herein serve to illustrate the present invention and the invention is not limited to the examples given.

The following table lists the abbreviations used in this paragraph, and in the examples section.

| Abbreviation | |
|---|---|
| (+/−)-BINAP | (+/−)-(1,1'-Binaphthalene-2,2'-diyl)bis(diphenylphosphine) |
| DCM | Dichloromethane |
| DIPEA | N-Ethyl-N-isopropylpropan-2-amine |
| DMF | N,N-Dimethylformamide |
| DMSO | Dimethyl sulfoxide |
| EE | Ethyl acetate |
| HATU | N-[(Dimethylamino)(3H-[1,2,3]triazolo[4,5-b]pyridin-3-yloxy)methylene]-N-methylmethanaminium hexafluorophosphate |
| HCl | Hydrochloric acid |
| HPLC | High pressure liquid chromatography |
| K2CO3 | Potassium carbonate |
| M | Molar |
| MgSO4 | Magnesium sulfate |
| min | Minute(s) |
| N | Normal |
| Na2CO3 | Sodium carbonate |
| NaHCO3 | Sodium bicarbonate |
| NaOH | Sodium hydroxide |
| Na2SO4 | Sodium sulfate |
| NH4Cl | Ammonium chloride |
| NMR | Nuclear magnetic resonance spectroscopy |
| RT | Room temperature |
| Rt | Retention time |
| sat. | Saturated |
| TBAI | Tetra-N-butylammonium iodide |
| tBu | Tert-butyl |
| TEA | Triethylamine |
| TFA | Trifluoroacetic acid |
| THF | Tetrahydrofuran |

HPLC Methods
Analytical HPLC, Method 1:
System: Agilent: 1260 AS, MWD, Aurora SFC-Modul; Column: Chiralpak ID 3 µm 100×4.6 mm; Temperature: 37.5° C.; Detection: DAD 254 nm.

Analytical HPLC, Method 2:
System: Dionex: Pump 680, ASI 100, UVD 170U; Column: Chiralpak AD-H 5 µm 150×4.6 mm; Temperature: 25° C.; Detection: UV 254 nm.

Analytical HPLC, Method 3:
System: Waters: Alliance 2695, DAD 996, ESA: Corona; Column: Chiralpak ID-3 100×4.6 mm; Temperature: 25° C.; Detection: DAD 254 nm.

Analytical HPLC, Method 4:
System: Agilent: 1260/Agilent 1290; Column: Chiralpak IA 3 µm 100×4.6 mm; Temperature: 25° C.; Detection: DAD 254 nm.

Analytical HPLC, Method 5:
System: Agilent: 1200; Column: Chiralpak IA 3 µm 100×4.6 mm; Temperature: 25° C.; Detection: DAD 254 nm.

Analytical HPLC, Method 6:
System: Waters: Alliance 2695, DAD 996, ESA: Corona; Column: Chiralpak IE 3 µm 100×4.6 mm; Temperature: 25° C.; Detection: DAD 254 nm.

Analytical HPLC, Method 7:
System: Waters: Alliance 2695, DAD 996, ESA: Corona; Column: Chiralpak IA 3 µm 100×4.6 mm; Temperature: 25° C.; Detection: DAD 254 nm.

Analytical HPLC, Method 8:
System: Waters: Alliance 2695, DAD 996, ESA: Corona; Column: Chiralpak IB 3 µm 100×4.6 mm; Temperature: 25° C.; Detection: DAD 254 nm.

Analytical HPLC, Method 9:
System: Agilent: 1200; Column: Chiralpak ID 3 µm 150×4.6 mm; Temperature: 25° C.; Detection: DAD 254 nm.

Analytical HPLC, Method 10:
System: Agilent: 1260 AS, MWD, Aurora SFC-Modul; Column: Chiralpak IA 5 µm 100×4.6 mm; Temperature: 37.5° C.; Detection: DAD 254 nm.

Analytical HPLC, Method 11:
System: Agilent: 1260/Agilent 1290; Column: Chiralpak IC 3 µm 100×4.6 mm; Temperature: 25° C.; Detection: DAD 254 nm.

Analytical HPLC, Method 12:
System: Agilent: 1260/Agilent 1290; Column: Chiralpak ID 3 µm 100×4.6 mm; Temperature: 25° C.; Detection: DAD 254 nm.

Analytical HPLC, Method 13:
System: Waters Acquity UPLC-MS: Binary Solvent Manager, Sample Manager/Organizer, Column Manager, PDA, ELSD, SQD 3001; Column: Acquity BEH C18 1.7 µm 2.1×50 mm; Temperature: 60° C.; Injection: 2 µL; Detection: DAD scan range 210-400 nm, MS ESI+ scan range 170-800 m/z; Solvent: A=H2O+0.1% HCOOH, B=Acetonitrile; Flow: 0.8 mL/min; Gradient: 0-1.6 min 1-99% B, 1.6-2.0 min 99% B Preparative HPLC, Method 1:
System: Sepiatec: Prep SFC100; Column: Chiralpak ID 5 µm 250×20 mm; Temperature: 40° C., Detection: UV 254 nm.

Preparative HPLC, Method 2:
System: Agilent: Prep 1200, 2×Prep Pump, DLA, MWD, Prep FC; Column: Chiralpak AD-H 5 µm 250×30 mm; Temperature: RT; Detection: UV 254 nm.

Preparative HPLC, Method 3:
System: 2× Labomatic Pump HD-3000, SD3000, Labomatic AS-3000, Knauer DAD 2600, Labomatic Labcol Vario 4000 PLus; Column: Chiralpak ID 5 µm 250×50 mm; Temperature: RT; Detection: UV 254 nm.

Preparative HPLC, Method 4:
System: Agilent: Prep 1200, 2×Prep Pump, DLA, MWD; Column: Chiralpak IA 5 µm 250×30 mm; Temperature: RT; Detection: UV 254 nm.

Preparative HPLC, Method 5:
System: Agilent: Prep 1200, 2×Prep Pump, DLA, MWD; Column: Chiralpak IB 5 μm 250×30 mm; Temperature: RT; Detection: UV 254 nm.
Preparative HPLC, Method 6:
System: Agilent: Prep 1200, 2×Prep Pump, DLA, MWD; Column: Chiralpak IE 5 μm 250×20 mm; Temperature: RT; Detection: UV 254 nm.
Preparative HPLC, Method 7:
System: Sepiatec: Prep SFC100; Column: Chiralpak ID 5 μm 250×30 mm; Temperature: 40° C., Detection: UV 254 nm.
Preparative HPLC, Method 8:
System: Sepiatec: Prep SFC100; Column: Chiralpak IA 5 μm 250×20 mm; Temperature: 40° C., Detection: UV 254 nm.

Absolute Configuration Determination by VCD Measurements

Determination was determined as fee for service by Biotools, 17546 Bee Line Hwy • Jupiter, Fla. • 33458.
Configuration Determination, Method 1:
System: ChirallIR2X with Dual PEM; Solvent: DMSO-d6; Aquisition time: 20 h; Concentration: 7.8 mL/0.2 mL; Pathlength 100 μM; Gaussian Version: Gaussian 09; DFT-level of theory: B3LYP/6-31G(d).

Chemical naming of the examples and intermediates was performed using ACD software by ACD/Labs (Name Batch version 12.01)

Reaction times are either specified explicitly in the protocols of the experimental section, or reactions were run until completion. Chemical reactions were monitored and their completion was judged using methods well known to the person skilled in the art, such as thin layer chromatography, e.g. on plates coated with silica gel, or by LC/MS methods (eg analytical HPLC method 13).

The starting materials for compound of general formula (I) were synthesized as follows:

Intermediate 1

(R/S) (4-bromophenyl)(cyclopentyl)acetic acid

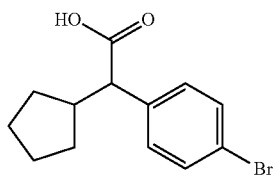 [SMILES: O=C(O)C(c1ccc(Br)cc1)C1CCCC1]

Step 1.1: (R/S) Ethyl (4-bromophenyl)(cyclopentyl)acetate

A solution of 25 g ethyl (4-bromophenyl)acetate in 100 ml DMF was added dropwise to 13.8 g potassium-tert.butylate in 150 ml DMF at 0° C. and stirred for additional 30 min at 0° C. Then 18.4 g bromocyclopentane were added dropwise at 0° C. and the reaction mixture was stirred until reaction completion. The mixture was given on water, extracted with EE, the combined organic layers washed with water and brine, dried with Na$_2$SO$_4$, filtered and evaporated to dryness. Yield: 35.6 g, used without further purification in the next step.

Step 1.2: (R/S) (4-Bromophenyl)(cyclopentyl)acetic acid 571 ml 2N NaOH were added to 35.6 g (R/S) Ethyl (4-bromophenyl)(cyclopentyl)acetate in 775 ml ethanol. The reaction was heated under reflux until complete conversion. The mixture was diluted with water, adjusted to pH 1-2 using diluted hydrochloric acid and extracted with EE. The combined organic layers were dried with Na$_2$SO$_4$, filtered and evaporated to dryness. Yield: 29.4 g.

$^1$H NMR (300 MHz, DMSO-d$_6$) δ ppm 0.96 (d, 1 H) 1.12-1.70 (m, 6 H) 1.82 (d, 1 H) 2.39 (d, 1 H) 3.25 (d, 1 H) 7.21-7.37 (m, 2 H) 7.43-7.59 (m, 2 H) 11.92-12.76 (m, 1 H).

Intermediate 2 tert-Butyl 3-(3-amino-2-methylphenyl)propanoate

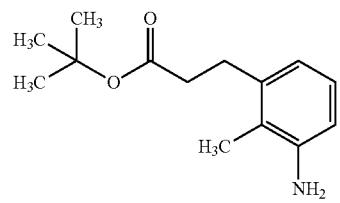 [SMILES: Cc1c(N)cccc1CCC(=O)OC(C)(C)C]

Step 2.1: tert-Butyl (2E)-3-(2-methyl-3-nitrophenyl)acrylate 201 ml tert-Butyl acrylate were added to 100 g 1-bromo-2-methyl-3-nitrobenzene, 28.2 g Tri-2-tolylphosphine, 10.4 g palladium(II) acetate and 322 ml TEA in 2 l DMF. The mixture was stirred over night at 125° C. The reaction mixture was stirred into sat. NH$_4$CL-solution, extracted with EE, the combined organic layers washed with brine, dried with Na$_2$SO$_4$, filtered and evaporated to dryness. The resulting material was purified by chromatography using silica gel (hexane/EE 9:1). Yield: 123 g.

$^1$H NMR (300 MHz, CHLOROFORM-d) δ ppm 1.55 (d, 9 H) 2.50 (s, 3 H) 6.30 (d, 1 H) 7.29-7.40 (m, 1 H) 7.72 (dd, 8.01 Hz, 2 H) 7.88 (d, 1 H).

Step 2.2: tert-Butyl 3-(3-amino-2-methylphenyl)propanoate 25 g Palladium/charcoal (10%) were added to a solution of 121 g tert-Butyl (2E)-3-(2-methyl-3-nitrophenyl)acrylate in 1.2 l ethanol and stirred at RT under hydrogen atmosphere until complete conversion. The catalyst was filtered off, the filter cake washed with ethanol and the resulting solution evaporated to dryness. Yield: 99 g.

$^1$H NMR (400 MHz, CHLOROFORM-d) δ ppm 1.47 (s, 9 H) 2.13 (s, 3 H) 2.43-2.54 (m, 2 H) 2.87-2.99 (m, 2 H) 6.57-6.70 (m, 2 H) 6.96 (t, 1 H).

Intermediate 3

(R/S) tert-Butyl 3-(3-{[(4-bromophenyl)(cyclopentyl)acetyl]amino}-2-methylphenyl)propanoate

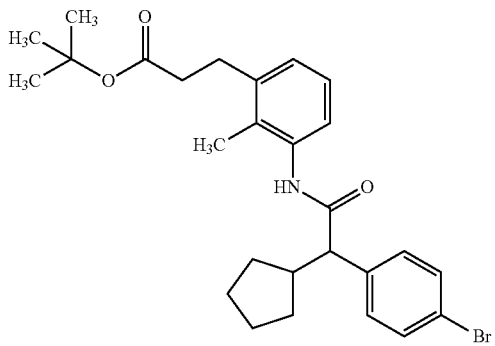 [SMILES: Cc1c(CCC(=O)OC(C)(C)C)cccc1NC(=O)C(c1ccc(Br)cc1)C1CCCC1]

53.3 g HATU and 67 ml DIPEA were added to 30 g intermediate 2 and 39.7 g intermediate 1 in 150 ml DMF. The reaction mixture was stirred until complete conversion at RT. The reaction mixture was stirred into 500 ml water, extracted with EE, the combined organic layers washed with sat. NH$_4$CL-solution and brine, dried with Na$_2$SO$_4$, filtered and evaporated to dryness. The resulting material was purified by chromatography using silica gel (gradient: hexane/EE). Yield: 43 g.

$^1$H NMR (300 MHz, DMSO-d$_6$) δ ppm 0.88-1.05 (m, 1 H) 1.27-1.42 (m, 12 H) 1.43-1.74 (m, 3 H) 1.76-1.91 (m, 1 H) 1.99 (s, 3 H) 2.37-2.46 (m, 2 H) 2.53-2.62 (m, 1 H) 2.79 (t, 2 H) 3.47 (d, 1 H) 6.95-7.08 (m, 3 H) 7.38 (d, 2 H) 7.52 (d, 2 H) 9.53 (s, 1 H).

Intermediate 4

(R/S) tert-Butyl 3-(3-{[(4-bromophenyl)(cyclopropyl)acetyl]amino}-2-methylphenyl)propanoate

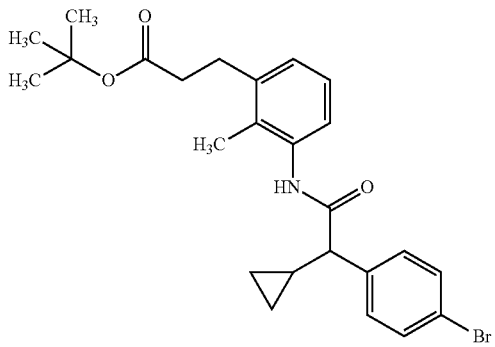 [SMILES: Cc1c(CCC(=O)OC(C)(C)C)cccc1NC(=O)C(c1ccc(Br)cc1)C1CC1]

Step 4.1: (E/Z)-2-(4-Bromophenyl)-2-cyclopropylvinyl methyl ether

To a solution of 6.85 g (methoxymethyl)(triphenyl)phosphonium chloride in 40 ml THF at 0° C. 40 ml 0.5 M potassium bis-(trimethylsilyl)amide solution in toluene were added and stirred for 1.5 hours at RT followed by the addition of 3.0 g (4-bromphenyl)(cyclopropyl)methanone in 10 ml THF. The reaction mixture was stirred until complete conversion at RT, cooled down to 0° C., quenched with 100 ml water and extracted with EE. The combined organic layers were washed with water and brine, dried with Na$_2$SO$_4$, filtered and evaporated to dryness. The crude material was purified by chromatography using silica gel (gradient: hexane/EE). Yield: 3.37 g as a mixture of E/Z isomers.

$^1$H NMR (300 MHz, DMSO-d$_6$) δ ppm 0.31-0.40 (m, 2×2 H) 0.66-0.77 (m, 2×2 H) 1.43-1.59 (m, 2×1 H) 3.66 (s, 2×3 H) 6.35 & 6.54 (je ein d, je 1 H) 7.20-7.31 (m, 2×1 H) 7.42-7.52 (m, 2×2 H) 7.63-7.68 (m, 2×1 H).

Step 4.2: (R/S) (4-Bromophenyl)(cyclopropyl)acetaldehyde

To a solution of 3.37 g (E/Z)-2-(4-bromophenyl)-2-cyclopropylvinyl methyl ether in 50 ml THF 6 ml 6 M hydrochloric acid were added. The reaction mixture was refluxed until complete conversion, cooled down to RT, quenched with water and extracted with DCM. The combined organic layers were washed with sat. NaHCO$_3$-solution, dried with Na$_2$SO$_4$, filtered and evaporated to dryness. The crude material was purified by chromatography using silica gel (gradient: hexane/EE). Yield: 2.8 g.

Step 4.3: (R/S) (4-Bromophenyl)(cyclopropyl)acetic acid

To a solution of 2.8 g of the before mentioned aldehyde in THF at 0° C. 19.6 ml 2-methyl-2-butene, 24.2 ml 10% sodium dihydrogen phosphate monohydrate and 13.1 ml 25% sodium chlorite were added and stirred until complete conversion at 0° C. At 0° C. 9.8 ml of ice-cold 10% sodium thiosulfate were added and stirred for additional 30 min. The reaction mixture was extracted with EE, dried with Na$_2$SO$_4$, filtered and evaporated to dryness. Yield: 3.72 g of the title compound which was used without further purification in the next step.

$^1$H NMR (300 MHz, DMSO-d$_6$) δ ppm 0.06-0.19 (m, 1 H) 0.26-0.49 (m, 2 H) 0.51-0.67 (m, 1 H) 1.25-1.36 (m, 1 H) 2.81 (m, 1 H) 7.27-7.37 (m, 2 H) 7.48-7.58 (m, 2 H) 12.42 (br. s., 1 H).

Step 4.4: (R/S) tert-Butyl 3-(3-{[(4-bromophenyl)(cyclopropyl)acetyl]amino}-2-methylphenyl) propanoate In analogy to intermediate 3 reaction of 839 mg intermediate 2 with 1.0 g of (R/S) (4-bromophenyl)(cyclopropyl) acetic acid gave 2.25 g of the title compound which was used without further purification in the next step.

Intermediate 5

(R/S) [4-(5-Chloropyridin-3-yl)phenyl](cyclopentyl) acetic acid

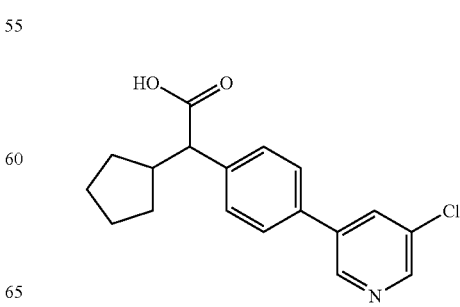

In analogy to coupling conditions under example 1 4.5 g intermediate 1 and 3.0 g (5-chlorpyridin-3-yl)boronic acid were heated under reflux until complete conversion. The reaction mixture was cooled down to RT, treated with water, acidified to a pH-value of 3 and extracted with EE. The combined organic layers were washed with water and brine, dried with $Na_2SO_4$, filtered and evaporated to dryness. The crude material was purified by chromatography using silica gel (gradient: hexane/EE). Yield: 3.2 g.

$^1$H NMR (300 MHz, DMSO-$d_6$) δ ppm 0.91-1.08 (m, 1 H) 1.21-1.69 (m, 6 H) 1.79-1.94 (m, 1 H) 7.46 (d, 2 H) 7.74 (d, 2 H) 8.24 (s, 1 H) 8.61 (d, 1 H) 8.86 (d, 1 H) 12.09-12.67 (m, 1 H).

Intermediate 6

(R/S) Methyl (3-{[(4-bromophenyl)(cyclopentyl)acetyl]amino}-2-methylphenoxy)acetate

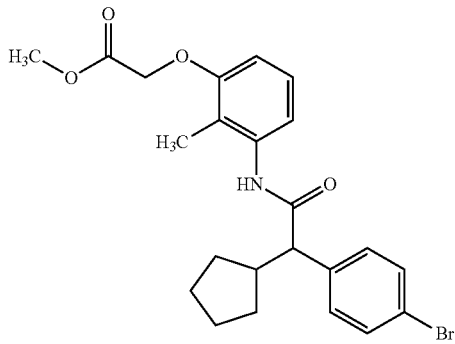 [SMILES: COC(=O)COc1cccc(NC(=O)C(c2ccc(Br)cc2)C2CCCC2)c1C]

Step 6.1: Methyl (2-methyl-3-nitrophenoxy)acetate

To a solution of 2.0 g 2-methyl-3-nitrophenol in 12 ml DMF, 3.61 g $K_2CO_3$, 7.24 g TBAI and 1.72 ml methyl chloroacetate were added and stirred until complete conversion at RT. The reaction mixture was quenched with water, extracted with EE, the combined organic layers washed with brine, dried with $Na_2SO_4$, filtered and evaporated to dryness. The resulting material was purified by chromatography using silica gel (gradient: hexane/EE). Yield: 2.09 g.

$^1$H NMR (400 MHz, DMSO-$d_6$) δ ppm 2.30 (s, 3 H) 3.71 (s, 3 H) 4.96 (s, 2 H) 7.27 (s, 1 H) 7.38 (s, 1 H) 7.48 (d, J=0.76 Hz, 1 H).

Step 6.2: Methyl-(3-amino-2-methylphenoxy)acetate 2.45 g Palladium/charcoal (10%) were added to a solution of 2.09 g methyl (2-methyl-3-nitrophenoxy)acetate in methanol and stirred at RT under hydrogen atmosphere until complete conversion. The catalyst was filtered off, the filter cake washed with methanol and the resulting solution evaporated to dryness. Yield: 1.87 g of the title compound which was used without further purification in the next step.

$^1$H NMR (400 MHz, DMSO-$d_6$) δ ppm 1.94 (s, 3 H) 3.68 (s, 3 H) 4.67 (s, 2 H) 4.83 (s, 2 H) 6.05 (d, 1 H) 6.29 (d, 1 H) 6.72-6.82 (m, 1 H).

Step 6.3: (R/S) Methyl (3-{[(4-bromophenyl)(cyclopentyl)acetyl]amino}-2-methylphenoxy)acetate In analogy to intermediate 3 reaction of 2.98 g intermediate 1 with 1.87 g the before mentioned aniline gave 2.13 g of the title compound.

$^1$H NMR (400 MHz, DMSO-$d_6$) δ ppm 0.90-1.03 (m, 1 H) 1.30-1.71 (m, 6 H) 1.78-1.89 (m, 1 H) 1.96 (s, 3 H) 2.53-2.61 (m, 1 H) 3.44-3.51 (m, 1 H) 3.68 (s, 3 H) 4.79 (s, 2 H) 6.66-6.72 (m, 1 H) 6.80-6.87 (m, 1 H) 7.00-7.09 (m, 1 H) 7.33-7.42 (m, 2 H) 7.50-7.55 (m, 2 H) 9.49-9.57 (m, 1 H).

Intermediate 7

(R/S) tert-Butyl 3-(3-{[(4-bromophenyl)(cyclopentyl)acetyl]amino}-6-methoxy-2-methylphenyl)propanoate

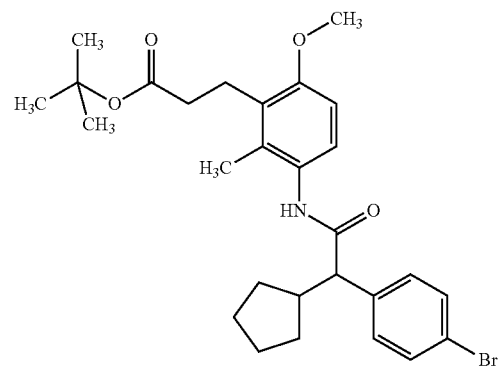 [SMILES: COc1ccc(NC(=O)C(c2ccc(Br)cc2)C2CCCC2)c(C)c1CCC(=O)OC(C)(C)C]

Step 7.1: tert-Butyl (2E)-3-(6-methoxy-2-methyl-3-nitrophenyl)acrylate

In analogy to Heck coupling conditions described in step 2.1 reaction of 2.52 g of a mixture containing 2-bromo-1-methoxy-3-methyl-4-nitrobenzene and 1-bromo-2-methoxy-4-methyl-5-nitrobenzene with 13.4 g tert-butyl acrylate and subsequent purification via HPLC gave 1.13 g of the title compound together with 393 mg tert-butyl (2E)-3-(2-methoxy-4-methyl-5-nitrophenyl)acrylate.

$^1$H NMR (300 MHz, DMSO-$d_6$) δ ppm 1.49 (s, 9 H) 2.43 (s, 3 H) 3.93 (s, 3 H) 6.35 (d, 1 H) 7.15 (d, 1 H) 7.60 (d, 1 H) 7.98 (d, 1 H).

Step 7.2: tert-Butyl 3-(3-amino-6-methoxy-2-methylphenyl)propanoate

In analogy to hydrogenation conditions described in step 2.2 reaction of 1.13 g tert-Butyl (2E)-3-(6-methoxy-2-methyl-3-nitrophenyl)acrylate in methanol/THF (100 ml, 1:1) gave 950 mg of the title compound which was used without further purification in the next step.

$^1$H NMR (300 MHz, DMSO-$d_6$) δ ppm 1.39 (s, 9 H) 1.98 (s, 3 H) 2.23 (dd, 2 H) 2.77 (dd, 2 H) 3.64 (s, 3 H) 4.31 (s, 2 H) 6.43-6.52 (m, 1 H) 6.52-6.61 (m, 1 H).

Step 7.3: (R/S) tert-Butyl 3-(3-{[(4-bromophenyl)(cyclopentyl)acetyl]amino}-6-methoxy-2-methylphenyl) propanoate In analogy to intermediate 3 reaction of 1.0 g tert-Butyl 3-(3-amino-6-methoxy-2-methylphenyl)propanoate and 1.17 g intermediate 1 and subsequent purification by chromatography using silica gel (gradient: hexane/EE) gave 1.46 g of the title compound.

$^1$H NMR (300 MHz, DMSO-$d_6$) δ ppm 0.89-1.03 (m, 1 H) 1.36-1.71 (m, 15 H) 1.76-1.90 (m, 1 H) 1.96 (s, 3 H)

2.19-2.31 (m, 2 H) 2.54-2.62 (m, 1 H) 2.74-2.84 (m, 2 H) 3.41 (d, 1 H) 3.74 (s, 3 H) 6.75 (d, 1 H) 6.92 (d, 1 H) 7.36 (d, 2 H) 7.52 (d, 2 H) 9.42 (s, 1 H).

Intermediate 8

(R/S) tert-butyl 3-(3-{[(4-bromo-3-methylphenyl)(cyclopentyl)acetyl]amino}-2-methylphenyl)propanoate

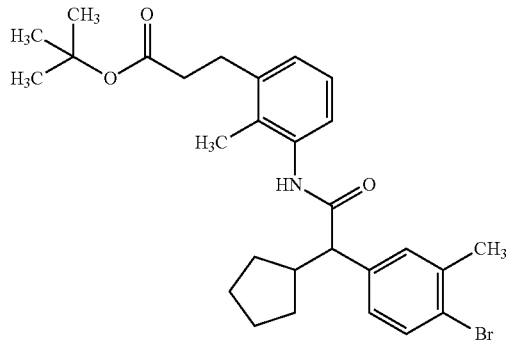 [SMILES: Cc1cc(C(C(=O)Nc2cccc(CCC(=O)OC(C)(C)C)c2C)C2CCCC2)ccc1Br]

Step 8.1: (R/S) Methyl (4-bromo-3-methylphenyl)(cyclopentyl)acetate

In analogy to alkylation condition described in step 1.1 reaction of 1.48 g methyl (4-bromo-3-methylphenyl)acetate with 2.17 g bromocyclopentane gave 2.04 g of the title compound which was used without further purification in the next step.

Step 8.2: (R/S) (4-Bromo-3-methylphenyl)(cyclopentyl)acetic acid

In analogy to saponification condition described in step 1.2 2.03 g (R/S) Methyl (4-bromo-3-methylphenyl)(cyclopentyl)acetate in methanol gave 1.84 g of the title compound which was used without further purification in the next step.

$^1$H NMR (300 MHz, DMSO-d$_6$) δ ppm 0.86-1.02 (m, 1 H) 1.56 (m, 6 H) 1.76-1.89 (m, 1 H) 2.32 (s, 3 H) 2.35-2.46 (m, 1 H) 3.20 (d, 1 H) 7.10 (d, 1 H) 7.30 (d, 1 H) 7.51 (d, 1 H) 12.19-12.53 (m, 1 H).

Step 8.3: (R/S) tert-butyl 3-(3-{[(4-bromo-3-methylphenyl)(cyclopentyl)acetyl]amino}-2-methylphenyl) propanoate In analogy to intermediate 3 reaction of 1.83 g (R/S) (4-Bromo-3-methylphenyl)(cyclopentyl)acetic acid with 1.59 g intermediate 2 and subsequent purification by chromatography using silica gel (gradient: hexane/EE) gave 2.41 g of the title compound.

$^1$H NMR (400 MHz, DMSO-d$_6$) δ ppm 1.30-1.74 (m, 16 H) 1.78-1.89 (m, 1 H) 1.97-2.02 (m, 3 H) 2.34 (s, 3 H) 2.42 (t, 2 H) 2.53-2.61 (m, 1 H) 2.76-2.83 (m, 2 H) 3.42 (d, 1 H) 6.94-7.07 (m, 3 H) 7.15-7.22 (m, 1 H) 7.39 (d, 1 H) 7.52 (d, 1 H) 9.48 (s, 1H).

Intermediate 9

(R/S) tert-Butyl 3-(3-{[(4-bromo-3-fluorophenyl)(cyclopentyl)acetyl]amino}-2-methylphenyl)propanoate

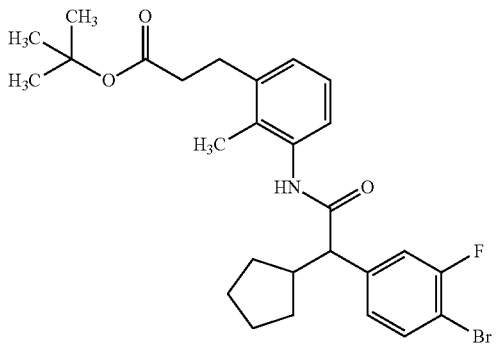 [SMILES: Cc1c(CCC(=O)OC(C)(C)C)cccc1NC(=O)C(c1ccc(Br)c(F)c1)C1CCCC1]

Step 9.1: (R/S) Ethyl (4-bromo-3-fluorophenyl)(cyclopentyl)acetate

In analogy to alkylation condition described in step 1.1 2 g ethyl (4-bromo-3-fluorophenyl)acetate with 1.37 g bromocyclopentane and subsequent purification by chromatography using silica gel (gradient: hexane/EE) gave 2.39 g of the title compound.

Step 9.2: (R/S) (4-Bromo-3-fluorophenyl)(cyclopentyl)acetic acid

In analogy to saponification condition described in step 1.2 2.39 g (R/S) Ethyl (4-bromo-3-fluorophenyl)(cyclopentyl)acetate in ethanol gave 2.35 g of the title compound which was used without further purification in the next step.

Step 9.3: (R/S) tert-Butyl 3-(3-{[(4-bromo-3-fluorophenyl)(cyclopentyl)acetyl]amino}-2-methylphenyl) propanoate In analogy to intermediate 3 reaction of 2 g (R/S) (4-Bromo-3-fluorophenyl)(cyclopentyl)acetic acid with 1.42 g intermediate 2 at 60° C. and subsequent purification by chromatography using silica gel (gradient: hexane/EE) gave 2.44 g of the title compound.

$^1$H NMR (400 MHz, DMSO-d$_6$) δ ppm 0.92-1.06 (m, 1 H) 1.32-1.72 (m, 15 H) 1.76-1.90 (m, 1 H) 2.00 (s, 3 H) 2.42 (t, 2 H) 2.52-2.61 (m, 1 H) 2.80 (t, 2 H) 3.51 (d, 1 H) 6.95-7.08 (m, 3 H) 7.21 (dd, 1 H) 7.39 (dd, 1 H) 7.67 (t, 1 H) 9.55 (s, 1 H).

Intermediate 10

(R/S) tert-Butyl 3-(3-{[(4-bromo-2-fluorophenyl)(cyclopentyl)acetyl]amino}-2-methylphenyl)propanoate

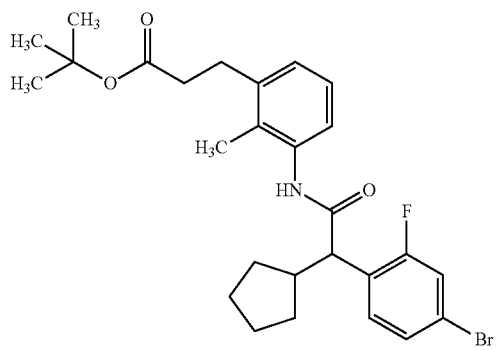 [SMILES: Cc1c(CCC(=O)OC(C)(C)C)cccc1NC(=O)C(c1ccc(Br)cc1F)C1CCCC1]

Step 10.1: (R/S) Ethyl (4-bromo-2-fluorophenyl)(cyclopentyl)acetate

In analogy to alkylation condition described in step 1.1 2 g ethyl (4-bromo-2-fluorophenyl)acetate with 1.37 g bromocyclopentane and subsequent purification by chromatography using silica gel (gradient: hexane/EE) gave 2.17 g of the title compound.

Step 10.2: (R/S) (4-Bromo-2-fluorophenyl)(cyclopentyl)acetic acid

In analogy to saponification condition described in step 1.2 2.17 g (R/S) Ethyl (4-bromo-2-fluorophenyl)(cyclopentyl)acetate in ethanol gave 2.15 g of the title compound which was used without further purification in the next step.

Step 10.3: (R/S) tert-Butyl 3-(3-{[(4-bromo-2-fluorophenyl)(cyclopentyl)acetyl]amino}-2-methylphenyl)propanoate In analogy to intermediate 3 reaction of 2 g (R/S) (4-Bromo-2-fluorophenyl)(cyclopentyl)acetic acid with 1.42 g intermediate 2 at 60° C. and subsequent purification by chromatography using silica gel (gradient: hexane/EE) gave 2.42 g of the title compound.

$^1$H NMR (400 MHz, DMSO-$d_6$) δ ppm 0.95-1.07 (m, 1 H) 1.34-1.62 (m, 14 H) 1.65-1.76 (m, 1 H) 1.78-1.90 (m, 1 H) 2.01 (s, 3 H) 2.43 (t, 2 H) 2.52-2.58 (m, 1 H) 2.80 (t, 2 H) 3.83 (d, 1 H) 6.97-7.08 (m, 3 H) 7.41 (dd, 1 H) 7.53 (dd, 1 H) 7.58-7.66 (m, 1 H) 9.63 (s, 1 H).

Intermediate 11

(R/S) tert-Butyl 3-(3-{[(4-bromophenyl)(cyclobutyl)acetyl]amino}-2-methylphenyl)propanoate

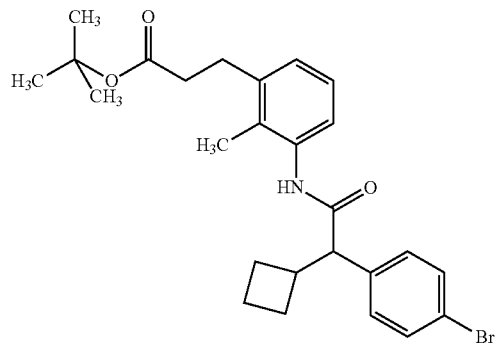 [SMILES: Cc1c(CCC(=O)OC(C)(C)C)cccc1NC(=O)C(c1ccc(Br)cc1)C1CCC1]

Step 11.1: (R/S) Ethyl (4-bromophenyl)(cyclobutyl)acetate

In analogy to alkylation condition described in step 1.1 1 g ethyl (4-bromophenyl)acetate with 666 mg bromocyclobutane and subsequent purification by chromatography using silica gel (gradient: hexane/EE) gave 1.06 g of the title compound.

Step 11.2: (R/S) (4-Bromophenyl)(cyclobutyl)acetic acid

In analogy to saponification condition described in step 1.2 1.06 g (R/S) ethyl (4-bromophenyl)(cyclobutyl)acetate in ethanol gave 800 mg of the title compound which was used without further purification in the next step.

Step 11.3: (R/S) tert-Butyl 3-(3-{[(4-bromophenyl)(cyclobutyl)acetyl]amino}-2-methylphenyl) propanoate In analogy to intermediate 3 reaction of 800 mg (R/S) (4-bromophenyl)(cyclobutyl)acetic acid with 636 mg intermediate 2 at 60° C. and subsequent purification by chromatography using silica gel (gradient: hexane/EE) gave 700 mg of the title compound.

$^1$H NMR (300 MHz, DMSO-$d_6$) δ ppm 1.33-1.41 (m, 9 H) 1.51-1.63 (m, 1 H) 1.75-1.91 (m, 4 H) 2.00 (s, 3 H) 2.05-2.16 (m, 1 H) 2.42 (t, 2 H) 2.75-2.84 (m, 2 H) 2.91-3.03 (m, 1 H) 3.73 (d, 1 H) 6.96-7.06 (m, 3 H) 7.33 (d, 2 H) 7.52 (d, 2 H) 9.55 (s, 1 H).

47

Intermediate 12

(R/S) tert-Butyl 3-(3-{[(4-bromophenyl)(cyclo-hexyl)acetyl]amino}-2-methylphenyl)propanoate

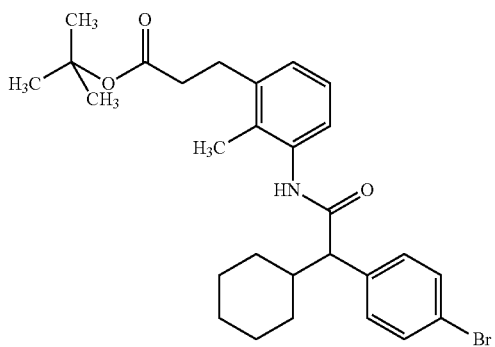 [SMILES: Cc1c(CCC(=O)OC(C)(C)C)cccc1NC(=O)C(c1ccc(Br)cc1)C1CCCCC1]

Step 12.1: (R/S) Ethyl (4-bromophenyl)(cyclohexyl)acetate

In analogy to alkylation condition described in step 1.1 reaction of 1 g ethyl (4-bromophenyl)acetate with 805 mg bromocyclohexane and subsequent purification by chromatography using silica gel (gradient: hexane/EE) gave 610 mg of the title compound.

Step 12.2: (R/S) (4-Bromophenyl)(cyclohexyl)acetic acid

In analogy to saponification condition described in step 1.2 saponification of 600 mg (R/S) ethyl (4-bromophenyl)(cyclohexyl)acetate in ethanol gave 506 mg of the title compound which was used without further purification in the next step.

Step 12.3: (R/S) tert-Butyl 3-(3-{[(4-bromophenyl)(cyclohexyl)acetyl]amino}-2-methylphenyl) propanoate In analogy to intermediate 3 reaction of 506 mg (R/S) (4-bromophenyl)(cyclohexyl)acetic acid with 366 mg intermediate 2 at 60° C. and subsequent purification by chromatography using silica gel (gradient: hexane/EE) gave 410 mg of the title compound.

$^1$H NMR (300 MHz, DMSO-$d_6$) δ ppm 0.66-0.89 (m, 1 H) 1.00-1.30 (m, 5 H) 1.32-1.40 (m, 9 H) 1.58 (m, 2 H) 1.68-1.78 (m, 1 H) 1.80-1.91 (m, 1 H) 1.93-2.07 (m, 4 H) 2.36-2.46 (m, 2 H) 2.74-2.85 (m, 2 H) 3.43 (d, 1 H) 6.95-7.05 (m, 3 H) 7.34 (d, 2 H) 7.52 (d, 2 H) 9.53 (s, 1 H).

48

Intermediate 13

Ethyl (2R/S)-3-(3-{[(2R/S)-2-(4-bromophenyl)-2-cyclopentylacetyl]amino}-2-methylphenyl)-2-methylpropanoate

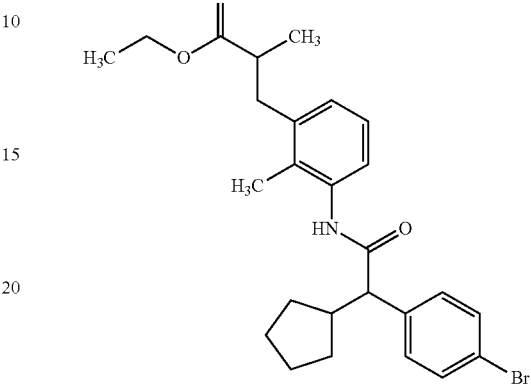

Step 13.1: Ethyl (2E)-2-methyl-3-(2-methyl-3-nitrophenyl)acrylate

To a solution of 1 g 2-methyl-3-nitrobenzaldehyde and 1.44 g ethyl 2-(diethoxyphosphoryl)propanoate in DMF at 0° C. 266 mg sodium hydride (60%) were added. The reaction mixture was stirred at RT until complete conversion, water was added and the mixture stirred for additional 30 min at RT. The reaction mixture was extracted with EE, washed with water and brine, dried with $Na_2SO_4$, filtered and evaporated to dryness. The resulting material was purified by chromatography using silica gel (hexane/EE). Yield: 958 mg.

$^1$H NMR (300 MHz, DMSO-$d_6$) δ ppm 1.28 (t, 3 H) 1.82 (d, 3 H) 2.30 (s, 3 H) 4.23 (q, 2 H) 7.44-7.58 (m, 2 H) 7.66 (s, 1 H) 7.87 (dd, 1 H).

Step 13.2: (R/S) Ethyl 3-(3-amino-2-methylphenyl)-2-methylpropanoate

In analogy to hydrogenation conditions described in step 2.2 hydrogenation of 958 mg ethyl (2E)-2-methyl-3-(2-methyl-3-nitrophenyl)acrylate in methanol/THF (2:1) and subsequent purification by chromatography using silica gel (gradient: hexane/EE) gave 790 mg of the title compound.

$^1$H NMR (300 MHz, DMSO-$d_6$) δ ppm 1.02-1.07 (d, 3 H) 1.08-1.14 (t, 3 H) 1.96 (s, 3 H) 2.53-2.64 (m, 2 H) 2.79-2.92 (m, 1 H) 4.00 (q, 2 H) 4.73 (s, 2 H) 6.31 (d, 1 H) 6.48 (d, 1 H) 6.71-6.81 (m, 1 H).

Step 13.3: Ethyl (2R/S)-3-(3-{[(2R/S)-2-(4-bromophenyl)-2-cyclopentylacetyl]amino}-2-methylphenyl)-2-methylpropanoate In analogy to intermediate 3 reaction of 790 mg (R/S) ethyl 3-(3-amino-2-methylphenyl)-2-methylpropanoate with 1.11 g intermediate 1 at 60° C. and subsequent purification by chromatography using silica gel (gradient: hexane/EE) gave 1.68 g of the title compound.

$^1$H NMR (400 MHz, DMSO-$d_6$) δ ppm 0.90-1.00 (m, 1 H) 1.04-1.12 (m, 6 H) 1.30-1.70 (m, 6 H) 1.78-1.90 (m, 1 H)

1.99 (d, 3 H) 2.54-2.68 (m, 3 H) 2.83-2.94 (m, 1 H) 3.46 (d, 1 H) 3.94-4.02 (m, 2 H) 6.93 (d, 1 H) 6.99-7.05 (m, 2 H) 7.38 (d, 2 H) 7.53 (d, 2 H) 9.52 (s, 1 H).

Intermediate 13-1

Ethyl 3-(3-{[2-(4-bromophenyl)-2-cyclopentylacetyl]amino}-2-methylphenyl)-2-methylpropanoate, Diastereomer 1

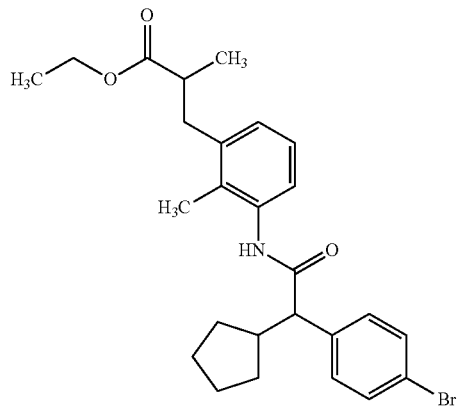 [SMILES: CCOC(=O)C(C)Cc1cccc(NC(=O)C(c2ccc(Br)cc2)C2CCCC2)c1C]

Step 13-1.1: (+) Ethyl 3-(3-amino-2-methylphenyl)-2-methylpropanoate

In analogy to hydrogenation conditions described in step 2.2 hydrogenation of 1.67 g ethyl (2E)-2-methyl-3-(2-methyl-3-nitrophenyl)acrylate in THF at 25 bar and 50° C. gave 1.54 g (R/S) ethyl 3-(3-amino-2-methylphenyl)-2-methylpropanoate which was separated into the two enantiomers using preparative chiral HPLC (method 2; solvent: hexane/2-propanol/diethylamine 70:30:0.1 (v/v/v); flow rate: 50 ml/min; solution: 1.54 g in 15 ml DCM/ ethanol; injection volume: 30×0.5 ml) to yield 585 mg (+) ethyl 3-(3-amino-2-methylphenyl)-2-methylpropanoate (Rt: 5.6-6.4 min) along with 545 mg of the corresponding (−)-enantiomer.

Analytical HPLC, method 3: solvent: hexane/2-propanol/ diethylamine 70:30:0.1 (v/v/v); flow rate: 1.0 ml/min; solution: 1.0 mg/ml ethanol/methanol (1:1), injection volume: 5 µl; Rt: 3.04 min Optical rotation: +56.9° (at 589 nm, 20° C., 7.6 mg/ml methanol).

Step 13-1.2: Ethyl 3-(3-{[2-(4-bromophenyl)-2-cyclopentylacetyl]amino}-2-methylphenyl)-2-methylpropanoate, Diastereomer 1

In analogy to intermediate 3 reaction of 585 mg (+) ethyl 3-(3-amino-2-methylphenyl)-2-methylpropanoate with 898 mg intermediate 1 at 60° C. and subsequent purification by chromatography using silica gel (gradient: hexane/EE) gave 630 mg of the title compound.

Intermediate 13-2

Ethyl 3-(3-{[2-(4-bromophenyl)-2-cyclopentylacetyl]amino}-2-methylphenyl)-2-methylpropanoate, Diastereomer 2

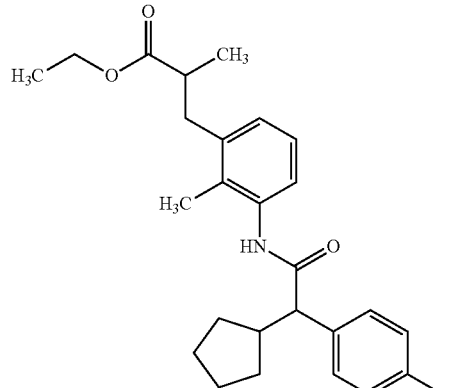

Step 13-2.1: (−) Ethyl 3-(3-amino-2-methylphenyl)-2-methylpropanoate

In analogy to hydrogenation conditions described in step 2.2 hydrogenation of 1.67 g ethyl (2E)-2-methyl-3-(2-methyl-3-nitrophenyl)acrylate in THF at 25 bar and 50° C. gave 1.54 g (R/S) ethyl 3-(3-amino-2-methylphenyl)-2-methylpropanoate which was separated into the two enantiomers using preparative chiral HPLC (method 2) to yield 545 mg (−) ethyl 3-(3-amino-2-methylphenyl)-2-methylpropanoate (Rt: 4.9-5.4 min) along with 585 mg of the corresponding (+)-enantiomer.

Analytical HPLC, method 3: Rt: 2.58 min

Optical rotation: −70.9° (at 589 nm, 20° C., 5.4 mg/ml methanol).

Step 13-2.2: Ethyl 3-(3-{[2-(4-bromophenyl)-2-cyclopentylacetyl]amino}-2-methylphenyl)-2-methylpropanoate, Diastereomer 2

In analogy to intermediate 3 reaction of 540 mg (−) ethyl 3-(3-amino-2-methylphenyl)-2-methylpropanoate with 829 mg intermediate 1 at 60° C. and subsequent purification by chromatography using silica gel (gradient: hexane/EE) gave 1.04 g of the title compound.

Intermediate 14

Ethyl (2E)-3-(3-{[(4-bromophenyl)(cyclopentyl)acetyl]amino}-2-methylphenyl)-2-methylacrylate

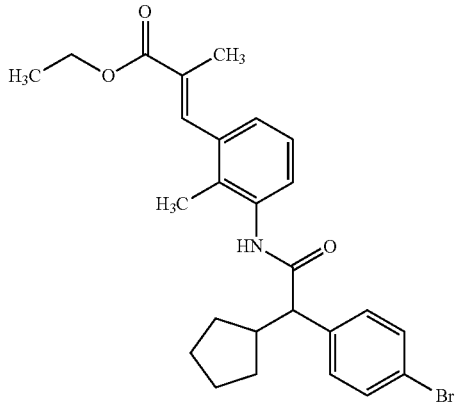 [SMILES: CCOC(=O)/C(C)=C/c1cccc(NC(=O)C(c2ccc(Br)cc2)C2CCCC2)c1C]

Step 14.1: Ethyl (2E)-3-(3-amino-2-methylphenyl)-2-methylacrylate 272 mg Palladium/charcoal (10%) were added to a solution of 6.37 g ethyl (2E)-2-methyl-3-(2-methyl-3-nitrophenyl)acrylate in 100 ml THF and stirred at RT under 1 bar hydrogen atmosphere until complete conversion. The catalyst was filtered off, the filter cake washed with THF, the resulting solution evaporated to dryness and purified by chromatography using silica gel (gradient: hexane/EE) to yield 1.67 g of the title compound as major component of a compound mixture.

Step 14.2: Ethyl (2E)-3-(3-{[(4-bromophenyl)(cyclopentyl)acetyl]amino}-2-methylphenyl)-2-methylacrylate In analogy to intermediate 3 reaction of 2.1 g Ethyl (2E)-3-(3-amino-2-methylphenyl)-2-methylacrylate with 2.96 g intermediate 1 at 60° C. and subsequent purification by chromatography using silica gel (gradient: hexane/EE) gave 1.1 g of the title compound as major component of a compound mixture.

Intermediate 15 tert-Butyl (3R/S)-3-(3-{[(2R/S)-2-(4-bromophenyl)-2-cyclopentylacetyl]amino}-2-methylphenyl)butanoate

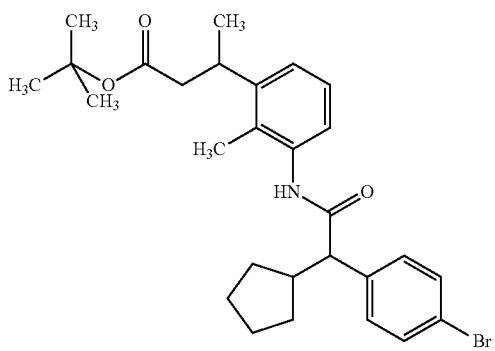 [SMILES: Cc1c(NC(=O)C(c2ccc(Br)cc2)C2CCCC2)cccc1C(C)CC(=O)OC(C)(C)C]

Step 15.1: 1-(2-methyl-3-nitrophenyl)ethanone methyl N-(3-amino-2-methylphenyl)-N-methylglycinate 8.2 g 1-Bromo-2-methyl-3-nitrobenzene and 2.12 g dichlorobis(triphenylphosphine)palladium(II) in 100 ml 1,4-dioxane were treated with 13.4 ml tributyl(1-ethoxyvinyl)stannane and stirred at 100° C. for one hour. The reaction mixture was cooled to 0° C. and treated with 20 ml 2N hydrochloric acid and stirred for another hour. The reaction mixture was adjusted to pH ~8 with 6 ml of a NaOH-solution (made from 5 g sodium chloride, 30 g sodium hydroxide, 90 ml water), extracted with EE, evaporated to dryness and purified by chromatography using silica gel (gradient: hexane/EE) to yield 4.85 g of the title compound.

$^1$H NMR (400 MHz, DMSO-$d_6$) δ ppm 2.37 (s, 3 H) 2.60 (s, 3 H) 7.56 (t, J=7.96 Hz, 1 H) 7.98 (dd, J=7.83, 2.78 Hz, 2 H).

Step 15.2: tert-Butyl (2E)-3-(2-methyl-3-nitrophenyl)but-2-enoate

To a solution of 4.85 g 1-(2-methyl-3-nitrophenyl)ethanone and 6.83 g tert-butyl (diethoxyphosphoryl)acetate in 97 ml DMF at 0° C. 1.19 g sodium hydride (60%) was added. The reaction mixture was stirred at RT until complete conversion. The reaction mixture was cooled to 0° C., diluted with EE, water was added and the mixture stirred for additional 30 min at RT. The reaction mixture was extracted with EE, washed with water, dried with $Na_2SO_4$, filtered and evaporated to dryness. The resulting material was purified by chromatography using silica gel (hexane/EE) to yield 4.46 g of the title compound.

$^1$H NMR (300 MHz, DMSO-$d_6$) δ ppm 1.11 (s, 9 H) 2.08 (d, 3 H) 2.23 (s, 3 H) 6.00 (d, 1 H) 7.29-7.36 (m, 1 H) 7.39-7.48 (m, 1 H) 7.80 (dd, 1 H).

Step 15.3: (R/S) tert-Butyl 3-(3-amino-2-methylphenyl)butanoate 1.72 g Palladium/charcoal (10%) were added to a solution of 4.4 g tert-Butyl (2E)-3-(2-methyl-3-nitrophenyl)but-2-enoate in 238 ml methanol and stirred at RT under hydrogen atmosphere until complete conversion. The catalyst was filtered off, the filter cake washed with methanol and the resulting solution evaporated to dryness to yield 3.75 g of the title compound.

$^1$H NMR (400 MHz, DMSO-$d_6$) δ ppm 1.11 (d, 3 H) 1.30 (s, 9 H) 2.01 (s, 3 H) 2.39 (dd, 2 H) 3.33-3.40 (m, 1 H) 4.69 (s, 2 H) 6.41-6.49 (m, 2 H) 6.79-6.85 (m, 1 H).

Step 15.4: tert-Butyl (3R/S)-3-(3-{[(2R/S)-2-(4-bromophenyl)-2-cyclopentylacetyl]amino}-2-methylphenyl)butanoate 5.45 g HATU and 6.8 ml DIPEA were added to 3.25 g (R/S) tert-Butyl 3-(3-amino-2-methylphenyl)butanoate and 4.06 g intermediate 1 in 15 ml DMF. The reaction mixture was stirred at 60° C. overnight. The reaction mixture was evaporated to dryness, water and DCM were added, the phases separated and the aqueous phase extracted four times with DCM. The combined organic layers were washed with sat. $Na_2CO_3$-solution and water, dried with $Na_2SO_4$, filtered and evaporated to dryness. The resulting material was purified by chromatography using silica gel (gradient: hexane/EE) to yield 2.54 g intermediate 15.

¹H NMR (400 MHz, DMSO-d₆) δ ppm 0.93-1.02 (m, 1 H) 1.12 (t, 3 H) 1.26 (d, 9 H) 1.33-1.73 (m, 6 H) 1.78-1.89 (m, 1 H) 2.04 (d, 3 H) 2.44-2.48 (m, 2 H) 3.35-3.41 (m, 1 H) 3.43-3.49 (m, 1 H) 6.93-7.01 (m, 1 H) 7.04-7.10 (m, 2 H) 7.38 (d, 2 H) 7.52 (d, 2 H) 9.53 (d, 1 H).

Intermediate 16

Methyl (3R/S)-3-(3-{[(2R/S)-2-(4-bromophenyl)-2-cyclopentylacetyl]amino}-2-methylphenyl)pentanoate

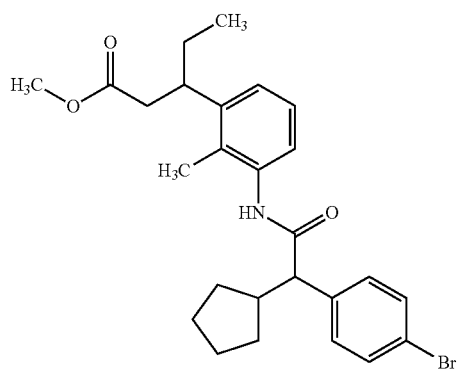 [SMILES: CCC(CC(=O)OC)c1cccc(NC(=O)C(c2ccc(Br)cc2)C2CCCC2)c1C]

Step 16.1: Methyl (3R/S)-3-(3-amino-2-methylphenyl)pentanoate

The reaction was carried out under argon atmosphere. 206 mg (+/−)-BINAP and 72 mg chloro(1,5-cyclooctadiene)rhodium(I) dimer were treated with 2.6 ml THF and stirred for 25 minutes at RT. This solution was added to a mixture of 1.11 g methyl (2E)-pent-2-enoate, 2.5 g 2-methyl-3-(4,4,5,5-tetramethyl-1,3,2-dioxaborolan-2-yl)aniline, 656 mg powdered potassium hydroxide and 1.41 g 1,1,1-tris(hydroxymethyl)ethane in 40 ml THF and stirred at 60° C. for 14 hours. Water was added, the mixture stirred for 10 minutes and the phases were separated. The organic layer was evaporated to dryness. The resulting material was purified by chromatography using silica gel (gradient: hexane/EE) to yield 820 mg of the title compound.

¹H NMR (400 MHz, DMSO-d₆) δ ppm 0.70 (t, 3 H) 1.42-1.63 (m, 2 H) 2.01 (s, 3 H) 2.54-2.63 (m, 1 H) 3.21-3.30 (m, 1 H) 3.50 (s, 3 H) 4.69 (s, 2 H) 6.41 (d, 1 H) 6.44-6.49 (m, 1 H) 6.83 (t, 1 H).

Step 16.2: Methyl (3R/S)-3-(3-{[(2R/S)-2-(4-bromophenyl)-2-cyclopentylacetyl]amino}-2-methylphenyl)pentanoate 2.26 g HATU and 3.18 ml DIPEA were added to 822 mg methyl (3R/S)-3-(3-amino-2-methylphenyl)pentanoate and 1.58 g intermediate 1 in 12 ml DMF. The reaction mixture was stirred at 60° C. overnight. The reaction mixture was treated with water, extracted with EE. The combined organic layers were washed with sat. NaHCO₃-solution, water and brine, dried with Na₂SO₄, filtered and evaporated to dryness. The resulting material was purified by chromatography using silica gel (gradient: hexane/EE) to yield 1.56 g intermediate 16.

¹H NMR (300 MHz, DMSO-d₆) δ ppm 0.62-0.74 (m, 3 H) 0.91-1.05 (m, 1 H) 1.28-1.70 (m, 8 H) 1.77-1.90 (m, 1 H) 2.04 (d, 3 H) 2.55-2.66 (m, 2 H) 3.21-3.30 (m, 1 H) 3.47 (d, 3 H) 6.94-7.01 (m, 1 H) 7.02-7.13 (m, 2 H) 7.38 (d, 2 H) 7.53 (d, 2 H) 9.54 (s, 1 H).

Intermediate 17 tert-Butyl (3R/S)-3-(3-{[(2R/S)-2-(4-bromophenyl)-2-cyclopentylacetyl]amino}-2-methylphenyl)-3-cyclopropylpropanoate

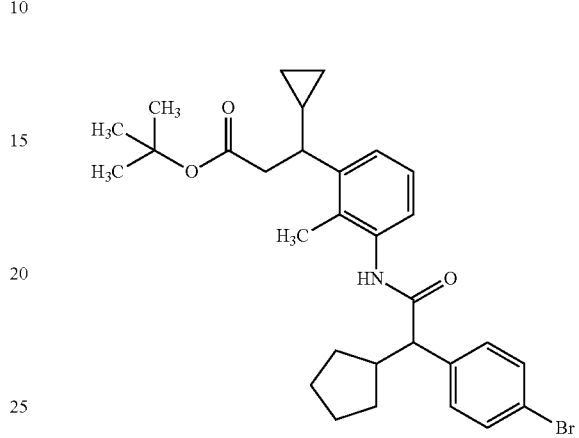

Step 17.1: tert-Butyl (3R/S)-3-(3-amino-2-methylphenyl)-3-cyclopropylpropanoate

The reaction was carried out under argon atmosphere. 189 mg (+/−)-BINAP and 66 mg chloro(1,5-cyclooctadiene)rhodium(I) dimer were treated with 2.5 ml THF and stirred for 30 minutes at RT. This solution was added to a mixture of 1.5 g tert-butyl (2E)-3-cyclopropylacrylate, 2.3 g 2-methyl-3-(4,4,5,5-tetramethyl-1,3,2-dioxaborolan-2-yl)aniline, 600 mg powdered potassium hydroxide and 1.28 g 1,1,1-tris(hydroxymethyl)ethane in 40 ml THF and stirred at 60° C. for 16 hours. Water and EE were added and the phases separated. The aqueous phase was extracted three times with EE and the combined organic phases were evaporated to dryness. The resulting material was purified by chromatography using silica gel (gradient: hexane/EE) to yield 1.57 g of the title compound.

¹H NMR (300 MHz, DMSO-d₆) δ ppm −0.08-0.03 (m, 1 H) 0.11-0.22 (m, 1 H) 0.22-0.33 (m, 1 H) 0.40-0.52 (m, 1 H) 0.95-1.08 (m, 1 H) 1.26 (s, 9 H) 1.96 (s, 3 H) 2.61-2.70 (m, 1 H) 4.69 (s, 2 H) 6.43-6.49 (m, 1 H) 6.50-6.57 (m, 1 H) 6.78-6.87 (m, 1 H).

Step 17.2: tert-Butyl (3R/S)-3-(3-{[(2R/S)-2-(4-bromophenyl)-2-cyclopentylacetyl]amino}-2-methylphenyl)-3-cyclopropylpropanoate 1.16 g HATU and 1.55 ml DIPEA were added to 577 mg methyl tert-Butyl (3R/S)-3-(3-amino-2-methylphenyl)-3-cyclopropylpropanoate and 809 mg intermediate 1 in 6.5 ml DMF. The reaction mixture was stirred at 60° C. for 24 hours. The reaction mixture was treated with water, extracted with EE. The combined organic layers were washed with sat. NaHCO₃-solution, water and brine, dried with Na₂SO₄, filtered and evaporated to dryness. The resulting material was purified by chromatography using silica gel (gradient: hexane/EE) to yield 520 mg intermediate 17.

¹H NMR (400 MHz, DMSO-d₆) δ ppm −0.06-0.04 (m, 1 H) 0.12-0.21 (m, 1 H) 0.23-0.33 (m, 1 H) 0.43-0.52 (m, 1 H)

0.96-1.09 (m, 2 H) 1.23 (d, 9 H) 1.40 (s, 6 H) 1.79-1.88 (m, 1 H) 1.97-1.99 (m, 3 H) 2.55 (m, 2 H) 2.64-2.71 (m, 1 H) 3.45 (d, 1 H) 6.94-7.03 (m, 1 H) 7.05-7.12 (m, 1 H) 7.16 (s, 1 H) 7.38 (dd, 2 H) 7.52 (dd, 2 H) 9.49 (d, 1 H).

Intermediate 18

Methyl (3R/S)-3-(3-{[(2R/S)-2-(4-bromo-3-fluorophenyl)-2-cyclopentylacetyl]amino}-2-methylphenyl)butanoate

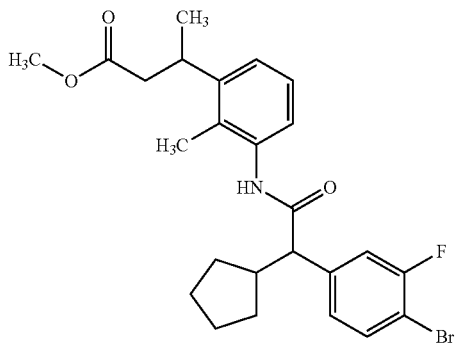 [SMILES: COC(=O)CC(C)c1cccc(NC(=O)C(c2ccc(Br)c(F)c2)C2CCCC2)c1C]

Step 18.1: Methyl (3R/S)-3-(3-amino-2-methylphenyl)butanoate

The reaction was carried out under argon atmosphere. 410 mg (+/−)-BINAP and 143 mg chloro(1,5-cyclooctadiene)rhodium(I) dimer were treated with 4.4 ml THF and stirred for 30 minutes at RT. This solution was added to a mixture of 2.32 g methyl (2E)-but-2-enoate, 4.51 g 2-methyl-3-(4,4,5,5-tetramethyl-1,3,2-dioxaborolan-2-yl)aniline, 1.3 mg powdered potassium hydroxide and 2.79 g 1,1,1-tris(hydroxymethyl)ethane in 66 ml THF and stirred at 60° C. for 16 hours. Acetic acid, water and EE were added and the phases separated. The aqueous phase was extracted three times with EE and the combined organic phases were evaporated to dryness. The resulting material was purified by chromatography using silica gel (gradient: hexane/EE) to yield 1.7 g of the title compound.
$^1$H NMR (400 MHz, DMSO-d$_6$) δ ppm 1.12 (d, 3 H) 2.00 (s, 3 H) 2.54 (dd, 1 H) 3.37-3.44 (m, 1 H) 3.54 (s, 3 H) 4.71 (s, 2 H) 6.40-6.51 (m, 2 H) 6.83 (s, 1 H).

Step 18.2: Methyl (3R/S)-3-(3-{[(2R/S)-2-(4-bromo-3-fluorophenyl)-2-cyclopentylacetyl]amino}-2-methylphenyl)butanoate 1.57 g HATU and 2.4 ml DIPEA were added to 628 mg methyl (3R/S)-3-(3-amino-2-methylphenyl)butanoate and 830 mg (R/S) (4-bromo-3-fluorophenyl)(cyclopentyl)acetic acid (prepared in step 9.2) in 20 ml DMF. The reaction mixture was stirred at 75° C. for 2 hours. The reaction mixture was treated with water and EE and the phases were separated. The aqueous layer was extracted with EE three times and the combined organic layers were evaporated to dryness. The resulting material was purified by chromatography using silica gel (gradient: hexane/EE) to yield 990 mg intermediate 18.
$^1$H NMR (400 MHz, DMSO-d$_6$) δ ppm 0.95-1.05 (m, 1 H) 1.11-1.16 (m, 3 H) 1.31-1.72 (m, 6 H) 1.79-1.89 (m, 1 H) 2.05 (d, 3 H) 2.59 (m, 2 H) 3.39-3.47 (m, 1 H) 3.52 (d, 3 H) 6.95-7.03 (m, 1 H) 7.09 (d, 2 H) 7.18-7.25 (m, 1 H) 7.35-7.43 (m, 1 H) 7.67 (s, 1 H) 9.58 (s, 1 H).

Intermediate 19

Methyl (3R/S)-3-(3-{[(2R/S)-2-(4-bromophenyl)-2-cyclobutylacetyl]amino}-2-methylphenyl)butanoate

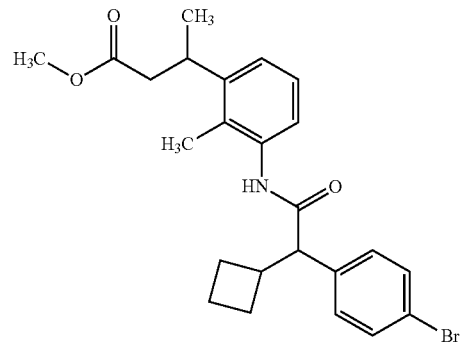 [SMILES: COC(=O)CC(C)c1cccc(NC(=O)C(c2ccc(Br)cc2)C2CCC2)c1C]

1.79 g HATU and 2.73 ml DIPEA were added to 715 mg methyl (3R/S)-3-(3-amino-2-methylphenyl)butanoate (prepared in step 18.1) and 843 mg (R/S) (4-bromophenyl)(cyclobutyl)acetic acid (prepared in step 11.2) in 20 ml DMF. The reaction mixture was stirred at 75° C. for 16 hours and evaporated to dryness. The resulting material was purified by chromatography using silica gel (gradient: hexane/EE) to yield 1.13 g intermediate 19.
$^1$H NMR (400 MHz, DMSO-d$_6$) δ ppm 1.10-1.15 (m, 3 H) 1.52-1.61 (m, 1 H) 1.76-1.91 (m, 4 H) 2.05 (d, 3 H) 2.11 (m, 1 H) 2.59 (ddd, 2 H) 2.92-3.03 (m, 1 H) 3.38-3.48 (m, 1 H) 3.51 (d, 3 H) 3.73 (d, 1 H) 6.94-7.02 (m, 1 H) 7.07-7.12 (m, 2 H) 7.31-7.37 (m, 2 H) 7.49-7.56 (m, 2 H) 9.54 (s, 1 H).

Intermediate 20

Methyl (3R/S)-3-(3-{[(2R/S)-2-(4-bromo-3-fluorophenyl)-2-cyclobutylacetyl]amino}-2-methylphenyl)butanoate

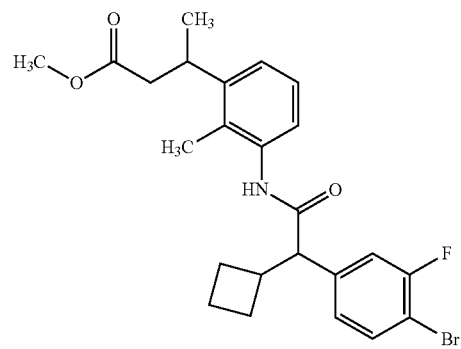 [SMILES: COC(=O)CC(C)c1cccc(NC(=O)C(c2ccc(Br)c(F)c2)C2CCC2)c1C]

Step 20.1: Ethyl (2R/S)-(4-bromo-3-fluorophenyl)(cyclobutyl)acetate

In analogy to alkylation condition described in step 1.1 2.0 g ethyl (4-bromo-3-fluorophenyl)acetate with 1.24 g bromocyclobutane and subsequent purification by chromatography using silica gel (gradient: hexane/EE) gave 1.69 g of the title compound.

Step 20.2: (R/S) (4-Bromo-3-fluorophenyl)(cyclobutyl)acetic acid

In analogy to saponification condition described in step 1.2 1.69 g ethyl (2R/S)-(4-bromo-3-fluorophenyl)(cyclobutyl)acetate were treated with 6.7 g NaOH (32%) in ethanol/water (30 ml/10 ml) to give after chromatography using silica gel (gradient: hexane/EE) 600 mg of the title compound.

$^1$H NMR (400 MHz, DMSO-$d_6$) δ ppm 1.46-1.63 (m, 1 H) 1.65-1.89 (m, 4 H) 2.03-2.14 (m, 1 H) 2.73-2.90 (m, 1 H) 3.61 (d, 1 H) 7.10 (dd, 1 H) 7.29 (dd, 1 H) 7.58-7.70 (m, 1 H) 12.28-12.63 (m, 1 H).

Step 20.3: Methyl (3R/S)-3-(3-{[(2R/S)-2-(4-bromo-3-fluorophenyl)-2-cyclobutylacetyl]amino}-2-methylphenyl)butanoate 1.19 g HATU and 1.82 ml DIPEA were added to 476 mg methyl (3R/S)-3-(3-amino-2-methylphenyl)butanoate (prepared in step 18.1) and 600 mg (R/S) (4-bromo-3-fluorophenyl)(cyclobutyl)acetic acid in 20 ml DMF. The reaction mixture was stirred at 75° C. for 16 hours and evaporated to dryness. The resulting material was purified by chromatography using silica gel (gradient: hexane/EE) to yield 640 mg intermediate 20.

$^1$H NMR (400 MHz, DMSO-$d_6$) δ ppm 1.14 (m, 3 H) 1.55-1.64 (m, 1 H) 1.78-1.91 (m, 4 H) 2.03-2.08 (d, 3 H) 2.08-2.15 (m, 1 H) 2.56-2.62 (m, 2 H) 2.93 (s, 1 H) 3.39-3.47 (m, 2 H) 3.52 (d, 3 H) 3.78 (d, 1 H) 7.00 (s, 1 H) 7.07-7.12 (m, 2 H) 7.18 (dd, 1 H) 7.35 (dd, 1 H) 7.67 (t, 1 H) 9.58 (s, 1 H).

Intermediate 21 methyl 2-(3-{[(4-bromophenyl)(cyclopentyl)acetyl]amino}-2-methylphenyl)cyclopropanecarboxylate

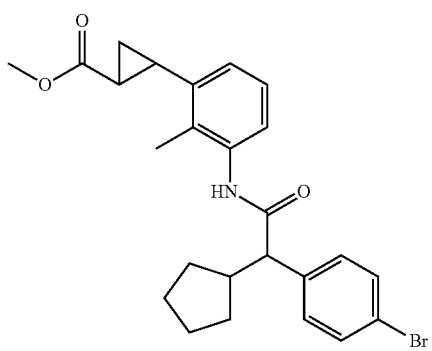 [SMILES: COC(=O)C1CC1c1cccc(NC(=O)C(c2ccc(Br)cc2)C2CCCC2)c1C]

310 mg (529 μmol) methyl 2-(3-amino-2-methylphenyl)cyclopropanecarboxylate which was prepared according to intermediate 22 were reacted with intermediate 1 in analogy to intermediate 3 to give after working up and purification 187 mg (75%) of the title compound.

$^1$H-NMR (DMSO-d6): δ=0.98 (1H), 1.24-1.93 (11H), 2.06 (3H), 2.40 (1H), 3.47 (1H), 3.66 (3H), 6.92 (1H), 7.01-7.22 (2H), 7.38 (2H), 7.53 (2H), 9.60 (1H) ppm.

Intermediate 22 methyl 2-(3-amino-2-methylphenyl)cyclopropanecarboxylate

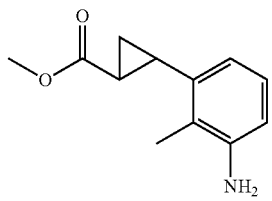

Step 22.1: methyl (2E)-3-{3-[(tert-butoxycarbonyl)amino]-2-methylphenyl}prop-2-enoate 2.0 g (6989 μmol) tert-butyl (3-bromo-2-methylphenyl)carbamate were transformed with methyl prop-2-enoate in analogy to intermediate 2, step 2.1 to give 3.01 g of the crude title compound which was used in the next step without further purification.

$^1$H-NMR (DMSO-d6): δ=1.44 (9H), 2.21 (3H), 3.73 (3H), 6.46 (1H), 7.18-7.22 (1H), 7.27-7.34 (1H), 7.50 (1H), 7.90 (1H), 7.94 (1H), 8.68 (1H) ppm.

Step 22.2: methyl 2-{3-[(tert-butoxycarbonyl)amino]-2-methylphenyl}cyclopropanecarboxylate To a stirred solution of 3.07 g (13.94 mmol) trimethylsulfoxonium iodide in 20 mL DMSO were added 1.98 g (13.76 mmol) sodium hydride at room temperature. After 1 h, 2.9 g (6.97 mmol) methyl (2E)-3-{3-[(tert-butoxycarbonyl)amino]-2-methylphenyl}prop-2-enoate were added and the mixture was heated at 100° C. for 2 h, to give, after working up and purification, 486 mg (23%) of the title compound.

$^1$H-NMR (DMSO-d6): δ=1.36-1.47 (11H), 1.58-1.77 (1H), 2.15 (3H), 2.40 (1H), 3.66 (3H), 6.86 (1H), 7.05 (1H), 7.13 (1H), 8.57 (1H) ppm.

Step 22.3: methyl 2-(3-amino-2-methylphenyl)cyclopropanecarboxylate 241 mg (552 μmol) methyl 2-{3-[(tert-butoxycarbonyl)amino]-2-methylphenyl}cyclopropanecarboxylate were stirred for 3 h at RT in 20 mL TFA/DCM 1:1 to yield, after evaporation, 294 mg of the crude title compound which was used in the next step without further purification.

Intermediate 23 methyl 2-(3-{[(4-bromophenyl)(cyclopentyl)acetyl]amino}-2-methylphenoxy)propanoate

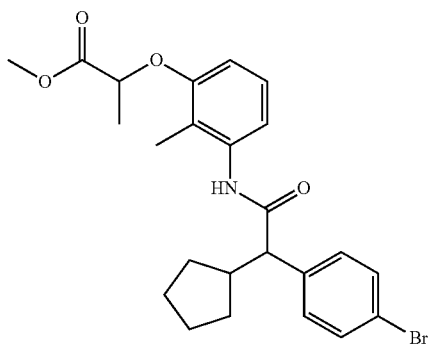 [SMILES: COC(=O)C(C)Oc1cccc(NC(=O)C(c2ccc(Br)cc2)C2CCCC2)c1C]

5 g (23.9 mmol) (R/S) methyl 2-(3-amino-2-methylphenoxy)propanoate which was prepared according to intermediate 24 were reacted with intermediate 1 in analogy to intermediate 3 to give after working up and purification 7.42 g (65%) of the title compound.

$^1$H-NMR (DMSO-d6): δ=0.88-1.04 (1H), 1.22-1.41 (2H), 1.41-1.69 (6H), 1.73-1.88 (1H), 1.94 (3H), 2.57 (1H), 3.48 (1H), 3.64 (3H), 4.92 (1H), 6.62 (1H), 6.83 (1H), 7.02 (1H), 7.37 (2H), 7.52 (2H), 9.53 (1H) ppm.

Intermediate 24

(R/S) methyl 2-(3-{[(4-bromophenyl)(cyclopentyl)acetyl]amino}-2-methylphenoxy)propanoate

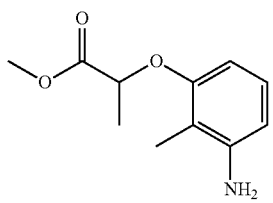

Step 24.1: (R/S) methyl 2-(2-methyl-3-nitrophenoxy)propanoate 14.95 g (97.6 mmol) 2-methyl-3-nitrophenol were reacted with methyl 2-chloropropanoate in analogy to intermediate 6, step 6.1 to give after working up and purification 19.66 g (84%) of the title compound.

$^1$H-NMR (DMSO-d6): δ=1.56 (3H), 2.29 (3H), 3.68 (3H), 5.15 (1H), 7.19 (1H), 7.35 (1H), 7.43-7.51 (1H) ppm.

Step 24.2: (R/S) methyl 2-{3-[(tert-butoxycarbonyl)amino]-2-methylphenyl}cyclopropanecarboxylate 18.6 g (77.9 mmol) methyl 2-(2-methyl-3-nitrophenoxy)propanoate which was prepared according to step 24.1 were transformed in analogy to intermediate 6, step 6.2 to give after working up and purification 16.1 g (98%) of the title compound.

$^1$H-NMR (DMSO-d6): δ=1.49 (3H), 1.94 (3H), 3.66 (3H), 4.78 (1H), 4.87 (2H), 6.01 (1H), 6.29 (1H), 6.74-6.96 (1H) ppm.

Intermediate 25 methyl 2-(3-{[(4-bromophenyl)(cyclopentyl)acetyl]amino}-2-methylphenoxy)propanoate

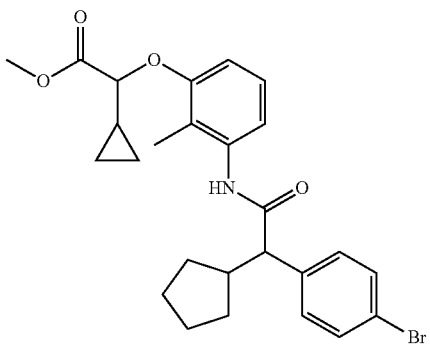 [SMILES: COC(=O)C(Oc1cccc(NC(=O)C(c2ccc(Br)cc2)C2CCCC2)c1C)C1CC1]

2.5 g (10 mmol) (R/S) ethyl (3-amino-2-methylphenoxy)(cyclopropyl)acetate which was prepared according to intermediate 26 were reacted with intermediate 1 in analogy to intermediate 3 to give after working up and purification 3.26 g (63%) of the title compound.

$^1$H-NMR (DMSO-d6): δ=0.53 (2H), 0.61 (2H), 0.97 (1H), 1.15 (3H), 1.21-1.42 (4H), 1.44-1.71 (4H), 1.84 (1H), 1.97 (3H), 2.58 (1H), 3.48 (1H), 4.08-4.19 (2H), 4.31 (1H), 6.56 (1H), 6.84 (1H), 7.01 (1H), 7.38 (2H), 7.53 (2H), 9.53 (1H) ppm.

Intermediate 26

(R/S) methyl 2-(3-{[(4-bromophenyl)(cyclopentyl)acetyl]amino}-2-methylphenoxy)propanoate

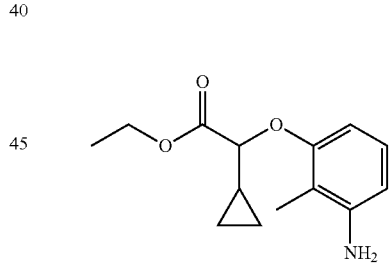

Step 26.1: (R/S) ethyl cyclopropyl(2-methyl-3-nitrophenoxy)acetate 3.45 g (22.5 mmol) 2-methyl-3-nitrophenol were reacted with ethyl bromo(cyclopropyl)acetate in analogy to intermediate 6, step 6.1 to give after working up and purification 6.11 g (97%) of the title compound.

$^1$H-NMR (DMSO-d6): δ=0.52-0.59 (2H), 0.60-0.67 (2H), 1.15 (3H), 1.36 (1H), 2.30 (3H), 4.09-4.19 (2H), 4.54 (1H), 7.11 (1H), 7.34 (1H), 7.46 (1H) ppm.

Step 26.2: (R/S) methyl 2-{3-[(tert-butoxycarbonyl)amino]-2-methylphenyl}cyclopropanecarboxylate 6.1 g (21.9 mmol) ethyl cyclopropyl(2-methyl-3-nitrophenoxy)acetate which was prepared according to step 26.1 were transformed in analogy to intermediate 6, step 6.2 to give after working up and purification 5.4 g (99%) of the title compound.

¹H-NMR (DMSO-d6):
0.46-0.62 (4H), 1.12-1.19 (3H), 1.28 (1H), 1.94 (3H), 4.06-4.20 (3H), 5.95 (1H), 6.27 (1H), 6.74 (1H) ppm.

Intermediate 27

(R/S) tert-butyl 3-(3-{[(4-bromophenyl)(cyclopentyl)acetyl]amino}-5-fluoro-2-methylphenyl)propanoate

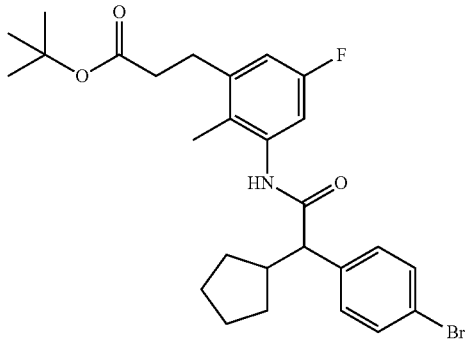 [SMILES: Cc1c(CCC(=O)OC(C)(C)C)cc(F)cc1NC(=O)C(c1ccc(Br)cc1)C1CCCC1]

3 g (11.84 mmol) tert-butyl 3-(3-amino-5-fluoro-2-methylphenyl)propanoate which was prepared according to intermediate 28 were reacted in analogy to intermediate 3 with (4-bromophenyl)(cyclopentyl)acetic acid which was prepared according to intermediate 1 to give after working-up and purification 4.04 g (66%) of the crude title compound.

¹H-NMR (DMSO-d6): δ=0.93-1.16 (1H), 1.18-1.42 (12H), 1.44-1.71 (4H), 1.83 (1H), 1.92-2.02 (3H), 2.40-2.64 (3H), 2.80 (2H), 3.52 (1H), 6.85 (1H), 6.99 (1H), 7.35-7.45 (2H), 7.48-7.59 (2H), 9.59 (1H) ppm.

Intermediate 28 tert-butyl 3-(3-amino-5-fluoro-2-methylphenyl)propanoate

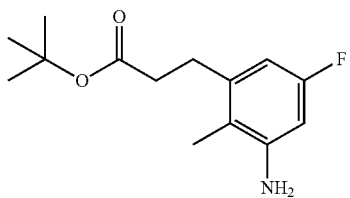 [SMILES: Cc1c(N)cc(F)cc1CCC(=O)OC(C)(C)C]

Step 28.1: tert-butyl (2E)-3-(5-fluoro-2-methyl-3-nitrophenyl)prop-2-enoate 9 g (38.5 mmol) 1-bromo-5-fluoro-2-methyl-3-nitrobenzene were reacted with tert-butyl prop-2-enoate in analogy to intermediate 2, step 2.1 to give after working up 15.4 g (142%) of the crude title compound which was used without further purification in the next step.

¹H-NMR (DMSO-d6): δ=1.49 (9H), 2.35 (3H), 6.59 (1H), 7.75 (1H), 7.87 (1H), 7.95 (1H) ppm.

Step 28.2: tert-butyl 3-(3-amino-5-fluoro-2-methylphenyl)propanoate 12.5 g (44.5 mmol) tert-butyl (2E)-3-(5-fluoro-2-methyl-3-nitrophenyl)prop-2-enoate which was prepared according to step 28.1 were transformed in analogy to intermediate 2, step 2.2 to give after working up 8.3 g (73%) of the title compound.

¹H-NMR (DMSO-d6): δ=1.39 (9H), 1.92 (3H), 2.38 (2H), 2.71 (2H), 5.1 (2H), 6.15 (1H), 6.29 (1H) ppm.

Intermediate 29 methyl N-(3-{[(4-bromophenyl)(cyclopentyl)acetyl]amino}-2-methylphenyl)glycinate

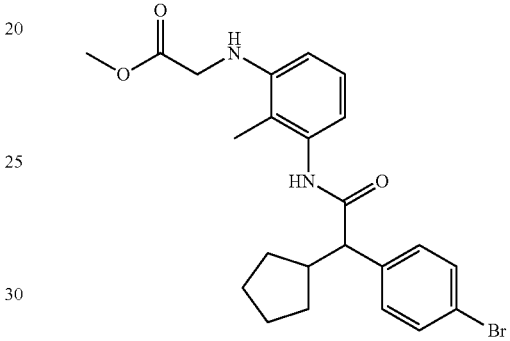

5 g (25.7 mmol) methyl N-(3-amino-2-methylphenyl)glycinate which was prepared according to intermediate 30 were reacted with intermediate 1 in analogy to intermediate 3 to give after working up and purification 9.52 g (80%) of the title compound.

¹H-NMR (DMSO-d6): δ=0.90-1.05 (1H), 1.23 (1H), 1.25-1.40 (2H), 1.46 (1H), 1.50-1.61 (2H), 1.66 (1H), 1.77-1.87 (4H), 2.51-2.58 (1H), 3.42 (1H), 3.62 (3H), 3.92 (2H), 5.32 (1H), 6.20 (1H), 6.42 (1H), 6.89 (1H), 7.36 (2H), 7.51 (2H), 9.46 (1H) ppm.

Intermediate 30 methyl N-(3-amino-2-methylphenyl)glycinate

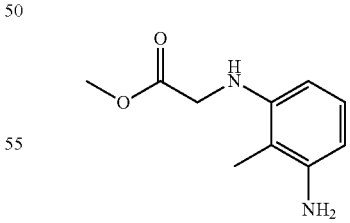

Step 30.1: methyl N-(2-methyl-3-nitrophenyl)glycinate 15 g (98.5 mmol) 2-methyl-3-nitroaniline were reacted with methyl bromoacetate in analogy to intermediate 6, step 6.1 to give after working up and purification 20.76 g (94%) of the title compound.

¹H-NMR (DMSO-d6): δ=2.13 (3H), 4.05 (2H), 6.01 (1H), 6.67 (1H), 6.99-7.06 (1H), 7.16-7.35 (1H) ppm.

Step 30.2: methyl N-(3-amino-2-methylphenyl)glycinate 19.8 g (88.1 mmol) methyl N-(2-methyl-3-nitrophenyl)glycinate which was prepared according to step 30.1 were transformed in analogy to intermediate 6, step 6.2 to give after working up and purification 16.94 g (99%) of the title compound.

¹H-NMR (DMSO-d6):
0.46-0.62 (4H), 1.12-1.19 (3H), 1.28 (1H), 1.94 (3H), 4.06-4.20 (3H), 5.95 (1H), 6.27 (1H), 6.74 (1H) ppm.

Intermediate 31

(R/S) tert-butyl 3-(3-{[(4-bromo-2-chloro-5-methylphenyl)(cyclopentyl)acetyl]amino}-2-methylphenyl)propanoate

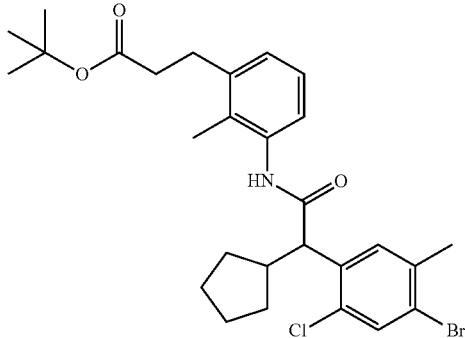 [SMILES: Cc1cc(C(C(=O)Nc2cccc(CCC(=O)OC(C)(C)C)c2C)C2CCCC2)c(Cl)cc1Br]

451 mg (1918 μmol) tert-butyl 3-(3-amino-2-methylphenyl)propanoate which was prepared according to intermediate 2 were reacted in analogy to intermediate 3 with (R/S) (4-bromo-2-chloro-5-methylphenyl)(cyclopentyl)acetic acid which was prepared according to intermediate 32 to give after working-up 1490 mg (150%) of the crude title compound which was used without further purification in the next step.

Intermediate 32

(R/S) (4-bromo-2-chloro-5-methylphenyl)(cyclopentyl)acetic acid

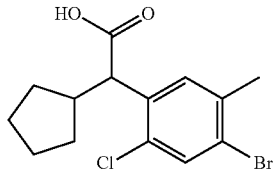 [SMILES: Cc1cc(C(C(=O)O)C2CCCC2)c(Cl)cc1Br]

Step 32.1: (R/S) methyl (4-bromo-2-chloro-5-methylphenyl)(cyclopentyl)acetate 2.25 g (8.1 mmol) methyl (4-bromo-2-chloro-5-methylphenyl)acetate were reacted with bromocyclopentane in analogy to intermediate 1, step 1.1 to give after working up and purification 2.42 g (86%) of the title compound.

¹H-NMR (DMSO-d6): δ=0.83-0.99 (1H), 1.21-1.38 (2H), 1.39-1.48 (1H), 1.48-1.68 (3H), 1.72-1.91 (1H), 2.16-2.36 (3H), 2.53 (1H), 3.57 (3H), 3.84 (1H), 7.46 (1H), 7.70 (1H) ppm.

Step 32.2: (R/S) (4-bromo-2-chloro-5-methylphenyl)(cyclopentyl)acetic acid 2.32 g (6.7 mmol) (R/S) methyl (4-bromo-2-chloro-5-methylphenyl)(cyclopentyl)acetate which was prepared according to step 32.1 were saponified in analogy to intermediate 1, step 1.2 to give after working up and purification 2.39 g (107%) of the title compound.

¹H-NMR (DMSO-d6): δ=0.85-0.99 (1H), 1.21-1.67 (6H), 1.72-1.91 (1H), 2.32 (3H), 2.53 (1H), 3.73 (1H), 7.46 (1H), 7.70 (1H), 12.33 (1H) ppm.

Intermediate 33

(R/S) {2-chloro-4-[5-(trifluoromethyl)pyridin-3-yl]phenyl}(cyclopentyl)acetic acid

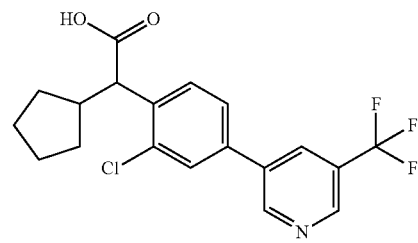 [SMILES: O=C(O)C(c1ccc(-c2cncc(C(F)(F)F)c2)cc1Cl)C1CCCC1]

60 mg (1800 μmol) (R/S) methyl (4-bromo-2-chlorophenyl)(cyclopentyl)acetate which was prepared according to intermediate 34 were reacted with [5-(trifluoromethyl)pyridin-3-yl]boronic acid in analogy to example 1 to give after methyl ester saponification with 1500 μL NaOH (2M in water) and subsequent working up 87 mg (48%) of the crude title compound which was used in the next step without further purification.

Intermediate 34

(R/S) methyl (4-bromo-2-chlorophenyl)(cyclopentyl)acetate

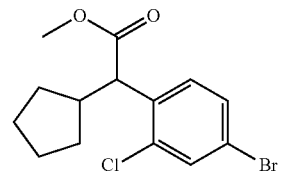 [SMILES: COC(=O)C(c1ccc(Br)cc1Cl)C1CCCC1]

150 mg (0.57 mmol) methyl (4-bromo-2-chlorophenyl)acetate were reacted with bromocyclopentane in analogy to intermediate 1, step 1.1 to give after working up 115 mg (93%) of the title compound.

¹H-NMR (DMSO-d6): δ=0.88-0.99 (1H), 1.22-1.38 (2H), 1.43 (1H), 1.47-1.68 (3H), 1.84 (1H), 2.51 (1H), 3.58 (3H), 3.88 (1H), 7.45 (1H), 7.56 (1H), 7.73 (1H) ppm.

Intermediate 35

(R/S) tert-butyl 3-(3-{[(4-bromo-3-chlorophenyl)(cyclopentyl)acetyl]amino}-2-methylphenyl)propanoate

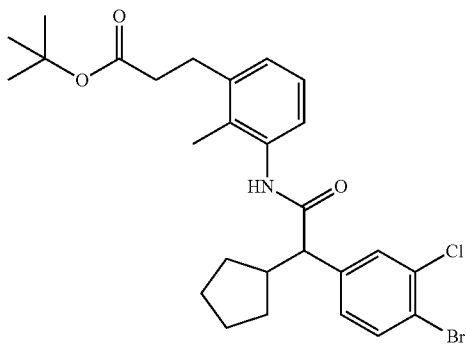

471 mg (2001 µmol) tert-butyl 3-(3-amino-2-methylphenyl)propanoate which was prepared according to intermediate 2 were reacted in analogy to intermediate 3 with (R/S) (4-bromo-3-chlorophenyl)(cyclopentyl)acetic acid which was prepared according to intermediate 36 to give after working-up 1650 mg (151%) of the crude title compound which was used without further purification in the next step.

Intermediate 36

(R/S) (4-bromo-3-chlorophenyl)(cyclopentyl)acetic acid

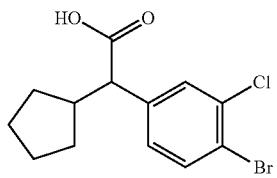 [SMILES: O=C(O)C(c1ccc(Br)c(Cl)c1)C1CCCC1]

Step 36.1: (R/S) methyl (4-bromo-3-chlorophenyl)(cyclopentyl)acetate 3 g (11.4 mmol) methyl (4-bromo-3-chlorophenyl)acetate were reacted with bromocyclopentane in analogy to intermediate 1, step 1.1 to give after working up 3.65 g (86%) of the title compound.

Step 36.2: (R/S) (4-bromo-3-chlorophenyl)(cyclopentyl)acetic acid 3.65 g (11 mmol) (R/S) methyl (4-bromo-3-chlorophenyl)(cyclopentyl)acetate which was prepared according to step 36.1 were saponified in analogy to intermediate 1, step 1.2 to give after working up 3.7 g (105%) of the title compound.

$^1$H-NMR (DMSO-d6): δ=0.83-1.06 (1H), 1.14-1.35 (2H), 1.37-1.64 (4H), 1.73-1.85 (1H), 2.32-2.47 (1H), 3.58 (1H), 7.26 (1H), 7.60 (1H), 7.70 (1H), 12.26 (1H) ppm.

Intermediate 37

(R/S) tert-butyl 3-(3-{[(4-bromo-2,5-difluorophenyl)(cyclopentyl)acetyl]amino}-2-methylphenyl)propanoate

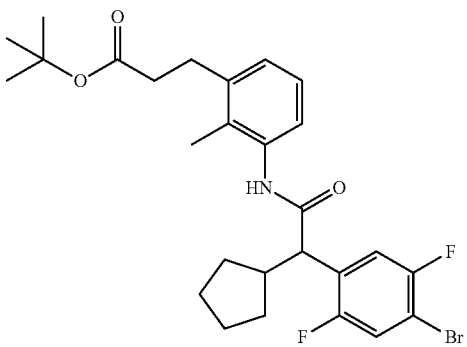 [SMILES: Cc1c(CCC(=O)OC(C)(C)C)cccc1NC(=O)C(c1cc(F)c(Br)cc1F)C1CCCC1]

469 mg (1994 µmol) tert-butyl 3-(3-amino-2-methylphenyl)propanoate which was prepared according to intermediate 2 were reacted in analogy to intermediate 3 with (R/S) (4-bromo-2,5-difluorophenyl)(cyclopentyl)acetic acid which was prepared according to intermediate 38 to give after working-up 1570 mg (146%) of the crude title compound which was used without further purification in the next step.

Intermediate 38

(R/S) (4-bromo-2,5-difluorophenyl)(cyclopentyl)acetic acid

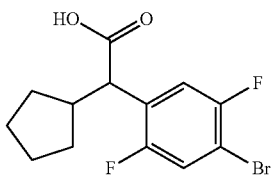 [SMILES: O=C(O)C(c1cc(F)c(Br)cc1F)C1CCCC1]

Step 38.1: (R/S) methyl (4-bromo-2,5-difluorophenyl)(cyclopentyl)acetate 4.85 g (18.3 mmol) methyl (4-bromo-2,5-difluorophenyl)acetate were reacted with bromocyclopentane in analogy to intermediate 1, step 1.1 to give after working up 6.09 g (97%) of the title compound.

Step 38.2: (R/S) (4-bromo-2,5-difluorophenyl)(cyclopentyl)acetic acid 6.09 g (18.3 mmol) methyl (4-bromo-2,5-difluorophenyl)(cyclopentyl)acetate which was prepared according to step 38.1 were saponified in analogy to intermediate 1, step 1.2 to give after working up 5.7 g (98%) of the title compound.

$^1$H-NMR (DMSO-d6): δ=0.93 (1H), 1.20-1.33 (1H), 1.35-1.64 (5H), 1.78-1.91 (1H), 2.38-2.49 (1H), 3.67 (1H), 7.46 (1H), 7.70 (1H), 12.53 (1H) ppm.

Intermediate 39

(R/S) tert-butyl 3-(3-{[(4-bromo-2-fluoro-5-methyl-phenyl)(cyclopentyl)acetyl]amino}-2-methylphenyl)propanoate

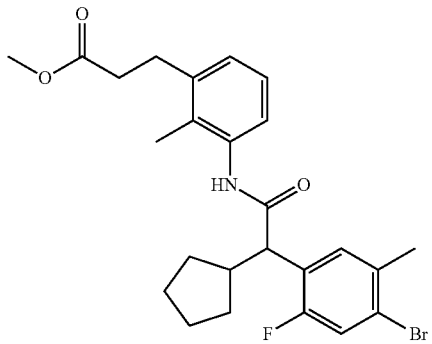 [SMILES: COC(=O)CCc1cccc(NC(=O)C(c2cc(C)c(Br)cc2F)C2CCCC2)c1C]

475 mg (2018 μmol) tert-butyl 3-(3-amino-2-methylphenyl)propanoate which was prepared according to intermediate 2 were reacted in analogy to intermediate 3 with (R/S) (4-bromo-2-fluoro-5-methylphenyl)(cyclopentyl)acetic acid which was prepared according to intermediate 40 to give after working-up 1630 mg (151%) of the crude title compound which was used without further purification in the next step.

Intermediate 40

(R/S) (4-bromo-2-fluoro-5-methylphenyl)(cyclopentyl)acetic acid

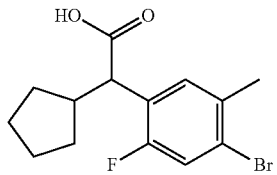 [SMILES: Cc1cc(C(C(=O)O)C2CCCC2)c(F)cc1Br]

Step 40.1: (R/S) methyl (4-bromo-2-fluoro-5-methylphenyl)(cyclopentyl)acetate 4.0 g (15.3 mmol) methyl (4-bromo-2-fluoro-5-methylphenyl)acetate were reacted with bromocyclopentane in analogy to intermediate 1, step 1.1 to give after working up and purification 2.17 g (43%) of the title compound.

$^1$H-NMR (DMSO-d6): δ=0.94 (1H), 1.10-1.31 (1H), 1.34-1.63 (5H), 1.71-1.92 (1H), 2.30 (3H), 2.49 (1H), 3.58 (3H), 3.61 (1H), 7.40 (1H), 7.50 (1H) ppm.

Step 40.2: (R/S) (4-bromo-2-fluoro-5-methylphenyl)(cyclopentyl)acetic acid 2.16 g (6.56 mmol) methyl (4-bromo-2-fluoro-5-methylphenyl)(cyclopentyl)acetate which was prepared according to step 40.1 were saponified in analogy to intermediate 1, step 1.2 to give after working up 2.0 g (97%) of the title compound.

$^1$H-NMR (DMSO-d6): δ=0.92 (1H), 1.10-1.31 (1H), 1.34-1.63 (5H), 1.71-1.92 (1H), 2.30 (3H), 2.44 (1H), 4.04 (1H), 7.40 (1H), 7.48 (1H), 12.14 (1H) ppm.

Intermediate 41 tert-butyl 3-(3-amino-6-fluoro-2-methylphenyl)propanoate

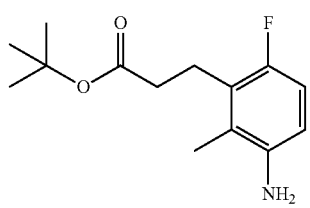 [SMILES: Cc1c(N)ccc(F)c1CCC(=O)OC(C)(C)C]

Step 41.1 tert-butyl (2E)-3-(3-amino-6-fluoro-2-methylphenyl)prop-2-enoate 4.47 g (21.9 mmol) 3-bromo-4-fluoro-2-methylaniline were reacted with tert-butyl prop-2-enoate in analogy to intermediate 2, step 2.1 to give after working up 3.2 g (58%) of the crude title compound which was used without further purification in the next step.

$^1$H-NMR (DMSO-d6): δ=1.49 (9H), 2.09 (3H), 4.87 (2H), 6.27 (1H), 6.68 (1H), 6.85 (1H), 7.61 (1H) ppm.

Step 41.2: tert-butyl 3-(3-amino-6-fluoro-2-methylphenyl)propanoate 3.2 g (12.7 mmol) tert-butyl (2E)-3-(3-amino-6-fluoro-2-methylphenyl)prop-2-enoate which was prepared according to step 41.1 were transformed in analogy to intermediate 2, step 2.2 to give after working up 3.1 g (97%) of the title compound.

$^1$H-NMR (DMSO-d6): δ=1.36 (9H), 1.98 (3H), 2.26-2.35 (2H), 2.66-2.81 (2H), 4.69 (2H), 6.48 (1H), 6.67 (1H) ppm.

Intermediate 42

(2R)-[4-(5-chloro-6-methylpyridin-3-yl)phenyl](cyclopentyl)ethanoic acid

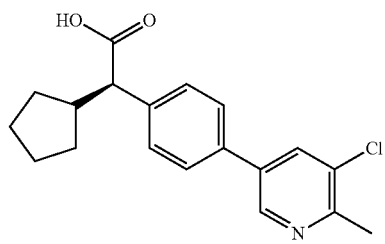 [SMILES: Cc1ncc(-c2ccc([C@H](C(=O)O)C3CCCC3)cc2)cc1Cl]

4.0 g intermediate 1 and 4.30 g 3-chloro-2-methyl-5-(4,4,5,5-tetramethyl-1,3,2-dioxaborolan-2-yl)pyridine were reacted in analogy to intermediate 5 to yield after workup and purification by flash chromatography 2.54 g of racemic [4-(5-chloro-6-methylpyridin-3-yl)phenyl](cyclopentyl)acetic acid.

Separation of 2.54 g (R/S) [4-(5-chloro-6-methylpyridin-3-yl)phenyl](cyclopentyl)acetic acid by preparative chiral HPLC (method 4; solvent: ethanol/methanol/HCOOH 50:50:0.1 (v/v/v); flow rate: 30 ml/min; solution: 2.54 g/25 ml DCM/methanol 2:1, injection volume: 17×1.5 ml) yielded 0.71 g of the title compound (Rt: 9.3-12.7 min) together with 0.77 g S-enantiomer (Rt: 12.7-19.6 min).

Analytical HPLC, method 7 ethanol/methanol/HCOOH 50:50:0.1 (v/v/v); flow rate: 1 ml/min; solution: 1 mg/ml EtOH/MeOH 1:1, injection volume: 5 µl; Rt: 3.20 min [(S)-enantiomer: Rt: 4.98 min].

$^1$H-NMR (DMSO-d6): δ=0.82-1.06 (1H), 1.13-1.38 (2H), 1.44 (1H), 1.49-1.68 (3H), 1.82-1.91 (1H), 2.47 (1H), 2.58 (3H), 3.10-3.33 (1H), 7.45 (2H), 7.71 (2H), 8.16 (1H), 8.74 (1H) ppm.

Intermediate 43-1 tert-butyl 3-(3-{[(2R)-2-(4-bromophenyl)-2-cyclopentylacetyl]amino}-2-methylphenyl)propanoate

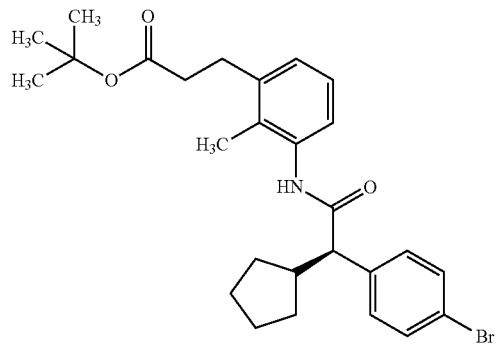 [SMILES: Cc1c(CCC(=O)OC(C)(C)C)cccc1NC(=O)[C@@H](c1ccc(Br)cc1)C1CCCC1]

15.0 g (R/S) tert-butyl 3-(3-{[(4-bromophenyl)(cyclopentyl)acetyl]amino}-2-methylphenyl)propanoate which was prepared according to intermediate 3 were separated by preparative chiral HPLC (method 2; solvent: CO$_2$/2-propanol; gradient isocratic 20% 2-propanol; flow rate: 100 ml/min; solution: 15.0 g/40 ml DCM/MeOH 1:1, injection volume: 140×0.3 ml) to yield 4.56 g of the title compound (Rt: 14.0-16.5 min) together with 4.14 g S-enantiomer (Rt: 10.0-11.0 min).

Analytical HPLC, method 1: CO2/2-propanol 76:24 (v/v); flow rate: 4 ml/min; solution: 1 mg/ml EtOH/MeOH 1:1, injection volume: 5 µl; Rt: 10.07 min [(+)-enantiomer: Rt: 6.95 min].

Optical rotation: −42.8° (2.8 mg/ml in DMSO, temperature: 20° C., wave length: 589 nM).

Intermediate 43-2 tert-butyl 3-(3-{[(2R)-2-(4-bromophenyl)-2-cyclopentylacetyl]amino}-2-methylphenyl)propanoate

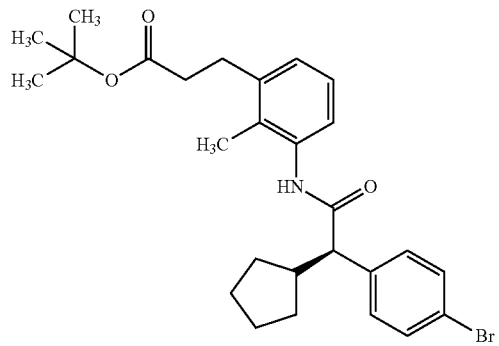 [SMILES: Cc1c(CCC(=O)OC(C)(C)C)cccc1NC(=O)[C@@H](c1ccc(Br)cc1)C1CCCC1]

To a solution of 34.20 g (145.32 mmol) tert-butyl 3-(3-amino-2-methylphenyl)propanoate which was prepared according to intermediate 2 in DCM (430 mL) were added 20.26 mL triethylamine and 43.83 g (2R)-(4-bromophenyl)(cyclopentyl)acetyl chloride which was prepared according to intermediate 47. The mixture was stirred for 1 h at RT to give after working up 72.46 g (100%) of the title compound.

Intermediate 44-1 tert-butyl 3-[3-({(2R)-2-[4-(5-chloropyridin-3-yl)phenyl]-2-cyclopentylacetyl}amino)-2-methylphenyl]propanoate

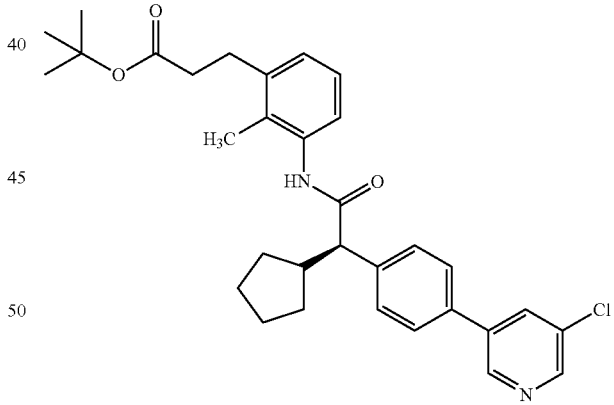

36.13 g (72.19 mmol) tert-butyl 3-(3-{[(2R)-2-(4-bromophenyl)-2-cyclopentylacetyl]amino}-2-methylphenyl)propanoate which was prepared according to intermediate 43 were reacted in analogy to example 16 with (5-chloropyridin-3-yl)boronic acid to give after working up and purification by flash chromatography (gradient EE/hexane) 33.64 g (87%) of the title compound.

$^1$H NMR (400 MHz, DMSO-d$_6$) δ ppm 0.97-1.20 (1H), 1.34-1.51 (12H), 1.54-1.62 (2H), 1.64-1.74 (1H), 1.87 (1H), 2.01 (3H), 2.41 (2H), 2.57-2.68 (1H), 2.79 (2H), 3.54 (1H), 6.95-7.05 (3H), 7.56 (2H), 7.76 (2H), 8.24 (1H), 8.60 (1H), 8.87 (1H), 9.52 (1H).

Analytical HPLC, method 9: solvent: acetonitrile/diethylamine 100:0.1 (v/v); flow rate: 1 ml/min; solution: 1 mg/ml EtOH/MeOH 2:1, injection volume: 5 µl; Rt: 3.66 min [(+)-enantiomer: Rt: 4.48 min].

Intermediate 44-2 tert-butyl 3-[3-({(2R)-2-[4-(5-chloropyridin-3-yl)phenyl]-2-cyclopentylacetyl}amino)-2-methylphenyl]propanoate

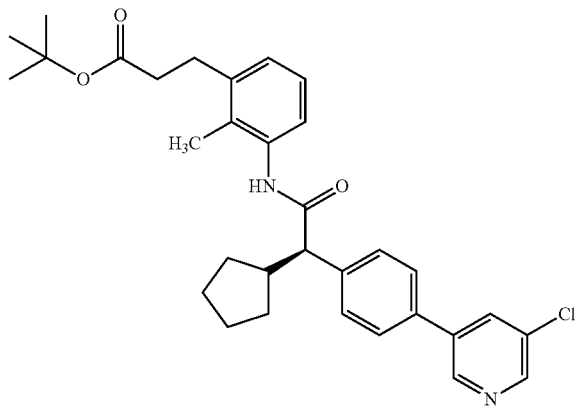 [SMILES: Cc1c(CCC(=O)OC(C)(C)C)cccc1NC(=O)[C@@H](c1ccc(-c2cncc(Cl)c2)cc1)C1CCCC1]

31.58 mg (0.1 mmol) (2R)-[4-(5-chloropyridin-3-yl)phenyl](cyclopentyl)ethanoic acid which was prepared according to intermediate 45 were reacted in analogy to intermediate 3 with tert-butyl 3-(3-amino-2-methylphenyl)propanoate to give after working up and purification by HPLC 13 mg (24%) of the title compound.

Intermediate 45

(2R)-[4-(5-chloropyridin-3-yl)phenyl](cyclopentyl)acetic acid

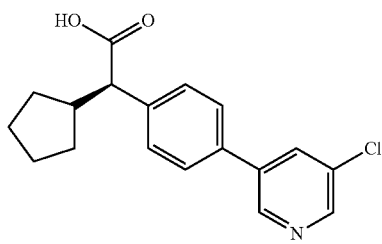 [SMILES: O=C(O)[C@@H](c1ccc(-c2cncc(Cl)c2)cc1)C1CCCC1]

10 g (R/S) [4-(5-chloropyridin-3-yl)phenyl](cyclopentyl)acetic acid which was prepared according to intermediate 5 were separated by preparative chiral HPLC (method 8; solvent: CO2/methanol; gradient isocratic 35% methanol; flow rate: 80 ml/min; solution: 10.0 g/90 ml DMSO/THF 2:1, injection volume: 200×0.45 ml) to yield 3.40 g of the title compound (Rt: 4.0-5.5 min) together with 3.70 g S-enantiomer (Rt: 6.0-9.5 min).

Analytical HPLC, method 10: CO2/methanol 65:35 (v/v); flow rate: 4 ml/min; solution: 1 mg/ml EtOH/MeOH 1:1; injection volume: 5 µl; Rt: 2.95 min [(S)-enantiomer: Rt: 5.75 min].

Optical rotation: −69.7° (10.6 mg/ml in DMSO, temperature: 20° C., wave length: 589 nM).

Intermediate 46

(2R)-(4-bromophenyl)(cyclopentyl)ethanoic acid

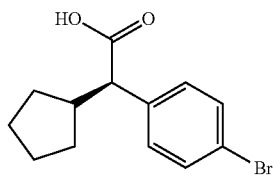 [SMILES: O=C(O)[C@@H](c1ccc(Br)cc1)C1CCCC1]

26.05 g (R/S) (4-bromophenyl)(cyclopentyl)acetic acid which was prepared according to intermediate 1 were dissolved in 240 n mL ethanol and 58 mL water under stirring: 12.29 mL (11.71 g) (1R)-1-phenylethanamine were added dropwise within 5 minutes, thereby forming a white precipitate. After further stirring at 60° C. for 2 h and stirring at RT overnight, the white solid was filtered off and washed with little water. The residue was acidified with 140 mL 1N HCl and extracted with ethyl acetate. The organic phase was washed three times with water, dried and evaporated to yield 12.47 g of the title compound Optical rotation:−58.6° (13 mg/ml in DMSO, temperature: 20° C., wave length: 589 nM).

Analytical HPLC, method 11: hexane/ethanol/TFA 98:2:0.1 (v/v/v); flow rate: 1 ml/min; solution: 1 mg/ml EtOH/MeOH 1:1, injection volume: 5 µl; Rt: 2.34 min [(S)-enantiomer: Rt: 2.70 min].

Intermediate 47

(2R)-(4-bromophenyl)(cyclopentyl)acetoyl chloride

41.50 g (146.55 mmol) (2R)-(4-bromophenyl)(cyclopentyl)ethanoic acid which was prepared according to intermediate 46 were stirred in thionylchloride (125 mL) for 3 h at 100° C. to give after evaporation and subsequent trituration and evaporation with toluene (two times) 43.8 g (99%) of the title compound.

$^1$H NMR (300 MHz, DMSO-d$_6$) δ ppm 0.96 (d, 1 H) 1.12-1.70 (m, 6 H) 1.82 (d, 1 H) 2.39 (d, 1 H) 3.25 (d, 1 H) 7.21-7.37 (m, 2 H) 7.43-7.59 (m, 2 H)

Intermediate 48

(2R)-[4-(5-trifluormethyl)pyridin-3-yl)phenyl](cyclopentyl)ethanoic acid

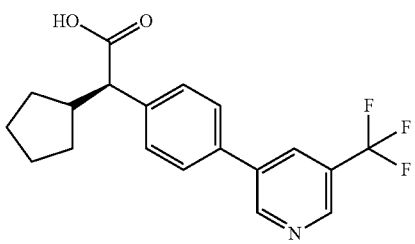 [SMILES: O=C(O)[C@@H](c1ccc(-c2cncc(C(F)(F)F)c2)cc1)C1CCCC1]

8.0 g intermediate 1 and 9.26 g 3-(4,4,5,5-tetramethyl-1,3,2-dioxaborolan-2-yl)-5-(trifluoromethyl)pyridine were reacted in analogy to intermediate 5 to yield after workup and purification by flash chromatography 6.52 g of racemic cyclopentyl{4-[5-(trifluoromethyl)pyridin-3-yl]phenyl}acetic acid.

Separation of 6.52 g (R/S) cyclopentyl{4-[5-(trifluoromethyl)pyridin-3-yl]phenyl}acetic acid by preparative chiral HPLC (method 4; solvent: ethanol/methanol/HCOOH 50:50:0.1 (v/v/v); flow rate: 40 ml/min; solution: 6.52 g/50 ml DCM/methanol 2:1, injection volume: 100×0.5 ml) yielded 1.55 g of the title compound (Rt: 5.5-6.4 min) together with 1.63 g S-enantiomer (Rt: 6.5-6.2 min).

Analytical HPLC, method 7 ethanol/methanol/HCOOH 50:50:0.1 (v/v/v); flow rate: 1 ml/min; solution: 1 mg/ml EtOH/MeOH 1:1, injection volume: 5 μl; Rt: 2.39 min [(S)-enantiomer: Rt: 3.32 min].

$^1$H-NMR (DMSO-d6): δ=0.94-1.06 (1H), 1.21-1.37 (2H), 1.43 (1H), 1.49-1.67 (3H), 1.81-1.90 (1H), 2.51 (1H), 7.48 (2H), 7.79 (2H), 8.43 (1H), 8.92-8.96 (1H), 9.19 (1H) ppm.

Optical rotation: −61.3° (10.7 mg/ml in DMSO, temperature: 20° C., wave length: 589 nM).

Intermediate 49 methyl N-(3-amino-2-methylphenyl)-N-methylglycinate

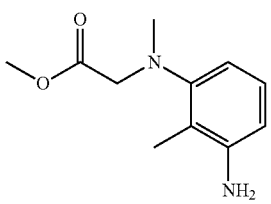

Step 49.1: methyl N-methyl-N-(2-methyl-3-nitrophenyl)glycinate 10 g (60.2 mmol) N,2-dimethyl-3-nitroaniline were reacted with methyl bromoacetate in analogy to intermediate 6, step 6.1 to give after working up and purification 13.71 g (95%) of the title compound.

$^1$H-NMR (DMSO-d6): δ=2.30 (3H), 2.81 (3H), 3.62 (3H), 3.87 (2H), 7.37 (1H), 7.41 (1H), 7.49 (1H) ppm.

Step 49.2: methyl N-(3-amino-2-methylphenyl)-N-methylglycinate 13.7 g (58 mmol) methyl N-methyl-N-(2-methyl-3-nitrophenyl)glycinate which was prepared according to step 49.1 were transformed in analogy to intermediate 6, step 6.2 to give after working up 12.4 g (105%) of the title compound.

$^1$H-NMR (DMSO-d6): δ=1.96 (3H), 2.65 (3H), 3.60 (3H), 3.63 (2H), 6.26-6.39 (2H), 6.78 (1H) ppm.

Intermediate 50

(−) cyclopentyl{3-fluoro-4-[5-(trifluoromethyl)pyridin-3-yl]phenyl}acetic acid, Single Enantiomer

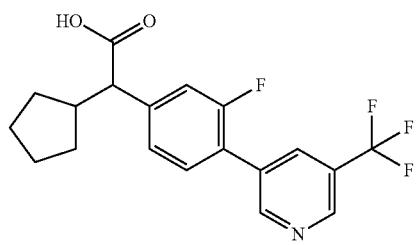 [SMILES: O=C(O)C(c1ccc(-c2cncc(C(F)(F)F)c2)c(F)c1)C1CCCC1]

(R/S) (4-Bromo-3-fluorophenyl)(cyclopentyl)acetic acid which was prepared according to intermediate 9, step 9.2 and [5-(trifluoromethyl)pyridin-3-yl]boronic acid were reacted in analogy to intermediate 5 to yield after workup and purification by flash chromatography racemic cyclopentyl{3-fluoro-4-[5-(trifluoromethyl)pyridin-3-yl]phenyl}acetic acid.

Separation of 4.86 g (R/S) cyclopentyl{3-fluoro-4-[5-(trifluoromethyl)pyridin-3-yl]phenyl}acetic acid by preparative chiral HPLC (method 4; solvent: ethanol/methanol/HCOOH 50:50:0.1 (v/v/v); flow rate: 30 ml/min; solution: 4.86 g/37 ml DCM/methanol 2:1, injection volume: 93×0.4 ml) yielded 2.03 g of the title compound (Rt: 5.8-7.0 min) together with 2.06 g (+)-enantiomer (Rt: 7.0-8.6 min).

Analytical HPLC, method 7 ethanol/methanol/HCOOH 50:50:0.1 (v/v/v); flow rate: 1 ml/min; solution: 1 mg/ml EtOH/MeOH 1:1, injection volume: 5 μl; Rt: 1.70 min [(+)-enantiomer: Rt: 2.30 min].

$^1$H-NMR (DMSO-d6): δ=0.97-1.08 (1H), 1.23-1.49 (3H), 1.49-1.67 (3H), 1.84 (1H), 2.46 (1H), 3.40 (1H), 7.32-7.39 (2H), 7.66 (1H), 8.37 (1H), 8.98-9.01 (1H), 9.06 (1H), 12.48 (1H) ppm.

Optical rotation: −52.5° (10 mg/ml in DMSO, temperature: 20° C., wave length: 589 nM).

Intermediate 51

(R/S) tert-butyl 3-(3-amino-2-methylphenyl)-3-hydroxypropanoate

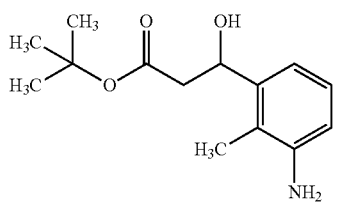 [SMILES: Cc1c(N)cccc1C(O)CC(=O)OC(C)(C)C]

Step 51.1: magnesium bis(3-tert-butoxy-3-oxopropanoate)

To a stirred solution of 3-tert-butoxy-3-oxopropanoic acid (150.0 g, 1.0 eq.) in 1.5 L THF was added magnesiumethoxide (128.7 g, 1.2 eq.) at RT. The resulting mixture was stirred at room temperature for 3 h. The reaction progress was monitored by TLC. After completion of the reaction the reaction, the white turbid solid was filtered and the crude compound was used as such for next step.

Step 51.2: tert-butyl 3-(2-methyl-3-nitrophenyl)-3-oxopropanoate

To a stirred solution of 2-methyl-3-nitro benzoic acid (100.0 g, 1.0 eq.) in THF was added CDI (134.2 g, 1.5 eq.) and the resulting contents were stirred at RT for 2 h, followed by addition of magnesium bis(3-tert-butoxy-3-oxopropanoate) (151.6 g, 1.5 eq). The resulting mixture was heated to reflux for 16 h. The reaction progress was monitored by TLC. After completion of the reaction (TLC), the reaction mixture was cooled to RT, acidified to pH ~2 using conc HCl, diluted with EtOAc (100 mL) and washed successively with 1N HCl solution, NaHCO3 solution and brine, dried over Na2SO4 filtered and concentrated under vacuum to yield the crude product. Purification of the residue via flash column chromatography on silica gel afforded 56.0 g (36%) of the title compound as off-white solid.

$^1$H-NMR (DMSO-d6): δ=1.31 (9H), 1.51 (1H), 2.33-2.44 (3H), 4.06 (2H), 7.46-7.62 (1H), 8.02 (2H) ppm.

Step 51.3: (R/S) tert-butyl 3-hydroxy-3-(2-methyl-3-nitrophenyl)propanoate

To a solution of intermediate 51.2 (40.0 g, 1.0 eq.) in ethanol (400 mL) under nitrogen atmosphere was added sodium borohydride (4.3 g, 0.8 eq) at −10° C. to room temperature. The resulting reaction mixture was stirred for 3 h at RT. The reaction progress was monitored by TLC. After completion of reaction (TLC), the reaction mixture was concentrated completely under vacuum, diluted with 1N HCl (100 mL) and extracted with ethyl acetate (2×100 mL), organics were washed with brine (100 mL), dried over Na2SO4, filtered and concentrated to get the crude product which was purified by silica gel (100-200 mesh) column chromatography to afford 26.0 g (65%) of the title compound as off-white solid.

$^1$H-NMR (DMSO-d6): δ=1.13-1.42 (9H), 2.32 (3H), 2.37-2.47 (1H), 2.52-2.71 (1H), 5.17-5.26 (1H), 5.64 (1H), 7.39-7.48 (1H), 7.67-7.80 (2H) ppm.

Step 51.4: (R/S) tert-butyl 3-(3-amino-2-methylphenyl)-3-hydroxypropanoate

To a solution of intermediate 51.3 (40.0 g, 1.0 eq.) in ethanol was added 10% Pd/C, and the mixture was reduced under hydrogen atmosphere at 40 PSI for 2 h. The reaction progress was monitored by TLC. After completion of the reaction (TLC), the reaction mixture was filtered through celite pad and was washed with ethanol (50 mL) twice, then concentrated to dryness under vacuum to afford 26.0 g (73%) of the title compound as light yellow solid.

$^1$H-NMR (DMSO-d6): δ=1.37 (9H), 1.98 (3H), 2.26-2.47 (2H), 4.72 (2H), 5.05-5.17 (2H), 6.48-6.56 (1H), 6.61-6.73 (1H), 6.77-6.92 (1H) ppm.

Intermediate 52

3-(3-{[(4-bromo-3-fluorophenyl)(cyclopentyl)acetyl]amino}-2-methylphenyl)pentanoic acid, Single Enantiomer

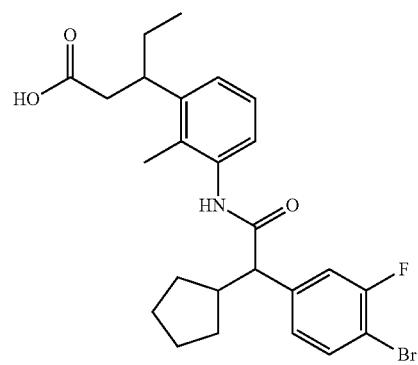 [SMILES: CCC(CC(=O)O)c1cccc(NC(=O)C(c2ccc(Br)c(F)c2)C2CCCC2)c1C]

Step 52.1: methyl 3-(3-{[(4-bromo-3-fluorophenyl)(cyclopentyl)acetyl]amino}-2-methylphenyl)pentanoate, Single Enantiomer 1 g (4519 μmol) (−) methyl 3-(3-amino-2-methylphenyl)pentanoate which was prepared according to intermediate 53 were reacted in analogy to intermediate 3 with (−) (4-bromo-3-fluorophenyl)(cyclopentyl)ethanoic acid which was prepared according to intermediate 54 to give after working-up 2350 mg (105%) of the title compound.

$^1$H-NMR (DMSO-d6): δ=0.65-0.71 (3H), 0.93-1.03 (1H), 1.29-1.42 (2H), 1.42-1.69 (6H), 1.79-1.90 (1H), 2.03 (3H), 2.51-2.67 (3H), 3.22-3.29 (1H), 3.45-3.52 (4H), 6.97-7.11 (3H), 7.21 (1H), 7.40 (1H), 7.37 (1H), 7.66 (1H), 9.55 (1H) ppm.

Step 52.2: 3-(3-{[(4-bromo-3-fluorophenyl)(cyclopentyl)acetyl]amino}-2-methylphenyl)pentanoic acid, Single Enantiomer 2.35 g (4519 μmol) methyl 3-(3-{[(4-bromo-3-fluorophenyl)(cyclopentyl)acetyl]amino}-2-methylphenyl)pentanoate, single enantiomer which was prepared according to step 52.1 was saponified with 40 mL MeOH and 24 mL aqueous NaOH (2M) to give after working-up 2130 mg (93%) of the title compound.

$^1$H-NMR (DMSO-d6): δ=0.66-0.73 (3H), 0.94-1.05 (1H), 1.34-1.44 (2H), 1.45-1.69 (6H), 1.80-1.93 (2H), 2.04-2.09 (3H), 2.33-2.49 (1H), 2.53-2.68 (2H), 3.21-3.30 (1H), 3.51 (1H), 6.98-7.12 (3H), 7.22 (1H), 7.41 (1H), 7.68 (1H), 9.57 (1H), 11.97 (1H) ppm.

Intermediate 53

(−) methyl 3-(3-amino-2-methylphenyl)pentanoate

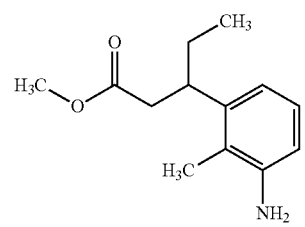 [SMILES: CCC(CC(=O)OC)c1cccc(N)c1C]

6.45 g racemic ester 16.1 were separated by preparative chiral HPLC (method 5; solvent: hexane/ethanol diethylamine 60:40:0.1 (v/v/v); flow rate: 40 ml/min; solution: 6450 mg/20 ml DMF/MeOH 1:1; injection volume: 16×0.75 ml) to yield 2820 mg of the title compound (Rt: 3.8-5.0 min) together with 2850 mg (+)-enantiomer (Rt: 5.5-10.5 min).

Analytical HPLC, method 12: solvent: hexane/ethanol/diethylamine 60:40:0.1 (v/v/v); flow rate: 1.0 ml/min; solution: 1 mg/ml ethanol/methanol 2:1; injection volume: 5.0 µl; Rt: 1.95 min ((+)-enantiomer Rt: 4.94 min).

Intermediate 54

(−) (4-bromo-3-fluorophenyl)(cyclopentyl)acetic acid

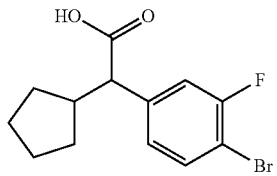

38.13 g (R/S) (4-bromo-3-fluorophenyl)(cyclopentyl)acetic acid which was prepared according to intermediate 9, step 9.2 were reacted in analogy to intermediate 46 with 16.92 mL (16.11 g) (1R)-1-phenylethanamine to yield 11.12 g (20.8%) of the title compound Optical rotation: −34.2° (13 mg/ml in DMSO, temperature: 20° C., wave length: 589 nM).

Analytical HPLC, method 11: hexane/ethanol/TFA 98:2:0.1 (v/v/v); flow rate: 1 ml/min; solution: 1 mg/ml EtOH/MeOH 1:1, injection volume: 5 µl; Rt: 2.01 min.

Intermediate 55

3-(3-{[(4-bromo-3-fluorophenyl)(cyclopentyl)acetyl]amino}-2-methylphenyl)propanoic acid, Single Enantiomer

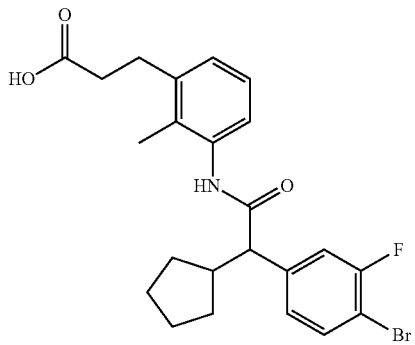 [SMILES: Cc1c(CCC(=O)O)cccc1NC(=O)C(c1ccc(Br)c(F)c1)C1CCCC1]

Step 55.1: tert-butyl 3-(3-{[(4-bromo-3-fluorophenyl)(cyclopentyl)acetyl]amino}-2-methylphenyl) propanoate, Single Enantiomer 1 g (3970 µmol) tert-butyl 3-(3-amino-2-methylphenyl) propanoate which was prepared according to intermediate 2 were reacted in analogy to intermediate 3 with (−) (4-bromo-3-fluorophenyl)(cyclopentyl)ethanoic acid which was prepared according to intermediate 54 to give after working-up and purification 2060 mg (94%) of the title compound.

$^1$H-NMR (DMSO-d6): δ=0.98 (1H), 1.25-1.42 (10H), 1.43-1.69 (4H), 1.82 (1H), 1.99 (3H), 2.41 (2H), 2.51-2.58 (1H), 2.79 (2H), 3.50 (1H), 6.96-7.06 (3H), 7.20 (1H), 7.40 (1H), 7.66 (1H), 9.54 (1H) ppm.

Step 55.2: 3-(3-{[(4-bromo-3-fluorophenyl)(cyclopentyl)acetyl]amino}-2-methylphenyl)propanoic acid, Single Enantiomer 2.06 g (3973 µmol tert-butyl 3-(3-{[(4-bromo-3-fluorophenyl)(cyclopentyl)acetyl]amino}-2-methylphenyl)propanoate, single enantiomer which was prepared according to step 55.1 were reacted with 15 mL TFA in 15 mL DCM to give after working-up 1810 mg (98%) of the title compound.

$^1$H-NMR (DMSO-d6): δ=0.94-1.06 (1H), 1.32-1.44 (2H), 1.45-1.70 (3H), 1.79-1.91 (1H), 2.01 (3H), 2.45 (2H), 2.53-2.60 (1H), 2.81 (2H), 3.53 (1H), 6.99-7.08 (3H), 7.22 (1H), 7.41 (1H), 7.68 (1H), 9.57 (1H), 12.15 (1H) ppm.

Intermediate 56

3-(3-{[(2R)-2-(4-bromophenyl)-2-cyclopentylacetyl] amino}-2-methylphenyl)pentanoic acid, Single Enantiomer

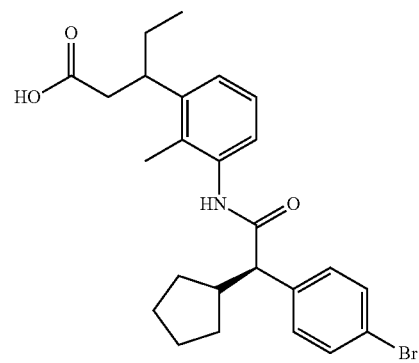 [SMILES: CCC(CC(=O)O)c1cccc(NC(=O)[C@@H](c2ccc(Br)cc2)C2CCCC2)c1C]

Step 56.1 methyl 3-(3-{[(2R)-2-(4-bromophenyl)-2-cyclopentylacetyl]amino}-2-methylphenyl)pentanoate 1 g (4519 µmol) (−) methyl 3-(3-amino-2-methylphenyl) pentanoate which was prepared according to intermediate 53 were reacted in analogy to intermediate 3 with (2R)-(4-bromophenyl)(cyclopentyl)ethanoic acid which was prepared according to intermediate 46 to give after working-up and purification 2130 mg (97%) of the title compound.

$^1$H-NMR (DMSO-d6): δ=0.66-0.72 (3H), 0.97 (1H), 1.17-1.43 (2H), 1.44-1.71 (5H), 1.77-1.90 (1H), 2.02-2.09 (3H), 2.53-2.69 (3H), 3.23-3.32 (1H), 3.35-3.49 (3H), 6.98-7.12 (3H), 7.39 (2H), 7.50-7.55 (2H), 9.54 (1H) ppm.

Step 55.2: 3-(3-{[(2R)-2-(4-bromophenyl)-2-cyclopentylacetyl]amino}-2-methylphenyl)pentanoic acid, Single Enantiomer 2.13 g (4379 µmol) methyl 3-(3-{[(2R)-2-(4-bromophenyl)-2-cyclopentylacetyl]amino}-2-methylphenyl)pentanoate which was prepared according to step 56.1 were saponified with 22 mL NaOH (2M) in 40 mL MeOH to give after working-up 2280 mg (107%) of the title compound.

¹H-NMR (DMSO-d6): δ=0.66-0.73 (3H), 0.97 (1H), 1.28-1.42 (2H), 1.43-1.71 (6H), 1.80-1.93 (2H), 1.99-2.07 (3H), 2.33-2.49 (1H), 2.53-2.67 (1H), 3.25 (1H), 3.47 (1H), 6.97-7.14 (3H), 7.39 (2H), 7.53 (2H), 9.53 (1H), 11.97 (1H) ppm.

Intermediate 57

3-(3-{[(4-bromo-3-fluorophenyl)(cyclobutyl)acetyl]amino}-2-methylphenyl)propanoic acid, Single Enantiomer

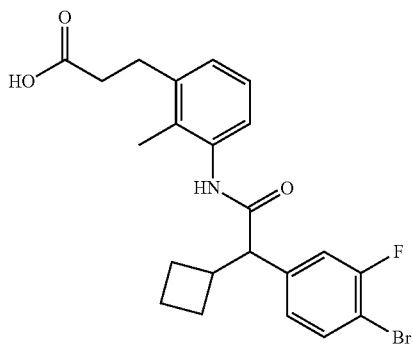 [SMILES: Cc1c(CCC(=O)O)cccc1NC(=O)C(c1ccc(Br)c(F)c1)C1CCC1]

Step 57.1: tert-butyl 3-(3-{[(4-bromo-3-fluorophenyl)(cyclobutyl)acetyl]amino}-2-methylphenyl)propanoate, Single Enantiomer 2.24 g (9498 µmol) tert-butyl 3-(3-amino-2-methylphenyl)propanoate, which was prepared according to intermediate 2 were reacted in analogy to intermediate 3 with (−)-(4-bromo-3-fluorophenyl)(cyclobutyl)ethanoic acid which was prepared according to intermediate 58 to give after working-up and purification 3430 mg (72%) of the title compound.

¹H-NMR (DMSO-d6): δ=1.20-1.40 (9H), 1.50-1.70 (1H), 1.77-1.94 (4H), 1.98-2.05 (3H), 2.06-2.17 (1H), 2.43 (2H), 2.81 (2H), 2.91-3.02 (1H), 3.79 (1H), 6.98-7.08 (3H), 7.19 (1H), 7.35 (1H), 7.67 (1H), 9.59 (1H) ppm.

Step 57.2: 3-(3-{[(4-bromo-3-fluorophenyl)(cyclobutyl)acetyl]amino}-2-methylphenyl)propanoic acid, Single Enantiomer 3.43 g (6799 µmol) tert-butyl 3-(3-amino-2-methylphenyl)propanoate, single enantiomer which was prepared according to step 57.1 were reacted with 10 mL TFA and 200 µL water in 10 mL DCM to give after working-up 3040 mg (100%) of the title compound.

¹H-NMR (DMSO-d6): δ=1.59 (1H), 1.75-1.92 (4H), 2.00 (3H), 2.09 (1H), 2.43 (2H), 2.51 (1H), 2.80 (2H), 2.88-3.01 (1H), 6.98-7.07 (3H), 7.17 (1H), 7.36 (1H), 7.66 (1H), 9.56 (1H) ppm.

Intermediate 58

(−)(4-bromo-3-fluorophenyl)(cyclobutyl)acetic acid

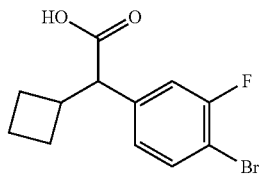 [SMILES: O=C(O)C(c1ccc(Br)c(F)c1)C1CCC1]

10.89 g (R/S) (4-bromo-3-fluorophenyl)(cyclobutyl)acetic acid which was prepared according to intermediate 11, step 11.2 were reacted in analogy to intermediate 46 with 5.069 mL (4.83 g) (1R)-1-phenylethanamine to yield 4.93 g (45%) of the title compound.

Optical rotation: −50.6° (10 mg/ml in DMSO, temperature: 20° C., wave length: 589 nM).

Analytical HPLC, method 4: hexane/isopropanol/diethylamine 95:5:0.1 (v/v/v) to 50:50:0.1 (v/v/v) in 10 min; flow rate: 1 ml/min; solution: 1 mg/ml EtOH/MeOH 2:1, injection volume: 5 µl; Rt: 3.04 min (other enantiomer at 3.27 min).

Intermediate 59

(R/S) tert-butyl 3-(3-{[(4-bromo-2-fluoro-5-methylphenyl)(cyclopentyl)acetyl]amino}-2-methylphenyl)propanoate

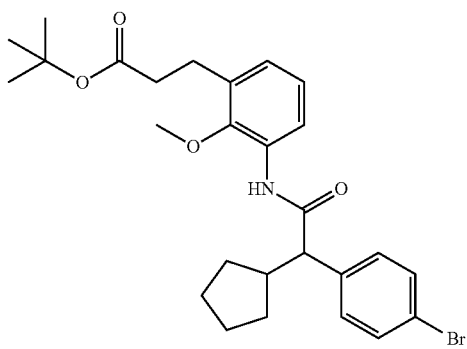 [SMILES: COc1c(CCC(=O)OC(C)(C)C)cccc1NC(=O)C(c1ccc(Br)cc1)C1CCCC1]

225 mg (895 µmol) tert-butyl 3-(3-amino-2-methoxyphenyl)propanoate which was prepared according to intermediate 60 were reacted in analogy to intermediate 3 with (R/S) (4-bromophenyl)(cyclopentyl)acetic acid which was prepared according to intermediate 1 to give after working-up and purification 271 mg (59%) of the title compound.

Intermediate 60 tert-butyl 3-(3-amino-2-methoxyphenyl)propanoate

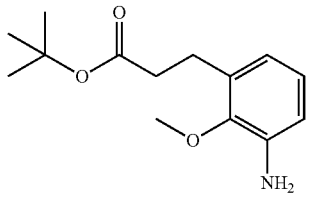 [SMILES: COc1c(N)cccc1CCC(=O)OC(C)(C)C]

Step 60.1: tert-butyl (2E)-3-(2-methoxy-3-nitrophenyl)prop-2-enoate 1 g (4.3 mmol) 1-bromo-2-methoxy-3-nitrobenzene were reacted with tert-butyl prop-2-enoate in analogy to intermediate 2, step 2.1 to give after working up and purification 427 mg (30%) of the title compound.

Step 60.2: tert-butyl 3-(3-amino-2-methoxyphenyl)propanoate 530 mg (1.9 mmol) tert-butyl (2E)-3-(2-methoxy-3-nitrophenyl)prop-2-enoate which was prepared according to step 60.1 were transformed in analogy to intermediate 2, step 2.2 to give after working up and purification 226 mg (47%) of the title compound.

$^1$H-NMR (DMSO-d6): δ=1.34 (9H), 2.40 (2H), 2.69 (3H), 3.58 (3H), 4.77 (2H), 6.31 (1H), 6.50 (1H), 6.67 (1H) ppm.

Intermediate 61 tert-butyl 3-[3-{[(2R)-2-(4-bromophenyl)-2-cyclopentylacetyl]amino}-2-(trifluoromethyl)phenyl]propanoate

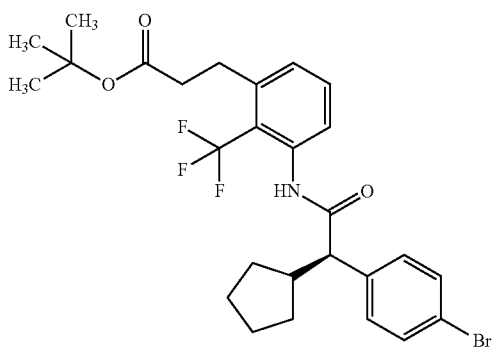 [SMILES: CC(C)(C)OC(=O)CCc1cccc(NC(=O)[C@@H](c2ccc(Br)cc2)C2CCCC2)c1C(F)(F)F]

To a solution of 239 mg (829 mmol) tert-butyl 3-[3-amino-2-(trifluoromethyl)phenyl]propanoate which was prepared according to intermediate 62 in NMP (50 mL) were added in analogy to intermediate 43-2 567 μL DIPEA and 500 mg (2R)-(4-bromophenyl)(cyclopentyl)acetyl chloride which was prepared according to intermediate 47. The mixture was stirred for 1 h at RT to give after working up 767 mg (100%) of the title compound.

Intermediate 62 tert-butyl 3-[3-amino-2-(trifluoromethyl)phenyl]propanoate

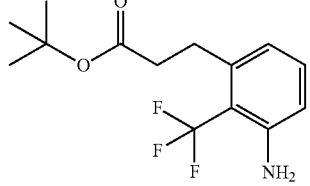

Step 62.1: tert-butyl (2E)-3-[3-nitro-2-(trifluoromethyl)phenyl]prop-2-enoate 5 g (18.5 mmol) 1-bromo-3-nitro-2-(trifluoromethyl)benzene were reacted with tert-butyl prop-2-enoate in analogy to intermediate 2, step 2.1 to give after working up and purification 2.41 g (41%) of the title compound.

$^1$H-NMR (DMSO-d6): δ=1.50 (9H), 6.67 (1H), 7.74 (1H), 7.95 (1H), 8.07 (1H), 8.23 (1H) ppm.

Step 62.2: tert-butyl 3-[3-amino-2-(trifluoromethyl)phenyl]propanoate 2410 mg (7.6 mmol) tert-butyl (2E)-3-[3-nitro-2-(trifluoromethyl)phenyl]prop-2-enoate which was prepared according to step 62.1 were transformed in analogy to intermediate 2, step 2.2 to give after working up and purification 2.01 g (91%) of the title compound.

$^1$H-NMR (DMSO-d6): δ=1.38 (9H), 2.38-2.49 (2H), 2.80-2.94 (2H), 5.50 (2H), 6.50 (1H), 6.70 (1H), 7.09-7.15 (1H) ppm.

Example 1

(R/S) 3-{3-[(Cyclopentyl{4-[5-(trifluoromethyl)pyridin-3-yl]phenyl}acetyl)amino]-2-methylphenyl}propanoic acid

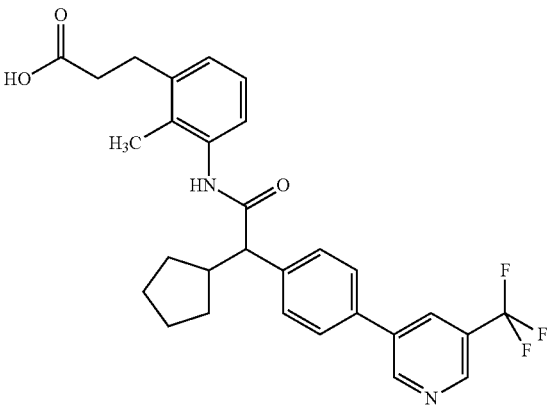 [SMILES: Cc1c(CCC(=O)O)cccc1NC(=O)C(c1ccc(-c2cncc(C(F)(F)F)c2)cc1)C1CCCC1]

(R/S) tert-Butyl 3-{3-[(cyclopentyl{4-[5-(trifluoromethyl)pyridin-3-yl]phenyl}acetyl)amino]-2-methylphenyl}propanoate 24.4 mg 1,1'-Bis(diphenylphosphino)ferrocenedichloropalladium(II) and 0.24 ml 1M $K_2CO_3$-solution were added to 100 mg intermediate 3 and 76.3 mg [5-(trifluoromethyl)pyridin-3-yl]boronic acid in 2 ml THF and heated under reflux until complete conversion. The reaction mixture was evaporated to dryness and the crude material (259 mg) used without further purification in the next step.

(R/S) 3-{3-[(Cyclopentyl{4-[5-(trifluoromethyl)pyridin-3-yl]phenyl}acetyl)amino]-2-methylphenyl}propanoic acid To a solution of 259 mg tert-butyl ester in 4.4 ml DCM and 3.5 ml TFA were added and stirred for 1 hour at RT. The mixture was repeatedly evaporated to dryness under toluene addition. The resulting material was purified by HPLC and resulted in 50 mg of the title compound.

$^1$H NMR (400 MHz, DMSO-$d_6$) δ ppm 0.94-1.14 (m, 1 H) 1.32-1.79 (m, 6 H) 1.82-1.94 (m, 1 H) 2.03 (s, 3 H) 2.44 (t, 2 H) 2.81 (t, 3 H) 3.56 (d, 1 H) 6.94-7.13 (m, 3 H) 7.59 (d, 2 H) 7.83 (d, 2 H) 8.46 (s, 1 H) 8.95 (d, 1 H) 9.22 (d, 1 H) 9.54 (s, 1 H) 12.01-12.21 (m, 1 H).

Example 2

(−) (R) 3-{3-[(Cyclopentyl{4-[5-(trifluoromethyl)pyridin-3-yl]phenyl}acetyl)amino]-2-methylphenyl}propanoic acid

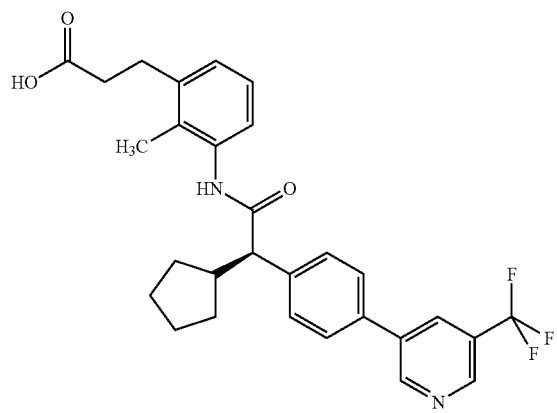 [SMILES: Cc1c(CCC(=O)O)cccc1NC(=O)[C@@H](c1ccc(-c2cncc(C(F)(F)F)c2)cc1)C1CCCC1]

37 mg racemic acid 1 were separated by preparative chiral HPLC (method 1; solvent: CO2/ethanol 80/20; flow rate: 80 ml/min; solution: 37 mg/ml DMF; injection volume: 5×0.2 ml) to yield 11 mg of the title compound (Rt: 5.95-8.0 min) together with 13 mg (+) (S)-enantiomer 3.

Analytical HPLC, method 1: solvent: CO2/ethanol 80/20; flow rate: 4 ml/min; solution: 1.0 mg/ml ethanol/methanol; injection volume: 10 µl; Rt: 4.3 min.

Optical rotation: −42.7° (1.8 mg/ml in DMSO, temperature: 20° C., wave length: 589 nM).

Example 2 was re-synthesized by alternative procedures using different intermediates. Comparison of retention times on chiral HPLC using identical conditions allowed unambiguous assignment of the stereochemistry also at intermediate level.

Example 3

(+) (S) 3-{3-[(Cyclopentyl{4-[5-(trifluoromethyl)pyridin-3-yl]phenyl}acetyl)amino]-2-methylphenyl}propanoic acid

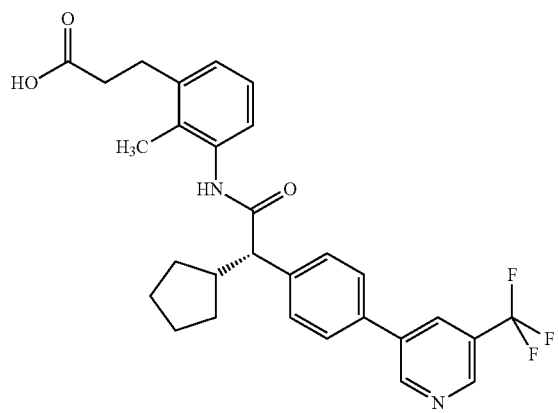

37 mg racemic acid 1 were separated by chiral HPLC (method 1, 37 mg/ml DMF, injection: 5×0.2 ml) to yield 13 mg of the title compound (Rt: 3.0 min) together with 11 mg (−) (R)-enantiomer 2.

Analytical HPLC, method 1: Rt: 3.0 min.

Optical rotation: +21.6° (7.3 mg/ml in CHCL3, temperature: 20° C., wave length: 589 nM).

Example 4

(R/S) 3-{3-[(Cyclopentyl{4-[6-(trifluoromethyl)pyridin-3-yl]phenyl}acetyl)amino]-2-methylphenyl}propanoic acid

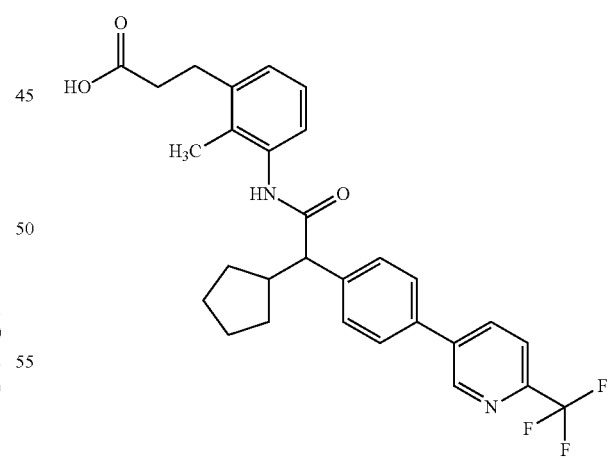

In analogy to example 1 reaction of 100 mg intermediate 3 with 76.3 mg [6-(trifluoromethyl)pyridin-3-yl]boronic acid followed by tert.-butyl ester cleavage and subsequent purification via HPLC gave 59.0 mg of the title compound.

$^1$H NMR (400 MHz, DMSO-$d_6$) δ ppm 0.93-1.11 (m, 1 H) 1.32-1.80 (m, 6 H) 1.81-1.94 (m, 1 H) 2.03 (s, 3 H) 2.44 (t, 2 H) 2.57-2.72 (m, 1 H) 2.81 (t, 2 H) 3.57 (d, 1 H) 6.94-7.10

(m, 3 H) 7.60 (d, 2 H) 7.81 (d, 2 H) 7.97 (d, 1 H) 8.37 (dd, 1 H) 9.10 (d, 1 H) 9.54 (s, 1 H) 12.12 (s, 1 H).

Example 5

(−) 3-{3-[(Cyclopentyl{4-[6-(trifluoromethyl)pyridin-3-yl]phenyl}acetyl)amino]-2-methylphenyl}propanoic acid

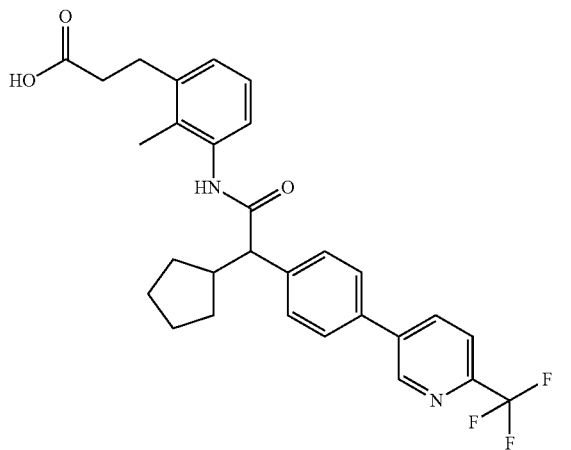 [SMILES: Cc1c(CCC(=O)O)cccc1NC(=O)C(c1ccc(-c2ccc(C(F)(F)F)nc2)cc1)C1CCCC1]

50 mg racemic acid 4 were separated by preparative chiral HPLC (method 1, solvent: CO2/ethanol 65/35; flow rate: 4.0 mL/min; solution: 39 mg/1.5 ml DMSO/EtOH 1:2, injection volume: 3×0.5 ml) to yield 15 mg of the title compound (Rt: 3.5-5.5 min) together with 12 mg (+)-enantiomer (Rt: 1.5-2.5 min).

Analytical HPLC, method 1: solvent: CO2/2-propanol 65/35; flow rate: 4.0 ml/min; solution: 1.0 mg/ml ethanol/methanol; injection volume: 10 μl; Rt: 3.50 min [(+)-enantiomer: Rt: 1.49 min].

Optical rotation: −43.0° (4.3 mg/ml in DMSO, temperature: 20° C., wave length: 589 nM)

Example 6

(R/S) 3-[3-({Cyclopentyl[4-(5-fluoropyridin-3-yl)phenyl]acetyl}amino)-2-methylphenyl]propanoic acid

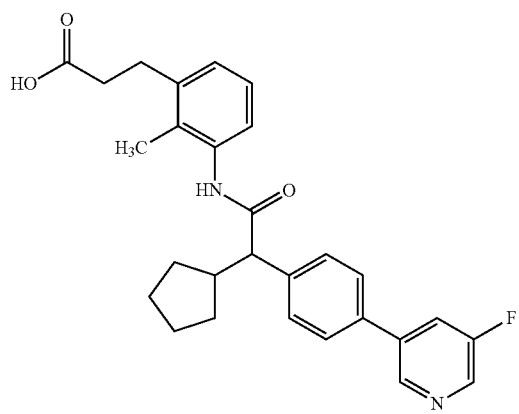

In analogy to example 1 reaction of 100 mg intermediate 3 with 42.2 mg (5-fluoropyridin-3-yl)boronic acid followed by tert.-butyl ester cleavage and subsequent purification via HPLC gave 25.0 mg of the title compound.

$^1$H NMR (300 MHz, DMSO-d$_6$) δ ppm 0.94-1.12 (m, 1 H) 1.32-1.76 (m, 6 H) 1.79-1.95 (m, 1 H) 2.02 (s, 3 H) 2.44 (m, 2 H) 2.58-2.70 (m, 1 H) 2.80 (d, 2 H) 3.55 (d, 1 H) 6.95-7.10 (m, 3 H) 7.57 (d, 2 H) 7.77 (d, 2 H) 7.98-8.13 (m, 1 H) 8.56 (d, 1 H) 8.81 (s, 1 H) 9.53 (s, 1 H) 12.12 (s, 1 H).

Example 7

(R/S) 3-[3-({[4-(6-Cyanopyridin-3-yl)phenyl](cyclopentyl)acetyl}amino)-2-methylphenyl]propanoic acid

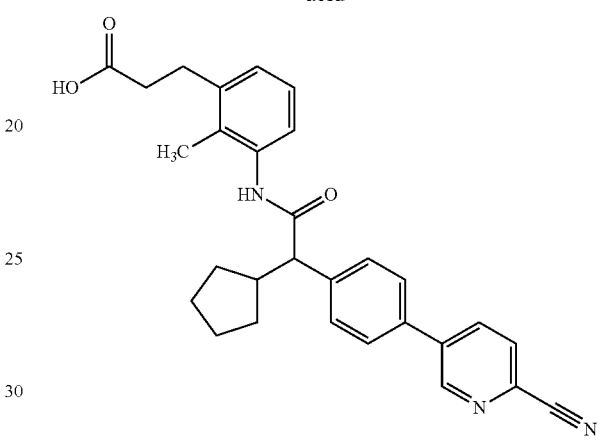

In analogy to example 1 reaction of 200 mg intermediate 3 with 110.3 mg 5-(4,4,5,5-tetramethyl-1,3,2-dioxaborolan-2-yl)pyridine-2-carbonitrile followed by tert.-butyl ester cleavage and subsequent purification via HPLC gave 45.0 mg of the title compound.

$^1$H NMR (300 MHz, DMSO-d$_6$) δ ppm 0.97-1.07 (m, 1 H) 1.33-1.76 (m, 6 H) 1.80-1.95 (m, 1 H) 2.02 (s, 3 H) 2.34-2.45 (m, 2 H) 2.57-2.70 (m, 1 H) 2.79 (t, 2 H) 3.56 (d, 1 H) 6.92-7.10 (m, 3 H) 7.60 (d, 2 H) 7.83 (d, 2 H) 8.12 (d, 1 H) 8.36 (dd, 1 H) 9.12 (d, 1 H) 9.57 (s, 1 H).

Example 8

(R/S) 3-[3-({Cyclopentyl[4-(5-ethoxypyridin-3-yl)phenyl]acetyl}amino)-2-methylphenyl]propanoic acid

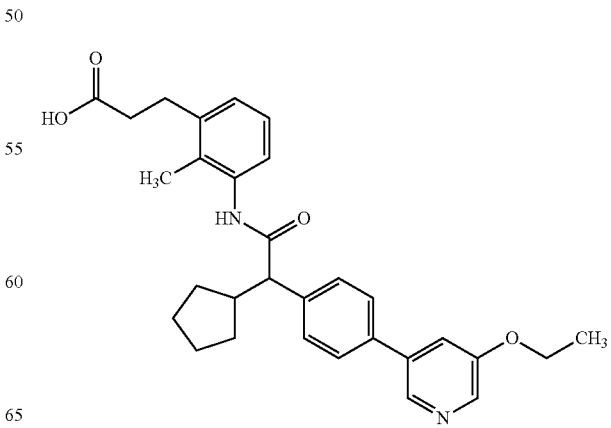

In analogy to example 1 reaction of 120 mg intermediate 3 with 71.7 mg 3-ethoxy-5-(4,4,5,5-tetramethyl-1,3,2-dioxaborolan-2-yl)pyridine followed by tert.-butyl ester cleavage and subsequent purification via HPLC gave 47.0 mg of the title compound.

$^1$H NMR (300 MHz, DMSO-$d_6$) δ ppm 0.98-1.08 (m, 1 H) 1.29-1.77 (m, 9 H) 1.79-1.95 (m, 1 H) 2.03 (s, 3 H) 2.37-2.47 (m, 2 H) 2.58-2.70 (m, 1 H) 2.75-2.88 (m, 2 H) 3.54 (d, 1 H) 4.08-4.29 (m, 2 H) 6.93-7.10 (m, 3 H) 7.47-7.64 (m, 3 H) 7.72 (d, 2 H) 8.25 (d, 1 H) 8.48 (d, 1 H) 9.52 (s, 1 H) 11.37-12.62 (m, 1H).

Example 9

(R/S) 3-{3-[(Cyclopentyl{4-[5-(2-hydroxypropan-2-yl)pyridin-3-yl]phenyl}acetyl)amino]-2-methylphenyl}propanoic acid

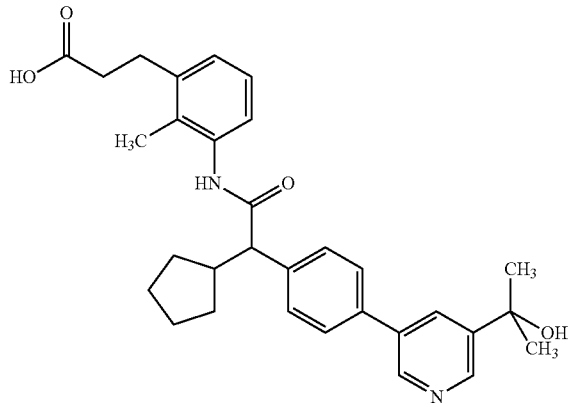 [SMILES: Cc1c(CCC(=O)O)cccc1NC(=O)C(c1ccc(-c2cncc(C(C)(C)O)c2)cc1)C1CCCC1]

In analogy to example 1 reaction of 120 mg intermediate 3 with 75.7 mg 2-[5-(4,4,5,5-tetramethyl-1,3,2-dioxaborolan-2-yl)pyridin-3-yl]propan-2-ol followed by tert.-butyl ester cleavage and subsequent purification via HPLC gave 49.0 mg of the title compound.

$^1$H NMR (400 MHz, DMSO-$d_6$) δ ppm 0.96-1.12 (m, 1 H) 1.52 (s, 12 H) 1.81-1.95 (m, 1 H) 2.03 (s, 3 H) 2.44 (t, 2 H) 2.58-2.70 (m, 1 H) 2.81 (t, 2 H) 3.55 (d, 1 H) 5.11-5.51 (m, 1 H) 6.96-7.09 (m, 3 H) 7.57 (d, 2 H) 7.71 (d, 2 H) 8.13 (t, 1 H) 8.69 (d, 1 H) 8.76 (d, 1 H) 9.53 (s, 1 H) 11.84-12.36 (m, 1 H).

Example 10

(R/S) 3-{3-[(Cyclopentyl{4-[5-(methoxymethyl)pyridin-3-yl]phenyl}acetyl)amino]-2-methylphenyl}propanoic acid

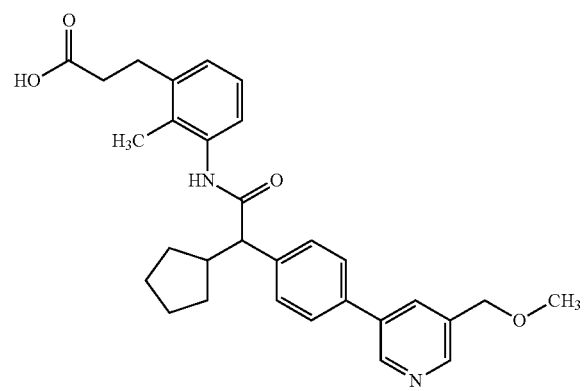 [SMILES: COCc1cncc(-c2ccc(C(C(=O)Nc3cccc(CCC(=O)O)c3C)C3CCCC3)cc2)c1]

In analogy to example 1 reaction of 120 mg intermediate 3 with 71.7 mg 3-(methoxymethyl)-5-(4,4,5,5-tetramethyl-1,3,2-dioxaborolan-2-yl)pyridine followed by tert.-butyl ester cleavage and subsequent purification via HPLC gave 22.0 mg of the title compound.

$^1$H NMR (400 MHz, DMSO-$d_6$) δ ppm 0.96-1.10 (m, 1 H) 1.37-1.77 (m, 6 H) 1.82-1.94 (m, 1 H) 2.02 (s, 3 H) 2.45 (d, 2 H) 2.59-2.70 (m, 1 H) 2.81 (s, 2 H) 3.35 (s, 3 H) 3.49-3.59 (m, 1 H) 4.53 (s, 2 H) 6.96-7.07 (m, 3 H) 7.56 (d, 2 H) 7.71 (d, 2 H) 8.00 (s, 1 H) 8.52 (d, 1 H) 8.83 (d, 1 H) 9.53 (s, 1 H) 11.98-12.25 (m, 1 H).

Example 11

(R/S) 3-[3-({Cyclopentyl[4-(5-methoxypyridin-3-yl)phenyl]acetyl}amino)-2-methylphenyl]propanoic acid

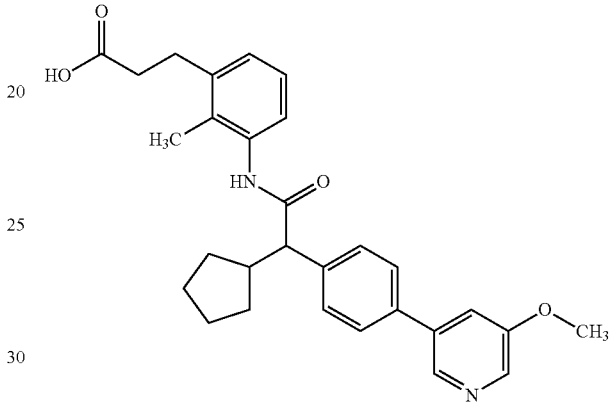

In analogy to example 1 reaction of 100 mg intermediate 3 with 45.8 mg (5-methoxypyridin-3-yl)boronic acid followed by tert.-butyl ester cleavage and subsequent purification via HPLC gave 29.0 mg of the title compound.

$^1$H NMR (300 MHz, DMSO-$d_6$) δ ppm 0.95-1.14 (m, 1 H) 1.36-1.78 (m, 6 H) 1.80-1.94 (m, 1 H) 2.03 (s, 3 H) 2.38-2.47 (m, 2 H) 2.58-2.70 (m, 1 H) 2.76-2.87 (m, 2 H) 3.54 (d, 1 H) 3.91 (s, 3 H) 6.96-7.07 (m, 3 H) 7.55 (d, 2 H) 7.62 (dd, 1 H) 7.72 (d, 2 H) 8.27 (d, 1 H) 8.49 (d, 1 H) 9.52 (s, 1 H) 12.12 (s, 1 H).

Example 12

(R/S) 3-[3-({Cyclopentyl[4-(4-methylpyridin-3-yl)phenyl]acetyl}amino)-2-methylphenyl]propanoic acid

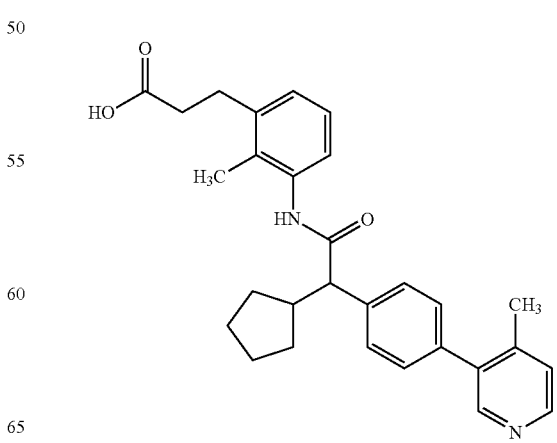

In analogy to example 1 reaction of 100 mg intermediate 3 with 41.0 mg (4-methylpyridin-3-yl)boronic acid followed by tert.-butyl ester cleavage and subsequent purification via HPLC gave 22.0 mg of the title compound.

$^1$H NMR (300 MHz, DMSO-d$_6$) δ ppm 0.98-1.12 (m, 1 H) 1.37-1.76 (m, 6 H) 1.81-1.95 (m, 1 H) 2.02 (s, 3 H) 2.27 (s, 3 H) 2.37-2.47 (m, 2 H) 2.58-2.70 (m, 1 H) 2.80 (d, 2 H) 3.49-3.63 (m, 1 H) 6.95-7.11 (m, 3 H) 7.27-7.43 (m, 3 H) 7.54 (d, 2 H) 8.31-8.49 (m, 2 H) 9.52 (s, 1 H) 12.12 (s, 1 H).

Example 13

(R/S) 3-[3-({Cyclopentyl[4-(5-ethylpyridin-3-yl)phenyl]acetyl}amino)-2-methylphenyl]propanoic acid

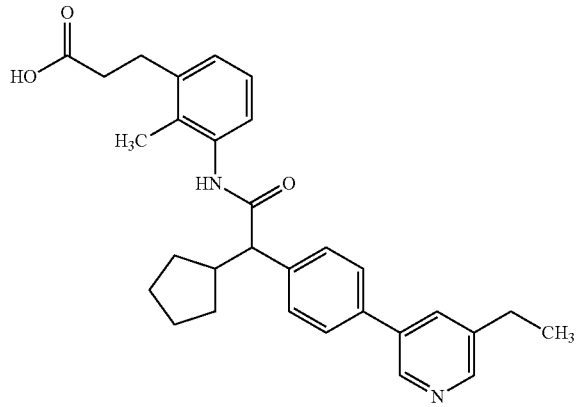 [SMILES: CCc1cncc(-c2ccc(C(C(=O)Nc3cccc(CCC(=O)O)c3C)C3CCCC3)cc2)c1]

In analogy to example 1 reaction of 200 mg intermediate 3 with 65.1 mg (5-ethylpyridin-3-yl)boronic acid followed by tert.-butyl ester cleavage and subsequent purification via HPLC gave 17.0 mg of the title compound.

$^1$H NMR (300 MHz, DMSO-d$_6$) δ ppm 0.98-1.08 (m, 1 H) 1.25 (t, 3 H) 1.32-1.77 (m, 6 H) 1.79-1.95 (m, 1 H) 2.02 (s, 3 H) 2.38-2.47 (m, 2 H) 2.57-2.75 (m, 3 H) 2.79 (d, 2 H) 3.52 (s, 1 H) 6.95-7.08 (m, 3 H) 7.55 (d, 2 H) 7.70 (d, 2 H) 7.92 (s, 1 H) 8.42 (s, 1 H) 8.71 (d, 1 H) 9.54 (s, 1 H) 11.58-12.55 (m, 1 H).

Example 14

(R/S) 3-[3-({Cyclopentyl[4-(5-cyclopropylpyridin-3-yl)phenyl]acetyl}amino)-2-methylphenyl]propanoic acid

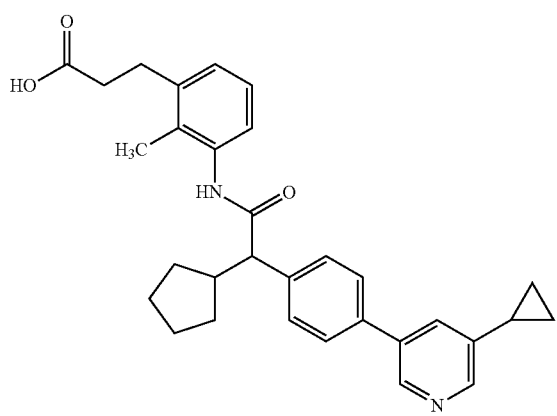 [SMILES: Cc1c(CCC(=O)O)cccc1NC(=O)C(c1ccc(-c2cncc(C3CC3)c2)cc1)C1CCCC1]

In analogy to example 1 reaction of 200 mg intermediate 3 with 70.3 mg (5-cyclopropylpyridin-3-yl)boronic acid followed by tert.-butyl ester cleavage and subsequent purification via HPLC gave 32.0 mg of the title compound.

$^1$H NMR (300 MHz, DMSO-d$_6$) δ ppm 0.86 (m, 2 H) 1.02 (m, 3 H) 1.27-1.78 (m, 7 H) 1.79-1.94 (m, 1 H) 2.02 (s, 3 H) 2.45 (d, 2 H) 2.59-2.69 (m, 1 H) 2.79 (d, 2 H) 3.49-3.60 (m, 1 H) 6.92-7.10 (m, 3 H) 7.53 (d, 2 H) 7.59-7.74 (m, 3 H) 8.38 (d, 1 H) 8.65 (d, 1 H) 9.54 (s, 1 H) 11.86-12.48 (m, 1 H).

Example 15

(R/S) 3-{3-[(Cyclopentyl{4-[5-(tetrahydro-2H-pyran-4-yloxy)pyridin-3-yl]phenyl}acetyl)amino]-2-methylphenyl}propanoic acid

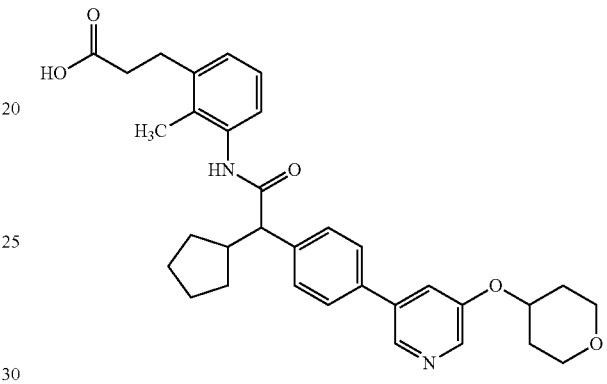

In analogy to example 1 reaction of 150 mg intermediate 3 with 80.2 mg [5-(tetrahydro-2H-pyran-4-yloxy)pyridin-3-yl]boronic acid followed by tert.-butyl ester cleavage and subsequent purification via HPLC gave 67.0 mg of the title compound.

$^1$H NMR (400 MHz, DMSO-d$_6$) δ ppm 0.95-1.10 (m, 1 H) 1.32-1.77 (m, 8 H) 1.81-1.93 (m, 1 H) 1.95-2.07 (m, 5 H) 2.43 (t, 2 H) 2.56-2.70 (m, 1 H) 2.80 (t, 2 H) 3.45-3.60 (m, 3 H) 3.87 (d, 2 H) 4.72-4.89 (m, 1 H) 6.94-7.10 (m, 3 H) 7.54 (d, 2 H) 7.64-7.77 (m, 3 H) 8.29 (d, 1 H) 8.47 (d, 1 H) 9.52 (s, 1 H) 10.80-12.73 (m, 1 H).

Example 16

(R/S) 3-[3-({[4-(5-Chloropyridin-3-yl)phenyl](cyclopentyl)acetyl}amino)-2-methylphenyl]propanoic acid

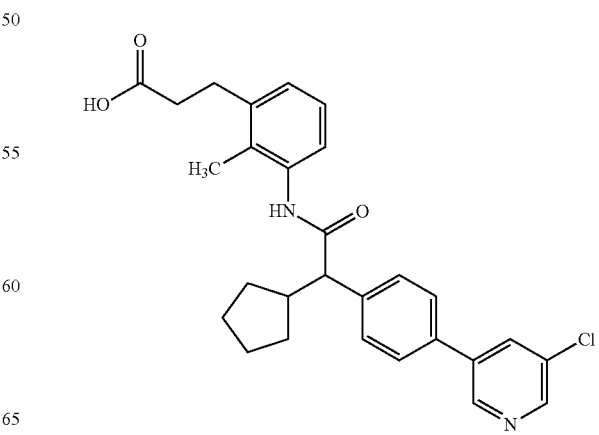

In analogy to example 1 reaction of 5.0 g intermediate 3 with 3.14 g (5-chloropyridin-3-yl)boronic acid followed by tert.-butyl ester cleavage and subsequent purification via chromatography using silica gel (gradient: hexane/EE) gave 3.69 g of the title compound.

$^1$H NMR (400 MHz, DMSO-$d_6$) δ ppm 0.96-1.09 (m, 1 H) 1.34-1.76 (m, 6 H) 1.81-1.93 (m, 1 H) 2.02 (s, 3 H) 2.44 (m, 2 H) 2.59-2.70 (m, 1 H) 2.81 (m, 2 H) 3.48-3.60 (m, 1 H) 7.03 (s, 3 H) 7.57 (d, 2 H) 7.77 (d, 2 H) 8.25 (s, 1 H) 8.61 (d, 1 H) 8.88 (d, 1 H) 9.53 (s, 1 H) 11.90-12.32 (m, 1 H).

Example 17-1

(−) (R) 3-[3-({[4-(5-Chloropyridin-3-yl)phenyl](cyclopentyl)acetyl}amino)-2-methylphenyl]propanoic acid solution: 1 mg/ml EtOH/MeOH 1:1, injection volume: 5 μl; Rt: 10.07 min [(+) (S)-enantiomer: Rt: 6.95 min].

Optical rotation: −32.4° (10 mg/ml in DMSO, temperature: 20° C., wave length: 589 nM).

The chiral center was determined to be in R-configuration by VCD spectroscopy with a confidence level of 100% (method 1).

Example 17 was re-synthesized by alternative procedures using different intermediates. Comparison of retention times on chiral HPLC using identical conditions allowed unambiguous assignment of the stereochemistry also at intermediate level.

Example 17-2

(−) (R) 3-[3-({[4-(5-Chloropyridin-3-yl)phenyl](cyclopentyl)acetyl}amino)-2-methylphenyl]propanoic acid

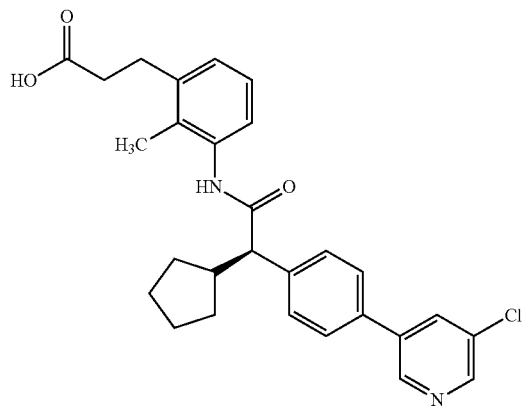 [SMILES: Cc1c(CCC(=O)O)cccc1NC(=O)[C@@H](c1ccc(-c2cncc(Cl)c2)cc1)C1CCCC1]

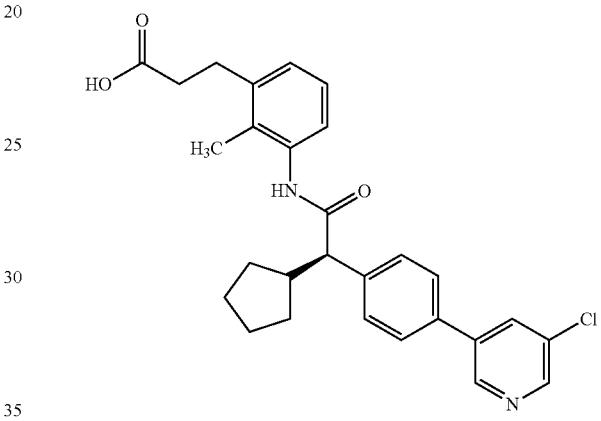

5.72 g racemic acid 16 were separated by preparative chiral HPLC (method 2; solvent: hexane/2-propanol/formic acid (99%) 70:30:0.1 (v/v/v); flow rate: 40 ml/min; solution: 5.72 g/90 ml EtOH/MeOH 1:1, injection volume: 60×1.5 ml) to yield 1.94 g of the title compound (Rt: 11.6-14.7 min) together with 1.07 g (+) -enantiomer (Rt: 8.7-11.1 min).

Analytical HPLC, method 2: solvent: hexane/2-propanol/formic acid (99%) 70:30:0.1 (v/v/v); flow rate: 1 ml/min;

33.64 g (63.10 mmol) tert-butyl 3-[3-({(2R)-2-[4-(5-chloropyridin-3-yl)phenyl]-2-cyclopentylacetyl}amino)-2-methylphenyl]propanoate which was prepared according to intermediate 44 were treated with TFA/DCM 3:1 for 1 h at RT to give after working up 20.09 g (67%) of the title compound.

The following examples were prepared in analogy to example 1:

| Example | Structure | IUPAC-Name | Analytics |
|---|---|---|---|
| 18 | 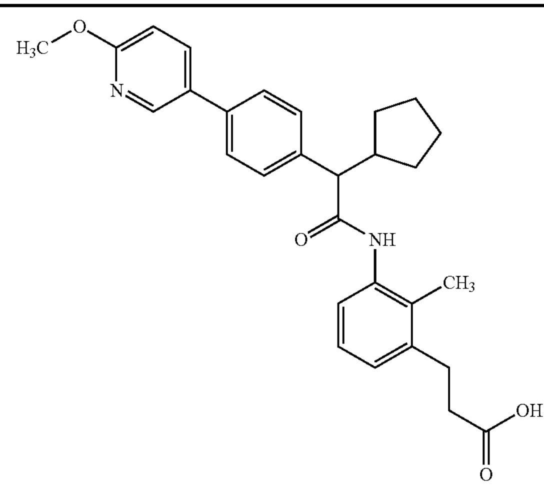 | (R/S) 3-[3-({Cyclopentyl[4-(6-methoxypyridin-3-yl)-phenyl]acetyl}amino)-2-methylphenyl]propanoic acid | Analytical HPLC, method 13 Rt 1.32 min, MW$_{calc}$ 473, MW$_{found}$ 474 |

| Example | Structure | IUPAC-Name | Analytics |
|---|---|---|---|
| 19 | 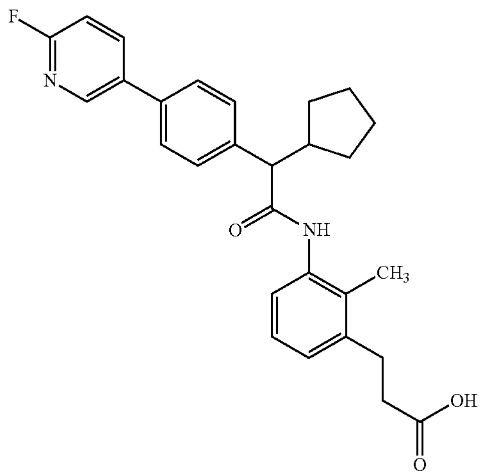 [SMILES: Cc1c(CCC(=O)O)cccc1NC(=O)C(c1ccc(-c2ccc(F)nc2)cc1)C1CCCC1] | (R/S) 3-[3-({Cyclopentyl[4-(6-fluoropyridin-3-yl)-phenyl]acetyl}amino)-2-methylphenyl]propanoic acid | Analytical HPLC, method 13 Rt 1.27 min, $MW_{calc}$ 461, $MW_{found}$ 462 |
| 20 | 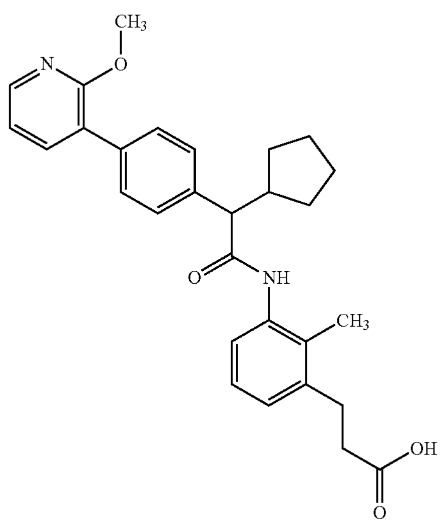 [SMILES: COc1ncccc1-c1ccc(C(C(=O)Nc2cccc(CCC(=O)O)c2C)C2CCCC2)cc1] | (R/S) 3-[3-({Cyclopentyl[4-(2-methoxypyridin-3-yl)-phenyl]acetyl}amino)-2-methylphenyl]propanoic acid | Analytical HPLC, method 13 Rt 1.32 min, $MW_{calc}$ 473, $MW_{found}$ 474 |
| 21 | 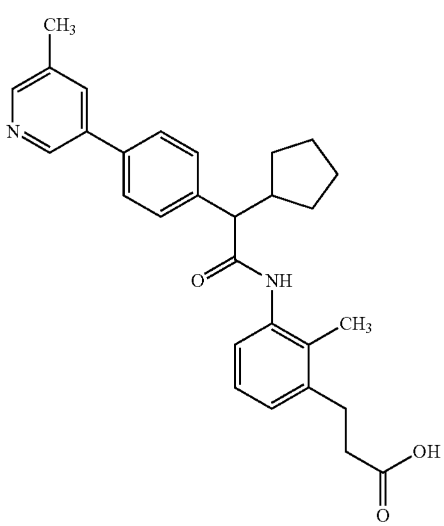 [SMILES: Cc1cncc(-c2ccc(C(C(=O)Nc3cccc(CCC(=O)O)c3C)C3CCCC3)cc2)c1] | (R/S) 3-[3-({Cyclopentyl[4-(5-methylpyridin-3-yl)-phenyl]acetyl}amino)-2-methylphenyl]propanoic acid | Analytical HPLC, method 13 Rt 1.00 min, $MW_{calc}$ 457, $MW_{found}$ 458 |

-continued

| Example | Structure | IUPAC-Name | Analytics |
|---|---|---|---|
| 22 | 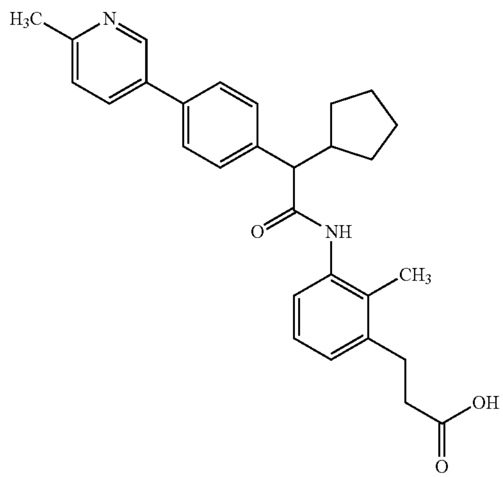 [SMILES: Cc1ccc(-c2ccc(C(C(=O)Nc3cccc(CCC(=O)O)c3C)C3CCCC3)cc2)cn1] | (R/S) 3-[3-({Cyclopentyl[4-(6-methylpyridin-3-yl)-phenyl]acetyl}amino)-2-methylphenyl]propanoic acid | Analytical HPLC, method 13 Rt 0.93 min, $MW_{calc}$ 457, $MW_{found}$ 458 |
| 23 | 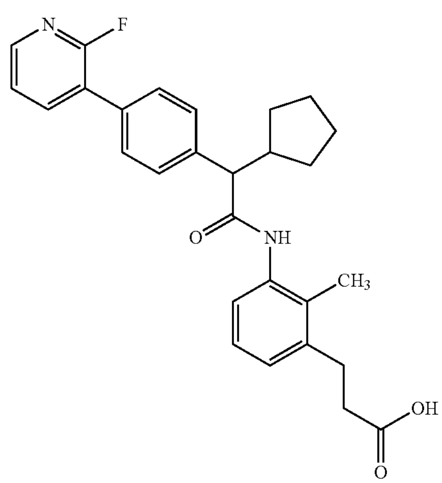 [SMILES: Cc1c(CCC(=O)O)cccc1NC(=O)C(c1ccc(-c2cccnc2F)cc1)C1CCCC1] | (R/S) 3-[3-({cyclopentyl[4-(2-fluoro-pyridin-3-yl)-phenyl]-acetyl}amino)-2-methyl-phenyl]propanoic acid | Analytical HPLC, method 13 Rt 1.25 min, $MW_{calc}$ 461, $MW_{found}$ 462 |

Example 24

(R/S) 3-[3-({[4-(5-Chloro-6-methylpyridin-3-yl)phenyl](cyclopentyl)acetyl}amino)-2-methylphenyl]propanoic acid

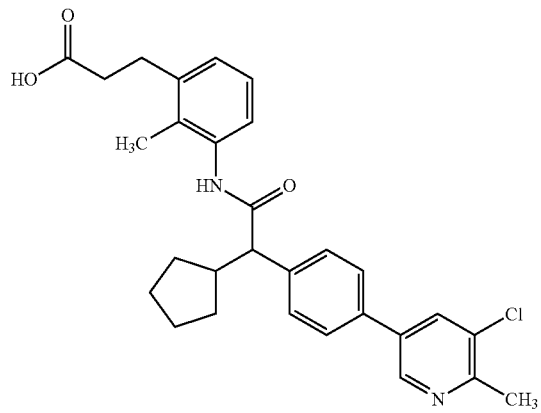 [SMILES: Cc1ncc(-c2ccc(C(C(=O)Nc3cccc(CCC(=O)O)c3C)C3CCCC3)cc2)cc1Cl]

In analogy to example 1 reaction of 150 mg intermediate 3 with 84 mg 3-chloro-2-methyl-5-(4,4,5,5-tetramethyl-1,3,2-dioxaborolan-2-yl)pyridine followed by tert.-butyl ester cleavage and subsequent via HPLC gave 50 mg of the title compound.

$^1$H NMR (300 MHz, DMSO-d$_6$) δ ppm 0.95-1.10 (m, 1 H) 1.34-1.75 (m, 6 H) 1.86 (m, 1 H) 2.02 (s, 3 H) 2.36-2.46 (m, 2 H) 2.54-2.68 (m, 4 H) 2.75-2.87 (m, 2 H) 3.54 (d, 1 H) 6.95-7.08 (m, 3 H) 7.54 (d, 2 H) 7.74 (d, 2 H) 8.17 (d, 1 H) 8.75 (d, 1 H) 9.54 (s, 1 H).

Example 25

(+) (S) 3-[3-({[4-(5-Chloro-6-methylpyridin-3-yl)phenyl](cyclopentyl)acetyl}amino)-2-methylphenyl]propanoic acid

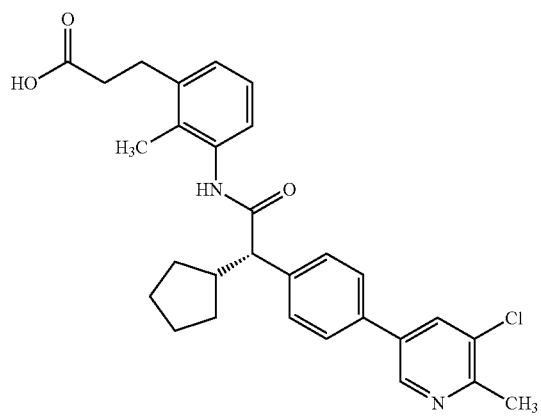 [SMILES: Cc1ncc(-c2ccc([C@@H](C(=O)Nc3cccc(CCC(=O)O)c3C)C3CCCC3)cc2)cc1Cl]

842 mg racemic acid 24 were separated by preparative chiral HPLC (method 3; solvent: hexane/ethanol/formic acid 70:30:1 (v/v/v); flow rate: 40 ml/min; solution: 842 mg/7 ml ethanol; injection volume: 5×1.4 ml) to yield 330 mg of the title compound (Rt: 6.3-8.7 min) together with 360 mg (−)-enantiomer 26.

Analytical HPLC: solvent: hexane/ethanol/formic acid 70:30:1 (v/v/v); flow rate: 1.0 ml/min; solution: 1 mg/ml ethanol/methanol 1:1; injection volume: 5.0 µl; Rt: 3.84 min.

Optical rotation: +42.2° (5 mg/ml in DMSO, temperature: 20° C., wave length: 589 nM).

Example 26

(−) (R) 3-[3-({[4-(5-Chloro-6-methylpyridin-3-yl)phenyl](cyclopentyl)acetyl}amino)-2-methylphenyl]propanoic acid

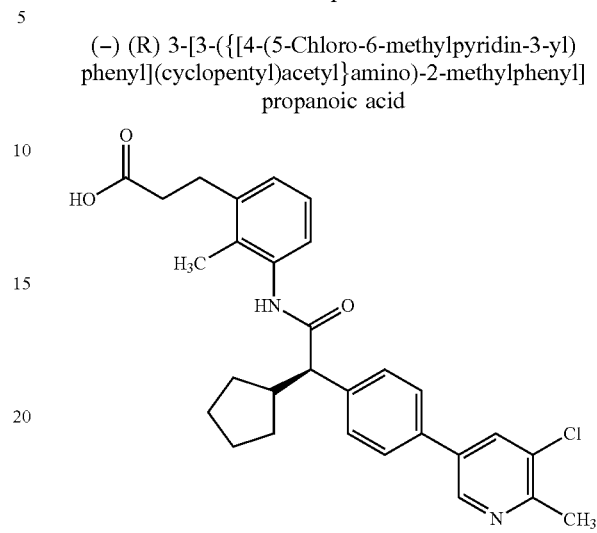

842 mg racemic acid 24 were separated by preparative chiral HPLC (method 3; solvent: hexane/ethanol/formic acid 70:30:1 (v/v/v); flow rate: 40 ml/min; solution: 842 mg/7 ml ethanol; injection volume: 5×1.4 ml) to yield 360 mg the title compound (Rt: 9.4-11.8 min) together with 330 mg (+)-enantiomer 25.

Analytical HPLC: solvent: hexane/ethanol/formic acid 70:30:1 (v/v/v); flow rate: 1.0 ml/min; solution: 1 mg/ml ethanol/methanol 1:1; injection volume: 5.0 µl; Rt: 5.13 min.

Optical rotation: −37.1 (5.3 mg/ml in DMSO, temperature: 20° C., wave length: 589 nM).

Example 26 was synthesized by alternative procedures using different intermediates. Comparison of retention times on chiral HPLC using identical conditions allowed unambiguous assignment of the stereochemistry also at intermediate level.

Example 27

(R/S) 3-[3-({Cyclopentyl[4-(5,6-dimethylpyridin-3-yl)phenyl]acetyl}amino)-2-methylphenyl]propanoic acid

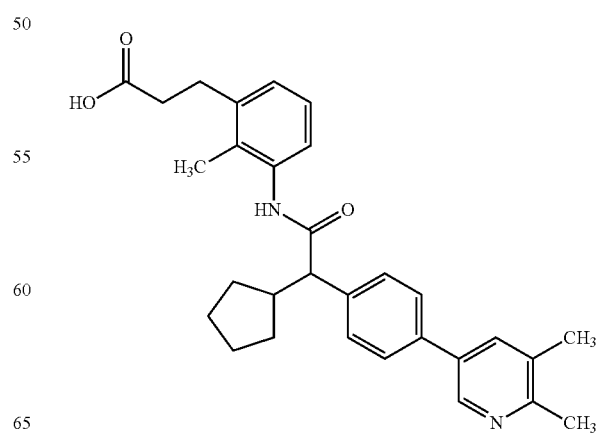

In analogy to example 1 reaction of 150 mg bromide intermediate 3 with 105 mg 2,3-dimethyl-5-(4,4,5,5-tetramethyl-1,3,2-dioxaborolan-2-yl)pyridine followed by tert.-butyl ester cleavage and subsequent purification via HPLC gave 74.1 mg of the title compound.

$^1$H NMR (300 MHz, DMSO-d$_6$) δ ppm 0.93-1.09 (m, 1 H) 1.31-1.74 (m, 6 H) 1.79-1.92 (m, 1 H) 2.02 (s, 3 H) 2.31 (s, 3 H) 2.41-2.47 (m, 3 H) 2.57-2.70 (m, 1 H) 2.74-2.84 (m, 2 H) 3.52 (d, 1 H) 6.94-7.06 (m, 3 H) 7.52 (d, 2 H) 7.60-7.70 (m, 2 H) 7.81 (s, 1 H) 8.56 (s, 1 H) 9.53 (s, 1 H).

Example 28

(R/S) 3-{3-[(Cyclopentyl{4-[5-(difluoromethoxy)pyridin-3-yl]phenyl}acetyl)amino]-2-methylphenyl}propanoic acid

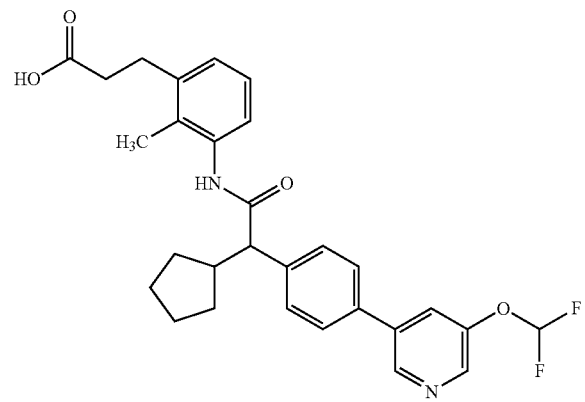

In analogy to example 1 reaction of 150 mg intermediate 3 with 150 mg potassium [5-(difluoromethoxy)pyridin-3-yl](trifluoro)borate followed by tert.-butyl ester cleavage and subsequent purification via HPLC gave 54.0 mg of the title compound.

$^1$H NMR (300 MHz, DMSO-d$_6$) δ ppm 0.77-1.13 (m, 1 H) 1.29-1.73 (m, 6 H) 1.77-1.92 (m, 1 H) 1.94-2.06 (m, 3 H) 2.37-2.46 (m, 2 H) 2.78 (d, 2 H) 3.51-3.60 (m, 1 H) 6.93-8.87 (m, 9 H) 9.53 (s, 1 H).

Example 29

(R/S) 3-{3-[(Cyclopentyl{4-[5-(difluoromethyl)pyridin-3-yl]phenyl}acetyl)amino]-2-methylphenyl}propanoic acid

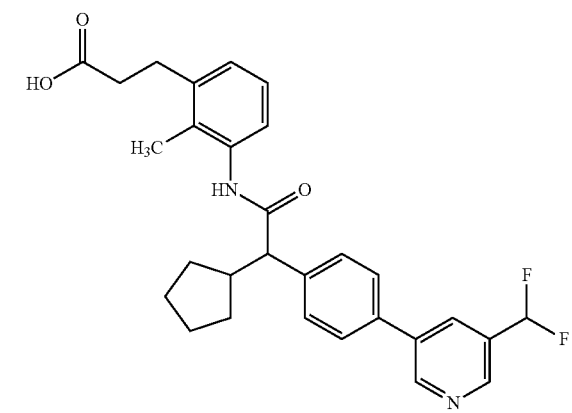 [SMILES: Cc1c(CCC(=O)O)cccc1NC(=O)C(c1ccc(-c2cncc(C(F)F)c2)cc1)C1CCCC1]

In analogy to example 1 reaction of 75 mg intermediate 3 with 38.9 mg 5-difluoromethyl-pyridine-3-boronic acid followed by tert.-butyl ester cleavage and subsequent purification via HPLC gave 48.0 mg of the title compound.

$^1$H NMR (400 MHz, DMSO-d$_6$) δ ppm 0.97-1.10 (m, 1 H) 1.34-1.76 (m, 6 H) 1.82-1.93 (m, 1 H) 2.02 (s, 3 H) 2.39-2.47 (m, 2 H) 2.59-2.71 (m, 1 H) 2.80 (t, 2 H) 3.56 (d, 1H) 6.97-7.08 (m, 3 H) 7.58 (d, 2 H) 7.78 (d, 2 H) 8.27 (s, 1 H) 8.77 (d, 1 H) 9.09 (d, 1 H) 9.55 (s, 1 H).

Example 30

(R/S) 3-{3-[(Cyclopentyl{4-[5-(fluoromethyl)pyridin-3-yl]phenyl}acetyl)amino]-2-methylphenyl}propanoic acid

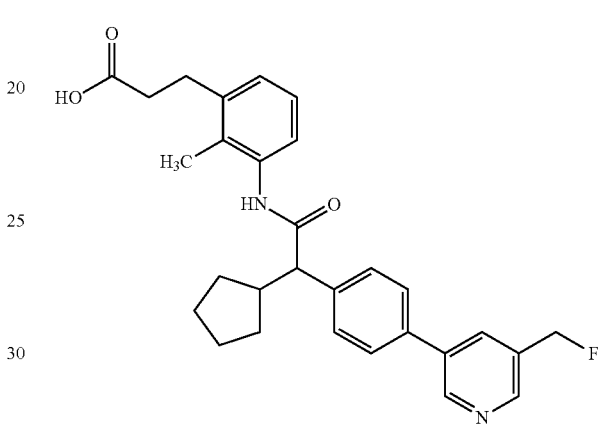

(R/S) tert-Butyl 3-{3-[(cyclopentyl{4-[5-(hydroxymethyl)pyridin-3-yl]phenyl}acetyl)amino]-2-methylphenyl}propanoate In analogy to example 1 reaction of 500 mg intermediate 3 with 352 mg [5-(4,4,5,5-tetramethyl-1,3,2-dioxaborolan-2-yl)pyridin-3-yl]methanol and subsequent purification by chromatography using silica gel (hexane/EE) gave 309 mg of the title compound.

$^1$H NMR (300 MHz, DMSO-d$_6$) δ ppm 0.95-1.10 (m, 1 H) 1.36 (m, 15 H) 1.80-1.94 (m, 1 H) 2.02 (s, 3 H) 2.43 (m, 2 H) 2.59-2.66 (m, 1 H) 2.79 (m, 2 H) 3.48-3.59 (m, 1 H) 4.61 (d, 2 H) 5.38 (t, 1 H) 6.95-7.09 (m, 3 H) 7.56 (d, 2 H) 7.70 (d, 2 H) 7.98 (s, 1 H) 8.51 (s, 1 H) 8.77 (d, 1 H) 9.54 (s, 1 H).

(R/S) tert-Butyl 3-{3-[(cyclopentyl{4-[5-(fluoromethyl)pyridin-3-yl]phenyl}acetyl)amino]-2-methylphenyl}propanoate To a solution of 309 mg of the before mentioned alcohol in DCM 1 g molecular sieve was added and the mixture cooled to 10° C. 0.50 ml 2-methoxy-N-(2-methoxyethyl)-N-(trifluoro-lambda$^4$-sulfanyl)ethanamine (50%) was added and the resulting mixture stirred at RT until complete consumption of the starting material. The mixture was cooled down to 10° C., sat. NaHCO$_3$-solution was carefully added and the mixture stirred for 10 minutes. The organic phase was separated, washed with brine, dried with Na$_2$SO$_4$, filtered and evaporated to dryness. The resulting material was purified by chromatography using silica gel (gradient: hexane/EE) and subsequently by preparative HPLC to give 20 mg of the title compound.

(R/S) 3-{3-[(Cyclopentyl{4-[5-(fluoromethyl)pyridin-3-yl]phenyl}acetyl)amino]-2-methylphenyl}propanoic acid In analogy to example 1 ester cleavage of 20 mg tert.-butyl ester in 0.14 ml TFA and 0.41 ml DCM and subsequent purification via HPLC gave 10.4 mg of the title compound.
¹H NMR (300 MHz, DMSO-d₆) δ ppm 0.94-1.13 (m, 1 H) 1.32-1.78 (m, 6 H) 1.79-1.95 (m, 1 H) 2.02 (s, 3 H) 2.38-2.47 (m, 2 H) 2.61-2.69 (m, 1 H) 2.75-2.85 (m, 2 H) 3.50-3.59 (m, 1 H) 5.39-5.71 (m, 2 H) 7.03 (s, 3 H) 7.50-7.64 (m, 2 H) 7.68-7.81 (m, 2 H) 8.11-8.23 (m, 1 H) 8.57-8.70 (m, 1 H) 8.87-9.02 (m, 1 H) 9.42-9.64 (m, 1 H) 11.73-12.45 (m, 1 H).

Example 31

(R/S) 3-[3-({[4-(5-Chloropyridin-3-yl)phenyl](cyclopropyl)acetyl}amino)-2-methylphenyl]propanoic acid

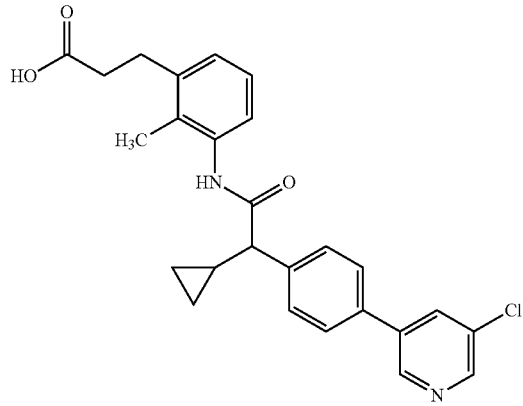 [SMILES: Cc1c(CCC(=O)O)cccc1NC(=O)C(c1ccc(-c2cncc(Cl)c2)cc1)C1CC1]

In analogy to example 1 reaction of 200 mg intermediate 4 with 99.9 mg (5-chloropyridin-3-yl)boronic acid followed by tert.-butyl ester cleavage and subsequent purification via HPLC gave 28.9 mg of the title compound.
¹H NMR (400 MHz, DMSO-d₆) δ ppm 0.15-0.26 (m, 1 H) 0.43-0.70 (m, 3 H) 1.46-1.57 (m, 1 H) 2.08 (s, 3 H) 2.45 (t, 2 H) 2.83 (t, 2 H) 3.06 (d, 1 H) 6.95-7.15 (m, 3 H) 7.60 (d, 2 H) 7.78 (d, 2 H) 8.25 (t, 1 H) 8.61 (d, 1 H) 8.88 (d, 1 H) 9.47 (s, 1 H) 11.66-12.60 (m, 1 H).

Example 32

(R/S) 3-{3-[(Cyclopropyl{4-[5-(trifluoromethyl)pyridin-3-yl]phenyl}acetyl)amino]-2-methylphenyl}propanoic acid

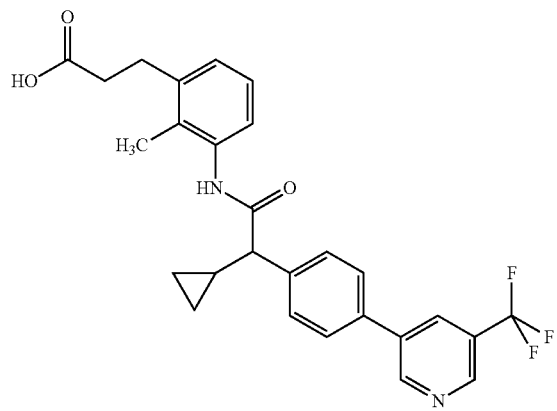 [SMILES: Cc1c(CCC(=O)O)cccc1NC(=O)C(c1ccc(-c2cncc(C(F)(F)F)c2)cc1)C1CC1]

In analogy to example 1 reaction of 200 mg intermediate 4 with 121.2 mg [5-(trifluoromethyl)pyridin-3-yl]boronic acid followed by tert.-butyl ester cleavage and subsequent purification via HPLC gave 50.3 mg of the title compound.
¹H NMR (400 MHz, METHANOL-d₄) δ ppm 0.30 (dd, 1 H) 0.55 (dd, 1 H) 0.67 (dd, 1 H) 0.72-0.82 (m, 1 H) 1.61 (d, 1 H) 2.15 (s, 3 H) 2.54 (t, 2 H) 2.95 (t, 2 H) 3.02 (d, 1 H) 7.05-7.17 (m, 3 H) 7.65-7.72 (m, 2 H) 7.72-7.80 (m, 2 H) 8.37 (br. s., 1 H) 8.85 (s, 1 H) 9.10 (s, 1 H).

Example 33

(R/S) {3-[(Cyclopentyl{4-[5-(trifluoromethyl)pyridin-3-yl]phenyl}acetyl)amino]-2-methylphenoxy}acetic acid

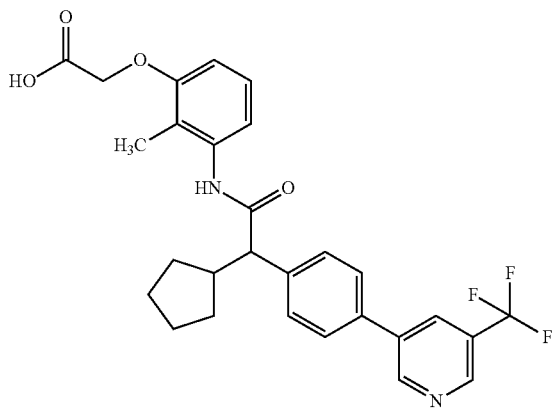 [SMILES: Cc1c(NC(=O)C(c2ccc(-c3cncc(C(F)(F)F)c3)cc2)C2CCCC2)cccc1OCC(=O)O]

Suzuki coupling condition in analogy to example 1 using 200 mg intermediate 6 and 103.3 mg [5-(trifluoromethyl)pyridin-3-yl]boronic acid followed by ester saponification in analogy to step 1.2 using MeOH as solvent and subsequent purification via HPLC gave 123.0 mg of the title compound.
¹H NMR (400 MHz, DMSO-d₆) δ ppm 0.97-1.11 (m, 1 H) 1.33-1.75 (m, 6 H) 1.82-1.93 (m, 1 H) 1.99 (s, 3 H) 2.58-2.72 (m, 1 H) 3.57 (d, 1 H) 4.67 (s, 2 H) 6.67 (d, 1 H) 6.85 (d, 1 H) 7.04 (s, 1 H) 7.59 (d, 2 H) 7.83 (d, 2 H) 8.46 (s, 1 H) 8.95 (s, 1 H) 9.22 (d, 1 H) 9.55 (s, 1 H) 12.58-13.17 (m, 1 H).

Example 34

(−) {3-[(Cyclopentyl{4-[5-(trifluoromethyl)pyridin-3-yl]phenyl}acetyl)amino]-2-methylphenoxy}acetic acid

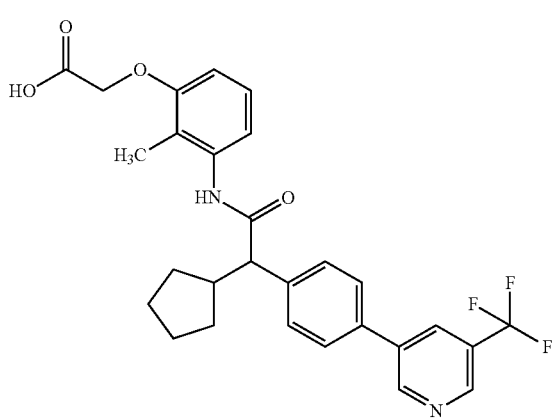 [SMILES: Cc1c(NC(=O)C(c2ccc(-c3cncc(C(F)(F)F)c3)cc2)C2CCCC2)cccc1OCC(=O)O]

123 mg racemic acid 33 were separated by preparative chiral HPLC (method 2; solvent: hexane/ethanol/formic acid (99%) 70:30:0.1 (v/v/v); flow rate: 30 ml/min; solution 123 mg/3.5 ml ethanol/DCM 1:1, injection: 5×0.7 ml) to yield 30 mg of the title compound (Rt: 6.6-7.8 min), together with 32 mg (+)-enantiomer 35 (Rt: 5.7-6.6 min).

Analytical HPLC, method 2: solvent: hexane/ethanol/formic acid (99%) 70:30:0.1 (v/v/v); flow rate: 1 ml/min; solution 1 mg/ml ethanol/methanol 1:1, injection: 5 μl; Rt: 4.88 min.

Optical rotation: −33.9° (6.6 mg/ml in DMSO, temperature: 20° C., wave length: 589 nM).

Example 35

(+) {3-[(Cyclopentyl{4-[5-(trifluoromethyl)pyridin-3-yl]phenyl}acetyl)amino]-2-methylphenoxy}acetic acid

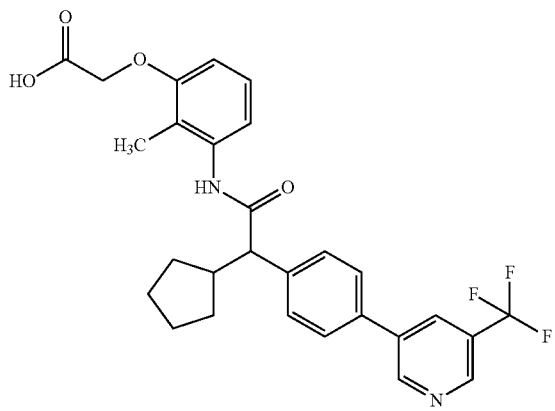 [SMILES: Cc1c(NC(=O)C(c2ccc(-c3cncc(C(F)(F)F)c3)cc2)C2CCCC2)cccc1OCC(=O)O]

123 mg racemic acid 33 were separated by preparative chiral HPLC (method 2; solvent: hexane/ethanol/formic acid (99%) 70:30:0.1 (v/v/v); flow rate: 30 ml/min; solution 123 mg/3.5 ml ethanol/DCM 1:1, injection: 5×0.7 ml) to yield 32 mg of the title compound (Rt: 5.7-6.6 min) together with 30 mg (−)-enantiomer 34.

Analytical HPLC, method 2: Rt: 4.13 min.

Optical rotation: +46.5° (5.8 mg/ml in DMSO, temperature: 20° C., wave length: 589 nM).

Example 36

(R/S) [3-({[4-(5-Chloropyridin-3-yl)phenyl](cyclopentyl)acetyl}amino)-2-methylphenoxy]acetic acid

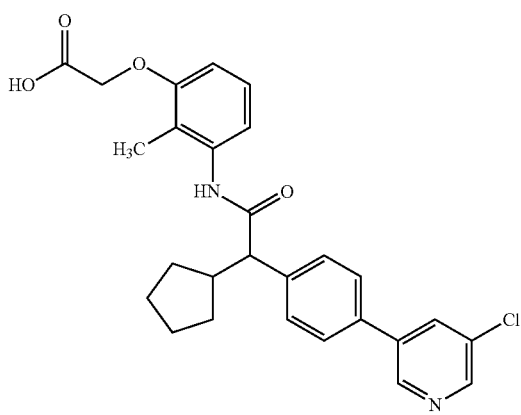

In analogy to example 33 reaction of 200 mg intermediate 6 with 65.1 (5-chloropyridin-3-yl)boronic acid followed by ester saponification and subsequent purification via HPLC gave 32.0 mg of the title compound.

$^1$H NMR (300 MHz, DMSO-$d_6$) δ ppm 0.90-1.11 (m, 1 H) 1.58 (m, 6 H) 1.79-1.93 (m, 1 H) 1.98 (s, 3 H) 2.57-2.70 (m, 1 H) 3.56 (d, 1 H) 4.55 (s, 2 H) 6.63 (d, 1 H) 6.81 (d, 1 H) 6.95-7.09 (m, 1 H) 7.56 (d, 2 H) 7.77 (d, 2 H) 8.25 (t, 1 H) 8.61 (d, 1 H) 8.88 (d, 1 H) 9.55 (s, 1 H).

Example 37

(−) [3-({[4-(5-Chloropyridin-3-yl)phenyl](cyclopentyl)acetyl}amino)-2-methylphenoxy]acetic acid

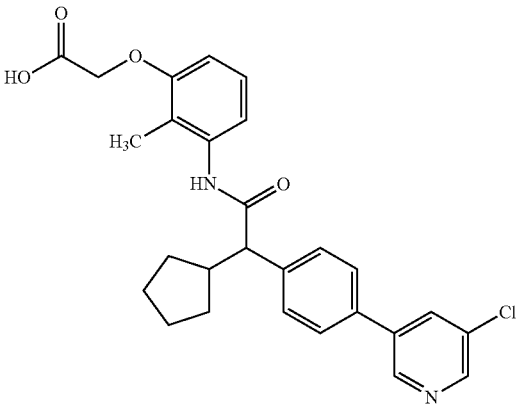 [SMILES: Cc1c(NC(=O)C(c2ccc(-c3cncc(Cl)c3)cc2)C2CCCC2)cccc1OCC(=O)O]

116 mg racemic acid 36 were separated by preparative chiral HPLC (method 2; solvent: hexane/ethanol/formic acid (99%) 70:30:0.1 (v/v/v); flow rate: 30 ml/min; solution 116 mg/3.6 ml ethanol/DCM 1:1, injection: 3×1.2 ml) to yield 41 mg of the title compound (Rt: 9.3-11.3 min) together with 43 mg (+)-enantiomer (Rt: 6.7-8.4 min).

Analytical HPLC, method 2: solvent: hexane/ethanol/formic acid (99%) 70:30:0.1 (v/v/v); flow rate: 1 ml/min; solution 1 mg/ml ethanol/methanol 1:1, injection: 5 μl; Rt: 7.63 min [(+)-enantiomer: 5.4 min].

Optical rotation: −42.7° (5.4 mg/ml in DMSO, temperature: 20° C., wave length: 589 nM).

Example 38

(R/S) 3-[3-({[4-(5-Chloropyridin-3-yl)phenyl](cyclopentyl)acetyl}amino)-6-methoxy-2-methylphenyl]propanoic acid

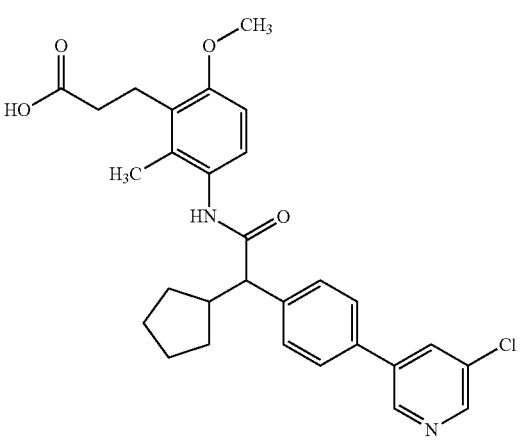 [SMILES: COc1ccc(NC(=O)C(c2ccc(-c3cncc(Cl)c3)cc2)C2CCCC2)c(C)c1CCC(=O)O]

In analogy to example 1 reaction of 612 mg intermediate 7 with 272 mg (5-chloropyridin-3-yl)boronic acid followed by tert.-butyl ester cleavage and subsequent purification by chromatography using silica gel (gradient: hexane/EE) gave 540 mg of the title compound.

¹H NMR (400 MHz, DMSO-d₆) δ ppm 0.95-1.08 (m, 1 H) 1.34-1.73 (m, 6 H) 1.80-1.94 (m, 1 H) 2.00 (s, 3 H) 2.27 (d, 2 H) 2.57-2.70 (m, 1 H) 2.80 (br. s., 2 H) 3.50 (d, 1 H) 3.74 (s, 3 H) 6.75 (d, 1 H) 6.94 (d, 1 H) 7.55 (d, 2 H) 7.77 (d, 2 H) 8.25 (t, 1 H) 8.61 (d, 1 H) 8.88 (d, 1 H) 9.42 (s, 1 H) 11.62-12.47 (m, 1 H).

Example 39

(−) 3-[3-({[4-(5-Chloropyridin-3-yl)phenyl](cyclopentyl)acetyl}amino)-6-methoxy-2-methylphenyl]propanoic acid

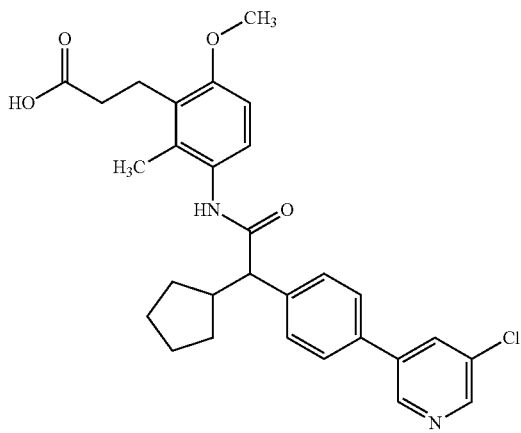 [SMILES: COc1ccc(NC(=O)C(c2ccc(-c3cncc(Cl)c3)cc2)C2CCCC2)c(C)c1CCC(=O)O]

540 mg racemic acid 38 were separated by preparative chiral HPLC (method 2; solvent: ethanol/methanol/formic acid (99%) 50:50:0.1 (v/v/v); flow rate: 40 ml/min; solution 540 mg/16 ml methanol/DCM, injection: 8×2 ml) to yield 200 mg of the title compound (Rt: 8.8-12.3 min) together with 180 mg (+)-enantiomer (Rt: 6.2-8.0 min).

Analytical HPLC, method 3: solvent: ethanol/methanol/formic acid (99%) 50:50:0.1 (v/v/v); flow rate: 1 ml/min; solution 1 mg/ml ethanol/methanol 1:1, injection: 5 µl; Rt: 4.43 min [(+)-enantiomer: 2.9 min].

Optical rotation: −66.6° (10.2 mg/ml in methanol, temperature: 20° C., wave length: 589 nM).

Example 40

(R/S) 3-{3-[(Cyclopentyl{4-[5-(trifluoromethyl)pyridin-3-yl]phenyl}acetyl)amino]-6-methoxy-2-methylphenyl}propanoic acid

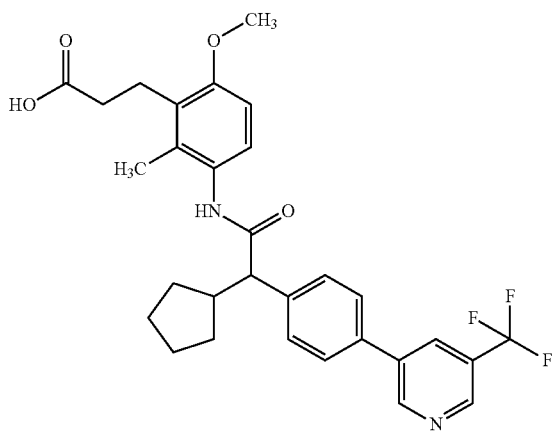 [SMILES: COc1ccc(NC(=O)C(c2ccc(-c3cncc(C(F)(F)F)c3)cc2)C2CCCC2)c(C)c1CCC(=O)O]

In analogy to example 1 reaction of 150 mg intermediate 7 with 116 mg 3-(4,4,5,5-tetramethyl-1,3,2-dioxaborolan-2-yl)-5-(trifluoromethyl)pyridine followed by tert.-butyl ester cleavage and subsequent via HPLC gave 43 mg of the title compound.

¹H NMR (300 MHz, DMSO-d₆) δ ppm 0.92-1.11 (m, 1 H) 1.32-1.74 (m, 6 H) 1.80-1.94 (m, 1 H) 2.00 (s, 3 H) 2.18-2.32 (m, 2 H) 2.57-2.69 (m, 1 H) 2.78 (d, 2 H) 3.51 (d, 1 H) 3.74 (s, 3 H) 6.75 (d, 1 H) 6.94 (d, 1 H) 7.58 (d, 2 H) 7.83 (d, 2 H) 8.47 (s, 1 H) 8.96 (s, 1 H) 9.23 (d, 1 H) 9.46 (s, 1 H) 10.62-12.39 (m, 1 H).

Example 41

(R/S) 3-{3-[(Cyclopentyl{3-methyl-4-[5-(trifluoromethyl)pyridin-3-yl]phenyl}acetyl)amino]-2-methylphenyl}propanoic acid

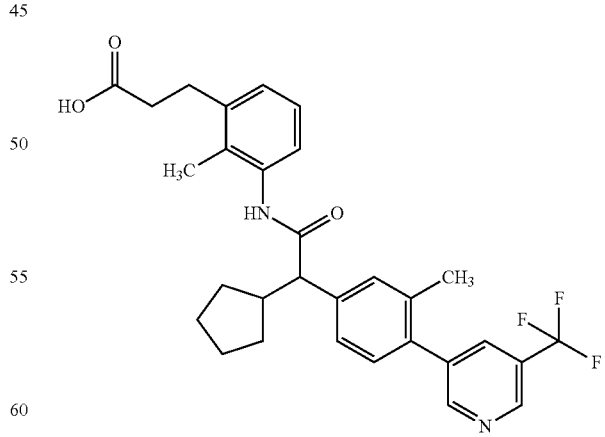

In analogy to example 1 reaction of 200 mg bromide intermediate 8 with 106 mg 3-(4,4,5,5-tetramethyl-1,3,2-dioxaborolan-2-yl)-5-(trifluoromethyl)pyridine followed by tert.-butyl ester cleavage and subsequent via HPLC gave 84 mg of the title compound.

¹H NMR (400 MHz, DMSO-d₆) δ ppm 1.01-1.11 (m, 1 H) 1.35-1.73 (m, 6 H) 1.81-1.93 (m, 1 H) 2.06 (s, 3 H) 2.27 (s, 3 H) 2.45 (br. s., 2 H) 2.59-2.69 (m, 1 H) 2.82 (br. s., 2 H) 3.51 (s, 1 H) 6.96-7.03 (m, 1 H) 7.04-7.09 (m, 2 H) 7.30 (d, 1 H) 7.41 (d, 2 H) 8.23 (s, 1 H) 8.90 (d, 1 H) 8.97 (d, 1 H) 9.51 (s, 1 H) 12.05-12.20 (m, 1 H).

Example 42

(R/S) 3-[3-({[4-(5-Chloropyridin-3-yl)-3-methylphenyl](cyclopentyl)acetyl}amino)-2-methylphenyl]propanoic acid

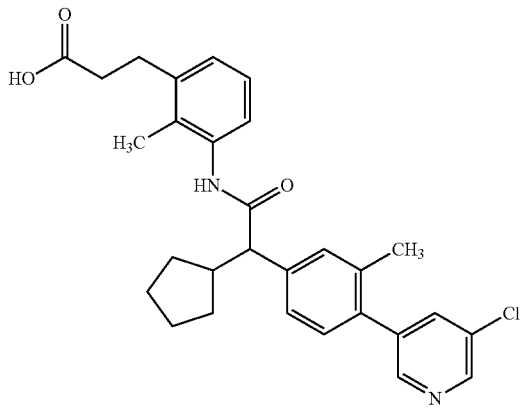 [SMILES: Cc1cc(C(C(=O)Nc2cccc(CCC(=O)O)c2C)C2CCCC2)ccc1-c1cncc(Cl)c1]

In analogy to example 1 reaction of 200 mg intermediate 8 with 76 mg (5-chloropyridin-3-yl)boronic acid followed by tert.-butyl ester cleavage and subsequent via HPLC gave 48 mg of the title compound.

¹H NMR (300 MHz, DMSO-d₆) δ ppm 0.96-1.11 (m, 1 H) 1.59 (m, 6 H) 1.80-1.94 (m, 1 H) 2.05 (s, 3 H) 2.27 (s, 3 H) 2.40-2.48 (m, 2 H) 2.56-2.70 (m, 1 H) 2.82 (t, 2 H) 3.51 (d, 1 H) 6.93-7.10 (m, 3 H) 7.25 (d, 1 H) 7.32-7.45 (m, 2 H) 7.99 (t, 1 H) 8.54 (d, 1 H) 8.63 (d, 1 H) 9.50 (s, 1 H) 11.91-12.42 (m, 1 H).

Example 43

(R/S) 3-[3-({[4-(5-Chloropyridin-3-yl)-3-fluorophenyl](cyclopentyl)acetyl}amino)-2-methylphenyl]propanoic acid

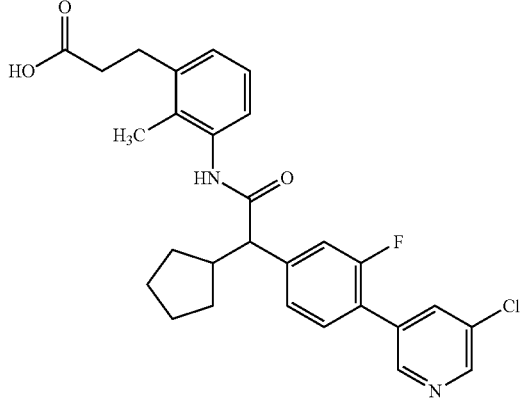 [SMILES: Cc1c(CCC(=O)O)cccc1NC(=O)C(c1ccc(-c2cncc(Cl)c2)c(F)c1)C1CCCC1]

In analogy to example 1 reaction of 150 mg intermediate 9 with 50 mg (5-chloropyridin-3-yl)boronic acid followed by tert.-butyl ester cleavage and subsequent via HPLC gave 66 mg of the title compound.

¹H NMR (300 MHz, DMSO-d₆) δ ppm 0.95-1.13 (m, 1 H) 1.32-1.76 (m, 6 H) 1.79-1.94 (m, 1 H) 2.04 (s, 3 H) 2.36-2.45 (m, 2 H) 2.56-2.68 (m, 1 H) 2.80 (t, 2 H) 3.59 (d, 1 H) 6.94-7.09 (m, 3 H) 7.34-7.48 (m, 2 H) 7.65 (t, 1 H) 8.16 (s, 1 H) 8.66 (d, 1 H) 8.74 (s, 1 H) 9.60 (s, 1 H).

Example 44

(−) 3-[3-({[4-(5-Chloropyridin-3-yl)-3-fluorophenyl](cyclopentyl)acetyl}amino)-2-methylphenyl]propanoic acid

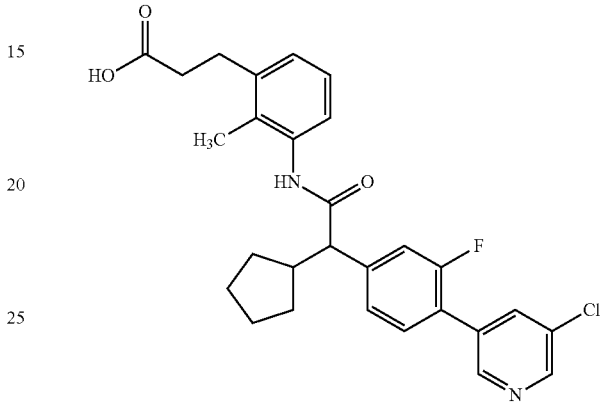

196 mg racemic acid 43 prepared from 300 mg intermediate 9 in analogy to example 43 were separated by preparative chiral HPLC (method 2; solvent: hexane/ethanol/formic acid (99%) 80:20:0.1 (v/v/v); flow rate: 50 ml/min; solution 196 mg/4 ml methanol/DCM, injection: 4×1 ml) to yield 65 mg of the title compound (Rt: 8.4-11.0 min) together with 78 mg (+)-enantiomer 45 (Rt: 7.0-8.4 min).

Analytical HPLC, method 3: solvent: hexane/ethanol/formic acid (99%) 70:30:0.1 (v/v/v); flow rate: 1 ml/min; solution 1 mg/ml ethanol/methanol 1:1, injection: 5 μl; Rt: 6.05 min.

Optical rotation: −23.1 (3.0 mg/ml in DMSO, temperature: 20° C., wave length: 589 nM).

Example 45

(+) 3-[3-({[4-(5-Chloropyridin-3-yl)-3-fluorophenyl](cyclopentyl)acetyl}amino)-2-methylphenyl]propanoic acid

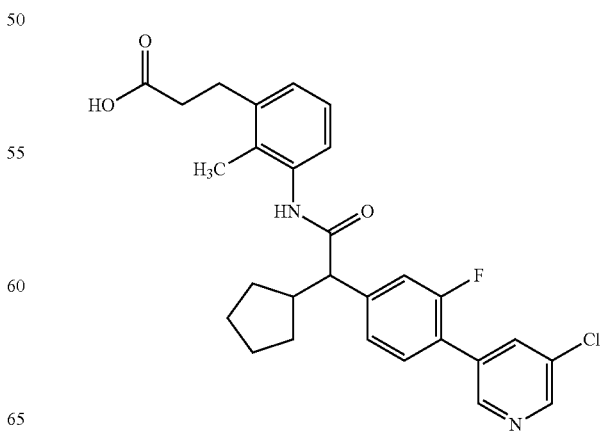

196 mg racemic acid 43 prepared from 300 mg intermediate 9 in analogy to example 43 were separated by preparative chiral HPLC (method 2; solvent: hexane/ethanol/formic acid (99%) 80:20:0.1 (v/v/v); flow rate: 50 ml/min; solution 196 mg/4 ml methanol/DCM, injection: 4×1 ml) to yield 78 mg of the title compound (Rt: 7.0-8.4 min) together with 65 mg (−)-enantiomer 44.

Analytical HPLC, method 3: Rt: 2.99 min.

Optical rotation: +20.5° (3.0 mg/ml in DMSO, temperature: 20° C., wave length: 589 nM).

Example 46

(R/S) 3-[3-({Cyclopentyl[4-(5-ethoxypyridin-3-yl)-3-fluorophenyl]acetyl}amino)-2-methylphenyl]propanoic acid

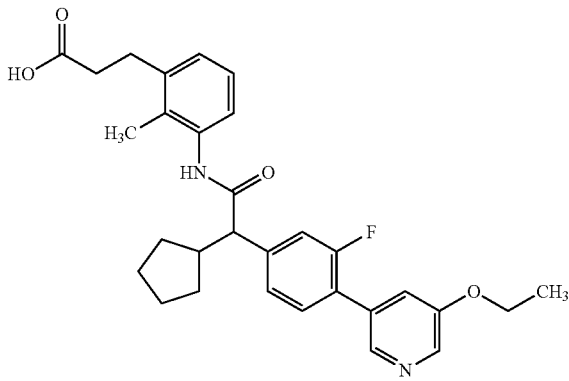 [SMILES: CCOc1cncc(-c2ccc(C(C(=O)Nc3cccc(CCC(=O)O)c3C)C3CCCC3)cc2F)c1]

In analogy to example 1 reaction of 150 mg intermediate 9 with 79 mg 3-ethoxy-5-(4,4,5,5-tetramethyl-1,3,2-dioxaborolan-2-yl)pyridine followed by tert.-butyl ester cleavage and subsequent via HPLC gave 28 mg of the title compound.

$^1$H NMR (400 MHz, DMSO-$d_6$) δ ppm 0.98-1.14 (m, 1 H) 1.30-1.74 (m, 9 H) 1.78-1.94 (m, 1 H) 2.05 (s, 3 H) 2.37-2.45 (m, 2 H) 2.57-2.69 (m, 1 H) 2.81 (t, 2 H) 3.58 (d, 1 H) 4.07-4.27 (m, 2 H) 6.94-7.12 (m, 3 H) 7.31-7.45 (m, 2 H) 7.47-7.65 (m, 2 H) 8.32 (d, 2 H) 9.57 (s, 1 H).

Example 47

(R/S) 3-{3-[(Cyclopentyl{3-fluoro-4-[5-(trifluoromethyl)pyridin-3-yl]phenyl}acetyl)amino]-2-methylphenyl}propanoic acid

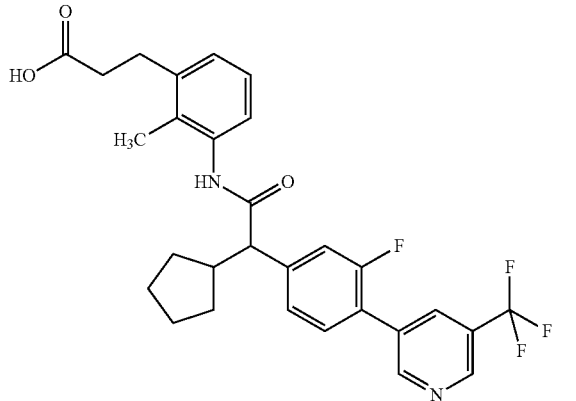 [SMILES: Cc1c(CCC(=O)O)cccc1NC(=O)C(c1ccc(-c2cncc(C(F)(F)F)c2)c(F)c1)C1CCCC1]

In analogy to example 1 reaction of 150 mg intermediate 9 with 61 mg [5-(trifluoromethyl)pyridin-3-yl]boronic acid followed by tert.-butyl ester cleavage and subsequent via HPLC gave 30 mg of the title compound.

$^1$H NMR (400 MHz, DMSO-$d_6$) δ ppm 0.98-1.12 (m, 1 H) 1.33-1.74 (m, 6 H) 1.80-1.93 (m, 1 H) 2.00-2.07 (m, 3 H) 2.23 (m, 2 H) 2.56-2.66 (m, 1 H) 2.75 (d, 2 H) 3.59 (m, 1 H) 6.92-7.07 (m, 3 H) 7.36-7.49 (m, 2 H) 7.70 (s, 1 H) 8.39 (s, 1 H) 9.00 (s, 1 H) 9.09 (s, 1 H) 9.59 (s, 1 H).

Example 48

(−) 3-{3-[(Cyclopentyl{3-fluoro-4-[5-(trifluoromethyl)pyridin-3-yl]phenyl}acetyl)amino]-2-methylphenyl}propanoic acid

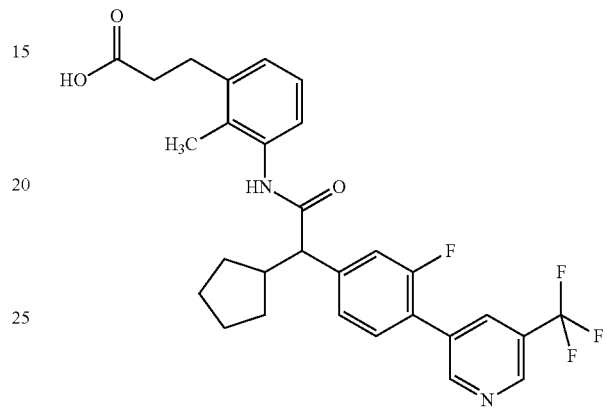

250 mg racemic acid 47 prepared from 300 mg intermediate 9 in analogy to example 47 were separated by preparative chiral HPLC (method 2; solvent: hexane/ethanol/formic acid (99%) 80:20:0.1 (v/v/v); flow rate: 50 ml/min; solution 250 mg/4.8 ml methanol/DCM, injection: 6×0.8 ml) to yield 65 mg of the title compound (Rt: 6.1-8.4 min) together with 70 mg (+)-enantiomer 49 (Rt: 5.3-6.1 min).

Analytical HPLC, method 3: solvent: hexane/ethanol/formic acid (99%) 70:30:0.1 (v/v/v); flow rate: 1 ml/min; solution 1 mg/ml ethanol/methanol 1:1, injection: 5 µl; Rt: 3.38 min.

Optical rotation: −24.9° (3.0 mg/ml in DMSO, temperature: 20° C., wave length: 589 nM).

Example 49

(+) 3-{3-[(Cyclopentyl{3-fluoro-4-[5-(trifluoromethyl)pyridin-3-yl]phenyl}acetyl)amino]-2-methylphenyl}propanoic acid

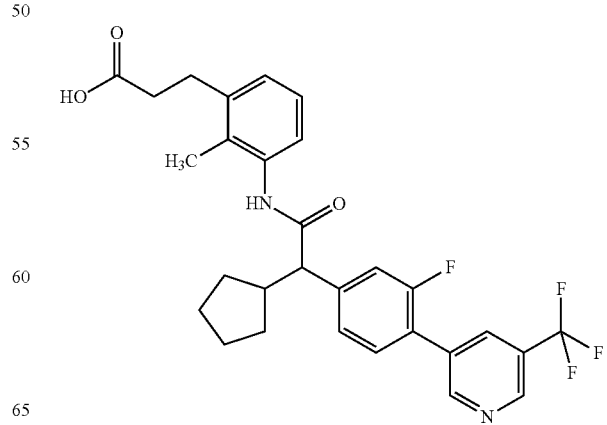

250 mg racemic acid 47 prepared from 300 mg intermediate 9 in analogy to example 47 were separated by preparative chiral HPLC (method 2; solvent: hexane/ethanol/formic acid (99%) 80:20:0.1 (v/v/v); flow rate: 50 ml/min; solution 250 mg/4.8 ml methanol/DCM, injection: 6×0.8 ml) to yield 70 mg of the title compound (Rt: 5.3-6.1 min) together with 65 mg (−)-enantiomer 48 (Rt: 6.1-8.4 min).

Analytical HPLC, method 3: Rt: 2.30 min.

Optical rotation: +22.8° (3.0 mg/ml in DMSO, temperature: 20° C., wave length: 589 nM).

Example 50

(R/S) 3-{3-[(cyclopentyl{4-[5-(difluoromethyl)pyridin-3-yl]-3-fluorophenyl}acetyl)amino]-2-methylphenyl}propanoic acid

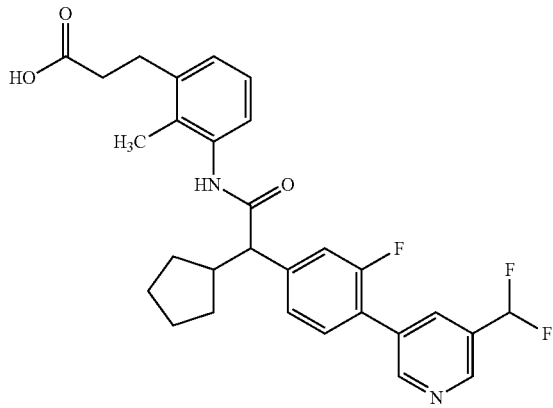 [SMILES: Cc1c(CCC(=O)O)cccc1NC(=O)C(c1ccc(-c2cncc(C(F)F)c2)c(F)c1)C1CCCC1]

In analogy to example 1 reaction of 75 mg intermediate 9 with 37.5 mg 5-difluoromethyl-pyridine-3-boronic acid followed by tert.-butyl ester cleavage and subsequent via HPLC gave 40 mg of the title compound.

$^1$H NMR (400 MHz, DMSO-d$_6$) δ ppm 0.96-1.11 (m, 1 H) 1.32-1.76 (m, 6 H) 1.81-1.93 (m, 1 H) 2.04 (s, 3 H) 2.44 (d, 2 H) 2.59-2.69 (m, 2 H) 2.80 (d, 2 H) 3.56-3.64 (m, 1 H) 6.97-7.09 (m, 4 H) 7.39-7.48 (m, 2 H) 7.66 (s, 1 H) 8.19 (s, 1 H) 8.82 (s, 1 H) 8.95 (s, 1 H) 9.60 (s, 1 H).

Example 51

(R/S) 3-[3-({[4-(5-Chloropyridin-3-yl)-2-fluorophenyl](cyclopentyl)acetyl}amino)-2-methylphenyl]propanoic acid

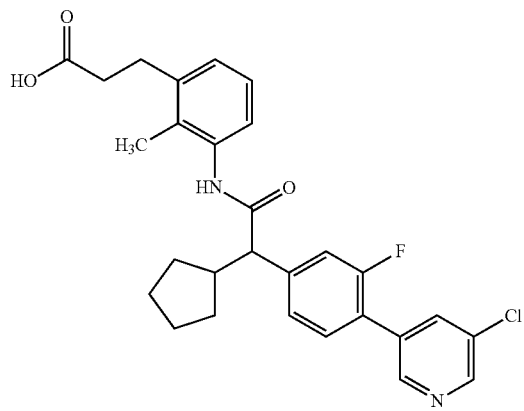 [SMILES: Cc1c(CCC(=O)O)cccc1NC(=O)C(c1ccc(-c2cncc(Cl)c2)c(F)c1)C1CCCC1]

In analogy to example 1 reaction of 150 mg intermediate 10 with 50 mg (5-chloropyridin-3-yl)boronic acid followed by tert.-butyl ester cleavage and subsequent via HPLC gave 53 mg of the title compound.

$^1$H NMR (400 MHz, DMSO-d$_6$) δ ppm 0.99-1.13 (m, 1 H) 1.44-1.65 (m, 5 H) 1.67-1.78 (m, 1 H) 1.81-1.93 (m, 1 H) 2.04 (s, 3 H) 2.33 (br. s., 2 H) 2.57-2.64 (m, 1 H) 2.78 (d, 2 H) 3.91 (d, 1 H) 7.02 (br. s., 3 H) 7.62-7.83 (m, 3 H) 8.32 (br. s., 1 H) 8.64 (s, 1 H) 8.92 (s, 1 H) 9.65 (br. s., 1 H).

Example 52

(R/S) 3-[3-({Cyclopentyl[4-(5-ethoxypyridin-3-yl)-2-fluorophenyl]acetyl}amino)-2-methylphenyl]propanoic acid

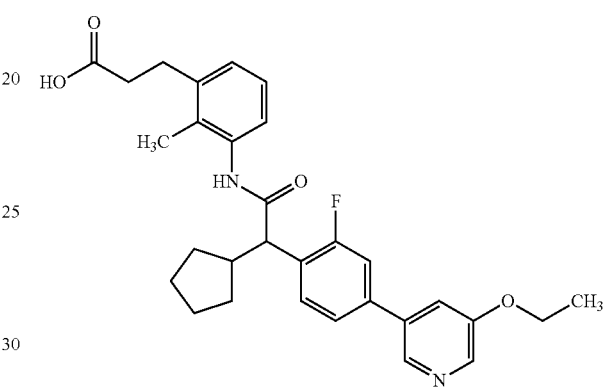

In analogy to example 1 reaction of 150 mg intermediate 10 with 79 mg 3-ethoxy-5-(4,4,5,5-tetramethyl-1,3,2-dioxaborolan-2-yl)pyridine followed by tert.-butyl ester cleavage and subsequent via HPLC gave 45 mg of the title compound.

$^1$H NMR (300 MHz, DMSO-d$_6$) δ ppm 1.07 (m, 1 H) 1.37 (t, 3 H) 1.42-1.77 (m, 6 H) 1.86 (m, 1 H) 2.05 (s, 3 H) 2.41 (t, 2 H) 2.58 (m, 1 H) 2.80 (t, 2 H) 3.90 (d, 1 H) 4.20 (q, 2 H) 6.97-7.09 (m, 3 H) 7.57-7.70 (m, 3 H) 7.71-7.81 (m, 1 H) 8.28 (d, 1 H) 8.52 (d, 1 H) 9.67 (s, 1 H).

Example 53

(R/S) 3-{3-[(Cyclopentyl{2-fluoro-4-[5-(trifluoromethyl)pyridin-3-yl]phenyl}acetyl)amino]-2-methylphenyl}propanoic acid

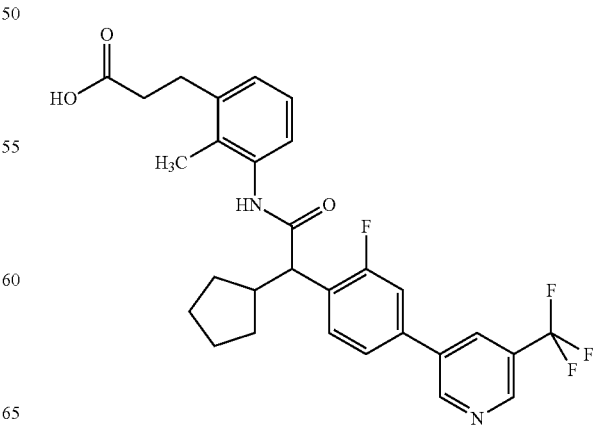

In analogy to example 1 reaction of 150 mg intermediate 10 with 61 mg [5-(trifluoromethyl)pyridin-3-yl]boronic acid followed by tert.-butyl ester cleavage and subsequent via HPLC gave 16 mg of the title compound.

$^1$H NMR (400 MHz, DMSO-d$_6$) δ ppm 1.07 (m, 1 H) 1.43-1.65 (m, 5 H) 1.71 (m, 1 H) 1.87 (m, 1 H) 2.03 (d, 3 H) 2.23 (br. s., 2 H) 2.59 (m, 1 H) 2.74 (d, 2 H) 3.92 (d, 1 H) 6.93-7.06 (m, 3 H) 7.72 (d, 1 H) 7.79 (d, 2 H) 8.53 (br. s., 1 H) 8.98 (br. s., 1 H) 9.26 (s, 1 H) 9.65 (s, 1 H).

Example 54

(R/S) 3-{3-[(Cyclobutyl{4-[5-(trifluoromethyl)pyridin-3-yl]phenyl}acetyl)amino]-2-methylphenyl}propanoic acid

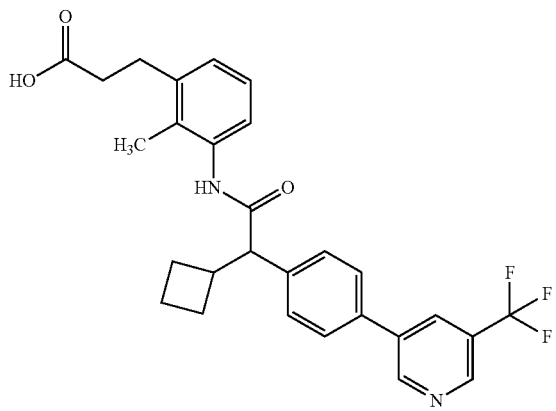 [SMILES: Cc1c(CCC(=O)O)cccc1NC(=O)C(c1ccc(-c2cncc(C(F)(F)F)c2)cc1)C1CCC1]

In analogy to example 1 reaction of 380 mg intermediate 11 with 217 mg [5-(trifluoromethyl)pyridin-3-yl]boronic acid followed by tert.-butyl ester cleavage and subsequent via HPLC gave 300 mg of the title compound.

$^1$H NMR (300 MHz, DMSO-d$_6$) δ ppm 1.52-1.71 (m, 1 H) 1.86 (m, 4 H) 2.03 (s, 3 H) 2.12 (s, 1 H) 2.35-2.45 (m, 2 H) 2.80 (d, 2 H) 2.93-3.14 (m, 1 H) 3.82 (s, 1 H) 6.96-7.12 (m, 3 H) 7.55 (d, 2 H) 7.83 (d, 2 H) 8.46 (s, 1 H) 8.95 (s, 1 H) 9.21 (s, 1 H) 9.58 (s, 1 H) 11.77-12.55 (m, 1 H)

Example 55

(−) 3-{3-[(Cyclobutyl{4-[5-(trifluoromethyl)pyridin-3-yl]phenyl}acetyl)amino]-2-methylphenyl}propanoic acid

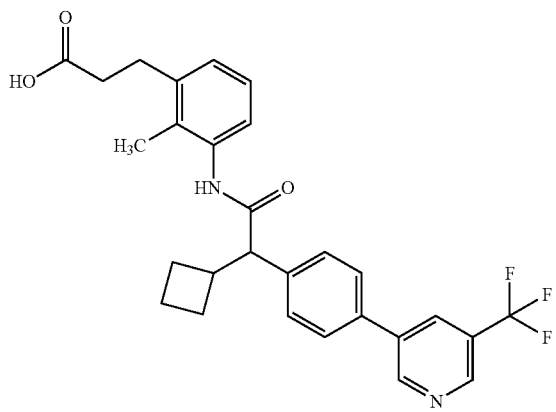 [SMILES: Cc1c(CCC(=O)O)cccc1NC(=O)C(c1ccc(-c2cncc(C(F)(F)F)c2)cc1)C1CCC1]

300 mg racemic acid 54 were separated by preparative chiral HPLC (method 2; solvent: hexane/ethanol/formic acid (99%) 70:30:0.1 (v/v/v); flow rate: 50 ml/min; solution 3000 mg/6 ml methanol/DCM, injection: 6×1.0 ml) to yield 91 mg of the title compound (Rt: 6.0-8.1 min) together with 91 mg (+)-enantiomer 56 (Rt: 4.7-6.0 min).

Analytical HPLC, method 3: solvent: hexane/ethanol/formic acid (99%) 70:30:0.1 (v/v/v); flow rate: 1 ml/min; solution 1 mg/ml ethanol/methanol 1:1, injection: 5 μl; Rt: 5.23 min.

Optical rotation: −56.8° (2.8 mg/ml in DMSO, temperature: 20° C., wave length: 589 nM).

Example 56

(+) 3-{3-[(Cyclobutyl{4-[5-(trifluoromethyl)pyridin-3-yl]phenyl}acetyl)amino]-2-methylphenyl}propanoic acid

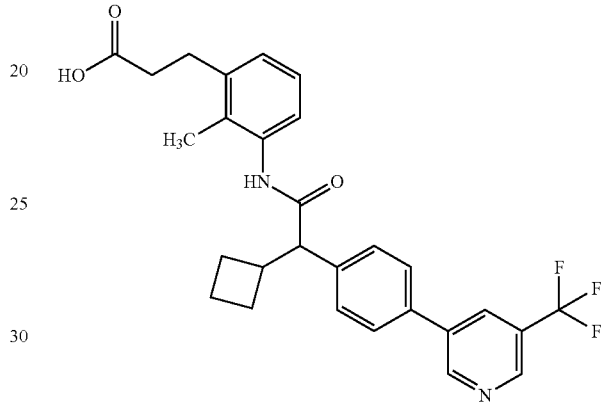

300 mg racemic acid 54 were separated by preparative chiral HPLC (method 2; solvent: hexane/ethanol/formic acid (99%) 70:30:0.1 (v/v/v); flow rate: 50 ml/min; solution 3000 mg/6 ml methanol/DCM, injection: 6×1.0 ml) to yield 91 mg of the title compound (Rt: 4.7-6.0 min) together with 91 mg (−)-enantiomer 55 (Rt: 6.0-8.1 min).

Analytical HPLC, method 3: Rt: 2.93 min.

Optical rotation: +54.1° (2.8 mg/ml in DMSO, temperature: 20° C., wave length: 589 nM).

Example 57

(R/S) 3-[3-({[4-(5-Chloropyridin-3-yl)phenyl](cyclobutyl)acetyl}amino)-2-methylphenyl]propanoic acid

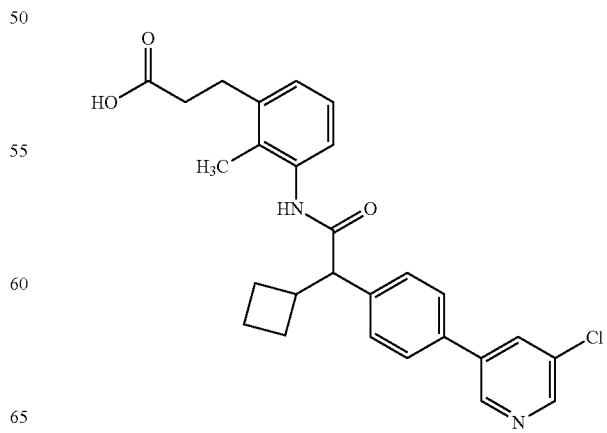

In analogy to example 1 reaction of 150 mg intermediate 11 with 52 mg (5-chloropyridin-3-yl)boronic acid followed by tert.-butyl ester cleavage and subsequent via HPLC gave 67 mg of the title compound.

$^1$H NMR (400 MHz, DMSO-d$_6$) δ ppm 1.56-1.69 (m, 1 H) 1.79-1.95 (m, 4 H) 2.03 (s, 3 H) 2.10-2.19 (m, 1 H) 2.42 (t, 2 H) 2.80 (t, 2 H) 2.98-3.10 (m, 1 H) 3.83 (d, 1 H) 6.97-7.06 (m, 3 H) 7.52 (d, 2 H) 7.76 (d, 2 H) 8.24 (t, 1 H) 8.60 (d, 1 H) 8.87 (d, 1 H) 9.55 (s, 1 H).

Example 58

(R/S) 3-[3-({Cyclobutyl[4-(5-ethoxypyridin-3-yl)phenyl]acetyl}amino)-2-methylphenyl]propanoic acid

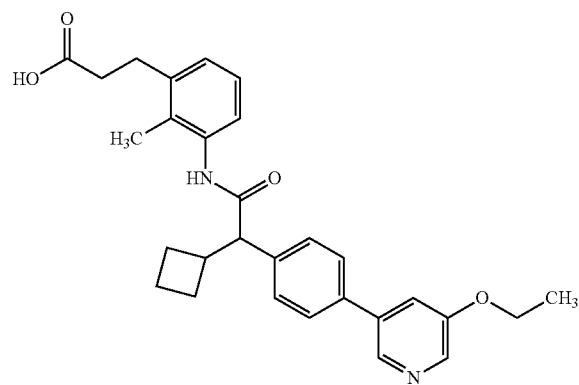 [SMILES: CCOc1cncc(-c2ccc(C(C(=O)Nc3cccc(CCC(=O)O)c3C)C3CCC3)cc2)c1]

In analogy to example 1 reaction of 150 mg intermediate 11 with 3-ethoxy-5-(4,4,5,5-tetramethyl-1,3,2-dioxaborolan-2-yl)pyridine followed by tert.-butyl ester cleavage and subsequent via HPLC gave 63 mg of the title compound.

$^1$H NMR (400 MHz, DMSO-d$_6$) δ ppm 1.37 (t, 3 H) 1.61 (m, 1 H) 1.86 (m, 4 H) 2.04 (s, 3 H) 2.14 (d, 1 H) 2.42 (t, 2 H) 2.80 (t, 2 H) 3.04 (br. s., 1 H) 3.82 (d, 1 H) 4.20 (q, 2 H) 6.97-7.08 (m, 3 H) 7.50 (d, 2 H) 7.60 (br. s., 1 H) 7.71 (d, 2 H) 8.25 (d, 1 H) 8.47 (s, 1 H) 9.54 (s, 1 H).

Example 59

(R/S) 3-[3-({Cyclobutyl[4-(5,6-dimethylpyridin-3-yl)phenyl]acetyl}amino)-2-methylphenyl]propanoic acid

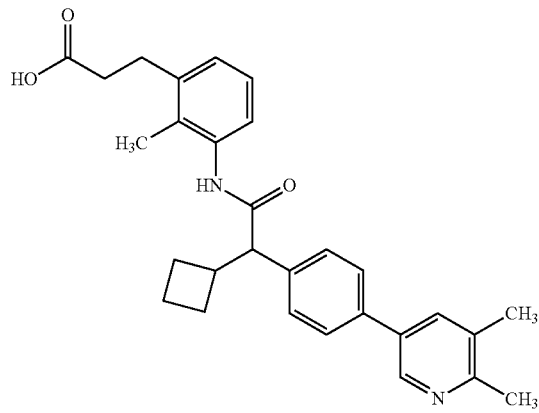 [SMILES: Cc1cc(-c2ccc(C(C(=O)Nc3cccc(CCC(=O)O)c3C)C3CCC3)cc2)cnc1C]

In analogy to example 1 reaction of 150 mg intermediate 11 with 86 mg 2,3-dimethyl-5-(4,4,5,5-tetramethyl-1,3,2-dioxaborolan-2-yl)pyridine followed by tert.-butyl ester cleavage and subsequent via HPLC gave 54 mg of the title compound.

$^1$H NMR (400 MHz, DMSO-d$_6$) δ ppm 1.54-1.68 (m, 1 H) 1.79-1.94 (m, 4 H) 2.03 (s, 3 H) 2.10-2.20 (m, 1 H) 2.31 (s, 3 H) 2.45 (s, 5 H) 2.75-2.89 (m, 2 H) 2.95-3.12 (m, 1 H) 3.72-3.89 (m, 1 H) 7.03 (s, 3 H) 7.49 (s, 2 H) 7.64 (s, 2 H) 7.76-7.88 (m, 1 H) 8.48-8.64 (m, 1 H) 9.46-9.61 (m, 1 H) 12.04-12.27 (m, 1 H).

Example 60

(R/S) 3-[3-({Cyclobutyl[4-(5-fluoropyridin-3-yl)phenyl]acetyl}amino)-2-methylphenyl]propanoic acid

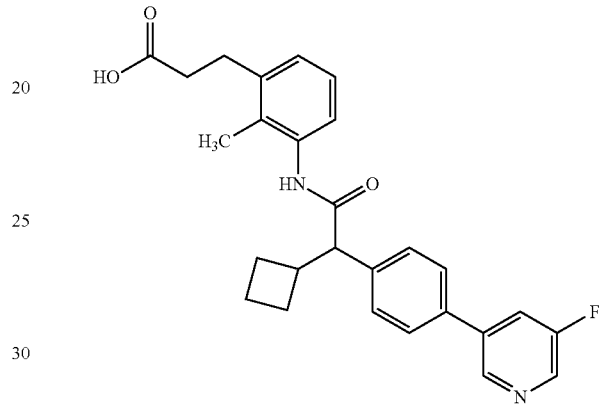

In analogy to example 1 reaction of 150 mg intermediate 11 with 87 mg (5-fluoropyridin-3-yl)boronic acid followed by tert.-butyl ester cleavage and subsequent via HPLC gave 60 mg of the title compound.

$^1$H NMR (300 MHz, DMSO-d$_6$) δ ppm 1.55-1.68 (m, 1 H) 1.85 (m, 4 H) 1.98-2.17 (m, 6 H) 2.72 (br. s., 2 H) 2.97-3.10 (m, 1 H) 3.78-3.87 (m, 1 H) 6.98 (s, 3 H) 7.52 (d, 2 H) 7.76 (d, 2 H) 8.01-8.13 (m, 1 H) 8.56 (d, 1 H) 8.80 (s, 1 H) 9.58 (s, 1 H).

Example 61

(R/S) 3-[3-({[4-(5-chloro-6-methylpyridin-3-yl)phenyl](cyclobutyl)acetyl}amino)-2-methylphenyl]propanoic acid

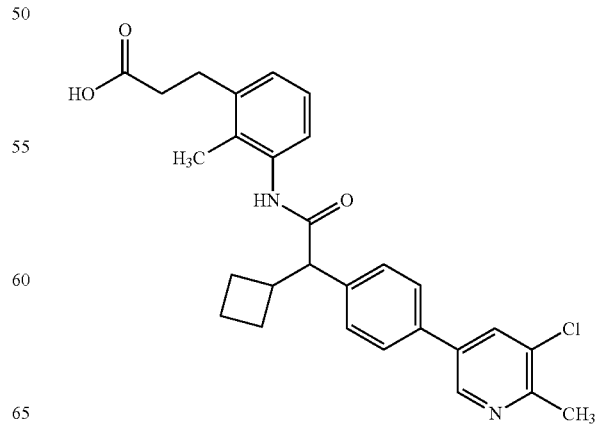

In analogy to example 1 reaction of 100 mg intermediate 11 with 78 mg 3-chloro-2-methyl-5-(4,4,5,5-tetramethyl-1,3,2-dioxaborolan-2-yl)pyridine followed by tert.-butyl ester cleavage and subsequent via HPLC gave 27.5 mg of the title compound.

$^1$H NMR (400 MHz, DMSO-d$_6$) δ ppm 1.54-1.68 (m, 1 H) 1.78-1.96 (m, 4 H) 2.03 (s, 3 H) 2.09-2.21 (m, 1 H) 2.44 (s, 2 H) 2.58 (s, 3 H) 2.81 (s, 2 H) 2.97-3.11 (m, 1 H) 3.77-3.85 (m, 1 H) 7.03 (m, 3 H) 7.50 (d, 2 H) 7.73 (d, 2 H) 8.16 (d, 1 H) 8.74 (d, 1 H) 9.55 (s, 1 H).

Example 62

(R/S) 3-[3-({[4-(5-Fluoro-6-methylpyridin-3-yl)phenyl](cyclobutyl)acetyl}amino)-2-methylphenyl]propanoic acid

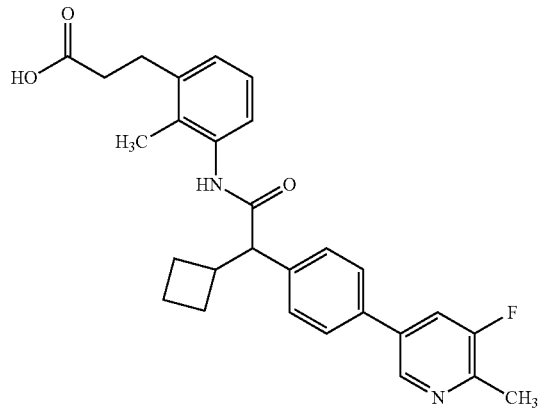 [SMILES: Cc1ncc(-c2ccc(C(C(=O)Nc3cccc(CCC(=O)O)c3C)C3CCC3)cc2)cc1F]

In analogy to example 1 reaction of 100 mg intermediate 11 with 48 mg (5-fluoro-6-methylpyridin-3-yl)boronic acid followed by tert.-butyl ester cleavage and subsequent via HPLC gave 20 mg of the title compound.

$^1$H NMR (400 MHz, DMSO-d$_6$) δ ppm 1.56-1.66 (m, 1 H) 1.87 (m, 4 H) 2.03 (s, 3 H) 2.09-2.21 (m, 1 H) 2.80 (d, 2 H) 2.96-3.10 (m, 1 H) 3.81 (d, 1 H) 6.93-7.09 (m, 3 H) 7.50 (d, 2 H) 7.72 (d, 2 H) 7.91-8.01 (m, 1 H) 8.65 (s, 1 H) 9.54 (s, 1 H).

Example 63

(R/S) 3-{3-[(Cyclobutyl{4-[5-(difluoromethoxy)pyridin-3-yl]phenyl}acetyl)amino]-2-methylphenyl}propanoic acid

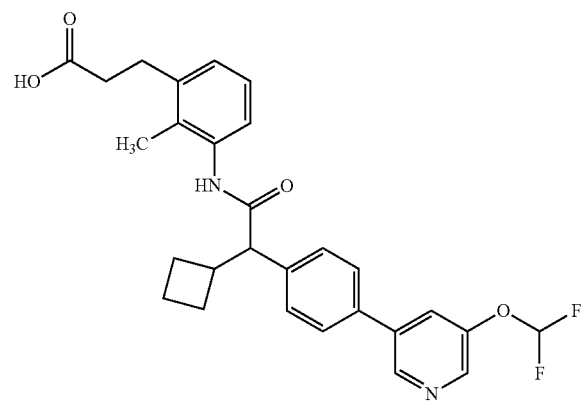 [SMILES: Cc1c(CCC(=O)O)cccc1NC(=O)C(c1ccc(-c2cncc(OC(F)F)c2)cc1)C1CCC1]

In analogy to example 1 reaction of 150 mg intermediate 11 with 116 mg potassium [5-(difluoromethoxy)pyridin-3-yl](trifluoro)borate followed by tert.-butyl ester cleavage and subsequent via HPLC gave 17.5 mg of the title compound.

$^1$H NMR (400 MHz, DMSO-d$_6$) δ ppm 1.57-1.68 (m, 1 H) 1.80-1.96 (m, 4 H) 2.03 (s, 3 H) 2.10-2.23 (m, 3 H) 2.69-2.79 (m, 2 H) 2.99-3.09 (m, 1 H) 3.78-3.87 (m, 1 H) 6.99 (m, 3 H) 7.43 (t, 1 H) 7.50-7.56 (m, 2 H) 7.70-7.79 (m, 2 H) 7.91-7.99 (m, 1 H) 8.43-8.51 (m, 1 H) 8.76-8.85 (m, 1 H) 9.50-9.59 (m, 1 H).

Example 64

(R/S) 3-[3-({Cyclobutyl[4-(5-methylpyridin-3-yl)phenyl]acetyl}amino)-2-methylphenyl]propanoic acid

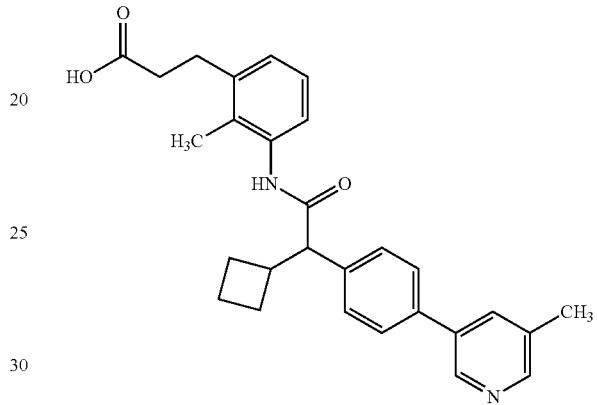

In analogy to example 1 reaction of 150 mg intermediate 11 with 84 mg (5-methylpyridin-3-yl)boronic acid followed by tert.-butyl ester cleavage and subsequent via HPLC gave 22 mg of the title compound.

$^1$H NMR (400 MHz, DMSO-d$_6$) δ ppm 1.55-1.66 (m, 1 H) 1.79-1.94 (m, 4 H) 2.03 (s, 3 H) 2.09-2.19 (m, 1 H) 2.36 (s, 3 H) 2.41-2.46 (m, 2 H) 2.76-2.85 (m, 2 H) 2.97-3.11 (m, 1 H) 3.76-3.85 (m, 1 H) 6.96-7.08 (m, 3 H) 7.47-7.54 (m, 2 H) 7.65-7.72 (m, 2 H) 7.84-7.92 (m, 1 H) 8.35-8.44 (m, 1 H) 8.64-8.72 (m, 1 H) 9.51-9.60 (m, 1 H) 11.99-12.33 (m, 1 H).

Example 65

(R/S) 3-[3-({[4-(5-Chloropyridin-3-yl)phenyl](cyclohexyl)acetyl}amino)-2-methylphenyl]propanoic acid

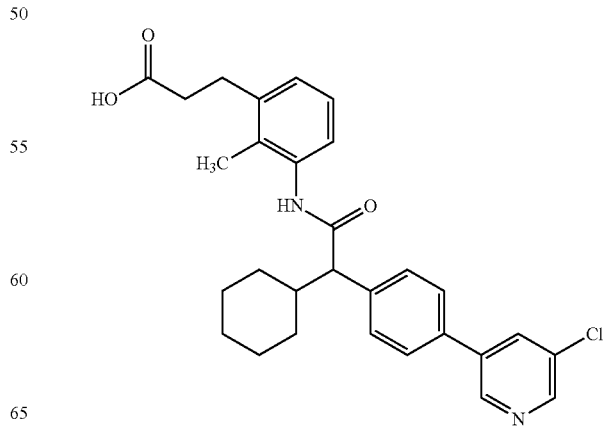

In analogy to example 1 reaction of 100 mg intermediate 12 with 33 mg (5-chloropyridin-3-yl)boronic acid followed by tert.-butyl ester cleavage and subsequent via HPLC gave 41 mg of the title compound.

$^1$H NMR (400 MHz, DMSO-d$_6$) δ ppm 0.73-0.89 (m, 1 H) 1.09-1.35 (m, 5 H) 1.60 (m, 2 H) 1.75 (d, 1 H) 1.90 (d, 1 H) 2.01 (s, 3 H) 2.07 (d, 1 H) 2.41 (t, 2 H) 2.79 (t, 2 H) 3.52 (d, 1 H) 6.94-7.08 (m, 3 H) 7.53 (d, 2 H) 7.76 (d, 2 H) 8.24 (s, 1 H) 8.60 (d, 1 H) 8.88 (s, 1 H) 9.53 (s, 1 H).

Example 66

(R/S) 3-{3-[(Cyclohexyl{4-[5-(trifluoromethyl)pyridin-3-yl]phenyl}acetyl)amino]-2-methylphenyl}propanoic acid

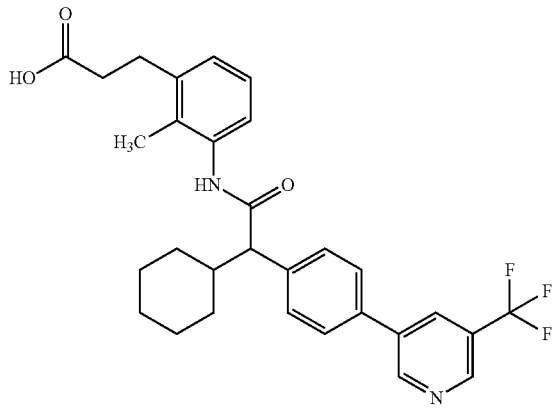 [SMILES: Cc1c(CCC(=O)O)cccc1NC(=O)C(c1ccc(-c2cncc(C(F)(F)F)c2)cc1)C1CCCCC1]

In analogy to example 1 reaction of 100 mg intermediate 12 with 40 mg [5-(trifluoromethyl)pyridin-3-yl]boronic acid followed by tert.-butyl ester cleavage and subsequent via HPLC gave 39 mg of the title compound.

$^1$H NMR (300 MHz, DMSO-d$_6$) δ ppm 0.73-0.90 (m, 1 H) 1.09-1.36 (m, 5 H) 1.60 (m, 2 H) 1.75 (d, 1 H) 1.90 (d, 1 H) 1.97-2.14 (m, 4 H) 2.37-2.45 (m, 2 H) 2.79 (t, 2 H) 3.53 (d, 1 H) 6.93-7.10 (m, 3 H) 7.56 (d, 2 H) 7.83 (d, 2 H) 8.47 (br. s., 1 H) 8.95 (s, 1 H) 9.22 (s, 1 H) 9.57 (s, 1 H).

Example 67

(R/S) 3-[3-({Cyclohexyl[4-(5-ethoxypyridin-3-yl)phenyl]acetyl}amino)-2-methylphenyl]propanoic acid

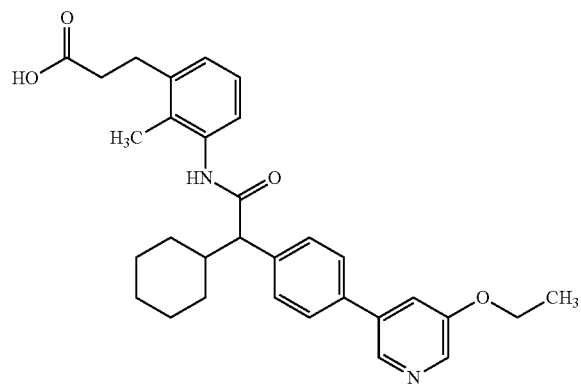 [SMILES: CCOc1cncc(-c2ccc(C(C(=O)Nc3cccc(CCC(=O)O)c3C)C3CCCCC3)cc2)c1]

In analogy to example 1 reaction of 100 mg intermediate 12 with 52 mg 3-ethoxy-5-(4,4,5,5-tetramethyl-1,3,2-dioxaborolan-2-yl)pyridine followed by tert.-butyl ester cleavage and subsequent via HPLC gave 36 mg of the title compound.

$^1$H NMR (300 MHz, DMSO-d$_6$) δ ppm 0.71-0.89 (m, 1 H) 1.09-1.41 (m, 8 H) 1.60 (br. s., 2 H) 1.74 (m, 1 H) 1.83-1.95 (m, 1 H) 2.01 (m, 4 H) 2.36-2.46 (m, 2 H) 2.79 (t, 2 H) 3.50 (d, 1 H) 4.19 (q, 2 H) 6.95-7.09 (m, 3 H) 7.51 (d, 2 H) 7.61 (br. s., 1 H) 7.72 (d, 2 H) 8.25 (d, 1 H) 8.47 (s, 1 H) 9.55 (s, 1 H).

Example 68

(2R/S)-3-(3-{[(2R/S)-2-Cyclopentyl-2-{4-[5-(trifluoromethyl)pyridin-3-yl]phenyl}acetyl]amino}-2-methylphenyl)-2-methylpropanoic acid

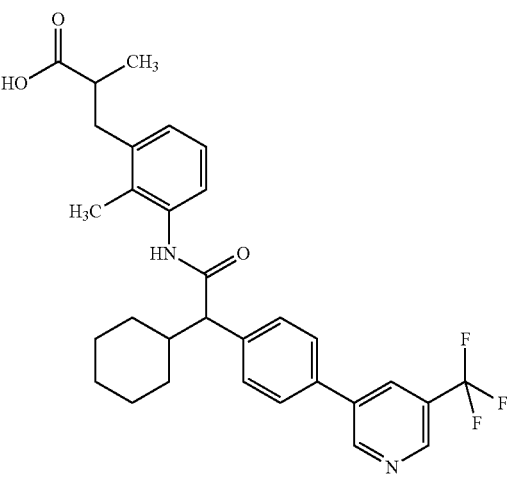 [SMILES: Cc1c(CC(C)C(=O)O)cccc1NC(=O)C(c1ccc(-c2cncc(C(F)(F)F)c2)cc1)C1CCCCC1]

In analogy to Suzuki coupling conditions in example 1 reaction of 150 mg intermediate 13 with 77 mg 3-(4,4,5,5-tetramethyl-1,3,2-dioxaborolan-2-yl)-5-(trifluoromethyl)pyridine followed by ethyl ester saponification using 2N NaOH in ethanol in analogy to step 1.2 and subsequent purification via HPLC gave 21 mg of the title compound.

$^1$H NMR (400 MHz, DMSO-d$_6$) δ ppm 0.98-1.09 (m, 4 H) 1.34-1.77 (m, 6 H) 1.82-1.95 (m, 1 H) 2.03 (d, 3 H) 2.53-2.60 (m, 2 H) 2.61-2.71 (m, 1 H) 2.86-3.01 (m, 1 H) 3.56 (d, 1 H) 6.91-6.99 (m, 1 H) 7.00-7.10 (m, 2 H) 7.59 (d, 2 H) 7.83 (d, 2 H) 8.46 (s, 1 H) 8.95 (s, 1 H) 9.22 (d, 1 H) 9.53 (s, 1 H) 11.14-12.12 (m, 1 H).

Example 69
3-{3-[(Cyclopentyl{4-[5-(trifluoromethyl)pyridin-3-yl]phenyl}acetyl)amino]-2-methylphenyl}-2-methyl-propanoic acid, Stereoisomer 1

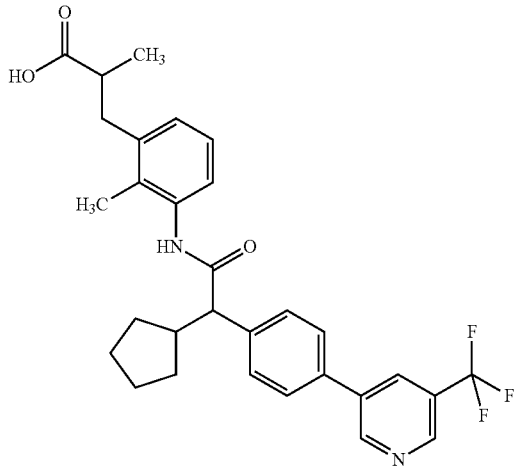 [SMILES: Cc1c(CC(C)C(=O)O)cccc1NC(=O)C(c1ccc(-c2cncc(C(F)(F)F)c2)cc1)C1CCCC1]

In analogy to Suzuki coupling conditions in example 1 reaction of 250 mg intermediate 13-2 with 384 mg [5-(trifluoromethyl)pyridin-3-yl]boronic acid followed by ethyl ester saponification with 0.52 g NaOH (32%) in 4 ml ethanol/water (3:1) and subsequent purification via HPLC gave 270 mg of a mixture of the two diastereomers which were separated into the two stereoisomers 1 (6.4 mg, example 69) & 2 (7.4 mg, example 70) via preparative chiral HPLC (method 2; solvent: hexane/ethanol 75:25 (v/v)+0.1% formic acid; flow rate: 15.5 ml/min; solution: 42 mg/1.5 mL DCM/MeOH; injection: 5×0.3 ml).

Preparative chiral HPLC: Rt: 6.0-6.8 min.

Analytical HPLC, method 4: solvent: hexane/ethanol 74:26 (v/v)+0.1% TFA; flow rate: 1 ml/min; solution 1 mg/ml ethanol/methanol 1:1, injection: 5 µl; Rt: 2.66 min.

Optical rotation: +15.5° (3.1 mg/ml DMSO, temperature: 20° C., wave length: 589 nM).

$^1$H NMR (400 MHz, DMSO-$d_6$) δ ppm 1.02 (d, 4 H) 1.33-1.77 (m, 6 H) 1.83-1.93 (m, 1 H) 2.03 (s, 3 H) 2.61-2.69 (m, 1 H) 2.89-2.99 (m, 1 H) 3.52-3.60 (m, 1 H) 6.92-6.99 (m, 1 H) 7.04 (m, 2 H) 7.59 (d, 2 H) 7.83 (d, 2 H) 8.43-8.49 (m, 1 H) 8.93-8.98 (m, 1 H) 9.20-9.25 (m, 1 H) 9.51-9.57 (m, 1 H).

Example 70
3-{3-[(Cyclopentyl{4-[5-(trifluoromethyl)pyridin-3-yl]phenyl}acetyl)amino]-2-methylphenyl}-2-methyl-propanoic acid, Stereoisomer 2

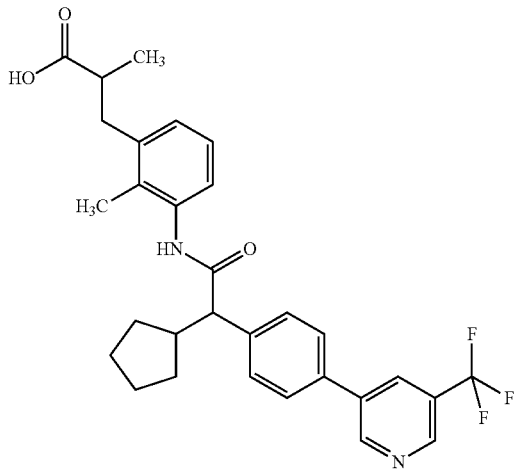 [SMILES: Cc1c(CC(C)C(=O)O)cccc1NC(=O)C(c1ccc(-c2cncc(C(F)(F)F)c2)cc1)C1CCCC1]

In analogy to Suzuki coupling conditions in example 1 reaction of 250 mg intermediate 13-2 with 384 mg [5-(trifluoromethyl)pyridin-3-yl]boronic acid followed by ethyl ester saponification with 0.52 g NaOH (32%) in 4 ml ethanol/water (3:1) and subsequent purification via HPLC gave 270 mg of a mixture of the two diastereomers which were separated into the two stereoisomers 1 (6.4 mg, example 69) & 2 (7.4 mg, example 70) via preparative chiral HPLC (method 2; solvent: hexane/ethanol 75:25 (v/v)+0.1% formic acid; flow rate: 15.5 ml/min; solution: 42 mg/1.5 mL DCM/MeOH; injection: 5×0.3 ml).

Preparative chiral HPLC: Rt: 7.7-8.8 min.

Analytical HPLC, method 4: solvent: hexane/ethanol 74:26 (v/v)+0.1% TFA; flow rate: 1 ml/min; solution 1 mg/ml ethanol/methanol 1:1, injection: 5 µl; Rt: 4.22 min.

$^1$H NMR (400 MHz, DMSO-$d_6$) δ ppm 1.03 (d, Hz, 4 H) 1.34-1.76 (m, 6 H) 1.82-1.94 (m, 1 H) 2.03 (s, 3 H) 2.63-2.69 (m, 1 H) 2.88-2.99 (m, 1 H) 3.52-3.59 (m, 1 H) 6.93-6.99 (m, 1 H) 7.04 (d, 2 H) 7.59 (d, 2 H) 7.83 (d, 2 H) 8.46 (s, 1 H) 8.95 (s, 1 H) 9.22 (d, 1 H) 9.54 (s, 1 H).

Example 71
3-{3-[(Cyclopentyl{4-[5-(trifluoromethyl)pyridin-3-yl]phenyl}acetyl)amino]-2-methylphenyl}-2-methyl-propanoic acid, Stereoisomer 3

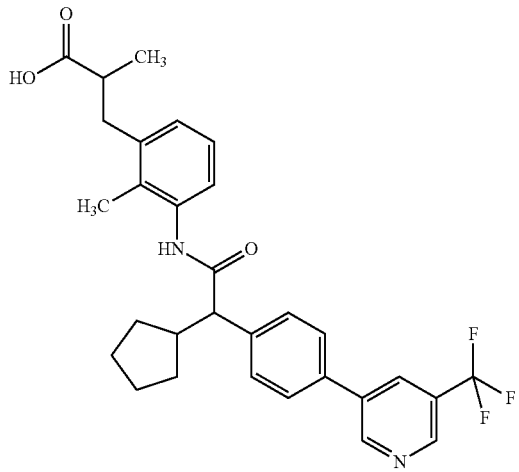 [SMILES: Cc1c(CC(C)C(=O)O)cccc1NC(=O)C(c1ccc(-c2cncc(C(F)(F)F)c2)cc1)C1CCCC1]

In analogy to Suzuki coupling conditions in example 1 reaction of 315 mg intermediate 13-1 with 148 mg [5-(trifluoromethyl)pyridin-3-yl]boronic acid followed by ethyl ester saponification with 0.63 g NaOH (32%) in 4.9 ml ethanol/water (3:1) and subsequent purification via HPLC gave 220 mg of a mixture of the two diastereomers which were separated into the two stereoisomers 3 (68 mg, example 71) & 4 (68 mg, example 72) via preparative chiral HPLC (method 4; solvent: hexane/2-propanol 76:24 (v/v)+0.1% formic acid; flow: 15 ml/min; solution: 176 mg/3 mL DCM/MeOH (1:1); injection: 15×0.2 ml).

Preparative chiral HPLC: Rt: 7.6-10.5 min.

Analytical HPLC, method 5: solvent: hexane/2-propanol 76:24 (v/v)+0.1% formic acid; flow rate: 1 ml/min; injection: 5 µl; Rt: 2.81 min.

Optical rotation: +43.8° (2.4 mg/ml DMSO, temperature: 20° C., wave length: 589 nM).

$^1$H NMR (400 MHz, DMSO-$d_6$) δ ppm 1.04 (d, 4 H) 1.35-1.74 (m, 6 H) 1.83-1.94 (m, 1 H) 2.03 (s, 3 H) 2.53-2.60

(m, 2 H) 2.62-2.69 (m, 1 H) 2.89-2.99 (m, 1 H) 3.52-3.61 (m, 1 H) 6.93-7.00 (m, 1 H) 7.02-7.07 (m, 2 H) 7.59 (d, 2 H) 7.83 (d, 2 H) 8.46 (s, 1 H) 8.95 (d, 1 H) 9.22 (d, 1 H) 9.53 (s, 1 H).

Example 72

3-{3-[(Cyclopentyl{4-[5-(trifluoromethyl)pyridin-3-yl]phenyl}acetyl)amino]-2-methylphenyl}-2-methylpropanoic acid, Stereoisomer 4

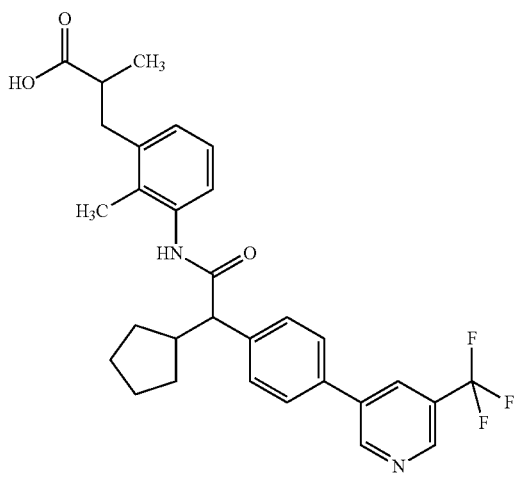 [SMILES: Cc1c(CC(C)C(=O)O)cccc1NC(=O)C(c1ccc(-c2cncc(C(F)(F)F)c2)cc1)C1CCCC1]

In analogy to Suzuki coupling conditions in example 1 reaction of 315 mg intermediate 13-1 with 148 mg [5-(trifluoromethyl)pyridin-3-yl]boronic acid followed by ethyl ester saponification with 0.63 g NaOH (32%) in 4.9 ml ethanol/water (3:1) and subsequent purification via HPLC gave 220 mg of a mixture of the two diastereomers which were separated into the two stereoisomers 3 (68 mg, example 71) & 4 (68 mg, example 72) via preparative chiral HPLC (method 4; solvent: hexane/2-propanol 76:24 (v/v)+ 0.1% formic acid; flow: 15 ml/min; solution: 176 mg/3 mL DCM/MeOH (1:1); injection: 15×0.2 ml).

Preparative chiral HPLC: Rt: 12.6-15.5 min.

Analytical HPLC, method 5: solvent: hexane/2-propanol 76:24 (v/v)+0.1% formic acid; flow rate: 1 ml/min; injection: 5 µl; Rt: 5.04 min.

Optical rotation: −12.8° (3 mg/ml DMSO, temperature: 20° C., wave length: 589 nM).

$^1$H NMR (400 MHz, DMSO-$d_6$) δ ppm 1.03 (d, 4 H) 1.35-1.75 (m, 6 H) 1.83-1.94 (m, 1 H) 2.03 (s, 3 H) 2.54 (m, 2 H) 2.62-2.69 (m, 1 H) 2.89-2.99 (m, 1 H) 3.55 (d, 1 H) 6.93-6.99 (m, 1 H) 7.02-7.07 (m, 2 H) 7.59 (d, 2 H) 7.83 (d, 2 H) 8.46 (s, 1 H) 8.95 (d, 1 H) 9.22 (d, 1 H) 9.53 (s, 1 H).

Example 73

(2R/S)-3-[3-({(2R/S)-2-[4-(5-Chloropyridin-3-yl)phenyl]-2-cyclopentylacetyl}amino)-2-methylphenyl]-2-methylpropanoic acid

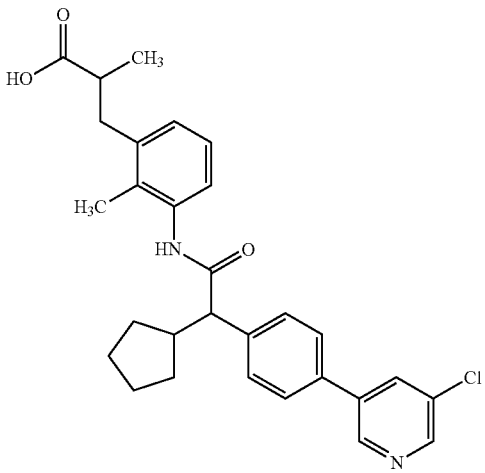 [SMILES: Cc1c(CC(C)C(=O)O)cccc1NC(=O)C(c1ccc(-c2cncc(Cl)c2)cc1)C1CCCC1]

In analogy to Suzuki coupling conditions in example 1 reaction of 150 mg intermediate 13 with 44 mg (5-chloropyridin-3-yl)boronic acid followed by ethyl ester saponification using 2N NaOH in ethanol in analogy to step 1.2 and subsequent purification via HPLC gave 22 mg of the title compound.

$^1$H NMR (400 MHz, DMSO-$d_6$) δ ppm 1.04 (m, 4 H) 1.34-1.74 (m, 6 H) 1.81-1.93 (m, 1 H) 2.03 (d, 3 H) 2.54 (m, 2 H) 2.61-2.69 (m, 1 H) 2.87-3.00 (m, 1 H) 3.50-3.60 (m, 1 H) 6.88-6.99 (m, 1 H) 7.04 (d, 2 H) 7.57 (d, 2 H) 7.77 (d, 2 H) 8.25 (s, 1 H) 8.61 (d1 H) 8.88 (d, 1 H) 9.52 (s, 1 H) 11.70-12.37 (m, 1 H).

Example 74

3-[3-[4-(5-Chloropyridin-3-yl)phenyl]-2-cyclopentylacetyl}amino)-2-methylphenyl]-2-methylpropanoic acid, Stereoisomer 1

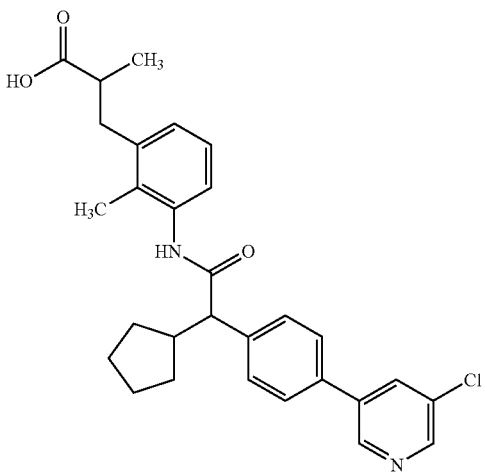 [SMILES: Cc1c(CC(C)C(=O)O)cccc1NC(=O)C(c1ccc(-c2cncc(Cl)c2)cc1)C1CCCC1]

In analogy to Suzuki coupling conditions in example 1 reaction of 250 mg intermediate 13-2 with 97 mg (5-chloropyridin-3-yl)boronic acid followed by ethyl ester saponification with 265 mg NaOH (32%) in 4 ml ethanol/water (3:1) and subsequent purification via HPLC gave 80 mg of a mixture of the two diastereomers which were separated into the two stereoisomers 1 (11.8 mg, example 74) & 2 (13.6 mg, example 75) via preparative chiral HPLC (method 4; solvent: hexane/ethanol 75:25 (v/v)+0.1% formic acid; flow rate: 15 ml/min; solution: 70 mg/2 mL DCM/MeOH (1:1); injection: 8×0.25 ml).

Preparative chiral HPLC: Rt: 7.0-9.5 min.

Analytical HPLC, method 4: solvent: hexane/ethanol 74:26 (v/v)+0.1% TFA; flow rate: 1 ml/min; solution 1 mg/ml ethanol/methanol (1:1), injection: 5 µl; Rt: 3.61 min.

Optical rotation: +15.5° (1.8 mg/ml DMSO, temperature: 20° C., wave length: 589 nM).

$^1$H NMR (400 MHz, DMSO-$d_6$) δ ppm 1.04 (d, 4 H) 1.34-1.76 (m, 6 H) 1.82-1.94 (m, 1 H) 2.03 (s, 3 H) 2.57-2.66 (m, 2 H) 2.87-2.99 (m, 1 H) 3.51-3.58 (m, 1 H) 6.92-6.99 (m, 1 H) 7.02-7.09 (m, 2 H) 7.56 (d, 2 H) 7.77 (d, 2 H) 8.25 (s, 1 H) 8.61 (s, 1 H) 8.88 (d, 1 H) 9.53 (s, 1 H) 11.98-12.24 (m, 1 H).

Example 75

3-[3-[4-(5-Chloropyridin-3-yl)phenyl]-2-cyclopentylacetyl}amino)-2-methylphenyl]-2-methylpropanoic acid, Stereoisomer 2

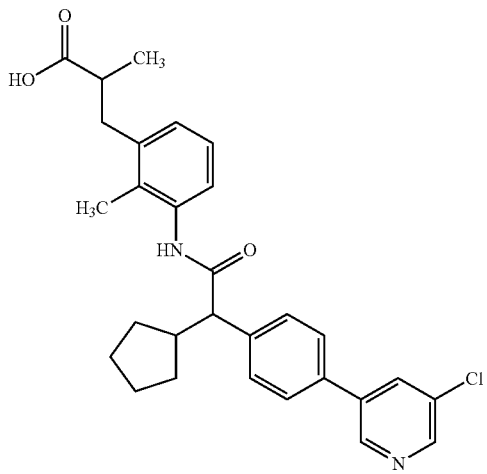 [SMILES: Cc1c(CC(C)C(=O)O)cccc1NC(=O)C(c1ccc(-c2cncc(Cl)c2)cc1)C1CCCC1]

In analogy to Suzuki coupling conditions in example 1 reaction of 250 mg intermediate 13-2 with 97 mg (5-chloropyridin-3-yl)boronic acid followed by ethyl ester saponification with 265 mg NaOH (32%) in 4 ml ethanol/water (3:1) and subsequent purification via HPLC gave 80 mg of a mixture of the two diastereomers which were separated into the two stereoisomers 2 (13.6 mg, example 75) & 1 (11.8 mg, example 74) via preparative chiral HPLC (method 4; solvent: hexane/ethanol 75:25 (v/v)+0.1% formic acid; flow rate: 15 ml/min; solution: 70 mg/2 mL DCM/MeOH (1:1); injection: 8×0.25 ml).

Preparative chiral HPLC: Rt: 11.5-15.5 min.

Analytical HPLC, method 4: solvent: hexane/ethanol 74:26 (v/v)+0.1% TFA; flow rate: 1 ml/min; solution 1 mg/ml ethanol/methanol (1:1), injection: 5 µl; Rt: 7.89 min.

Optical rotation: −43.8° (1.3 mg/ml DMSO, temperature: 20° C., wave length: 589 nM).

$^1$H NMR (400 MHz, DMSO-$d_6$) δ ppm 1.03 (d, 4 H) 1.34-1.76 (m, 6 H) 1.82-1.93 (m, 1 H) 2.02 (s, 3 H) 2.58-2.67 (m, 2 H) 2.88-2.99 (m, 1 H) 3.52-3.59 (m, 1 H) 6.93-6.99 (m, 1 H) 7.02-7.08 (m, 2 H) 7.56 (d, 2 H) 7.77 (d, 2 H) 8.25 (s, 1 H) 8.61 (d, 1 H) 8.88 (d, 1 H) 9.53 (s, 1 H).

Example 76

3-[3-[4-(5-Chloropyridin-3-yl)phenyl]-2-cyclopentylacetyl}amino)-2-methylphenyl]-2-methylpropanoic acid, Stereoisomer 3

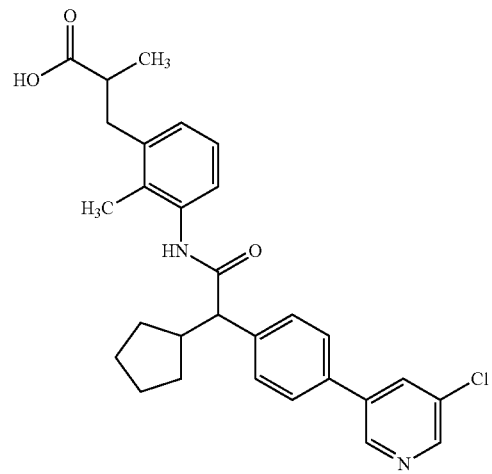 [SMILES: Cc1c(CC(C)C(=O)O)cccc1NC(=O)C(c1ccc(-c2cncc(Cl)c2)cc1)C1CCCC1]

In analogy to Suzuki coupling conditions in example 1 reaction of 315 mg intermediate 13-1 with 122 mg (5-chloropyridin-3-yl)boronic acid followed by ethyl ester saponification with 626 mg NaOH (32%) in 9.4 ml ethanol/water (3:1) and subsequent purification via HPLC gave 220 mg of a mixture of the two diastereomers which were separated into the two stereoisomers 3 (70 mg, example 76) & 4 (70 mg, example 77) via preparative chiral HPLC (method 4; solvent: hexane/ethanol 74:26 (v/v)+0.1% formic acid; flow rate: 15 ml/min; solution: 179 mg/3 mL DCM/MeOH (1:1); injection: 15×0.2 ml).

Preparative chiral HPLC: Rt: 7.0-9.5 min.

Analytical HPLC, method 5: solvent: hexane/ethanol 74:26 (v/v)+0.1% formic acid; flow rate: 1 ml/min; injection: 5 µl; Rt: 3.80 min.

Optical rotation: +39.1° (2.3 mg/ml DMSO, temperature: 20° C., wave length: 589 nM).

$^1$H NMR (400 MHz, DMSO-$d_6$) δ ppm 1.04 (d, 4 H) 1.36-1.74 (m, 6 H) 1.82-1.93 (m, 1 H) 2.03 (s, 3 H) 2.53-2.66 (m, 3 H) 2.88-2.99 (m, 1 H) 3.51-3.59 (m, 1 H) 6.93-6.99 (m, 1 H) 7.02-7.07 (m, 2 H) 7.56 (d, 2 H) 7.77 (d, 2 H) 8.21-8.28 (m, 1 H) 8.61 (d, 1 H) 8.88 (d, 1 H) 9.52 (s, 1 H).

Example 77

3-[3-[4-(5-Chloropyridin-3-yl)phenyl]-2-cyclopentylacetyl}amino)-2-methylphenyl]-2-methylpropanoic acid, Stereoisomer 4

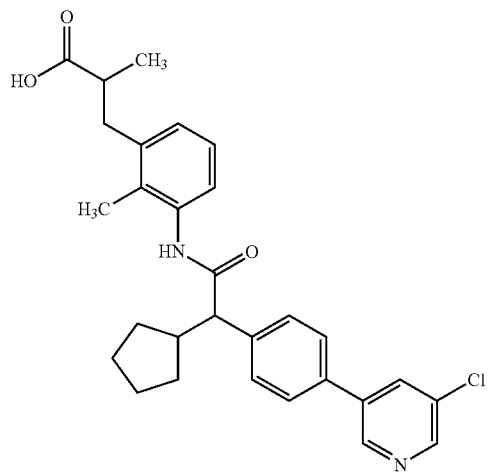 [SMILES: Cc1c(CC(C)C(=O)O)cccc1NC(=O)C(c1ccc(-c2cncc(Cl)c2)cc1)C1CCCC1]

In analogy to Suzuki coupling conditions in example 1 reaction of 315 mg intermediate 13-1 with 122 mg (5-chloropyridin-3-yl)boronic acid followed by ethyl ester saponification with 626 mg NaOH (32%) in 9.4 ml ethanol/water (3:1) and subsequent purification via HPLC gave 220 mg of a mixture of the two diastereomers which were separated into the two stereoisomers 4 (70 mg, example 77) & 3 (70 mg, example 76) via preparative chiral HPLC (method 4; solvent: hexane/ethanol 74:26 (v/v)+0.1% formic acid; flow rate: 15 ml/min; solution: 179 mg/3 mL DCM/MeOH (1:1); injection: 15×0.2 ml).

Preparative chiral HPLC: Rt: 11.5-15.5 min.

Analytical HPLC, method 5: solvent: hexane/ethanol 74:26 (v/v)+0.1% formic acid; flow rate: 1 ml/min; injection: 5 µl; Rt: 8.38 min.

Optical rotation: −15.5° (3.2 mg/ml DMSO, temperature: 20° C., wave length: 589 nM).

$^1$H NMR (400 MHz, DMSO-$d_6$) δ ppm 1.03 (d, 4 H) 1.34-1.74 (m, 6 H) 1.82-1.93 (m, 1 H) 2.03 (s, 3 H) 2.53 (m, 3 H) 2.90-2.99 (m, 1 H) 3.55 (d, 1 H) 6.93-6.99 (m, 1 H) 7.00-7.07 (m, 2 H) 7.56 (d, 2 H) 7.77 (d, 2 H) 8.25 (t, 1 H) 8.61 (d, 1 H) 8.88 (d, 1 H) 9.52 (s, 1 H).

Example 78

(2R/2S)-3-[3-({(2R/2S)-2-Cyclopentyl-2-[4-(5,6-dimethylpyridin-3-yl)phenyl]acetyl}amino)-2-methylphenyl]-2-methylpropanoic acid

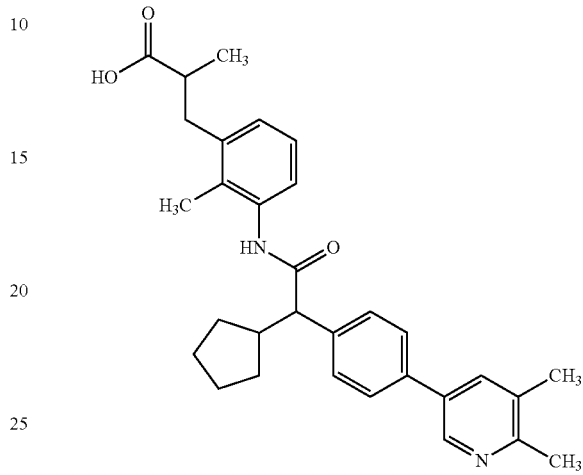

Step 78.1: (2E)-3-[3-({(2R)-2-Cyclopentyl-2-[4-(5,6-dimethylpyridin-3-yl)phenyl]acetyl}amino)-2-methylphenyl]-2-methylacrylic acid In analogy to Suzuki coupling conditions in example 1 reaction of 177 mg intermediate 14 with 127 mg 2,3-dimethyl-5-(4,4,5,5-tetramethyl-1,3,2-dioxaborolan-2-yl)pyridine followed by ethyl ester saponification with 195 mg NaOH (32%) in 6 ml ethanol/water (3:1) gave 50 mg of the title compound as major compound of a compound mixture.

Step 78.2: (2R/2S)-3-[3-({(2R/2S)-2-Cyclopentyl-2-[4-(5,6-dimethylpyridin-3-yl)phenyl]acetyl}amino)-2-methylphenyl]-2-methylpropanoic acid 50 mg crude methylacrylic acid 78.1 were dissolved in 10 ml THF/methanol 1:1, 50 mg palladium on charcoal (10%) were added and the reaction mixture stirred under 1 bar hydrogen atmosphere at RT until complete conversion. The catalyst was filtered off, the filtrate evaporated to dryness and purified via preparative HPLC to give 17.2 mg of the title compound.

$^1$H NMR (400 MHz, DMSO-$d_6$) δ ppm 1.03 (dd, 4 H) 1.33-1.75 (m, 6 H) 1.82-1.93 (m, 1 H) 2.03 (d, 3 H) 2.31 (s, 3 H) 2.45 (s, 3 H) 2.58-2.66 (m, 2 H) 2.87-2.99 (m, 1 H) 3.47-3.56 (m, 1 H) 6.93-6.98 (m, 1 H) 7.04 (s, 2 H) 7.52 (d, 2 H) 7.66 (d, 2 H) 7.78-7.85 (m, 1 H) 8.54-8.59 (m, 1 H) 9.44-9.55 (m, 1 H).

Example 79

(2R/2S)-3-[3-({(2R/2S)-2-Cyclopentyl-2-[4-(6-methylpyridin-3-yl)phenyl]acetyl}amino)-2-methylphenyl]-2-methylpropanoic acid

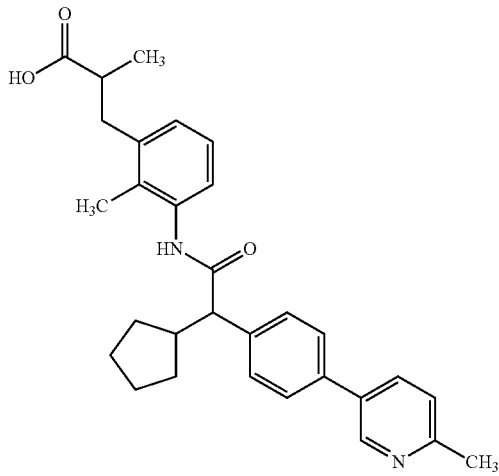 [SMILES: Cc1ccc(-c2ccc(C(C(=O)Nc3cccc(CC(C)C(=O)O)c3C)C3CCCC3)cc2)cn1]

Step 79.1: (2E)-3-[3-({(2R)-2-[4-(5-Chloro-6-methylpyridin-3-yl)phenyl]-2-cyclopentylacetyl}amino)-2-methylphenyl]-2-methylacrylic acid In analogy to Suzuki coupling conditions in example 1 reaction of 85 mg intermediate 14 with 66 mg 3-chloro-2-methyl-5-(4,4,5,5-tetramethyl-1,3,2-dioxaborolan-2-yl)pyridine followed by ethyl ester saponification with 164 mg NaOH (32%) in 6 ml ethanol/water (3:1) gave 58 mg of the title compound as major compound of a compound mixture.

Step 79.2: (2R/2S)-3-[3-({(2R/2S)-2-Cyclopentyl-2-[4-(6-methylpyridin-3-yl)phenyl]acetyl}amino)-2-methylphenyl]-2-methylpropanoic acid 58 mg crude methylacrylic acid 79.1 were dissolved in 10 ml THF/methanol 1:1, 50 mg palladium on charcoal (10%) were added and the reaction mixture stirred under 1 bar hydrogen atmosphere at RT until complete conversion. The catalyst was filtered off, the filtrate evaporated to dryness and purified via preparative HPLC to give 18 mg of the title compound.

$^1$H NMR (400 MHz, DMSO-$d_6$) δ ppm 1.03 (d, 4 H) 1.34-1.75 (m, 6 H) 1.79-1.93 (m, 1 H) 2.03 (d, 3 H) 2.56-2.65 (m, 3 H) 2.87-3.00 (m, 1 H) 3.47-3.58 (m, 1 H) 6.92-6.99 (m, 1 H) 7.04 (s, 2 H) 7.30-7.36 (m, 1 H) 7.54 (s, 2 H) 7.66 (s, 2 H) 7.92-8.01 (m, 1 H) 8.72-8.79 (m, 1 H) 9.47-9.57 (m, 1 H).

Example 80

(2R/2S)-3-(3-{[(2R/2S)-2-Cyclopentyl-2-{4-[5-(difluoromethoxy)pyridin-3-yl]phenyl}acetyl]amino}-2-methylphenyl)-2-methylpropanoic acid

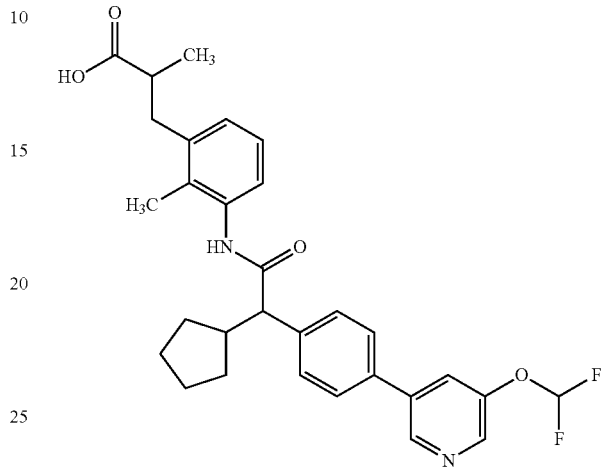

Step 80.1: (2E)-3-(3-{[(2R)-2-Cyclopentyl-2-{4-[5-(difluoromethoxy)pyridin-3-yl]phenyl}acetyl]amino}-2-methylphenyl)-2-methylacrylic acid In analogy to Suzuki coupling conditions in example 1 reaction of 177 mg intermediate 14 with 137 mg potassium [5-(difluoromethoxy)pyridin-3-yl](trifluoro)borate followed by ethyl ester saponification with 182 mg NaOH (32%) in 5.6 ml ethanol/water (3:1) gave 70 mg of the title compound as major compound of a compound mixture.

Step 80.2: (2R/2S)-3-(3-{[(2R/2S)-2-Cyclopentyl-2-{4-[5-(difluoromethoxy)pyridin-3-yl]phenyl}acetyl]amino}-2-methylphenyl)-2-methylpropanoic acid 70 mg crude methylacrylic acid 79.1 were dissolved in 10 ml THF/methanol 1:1, 50 mg palladium on charcoal (10%) were added and the reaction mixture stirred under 1 bar hydrogen atmosphere at RT until complete conversion. The catalyst was filtered off, the filtrate evaporated to dryness and purified via preparative HPLC to give 19 mg of the title compound.

$^1$H NMR (400 MHz, DMSO-$d_6$) δ ppm 0.97 (dd, 4 H) 1.34-1.74 (m, 6 H) 1.82-1.93 (m, 1 H) 2.03 (s, 3 H) 2.38-2.47 (m, 2 H) 2.58-2.66 (m, 1 H) 2.91-2.98 (m, 1 H) 3.55 (d, 1 H) 6.91-7.05 (m, 3 H) 7.23-7.64 (m, 3 H) 7.76 (d, 2 H) 7.95 (s, 3 H) 8.47 (d, 1 H) 8.81 (d, 1 H) 9.54 (s, 1 H).

Example 81

(2R/2S)-3-[3-({(2R/2S)-2-Cyclopentyl-2-[4-(5-methylpyridin-3-yl)phenyl]acetyl}amino)-2-methylphenyl]-2-methylpropanoic acid

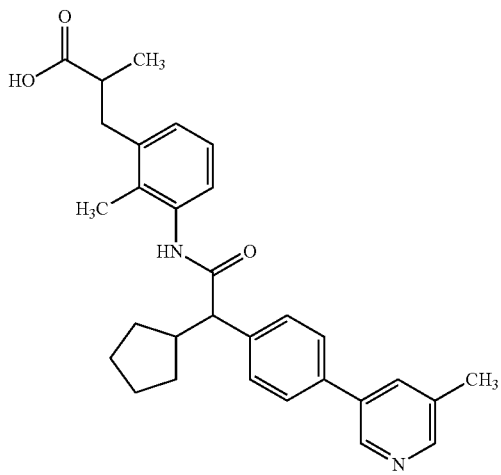 [SMILES: Cc1cncc(-c2ccc(C(C(=O)Nc3cccc(CC(C)C(=O)O)c3C)C3CCCC3)cc2)c1]

Step 81.1: (2E)-3-[3-({(2R)-2-cyclopentyl-2-[4-(5-methylpyridin-3-yl)phenyl]acetyl}amino)-2-methylphenyl]-2-methylacrylic acid In analogy to Suzuki coupling conditions in example 1 reaction of 177 mg intermediate 14 with 75 mg (5-methylpyridin-3-yl)boronic acid followed by ethyl ester saponification with 351 mg NaOH (32%) in 6 ml ethanol/water (3:1) gave 80 mg of the title compound as major compound of a compound mixture.

Step 81.2: (2R/2S)-3-[3-({(2R/2S)-2-Cyclopentyl-2-[4-(5-methylpyridin-3-yl)phenyl]acetyl}amino)-2-methylphenyl]-2-methylpropanoic acid 80 mg crude methylacrylic acid 81.1 were dissolved in 10 ml THF/methanol 1:1, 50 mg palladium on charcoal (10%) were added and the reaction mixture stirred under 1 bar hydrogen atmosphere at RT until complete conversion. The catalyst was filtered off, the filtrate evaporated to dryness and purified via preparative HPLC to give 6.3 mg of the title compound.

$^1$H NMR (400 MHz, DMSO-$d_6$) δ ppm 1.04 (dd, 4 H) 1.33-1.76 (m, 6 H) 1.81-1.94 (m, 1 H) 2.03 (d, 3 H) 2.37 (s, 3 H) 2.58-2.66 (m, 2 H) 2.86-3.00 (m, 1 H) 3.49-3.59 (m, 1 H) 6.91-6.98 (m, 1 H) 7.05 (s, 2 H) 7.55 (s, 2 H) 7.69 (d, 2 H) 7.87-7.95 (m, 1 H) 8.34-8.43 (m, 1 H) 8.67-8.73 (m, 1 H) 9.48-9.57 (m, 1 H) 11.91-12.31 (m, 1 H).

Example 82

(2R/2S)-3-[3-({(2R/2S)-2-Cyclopentyl-2-[4-(5-fluoro-6-methylpyridin-3-yl)phenyl]acetyl}amino)-2-methylphenyl]-2-methylpropanoic acid

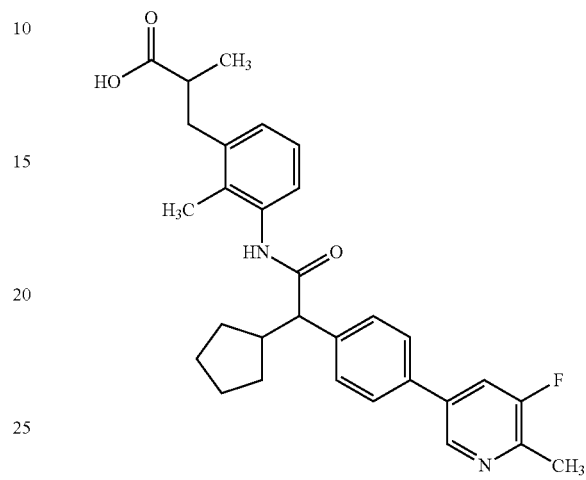

Step 82.1: (2E)-3-[3-({(2R/2S)-2-cyclopentyl-2-[4-(5-fluoro-6-methylpyridin-3-yl)phenyl]acetyl}amino)-2-methylphenyl]-2-methylacrylic acid In analogy to Suzuki coupling conditions in example 1 reaction of 85 mg intermediate 14 with 41 mg (5-fluoro-6-methylpyridin-3-yl)boronic acid followed by ethyl ester saponification with 73 mg NaOH (32%) in 4 ml ethanol/water (3:1) gave 16 mg of the title compound as major compound of a compound mixture.

Step 82.2: (2R/2S)-3-[3-({(2R/2S)-2-Cyclopentyl-2-[4-(5-fluoro-6-methylpyridin-3-yl)phenyl]acetyl}amino)-2-methylphenyl]-2-methylpropanoic acid 16 mg crude methylacrylic acid 82.1 were dissolved in 10 ml THF/methanol 1:1, 50 mg palladium on charcoal (10%) were added and the reaction mixture stirred under 1 bar hydrogen atmosphere at RT until complete conversion. The catalyst was filtered off, the filtrate evaporated to dryness and purified via preparative HPLC to give 5.1 mg of the title compound.

$^1$H NMR (400 MHz, DMSO-$d_6$) δ ppm 0.99-1.08 (m, 4 H) 1.30-1.74 (m, 6 H) 1.81-1.93 (m, 1 H) 2.03 (d, 3 H) 2.54 (s, 3 H) 2.59-2.65 (m, 2 H) 2.87-2.98 (m, 1 H) 3.50-3.58 (m, 1 H) 6.90-6.99 (m, 1 H) 7.00-7.10 (m, 2 H) 7.50-7.61 (m, 2 H) 7.70-7.78 (m, 2 H) 7.93-8.04 (m, 1 H) 8.61-8.71 (m, 1 H) 9.49-9.57 (m, 1 H) 11.94-12.38 (m, 1 H).

Example 83

3-[3-({[4-(5-Chloro-6-methylpyridin-3-yl)phenyl](cyclopentyl)acetyl}amino)-2-methylphenyl]-2-methylpropanoic acid, Stereoisomer 1

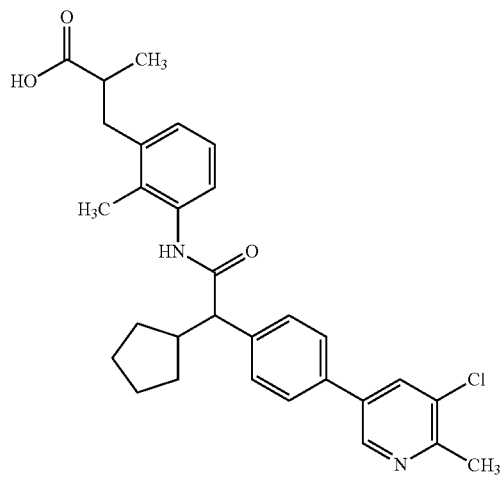

In analogy to Suzuki coupling conditions in example 1 reaction of 250 mg intermediate 13-2 with 156 mg 3-chloro-2-methyl-5-(4,4,5,5-tetramethyl-1,3,2-dioxaborolan-2-yl)pyridine followed by ethyl ester saponification with 141 mg NaOH (32%) in 4 ml ethanol/water (3:1) and subsequent purification via HPLC gave 30 mg of a mixture of the two diastereomers which were separated into the two stereoisomers 1 (6.3 mg, example 83) & 2 (5.7 mg, example 84) via preparative chiral HPLC (method 4; solvent: hexane/ethanol 75:25 (v/v)+0.1% formic acid; flow rate: 15 ml/min; solution: 30 mg/2 mL DCM/MeOH (1:1); injection: 4×0.5 ml).

Preparative chiral HPLC: Rt: 9.0-12.5 min.

Analytical HPLC, method 4: solvent: hexane/ethanol 74:26 (v/v)+0.1% TFA; flow rate: 1 ml/min; solution 1 mg/ml ethanol/methanol (1:1), injection: 5 µl; Rt: 3.39 min.

Optical rotation: +18.3° (1.4 mg/ml DMSO, temperature: 20° C., wave length: 589 nM).

$^1$H NMR (400 MHz, DMSO-$d_6$) δ ppm 1.02 (m, 4 H) 1.34-1.75 (m, 6 H) 1.82-1.93 (m, 1 H) 2.02 (s, 3 H) 2.58 (s, 3 H) 2.60-2.66 (m, 2 H) 2.87-2.99 (m, 1 H) 3.49-3.58 (m, 1 H) 6.91-7.09 (m, 3 H) 7.54 (d, 2 H) 7.73 (d, 2 H) 8.17 (d, 1 H) 8.75 (d, 1 H) 9.52 (s, 1 H).

Example 84

3-[3-({[4-(5-Chloro-6-methylpyridin-3-yl)phenyl](cyclopentyl)acetyl}amino)-2-methylphenyl]-2-methylpropanoic acid, Stereoisomer 2

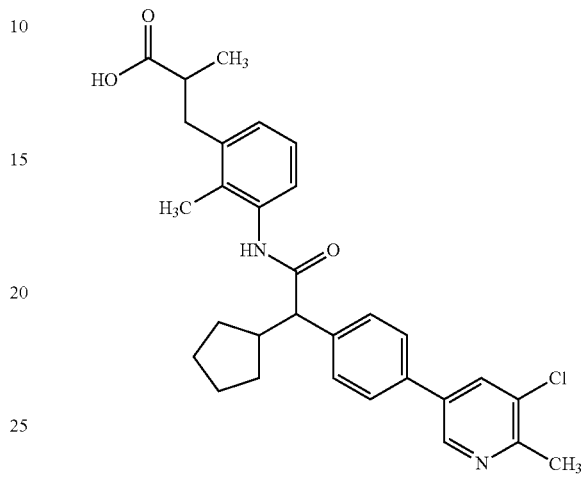

In analogy to Suzuki coupling conditions in example 1 reaction of 250 mg intermediate 13-2 with 156 mg 3-chloro-2-methyl-5-(4,4,5,5-tetramethyl-1,3,2-dioxaborolan-2-yl)pyridine followed by ethyl ester saponification with 141 mg NaOH (32%) in 4 ml ethanol/water (3:1) and subsequent purification via HPLC gave 30 mg of a mixture of the two diastereomers which were separated into the two stereoisomers 2 (5.7 mg, example 84) & 1 (6.3 mg, example 83) via preparative chiral HPLC (method 4; solvent: hexane/ethanol 75:25 (v/v)+0.1% formic acid; flow rate: 15 ml/min; solution: 30 mg/2 mL DCM/MeOH (1:1); injection: 4×0.5 ml).

Preparative chiral HPLC: Rt: 15.1-19.0 min.

Analytical HPLC, method 4: solvent: hexane/ethanol 74:26 (v/v)+0.1% TFA; flow rate: 1 ml/min; solution 1 mg/ml ethanol/methanol (1:1), injection: 5 µl; Rt: 6.85 min.

Optical rotation: −40.3° (1.2 mg/ml DMSO, temperature: 20° C., wave length: 589 nM).

$^1$H NMR (400 MHz, DMSO-$d_6$) δ ppm 1.03 (d, 4 H) 1.35-1.73 (m, 6 H) 1.81-1.92 (m, 1 H) 2.03 (s, 3 H) 2.58 (s, 5 H) 2.88-2.99 (m, 1 H) 3.49-3.57 (m, 1 H) 7.04 (m, 3 H) 7.56 (s, 2 H) 7.73 (s, 2 H) 8.14-8.20 (m, 1 H) 8.71-8.79 (m, 1 H) 9.47-9.56 (m, 1 H).

Example 85

(3R/S)-3-[3-({(2R/S)-2-[4-(5-Chloropyridin-3-yl)phenyl]-2-cyclopentylacetyl}amino)-2-methylphenyl]butanoic acid

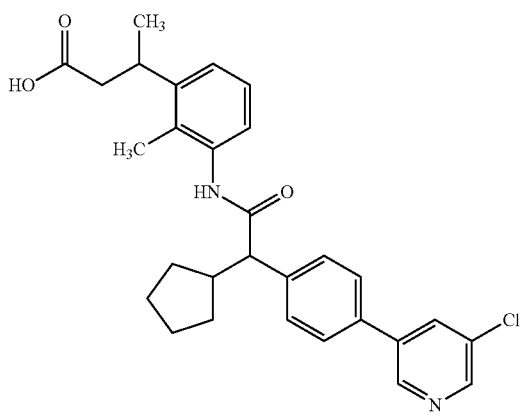 [SMILES: Cc1c(NC(=O)C(c2ccc(-c3cncc(Cl)c3)cc2)C2CCCC2)cccc1C(C)CC(=O)O]

In analogy to Suzuki coupling conditions in example 1 reaction of 150 mg intermediate 15 with 50.5 mg 5-chloropyridine-3-boronic acid followed by tert.-butyl ester cleavage and subsequent via HPLC gave 65 mg of the title compound.

$^1$H NMR (300 MHz, DMSO-$d_6$) δ ppm 0.97-1.07 (m, 1 H) 1.12 (t, 3 H) 1.35-1.74 (m, 6 H) 1.82-1.94 (m, 1 H) 2.07 (d, 3 H) 2.62 (m, 2 H) 3.39 (m, 2 H) 3.55 (d, 1 H) 6.95-7.11 (m, 3 H) 7.56 (d, 2 H) 7.77 (d, 2 H) 8.26 (s, 1 H) 8.61 (d, 1 H) 8.88 (s, 1 H) 9.56 (s, 1 H).

Example 86

3-[3-({[4-(5-Chloropyridin-3-yl)phenyl](cyclopentyl)acetyl}amino)-2-methylphenyl]butanoic acid, Stereoisomer 1

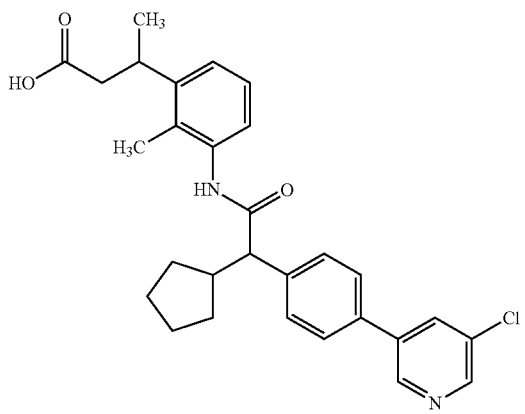 [SMILES: Cc1c(NC(=O)C(c2ccc(-c3cncc(Cl)c3)cc2)C2CCCC2)cccc1C(C)CC(=O)O]

In analogy to Suzuki coupling conditions in example 1 reaction of 1200 mg intermediate 15 with 550 mg 5-chloropyridine-3-boronic acid followed by tert.-butyl ester cleavage and subsequent via HPLC gave 850 mg of example 85 which was separated into the four stereoisomers (examples 86/87/88/89) via preparative chiral HPLC. A first HPLC separation (method 5; solvent: hexane/2-propanol 70:30 (v/v)+0.1% formic acid; flow rate: 50 ml/min; solution: 850 mg/7 mL DCM/MeOH; injection: 7×1 ml) gave a 337 mg of mixture of example 86/87 as well as 175 mg example 88 and 155 mg example 89. A second HPLC separation (method 4; solvent: hexane/ethanol 70:30 (v/v)+0.1% formic acid; flow rate: 50 ml/min; solution: 337 mg/6 mL DCM/MeOH; injection: 6×1 ml) gave a 95 mg example 86 and 110 mg example 87.

Preparative chiral HPLC, method 4: Rt: 5.4-6.9 min.

Analytical HPLC, method 3: solvent: hexane/ethanol 70:30 (v/v)+0.1% formic acid; flow rate: 1 ml/min; injection: 5 µl; 1 mg/ml ethanol/methanol (1:1); Rt: 3.38 min.

Optical rotation: +35.3° (5.0 mg/ml DMSO, temperature: 20° C., wave length: 589 nM).

$^1$H NMR (300 MHz, DMSO-$d_6$) δ ppm 0.97-1.07 (m, 1 H) 1.08-1.18 (m, 3 H) 1.33-1.74 (m, 6 H) 1.81-1.94 (m, 1 H) 2.08 (s, 3 H) 2.58-2.68 (m, 1 H) 3.37-3.47 (m, 2 H) 3.49-3.61 (m, 1 H) 6.94-7.12 (m, 3 H) 7.56 (d, 2 H) 7.77 (d, 2 H) 8.26 (t, 1 H) 8.61 (d, 1 H) 8.88 (d, 1 H) 9.55 (s, 1 H) 11.58-12.29 (m, 1 H).

Example 87

3-[3-({[4-(5-Chloropyridin-3-yl)phenyl](cyclopentyl)acetyl}amino)-2-methylphenyl]butanoic acid, Stereoisomer 2

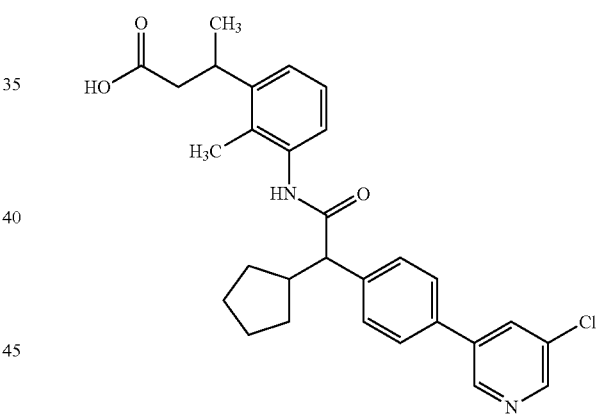

Preparative chiral HPLC, method 4: Rt: 7.0-9.1 min.

Analytical HPLC, method 3: solvent: hexane/ethanol 70:30 (v/v)+0.1% formic acid; flow rate: 1 ml/min; injection: 5 µl; 1 mg/ml ethanol/methanol (1:1); Rt: 4.84 min.

Optical rotation: −29.9° (5.0 mg/ml DMSO, temperature: 20° C., wave length: 589 nM).

$^1$H NMR (300 MHz, DMSO-$d_6$) δ ppm 0.94-1.06 (m, 1 H) 1.07-1.17 (m, 3 H) 1.33-1.75 (m, 6 H) 1.79-1.96 (m, 1 H) 2.06 (s, 3 H) 2.57-2.70 (m, 1 H) 3.38 (m, 2 H) 3.53 (d, 1 H) 6.96-7.14 (m, 3 H) 7.56 (d, 2 H) 7.77 (d, 2 H) 8.26 (t, 1 H) 8.61 (d, 1 H) 8.88 (d, 1 H) 9.55 (s, 1 H) 11.71-12.31 (m, 1 H).

Example 88

3-[3-({[4-(5-Chloropyridin-3-yl)phenyl](cyclopentyl)acetyl}amino)-2-methylphenyl]butanoic acid, Stereoisomer 3

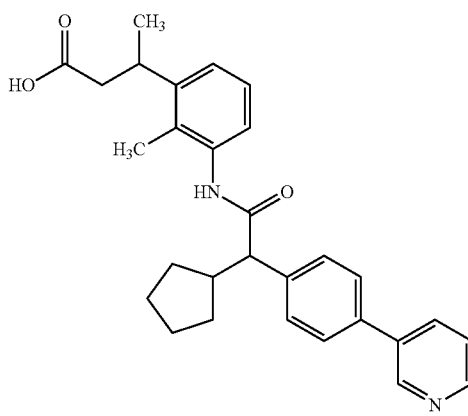

Preparative chiral HPLC, method 5: Rt: 7.0-9.3 min.
Analytical HPLC, method 3: solvent: hexane/2-propanol 70:30 (v/v)+0.1% formic acid; flow rate: 1 ml/min; injection: 5 μl; 1 mg/ml ethanol/methanol (1:1); Rt: 4.18 min.
Optical rotation: +29.3° (5.0 mg/ml DMSO, temperature: 20° C., wave length: 589 nM).
$^1$H NMR (300 MHz, DMSO-$d_6$) δ ppm 0.98-1.06 (m, 1 H) 1.13 (m, 3 H) 1.34-1.77 (m, 6 H) 1.81-1.95 (m, 1 H) 2.06 (s, 3 H) 2.58-2.70 (m, 1 H) 3.38 (m, 2 H) 3.53 (d, 1 H) 6.96-7.12 (m, 3 H) 7.56 (d, 2 H) 7.77 (d, 2 H) 8.26 (t, 1 H) 8.61 (d, 1 H) 8.88 (d, 1 H) 9.55 (s, 1 H) 11.83-12.26 (m, 1 H).

Example 89

3-[3-({[4-(5-Chloropyridin-3-yl)phenyl](cyclopentyl)acetyl}amino)-2-methylphenyl]butanoic acid, Stereoisomer 4

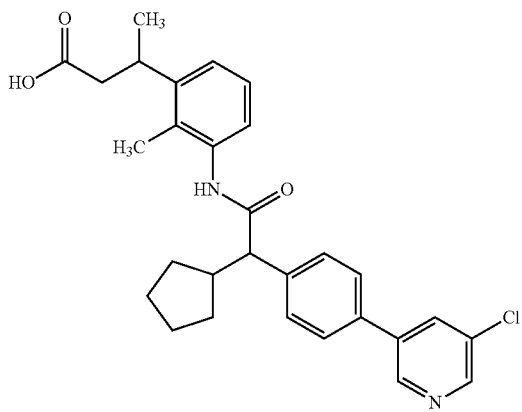 [SMILES: Cc1c(NC(=O)C(c2ccc(-c3cncc(Cl)c3)cc2)C2CCCC2)cccc1C(C)CC(=O)O]

Preparative chiral HPLC, method 5: Rt: 9.3-12.5 min.
Analytical HPLC, method 3: solvent: hexane/2-propanol 70:30 (v/v)+0.1% formic acid; flow rate: 1 ml/min; injection: 5 μl; 1 mg/ml ethanol/methanol (1:1); Rt: 5.93 min.
Optical rotation: −30.6° (5.0 mg/ml DMSO, temperature: 20° C., wave length: 589 nM).

$^1$H NMR (300 MHz, DMSO-$d_6$) δ ppm 0.98-1.07 (m, 1 H) 1.14 (d, 3 H) 1.34-1.75 (m, 6 H) 1.81-1.95 (m, 1 H) 2.08 (s, 3 H) 2.57-2.70 (m, 2 H) 3.36-3.46 (m, 2 H) 3.50-3.60 (m, 1 H) 6.95-7.12 (m, 3 H) 7.56 (d, 2 H) 7.77 (d, 2 H) 8.26 (s, 1 H) 8.61 (d, 1 H) 8.88 (d, 1 H) 9.55 (s, 1 H) 11.83-12.25 (m, 1 H).

Example 90

(3R/S)-3-[3-({(2R/S)-2-Cyclopentyl-2-[4-(5-ethoxypyridin-3-yl)phenyl]acetyl}amino)-2-methylphenyl]butanoic acid

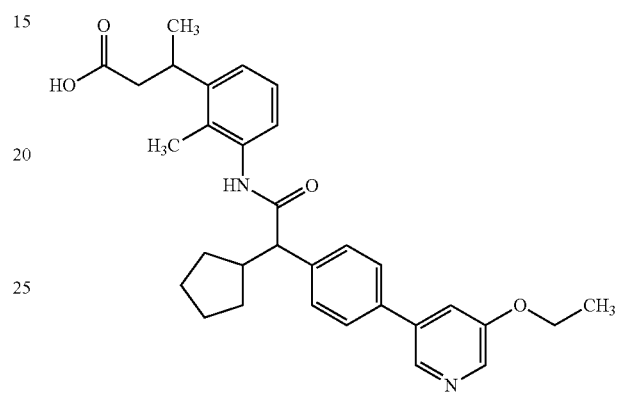

In analogy to Suzuki coupling conditions in example 1 reaction of 150 mg intermediate 15 with 80 mg 3-ethoxy-5-(4,4,5,5-tetramethyl-1,3,2-dioxaborolan-2-yl)pyridine followed by tert.-butyl ester cleavage and subsequent via HPLC gave 52 mg of the title compound.

$^1$H NMR (300 MHz, DMSO-$d_6$) δ ppm 1.03 (m, 1 H) 1.13 (t, 3 H) 1.37 (t, 3 H) 1.41-1.75 (m, 6 H) 1.88 (m, 1 H) 2.07 (d, 3 H) 2.41-2.47 (m, 2 H) 2.63 (d, 1 H) 3.40 (m, 1 H) 3.54 (d, 1 H) 4.20 (q, 2 H) 7.01 (dd, 1 H) 7.04-7.10 (m, 2 H) 7.54 (d, 2 H) 7.61 (s, 1 H) 7.72 (d, 2 H) 8.25 (d, 1 H) 8.48 (d, 1 H) 9.55 (s, 1 H).

Example 91

(3R/S)-3-(3-{[(2R/S)-2-Cyclopentyl-2-{4-[5-(trifluoromethyl)pyridin-3-yl]phenyl}acetyl]amino}-2-methylphenyl)butanoic acid

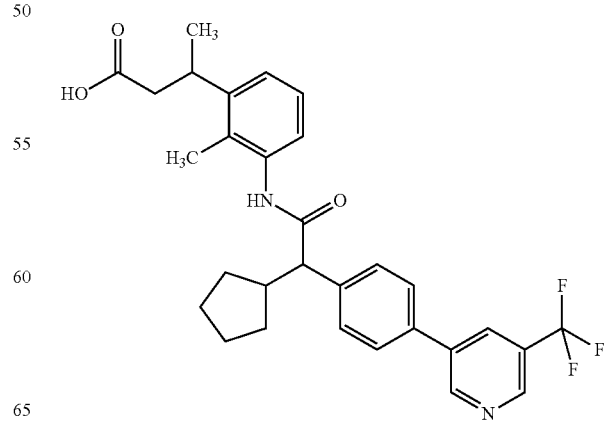

In analogy to Suzuki coupling conditions in example 1 reaction of 150 mg intermediate 15 with 61 mg 3 [5-(trifluoromethyl)pyridin-3-yl]boronic acid followed by tert.-butyl ester cleavage and subsequent via HPLC gave 75 mg of the title compound.

¹H NMR (400 MHz, DMSO-d₆) δ ppm 0.98-1.07 (m, 1 H) 1.13 (t, 3 H) 1.35-1.75 (m, 6 H) 1.83-1.94 (m, 1 H) 2.07 (d, 3 H) 2.46 (d, 2 H) 2.60-2.69 (m, 1 H) 3.40 (d, 1 H) 3.56 (d, 1 H) 7.00 (br. s., 1 H) 7.07 (s, 2 H) 7.59 (d, 2 H) 7.83 (d, 2 H) 8.46 (s, 1 H) 8.95 (s, 1 H) 9.22 (s, 1 H) 9.54 (s, 1 H).

Example 92

(3R/S)-3-[3-({(2R/S)-2-Cyclopentyl-2-[4-(5-ethyl-pyridin-3-yl)phenyl]acetyl}amino)-2-methylphenyl]butanoic acid

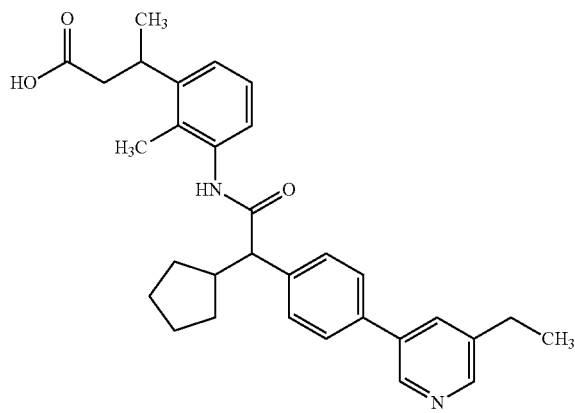 [SMILES: CCc1cncc(-c2ccc(C(C(=O)Nc3cccc(C(C)CC(=O)O)c3C)C3CCCC3)cc2)c1]

In analogy to Suzuki coupling conditions in example 1 reaction of 75 mg intermediate 15 with 33 mg (5-ethylpyridin-3-yl)boronic acid followed by tert.-butyl ester cleavage and subsequent purification via HPLC gave 32 mg of the title compound.

¹H NMR (400 MHz, DMSO-d₆) δ ppm 0.93-1.08 (m, 1 H) 1.13 (t, 3 H) 1.25 (t, 3 H) 1.33-1.77 (m, 6 H) 1.79-1.95 (m, 1 H) 2.00-2.14 (m, 3 H) 2.69 (m, 3 H) 3.51-3.59 (m, 1 H) 6.95-7.14 (m, 3 H) 7.50-7.60 (m, 2 H) 7.70 (d, 2 H) 7.92 (s, 1 H) 8.43 (d, 1 H) 8.71 (d, 1 H) 9.54 (s, 1 H) 11.47-12.28 (m, 1 H).

Example 93

(3R/S)-3-[3-({(2R/S)-2-Cyclopentyl-2-[4-(5,6-dimethylpyridin-3-yl)phenyl]acetyl}amino)-2-methylphenyl]butanoic acid

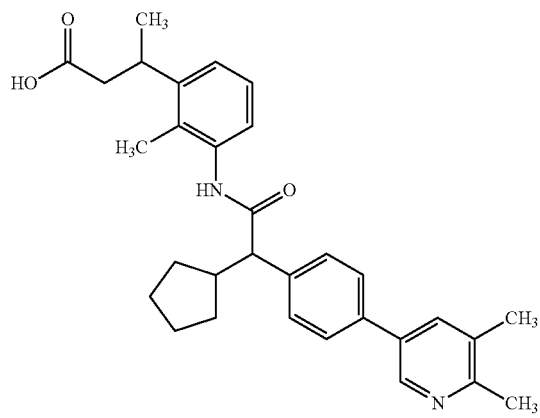

In analogy to Suzuki coupling conditions in example 1 reaction of 75 mg intermediate 15 with 51 mg 2,3-dimethyl-5-(4,4,5,5-tetramethyl-1,3,2-dioxaborolan-2-yl)pyridine followed by tert.-butyl ester cleavage and subsequent purification via HPLC gave 25 mg of the title compound.

¹H NMR (400 MHz, DMSO-d₆) δ ppm 0.97-1.08 (m, 1 H) 1.10-1.17 (m, 3 H) 1.33-1.76 (m, 6 H) 1.82-1.93 (m, 1 H) 2.07 (d, 3 H) 2.31 (s, 3 H) 2.45 (s, 3 H) 2.58-2.71 (m, 1 H) 3.49-3.58 (m, 1 H) 6.94-7.14 (m, 3 H) 7.52 (d, 2 H) 7.66 (d, 2 H) 7.82 (d, 1 H) 8.56 (d, 1 H) 9.53 (s, 1 H) 11.67-12.28 (m, 1 H).

Example 94

(3R/S)-3-[3-({(2R/S)-2-Cyclopentyl-2-[4-(5-methyl-pyridin-3-yl)phenyl]acetyl}amino)-2-methylphenyl]butanoic acid

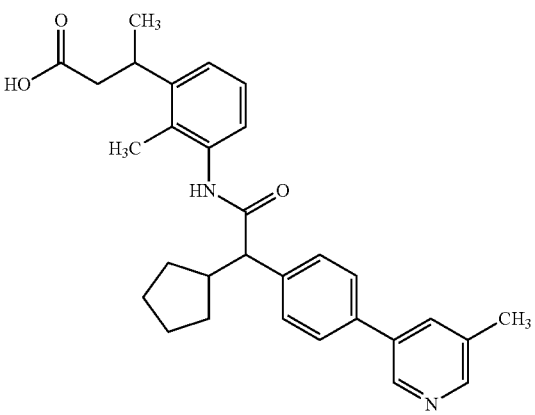 [SMILES: Cc1cncc(-c2ccc(C(C(=O)Nc3cccc(C(C)CC(=O)O)c3C)C3CCCC3)cc2)c1]

In analogy to Suzuki coupling conditions in example 1 reaction of 75 mg intermediate 15 with 30 mg (5-methylpyridin-3-yl)boronic acid followed by tert.-butyl ester cleavage and subsequent purification via HPLC gave 28 mg of the title compound.

¹H NMR (400 MHz, DMSO-d₆) δ ppm 0.95-1.08 (m, 1 H) 1.13 (t, 3 H) 1.34-1.77 (m, 6 H) 1.82-1.94 (m, 1 H) 2.07 (d, 3 H) 2.34-2.40 (m, 3 H) 2.59-2.70 (m, 1 H) 3.48-3.59 (m, 1 H) 6.93-7.13 (m, 3 H) 7.54 (d, 2 H) 7.69 (d, 2 H) 7.90 (s, 1 H) 8.40 (d, 1 H) 8.69 (d, 1 H) 9.54 (s, 1 H) 11.59-12.33 (m, 1 H).

Example 95

(3R/S)-3-[3-({(2R/S)-2-Cyclopentyl-2-[4-(5-fluoro-pyridin-3-yl)phenyl]acetyl}amino)-2-methylphenyl]butanoic acid

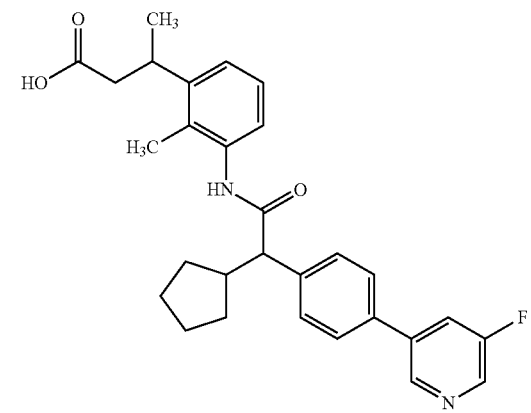 [SMILES: Cc1c(NC(=O)C(c2ccc(-c3cncc(F)c3)cc2)C2CCCC2)cccc1C(C)CC(=O)O]

In analogy to Suzuki coupling conditions in example 1 reaction of 75 mg intermediate 15 with 31 mg (5-fluoropyridin-3-yl)boronic acid followed by tert.-butyl ester cleavage and subsequent purification via HPLC gave 29 mg of the title compound.

$^1$H NMR (400 MHz, DMSO-d$_6$) δ ppm 0.97-1.08 (m, 1 H) 1.13 (t, 3 H) 1.33-1.77 (m, 6 H) 1.82-1.94 (m, 1 H) 2.07 (d, 3 H) 2.59-2.70 (m, 1 H) 3.51-3.59 (m, 1 H) 6.94-7.15 (m, 3 H) 7.57 (d, 2 H) 7.77 (d, 2 H) 8.03-8.12 (m, 1 H) 8.56 (d, 1 H) 8.82 (s, 1 H) 9.55 (s, 1 H) 11.30-12.38 (m, 1 H).

Example 96

(3R/S)-3-[3-({(2R/S)-2-[4-(5-Fluoro-6-methylpyridin-3-yl)phenyl]-2-cyclopentylacetyl}amino)-2-methylphenyl]butanoic acid

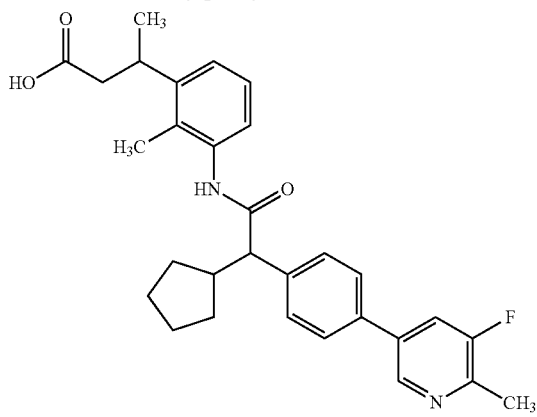 [SMILES: Cc1ncc(-c2ccc(C(C(=O)Nc3cccc(C(C)CC(=O)O)c3C)C3CCCC3)cc2)cc1Cl]

In analogy to Suzuki coupling conditions in example 1 reaction of 75 mg intermediate 15 with 68 mg (5-fluoro-6-methylpyridin-3-yl)boronic acid followed by tert.-butyl ester cleavage and subsequent purification via HPLC gave 11 mg of the title compound.

$^1$H NMR (400 MHz, DMSO-d$_6$) δ ppm 0.95-1.08 (m, 1 H) 1.13 (t, 3 H) 1.33-1.74 (m, 6 H) 1.81-1.94 (m, 1 H) 2.07 (d, 3 H) 2.58-2.66 (m, 1 H) 3.49-3.58 (m, 1 H) 6.96-7.04 (m, 1 H) 7.05-7.12 (m, 2 H) 7.54 (d, 2 H) 7.73 (d, 2 H) 7.92-8.03 (m, 1 H) 8.66 (s, 1 H) 9.54 (s, 1 H) 11.60-12.25 (m, 1 H).

Example 97

(3R/S)-3-[3-({(2R/S)-2-[4-(5-Chloro-6-methylpyridin-3-yl)phenyl]-2-cyclopentylacetyl}amino)-2-methylphenyl]butanoic acid

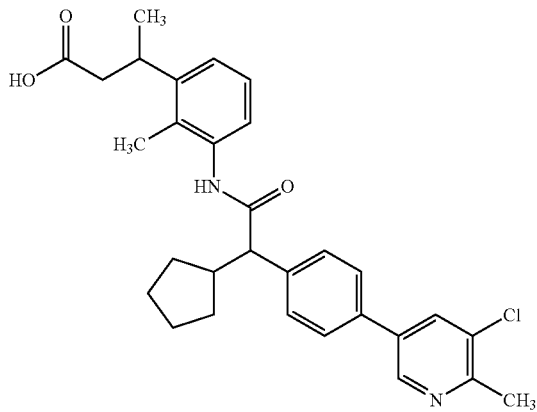

In analogy to Suzuki coupling conditions in example 1 reaction of 75 mg intermediate 15 with 55 mg 3-chloro-2-methyl-5-(4,4,5,5-tetramethyl-1,3,2-dioxaborolan-2-yl)pyridine followed by tert.-butyl ester cleavage and subsequent purification via HPLC gave 38 mg of the title compound.

$^1$H NMR (400 MHz, DMSO-d$_6$) δ ppm 0.97-1.07 (m, 1 H) 1.09-1.18 (m, 3 H) 1.31-1.76 (m, 6 H) 1.81-1.92 (m, 1 H) 2.03-2.12 (m, 3 H) 2.58 (s, 3 H) 2.61-2.70 (m, 1 H) 3.50-3.56 (m, 1 H) 6.96-7.04 (m, 1 H) 7.04-7.13 (m, 2 H) 7.52-7.60 (m, 2 H) 7.70-7.79 (m, 2 H) 8.15-8.22 (m, 1 H) 8.73-8.80 (m, 1 H) 9.50-9.58 (m, 1 H).

Example 98

(3R/S)-3-(3-{[(2R/S)-2-Cyclopentyl-2-{4-[5-(difluoromethyl)pyridin-3-yl]phenyl}acetyl]amino}-2-methylphenyl)butanoic acid

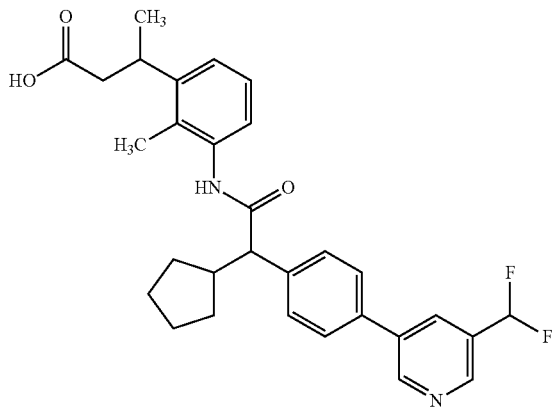 [SMILES: Cc1c(NC(=O)C(c2ccc(-c3cncc(C(F)F)c3)cc2)C2CCCC2)cccc1C(C)CC(=O)O]

In analogy to Suzuki coupling conditions in example 1 reaction of 75 mg intermediate 15 with 38 mg [5-(difluoromethyl)pyridin-3-yl]boronic acid followed by tert.-butyl ester cleavage and subsequent purification via HPLC gave 32 mg of the title compound.

$^1$H NMR (400 MHz, DMSO-d$_6$) δ ppm 0.98-1.08 (m, 1 H) 1.09-1.17 (m, 3 H) 1.35-1.75 (m, 6 H) 1.82-1.93 (m, 1 H) 2.07 (d, 3 H) 2.60-2.71 (m, 1 H) 3.55 (d, 1 H) 6.97-7.14 (m, 3 H) 7.18-7.39 (m, 1 H) 7.58 (d, 2 H) 7.78 (d, 2 H) 8.27 (s, 1 H) 8.77 (d, 1 H) 9.09 (d, 1 H) 9.55 (s, 1 H).

Example 99

(3R/S)-3-[3-({(2R/S)-2-[4-(5-Chloropyridin-3-yl)phenyl]-2-cyclopentylacetyl}amino)-2-methylphenyl]pentanoic acid

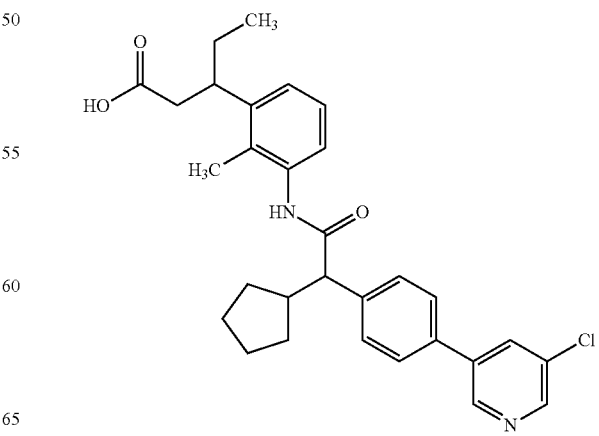

In analogy to Suzuki coupling conditions in example 1 reaction of 75 mg intermediate 16 with 36 mg (5-chloropyridin-3-yl)boronic acid followed by methyl ester saponification with 193 mg NaOH (32%) in methanol/water (5.5 ml/2.6 ml) and subsequent purification via HPLC gave 25 mg of the title compound.

¹H NMR (400 MHz, DMSO-d₆) δ ppm 0.61-0.75 (m, 3 H) 0.96-1.08 (m, 1 H) 1.59 (m, 8 H) 1.82-1.93 (m, 1 H) 2.07 (d, 3 H) 2.38-2.47 (m, 1 H) 2.59-2.69 (m, 1 H) 3.51-3.58 (m, 1 H) 6.97-7.13 (m, 3 H) 7.56 (d, 2 H) 7.77 (dd, 2 H) 8.25 (t, 1 H) 8.61 (d, 1 H) 8.88 (d, 1 H) 9.55 (d, 1 H).

Example 100

3-[3-({[4-(5-Chloropyridin-3-yl)phenyl](cyclopentyl)acetyl}amino)-2-methylphenyl]pentanoic acid, Stereoisomer 1

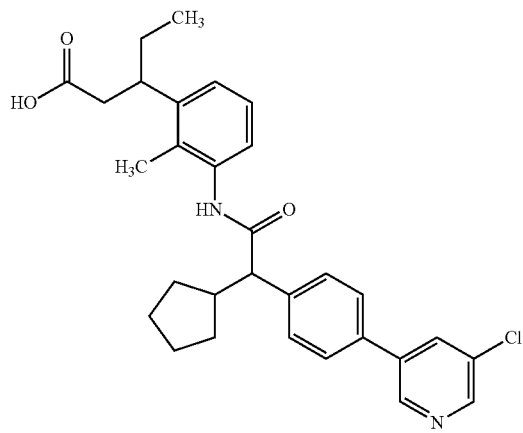 [SMILES: CCC(CC(=O)O)c1cccc(NC(=O)C(c2ccc(-c3cncc(Cl)c3)cc2)C2CCCC2)c1C]

In analogy to Suzuki coupling conditions in example 1 reaction of 310 mg intermediate 16 with 150 mg (5-chloropyridin-3-yl)boronic acid followed by methyl ester saponification with 958 mg NaOH (32%) in 21 ml THF/ethanol/water (3:3:1) gave 360 mg of example 99 which was separated into the four stereoisomers (examples 100/101/102/103) via preparative chiral HPLC. A first HPLC separation (method 6; solvent: hexane/ethanol 70:30 (v/v)+0.1% formic acid; flow rate: 25 ml/min; solution: 360 mg/3.75 mL DCM/MeOH; injection: 15×0.25 ml) gave 72 mg example 100 and 75 mg example 101 as well as 128 mg of a mixture of example 102/103. A second HPLC separation (method 4; solvent: hexane/2-propanol 70:30 (v/v)+0.1% formic acid; flow rate: 20 ml/min; solution: 128 mg/2.5 mL DCM/MeOH; injection: 5×0.5 ml) gave a 57 mg example 102 and 55 mg example 103.

Preparative chiral HPLC, method 6: Rt: 8.8-9.5 min.

Analytical HPLC, method 6: solvent: hexane/ethanol 70:30 (v/v)+0.1% formic acid; flow rate: 1 ml/min; injection: 5 μl; 1 mg/ml ethanol/methanol (1:1); Rt: 4.69 min.

Optical rotation: −52.6° (1.8 mg/ml methanol, temperature: 20° C., wave length: 589 nM).

¹H NMR (400 MHz, DMSO-d₆) δ ppm 0.68 (t, 3 H) 0.94-1.09 (m, 1 H) 1.31-1.76 (m, 8 H) 1.81-1.94 (m, 1 H) 2.07 (s, 3 H) 2.60-2.71 (m, 1 H) 3.47-3.62 (m, 1 H) 7.03 (s, 3 H) 7.57 (d, 2 H) 7.77 (d, 2 H) 8.25 (s, 1 H) 8.61 (d, 1 H) 8.88 (d, 1 H) 9.53 (s, 1 H) 11.64-12.19 (m, 1 H).

Example 101

3-[3-({[4-(5-Chloropyridin-3-yl)phenyl](cyclopentyl)acetyl}amino)-2-methylphenyl]pentanoic acid, Stereoisomer 2

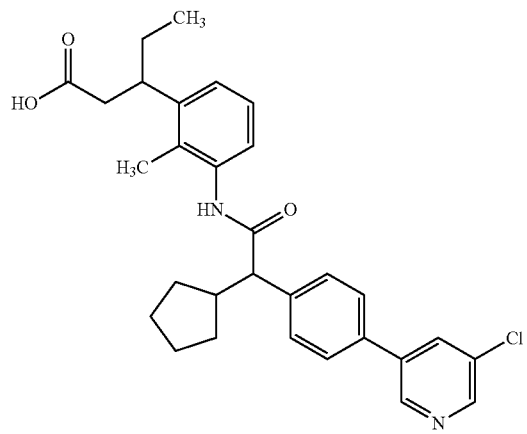 [SMILES: CCC(CC(=O)O)c1cccc(NC(=O)C(c2ccc(-c3cncc(Cl)c3)cc2)C2CCCC2)c1C]

Preparative chiral HPLC, method 6: Rt: 9.5-10.5 min.

Analytical HPLC, method 6: solvent: hexane/ethanol 70:30 (v/v)+0.1% formic acid; flow rate: 1 ml/min; injection: 5 μl; 1 mg/ml ethanol/methanol (1:1); Rt: 5.69 min.

Optical rotation: +55.0° (2.5 mg/ml methanol, temperature: 20° C., wave length: 589 nM).

¹H NMR (400 MHz, DMSO-d₆) δ ppm 0.70 (t, 3 H) 0.98-1.07 (m, 1 H) 1.33-1.73 (m, 8 H) 1.82-1.96 (m, 1 H) 2.08 (s, 3 H) 2.59-2.71 (m, 1 H) 3.53 (d, 1 H) 6.96-7.13 (m, 3 H) 7.56 (d, 2 H) 7.77 (d, 2 H) 8.25 (t, 1 H) 8.61 (d, 1 H) 8.88 (d, 1 H) 9.53 (s, 1 H) 11.65-12.22 (m, 1 H).

Example 102

3-[3-({[4-(5-Chloropyridin-3-yl)phenyl](cyclopentyl)acetyl}amino)-2-methylphenyl]pentanoic acid, Stereoisomer 3

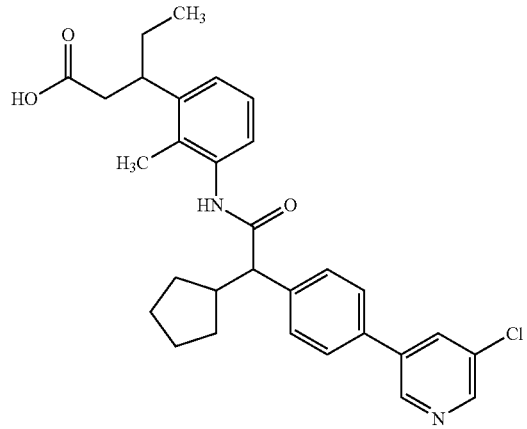 [SMILES: CCC(CC(=O)O)c1cccc(NC(=O)C(c2ccc(-c3cncc(Cl)c3)cc2)C2CCCC2)c1C]

Preparative chiral HPLC, method 4: Rt: 5.3-6.7 min.

Analytical HPLC, method 7: solvent: hexane/2-propanol 70:30 (v/v)+0.1% formic acid; flow rate: 1 ml/min; injection: 5 μl; 1 mg/ml ethanol/methanol (1:1); Rt: 2.41 min.

Optical rotation: +53.6° (2.3 mg/ml methanol, temperature: 20° C., wave length: 589 nM).

$^1$H NMR (400 MHz, DMSO-$d_6$) δ ppm 0.68 (t, 3 H) 0.98-1.08 (m, 1 H) 1.60 (m, 8 H) 1.82-1.94 (m, 1 H) 2.07 (s, 3 H) 2.59-2.69 (m, 1 H) 3.55 (d, 1 H) 7.06 (dd, 3 H) 7.57 (d, 2 H) 7.77 (d, 2 H) 8.25 (t, 1 H) 8.61 (d, 1 H) 8.88 (d, 1 H) 9.53 (s, 1 H) 11.74-12.17 (m, 1 H).

Example 103

3-[3-({[4-(5-Chloropyridin-3-yl)phenyl](cyclopentyl)acetyl}amino)-2-methylphenyl]pentanoic acid, Stereoisomer 4

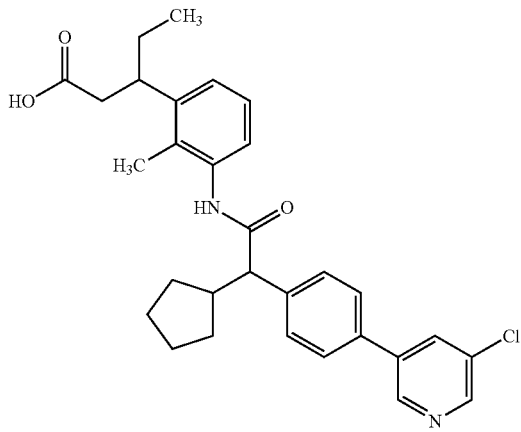 [SMILES: CCC(CC(=O)O)c1cccc(NC(=O)C(c2ccc(-c3cncc(Cl)c3)cc2)C2CCCC2)c1C]

Preparative chiral HPLC, method 4: Rt: 8.0-10.0 min.

Analytical HPLC, method 7: solvent: hexane/2-propanol 70:30 (v/v)+0.1% formic acid; flow rate: 1 ml/min; injection: 5 μl; 1 mg/ml ethanol/methanol (1:1); Rt: 3.97 min.

Optical rotation: −56.4° (3.1 mg/ml methanol, temperature: 20° C., wave length: 589 nM).

$^1$H NMR (400 MHz, DMSO-$d_6$) δ ppm 0.70 (t, 3 H) 0.97-1.07 (m, 1 H) 1.36-1.74 (m, 8 H) 1.83-1.94 (m, 1 H) 2.08 (s, 3 H) 2.60-2.71 (m, 1 H) 3.54 (d, 1 H) 6.95-7.13 (m, 3 H) 7.56 (d, 2 H) 7.77 (d, 2 H) 8.25 (t, 1 H) 8.60 (d, 1 H) 8.88 (d, 1 H) 9.53 (s, 1 H) 11.69-12.17 (m, 1 H).

Example 104

(3R/S)-3-[3-({(2RS)-2-Cyclopentyl-2-[4-(5-methylpyridin-3-yl)phenyl]acetyl}amino)-2-methylphenyl]pentanoic acid

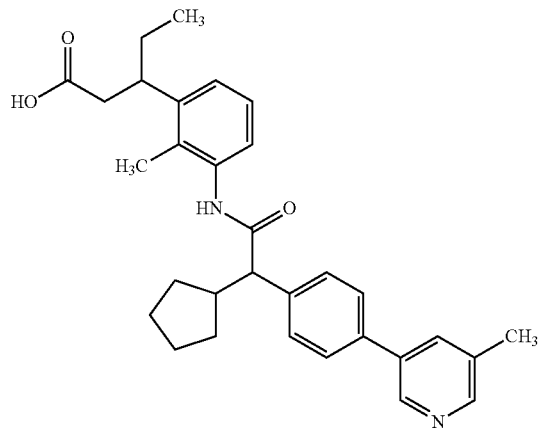 [SMILES: CCC(CC(=O)O)c1cccc(NC(=O)C(c2ccc(-c3cncc(C)c3)cc2)C2CCCC2)c1C]

In analogy to Suzuki coupling conditions in example 1 reaction of 75 mg intermediate 16 with 32 mg (5-methylpyridin-3-yl)boronic acid followed by methyl ester saponification with 200 mg NaOH (32%) in 11 ml methanol/water (3:1) and subsequent purification via HPLC gave 22 mg of the title compound.

$^1$H NMR (400 MHz, DMSO-$d_6$) δ ppm 0.69 (d, 3 H) 0.97-1.09 (m, 1 H) 1.34-1.73 (m, 8 H) 1.82-1.93 (m, 1 H) 2.07 (d, 3 H) 2.37 (s, 3 H) 2.60-2.68 (m, 1 H) 3.49-3.57 (m, 1 H) 7.04 (d, 3 H) 7.55 (d, 2 H) 7.69 (dd, 2 H) 7.90 (s, 1 H) 8.40 (d, 1 H) 8.69 (d, 1 H) 9.50-9.55 (m, 1 H).

Example 105

(3R/S)-3-[3-({(2R/S)-2-Cyclopentyl-2-[4-(5-ethylpyridin-3-yl)phenyl]acetyl}amino)-2-methylphenyl]pentanoic acid

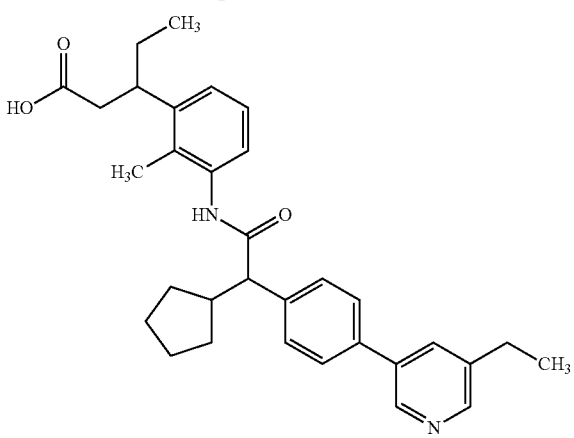 [SMILES: CCc1cncc(-c2ccc(C(C(=O)Nc3cccc(C(CC)CC(=O)O)c3C)C3CCCC3)cc2)c1]

In analogy to Suzuki coupling conditions in example 1 reaction of 75 mg intermediate 16 with 35 mg (5-ethylpyridin-3-yl)boronic acid followed by methyl ester saponification with 190 mg NaOH (32%) in methanol/water (5.6 ml/2.7 ml) and subsequent purification via HPLC gave 16 mg of the title compound.

$^1$H NMR (400 MHz, DMSO-$d_6$) δ ppm 0.69 (d, 3 H) 0.99-1.07 (m, 1 H) 1.25 (t, 3 H) 1.34-1.74 (m, 8 H) 1.82-1.94 (m, 1 H) 2.07 (d, 3 H) 2.39-2.48 (m, 1 H) 2.69 (d, 3 H) 3.49-3.58 (m, 1 H) 7.05 (s, 3 H) 7.55 (d, 2 H) 7.70 (dd, 2 H) 7.91 (s, 1 H) 8.39-8.48 (m, 1 H) 8.67-8.76 (m, 1 H) 9.48-9.57 (m, 1 H) 11.63-12.25 (m, 1 H).

Example 106

3-[3-({[4-(5-Fluoropyridin-3-yl)phenyl](cyclopentyl)acetyl}amino)-2-methylphenyl]pentanoic acid, Stereoisomer 4

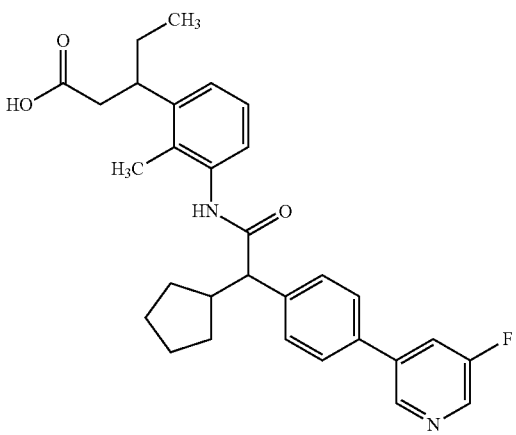 [SMILES: CCC(CC(=O)O)c1cccc(NC(=O)C(c2ccc(-c3cncc(F)c3)cc2)C2CCCC2)c1C]

In analogy to Suzuki coupling conditions in example 1 reaction of 75 mg intermediate 16 with 33 mg (5-fluoropyridin-3-yl)boronic acid followed by methyl ester saponification with 199 mg NaOH (32%) in methanol/water (5.7 ml/2.7 ml) and subsequent purification via HPLC gave 32 mg of the title compound.

$^1$H NMR (400 MHz, DMSO-d$_6$) δ ppm 0.63-0.74 (m, 3 H) 0.96-1.08 (m, 1 H) 1.34-1.73 (m, 8 H) 1.83-1.93 (m, 1 H) 2.07 (d, 3 H) 2.38-2.47 (m, 1 H) 2.60-2.68 (m, 1 H) 3.54 (d, 1 H) 6.97-7.12 (m, 3 H) 7.57 (d, 2 H) 7.77 (dd, 2 H) 8.07 (d, 1 H) 8.56 (d, 1 H) 8.81 (s, 1 H) 9.55 (s, 1 H).

Example 107

(3R/S)-3-[3-({(2R/S)-2-Cyclopentyl-2-[4-(5-ethoxypyridin-3-yl)phenyl]acetyl}amino)-2-methylphenyl]pentanoic acid

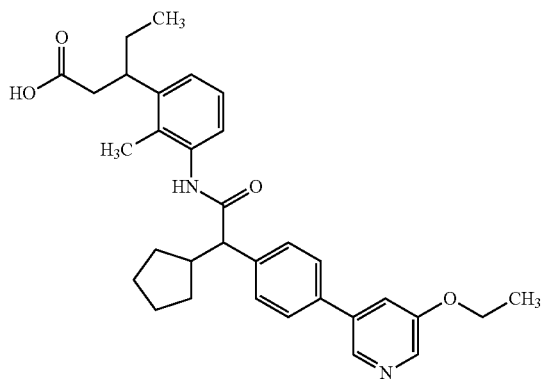 [SMILES: CCOc1cncc(-c2ccc(C(C(=O)Nc3cccc(C(CC)CC(=O)O)c3C)C3CCCC3)cc2)c1]

In analogy to Suzuki coupling conditions in example 1 reaction of 75 mg intermediate 16 with 39 mg (5-ethoxypyridin-3-yl)boronic acid followed by methyl ester saponification with 189 mg NaOH (32%) in methanol/water (5.4 ml/2.6 ml) and subsequent purification via HPLC gave 38 mg of the title compound.

$^1$H NMR (400 MHz, DMSO-d$_6$) δ ppm 0.97-1.07 (m, 1 H) 1.37 (t, 3 H) 1.58 (d, 8 H) 1.82-1.92 (m, 1 H) 2.08 (d, 3 H) 2.35-2.44 (m, 1 H) 2.59-2.68 (m, 1 H) 3.54 (d, 1 H) 4.20 (d, 2 H) 7.05 (dd, 3 H) 7.54 (d, 2 H) 7.59-7.63 (m, 1 H) 7.72 (dd, 2 H) 8.25 (d, 1 H) 8.48 (d, 1 H) 9.53 (d, 1 H).

Example 108

(3R/S)-3-[3-({(2R/S)-2-[4-(5-chloro-6-methylpyridin-3-yl)phenyl]-2-cyclopentylacetyl}amino)-2-methylphenyl]-3-cyclopropylpropanoic acid

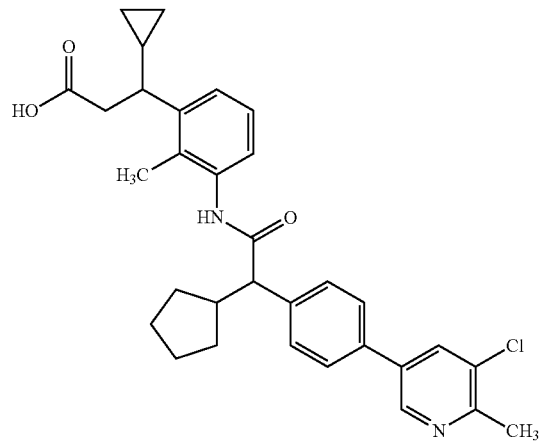 [SMILES: Cc1ncc(-c2ccc(C(C(=O)Nc3cccc(C(CC(=O)O)C4CC4)c3C)C3CCCC3)cc2)cc1Cl]

In analogy to Suzuki coupling conditions in example 1 reaction of 75 mg intermediate 17 with 53 mg 3-chloro-2-methyl-5-(4,4,5,5-tetramethyl-1,3,2-dioxaborolan-2-yl)pyridine followed by tert.-butyl ester cleavage and subsequent purification via HPLC gave 36 mg of the title compound.

$^1$H NMR (300 MHz, DMSO-d$_6$) δ ppm −0.09-0.05 (m, 1 H) 0.11-0.34 (m, 2 H) 0.39-0.53 (m, 1 H) 0.96-1.10 (m, 2 H) 1.33-1.74 (m, 6 H) 1.80-1.93 (m, 1 H) 2.03 (d, 3 H) 2.58 (s, 3 H) 2.63-2.75 (m, 2 H) 3.51 (s, 1 H) 6.96-7.04 (m, 1 H) 7.05-7.13 (m, 1 H) 7.16 (s, 1 H) 7.54 (d, 2 H) 7.74 (d, 2 H) 8.18 (d, 1 H) 8.75 (s, 1 H) 9.53 (s, 1 H).

Example 109

(3R/S)-3-(3-{[(2R/S)-2-cyclopentyl-2-{4-[5-(trifluoromethyl)pyridin-3-yl]phenyl}acetyl]amino}-2-methylphenyl)-3-cyclopropylpropanoic acid

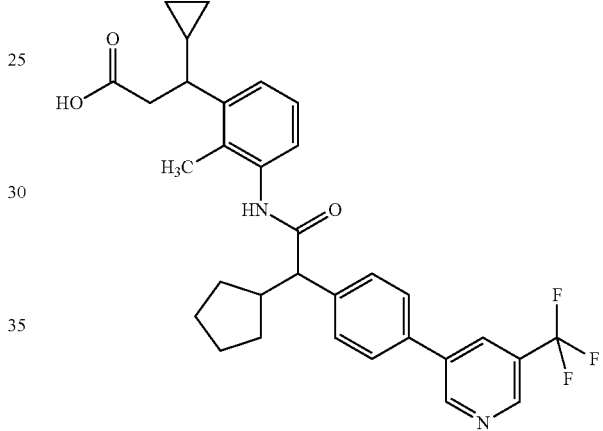

In analogy to Suzuki coupling conditions in example 1 reaction of 75 mg intermediate 17 with 40 mg [5-(trifluoromethyl)pyridin-3-yl]boronic acid followed by tert.-butyl ester cleavage and subsequent purification via HPLC gave 35 mg of the title compound.

$^1$H NMR (400 MHz, DMSO-d$_6$) δ ppm −0.06-0.03 (m, 1 H) 0.13-0.21 (m, 1 H) 0.23-0.32 (m, 1 H) 0.41-0.52 (m, 1 H) 0.97-1.10 (m, 2 H) 1.35-1.74 (m, 6 H) 1.82-1.93 (m, 1 H) 2.03 (d, 3 H) 2.58 (m, 2 H) 2.60-2.68 (m, 1 H) 2.69-2.77 (m, 1 H) 3.54 (d, 1 H) 6.98-7.05 (m, 1 H) 7.06-7.12 (m, 1 H) 7.16 (s, 1 H) 7.59 (d, 2 H) 7.83 (dd, 2 H) 8.46 (s, 1 H) 8.95 (s, 1 H) 9.22 (s, 1 H) 9.54 (s, 1 H).

Example 110

(3R/S)-3-[3-({(2R/S)-2-[4-(5-chloropyridin-3-yl)phenyl]-2-cyclopentylacetyl}amino)-2-methylphenyl]-3-cyclopropylpropanoic acid

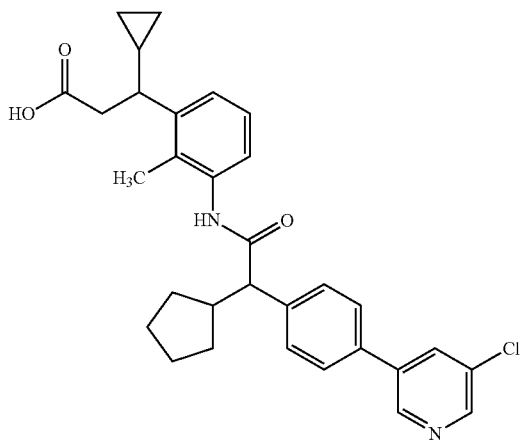 [SMILES: Cc1c(NC(=O)C(c2ccc(-c3cncc(Cl)c3)cc2)C2CCCC2)cccc1C(CC(=O)O)C1CC1]

In analogy to Suzuki coupling conditions in example 1 reaction of 75 mg intermediate 17 with 33 mg (5-chloropyridin-3-yl)boronic acid followed by tert.-butyl ester cleavage and subsequent purification via HPLC gave 29 mg of the title compound.

$^1$H NMR (400 MHz, DMSO-d$_6$) δ ppm −0.08-0.04 (m, 1 H) 0.12-0.22 (m, 1 H) 0.22-0.33 (m, 1 H) 0.42-0.52 (m, 1 H) 0.98-1.11 (m, 2 H) 1.34-1.73 (m, 6 H) 1.81-1.93 (m, 1 H) 2.03 (d, 3 H) 2.56-2.68 (m, 3 H) 2.69-2.76 (m, 1 H) 3.51-3.57 (m, 1 H) 6.98-7.05 (m, 1 H) 7.05-7.13 (m, 1 H) 7.15-7.21 (m, 1 H) 7.56 (d, 2 H) 7.76 (m, 2 H) 8.22-8.28 (m, 1 H) 8.58-8.63 (m, 1 H) 8.86-8.91 (m, 1 H) 9.52-9.56 (m, 1 H).

Example 111

(3R/S)-3-[3-({(2R/S)-2-cyclopentyl-2-[4-(5-ethoxypyridin-3-yl)phenyl]acetyl}amino)-2-methylphenyl]-3-cyclopropylpropanoic acid

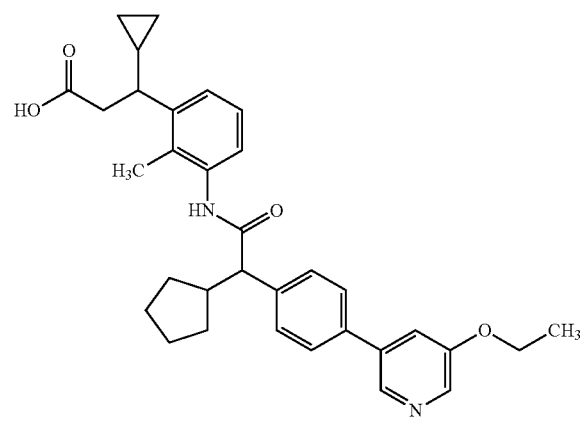 [SMILES: CCOc1cncc(-c2ccc(C(C(=O)Nc3cccc(C(CC(=O)O)C4CC4)c3C)C3CCCC3)cc2)c1]

In analogy to Suzuki coupling conditions in example 1 reaction of 75 mg intermediate 17 with 35 mg (5-ethoxypyridin-3-yl)boronic acid followed by tert.-butyl ester cleavage and subsequent purification via HPLC gave 29 mg of the title compound.

$^1$H NMR (400 MHz, DMSO-d$_6$) δ ppm −0.07-0.04 (m, 1 H) 0.13-0.21 (m, 1 H) 0.22-0.31 (m, 1 H) 0.42-0.51 (m, 1 H) 0.98-1.09 (m, 2 H) 1.37 (m, 9 H) 1.82-1.93 (m, 1 H) 2.00-2.06 (m, 3 H) 2.56-2.65 (m, 3 H) 2.70-2.77 (m, 1 H) 3.50-3.56 (d, 1 H) 4.15-4.24 (m, 2 H) 6.98-7.04 (m, 1 H) 7.05-7.12 (m, 1 H) 7.14-7.20 (m, 1 H) 7.55 (s, 2 H) 7.59-7.63 (m, 1 H) 7.68-7.74 (m, 2 H) 8.24-8.27 (m, 1 H) 8.46-8.49 (m, 1 H) 9.50-9.54 (m, 1 H).

Example 112

(3R/S)-3-[3-({(2R/S)-2-cyclopentyl-2-[4-(5-fluoropyridin-3-yl)phenyl]acetyl}amino)-2-methylphenyl]-3-cyclopropylpropanoic acid

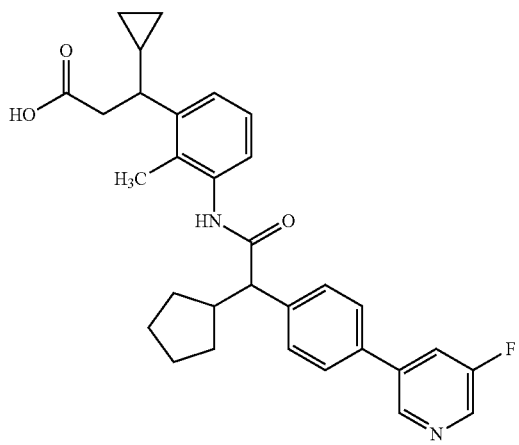 [SMILES: Cc1c(NC(=O)C(c2ccc(-c3cncc(F)c3)cc2)C2CCCC2)cccc1C(CC(=O)O)C1CC1]

In analogy to Suzuki coupling conditions in example 1 reaction of 75 mg intermediate 17 with 29 mg (5-fluoropyridin-3-yl)boronic acid followed by tert.-butyl ester cleavage and subsequent purification via HPLC gave 29 mg of the title compound.

$^1$H NMR (300 MHz, DMSO-d$_6$) δ ppm −0.08-0.04 (m, 1 H) 0.12-0.32 (m, 2 H) 0.40-0.52 (m, 1 H) 0.97-1.10 (m, 2 H) 1.35-1.73 (m, 6 H) 1.80-1.94 (m, 1 H) 2.03 (d, 3 H) 2.58 (m, 3 H) 2.70-2.77 (m, 1 H) 3.54 (d, 1 H) 6.96-7.05 (m, 1 H) 7.09 (s, 1 H) 7.16 (s, 1 H) 7.56 (d, 2 H) 7.77 (d, 2 H) 8.03-8.12 (m, 1 H) 8.56 (d, 1 H) 8.81 (s, 1 H) 9.55 (s, 1 H).

Example 113

(3R/S)-3-[3-({(2R/S)-2-cyclopentyl-2-[4-(5-methyl-pyridin-3-yl)phenyl]acetyl}amino)-2-methylphenyl]-3-cyclopropylpropanoic acid

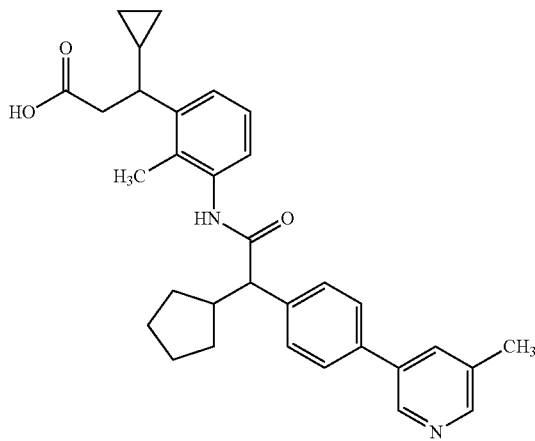 [SMILES: Cc1cncc(-c2ccc(C(C(=O)Nc3cccc(C(CC(=O)O)C4CC4)c3C)C3CCCC3)cc2)c1]

In analogy to Suzuki coupling conditions in example 1 reaction of 75 mg intermediate 17 with 29 mg (5-methyl-pyridin-3-yl)boronic acid followed by tert.-butyl ester cleavage and subsequent purification via HPLC gave 22 mg of the title compound.

$^1$H NMR (300 MHz, DMSO-d$_6$) δ ppm −0.09-0.05 (m, 1 H) 0.12-0.32 (m, 2 H) 0.40-0.53 (m, 1 H) 0.96-1.11 (m, 2 H) 1.33-1.75 (m, 6 H) 1.81-1.93 (m, 1 H) 2.03 (d, 3 H) 2.37 (s, 3 H) 2.59 (m, 3 H) 2.70-2.75 (m, 1 H) 3.50-3.56 (d, 1 H) 6.98-7.04 (m, 1 H) 7.10 (m, 1 H) 7.15-7.20 (m, 1 H) 7.54 (d, 2 H) 7.69 (d, 2 H) 7.89-7.95 (m, 1 H) 8.38-8.43 (m, 1 H) 8.67-8.73 (m, 1 H) 9.53 (s, 1 H) 11.90-12.06 (m, 1 H).

Example 114: (3R/S)-3-[3-({(2R/S)-2-cyclopentyl-2-[4-(5-ethylpyridin-3-yl)phenyl]acetyl}amino)-2-methylphenyl]-3-cyclopropylpropanoic acid

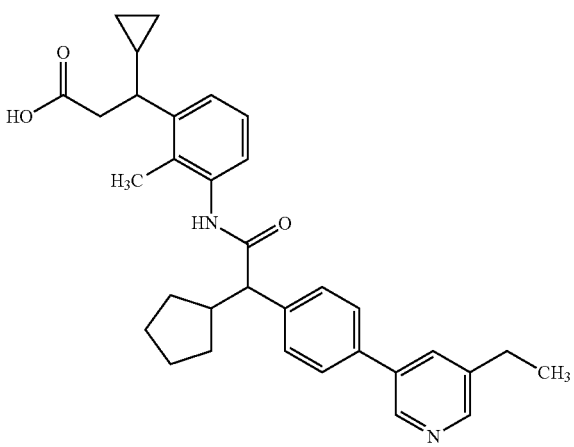 [SMILES: CCc1cncc(-c2ccc(C(C(=O)Nc3cccc(C(CC(=O)O)C4CC4)c3C)C3CCCC3)cc2)c1]

In analogy to Suzuki coupling conditions in example 1 reaction of 75 mg intermediate 17 with 31 mg (5-ethylpyridin-3-yl)boronic acid followed by tert.-butyl ester cleavage and subsequent purification via HPLC gave 33 mg of the title compound.

$^1$H NMR (300 MHz, DMSO-d$_6$) δ ppm −0.08-0.03 (m, 1 H) 0.12-0.31 (m, 2 H) 0.40-0.52 (m, 1 H) 0.97-1.09 (m, 2 H) 1.25 (t, 3 H) 1.33-1.73 (m, 6 H) 1.80-1.93 (m, 1 H) 2.03 (d, 3 H) 2.58 (m, 2 H) 2.63-2.75 (m, 4 H) 3.52 (d, 1 H) 6.96-7.04 (m, 1 H) 7.09 (s, 1 H) 7.16 (s, 1 H) 7.54 (d, 2 H) 7.69 (d, 2 H) 7.91 (s, 1 H) 8.42 (s, 1 H) 8.71 (s, 1 H) 9.53 (s, 1 H).

Example 115

(3R/S)-3-(3-{[(2R/S)-2-Cyclopentyl-2-{3-fluoro-4-[5-(trifluoromethyl)pyridin-3-yl]phenyl}acetyl]amino}-2-methylphenyl)butanoic acid

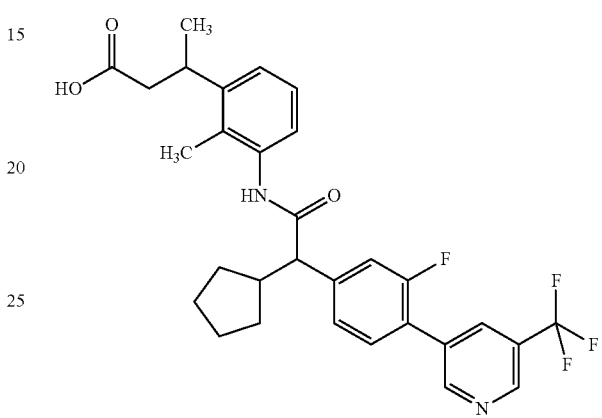

In analogy to Suzuki coupling conditions in example 1 reaction of 330 mg intermediate 18 with 154 mg [5-(trifluoromethyl)pyridin-3-yl]boronic acid followed by methyl ester saponification with 186 mg NaOH (32%) in ethanol/water (7.5 ml/2.5 ml) and subsequent purification via HPLC gave 230 mg of the title compound.

$^1$H NMR (400 MHz, DMSO-d$_6$) δ ppm 0.99-1.10 (m, 1 H) 1.15 (t, 3 H) 1.36-1.76 (m, 6 H) 1.82-1.96 (m, 1 H) 2.10 (d, 3 H) 2.59-2.71 (m, 1 H) 3.42 (m, 1 H) 3.61 (d, 1 H) 7.04 (dd, 1 H) 7.07-7.15 (m, 2 H) 7.38-7.48 (m, 2 H) 7.71 (t1 H) 8.40 (s, 1 H) 9.02 (d, 1 H) 9.10 (s, 1 H) 9.61 (s, 1 H) 11.91-12.21 (m, 1 H).

Example 116

3-{3-[(Cyclopentyl{3-fluoro-4-[5-(trifluoromethyl)pyridin-3-yl]phenyl}acetyl)amino]-2-methylphenyl}butanoic acid, Stereoisomer 1

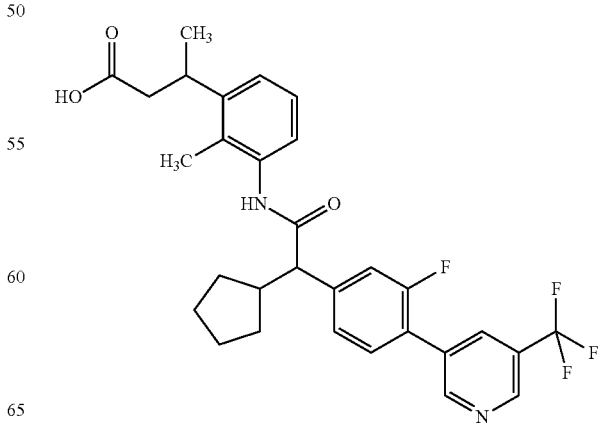

230 mg of example 115 were separated into the four stereoisomers (examples 116/117/118/119) via preparative chiral HPLC. A first HPLC separation (method 6; solvent: hexane/ethanol 70:30 (v/v)+0.1% formic acid; flow rate: 25 ml/min; solution: 230 mg/3.0 mL DCM/MeOH; injection: 10×0.3 ml) gave 46 mg example 116 and 142 mg of a mixture of example 117/118/119. A second HPLC separation (method 4; solvent: hexane/2-propanol 70:30 (v/v)+0.1% formic acid; flow rate: 20 ml/min; solution: 142 mg/2.4 mL DCM/MeOH; injection: 4×0.6 ml) gave a 44 mg example 117 and 92 mg of a mixture of example 118/119. A third HPLC separation (method 5; solvent: hexane/2-propanol 80:20 (v/v)+0.1% formic acid; flow rate: 25 ml/min; solution: 92 mg/2.0 mL DCM/MeOH; injection: 2×1.0 ml) gave a 30 mg example 118 and 25 mg example 119.

Preparative chiral HPLC, method 6: Rt: 8.3-9.5 min.

Analytical HPLC, method 6: solvent: hexane/ethanol 80:20 (v/v)+0.1% TFA; flow rate: 1 ml/min; injection: 5 µl; 1 mg/ml ethanol/methanol (1:1); Rt: 6.00 min.

Optical rotation: −46.0° (3.2 mg/ml methanol, temperature: 20° C., wave length: 589 nM).

$^1$H NMR (400 MHz, DMSO-$d_6$) δ ppm 1.02-1.09 (m, 1 H) 1.10-1.17 (m, 3 H) 1.35-1.75 (m, 6 H) 1.81-1.95 (m, 1 H) 2.09 (s, 3 H) 2.61-2.68 (m, 1 H) 3.38-3.45 (m, 1 H) 3.60 (d, 1 H) 7.04 (s, 1 H) 7.06-7.15 (m, 2 H) 7.38-7.51 (m, 2 H) 7.71 (s, 1 H) 8.39 (s, 1 H) 9.01 (s, 1 H) 9.09 (s, 1 H) 9.60 (s, 1 H) 11.76-12.24 (m, 1 H).

Example 117

3-{3-[(Cyclopentyl{3-fluoro-4-[5-(trifluoromethyl) pyridin-3-yl]phenyl}acetyl)amino]-2-methylphenyl}butanoic acid, Stereoisomer 2

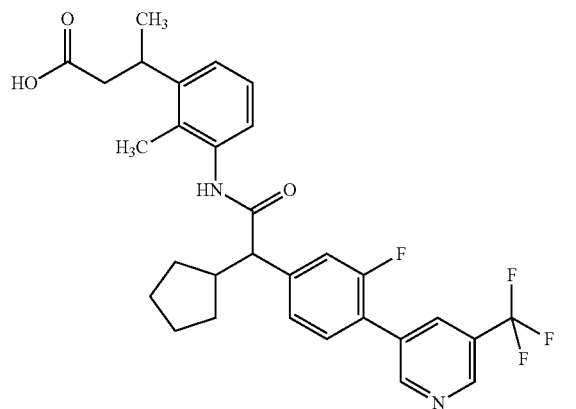 [SMILES: Cc1c(NC(=O)C(c2ccc(-c3cncc(C(F)(F)F)c3)c(F)c2)C2CCCC2)cccc1C(C)CC(=O)O]

Preparative chiral HPLC, method 4: Rt: 6.2-8.0 min.

Analytical HPLC, method 7: solvent: hexane/2-propanol 80:20 (v/v)+0.1% TFA; flow rate: 1 ml/min; injection: 5 µl; 1 mg/ml ethanol/methanol (1:1); Rt: 4.59 min.

Optical rotation: −40.5° (2.8 mg/ml methanol, temperature: 20° C., wave length: 589 nM).

$^1$H NMR (400 MHz, DMSO-$d_6$) δ ppm 1.02-1.09 (m, 1 H) 1.15 (d, 3 H) 1.34-1.76 (m, 6 H) 1.81-1.94 (m, 1 H) 2.10 (s, 3 H) 2.62-2.69 (m, 1 H) 3.39-3.45 (m, 1 H) 3.56-3.65 (m, 1 H) 6.97-7.05 (m, 1 H) 7.06-7.15 (m, 2 H) 7.36-7.51 (m, 2 H) 7.71 (s, 1 H) 8.40 (s, 1 H) 9.01 (d, 1 H) 9.09 (s, 1 H) 9.60 (s, 1 H) 11.62-12.20 (m, 1 H).

Example 118

3-{3-[(Cyclopentyl{3-fluoro-4-[5-(trifluoromethyl) pyridin-3-yl]phenyl}acetyl)amino]-2-methylphenyl}butanoic acid, Stereoisomer 3

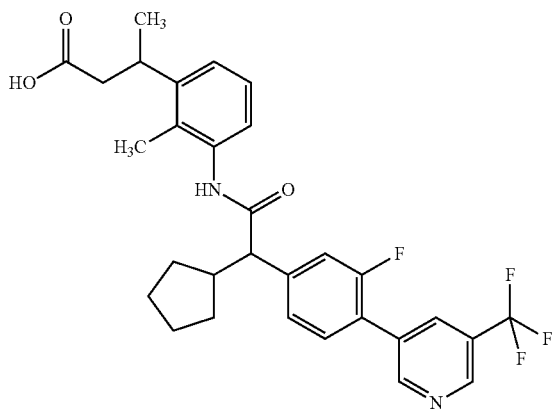 [SMILES: Cc1c(NC(=O)C(c2ccc(-c3cncc(C(F)(F)F)c3)c(F)c2)C2CCCC2)cccc1C(C)CC(=O)O]

Preparative chiral HPLC, method 5: Rt: 2.5-3.7 min.

Analytical HPLC, method 8: solvent: hexane/2-propanol 80:20 (v/v)+0.1% TFA; flow rate: 1 ml/min; injection: 5 µl; 1 mg/ml ethanol/methanol (1:1); Rt: 1.84 min.

Optical rotation: +55.4° (2.2 mg/ml methanol, temperature: 20° C., wave length: 589 nM).

$^1$H NMR (400 MHz, DMSO-$d_6$) δ ppm 1.01-1.09 (m, 1 H) 1.15 (d, 3 H) 1.60 (m, 6 H) 1.81-1.95 (m, 1 H) 2.10 (s, 3 H) 2.61-2.69 (m, 1 H) 3.41 (m, 1 H) 3.60 (d, 1 H) 7.02 (d, 1 H) 7.06-7.15 (m, 2 H) 7.38-7.51 (m, 2 H) 7.71 (s, 1 H) 8.40 (s, 1 H) 9.01 (d, 1 H) 9.09 (s, 1 H) 9.60 (s, 1 H) 11.84-12.22 (m, 1 H).

Example 119

3-{3-[(Cyclopentyl{3-fluoro-4-[5-(trifluoromethyl) pyridin-3-yl]phenyl}acetyl)amino]-2-methylphenyl}butanoic acid, Stereoisomer 4

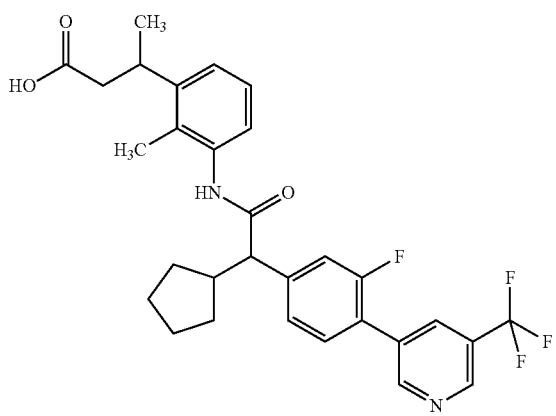 [SMILES: Cc1c(NC(=O)C(c2ccc(-c3cncc(C(F)(F)F)c3)c(F)c2)C2CCCC2)cccc1C(C)CC(=O)O]

Preparative chiral HPLC, method 5: Rt: 5.1-6.4 min.

Analytical HPLC, method 8: solvent: hexane/2-propanol 80:20 (v/v)+0.1% TFA; flow rate: 1 ml/min; injection: 5 µl; 1 mg/ml ethanol/methanol (1:1); Rt: 4.23 min.

Optical rotation: +55.2° (2.7 mg/ml methanol, temperature: 20° C., wave length: 589 nM).

$^1$H NMR (400 MHz, DMSO-d$_6$) δ ppm 1.02-1.09 (m, 1 H) 1.13 (d, 3 H) 1.60 (m, 7 H) 1.83-1.94 (m, 1 H) 2.09 (s, 3 H) 2.61-2.68 (m, 1 H) 3.38-3.44 (m, 1 H) 3.60 (d, 1 H) 7.04 (d, 1 H) 7.06-7.16 (m, 2 H) 7.38-7.51 (m, 2 H) 7.71 (s, 1 H) 8.40 (s, 1 H) 9.01 (s, 1 H) 9.09 (s, 1 H) 9.60 (s, 1 H) 11.78-12.31 (m, 1 H).

Example 120

(3R/S)-3-[3-({(2R/S)-2-[4-(5-Chloro-6-methylpyridin-3-yl)-3-fluorophenyl]-2-cyclopentylacetyl}amino)-2-methylphenyl]butanoic acid

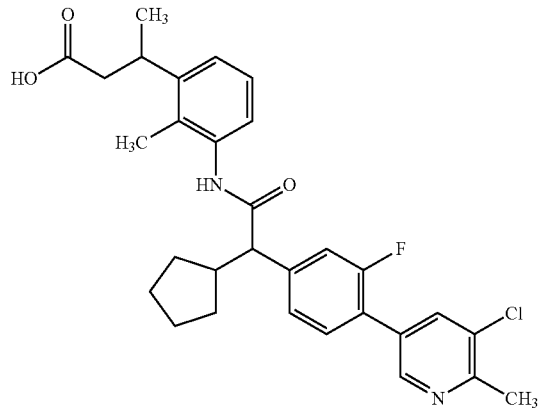 [SMILES: Cc1ncc(-c2ccc(C(C(=O)Nc3cccc(C(C)CC(=O)O)c3C)C3CCCC3)cc2F)cc1Cl]

In analogy to Suzuki coupling conditions in example 1 reaction of 330 mg intermediate 18 with 205 mg 3-chloro-2-methyl-5-(4,4,5,5-tetramethyl-1,3,2-dioxaborolan-2-yl)pyridine followed by methyl ester saponification with 372 mg NaOH (32%) in ethanol/water (7.5 ml/2.5 ml) and subsequent purification via HPLC gave 130 mg of the title compound.

$^1$H NMR (400 MHz, DMSO-d$_6$) δ ppm 0.99-1.08 (m, 1 H) 1.14 (t3 H) 1.33-1.75 (m, 6H) 1.81-1.93 (m, 1 H) 2.09 (d, 3 H) 2.60 (s, 4 H) 3.54-3.62 (d, 1 H) 6.97-7.05 (m, 1 H) 7.06-7.14 (m, 2 H) 7.39 (d, 2 H) 7.62 (s, 1 H) 8.08 (s, 1 H) 8.60-8.66 (m, 1 H) 9.59 (s, 1 H) 11.76-12.28 (m, 1 H).

Example 121

3-[3-({[4-(5-Chloro-6-methylpyridin-3-yl)-3-fluorophenyl](cyclopentyl)acetyl}amino)-2-methylphenyl]butanoic acid, Stereoisomer 1

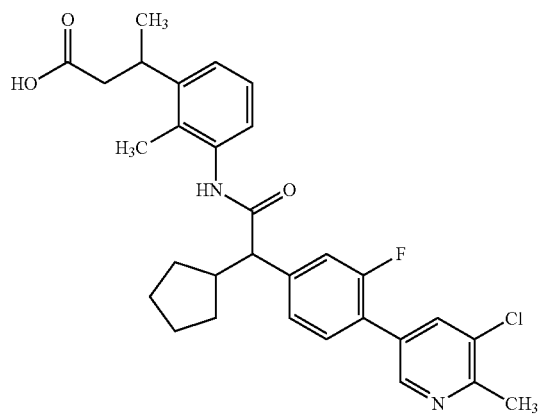 [SMILES: Cc1ncc(-c2ccc(C(C(=O)Nc3cccc(C(C)CC(=O)O)c3C)C3CCCC3)cc2F)cc1Cl]

130 mg example 120 were separated into the four stereoisomers (examples 121/122/123/124) via preparative chiral HPLC. A first HPLC separation (method 5; solvent: hexane/2-propanol 70:30 (v/v)+0.1% formic acid; flow rate: 50 ml/min; solution: 130 mg/3.0 mL DCM/MeOH; injection: 3×1.0 ml) gave 28 mg example 121, 28 mg of example 122 and 64 mg of a mixture of example 123/124. A second HPLC separation (method 4; solvent: hexane/2-propanol 80:20 (v/v)+0.1% formic acid; flow rate: 50 ml/min; solution: 64 mg/2.0 mL DCM/MeOH; injection: 2×1.0 ml) gave 20 mg of example 123 and 19 mg of example 124.

Preparative chiral HPLC, method 5: Rt: 6.7-8.4 min.

Analytical HPLC, method 8: solvent: hexane/2-propanol 70:30 (v/v)+0.1% TFA; flow rate: 1 ml/min; injection: 5 μl; 1 mg/ml ethanol/methanol (1:1); Rt: 4.49 min.

Optical rotation: +36.6° (1.4 mg/ml methanol, temperature: 20° C., wave length: 589 nM).

$^1$H NMR (400 MHz, DMSO-d$_6$) δ ppm 1.02-1.08 (m, 1 H) 1.13 (d, 3 H) 1.34-1.75 (m, 6 H) 1.82-1.92 (m, 1 H) 2.08 (s, 3 H) 2.47 (s, 1 H) 2.60 (m, 4 H) 3.54-3.62 (d, 1 H) 6.99-7.05 (m, 1 H) 7.06-7.11 (m, 2 H) 7.34-7.44 (m, 2 H) 7.62 (s, 1 H) 8.08 (s, 1 H) 8.62 (s, 1 H) 9.57 (s, 1 H).

Example 122

3-[3-({[4-(5-Chloro-6-methylpyridin-3-yl)-3-fluorophenyl](cyclopentyl)acetyl}amino)-2-methylphenyl]butanoic acid, Stereoisomer 2

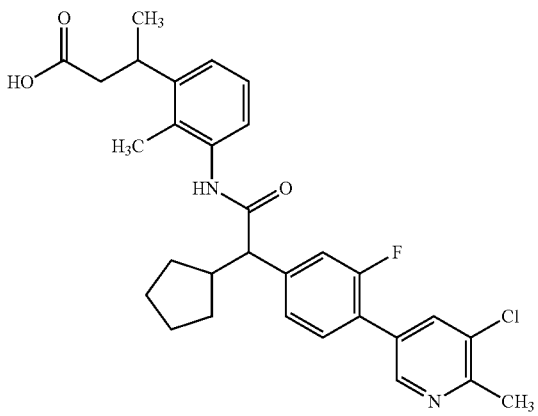 [SMILES: Cc1ncc(-c2ccc(C(C(=O)Nc3cccc(C(C)CC(=O)O)c3C)C3CCCC3)cc2F)cc1Cl]

Preparative chiral HPLC, method 5: Rt: 9.1-11.2 min.

Analytical HPLC, method 8: solvent: hexane/2-propanol 70:30 (v/v)+0.1% TFA; flow rate: 1 ml/min; injection: 5 μl; 1 mg/ml ethanol/methanol (1:1); Rt: 7.35 min.

Optical rotation: −52.1 (1.8 mg/ml methanol, temperature: 20° C., wave length: 589 nM).

$^1$H NMR (400 MHz, DMSO-d$_6$) δ ppm 1.04 (s, 1 H) 1.14 (d, 3 H) 1.32-1.73 (m, 6 H) 1.81-1.92 (m, 1 H) 2.10 (s, 3 H) 2.45 (m, 2 H) 2.60 (m, 4 H) 3.54-3.61 (d, 1 H) 6.98-7.04 (m, 1 H) 7.06-7.11 (m, 2 H) 7.39 (br. s., 2 H) 7.62 (s, 1 H) 8.08 (s, 1 H) 8.62 (s, 1 H) 9.57 (s, 1 H).

Example 123

3-[3-({[4-(5-Chloro-6-methylpyridin-3-yl)-3-fluorophenyl](cyclopentyl)acetyl}amino)-2-methylphenyl]butanoic acid, Stereoisomer 3

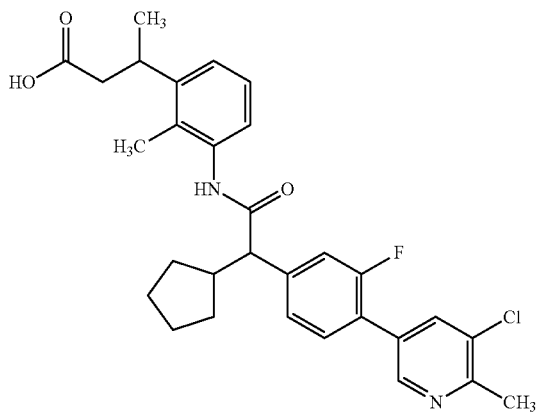

Preparative chiral HPLC, method 4: Rt: 5.8-7.2 min.
Analytical HPLC, method 7: solvent: hexane/2-propanol 70:30 (v/v)+0.1% TFA; flow rate: 1 ml/min; injection: 5 µl; 1 mg/ml ethanol/methanol (1:1); Rt: 3.68 min.
Optical rotation: +43.0° (1.4 mg/ml methanol, temperature: 20° C., wave length: 589 nM).
$^1$H NMR (400 MHz, DMSO-$d_6$) δ ppm 1.02-1.08 (m, 1 H) 1.15 (d, 3 H) 1.35-1.73 (m, 6 H) 1.81-1.92 (m, 1 H) 2.10 (s, 3 H) 2.47 (m, 1 H) 2.60 (m, 4 H) 3.38-3.45 (m, 1 H) 3.55-3.61 (d, 1 H) 6.99-7.04 (m, 1 H) 7.06-7.11 (m, 2 H) 7.35-7.43 (m, 2 H) 7.62 (s, 1 H) 8.08 (s, 1 H) 8.62 (s, 1 H) 9.57 (s, 1 H).

Example 124

3-[3-({[4-(5-Chloro-6-methylpyridin-3-yl)-3-fluorophenyl](cyclopentyl)acetyl}amino)-2-methylphenyl]butanoic acid, Stereoisomer 4

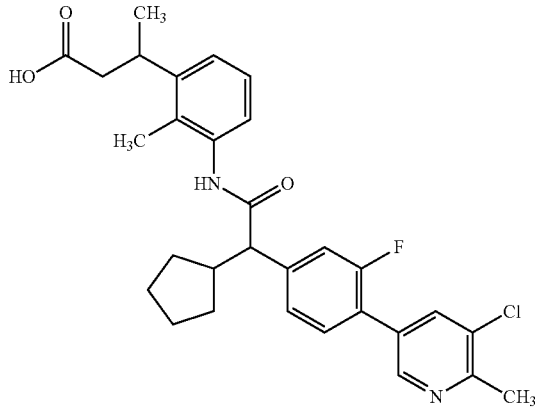 [SMILES: Cc1ncc(-c2ccc(C(C(=O)Nc3cccc(C(C)CC(=O)O)c3C)C3CCCC3)cc2F)cc1Cl]

Preparative chiral HPLC, method 4: Rt: 9.2-11.2 min.
Analytical HPLC, method 7: solvent: hexane/2-propanol 70:30 (v/v)+0.1% TFA; flow rate: 1 ml/min; injection: 5 µl; 1 mg/ml ethanol/methanol (1:1); Rt: 6.44 min.
Optical rotation: −40.5° (2.0 mg/ml methanol, temperature: 20° C., wave length: 589 nM).
$^1$H NMR (400 MHz, DMSO-$d_6$) δ ppm 1.03-1.08 (m, 1 H) 1.13 (d, 3 H) 1.34-1.74 (m, 6 H) 1.81-1.93 (m, 1 H) 2.08 (s, 3 H) 2.60 (m, 4 H) 3.37-3.44 (m, 1 H) 3.57 (d, 1 H) 7.04 (s, 1 H) 7.06-7.12 (m, 2 H) 7.34-7.43 (m, 2 H) 7.62 (s, 1 H) 8.08 (s, 1 H) 8.62 (s, 1 H) 9.57 (s, 1 H).

Example 125

(3R/S)-3-[3-({(2R/S)-2-[4-(5-Chloropyridin-3-yl)-3-fluorophenyl]-2-cyclopentylacetyl}amino)-2-methylphenyl]butanoic acid

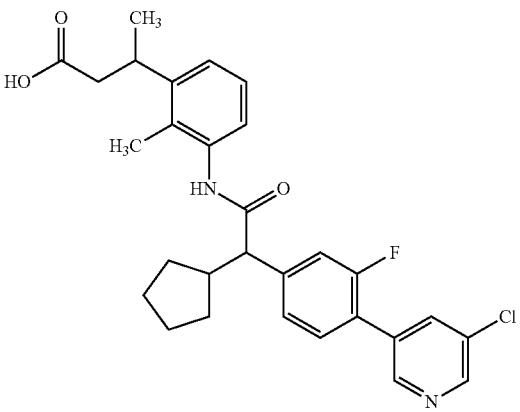 [SMILES: Cc1c(NC(=O)C(c2ccc(-c3cncc(Cl)c3)c(F)c2)C2CCCC2)cccc1C(C)CC(=O)O]

In analogy to Suzuki coupling conditions in example 1 reaction of 330 mg intermediate 18 with 127 mg (5-chloropyridin-3-yl)boronic acid followed by methyl ester saponification with 645 mg NaOH (32%) in ethanol/water (7.5 ml/2.5 ml) and subsequent purification via HPLC gave 230 mg of the title compound.
$^1$H NMR (400 MHz, DMSO-$d_6$) δ ppm 1.00-1.07 (m, 1 H) 1.14 (t, 3 H) 1.34-1.75 (m, 6 H) 1.81-1.93 (m, 1 H) 2.09 (d, 3 H) 2.57-2.70 (m, 1 H) 3.39-3.45 (m, 1 H) 3.59 (d, 1 H) 6.98-7.06 (m, 1 H) 7.06-7.15 (m, 2 H) 7.35-7.47 (m, 2 H) 7.65 (t, 1 H) 8.16 (s, 1 H) 8.66 (d, 1 H) 8.75 (s, 1 H) 9.59 (s, 1 H) 12.04 (s, 1 H).

Example 126

3-[3-({[4-(5-Chloropyridin-3-yl)-3-fluorophenyl](cyclopentyl)acetyl}amino)-2-methylphenyl]butanoic acid, Stereoisomer 1

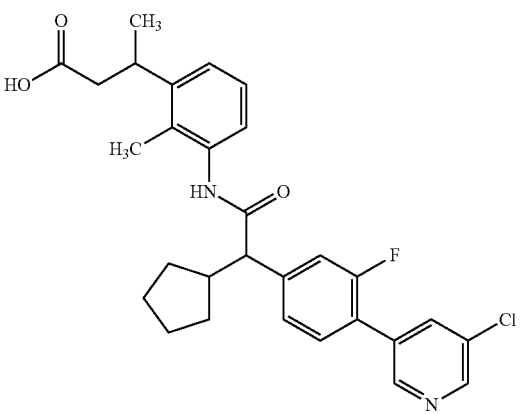 [SMILES: Cc1c(NC(=O)C(c2ccc(-c3cncc(Cl)c3)c(F)c2)C2CCCC2)cccc1C(C)CC(=O)O]

200 mg example 125 were separated into the four stereoisomers (examples 126/127/128/129) via preparative chiral HPLC. A first HPLC separation (method 5; solvent: hexane/2-propanol 70:30 (v/v)+0.1% formic acid; flow rate: 50 ml/min; solution: 200 mg/4.4 mL DCM/MeOH; injection: 4×1.1 ml) gave 57 mg example 126, 66 mg of example 127 and 140 mg of a mixture of example 128/129. A second HPLC separation (method 4; solvent: hexane/2-propanol 80:20 (v/v)+0.1% formic acid; flow rate: 50 ml/min; solution: 140 mg/3.0 mL DCM/MeOH; injection: 4×0.75 ml) gave 35 mg of example 128 and 47 mg of example 129.

Preparative chiral HPLC, method 5: Rt: 3.5-5.5 min.

Analytical HPLC, method 8: solvent: hexane/2-propanol 70:30 (v/v)+0.1% TFA; flow rate: 1 ml/min; injection: 5 µl; 1 mg/ml ethanol/methanol (1:1); Rt: 4.90 min.

Optical rotation: +39.2° (2.3 mg/ml methanol, temperature: 20° C., wave length: 589 nM).

$^1$H NMR (400 MHz, DMSO-$d_6$) δ ppm 1.02-1.08 (m, 1 H) 1.13 (d, 3 H) 1.35-1.74 (m, 6 H) 1.82-1.94 (m, 1 H) 2.08 (s, 3 H) 2.57-2.69 (m, 1 H) 3.59 (d, 1 H) 7.04 (s, 1 H) 7.06-7.12 (m, 2 H) 7.37-7.45 (m, 2 H) 7.65 (s, 1 H) 8.16 (s, 1 H) 8.66 (d, 1 H) 8.74 (s, 1 H) 9.58 (s, 1 H).

Example 127

3-[3-({[4-(5-Chloropyridin-3-yl)-3-fluorophenyl](cyclopentyl)acetyl}amino)-2-methylphenyl]butanoic acid, Stereoisomer 2

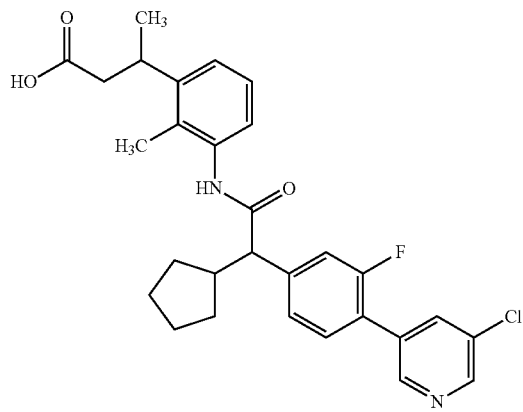 [SMILES: Cc1c(NC(=O)C(c2ccc(-c3cncc(Cl)c3)c(F)c2)C2CCCC2)cccc1C(C)CC(=O)O]

Preparative chiral HPLC, method 5: Rt: 8.5-10.1 min.

Analytical HPLC, method 8: solvent: hexane/2-propanol 70:30 (v/v)+0.1% TFA; flow rate: 1 ml/min; injection: 5 µl; 1 mg/ml ethanol/methanol (1:1); Rt: 6.07 min.

Optical rotation: −40.1 (2.0 mg/ml methanol, temperature: 20° C., wave length: 589 nM).

$^1$H NMR (400 MHz, DMSO-$d_6$) δ ppm 1.02-1.08 (m, 1 H) 1.15 (d, 3 H) 1.34-1.74 (m, 6 H) 1.82-1.93 (m, 1 H) 2.10 (s, 3 H) 2.57-2.69 (m, 1 H) 3.59 (d, 1 H) 7.02 (s, 1 H) 7.06-7.12 (m, 2 H) 7.36-7.46 (m, 2 H) 7.64 (s, 1 H) 8.16 (s, 1 H) 8.66 (d, 1 H) 8.75 (s, 1 H) 9.58 (s, 1 H).

Example 128

3-[3-({[4-(5-Chloropyridin-3-yl)-3-fluorophenyl](cyclopentyl)acetyl}amino)-2-methylphenyl]butanoic acid, Stereoisomer 3

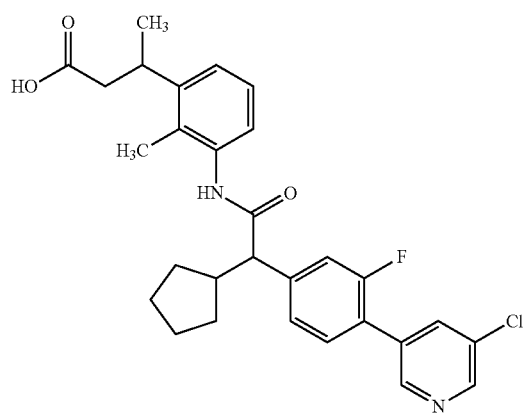 [SMILES: Cc1c(NC(=O)C(c2ccc(-c3cncc(Cl)c3)c(F)c2)C2CCCC2)cccc1C(C)CC(=O)O]

Preparative chiral HPLC, method 4: Rt: 6.6-8.0 min.

Analytical HPLC, method 7: solvent: hexane/2-propanol 80:20 (v/v)+0.1% TFA; flow rate: 1 ml/min; injection: 5 µl; 1 mg/ml ethanol/methanol (1:1); Rt: 4.21 min.

Optical rotation: +56.0° (2.3 mg/ml methanol, temperature: 20° C., wave length: 589 nM).

$^1$H NMR (400 MHz, DMSO-$d_6$) δ ppm 1.01-1.08 (m, 1 H) 1.15 (d, 3 H) 1.60 (m, 6 H) 1.82-1.93 (m, 1 H) 2.10 (s, 3 H) 2.56-2.69 (m, 1 H) 3.41 (m, 1 H) 3.59 (d, 1 H) 7.02 (d, 1 H) 7.06-7.13 (m, 2 H) 7.36-7.46 (m, 2 H) 7.60-7.69 (m, 1 H) 8.16 (s, 1 H) 8.66 (d, 1 H) 8.75 (s, 1 H) 9.58 (s, 1 H).

Example 129

3-[3-({[4-(5-Chloropyridin-3-yl)-3-fluorophenyl](cyclopentyl)acetyl}amino)-2-methylphenyl]butanoic acid, Stereoisomer 4

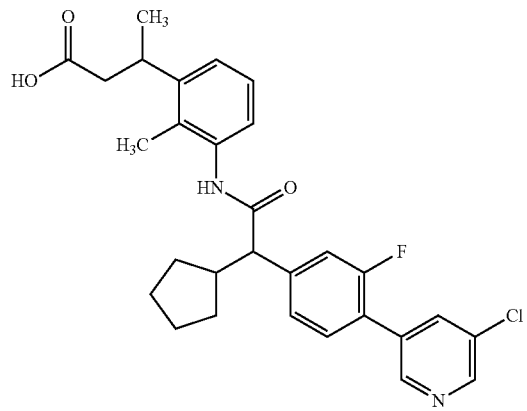

Preparative chiral HPLC, method 4: Rt: 8.0-10.0 min.

Analytical HPLC, method 7: solvent: hexane/2-propanol 80:20 (v/v)+0.1% TFA; flow rate: 1 ml/min; injection: 5 µl; 1 mg/ml ethanol/methanol (1:1); Rt: 5.50 min.

Optical rotation: −37.2° (3.4 mg/ml methanol, temperature: 20° C., wave length: 589 nM).

¹H NMR (400 MHz, DMSO-d₆) δ ppm 1.01-1.09 (m, 1 H) 1.13 (d, 3 H) 1.34-1.75 (m, 6 H) 1.82-1.94 (m, 1 H) 2.08 (s, 3 H) 2.46 (m, 1 H) 2.58-2.68 (m, 1 H) 3.38-3.45 (m, 1 H) 3.59 (d, 1 H) 7.04 (d, 1 H) 7.07-7.12 (m, 2 H) 7.37-7.45 (m, 2 H) 7.61-7.69 (m, 1 H) 8.16 (d, 1 H) 8.66 (d, 1 H) 8.75 (t, 1 H) 9.58 (s, 1 H).

Example 130

(3R/S)-3-(3-{[(2R/S)-2-Cyclobutyl-2-{4-[5-(trifluoromethyl)pyridin-3-yl]phenyl}acetyl]amino}-2-methylphenyl)butanoic acid

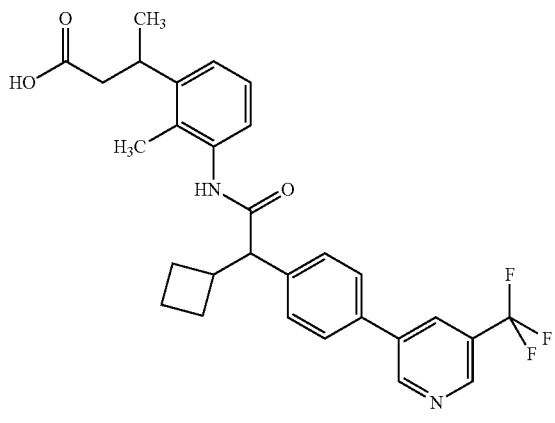 [SMILES: Cc1c(NC(=O)C(c2ccc(-c3cncc(C(F)(F)F)c3)cc2)C2CCC2)cccc1C(C)CC(=O)O]

In analogy to Suzuki coupling conditions in example 1 reaction of 375 mg intermediate 19 with 234 mg [5-(trifluoromethyl)pyridin-3-yl]boronic acid followed by methyl ester saponification with 810 mg NaOH (32%) in ethanol/water (17.5 ml/5.8 ml) and subsequent purification via HPLC gave 300 mg of the title compound.

¹H NMR (400 MHz, DMSO-d₆) δ ppm 1.14 (dd, 3 H) 1.58-1.68 (m, 1 H) 1.80-1.95 (m, 4 H) 2.09 (d, 3 H) 2.12-2.20 (m, 1 H) 2.98-3.12 (m, 1 H) 3.35-3.47 (m, 1 H) 3.84 (d, 1 H) 7.01 (dd, 1 H) 7.06-7.12 (m, 2 H) 7.55 (d, 2 H) 7.83 (d, 2 H) 8.45 (s, 1 H) 8.95 (d, 1 H) 9.21 (d, 1 H) 9.57 (s, 1 H) 11.92-12.13 (m, 1 H).

Example 131

3-{3-[(Cyclobutyl{4-[5-(trifluoromethyl)pyridin-3-yl]phenyl}acetyl)amino]-2-methylphenyl}butanoic acid, Stereoisomer 1

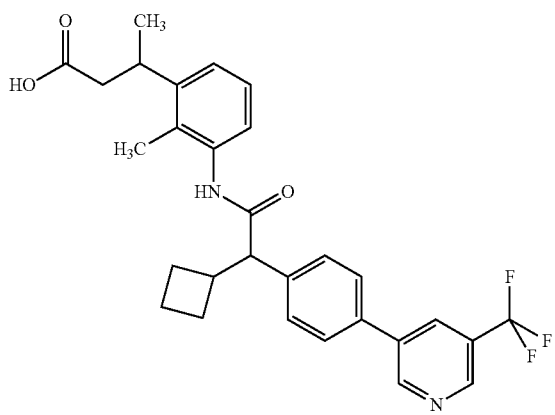 [SMILES: Cc1c(NC(=O)C(c2ccc(-c3cncc(C(F)(F)F)c3)cc2)C2CCC2)cccc1C(C)CC(=O)O]

300 mg example 130 were separated into the four stereoisomers (examples 131/132/133/134) via preparative chiral HPLC. A first HPLC separation (method 5; solvent: hexane/2-propanol 70:30 (v/v)+0.1% formic acid; flow rate: 50 ml/min; solution: 300 mg/6 mL DCM/MeOH; injection: 6×1.0 ml) gave 72 mg example 131, 63 mg of example 132 and 165 mg of a mixture of example 133/134. A second HPLC separation (method 4; solvent: hexane/2-propanol 70:30 (v/v)+0.1% formic acid; flow rate: 20 ml/min; solution: 165 mg/1.5 mL DCM/MeOH; injection: 1×1.5 ml) gave 49 mg of example 133 and 63 mg of example 134.

Preparative chiral HPLC, method 5: Rt: 6.0-8.1 min.

Analytical HPLC, method 8: solvent: hexane/2-propanol 70:30 (v/v)+0.1% TFA; flow rate: 1 ml/min; injection: 5 µl; 1 mg/ml ethanol/methanol (1:1); Rt: 4.10 min.

Optical rotation: +53.2° (2.1 mg/ml methanol, temperature: 20° C., wave length: 589 nM).

¹H NMR (400 MHz, DMSO-d₆) δ ppm 1.13 (d, 3 H) 1.57-1.67 (m, 1 H) 1.87 (m, 4 H) 2.08 (s, 3 H) 2.11-2.20 (m, 1 H) 2.99-3.11 (m, 1 H) 3.84 (d, 1 H) 6.98-7.04 (m, 1H) 7.06-7.11 (m, 2 H) 7.55 (d, 2 H) 7.83 (d, 2 H) 8.45 (s, 1 H) 8.95 (d, 1 H) 9.21 (d, 1 H) 9.56 (s, 1 H).

Example 132

3-{3-[(Cyclobutyl{4-[5-(trifluoromethyl)pyridin-3-yl]phenyl}acetyl)amino]-2-methylphenyl}butanoic acid, Stereoisomer 2

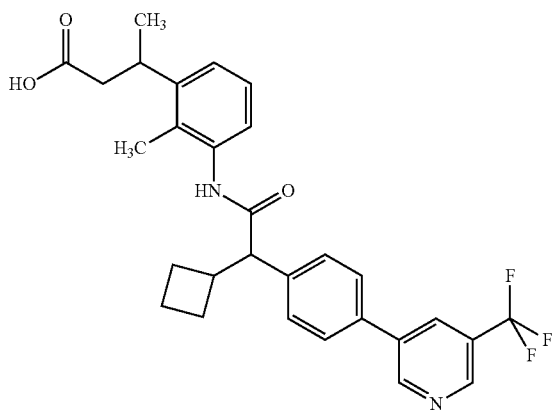 [SMILES: Cc1c(NC(=O)C(c2ccc(-c3cncc(C(F)(F)F)c3)cc2)C2CCC2)cccc1C(C)CC(=O)O]

Preparative chiral HPLC, method 5: Rt: 8.8-11.4 min.

Analytical HPLC, method 8: solvent: hexane/2-propanol 70:30 (v/v)+0.1% TFA; flow rate: 1 ml/min; injection: 5 µl; 1 mg/ml ethanol/methanol (1:1); Rt: 7.58 min.

Optical rotation: −60.5° (2.1 mg/ml methanol, temperature: 20° C., wave length: 589 nM).

¹H NMR (400 MHz, DMSO-d₆) δ ppm 1.14 (d, 3 H) 1.57-1.67 (m, 1 H) 1.86 (m, 4 H) 2.09 (s, 3 H) 2.12-2.20 (m, 1 H) 2.97-3.11 (m, 1 H) 3.84 (d, 1 H) 7.00 (d, 1 H) 7.06-7.12 (m, 2 H) 7.55 (d, 2 H) 7.83 (d, 2 H) 8.45 (s, 1 H) 8.95 (s, 1 H) 9.22 (s, 1 H) 9.57 (s, 1 H).

Example 133

3-{3-[(Cyclobutyl{4-[5-(trifluoromethyl)pyridin-3-yl]phenyl}acetyl)amino]-2-methylphenyl}butanoic acid, Stereoisomer 3

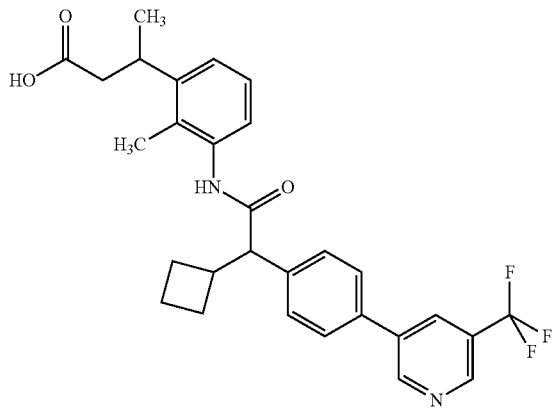

Preparative chiral HPLC, method 4: Rt: 6.3-7.8 min.

Analytical HPLC, method 7: solvent: hexane/2-propanol 80:20 (v/v)+0.1% TFA; flow rate: 1 ml/min; injection: 5 µl; 1 mg/ml ethanol/methanol (1:1); Rt: 4.53 min.

Optical rotation: +66.5° (2.2 mg/ml methanol, temperature: 20° C., wave length: 589 nM).

$^1$H NMR (400 MHz, DMSO-$d_6$) δ ppm 1.15 (d, 3 H) 1.57-1.67 (m, 1 H) 1.78-1.95 (m, 4 H) 2.09 (s, 3 H) 2.12-2.20 (m, 1 H) 2.99-3.12 (m, 1 H) 3.38-3.45 (m, 1 H) 3.84 (d, 1 H) 6.97-7.03 (m, 1 H) 7.06-7.13 (m, 2 H) 7.55 (d, 2 H) 7.82 (d, 2 H) 8.45 (s, 1 H) 8.95 (d, 1 H) 9.21 (d, 1 H) 9.57 (s, 1 H).

Example 134

3-{3-[(Cyclobutyl{4-[5-(trifluoromethyl)pyridin-3-yl]phenyl}acetyl)amino]-2-methylphenyl}butanoic acid, Stereoisomer 4

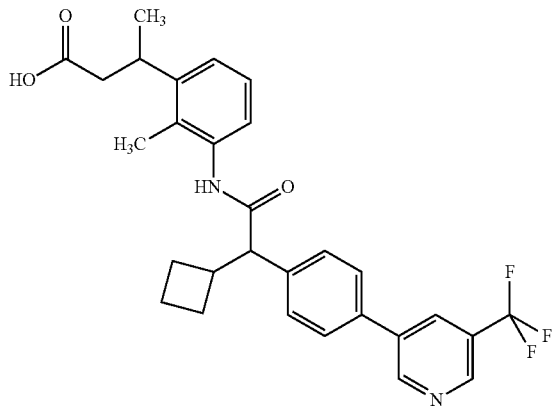 [SMILES: Cc1c(NC(=O)C(c2ccc(-c3cncc(C(F)(F)F)c3)cc2)C2CCC2)cccc1C(C)CC(=O)O]

Preparative chiral HPLC, method 4: Rt: 7.8-11.8 min.
Analytical HPLC, method 7: solvent: hexane/2-propanol 80:20 (v/v)+0.1% TFA; flow rate: 1 ml/min; injection: 5 µl; 1 mg/ml ethanol/methanol (1:1); Rt: 6.29 min.

Optical rotation: −53.6° (2.2 mg/ml methanol, temperature: 20° C., wave length: 589 nM).

$^1$H NMR (400 MHz, DMSO-$d_6$) δ ppm 1.13 (d, 3 H) 1.57-1.68 (m, 1 H) 1.87 (m, 4 H) 2.08 (s, 3 H) 2.12-2.19 (m, 1 H) 2.97-3.12 (m, 1 H) 3.37-3.45 (m, 1 H) 3.84 (d, 1 H) 7.02 (s, 1 H) 7.05-7.13 (m, 2 H) 7.55 (d, 2 H) 7.83 (d, 2 H) 8.45 (s, 1 H) 8.95 (d, 1 H) 9.21 (d, 1 H) 9.56 (s, 1 H).

Example 135

(3R/S)-3-[3-({(2R/S)-2-[4-(5-Chloropyridin-3-yl)phenyl]-2-cyclobutylacetyl}amino)-2-methylphenyl]butanoic acid

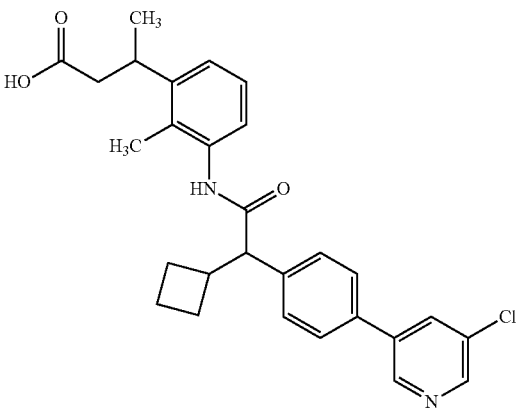 [SMILES: Cc1c(NC(=O)C(c2ccc(-c3cncc(Cl)c3)cc2)C2CCC2)cccc1C(C)CC(=O)O]

In analogy to Suzuki coupling conditions in example 1 reaction of 375 mg intermediate 19 with 193 mg (5-chloropyridin-3-yl)boronic acid followed by methyl ester saponification with 815 mg NaOH (32%) in ethanol/water (7.5 ml/2.5 ml) and subsequent purification via HPLC gave 260 mg of the title compound.

$^1$H NMR (400 MHz, DMSO-$d_6$) δ ppm 1.14 (dd, 3 H) 1.55-1.70 (m, 1 H) 1.80-1.98 (m, 4 H) 2.08 (d, 3 H) 2.12-2.21 (m, 1 H) 2.97-3.11 (m, 1 H) 3.82 (d, 1 H) 6.95-7.04 (m, 1 H) 7.05-7.13 (m, 2 H) 7.52 (d, 2 H) 7.76 (d, 2 H) 8.25 (t, 1 H) 8.61 (d, 1 H) 8.87 (d, 1 H) 9.57 (s, 1 H) 11.86-12.24 (m, 1 H).

Example 136

(3-[3-({[4-(5-Chloropyridin-3-yl)phenyl](cyclobutyl)acetyl}amino)-2-methylphenyl]butanoic acid, Stereoisomer 1

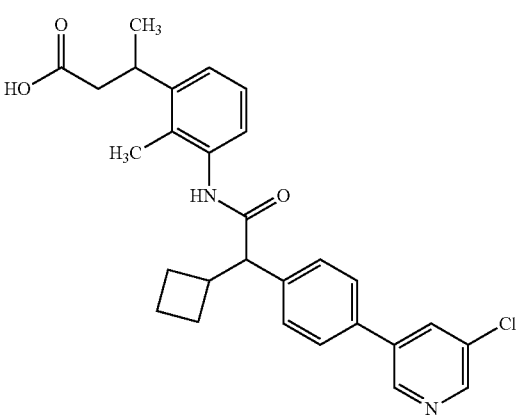 [SMILES: Cc1c(NC(=O)C(c2ccc(-c3cncc(Cl)c3)cc2)C2CCC2)cccc1C(C)CC(=O)O]

260 mg example 135 were separated into the four stereoisomers (examples 136/137/138/139) via preparative chiral HPLC (method 5; solvent: hexane/2-propanol 70:30 (v/v)+0.1% formic acid; flow rate: 50 ml/min; solution: 260 mg/3 mL DCM/MeOH; injection: 6×0.5 ml) gave 52 mg example 136, 58 mg of example 137, 55 mg example 138 and 49 mg example 139.

Preparative chiral HPLC, method 5: Rt: 4.7-5.7 min.

Analytical HPLC, method 8: solvent: hexane/2-propanol 70:30 (v/v)+0.1% TFA; flow rate: 1 ml/min; injection: 5 µl; 1 mg/ml ethanol/methanol (1:1); Rt: 2.37 min.

Optical rotation: +71.5° (2.7 mg/ml methanol, temperature: 20° C., wave length: 589 nM).

$^1$H NMR (400 MHz, DMSO-$d_6$) δ ppm 1.14 (d, 3 H) 1.57-1.68 (m, 1 H) 1.79-1.96 (m, 4 H) 2.09 (s, 3 H) 2.11-2.20 (m, 1 H) 2.96-3.11 (m, 1 H) 3.82 (d, 1 H) 7.00 (d, 1 H) 7.05-7.14 (m, 2 H) 7.52 (d, 2 H) 7.76 (d, 2 H) 8.25 (t1 H) 8.61 (d, 1 H) 8.87 (d, 1 H) 9.57 (s, 1 H).

Example 137

(3-[3-({[4-(5-Chloropyridin-3-yl)phenyl](cyclobutyl)acetyl}amino)-2-methylphenyl]butanoic acid, Stereoisomer 2

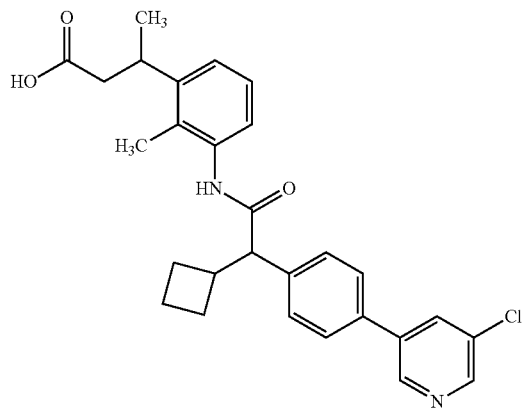 [SMILES: Cc1c(NC(=O)C(c2ccc(-c3cncc(Cl)c3)cc2)C2CCC2)cccc1C(C)CC(=O)O]

Preparative chiral HPLC, method 5: Rt: 5.7-7.0 min.

Analytical HPLC, method 8: solvent: hexane/2-propanol 70:30 (v/v)+0.1% TFA; flow rate: 1 ml/min; injection: 5 µl; 1 mg/ml ethanol/methanol (1:1); Rt: 2.94 min.

Optical rotation: −41.5° (2.4 mg/ml methanol, temperature: 20° C., wave length: 589 nM).

$^1$H NMR (400 MHz, DMSO-$d_6$) δ ppm 1.13 (d, 3 H) 1.56-1.68 (m, 1 H) 1.87 (m, 4 H) 2.03-2.10 (m, 3 H) 2.11-2.19 (m, 1 H) 2.95-3.11 (m, 1 H) 3.82 (d, 1 H) 7.01 (dl H) 7.04-7.13 (m, 2 H) 7.52 (d, 2 H) 7.76 (d, 2 H) 8.25 (t, 1 H) 8.61 (d, 1 H) 8.87 (d, 1 H) 9.57 (s, 1 H).

Example 138

(3-[3-({[4-(5-Chloropyridin-3-yl)phenyl](cyclobutyl)acetyl}amino)-2-methylphenyl]butanoic acid, Stereoisomer 3

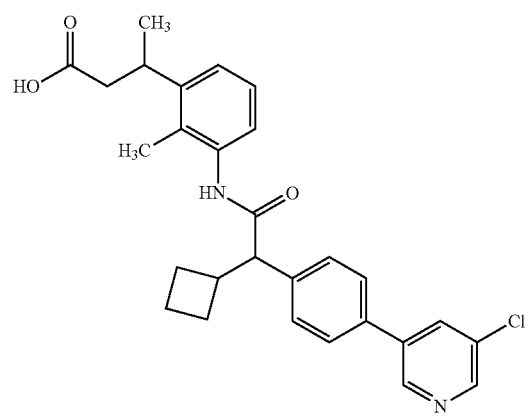 [SMILES: Cc1c(NC(=O)C(c2ccc(-c3cncc(Cl)c3)cc2)C2CCC2)cccc1C(C)CC(=O)O]

Preparative chiral HPLC, method 5: Rt: 8.5-10.3 min.

Analytical HPLC, method 8: solvent: hexane/2-propanol 70:30 (v/v)+0.1% TFA; flow rate: 1 ml/min; injection: 5 µl; 1 mg/ml ethanol/methanol (1:1); Rt: 4.80 min.

Optical rotation: +58.8° (2.2 mg/ml methanol, temperature: 20° C., wave length: 589 nM).

$^1$H NMR (400 MHz, DMSO-$d_6$) δ ppm 1.13 (d, 3 H) 1.57-1.66 (m, 1 H) 1.79-1.94 (m, 4 H) 2.07 (s, 3 H) 2.11-2.20 (m, 1 H) 2.96-3.10 (m, 1 H) 3.82 (d, 1 H) 7.01 (d, 1 H) 7.05-7.13 (m, 2 H) 7.52 (d, 2 H) 7.76 (d, 2 H) 8.25 (t, 1 H) 8.61 (d, 1 H) 8.87 (d, 1 H) 9.57 (s, 1 H).

Example 139

(3-[3-({[4-(5-Chloropyridin-3-yl)phenyl](cyclobutyl)acetyl}amino)-2-methylphenyl]butanoic acid, Stereoisomer 4

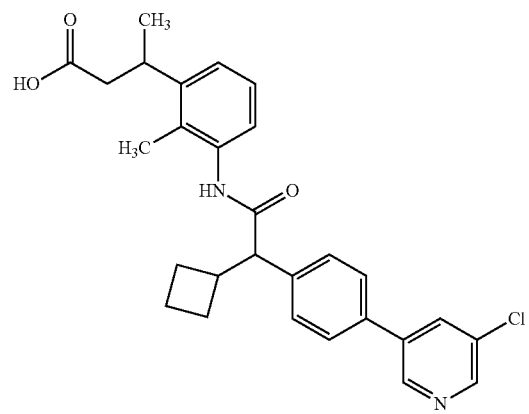 [SMILES: Cc1c(NC(=O)C(c2ccc(-c3cncc(Cl)c3)cc2)C2CCC2)cccc1C(C)CC(=O)O]

Preparative chiral HPLC, method 5: Rt: 18.0-20.6 min.

Analytical HPLC, method 8: solvent: hexane/2-propanol 70:30 (v/v)+0.1% TFA; flow rate: 1 ml/min; injection: 5 µl; 1 mg/ml ethanol/methanol (1:1); Rt: 11.48 min.

Optical rotation: −64.4° (2.5 mg/ml methanol, temperature: 20° C., wave length: 589 nM).

¹H NMR (400 MHz, DMSO-d₆) δ ppm 1.14 (d, 3 H) 1.56-1.69 (m, 1 H) 1.78-1.95 (m, 4 H) 2.09 (s, 3 H) 2.11-2.21 (m, 1 H) 2.97-3.11 (m, 1 H) 3.82 (d, 1 H) 7.00 (d, 1 H) 7.04-7.13 (m, 2 H) 7.52 (d, 2 H) 7.76 (d, 2 H) 8.25 (t, 1 H) 8.61 (d, 1 H) 8.87 (d, 1 H) 9.57 (s, 1 H).

Example 140

(3R/S)-3-[3-({(2R/S)-2-[4-(5-Chloro-6-methylpyridin-3-yl)phenyl]-2-cyclobutylacetyl}amino)-2-methylphenyl]butanoic acid

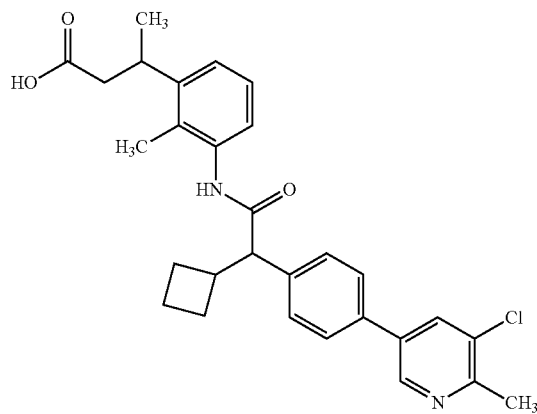 [SMILES: Cc1ncc(-c2ccc(C(C(=O)Nc3cccc(C(C)CC(=O)O)c3C)C3CCC3)cc2)cc1Cl]

In analogy to Suzuki coupling conditions in example 1 reaction of 375 mg intermediate 19 with 311 mg 3-chloro-2-methyl-5-(4,4,5,5-tetramethyl-1,3,2-dioxaborolan-2-yl)pyridine followed by methyl ester saponification with 346 mg NaOH (32%) in ethanol/water (7.5 ml/2.5 ml) and subsequent purification via HPLC gave 110 mg of the title compound.

¹H NMR (400 MHz, DMSO-d₆) δ ppm 1.14 (dd, 3 H) 1.56-1.66 (m, 1 H) 1.86 (m, 4 H) 2.08 (d, 3 H) 2.11-2.19 (m, 1 H) 2.58 (s, 3 H) 2.97-3.10 (m, 1 H) 3.80 (d, 1 H) 6.97-7.04 (m, 1 H) 7.05-7.11 (m, 2 H) 7.50 (d, 2 H) 7.73 (d, 2 H) 8.17 (dl H) 8.74 (d, 1 H) 9.55 (s, 1 H).

Example 141

3-[3-({[4-(5-Chloro-6-methylpyridin-3-yl)phenyl](cyclobutyl)acetyl}amino)-2-methylphenyl]butanoic acid, Stereoisomer 1

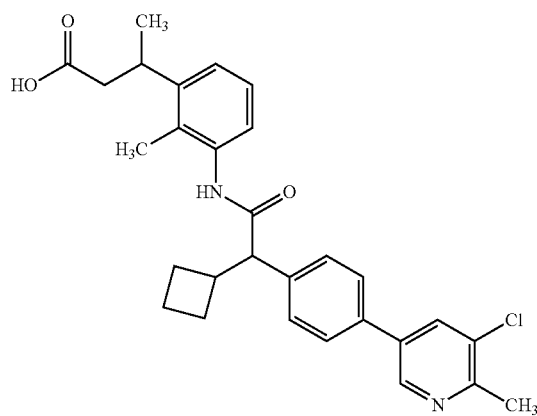 [SMILES: Cc1ncc(-c2ccc(C(C(=O)Nc3cccc(C(C)CC(=O)O)c3C)C3CCC3)cc2)cc1Cl]

110 mg example 140 were separated into the four stereoisomers (examples 141/142/143/144) via preparative chiral HPLC (method 5; solvent: hexane/2-propanol 70:30 (v/v)+0.1% formic acid; flow rate: 50 ml/min; solution: 110 mg/1.5 mL DCM/MeOH; injection: 3×0.5 ml) gave 20 mg example 141, 21 mg of example 142, 21 mg example 143 and 17 mg example 144.

Preparative chiral HPLC, method 5: Rt: 4.6-5.7 min.

Analytical HPLC, method 8: solvent: hexane/2-propanol 70:30 (v/v)+0.1% TFA; flow rate: 1 ml/min; injection: 5 μl; 1 mg/ml ethanol/methanol (1:1); Rt: 2.23 min.

¹H NMR (400 MHz, DMSO-d₆) δ ppm 1.14 (d, 3 H) 1.57-1.66 (m, 1 H) 1.80-1.94 (m, 4 H) 2.09 (m, 4 H) 2.58 (s, 3 H) 2.96-3.11 (m, 1 H) 3.76-3.85 (d, 1 H) 6.94-7.02 (m, 1 H) 7.04-7.12 (m, 2 H) 7.50 (d, 2 H) 7.73 (d, 2 H) 8.17 (d, 1 H) 8.74 (d, 1 H) 9.56 (s, 1 H).

Example 142

3-[3-({[4-(5-Chloro-6-methylpyridin-3-yl)phenyl](cyclobutyl)acetyl}amino)-2-methylphenyl]butanoic acid, Stereoisomer 2

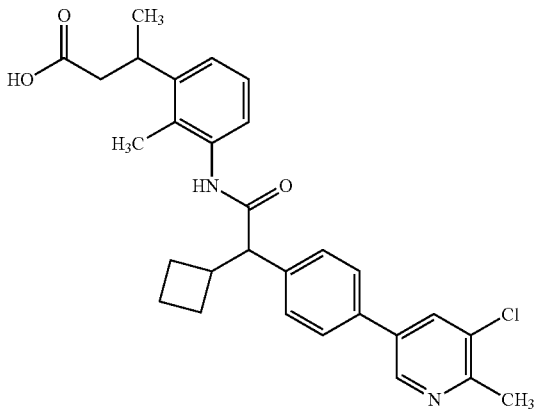 [SMILES: Cc1ncc(-c2ccc(C(C(=O)Nc3cccc(C(C)CC(=O)O)c3C)C3CCC3)cc2)cc1Cl]

Preparative chiral HPLC, method 5: Rt: 6.4-7.8 min.

Analytical HPLC, method 8: solvent: hexane/2-propanol 70:30 (v/v)+0.1% TFA; flow rate: 1 ml/min; injection: 5 μl; 1 mg/ml ethanol/methanol (1:1); Rt: 3.55 min.

¹H NMR (400 MHz, DMSO-d₆) δ ppm 1.13 (d, 3 H) 1.56-1.67 (m, 1 H) 1.80-1.94 (m, 4 H) 2.07 (s, 3 H) 2.10-2.19 (m, 1 H) 2.58 (s, 3 H) 2.96-3.10 (m, 1 H) 3.76-3.85 (d, 1 H) 6.96-7.04 (m, 1 H) 7.05-7.12 (m, 2 H) 7.50 (d, 2 H) 7.73 (d, 2 H) 8.17 (d, 1 H) 8.74 (d, 1 H) 9.56 (s, 1 H).

Example 143

3-[3-({[4-(5-Chloro-6-methylpyridin-3-yl)phenyl](cyclobutyl)acetyl}amino)-2-methylphenyl]butanoic acid, Stereoisomer 3

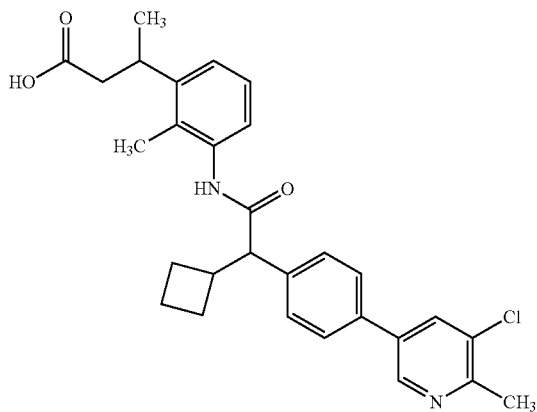 [SMILES: Cc1ncc(-c2ccc(C(C(=O)Nc3cccc(C(C)CC(=O)O)c3C)C3CCC3)cc2)cc1Cl]

Preparative chiral HPLC, method 5: Rt: 8.2-9.9 min.
Analytical HPLC, method 8: solvent: hexane/2-propanol 70:30 (v/v)+0.1% TFA; flow rate: 1 ml/min; injection: 5 µl; 1 mg/ml ethanol/methanol (1:1); Rt: 4.63 min.
$^1$H NMR (400 MHz, DMSO-$d_6$) δ ppm 1.13 (d, 3 H) 1.56-1.66 (m, 1 H) 1.86 (m, 4 H) 2.07 (s, 3 H) 2.11-2.18 (m, 1 H) 2.58 (s, 3 H) 2.97-3.11 (m, 1 H) 3.75-3.87 (d, 1 H) 6.96-7.04 (m, 1 H) 7.04-7.12 (m, 2 H) 7.50 (d, 2 H) 7.73 (d, 2 H) 8.17 (d, 1 H) 8.74 (d, 1 H) 9.56 (s, 1 H).

Example 144

3-[3-({[4-(5-Chloro-6-methylpyridin-3-yl)phenyl](cyclobutyl)acetyl}amino)-2-methylphenyl]butanoic acid, Stereoisomer 4

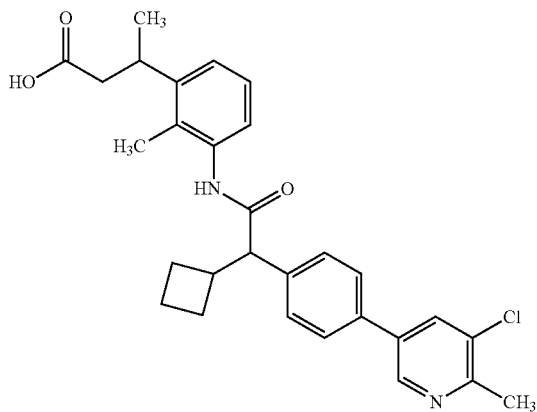 [SMILES: Cc1ncc(-c2ccc(C(C(=O)Nc3cccc(C(C)CC(=O)O)c3C)C3CCC3)cc2)cc1Cl]

Preparative chiral HPLC, method 5: Rt: 30.0-37.7 min.
Analytical HPLC, method 8: solvent: hexane/2-propanol 70:30 (v/v)+0.1% TFA; flow rate: 1 ml/min; injection: 5 µl; 1 mg/ml ethanol/methanol (1:1); Rt: 21.02 min.
$^1$H NMR (400 MHz, DMSO-$d_6$) δ ppm 1.14 (d, 3 H) 1.57-1.66 (m, 1 H) 1.79-1.94 (m, 4 H) 2.09 (m, 4 H) 2.58 (s, 3 H) 2.95-3.09 (m, 1 H) 3.76-3.87 (d, 1 H) 6.94-7.02 (m, 1 H) 7.04-7.12 (m, 2 H) 7.50 (d, 2 H) 7.73 (d, 2 H) 8.17 (d, 1 H) 8.74 (d, 1 H) 9.56 (s, 1 H).

Example 145

(3R/S)-3-(3-{[(2R/S)-2-Cyclobutyl-2-{3-fluoro-4-[5-(trifluoromethyl)pyridin-3-yl]phenyl}acetyl]amino}-2-methylphenyl)butanoic acid

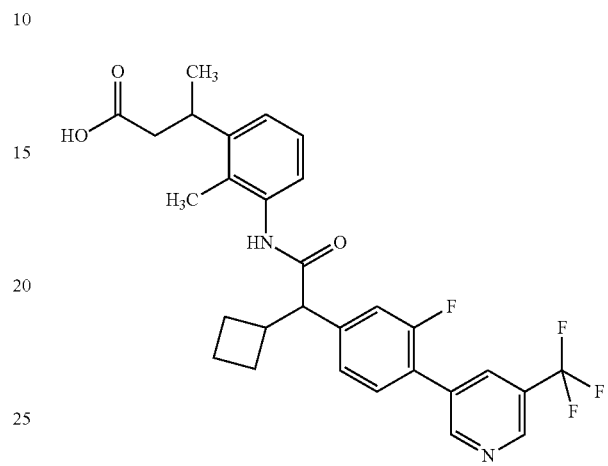

In analogy to Suzuki coupling conditions in example 1 reaction of 320 mg intermediate 20 with 154 mg [5-(trifluoromethyl)pyridin-3-yl]boronic acid followed by methyl ester saponification with 507 mg NaOH (32%) in ethanol/water (7.5 ml/2.5 ml) and subsequent purification via HPLC gave 200 mg of the title compound.
$^1$H NMR (400 MHz, DMSO-$d_6$) δ ppm 1.14 (dd, 3 H) 1.60-1.70 (m, 1 H) 1.82-1.95 (m, 4 H) 2.06-2.18 (m, 4 H) 3.00-3.10 (m, 1 H) 3.38-3.47 (m, 1 H) 3.87 (d, 1 H) 6.96-7.05 (m, 1 H) 7.07-7.15 (m, 2 H) 7.36-7.44 (m, 2 H) 7.70 (t, 1 H) 8.39 (s, 1 H) 9.01 (d, 1 H) 9.08 (s, 1 H) 9.63 (s, 1 H) 11.94-12.16 (m, 1 H).

Example 146

3-{3-[(Cyclobutyl{3-fluoro-4-[5-(trifluoromethyl)pyridin-3-yl]phenyl}acetyl)amino]-2-methylphenyl}butanoic acid, Stereoisomeric Mixture 1

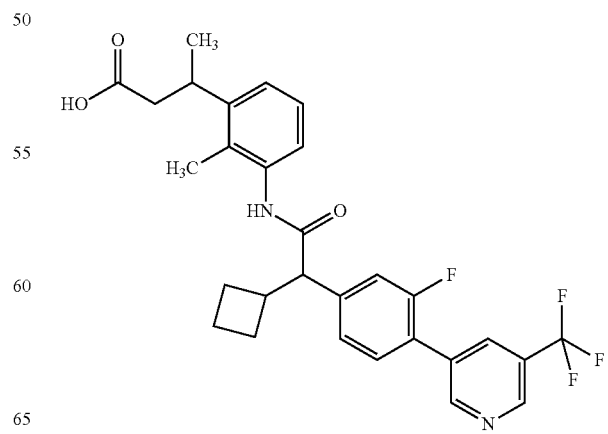

200 mg example 145 were separated into two stereoisomers as well as a stereoisomeric mixture of another two stereoisomers (examples 146/147/148) via preparative chiral HPLC (method 5; solvent: hexane/2-propanol 70:30 (v/v)+ 0.1% formic acid; flow rate: 50 ml/min; solution: 200 mg/4.4 mL DCM/MeOH; injection: 4×1.1 ml) gave 43 mg example 147, 40 mg of example 148 and 85 mg example 146 (stereoisomeric mixture 1).

Preparative chiral HPLC, method 5: Rt: 3.2-5.3 min.

Analytical HPLC, method 8: solvent: hexane/2-propanol 70:30 (v/v)+0.1% TFA; flow rate: 1 ml/min; injection: 5 µl; 1 mg/ml ethanol/methanol (1:1); Rt: 1.94/2.13 min.

Optical rotation: +1.4° (2.8 mg/ml methanol, temperature: 20° C., wave length: 589 nM).

$^1$H NMR (300 MHz, DMSO-$d_6$) δ ppm 1.14 (dd, 3.49 Hz, 3 H) 1.58-1.73 (m, 1 H) 1.90 (m, 4 H) 2.10 (m, 4 H) 2.99-3.13 (m, 1 H) 3.38-3.46 (m, 1 H) 3.78-3.94 (d, 1 H) 6.96-7.05 (m, 1 H) 7.06-7.14 (m, 2 H) 7.38 (s, 2 H) 7.70 (s, 1 H) 8.39 (s, 1 H) 9.01 (s, 1 H) 9.08 (s, 1 H) 9.63 (s, 1 H) 11.78-12.21 (m, 1 H).

Example 147

3-{3-[(Cyclobutyl{3-fluoro-4-[5-(trifluoromethyl)pyridin-3-yl]phenyl}acetyl)amino]-2-methylphenyl}butanoic acid, Stereoisomer 1

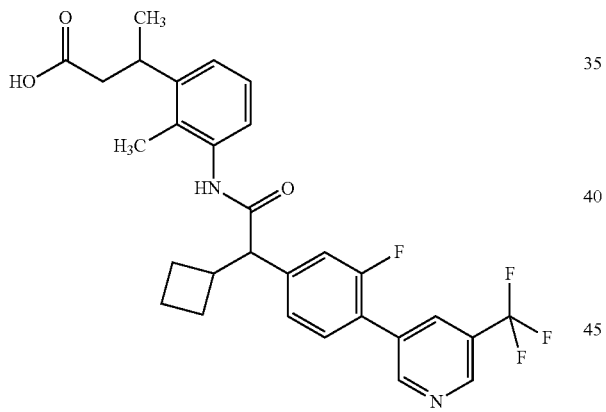

Preparative chiral HPLC, method 5: Rt: 6.7-8.4 min.

Analytical HPLC, method 8: solvent: hexane/2-propanol 70:30 (v/v)+0.1% TFA; flow rate: 1 ml/min; injection: 5 µl; 1 mg/ml ethanol/methanol (1:1); Rt: 4.14 min.

Optical rotation: +41.3° (2.0 mg/ml methanol, temperature: 20° C., wave length: 589 nM).

$^1$H NMR (300 MHz, DMSO-$d_6$) δ ppm 1.14 (d, 3 H) 1.59-1.70 (m, 1 H) 1.89 (m, 4 H) 2.10 (m, 4 H) 2.97-3.12 (m, 1 H) 3.88 (d, 1 H) 7.03 (d, 1 H) 7.07-7.13 (m, 2 H) 7.34-7.44 (m, 2 H) 7.70 (s, 1 H) 8.39 (s, 1 H) 9.01 (s, 1 H) 9.08 (s, 1 H) 9.63 (s, 1H).

Example 148

3-{3-[(Cyclobutyl{3-fluoro-4-[5-(trifluoromethyl)pyridin-3-yl]phenyl}acetyl)amino]-2-methylphenyl}butanoic acid, Stereoisomer 2

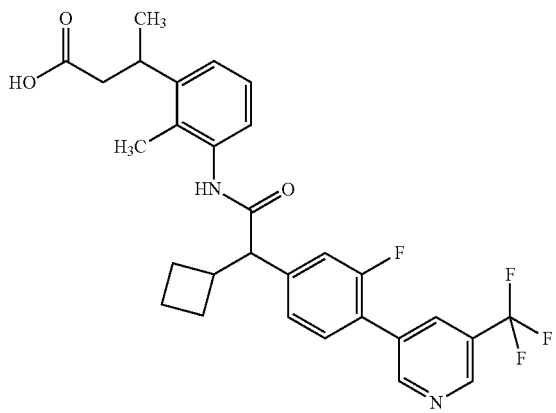 [SMILES: Cc1c(NC(=O)C(c2ccc(-c3cncc(C(F)(F)F)c3)c(F)c2)C2CCC2)cccc1C(C)CC(=O)O]

Preparative chiral HPLC, method 5: Rt: 9.9-12.2 min.

Analytical HPLC, method 8: solvent: hexane/2-propanol 70:30 (v/v)+0.1% TFA; flow rate: 1 ml/min; injection: 5 µl; 1 mg/ml ethanol/methanol (1:1); Rt: 6.09 min.

Optical rotation: −54.1 (2.5 mg/ml methanol, temperature: 20° C., wave length: 589 nM).

$^1$H NMR (300 MHz, DMSO-$d_6$) δ ppm 1.15 (d, 3 H) 1.58-1.70 (m, 1 H) 1.89 (m, 4 H) 2.11 (m, 4 H) 2.98-3.11 (m, 1 H) 3.85 (d, 1 H) 7.01 (d, 1 H) 7.06-7.13 (m, 2 H) 7.34-7.44 (m, 2 H) 7.70 (s, 1 H) 8.39 (s, 1 H) 9.01 (s, 1 H) 9.08 (s, 1 H) 9.63 (s, 1H).

Example 149

((3R/S)-3-[3-({(2R/S)-2-[4-(5-Chloropyridin-3-yl)-3-fluorophenyl]-2-cyclobutylacetyl}amino)-2-methylphenyl]butanoic acid

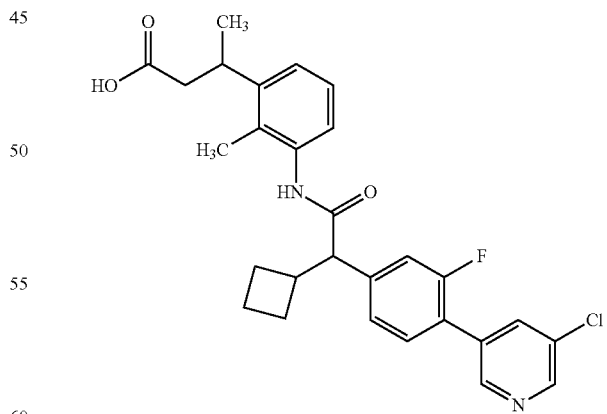

In analogy to Suzuki coupling conditions in example 1 reaction of 320 mg intermediate 20 with 127 mg (5-chloropyridin-3-yl)boronic acid followed by methyl ester saponification with 565 mg NaOH (32%) in ethanol/water (7.5 ml/2.5 ml) and subsequent purification via HPLC gave 190 mg of the title compound.

¹H NMR (400 MHz, DMSO-d₆) δ ppm 1.14 (dd, 3 H) 1.60-1.70 (m, 1 H) 1.82-1.95 (m, 4 H) 2.06-2.18 (m, 4 H) 2.99-3.11 (m, 1 H) 3.41 (s, 1 H) 3.86 (d, 1 H) 6.97-7.05 (m, 1 H) 7.06-7.13 (m, 2 H) 7.32-7.41 (m, 2 H) 7.64 (t, 1 H) 8.16 (d, 1 H) 8.66 (d, 1 H) 8.74 (t, 1 H) 9.62 (s, 1 H) 11.97-12.13 (m, 1 H).

Example 150

3-[3-({[4-(5-Chloropyridin-3-yl)-3-fluorophenyl](cyclobutyl)acetyl}amino)-2-methylphenyl]butanoic acid, Stereoisomer 1

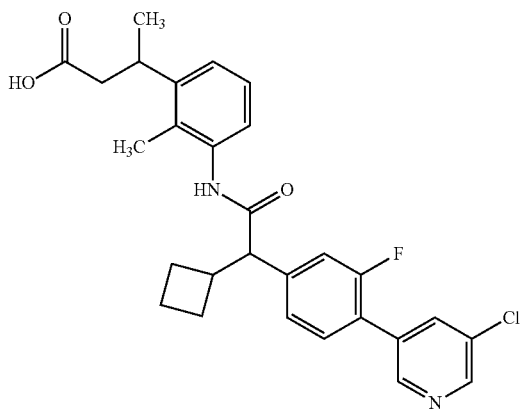 [SMILES: Cc1c(NC(=O)C(c2ccc(-c3cncc(Cl)c3)c(F)c2)C2CCC2)cccc1C(C)CC(=O)O]

190 mg example 149 were separated into the four stereoisomers (examples 150/151/152/153) via preparative chiral HPLC. A first HPLC separation (method 5; solvent: hexane/2-propanol 70:30 (v/v)+0.1% formic acid; flow rate: 50 ml/min; solution: 190 mg/3.6 mL DCM/MeOH; injection: 3×1.2 ml) gave 38 mg example 150, 38 mg of example 151 and 90 mg of a mixture of example 152/153. A second HPLC separation (method 4; solvent: hexane/2-propanol 80:20 (v/v)+0.1% formic acid; flow rate: 50 ml/min; solution: 90 mg/3.6 mL DCM/MeOH; injection: 2×1.8 ml) gave 27 mg of example 152 and 36 mg of example 153.

Preparative chiral HPLC, method 5: Rt: 9.5-10.5 min.
Analytical HPLC, method 8: solvent: hexane/2-propanol 70:30 (v/v)+0.1% TFA; flow rate: 1 ml/min; injection: 5 μl; 1 mg/ml ethanol/methanol (1:1); Rt: 4.76 min.
Optical rotation: +52.6° (2.1 mg/ml methanol, temperature: 20° C., wave length: 589 nM).
¹H NMR (400 MHz, DMSO-d₆) δ ppm 1.14 (d, 3 H) 1.59-1.69 (m, 1 H) 1.82-1.96 (m, 4 H) 2.09 (s, 3 H) 2.12-2.19 (m, 1 H) 2.96-3.09 (m, 1 H) 3.38-3.45 (m, 1 H) 3.86 (d, 1 H) 7.03 (d, 1 H) 7.07-7.12 (m, 2 H) 7.33-7.41 (m, 2 H) 7.59-7.68 (m, 1 H) 8.15 (d, 1 H) 8.66 (d, 1 H) 8.74 (t, 1 H) 9.60 (s, 1 H).

Example 151

3-[3-({[4-(5-Chloropyridin-3-yl)-3-fluorophenyl](cyclobutyl)acetyl}amino)-2-methylphenyl]butanoic acid, Stereoisomer 2

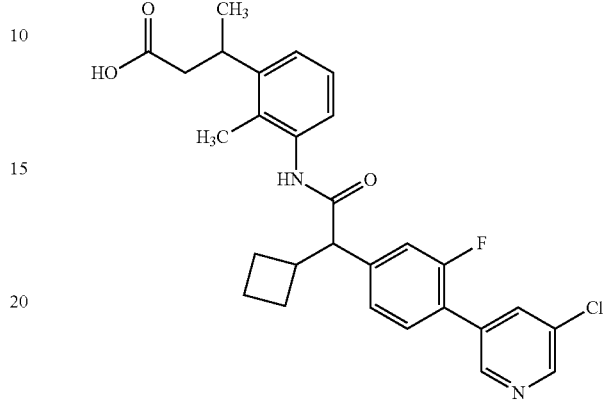

Preparative chiral HPLC, method 5: Rt: 11.1-12.6 min.
Analytical HPLC, method 8: solvent: hexane/2-propanol 70:30 (v/v)+0.1% TFA; flow rate: 1 ml/min; injection: 5 μl; 1 mg/ml ethanol/methanol (1:1); Rt: 8.98 min.
Optical rotation: −58.1 (2.6 mg/ml methanol, temperature: 20° C., wave length: 589 nM).
¹H NMR (400 MHz, DMSO-d₆) δ ppm 1.15 (d, 3 H) 1.60-1.69 (m, 1 H) 1.82-1.95 (m, 4 H) 2.11 (m, 4 H) 2.43-2.48 (m, 2 H) 2.98-3.09 (m, 1 H) 3.38-3.46 (m, 1 H) 3.86 (d, 1 H) 7.01 (d, 1 H) 7.07-7.11 (m, 2 H) 7.33-7.41 (m, 2 H) 7.64 (s, 1 H) 8.15 (s, 1 H) 8.66 (d, 1 H) 8.74 (s, 1 H) 9.61 (s, 1 H).

Example 152

3-[3-({[4-(5-Chloropyridin-3-yl)-3-fluorophenyl](cyclobutyl)acetyl}amino)-2-methylphenyl]butanoic acid, Stereoisomer 3

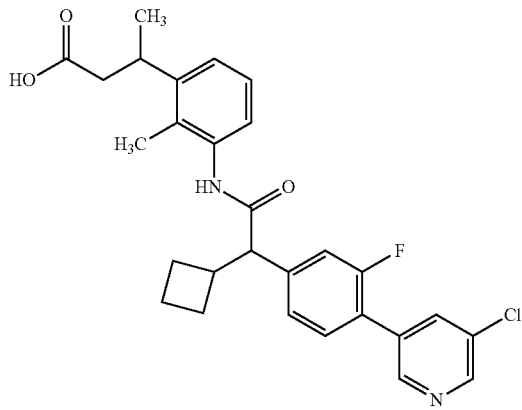 [SMILES: Cc1c(NC(=O)C(c2ccc(-c3cncc(Cl)c3)c(F)c2)C2CCC2)cccc1C(C)CC(=O)O]

Preparative chiral HPLC, method 4: Rt: 6.5-7.8 min.
Analytical HPLC, method 7: solvent: hexane/2-propanol 80:20 (v/v)+0.1% TFA; flow rate: 1 ml/min; injection: 5 μl; 1 mg/ml ethanol/methanol (1:1); Rt: 4.19 min.

Optical rotation: +65.1° (2.3 mg/ml methanol, temperature: 20° C., wave length: 589 nM).

$^1$H NMR (400 MHz, DMSO-d$_6$) δ ppm 1.15 (d, 3 H) 1.59-1.70 (m, 1 H) 1.81-1.97 (m, 4 H) 2.10 (m, 4 H) 2.97-3.10 (m, 1 H) 3.86 (d, 1 H) 7.01 (d, 1 H) 7.06-7.12 (m, 2 H) 7.31-7.41 (m, 2 H) 7.64 (s, 1 H) 8.16 (s, 1 H) 8.66 (d, 1 H) 8.74 (s, 1 H) 9.62 (s, 1 H).

Example 153

3-[3-({[4-(5-Chloropyridin-3-yl)-3-fluorophenyl](cyclobutyl)acetyl}amino)-2-methylphenyl]butanoic acid, Stereoisomer 4

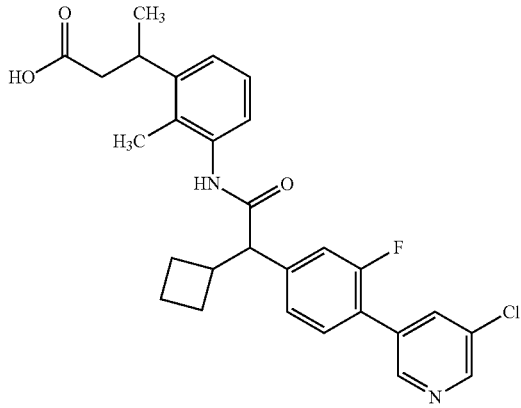 [SMILES: Cc1c(NC(=O)C(c2ccc(-c3cncc(Cl)c3)c(F)c2)C2CCC2)cccc1C(C)CC(=O)O]

Preparative chiral HPLC, method 4: Rt: 7.8-10.4 min.

Analytical HPLC, method 7: solvent: hexane/2-propanol 80:20 (v/v)+0.1% TFA; flow rate: 1 ml/min; injection: 5 µl; 1 mg/ml ethanol/methanol (1:1); Rt: 5.42 min.

Optical rotation: −31.4° (3.1 mg/ml methanol, temperature: 20° C., wave length: 589 nM).

$^1$H NMR (400 MHz, DMSO-d$_6$) δ ppm 1.14 (d, 3 H) 1.60-1.70 (m, 1 H) 1.81-1.96 (m, 4 H) 2.06-2.11 (s, 3 H) 2.12-2.19 (m, 1 H) 2.96-3.10 (m, 1 H) 3.38-3.45 (m, 1 H) 3.86 (d, 1 H) 7.03 (d, 1 H) 7.07-7.12 (m, 2 H) 7.33-7.42 (m, 2 H) 7.64 (s, 1 H) 8.15 (d, 1 H) 8.66 (d, 1 H) 8.74 (t, 1 H) 9.60 (s, 1 H).

Example 154

2-[3-({2-[4-(5-chloro-6-methylpyridin-3-yl)phenyl]-2-cyclopentylacetyl}amino)-2-methylphenyl]cyclopropanecarboxylic acid

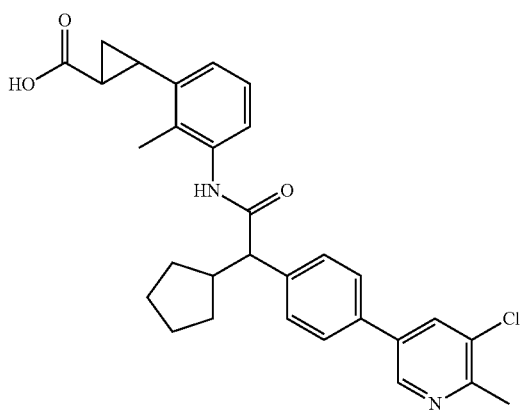 [SMILES: Cc1ncc(-c2ccc(C(C(=O)Nc3cccc(C4CC4C(=O)O)c3C)C3CCCC3)cc2)cc1Cl]

37 mg (78 µmol) methyl 2-(3-{[(4-bromophenyl)(cyclopentyl)acetyl]amino}-2-methylphenyl)cyclopropanecarboxylate which was prepared according to intermediate 21 were reacted with 3-chloro-2-methyl-5-(4,4,5,5-tetramethyl-1,3,2-dioxaborolan-2-yl)pyridine in analogy to example 1 to give after methyl ester saponification with 1248 µL NaOH (1M in water) and subsequent working up and purification 27 mg (63%) of the title compound.

$^1$H-NMR (DMSO-d6): δ=1.03-1.87 (10H), 2.09 (3H), 2.24-2.39 (1H), 2.57 (3H), 2.70 (1H), 3.53 (2H), 6.82-6.93 (1H), 7.05 (2H), 7.53 (2H), 7.65-7.77 (2H), 8.17 (1H), 8.74 (1H), 9.60 (1H), 12.32 (1H) ppm.

Example 155

2-[3-({2-cyclopentyl-2-[4-(5-ethoxypyridin-3-yl)phenyl]acetyl}amino)-2-methylphenyl]cyclopropanecarboxylic acid

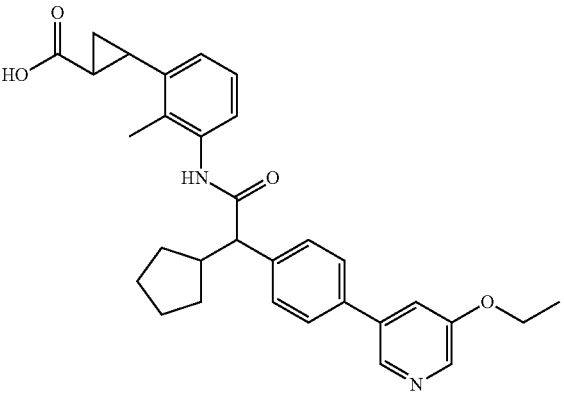 [SMILES: CCOc1cncc(-c2ccc(C(C(=O)Nc3cccc(C4CC4C(=O)O)c3C)C3CCCC3)cc2)c1]

37 mg (78 µmol) methyl 2-(3-{[(4-bromophenyl)(cyclopentyl)acetyl]amino}-2-methylphenyl)cyclopropanecarboxylate which was prepared according to intermediate 21 were reacted with 3-ethoxy-5-(4,4,5,5-tetramethyl-1,3,2-dioxaborolan-2-yl)pyridine in analogy to example 1 to give after methyl ester saponification with 1248 µL NaOH (1M in water) and subsequent working up and purification 13 mg (29%) of the title compound.

$^1$H-NMR (DMSO-d6): δ=1.04 (1H), 1.36 (3H), 1.56 (5H), 1.67 (2H), 1.79-1.94 (2H), 2.09 (3H), 2.25-2.45 (1H), 2.70 (1H), 2.88 (1H), 3.53 (1H), 4.19 (2H), 6.88 (1H), 6.99-7.09 (2H), 7.12-7.23 (1H), 7.31-7.65 (3H), 7.65-7.84 (1H), 8.25 (1H), 8.47 (1H), 9.59 (1H), 12.32 (1H) ppm.

Example 156

2-(3-{[2-cyclopentyl-2-{4-[5-(trifluoromethyl)pyridin-3-yl]phenyl}acetyl]amino}-2-methylphenyl)cyclopropanecarboxylic acid

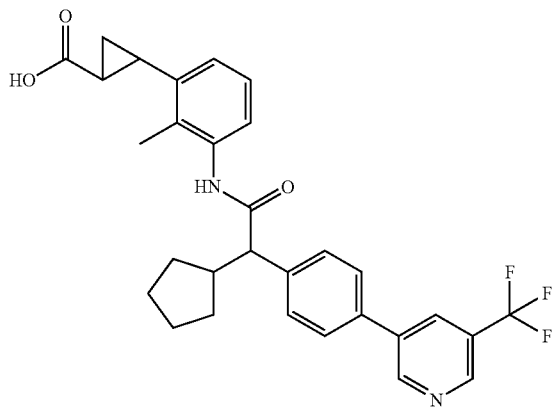 [SMILES: Cc1c(NC(=O)C(c2ccc(-c3cncc(C(F)(F)F)c3)cc2)C2CCCC2)cccc1C1CC1C(=O)O]

37 mg (78 µmol) methyl 2-(3-{[(4-bromophenyl)(cyclopentyl)acetyl]amino}-2-methylphenyl)cyclopropanecarboxylate which was prepared according to intermediate 21 were reacted with [5-(trifluoromethyl)pyridin-3-yl]boronic acid in analogy to example 1 to give after methyl ester saponification with 1248 µL NaOH (1M in water) and subsequent working up and purification 9 mg (22%) of the title compound.

$^1$H-NMR (DMSO-d6): δ=1.02 (1H), 1.27-1.64 (9H), 1.68 (1H), 1.76-1.94 (2H), 2.08 (3H), 2.22-2.47 (1H), 2.73 (1H), 2.88 (1H), 3.57 (1H), 6.87 (1H), 7.05 (2H), 7.46-7.62 (2H), 7.83 (2H), 8.46 (1H), 8.92-8.97 (1H), 9.21 (1H), 9.61 (1H) ppm.

Example 157

-2-(3-{[2-cyclopentyl-2-{4-[5-chloropyridin-3-yl]phenyl}acetyl]amino}-2-methylphenyl)cyclopropanecarboxylic acid

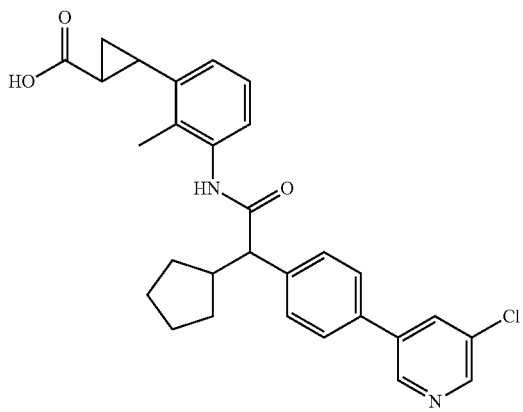 [SMILES: Cc1c(NC(=O)C(c2ccc(-c3cncc(Cl)c3)cc2)C2CCCC2)cccc1C1CC1C(=O)O]

28 mg (60 µmol) methyl 2-(3-{[(4-bromophenyl)(cyclopentyl)acetyl]amino}-2-methylphenyl)cyclopropanecarboxylate which was prepared according to intermediate 21 were reacted with (5-chloropyridin-3-yl)boronic acid in analogy to example 1 to give after methyl ester saponification with 780 µL NaOH (1M in water) and subsequent working up and purification 9 mg (22%) of the title compound.

$^1$H-NMR (DMSO-d6): δ=0.92-1.27 (1H), 1.29-1.64 (9H), 1.68 (1H), 1.76-1.97 (1H), 2.08 (3H), 2.33 (2H), 2.53-2.72 (1H), 3.52 (1H), 6.84-6.95 (1H), 7.00-7.21 (2H), 7.45-7.63 (2H), 7.76 (2H), 8.25 (1H), 8.60 (1H), 8.87 (1H), 9.60 (1H) ppm.

Example 158

2-[3-({2-[4-(5-chloropyridin-3-yl)phenyl]-2-cyclopentylacetyl}amino)-2-methylphenoxy]propanoic acid

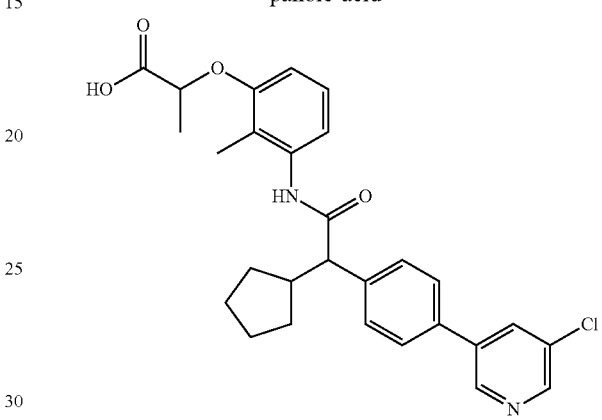

142 mg (300 µmol) methyl 2-(3-{[(4-bromophenyl)(cyclopentyl)acetyl]amino}-2-methylphenoxy)propanoate which was prepared according to intermediate 23 were reacted with (5-chloropyridin-3-yl)boronic acid in analogy to example 1 to give after methyl ester saponification with 1500 µL NaOH (2M in water) and subsequent working up and purification 102 mg (68%) of the title compound.

$^1$H-NMR (DMSO-d6): δ=1.01 (1H), 1.33-1.71 (6H), 1.79-1.90 (1H), 1.90-2.00 (3H), 2.06 (2H), 2.52-2.72 (2H), 3.55 (1H), 4.72-4.82 (1H), 6.60 (1H), 6.84 (1H), 6.98-7.06 (1H), 7.47-7.66 (2H), 7.76 (2H), 8.24 (1H), 8.60 (1H), 8.87 (1H), 9.53 (1H), 12.96 (1H) ppm.

Example 159

2-[3-({2-cyclopentyl-2-[4-(5-ethoxypyridin-3-yl)phenyl]acetyl}amino)-2-methylphenoxy]propanoic acid

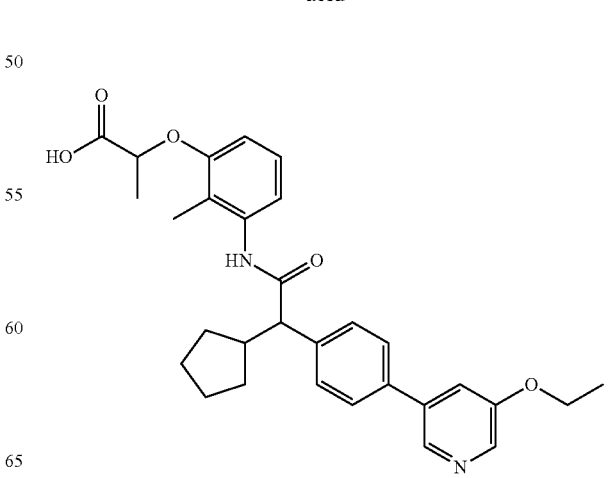

142 mg (300 μmol) methyl 2-(3-{[(4-bromophenyl)(cyclopentyl)acetyl]amino}-2-methylphenoxy)propanoate which was prepared according to intermediate 23 were reacted with 3-ethoxy-5-(4,4,5,5-tetramethyl-1,3,2-dioxaborolan-2-yl)pyridine in analogy to example 1 to give after methyl ester saponification with 1500 μL NaOH (2M in water) and subsequent working up and purification 11 mg (7%) of the title compound.

¹H-NMR (DMSO-d6): δ=0.94-1.16 (1H), 1.31-1.69 (11H), 1.75-2.02 (4H), 2.52-2.72 (2H), 3.54 (1H), 4.19 (2H), 4.76 (1H), 6.60 (1H), 6.84 (1H), 7.02 (1H), 7.47-7.65 (3H), 7.71 (2H), 8.25 (1H), 8.47 (1H), 9.52 (1H), 12.96 (1H) ppm.

Example 160

2-[3-({2-cyclopentyl-2-[4-(5-chloropyridin-3-yl)phenyl]acetyl}amino)-2-methylphenoxy]propanoic acid

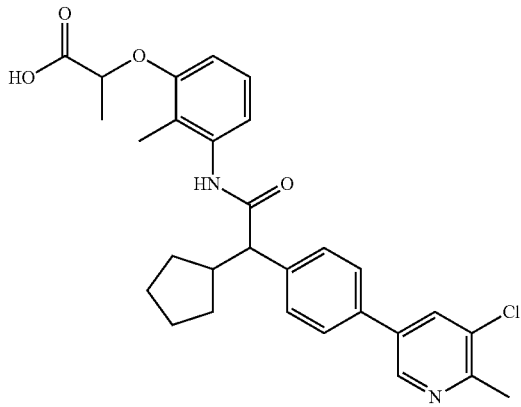 [SMILES: Cc1ncc(-c2ccc(C(C(=O)Nc3cccc(OC(C)C(=O)O)c3C)C3CCCC3)cc2)cc1Cl]

142 mg (300 μmol) methyl methyl 2-(3-{[(4-bromophenyl)(cyclopentyl)acetyl]amino}-2-methylphenoxy)propanoate which was prepared according to intermediate 23 were reacted with 3-chloro-2-methyl-5-(4,4,5,5-tetramethyl-1,3,2-dioxaborolan-2-yl)pyridine in analogy to example 1 to give after methyl ester saponification with 1500 μL NaOH (2M in water) and subsequent working up and purification 49 mg (32%) of the title compound.

¹H-NMR (DMSO-d6): δ=1.03 (1H), 1.34-1.54 (5H), 1.54-1.65 (2H), 1.69 (1H), 1.79-1.93 (1H), 1.98 (3H), 2.08 (1H), 2.53-2.68 (6H), 3.56 (1H), 4.78 (1H), 6.62 (1H), 6.85 (1H), 7.03 (1H), 7.55 (2H), 7.74 (2H), 8.18 (1H), 8.76 (1H), 9.53 (1H), 12.96 (1H) ppm.

Example 161

(R/S) 3-(3-{[{2-chloro-4-[5-(trifluoromethyl)pyridin-3-yl]phenyl}(cyclopentyl)acetyl]amino}-2-methylphenyl)propanoic acid

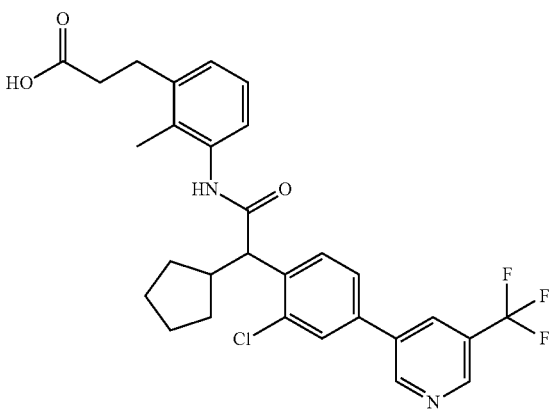 [SMILES: Cc1c(CCC(=O)O)cccc1NC(=O)C(c1ccc(-c2cncc(C(F)(F)F)c2)cc1Cl)C1CCCC1]

24 mg (100 μmol) tert-butyl 3-(3-amino-2-methylphenyl)propanoate which was prepared according to intermediate 2 were reacted in analogy to intermediate 3 with {2-chloro-4-[5-(trifluoromethyl)pyridin-3-yl]phenyl}(cyclopentyl)acetic acid which was prepared according to intermediate 33 to give the tBu ester protected product which was subjected to preparative HPLC. After tBu ester deprotection of the obtained solid with TFA in DCM (1:1) and subsequent working up 9 mg (9%) of the title compound were obtained.

¹H-NMR (DMSO-d6): δ=0.93-1.24 (2H), 1.44-1.65 (4H), 1.67-1.79 (1H), 1.82-1.93 (1H), 2.05 (3H), 2.44 (2H), 2.59-2.71 (1H), 2.81 (2H), 4.07 (1H), 6.95-7.08 (3H), 7.81-7.88 (2H), 8.00 (1H), 8.54 (1H), 8.97 (1H), 9.24 (1H), 9.64 (1H) ppm.

Example 162

2-(3-{[2-cyclopentyl-2-{4-[5-(trifluoromethyl)pyridin-3-yl]phenyl}acetyl]amino}-2-methylphenoxy)propanoic acid

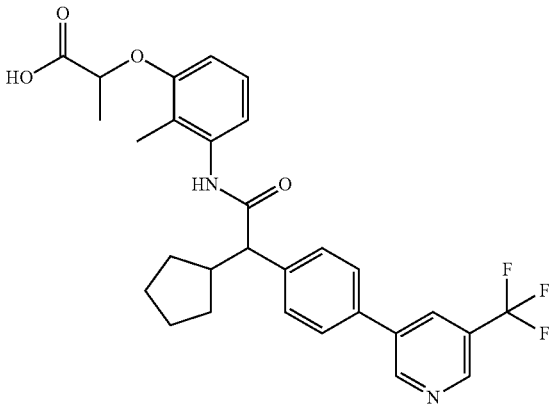 [SMILES: Cc1c(NC(=O)C(c2ccc(-c3cncc(C(F)(F)F)c3)cc2)C2CCCC2)cccc1OC(C)C(=O)O]

142 mg (300 μmol) methyl 2-(3-{[(4-bromophenyl)(cyclopentyl)acetyl]amino}-2-methylphenoxy)propanoate which was prepared according to intermediate 23 were reacted with [3-(trifluoromethyl)phenyl]boronic acid in analogy to example 1 to give after methyl ester saponification with 1500 µL NaOH (2M in water) and subsequent working up and purification 111 mg (70%) of the title compound.

$^1$H-NMR (DMSO-d6): δ=0.94-1.18 (1H), 1.34-1.54 (6H), 1.54-1.75 (3H), 1.80-1.93 (1H), 1.94-2.03 (3H), 2.33-2.47 (1H), 2.53-2.70 (2H), 3.58 (1H), 4.78 (1H), 6.62 (1H), 6.85 (1H), 6.99-7.12 (1H), 7.51-7.67 (2H), 7.84 (2H), 8.47 (1H), 8.93-9.00 (1H), 9.23 (1H), 9.55 (1H), 12.94 (1H) ppm.

Example 163

[3-({2-[4-(5-chloropyridin-3-yl)phenyl]-2-cyclopentylacetyl}amino)-2-methylphenoxy](cyclopropyl)ethanoic acid

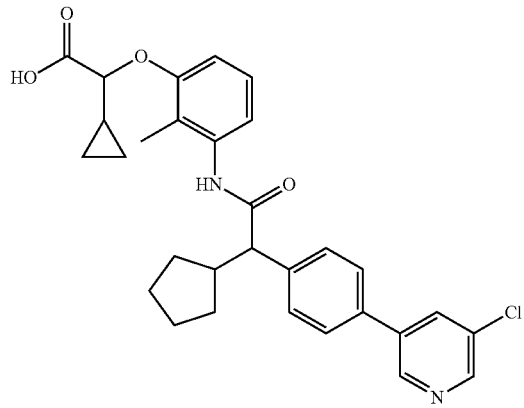 [SMILES: Cc1c(NC(=O)C(c2ccc(-c3cncc(Cl)c3)cc2)C2CCCC2)cccc1OC(C(=O)O)C1CC1]

154 mg (300 µmol) methyl 2-(3-{[(4-bromophenyl)(cyclopentyl)acetyl]amino}-2-methylphenoxy)propanoate which was prepared according to intermediate 25 were reacted with (5-chloropyridin-3-yl)boronic acid in analogy to example 1 to give after ethyl ester saponification with 1500 µL NaOH (2M in water) and subsequent working up and purification 13 mg (8%) of the title compound.

$^1$H-NMR (DMSO-d6): δ=0.43-0.64 (4H), 1.01 (1H), 1.28-1.64 (5H), 1.67 (1H), 1.86 (1H), 1.97 (3H), 2.06 (1H), 2.52-2.72 (1H), 3.55 (1H), 4.16 (1H), 6.53 (1H), 6.79-6.88 (1H), 7.00 (1H), 7.55 (2H), 7.76 (2H), 8.24 (1H), 8.60 (1H), 8.87 (1H), 9.53 (1H), 12.93 (1H) ppm.

Example 164

[3-({2-cyclopentyl-2-[4-(5-ethoxypyridin-3-yl)phenyl]acetyl}amino)-2-methylphenoxy](cyclopropyl)ethanoic acid

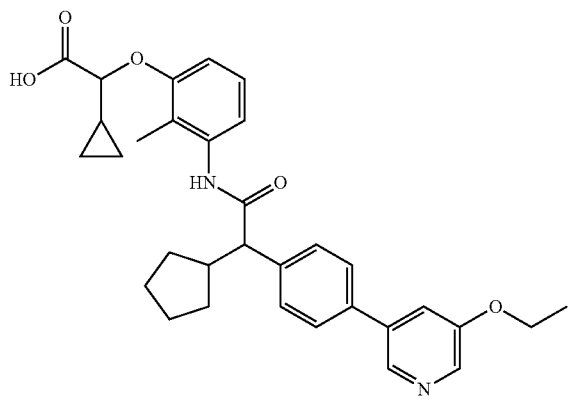 [SMILES: CCOc1cncc(-c2ccc(C(C(=O)Nc3cccc(OC(C(=O)O)C4CC4)c3C)C3CCCC3)cc2)c1]

154 mg (300 µmol) ethyl methyl 2-(3-{[(4-bromophenyl)(cyclopentyl)acetyl]amino}-2-methylphenoxy)propanoate which was prepared according to intermediate 25 were reacted with 3-ethoxy-5-(4,4,5,5-tetramethyl-1,3,2-dioxaborolan-2-yl)pyridine in analogy to example 1 to give after ethyl ester saponification with 1500 µL NaOH (2M in water) and subsequent working up and purification 11 mg (6%) of the title compound.

$^1$H-NMR (DMSO-d6): δ=0.44-0.64 (4H), 1.01 (1H), 1.29-1.63 (8H), 1.67 (1H), 1.74-2.04 (4H), 2.51-2.72 (2H), 3.54 (1H), 4.12-4.26 (3H), 6.53 (1H), 6.83 (1H), 7.00 (1H), 7.43-7.65 (3H), 7.71 (2H), 8.25 (1H), 8.47 (1H), 9.52 (1H), 12.94 (1H) ppm.

Example 165

[3-({2-[4-(5-chloro-6-methylpyridin-3-yl)phenyl]-2-cyclopentylacetyl}amino)-2-methylphenoxy](cyclopropyl)ethanoic acid

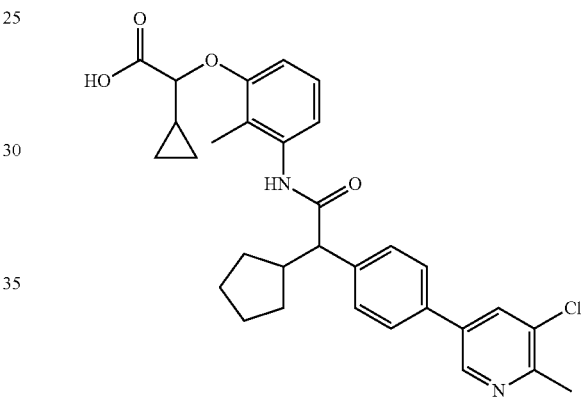

154 mg (300 µmol) methyl 2-(3-{[(4-bromophenyl)(cyclopentyl)acetyl]amino}-2-methylphenoxy)propanoate which was prepared according to intermediate 25 were reacted with 3-chloro-2-methyl-5-(4,4,5,5-tetramethyl-1,3,2-dioxaborolan-2-yl)pyridine in analogy to example 1 to give after ethyl ester saponification with 1500 µL NaOH (2M in water) and subsequent working up and purification 13 mg (8%) of the title compound.

$^1$H-NMR (DMSO-d6): δ=0.44-0.63 (4H), 0.94-1.09 (1H), 1.29-1.63 (6H), 1.85 (1H), 1.98 (3H), 2.52-2.71 (5H), 3.54 (1H), 4.16 (1H), 6.54 (1H), 6.83 (1H), 7.00 (1H), 7.53 (2H), 7.72 (2H), 8.16 (1H), 8.74 (1H), 9.53 (1H), 12.93 (1H) ppm.

Example 166

(3-{[2-cyclopentyl-2-{4-[5-(trifluoromethyl)pyridin-3-yl]phenyl}acetyl]amino}-2-methylphenoxy)(cyclopropyl)ethanoic acid

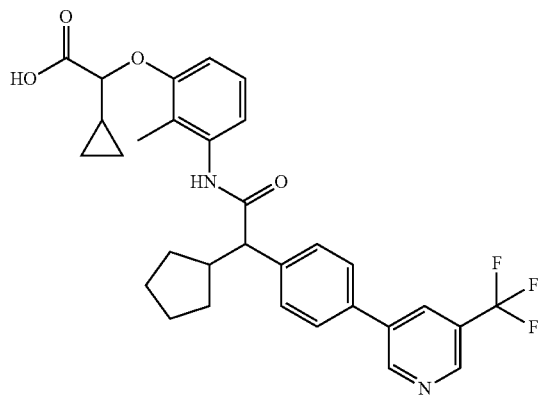 [SMILES: Cc1c(NC(=O)C(c2ccc(-c3cncc(C(F)(F)F)c3)cc2)C2CCCC2)cccc1OC(C(=O)O)C1CC1]

154 mg (300 μmol) methyl 2-(3-{[(4-bromophenyl)(cyclopentyl)acetyl]amino}-2-methylphenoxy)propanoate which was prepared according to intermediate 25 were reacted with [5-(trifluoromethyl)pyridin-3-yl]boronic acid in analogy to example 1 to give after ethyl ester saponification with 1500 μL NaOH (2M in water) and subsequent working up and purification 10 mg (6%) of the title compound.

$^1$H-NMR (DMSO-d6): δ=0.44-0.63 (4H), 1.02 (1H), 1.28-1.64 (6H), 1.68 (1H), 1.86 (1H), 1.93-2.04 (3H), 2.52-2.72 (2H), 3.58 (1H), 3.54 (1H), 4.16 (1H), 6.54 (1H), 6.83 (1H), 7.00 (1H), 7.58 (2H), 7.82 (2H), 8.46 (1H), 8.92-8.98 (1H), 9.21 (1H), 9.55 (1H), 12.85 (1H) ppm.

Example 167

(R/S) 3-{3-[(cyclopentyl{4-[5-(trifluoromethyl)pyridin-3-yl]phenyl}acetyl)amino]-5-fluoro-2-methylphenyl}propanoic acid

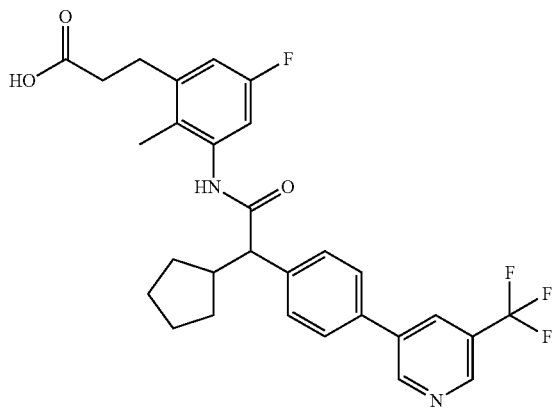 [SMILES: Cc1c(CCC(=O)O)cc(F)cc1NC(=O)C(c1ccc(-c2cncc(C(F)(F)F)c2)cc1)C1CCCC1]

175 mg (300 μmol) (R/S) tert-butyl 3-(3-{[(4-bromophenyl)(cyclopentyl)acetyl]amino}-5-fluoro-2-methylphenyl)propanoate which was prepared according to intermediate 27 were reacted with [5-(trifluoromethyl)pyridin-3-yl]boronic acid in analogy to example 1 to give after tBu ester deprotection with 7000 μL TFA and 100 μL water and subsequent working up and purification 131 mg (81%) of the title compound.

$^1$H-NMR (DMSO-d6): δ=0.95-1.19 (1H), 1.33-1.54 (3H), 1.54-1.65 (2H), 1.66-1.76 (1H), 1.81-1.95 (1H), 2.02 (3H), 2.53-2.59 (1H), 2.59-2.71 (1H), 2.81 (2H), 3.34 (1H), 3.62 (1H), 6.86 (1H), 7.02 (1H), 7.60 (2H), 7.84 (2H), 8.47 (1H), 8.96 (1H), 9.19-9.28 (1H), 9.62 (1H), 12.20 (1H) ppm.

Example 168

(R/S) 3-[3-({[4-(5-chloropyridin-3-yl)phenyl](cyclopentyl)acetyl}amino)-5-fluoro-2-methylphenyl]propanoic acid

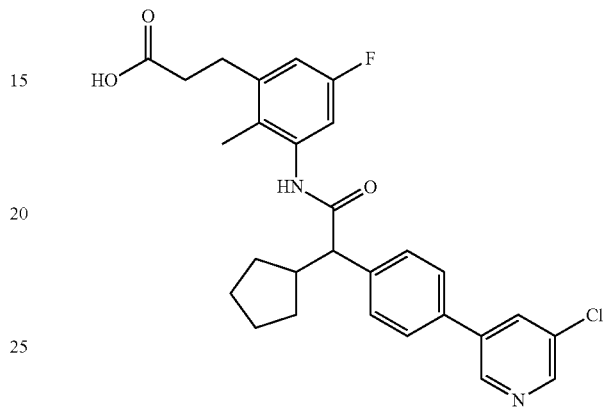

155 mg (300 μmol) (R/S) tert-butyl 3-(3-{[(4-bromophenyl)(cyclopentyl)acetyl]amino}-5-fluoro-2-methylphenyl)propanoate which was prepared according to intermediate 27 were reacted with (5-chloropyridin-3-yl)boronic acid in analogy to example 1 to give after tBu ester deprotection with 4000 μL TFA and 100 μL water and subsequent working up and purification 95 mg (61%) of the title compound.

$^1$H-NMR (DMSO-d6): δ=1.03 (1H), 1.27-1.46 (2H), 1.49 (1H), 1.53-1.64 (2H), 1.68 (1H), 1.87 (1H), 2.02 (3H), 2.33-2.49 (2H), 2.53-2.58 (1H), 2.64 (1H), 2.81 (2H), 3.61 (1H), 6.86 (1H), 7.00 (1H), 7.57 (2H), 7.78 (2H), 8.25 (1H), 8.61 (1H), 8.88 (1H), 9.61 (1H), 12.19 (1H) ppm.

Example 169

(R/S) 3-[3-({[4-(5-chloro-6-methylpyridin-3-yl)phenyl](cyclopentyl)acetyl}amino)-5-fluoro-2-methylphenyl]propanoic acid

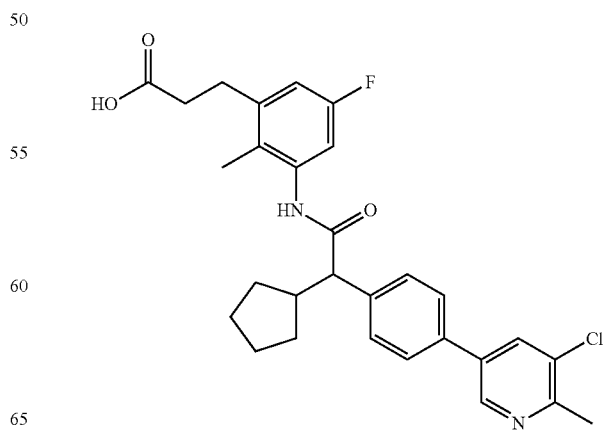

155 mg (300 µmol) (R/S) tert-butyl 3-(3-{[(4-bromophenyl)(cyclopentyl)acetyl]amino}-5-fluoro-2-methylphenyl)propanoate which was prepared according to intermediate 27 were reacted with 3-chloro-2-methyl-5-(4,4,5,5-tetramethyl-1,3,2-dioxaborolan-2-yl)pyridine in analogy to example 1 to give after tBu ester deprotection with 4000 µL TFA and 100 µL water and subsequent working up and purification 129 mg (84%) of the title compound.

¹H-NMR (DMSO-d6): δ=0.94-1.17 (1H), 1.32-1.53 (3H), 1.53-1.65 (2H), 1.66-1.76 (1H), 1.80-1.95 (1H), 2.02 (3H), 2.32-2.68 (6H), 2.81 (2H), 3.60 (1H), 6.86 (1H), 7.02 (1H), 7.55 (2H), 7.74 (2H), 8.18 (1H), 8.75 (1H), 9.60 (1H), 12.19 (1H) ppm.

Example 170

(R/S) 3-[3-({[4-(5-ethoxypyridin-3-yl)phenyl](cyclopentyl)acetyl}amino)-5-fluoro-2-methylphenyl]propanoic acid

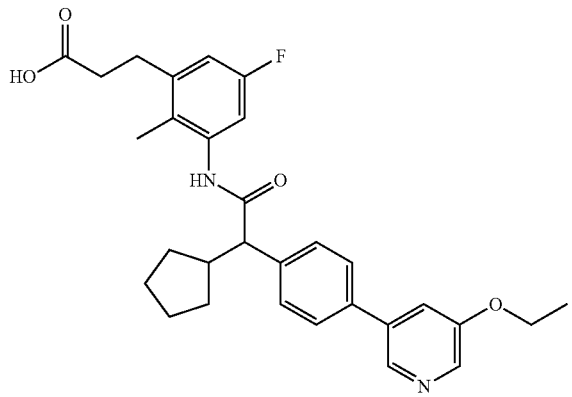 [SMILES: CCOc1cncc(-c2ccc(C(C(=O)Nc3cc(F)cc(CCC(=O)O)c3C)C3CCCC3)cc2)c1]

155 mg (300 µmol) (R/S) tert-butyl 3-(3-{[(4-bromophenyl)(cyclopentyl)acetyl]amino}-5-fluoro-2-methylphenyl)propanoate which was prepared according to intermediate 27 were reacted with 3-ethoxy-5-(4,4,5,5-tetramethyl-1,3,2-dioxaborolan-2-yl)pyridine in analogy to example 1 to give after tBu ester deprotection with 3000 µL TFA and 100 µL water and subsequent working up and purification 6 mg (4%) of the title compound.

¹H-NMR (DMSO-d6): δ=1.04 (1H), 1.31-1.69 (9H), 1.84 (1H), 2.00 (3H), 2.41-2.67 (3H), 2.80 (2H), 3.58 (1H), 4.18 (2H), 6.84 (1H), 7.01 (1H), 7.35-7.65 (3H), 7.71 (2H), 8.25 (1H), 8.47 (1H), 9.59 (1H), 12.20 (1H) ppm.

Example 171: (R/S) N-{3-[(cyclopentyl{4-[5-(trifluoromethyl)pyridin-3-yl]phenyl}acetyl)amino]-2-methylphenyl}glycine

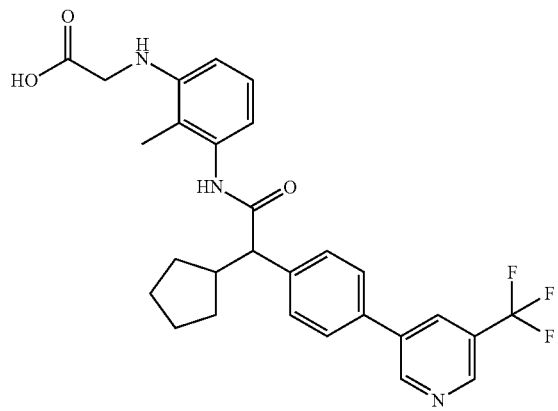 [SMILES: Cc1c(NCC(=O)O)cccc1NC(=O)C(c1ccc(-c2cncc(C(F)(F)F)c2)cc1)C1CCCC1]

138 mg (R/S) (300 µmol methyl N-(3-{[(4-bromophenyl)(cyclopentyl)acetyl]amino}-2-methylphenyl)glycinate which was prepared according to intermediate 29 were reacted with [5-(trifluoromethyl)pyridin-3-yl]boronic acid in analogy to example 1 to give after methyl ester saponification with 1500 µL NaOH (2M in water) and subsequent working up and purification 4 mg (1%) of the title compound.

¹H-NMR (DMSO-d6): δ=0.86-1.05 (1H), 1.10 (1H), 1.33-1.71 (6H), 1.76-1.92 (4H), 2.51-2.72 (1H), 3.54 (2H), 6.20 (1H), 6.38 (1H), 6.84-7.01 (1H), 7.58 (2H), 7.82 (2H), 8.46 (1H), 8.94 (1H), 9.21 (1H), 9.51 (1H) ppm.

Example 172

(R/S) 3-[3-({[2-chloro-4-(5-chloropyridin-3-yl)-5-methylphenyl](cyclopentyl)acetyl}amino)-2-methylphenyl]propanoic acid

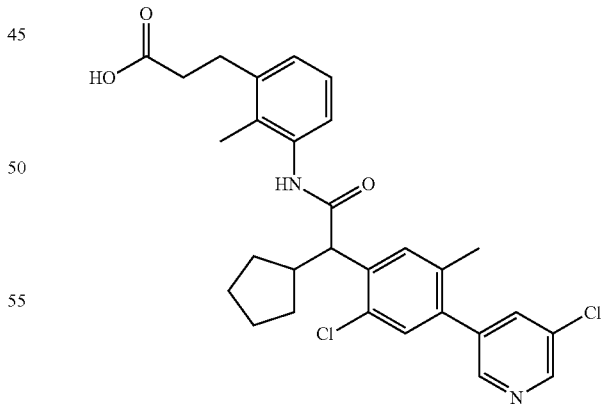

496 mg (900 µmol) (R/S) tert-butyl 3-(3-{[(4-bromo-2-chloro-5-methylphenyl)(cyclopentyl)acetyl]amino}-2-methylphenyl)propanoate which was prepared according to intermediate 31 were reacted with (5-chloropyridin-3-yl)boronic acid in analogy to example 1 to give after tBu ester deprotection with 25000 µL TFA and subsequent working up and purification 120 mg (23%) of the title compound.

¹H-NMR (DMSO-d6): δ=0.96-1.12 (1H), 1.40-1.68 (6H), 1.74 (1H), 1.80-1.97 (1H), 2.08 (3H), 2.21-2.29 (4H), 2.41-2.55 (1H), 2.83 (2H), 4.04 (1H), 7.00-7.18 (3H), 7.42 (1H), 7.70 (1H), 8.06 (1H), 8.58 (1H), 8.66 (1H), 9.62 (1H), 12.19 (1H) ppm.

Example 173

(R/S) 3-(3-{[{2-chloro-5-methyl-4-[5-(trifluoromethyl)pyridin-3-yl]phenyl}(cyclopentyl)acetyl]amino}-2-methylphenyl)propanoic acid

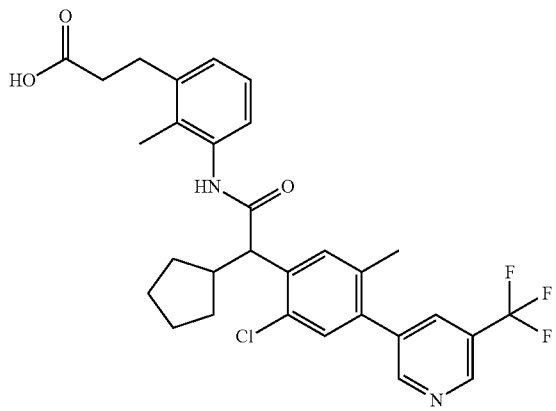 [SMILES: Cc1cc(C(C(=O)Nc2cccc(CCC(=O)O)c2C)C2CCCC2)c(Cl)cc1-c1cncc(C(F)(F)F)c1]

496 mg (900 µmol) (R/S) tert-butyl 3-(3-{[(4-bromo-2-chloro-5-methylphenyl)(cyclopentyl)acetyl]amino}-2-methylphenyl)propanoate which was prepared according to intermediate 31 were reacted with [5-(trifluoromethyl)pyridin-3-yl]boronic acid in analogy to example 1 to give after tBu ester deprotection with 25000 µL TFA and subsequent working up and purification 144 mg (24%) of the title compound.

¹H-NMR (DMSO-d6): δ=0.96-1.12 (1H), 1.24 (1H), 1.32-1.49 (1H), 1.51-1.67 (4H), 1.75 (1H), 1.80-1.97 (1H), 2.09 (3H), 2.25 (3H), 2.41-2.49 (1H), 2.68 (1H), 2.83 (2H), 4.07 (1H), 7.00-7.11 (2H), 7.47 (1H), 7.72 (1H), 8.31 (1H), 8.93 (1H), 9.01 (1H), 9.63 (1H), 12.21 (1H) ppm.

Example 174

(R/S) 3-[3-({[2-chloro-4-(5-chloro-6-methylpyridin-3-yl)-5-methylphenyl](cyclopentyl)acetyl}amino)-2-methylphenyl]propanoic acid

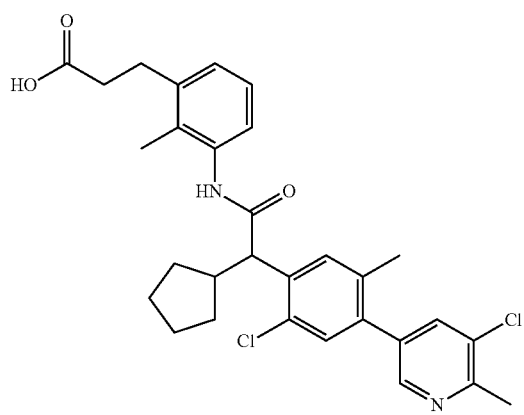

496 mg (900 µmol) (R/S) tert-butyl 3-(3-{[(4-bromo-2-chloro-5-methylphenyl)(cyclopentyl)acetyl]amino}-2-methylphenyl)propanoate which was prepared according to intermediate 31 were reacted with 3-chloro-2-methyl-5-(4,4,5,5-tetramethyl-1,3,2-dioxaborolan-2-yl)pyridine in analogy to example 1 to give after tBu ester deprotection with 25000 µL TFA and subsequent working up and purification 128 mg (24%) of the title compound.

¹H-NMR (DMSO-d6): δ=1.05 (1H), 1.41-1.67 (5H), 1.74 (1H), 1.88 (1H), 2.08 (3H), 2.25 (3H), 2.33 (1H), 2.41-2.49 (1H), 2.53-2.69 (4H), 2.83 (2H), 4.03 (1H), 7.00-7.13 (3H), 7.37 (1H), 7.68 (1H), 7.97 (1H), 8.45 (1H), 9.61 (1H), 12.16 (1H) ppm.

Example 175

(R/S) 3-[3-({[3-chloro-4-(5-(trifluoromethyl)pyridin-3-yl)phenyl](cyclopentyl)acetyl}amino)-2-methylphenyl]propanoic acid

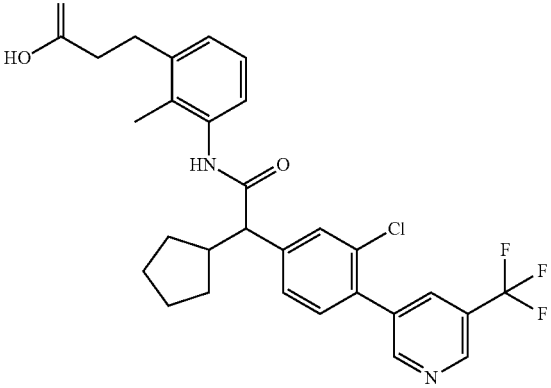

550 mg (1028 µmol) (R/S) tert-butyl 3-(3-{[(4-bromo-3-chlorophenyl)(cyclopentyl)acetyl]amino}-2-methylphenyl)propanoate which was prepared according to intermediate 35 were reacted in analogy to intermediate 3 with [5-(trifluoromethyl)pyridin-3-yl]boronic acid to give after tBu ester deprotection with 25000 µL TFA and subsequent working up and purification 83 mg (10%) of the title compound.

¹H-NMR (DMSO-d6): δ=1.02-1.16 (1H), 1.33-1.43 (1H), 1.44-1.56 (2H), 1.56-1.65 (2H), 1.66-1.76 (1H), 1.88 (1H), 2.06 (3H), 2.44 (2H), 2.57-2.69 (1H), 2.82 (2H), 3.60 (1H), 6.99-7.10 (3H), 7.52-7.60 (2H), 7.69 (1H), 8.31-8.36 (1H), 8.97-9.05 (2H), 9.59 (1H) ppm.

Example 176

(R/S) 3-[3-({[3-chloro-4-(5-chloro-6-methylpyridin-3-yl)phenyl](cyclopentyl)acetyl}amino)-2-methylphenyl]propanoic acid

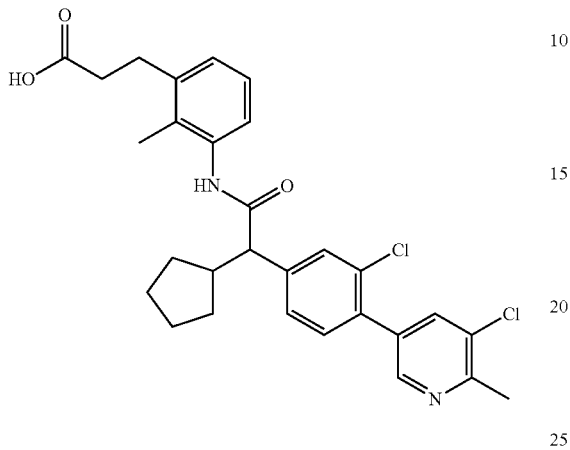

550 mg (1028 µmol) (R/S) tert-butyl 3-(3-{[(4-bromo-3-chlorophenyl)(cyclopentyl)acetyl]amino}-2-methylphenyl)propanoate which was prepared according to intermediate 35 were reacted in analogy to intermediate 3 with 3-chloro-2-methyl-5-(4,4,5,5-tetramethyl-1,3,2-dioxaborolan-2-yl)pyridine to give after tBu ester deprotection with 25000 µL TFA and subsequent working up and purification 158 mg (26%) of the title compound.

$^1$H-NMR (DMSO-d6): δ=0.98-1.12 (1H), 1.22-1.76 (6H), 1.80-1.94 (1H), 2.06 (3H), 2.41-2.49 (2H), 2.53-2.70 (4H), 2.83 (2H), 3.58 (1H), 7.06 (2H), 7.35-7.55 (3H), 7.66 (1H), 8.01 (1H), 8.51 (1H), 9.59 (1H), 12.18 (1H) ppm.

Example 177

(R/S) 3-[3-({[3-chloro-4-(5-chloropyridin-3-yl)phenyl](cyclopentyl)acetyl}amino)-2-methylphenyl]propanoic acid

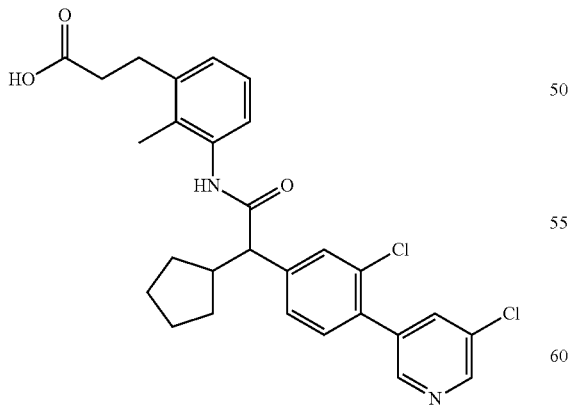

550 mg (1028 µmol) (R/S) tert-butyl 3-(3-{[(4-bromo-3-chlorophenyl)(cyclopentyl)acetyl]amino}-2-methylphenyl)propanoate which was prepared according to intermediate 35 were reacted in analogy to intermediate 3 with (5-chloropyridin-3-yl)boronic acid to give after tBu ester deprotection with 25000 µL TFA and subsequent working up and purification 84% of the title compound.

$^1$H-NMR (DMSO-d6): δ=1.04 (1H), 1.19-1.71 (6H), 1.84 (2H), 2.04 (3H), 2.36-2.46 (2H), 2.81 (2H), 3.57 (1H), 6.96-7.21 (2H), 7.40-7.59 (3H), 7.66 (1H), 8.05 (1H), 8.57-8.72 (2H), 9.59 (1H), 12.21 (1H) ppm.

Example 178

(R/S) 3-[3-({[4-(5-chloropyridin-3-yl)-2,5-difluorophenyl](cyclopentyl)acetyl}amino)-2-methylphenyl]propanoic acid

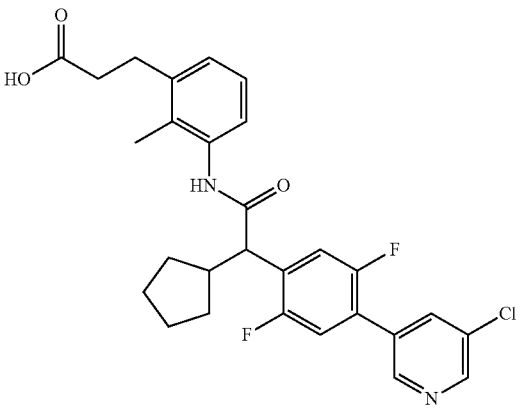 [SMILES: Cc1c(CCC(=O)O)cccc1NC(=O)C(c1cc(F)c(-c2cncc(Cl)c2)cc1F)C1CCCC1]

523 mg (975 µmol) (R/S) tert-butyl 3-(3-{[(4-bromo-2,5-difluorophenyl)(cyclopentyl)acetyl]amino}-2-methylphenyl)propanoate which was prepared according to intermediate 37 were reacted in analogy to intermediate 3 with (5-chloropyridin-3-yl)boronic acid to give after tBu ester deprotection with 25000 µL TFA and subsequent working up and purification 94 mg (17%) of the title compound.

$^1$H-NMR (DMSO-d6): δ=1.07 (1H), 1.51-1.66 (4H), 1.67-1.78 (1H), 1.80-1.93 (1H), 2.08 (3H), 2.41-2.49 (2H), 2.53-2.68 (2H), 2.83 (2H), 3.93 (1H), 7.00-7.22 (3H), 7.44-7.69 (2H), 8.22 (1H), 8.70 (1H), 8.78 (1H), 9.75 (1H), 12.16 (1H) ppm.

Example 179

(R/S) 3-{3-[(cyclopentyl{2,5-difluoro-4-[5-(trifluoromethyl)pyridin-3-yl]phenyl}acetyl)amino]-2-methylphenyl}propanoic acid

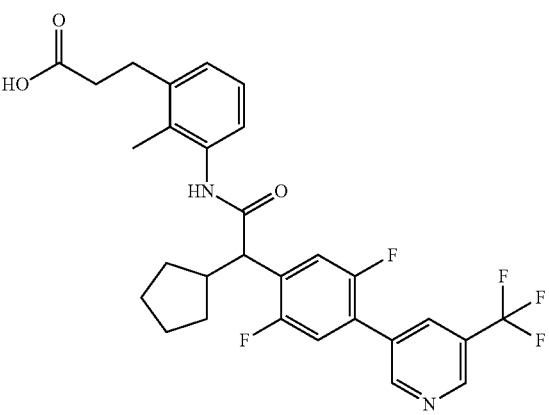 [SMILES: Cc1c(CCC(=O)O)cccc1NC(=O)C(c1cc(F)c(-c2cncc(C(F)(F)F)c2)cc1F)C1CCCC1]

523 mg (975 µmol) (R/S) tert-butyl 3-(3-{[(4-bromo-2,5-difluorophenyl)(cyclopentyl)acetyl]amino}-2-methylphenyl)propanoate which was prepared according to intermediate 37 were reacted in analogy to intermediate 3 with [5-(trifluoromethyl)pyridin-3-yl]boronic acid to give after tBu ester deprotection with 25000 µL TFA and subsequent working up and purification 87 mg (15%) of the title compound.

$^1$H-NMR (DMSO-d6): δ=1.09 (1H), 1.46-1.67 (5H), 1.68-1.79 (1H), 1.88 (1H), 2.08 (3H), 2.42-2.49 (3H), 2.83 (2H), 3.94 (1H), 7.01-7.24 (3H), 7.51-7.76 (2H), 8.46 (1H), 9.01-9.08 (1H), 9.12 (1H), 9.76 (1H), 12.16 (1H) ppm.

Example 180

(R/S) 3-[3-({[4-(5-chloro-6-methylpyridin-3-yl)-2,5-difluorophenyl](cyclopentyl)acetyl}amino)-2-methylphenyl]propanoic acid

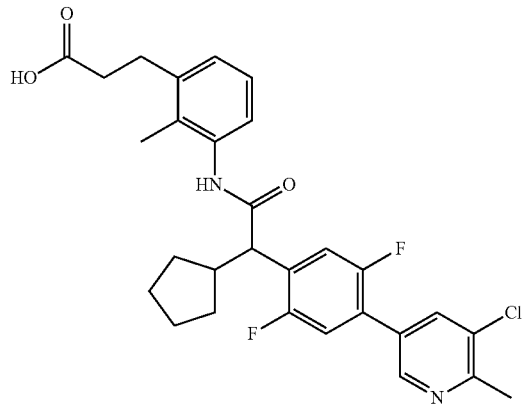 [SMILES: Cc1ncc(-c2cc(F)c(C(C(=O)Nc3cccc(CCC(=O)O)c3C)C3CCCC3)cc2F)cc1Cl]

523 mg (975 µmol) (R/S) tert-butyl 3-(3-{[(4-bromo-2,5-difluorophenyl)(cyclopentyl)acetyl]amino}-2-methylphenyl)propanoate which was prepared according to intermediate 37 were reacted in analogy to intermediate 3 with 3-chloro-2-methyl-5-(4,4,5,5-tetramethyl-1,3,2-dioxaborolan-2-yl)pyridine to give after tBu ester deprotection with 25000 µL TFA and subsequent working up and purification 89 mg (16%) of the title compound.

$^1$H-NMR (DMSO-d6): δ=1.06 (1H), 1.46-1.66 (5H), 1.72 (1H), 1.79-1.96 (1H), 2.07 (3H), 2.41-2.48 (3H), 2.61 (3H), 2.83 (2H), 3.92 (1H), 7.00-7.12 (3H), 7.60 (2H), 8.14 (1H), 8.66 (1H), 9.75 (1H), 12.16 (1H) ppm.

Example 181

(R/S) 3-[3-({[4-(5-chloropyridin-3-yl)-2-fluoro-5-methylphenyl](cyclopentyl)acetyl}amino)-2-methylphenyl]propanoic acid

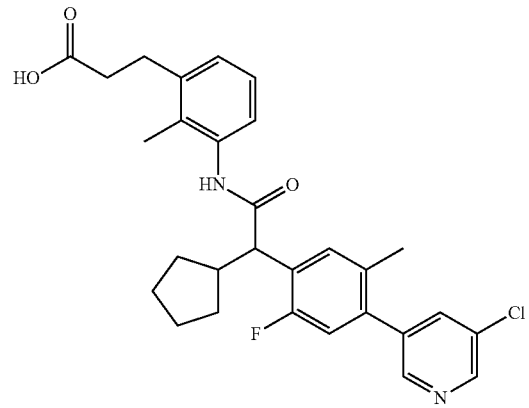 [SMILES: Cc1cc(C(C(=O)Nc2cccc(CCC(=O)O)c2C)C2CCCC2)c(F)cc1-c1cncc(Cl)c1]

543 mg (1020 µmol) (R/S) tert-butyl 3-(3-{[(4-bromo-2-fluoro-5-methylphenyl)(cyclopentyl)acetyl]amino}-2-methylphenyl)propanoate which was prepared according to intermediate 39 were reacted in analogy to intermediate 3 with (5-chloropyridin-3-yl)boronic acid to give after tBu ester deprotection with 25000 µL TFA and subsequent working up and purification 129 mg (22%) of the title compound.

$^1$H-NMR (DMSO-d6): δ=1.08 (1H), 1.43-1.67 (5H), 1.68-1.79 (1H), 1.80-1.95 (1H), 2.07 (3H), 2.23 (3H), 2.42-2.64 (3H), 2.83 (2H), 3.88 (1H), 7.00-7.11 (3H), 7.20 (1H), 7.62 (1H), 8.05 (1H), 8.58 (1H), 8.66 (1H), 9.65 (1H), 12.16 (1H) ppm.

Example 182

(R/S) 3-[3-({[4-(5-chloro-6-methylpyridin-3-yl)-2-fluoro-5-methylphenyl](cyclopentyl)acetyl}amino)-2-methylphenyl]propanoic acid

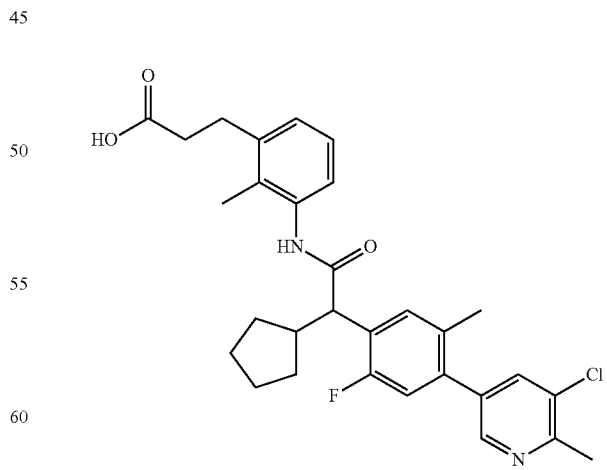

543 mg (1020 µmol) (R/S) tert-butyl 3-(3-{[(4-bromo-2-fluoro-5-methylphenyl)(cyclopentyl)acetyl]amino}-2-methylphenyl)propanoate which was prepared according to intermediate 39 were reacted in analogy to intermediate 3 with 3-chloro-2-methyl-5-(4,4,5,5-tetramethyl-1,3,2-dioxaborolan-2-yl)pyridine to give after tBu ester deprotection with 25000 μL TFA and subsequent working up and purification 148 mg (28%) of the title compound.

¹H-NMR (DMSO-d6): δ=1.08 (1H), 1.43-1.66 (6H), 1.66-1.78 (1H), 1.79-1.93 (1H), 2.07 (3H), 2.23 (3H), 2.41-2.48 (1H), 2.60 (3H), 2.68 (1H), 2.83 (2H), 3.88 (1H), 7.00-7.11 (3H), 7.16 (1H), 7.60 (1H), 7.91-8.01 (1H), 8.41-8.49 (1H), 9.64 (1H), 12.16 (1H) ppm.

Example 183

(R/S) 3-{3-[(cyclopentyl{2-fluoro-5-methyl-4-[5-(trifluoromethyl)pyridin-3-yl]phenyl}acetyl)amino]-2-methylphenyl}propanoic acid

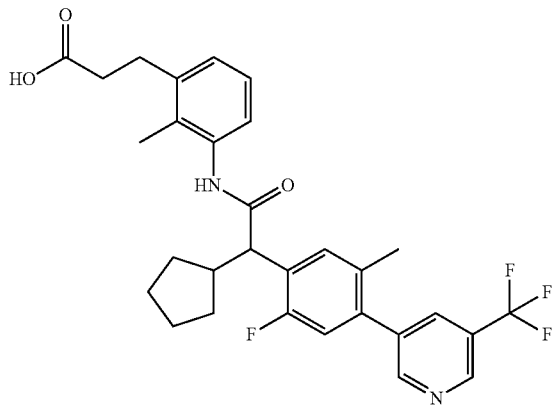 [SMILES: Cc1cc(C(C(=O)Nc2cccc(CCC(=O)O)c2C)C2CCCC2)c(F)cc1-c1cncc(C(F)(F)F)c1]

543 mg (1020 μmol) (R/S) tert-butyl 3-(3-{[(4-bromo-2-fluoro-5-methylphenyl)(cyclopentyl)acetyl]amino}-2-methylphenyl)propanoate which was prepared according to intermediate 39 were reacted in analogy to intermediate 3 with [5-(trifluoromethyl)pyridin-3-yl]boronic acid to give after tBu ester deprotection with 25000 μL TFA and subsequent working up and purification 74 mg (12%) of the title compound.

¹H-NMR (DMSO-d6): δ=1.07 (1H), 1.34-1.65 (5H), 1.71 (1H), 1.78-1.96 (1H), 2.06 (3H), 2.16-2.34 (1H), 2.36-2.53 (3H), 2.81 (2H), 3.88 (1H), 6.96-7.12 (3H), 7.23 (1H), 7.62 (1H), 8.28 (1H), 8.92 (1H), 8.99 (1H), 9.65 (1H), 12.16 (1H) ppm.

Example 184

3-[3-({(2R)-2-[4-(5-chloro-6-methylpyridin-3-yl)phenyl]-2-cyclopentylacetyl}amino)-6-fluoro-2-methylphenyl]propanoic acid

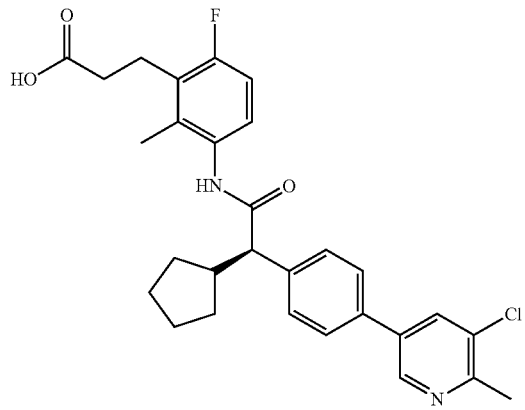

38 mg (150 μmol) tert-butyl 3-(3-amino-6-fluoro-2-methylphenyl)propanoate which was prepared according to intermediate 41 were reacted in analogy to intermediate 3 with (2R)-[4-(5-chloro-6-methylpyridin-3-yl)phenyl](cyclopentyl)ethanoic acid which was prepared according to intermediate 42 to give the tBu ester protected product which was subjected to preparative HPLC. After tBu ester deprotection of the obtained solid with TFA in DCM (1:1) and subsequent working up and purification 31 mg (41%) of the title compound were obtained.

¹H-NMR (DMSO-d6): δ=0.95-1.17 (1H), 1.34-1.63 (5H), 1.66-1.72 (1H), 1.80-1.93 (1H), 2.06 (3H), 2.32-2.49 (2H), 2.59 (3H), 2.81-2.89 (2H), 3.32 (1H), 3.52 (1H), 6.94 (1H), 7.04 (1H), 7.54 (1H), 7.68-7.78 (2H), 8.15-8.20 (1H), 8.73-8.77 (1H), 9.57 (1H), 12.23 (1H) ppm.

Analytical HPLC, method 11: solvent: acetonitrile/water+ 0.1% TFA, gradient 20% to 90% acetonitrile in 14 min; flow rate: 1 ml/min; solution: 1 mg/ml MeOH, injection volume: 5 μl; Rt: 8.65 min.

Optical rotation: −34.8° (9.4 mg/ml in DMSO, temperature: 20° C., wave length: 589 nM).

Example 185

3-[3-({(2R)-2-[4-(5-chloropyridin-3-yl)phenyl]-2-cyclopentylacetyl}amino)-6-fluoro-2-methylphenyl]propanoic acid

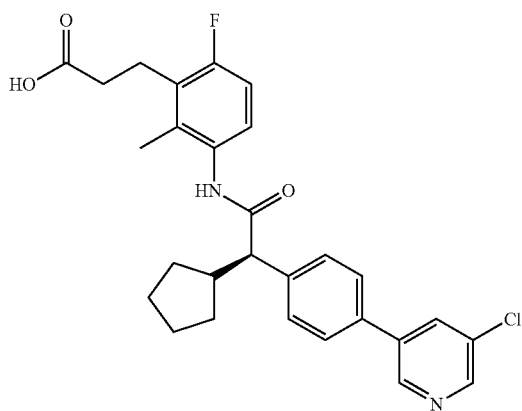 [SMILES: Cc1ncc(-c2ccc([C@H](C(=O)Nc3ccc(F)c(CCC(=O)O)c3C)C3CCCC3)cc2)cc1Cl]

38 mg (150 μmol) tert-butyl 3-(3-amino-6-fluoro-2-methylphenyl)propanoate which was prepared according to intermediate 41 were reacted in analogy to intermediate 3 with (2R)-[4-(5-chloropyridin-3-yl)phenyl](cyclopentyl)ethanoic acid which was prepared according to intermediate 45 to give the tBu ester protected product which was subjected to preparative HPLC. After tBu ester deprotection of the obtained solid with TFA in DCM (1:1) and subsequent working up and purification 37 mg (48%) of the title compound were obtained.

¹H-NMR (DMSO-d6): δ=0.97-1.12 (1H), 1.35-1.64 (5H), 1.66-1.73 (1H), 1.80-1.93 (1H), 2.05 (3H), 2.33-2.40 (2H), 2.58-2.72 (1H), 2.79-2.90 (2H), 3.52 (1H), 6.95 (1H), 7.04 (1H), 7.56 (2H), 7.72-7.81 (2H), 8.26 (1H), 8.62 (1H), 8.86-8.92 (1H), 9.58 (1H), 12.22 (1H) ppm.

Analytical HPLC, method 12: solvent: acetonitrile/water+ 0.1% TFA, gradient 20% to 90% acetonitrile in 14 min; flow rate: 1 ml/min; solution: 1 mg/ml MeOH, injection volume: 5 μl; Rt: 10.88 min.

Optical rotation: −34.0° (10.1 mg/ml in DMSO, temperature: 20° C., wave length: 589 nM).

Example 186

N-[3-({(2R)-2-[4-(5-chloropyridin-3-yl)phenyl]-2-cyclopentylacetyl}amino)-2-methylphenyl]-N-methylglycine

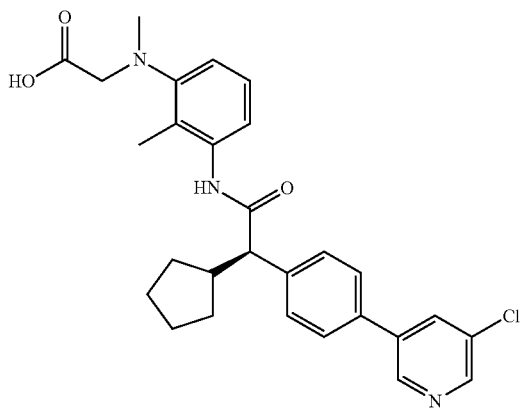 [SMILES: Cc1c(NC(=O)[C@@H](c2ccc(-c3cncc(Cl)c3)cc2)C2CCCC2)cccc1N(C)CC(=O)O]

40 mg (192 μmol) methyl N-(3-amino-2-methylphenyl)-N-methylglycinate which was prepared according to intermediate 49 were reacted analogy to intermediate 3 with (2R)-[4-(5-chloropyridin-3-yl)phenyl](cyclopentyl)ethanoic acid which was prepared according to intermediate 45 to give after methyl ester saponification with 750 μL NaOH (2M in water) and subsequent working up and purification 29 mg (36%) of the title compound.

¹H-NMR (DMSO-d6): δ=0.96-1.07 (1H), 1.33-1.62 (5H), 1.64-1.71 (1H), 1.86 (1H), 2.00 (3H), 2.58-2.76 (4H), 3.51-3.61 (3H), 6.88 (2H), 7.00-7.06 (1H), 7.55 (2H), 7.72-7.78 (2H), 8.22-8.25 (1H), 8.58-8.61 (1H), 8.84-8.89 (1H), 9.48 (1H), 12.36 (1H) ppm.

Example 187

N-[3-({(2R)-2-[4-(5-chloro-6-methylpyridin-3-yl)phenyl]-2-cyclopentylacetyl}amino)-2-methylphenyl]-N-methylglycine

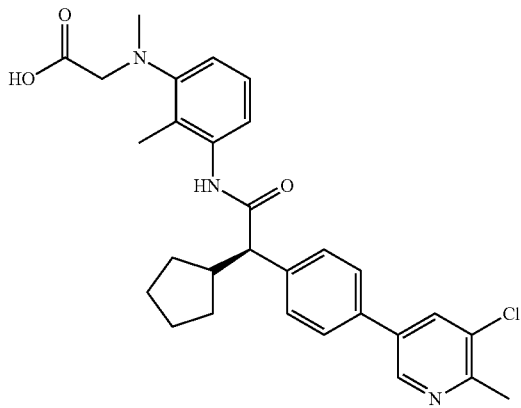 [SMILES: Cc1ncc(-c2ccc([C@H](C(=O)Nc3cccc(N(C)CC(=O)O)c3C)C3CCCC3)cc2)cc1Cl]

40 mg (192 μmol) methyl N-(3-amino-2-methylphenyl)-N-methylglycinate which was prepared according to intermediate 49 were reacted analogy to intermediate 3 with (2R)-[4-(5-chloro-6-methylpyridin-3-yl)phenyl](cyclopentyl)ethanoic acid which was prepared according to intermediate 42 to give after methyl ester saponification with 960 μL NaOH (2M in water) and subsequent working up and purification 39 mg (38%) of the title compound.

¹H-NMR (DMSO-d6): δ=0.95-1.06 (1H), 1.32-1.70 (6H), 1.80-1.91 (1H), 2.00 (3H), 2.51-2.61 (4H), 2.61-2.76 (3H), 3.49-3.62 (3H), 6.85-6.91 (2H), 6.99-7.06 (1H), 7.53 (2H), 7.68-7.75 (2H), 8.15-8.18 (1H), 8.72-8.75 (1H), 9.50 (1H), 12.38 (1H) ppm.

Example 188

(−) N-{3-[(cyclopentyl{3-fluoro-4-[5-(trifluoromethyl)pyridin-3-yl]phenyl}acetyl)amino]-2-methylphenyl}-N-methylglycine, Single Enantiomer

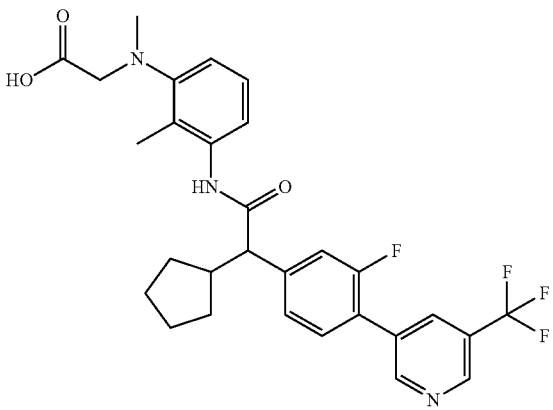 [SMILES: Cc1c(NC(=O)C(c2ccc(-c3cncc(C(F)(F)F)c3)c(F)c2)C2CCCC2)cccc1N(C)CC(=O)O]

52 mg (247 μmol) methyl N-(3-amino-2-methylphenyl)-N-methylglycinate which was prepared according to intermediate 49 were reacted analogy to intermediate 3 with (−)-cyclopentyl{3-fluoro-4-[5-(trifluoromethyl)pyridin-3-yl]phenyl}ethanoic acid which was prepared according to intermediate 50 to give after methyl ester saponification with 1235 μL NaOH (2M in water) and subsequent working up and purification 38 mg (27%) of the title compound.

¹H-NMR (DMSO-d6): δ=1.05 (1H), 1.35-1.63 (5H), 1.68 (1H), 1.77-1.95 (1H), 2.02 (3H), 2.53-2.68 (1H), 2.71 (3H), 3.43-3.69 (3H), 6.89 (2H), 7.03 (1H), 7.32-7.54 (2H), 7.69 (1H), 8.38 (1H), 8.99 (1H), 9.08 (1H), 9.53 (1H) ppm.

Optical rotation:—−7.9° (9 mg/ml in DMSO, temperature: 20° C., wave length: 589 nM).

Example 189

3-(3-{[(2R)-2-cyclopentyl-2-{4-[5-(2-methylpropyl)pyridin-3-yl]phenyl}acetyl]amino}-2-methylphenyl)propanoic acid

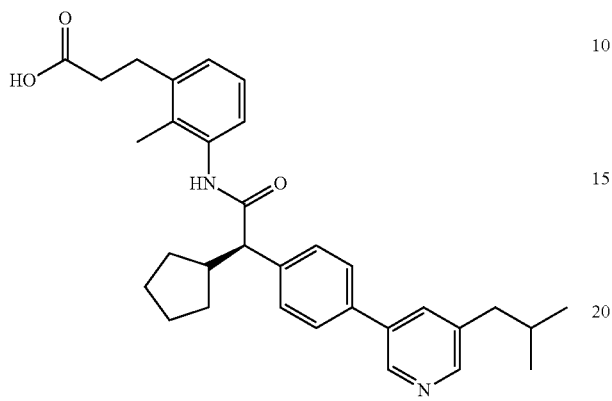

150 mg (300 μmol) tert-butyl 3-(3-{[(2R)-2-(4-bromophenyl)-2-cyclopentylacetyl]amino}-2-methylphenyl)propanoate which was prepared according to intermediate 43 were reacted with [5-(2-methylpropyl)pyridin-3-yl]boronic acid in analogy to example 1 to give after tBu ester deprotection with 20000 μL TFA and subsequent working up and purification 40 mg (26%) of the title compound.

$^1$H-NMR (DMSO-d6): δ=0.90 (6H), 1.04 (1H), 1.33-1.53 (3H), 1.60 (2H), 1.70 (1H), 1.82-1.99 (2H), 2.03 (3H), 2.45-2.55 (4H), 2.64 (1H), 2.81 (2H), 3.54 (1H), 6.97-7.09 (3H), 7.55 (2H), 7.71 (2H), 7.88 (1H), 8.37 (1H), 8.73 (1H), 9.54 (1H), 12.15 (1H) ppm.

Optical rotation:—−33.9° (10 mg/ml in DMSO, temperature: 20° C., wave length: 589 nM).

Example 190

3-(3-{[(2R)-2-cyclopentyl-2-{4-[5-(propan-2-yloxy)pyridin-3-yl]phenyl}acetyl]amino}-2-methylphenyl)propanoic acid

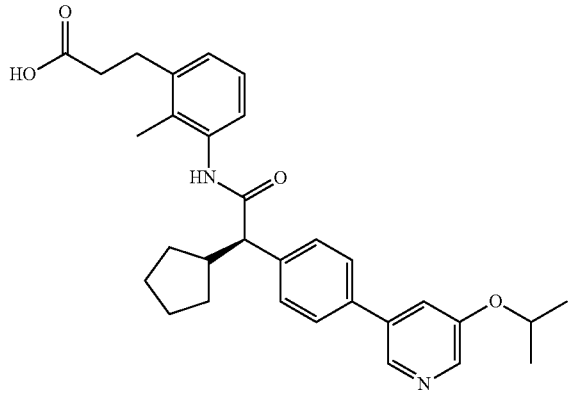 [SMILES: Cc1c(CCC(=O)O)cccc1NC(=O)[C@@H](c1ccc(-c2cncc(OC(C)C)c2)cc1)C1CCCC1]

150 mg (300 μmol) tert-butyl 3-(3-{[(2R)-2-(4-bromophenyl)-2-cyclopentylacetyl]amino}-2-methylphenyl)propanoate which was prepared according to intermediate 43 were reacted with [5-(propan-2-yloxy)pyridin-3-yl]boronic acid in analogy to example 1 to give after tBu ester deprotection with 20000 μL TFA and subsequent working up and purification 58 mg (43%) of the title compound.

$^1$H-NMR (DMSO-d6): δ=1.02 (1H), 1.28-1.52 (9H), 1.52-1.64 (2H), 1.65-1.74 (1H), 1.87 (1H), 2.02 (3H), 2.43 (2H), 2.57-2.68 (1H), 2.80 (2H), 3.53 (1H), 4.83 (1H), 6.96-7.07 (3H), 7.50-7.63 (3H), 7.70 (2H), 8.22 (1H), 8.45 (1H), 9.51 (1H), 12.13 (1H) ppm.

Optical rotation: −28.0° (9 mg/ml in DMSO, temperature: 20° C., wave length: 589 nM).

Example 191

3-(3-{[(2R)-2-cyclopentyl-2-{4-[5-(2,2,2-trifluoroethyl)pyridin-3-yl]phenyl}acetyl]amino}-2-methylphenyl)propanoic acid

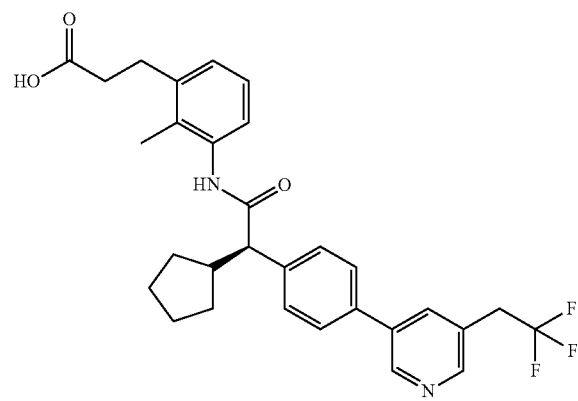 [SMILES: Cc1c(CCC(=O)O)cccc1NC(=O)[C@@H](c1ccc(-c2cncc(CC(F)(F)F)c2)cc1)C1CCCC1]

150 mg (300 μmol) tert-butyl 3-(3-{[(2R)-2-(4-bromophenyl)-2-cyclopentylacetyl]amino}-2-methylphenyl)propanoate which was prepared according to intermediate 43 were reacted with 3-(4,4,5,5-tetramethyl-1,3,2-dioxaborolan-2-yl)-5-(2,2,2-trifluoroethyl)pyridine in analogy to example 1 to give after tBu ester deprotection with 15000 μL TFA and subsequent working up and purification 55 mg (35%) of the title compound.

$^1$H-NMR (DMSO-d6): δ=1.03 (1H), 1.32-1.53 (3H), 1.53-1.63 (2H), 1.69 (1H), 1.87 (1H), 1.95-2.08 (3H), 2.34-2.53 (2H), 2.57-2.72 (1H), 2.81 (2H), 3.54 (1H), 3.80 (2H), 6.95-7.08 (3H), 7.57 (3H), 7.69 (2H), 8.09 (1H), 8.56 (1H), 8.89 (1H), 9.53 (1H), 12.12 (1H) ppm.

Optical rotation: −26.3° (8.59 mg/2 ml in DMSO, temperature: 20° C., wave length: 589 nM).

Example 192

3-(3-{[(2R)-2-cyclopentyl-2-{4-[6-methyl-5-(trifluoromethyl)pyridin-3-yl]phenyl}acetyl]amino}-2-methylphenyl)propanoic acid

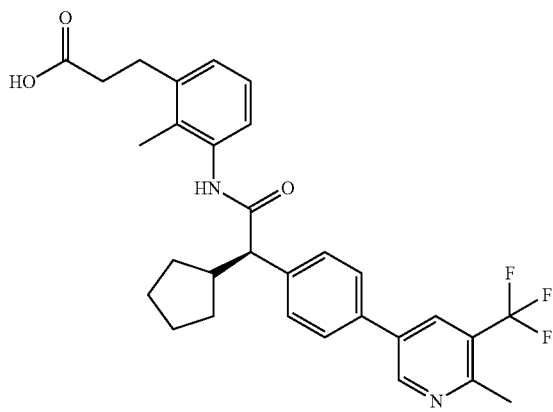 [SMILES: Cc1ncc(-c2ccc([C@H](C(=O)Nc3cccc(CCC(=O)O)c3C)C3CCCC3)cc2)cc1C(F)(F)F]

150 mg (300 µmol) tert-butyl 3-(3-{[(2R)-2-(4-bromophenyl)-2-cyclopentylacetyl]amino}-2-methylphenyl)propanoate which was prepared according to intermediate 43 were reacted with 2-methyl-5-(4,4,5,5-tetramethyl-1,3,2-dioxaborolan-2-yl)-3-(trifluoromethyl)pyridine in analogy to example 1 to give after tBu ester deprotection with 15000 µL TFA and subsequent working up and purification 8 mg (6%) of the title compound.

$^1$H-NMR (DMSO-d6): δ=0.97-1.10 (1H), 1.33-1.52 (3H), 1.52-1.63 (2H), 1.68 (1H), 1.82-1.92 (1H), 2.02 (3H), 2.43 (2H), 2.51-2.69 (4H), 2.80 (2H), 3.55 (1H), 6.97-7.06 (3H), 7.56 (2H), 7.78 (2H), 8.29 (1H), 9.03 (1H), 9.52 (1H), 12.11 (1H) ppm.

Optical rotation: −43.3° (10 mg/ml in methanol, temperature: 20° C., wave length: 589 nM).

Example 193

3-[3-({(2R)-2-[4-(5-chloropyridin-3-yl)phenyl]-2-cyclopentylacetyl}amino)-2-methylphenyl]-3-hydroxypropanoic acid

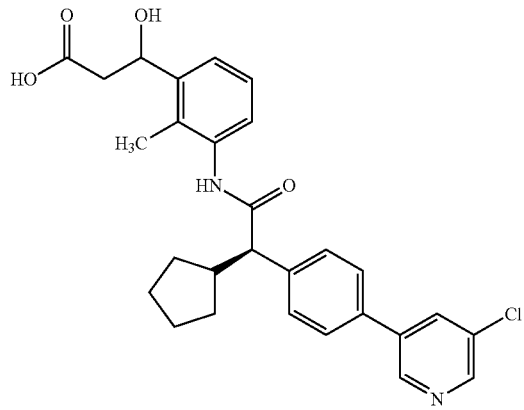 [SMILES: Cc1c(NC(=O)[C@@H](c2ccc(-c3cncc(Cl)c3)cc2)C2CCCC2)cccc1C(O)CC(=O)O]

75 mg (300 µmol) tert-butyl 3-(3-amino-2-methylphenyl)-3-hydroxypropanoate which was prepared according to intermediate 51 were reacted in analogy to intermediate 3 with (2R)-[4-(5-chloropyridin-3-yl)phenyl](cyclopentyl)acetic acid which was prepared according to intermediate 45 to give after tBu ester deprotection with 5000 µL TFA and subsequent working up and purification 85 mg (55%) of the title compound.

$^1$H-NMR (DMSO-d6): δ=1.02 (1H), 1.34-1.53 (3H), 1.53-1.64 (2H), 1.68 (1H), 1.82-1.91 (1H), 2.02-2.07 (3H), 2.31-2.47 (2H), 2.51-2.57 (1H), 2.57-2.67 (1H), 3.55 (1H), 5.14 (1H), 5.30 (1H), 7.04-7.14 (2H), 7.29 (1H), 7.56 (2H), 7.76 (2H), 8.24 (1H), 8.60 (1H), 8.87 (1H), 9.52 (1H), 12.11 (1H) ppm.

Optical rotation: −31.9° (9.4 mg/ml in DMSO, temperature: 20° C., wave length: 589 nM).

Example 194

3-[3-({cyclopentyl[3-fluoro-4-(5-isobutylpyridin-3-yl)phenyl]acetyl}amino)-2-methylphenyl]pentanoic acid, single enantiomer

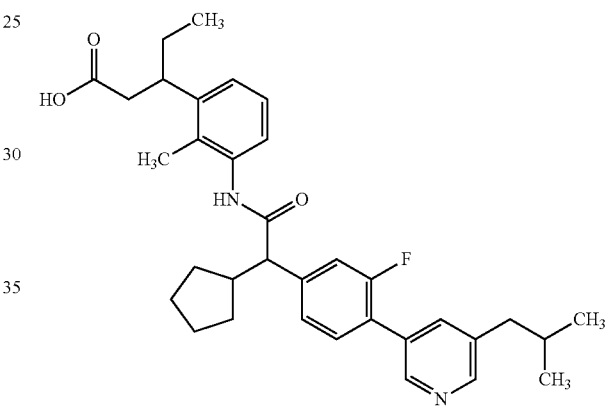

150 mg (306 µmol) 3-(3-{[(4-bromo-3-fluorophenyl)(cyclopentyl)acetyl]amino}-2-methylphenyl)pentanoic acid, single enantiomer which was prepared according to intermediate 52 were reacted with [5-(2-methylpropyl)pyridin-3-yl]boronic acid in analogy to example 1 to give after subsequent working up and purification 58 mg (34%) of the title compound.

$^1$H-NMR (DMSO-d6): δ=0.65-0.74 (3H), 0.88 (6H), 0.99-1.14 (1H), 1.37 (1H), 1.42-1.63 (6H), 1.67-1.70 (1H), 1.82-1.95 (2H), 2.05-2.11 (3H), 2.40-2.47 (1H), 2.51-2.66 (2H), 3.17-3.28 (1H), 3.56 (2H), 7.00-7.12 (3H), 7.35-7.43 (2H), 7.57 (1H), 7.71-7.79 (1H), 8.40 (1H), 8.58 (1H), 9.56 (1H), 11.95 (1H) ppm.

Optical rotation: −10.0° (9.9 mg/ml in DMSO, temperature: 20° C., wave length: 589 nM).

Example 195

3-[3-({cyclopentyl[4-(5-ethylpyridin-3-yl)-3-fluorophenyl]acetyl}amino)-2-methylphenyl]pentanoic acid, Single Enantiomer

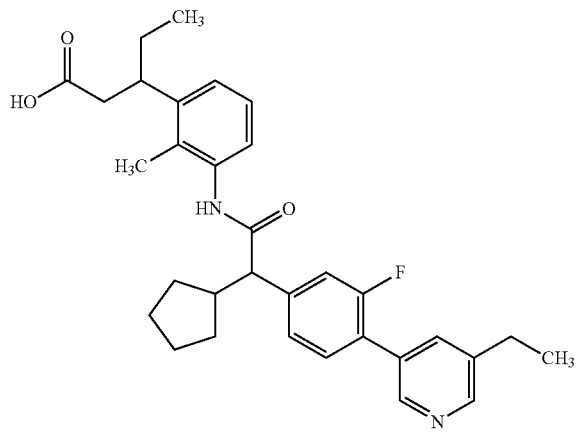 [SMILES: CCc1cncc(-c2ccc(C(C(=O)Nc3cccc(C(CC)CC(=O)O)c3C)C3CCCC3)cc2F)c1]

150 mg (306 μmol) 3-(3-{[(4-bromo-3-fluorophenyl)(cyclopentyl)acetyl]amino}-2-methylphenyl)pentanoic acid, single enantiomer which was prepared according to intermediate 52 were reacted with (5-ethylpyridin-3-yl)boronic acid in analogy to example 1 to give after subsequent working up and purification 36 mg (22%) of the title compound.

$^1$H-NMR (DMSO-d6): δ=0.60-0.69 (3H), 0.98-1.10 (1H), 1.23 (3H), 1.34-1.51 (4H), 1.53-1.71 (2H), 1.75 (1H), 1.81-1.93 (1H), 2.05-2.13 (3H), 2.13-2.32 (2H), 2.56-2.72 (3H), 3.25 (1H), 3.60 (1H), 6.94-7.06 (3H), 7.35-7.42 (2H), 7.55 (1H), 7.81 (1H), 8.43-8.47 (1H), 8.57 (1H), 9.65-9.71 (1H) ppm.

Optical rotation: −2.6° (9 mg/4 ml in DMSO, temperature: 20° C., wave length: 589 nM).

Example 196

(−) 3-{3-[(cyclopentyl{3-fluoro-4-[5-(2,2,2-trifluoroethyl)pyridin-3-yl]phenyl}acetyl)amino]-2-methylphenyl}propanoic acid, Single Enantiomer

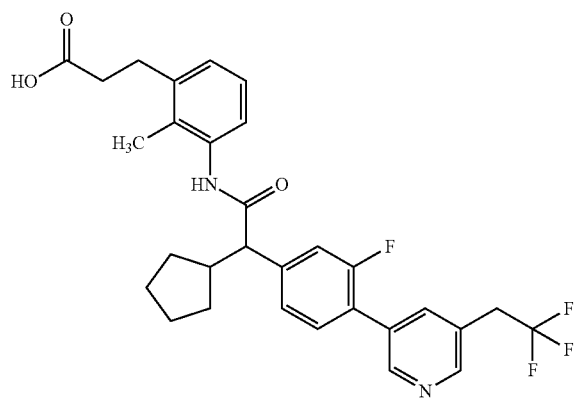 [SMILES: Cc1c(CCC(=O)O)cccc1NC(=O)C(c1ccc(-c2cncc(CC(F)(F)F)c2)c(F)c1)C1CCCC1]

138 mg (300 μmol) 3-(3-{[(4-bromo-3-fluorophenyl)(cyclopentyl)acetyl]amino}-2-methylphenyl)propanoic acid, single enantiomer which was prepared according to intermediate 55 were reacted with 3-(4,4,5,5-tetramethyl-1,3,2-dioxaborolan-2-yl)-5-(2,2,2-trifluoroethyl)pyridine in analogy to example 1 to give after subsequent working up and purification 82 mg (48%) of the title compound.

$^1$H-NMR (DMSO-d6): δ=1.06 (1H), 1.36-1.93 (5H), 2.00-2.09 (3H), 2.40 (2H), 2.53-2.58 (1H), 2.64 (1H), 2.80 (2H), 3.60 (1H), 3.83 (2H), 6.99-7.07 (3H), 7.38-7.45 (2H), 7.59 (1H), 8.02 (1H), 8.60 (1H), 8.77 (1H), 9.60 (1H) ppm.

Optical rotation: −31.1° (5 mg/ml in DMSO, temperature: 20° C., wave length: 589 nM).

Example 197

(−) 3-{3-[(cyclopentyl{3-fluoro-4-[6-methyl-5-(trifluoromethyl)pyridin-3-yl]phenyl}acetyl)amino]-2-methylphenyl}propanoic acid, Single Enantiomer

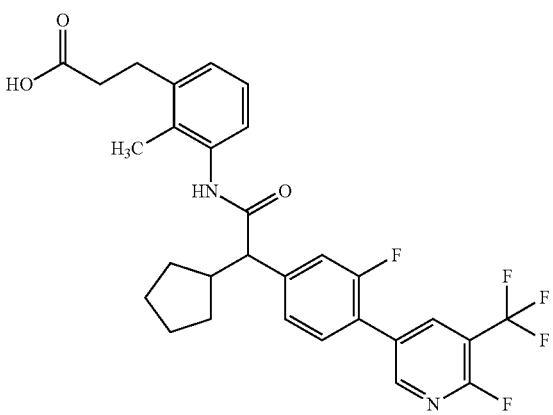 [SMILES: Cc1c(CCC(=O)O)cccc1NC(=O)C(c1ccc(-c2cnc(F)c(C(F)(F)F)c2)c(F)c1)C1CCCC1]

138 mg (300 μmol) 3-(3-{[(4-bromo-3-fluorophenyl)(cyclopentyl)acetyl]amino}-2-methylphenyl)propanoic acid, single enantiomer which was prepared according to intermediate 55 were reacted with 2-methyl-5-(4,4,5,5-tetramethyl-1,3,2-dioxaborolan-2-yl)-3-(trifluoromethyl)pyridine in analogy to example 1 to give after subsequent working up and purification 83 mg (48%) of the title compound.

$^1$H-NMR (DMSO-d6): δ=1.00-1.24 (1H), 1.36-1.65 (5H), 1.66-1.76 (1H), 1.82-1.93 (1H), 2.05 (3H), 2.43 (2H), 2.58-2.72 (4H), 2.81 (2H), 3.60 (1H), 6.99-7.08 (3H), 7.38-7.51 (2H), 7.68 (1H), 8.25 (1H), 8.93 (1H), 9.60 (1H) ppm.

Optical rotation: −9.5° (6 mg/ml in DMSO, temperature: 20° C., wave length: 589 nM).

Example 198

(−) 3-[3-({cyclopentyl[3-fluoro-4-(5-isobutyl-6-methylpyridin-3-yl)phenyl]acetyl}amino)-2-methylphenyl]propanoic acid, Single Enantiomer

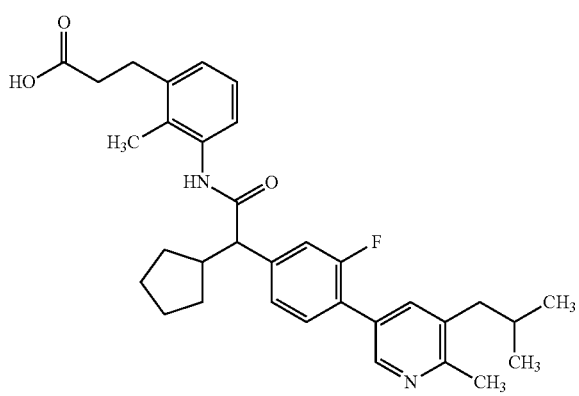 [SMILES: Cc1ncc(-c2ccc(C(C(=O)Nc3cccc(CCC(=O)O)c3C)C3CCCC3)cc2F)cc1CC(C)C]

138 mg (300 µmol) 3-(3-{[(4-bromo-3-fluorophenyl)(cyclopentyl)acetyl]amino}-2-methylphenyl)propanoic acid, single enantiomer which was prepared according to intermediate 55 were reacted with [5-(2-methylpropyl)pyridin-3-yl]boronic acid in analogy to example 1 to give after subsequent working up and purification 73 mg (45%) of the title compound.

$^1$H-NMR (DMSO-d6): δ=0.88 (6H), 1.04 (1H), 1.34-1.63 (5H), 1.65-1.77 (2H), 1.80-1.94 (2H), 2.00-2.17 (3H), 2.43 (2H), 2.51-2.66 (3H), 2.81 (2H), 3.54-3.62 (2H), 6.98-7.07 (3H), 7.35-7.44 (2H), 7.56 (1H), 7.69-7.79 (1H), 8.40 (1H), 8.58 (1H), 9.56 (1H) ppm.

Optical rotation: −16.5° (10 mg/ml in DMSO, temperature: 20° C., wave length: 589 nM).

Example 199

(−) 3-[3-({cyclopentyl[3-fluoro-4-(5-isopropoxypyridin-3-yl)phenyl]acetyl}amino)-2-methylphenyl]propanoic acid, Single Enantiomer

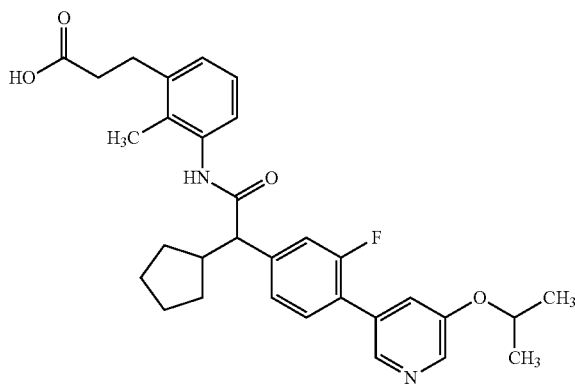 [SMILES: Cc1c(CCC(=O)O)cccc1NC(=O)C(c1ccc(-c2cncc(OC(C)C)c2)c(F)c1)C1CCCC1]

138 mg (300 µmol) 3-(3-{[(4-bromo-3-fluorophenyl)(cyclopentyl)acetyl]amino}-2-methylphenyl)propanoic acid, single enantiomer were reacted with [5-(propan-2-yloxy)pyridin-3-yl]boronic acid in analogy to example 1 to give after subsequent working up and purification 65 mg (40%) of the title compound.

$^1$H-NMR (DMSO-d6): δ=0.98-1.21 (1H), 1.30-1.34 (6H), 1.36-1.64 (4H), 1.66-1.73 (1H), 1.80-1.96 (1H), 2.01-2.09 (3H), 2.45 (2H), 2.53-2.68 (1H), 2.82 (2H), 3.59 (1H), 4.79 (1H), 6.99-7.08 (3H), 7.34-7.43 (2H), 7.50-7.63 (2H), 8.26-8.34 (2H), 9.59 (1H), 12.12 (1H) ppm.

Optical rotation: −16.5° (10 mg/ml in DMSO, temperature: 20° C., wave length: 589 nM).

Example 200

3-(3-{[(2R)-2-cyclopentyl-2-{4-[5-(2,2,2-trifluoroethyl)pyridin-3-yl]phenyl}acetyl]amino}-2-methylphenyl)pentanoic acid, Single Enantiomer

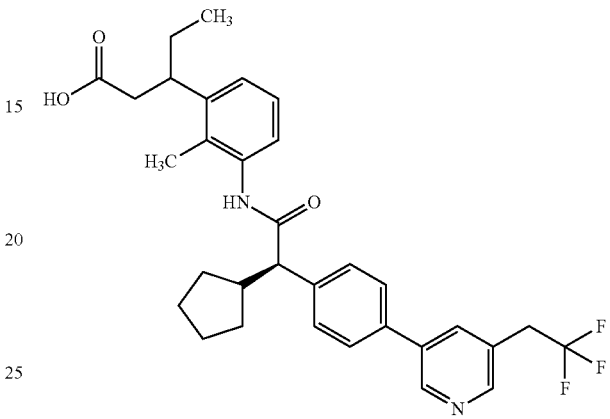

142 mg (300 µmol) 3-(3-{[(2R)-2-(4-bromophenyl)-2-cyclopentylacetyl]amino}-2-methylphenyl)pentanoic acid, single enantiomer acid which was prepared according to intermediate 56 were reacted with 3-(4,4,5,5-tetramethyl-1,3,2-dioxaborolan-2-yl)-5-(2,2,2-trifluoroethyl)pyridine in analogy to example 1 to give after subsequent working up and purification 96 mg (55%) of the title compound.

$^1$H-NMR (DMSO-d6): δ=0.63-0.70 (3H), 1.02 (1H), 1.35-1.53 (3H), 1.53-1.72 (3H), 1.82-1.91 (2H), 2.04-2.10 (3H), 2.31-2.47 (1H), 2.56-2.77 (1H), 3.16-3.39 (1H), 3.55 (1H), 3.80 (3H), 6.97-7.09 (3H), 7.57 (2H), 7.69 (2H), 8.08 (1H), 8.53-8.56 (1H), 8.88 (1H), 9.52 (1H) ppm.

Optical rotation: −9.2° (9 mg/ml in DMSO, temperature: 20° C., wave length: 589 nM).

Example 201

3-(3-{[(2R)-2-cyclopentyl-2-{4-[6-methyl-5-(trifluoromethyl)pyridin-3-yl]phenyl}acetyl]amino}-2-methylphenyl)pentanoic acid, Single Enantiomer

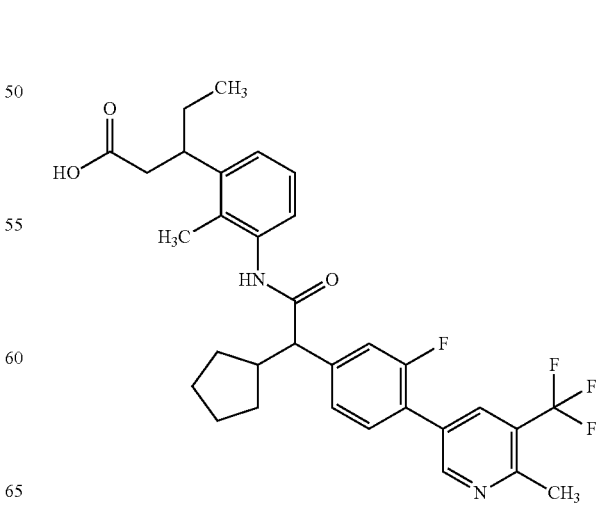

142 mg (300 µmol) 3-(3-{[(2R)-2-(4-bromophenyl)-2-cyclopentylacetyl]amino}-2-methylphenyl)pentanoic acid, single enantiomer which was prepared according to intermediate 56 were reacted with 2-methyl-5-(4,4,5,5-tetramethyl-1,3,2-dioxaborolan-2-yl)-3-(trifluoromethyl)pyridine in analogy to example 1 to give after subsequent working up and purification 115 mg (65%) of the title compound.

¹H-NMR (DMSO-d6): δ=0.63-0.72 (3H), 1.01 (1H), 1.35-1.62 (7H), 1.68 (1H), 1.82-1.92 (1H), 2.02-2.11 (3H), 2.31-2.47 (1H), 2.52-2.57 (1H), 2.58-2.70 (4H), 3.12-3.39 (1H), 3.54 (1H), 6.98-7.10 (3H), 7.57 (2H), 7.78 (2H), 8.27-8.31 (1H), 9.03 (1H), 9.52 (1H) ppm.

Optical rotation: −10.6° (7 mg/ml in DMSO, temperature: 20° C., wave length: 589 nM).

Example 202

3-[3-({(2R)-2-cyclopentyl-2-[4-(5-isobutylpyridin-3-yl)phenyl]acetyl}amino)-2-methylphenyl]pentanoic acid, Single Enantiomer

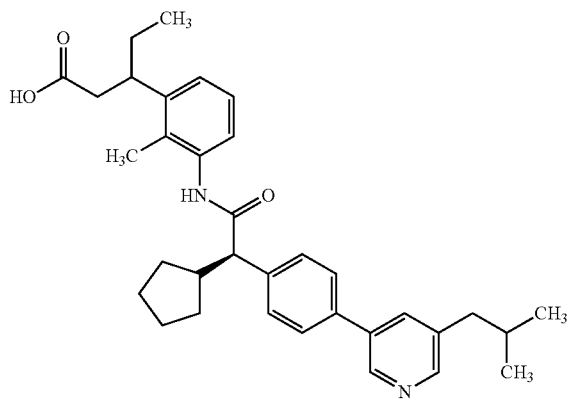 [SMILES: CCC(CC(=O)O)c1cccc(NC(=O)[C@@H](c2ccc(-c3cncc(CC(C)C)c3)cc2)C2CCCC2)c1C]

142 mg (300 µmol) 3-(3-{[(2R)-2-(4-bromophenyl)-2-cyclopentylacetyl]amino}-2-methylphenyl)pentanoic acid, single enantiomer which was prepared according to intermediate 56 were reacted with [5-(2-methylpropyl)pyridin-3-yl]boronic acid in analogy to example 1 to give after subsequent working up and purification 85 mg (51%) of the title compound.

¹H-NMR (DMSO-d6): δ=0.66 (3H), 0.83-0.94 (6H), 0.96-1.12 (1H), 1.33-1.53 (4H), 1.53-1.63 (3H), 1.68 (1H), 1.81-1.99 (3H), 2.00-2.10 (3H), 2.31-2.47 (2H), 2.51-2.57 (4H), 2.58-2.73 (1H), 3.14-3.39 (1H), 3.53 (1H), 6.97-7.09 (2H), 7.54 (2H), 7.69 (2H), 7.86 (1H), 8.34-8.45 (1H), 8.71 (1H), 9.51 (1H) ppm.

Optical rotation: −16.7° (7 mg/3 ml in DMSO, temperature: 20° C., wave length: 589 nM).

Example 203

3-[3-({(2R)-2-cyclopentyl-2-[4-(5-isopropoxypyridin-3-yl)phenyl]acetyl}amino)-2-methylphenyl]pentanoic acid, Single Enantiomer

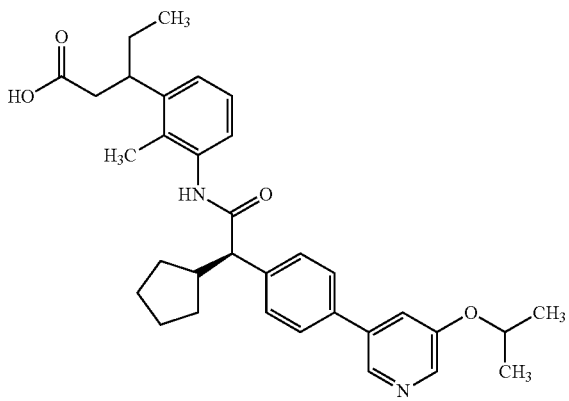 [SMILES: CCC(CC(=O)O)c1cccc(NC(=O)[C@@H](c2ccc(-c3cncc(OC(C)C)c3)cc2)C2CCCC2)c1C]

142 mg (300 µmol) 3-(3-{[(2R)-2-(4-bromophenyl)-2-cyclopentylacetyl]amino}-2-methylphenyl)pentanoic acid, single enantiomer which was prepared according to intermediate 56 were reacted with [5-(propan-2-yloxy)pyridin-3-yl]boronic acid in analogy to example 1 to give after subsequent working up and purification 132 mg (79%) of the title compound.

¹H-NMR (DMSO-d6): δ=0.62-0.71 (3H), 1.02 (1H), 1.25-1.52 (10H), 1.53-1.75 (4H), 1.78-1.95 (2H), 2.00-2.12 (3H), 2.22-2.39 (1H), 2.42 (1H), 2.53 (1H), 2.57-2.69 (1H), 3.25 (1H), 3.54 (1H), 4.83 (1H), 6.97-7.09 (3H), 7.48-7.62 (3H), 7.70 (2H), 8.22 (1H), 8.45 (1H), 9.51 (1H) ppm.

Analytical HPLC, method 4: solvent/gradient: hexane/isopropanol/diethylamine 95:5:0.1 (v/v/v) to 50:50:0.1 (v/v/v) in 10 min; flow rate: 1.0 ml/min; solution: 1 mg/ml ethanol/methanol 2:1; injection volume: 5.0 µl; Rt: 8.46 min.

Example 204

3-[3-({(2R)-2-cyclopentyl-2-[4-(5-ethylpyridin-3-yl)phenyl]acetyl}amino)-2-methylphenyl]pentanoic acid, Single Enantiomer

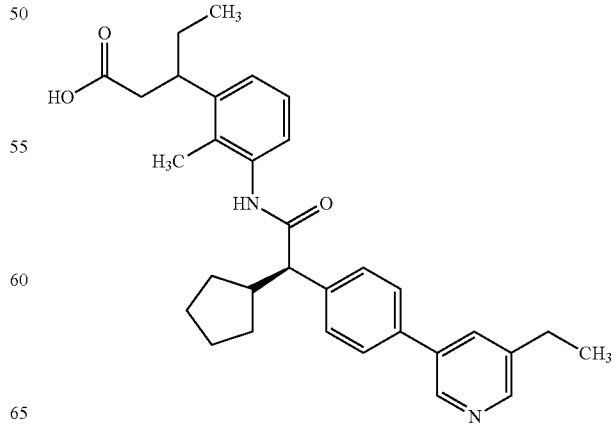

200 mg (423 µmol) 3-(3-{[(2R)-2-(4-bromophenyl)-2-cyclopentylacetyl]amino}-2-methylphenyl)pentanoic acid, single enantiomer which was prepared according to intermediate 56 were reacted with (5-ethylpyridin-3-yl)boronic acid in analogy to example 1 to give after subsequent working up and purification 155 mg (70%) of the title compound.

¹H-NMR (DMSO-d6): δ=0.60-0.82 (3H), 0.94-1.13 (1H), 1.24 (3H), 1.33-1.54 (4H), 1.59 (2H), 1.68 (1H), 1.75 (1H), 1.80-1.96 (1H), 2.06 (3H), 2.41 (1H), 2.57-2.77 (2H), 3.26 (1H), 3.39-3.63 (3H), 6.97-7.12 (3H), 7.54 (2H), 7.69 (2H), 7.90 (1H), 8.42 (1H), 8.70 (1H), 9.51 (1H), 11.87 (1H) ppm.

Analytical HPLC, method 4: solvent/gradient: hexane/isopropanol/TFA 95:5:0.1 (v/v/v) to 50:50:0.1 (v/v/v) in 10 min; flow rate: 1.0 ml/min; solution: 1 mg/ml ethanol/methanol 2:1; injection volume: 5.0 µl; Rt: 9.21 min.

Example 205

3-{3-[(cyclobutyl{3-fluoro-4-[5-(2,2,2-trifluoroethyl)pyridin-3-yl]phenyl}acetyl)amino]-2-methylphenyl}propanoic acid, Single Enantiomer

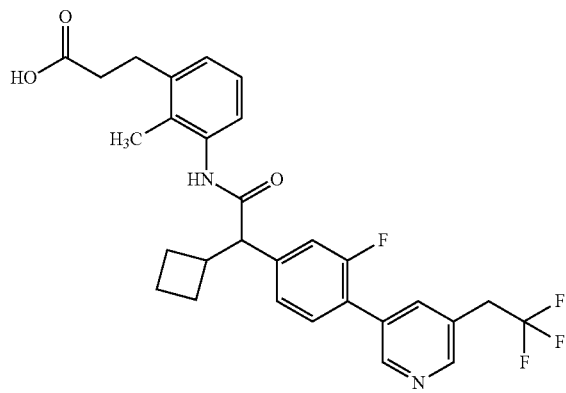 [SMILES: Cc1c(CCC(=O)O)cccc1NC(=O)C(c1ccc(-c2cncc(CC(F)(F)F)c2)c(F)c1)C1CCC1]

67 mg (150 µmol) 3-(3-{[(4-bromo-3-fluorophenyl)(cyclobutyl)acetyl]amino}-2-methylphenyl)propanoic acid, single enantiomer which was prepared according to intermediate 57 were reacted with 3-(4,4,5,5-tetramethyl-1,3,2-dioxaborolan-2-yl)-5-(2,2,2-trifluoroethyl)pyridine in analogy to example 1 to give after subsequent working up and purification 41 mg (43%) of the title compound.

¹H-NMR (DMSO-d6): δ=1.63 (1H), 1.78-1.96 (5H), 1.99-2.09 (4H), 2.09-2.32 (1H), 2.44 (2H), 2.66-2.91 (3H), 3.03 (1H), 3.75-3.88 (3H), 6.99-7.18 (3H), 7.26-7.46 (2H), 7.57 (1H), 7.99 (1H), 8.56-8.63 (1H), 8.75 (1H), 9.55-9.63 (1H) ppm.

Example 206

(−) 3-{3-[(cyclobutyl{3-fluoro-4-[6-methyl-5-(trifluoromethyl)pyridin-3-yl]phenyl}acetyl)amino]-2-methylphenyl}propanoic acid, Single Enantiomer

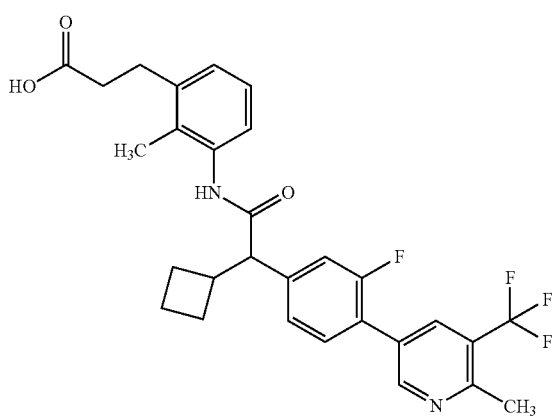 [SMILES: Cc1ncc(-c2ccc(C(C(=O)Nc3cccc(CCC(=O)O)c3C)C3CCC3)cc2F)cc1C(F)(F)F]

67 mg (150 µmol) 3-(3-{[(4-bromo-3-fluorophenyl)(cyclobutyl)acetyl]amino}-2-methylphenyl)propanoic acid, single enantiomer which was prepared according to intermediate 57 were reacted with 2-methyl-5-(4,4,5,5-tetramethyl-1,3,2-dioxaborolan-2-yl)-3-(trifluoromethyl)pyridine in analogy to example 1 to give after subsequent working up and purification 28 mg (32%) of the title compound.

¹H-NMR (DMSO-d6): δ=1.64 (1H), 1.79-1.96 (4H), 2.01-2.09 (3H), 2.09-2.20 (1H), 2.30-2.48 (2H), 2.64-2.71 (3H), 2.81 (2H), 3.03 (1H), 3.86 (1H), 6.99-7.07 (3H), 7.31-7.51 (2H), 7.66 (1H), 8.23 (1H), 8.90 (1H), 9.59 (1H), 12.13 (1H) ppm.

Optical rotation: −24.9° (8.4 mg/ml in DMSO, temperature: 20° C., wave length: 589 nM).

Example 207

3-[3-({cyclobutyl[3-fluoro-4-(5-isobutylpyridin-3-yl)phenyl]acetyl}amino)-2-methylphenyl]propanoic acid, Single Enantiomer

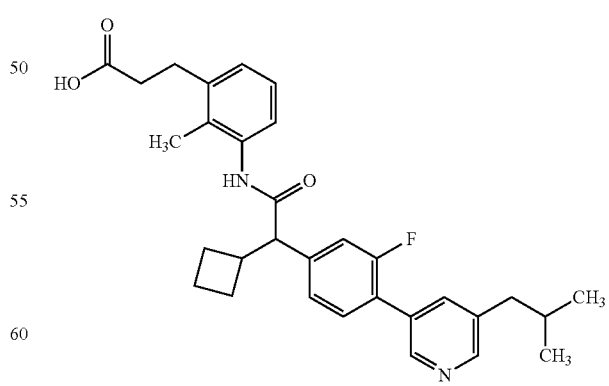

67 mg (150 µmol) 3-(3-{[(4-bromo-3-fluorophenyl)(cyclobutyl)acetyl]amino}-2-methylphenyl)propanoic acid, single enantiomer which was prepared according to intermediate 57 were reacted with [5-(2-methylpropyl)pyridin- 3-yl]boronic acid in analogy to example 1 to give after subsequent working up and purification 11 mg (13%) of the title compound.

$^1$H-NMR (DMSO-d6): δ=0.84-0.91 (6H), 1.64 (1H), 1.80-1.96 (5H), 2.01-2.08 (3H), 2.12 (1H), 2.40-2.47 (2H), 2.51-2.56 (2H), 2.81 (2H), 3.02 (1H), 3.84 (1H), 6.99-7.07 (3H), 7.31-7.38 (2H), 7.56 (1H), 7.76 (1H), 8.40 (1H), 8.57 (1H), 9.58 (1H) ppm.

Example 208

(−) 3-{3-[(cyclobutyl{3-fluoro-4-[5-(trifluoromethyl)pyridin-3-yl]phenyl}acetyl)amino]-2-methylphenyl}propanoic acid, Single Enantiomer

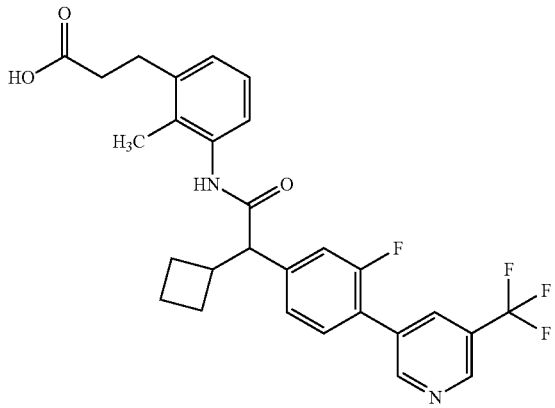

67 mg (150 μmol) 3-(3-{[(4-bromo-3-fluorophenyl)(cyclobutyl)acetyl]amino}-2-methylphenyl)propanoic acid, single enantiomer which was prepared according to intermediate 57 were reacted with [5-(trifluoromethyl)pyridin-3-yl]boronic acid in analogy to example 1 to give after subsequent working up and purification 32 mg (35%) of the title compound.

$^1$H-NMR (DMSO-d6): δ=1.65 (1H), 1.79-1.96 (4H), 1.98-2.10 (3H), 2.10-2.27 (1H), 2.33-2.49 (3H), 2.67-2.93 (2H), 3.04 (1H), 3.88 (1H), 6.99-7.20 (3H), 7.33-7.55 (2H), 7.55-7.73 (1H), 8.40 (1H), 9.01 (1H), 9.09 (1H), 9.57-9.66 (1H), 12.16 (1H) ppm.

Optical rotation: −22.5° (8.5 mg/ml in DMSO, temperature: 20° C., wave length: 589 nM).

Example 209

(−) 3-[3-({cyclobutyl[3-fluoro-4-(5-isopropoxypyridin-3-yl)phenyl]acetyl}amino)-2-methylphenyl]propanoic acid, Single Enantiomer

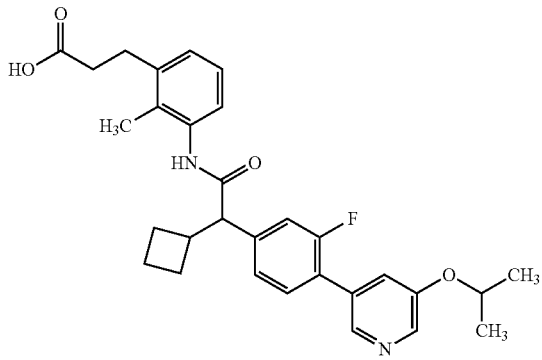 [SMILES: Cc1c(CCC(=O)O)cccc1NC(=O)C(c1ccc(-c2cncc(CC(C)C)c2)c(F)c1)C1CCC1]

67 mg (150 μmol) 3-(3-{[(4-bromo-3-fluorophenyl)(cyclobutyl)acetyl]amino}-2-methylphenyl)propanoic acid, single enantiomer which was prepared according to intermediate 57 were reacted with [5-(propan-2-yloxy)pyridin-3-yl]boronic acid in analogy to example 1 to give after subsequent working up and purification 18 mg (23%) of the title compound.

$^1$H-NMR (DMSO-d6): δ=1.31 (6H), 1.65 (1H), 1.80-1.97 (4H), 2.06 (3H), 2.14 (1H), 2.46 (2H), 2.82 (2H), 2.97-3.09 (1H), 3.85 (1H), 4.79 (1H), 7.00-7.09 (3H), 7.31-7.39 (2H), 7.48-7.63 (2H), 8.25-8.33 (2H), 9.63 (1H) ppm.

Optical rotation: −24.4° (8.7 mg/ml in DMSO, temperature: 20° C., wave length: 589 nM).

Example 210

(−) 3-[3-({cyclobutyl[4-(5-ethylpyridin-3-yl)-3-fluorophenyl]acetyl}amino)-2-methylphenyl]propanoic acid, Single Enantiomer

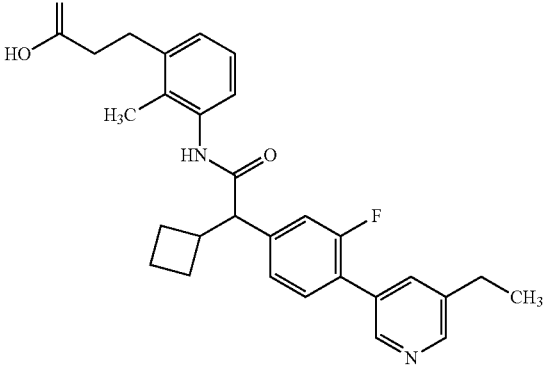

89 mg (200 μmol) 3-(3-{[(4-bromo-3-fluorophenyl)(cyclobutyl)acetyl]amino}-2-methylphenyl)propanoic acid, single enantiomer which was prepared according to intermediate 57 were reacted with (5-ethylpyridin-3-yl)boronic acid in analogy to example 1 to give after subsequent working up and purification 20 mg (21%) of the title compound.

$^1$H-NMR (DMSO-d6): δ=1.24 (3H), 1.52-1.76 (1H), 1.80-1.97 (4H), 2.06 (3H), 2.13 (1H), 2.41-2.49 (2H), 2.70 (2H), 2.83 (2H), 2.97-3.10 (1H), 3.86 (1H), 6.97-7.14 (3H), 7.25-7.45 (2H), 7.58 (1H), 7.82 (1H), 8.47 (1H), 8.58 (1H), 9.62 (1H), 12.18 (1H) ppm.

Optical rotation: −26.3° (8.2 mg/3 ml in DMSO, temperature: 20° C., wave length: 589 nM).

Example 211

(R/S) 3-[3-({cyclopentyl[4-(5-fluoro-6-methylpyridin-3-yl)phenyl]acetyl}amino)-2-methylphenyl]propanoic acid

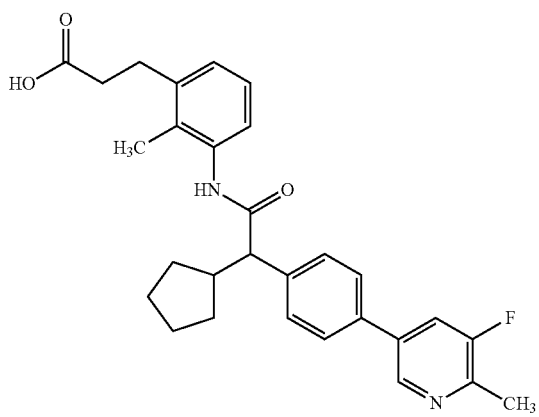

In analogy to example 1 reaction of 75 mg intermediate 3 with 34.8 mg (5-fluoro-6-methylpyridin-3-yl)boronic acid followed by tert.-butyl ester cleavage and subsequent purification via HPLC gave 31.5 mg (47%) of the title compound.

Example 212

3-[3-({[4-(5-chloropyridin-3-yl)phenyl](cyclopentyl)acetyl}amino)-2-methoxyphenyl]propanoic acid

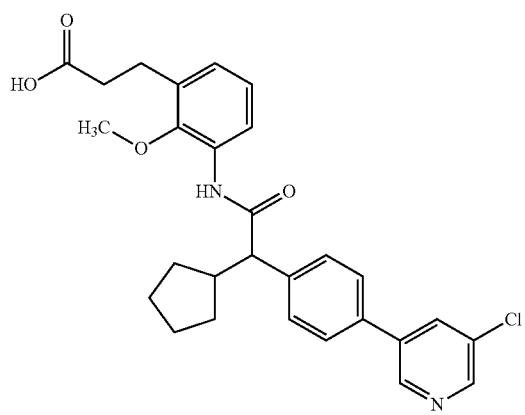 [SMILES: COc1c(CCC(=O)O)cccc1NC(=O)C(c1ccc(-c2cncc(Cl)c2)cc1)C1CCCC1]

90 mg (145 µmol) tert-butyl 3-(3-{[(4-bromophenyl)(cyclopentyl)acetyl]amino}-2-methoxyphenyl)propanoate which was prepared according to intermediate 60 were reacted with (5-chloropyridin-3-yl)boronic acid in analogy to example 1 to give after tBu ester deprotection with 1100 µL TFA in 1400 µL DCM and subsequent working up and purification 28 mg (39%) of the title compound.

$^1$H-NMR (DMSO-d6): δ=0.97 (1H), 1.27-1.41 (2H), 1.43-1.59 (3H), 1.60-1.70 (1H), 1.81 (1H), 2.44 (1H), 2.55-2.68 (1H), 2.77 (2H), 3.48 (3H), 3.78 (1H), 6.90-6.96 (2H), 7.55 (2H), 7.63 (1H), 7.72 (2H), 8.19 (1H), 8.56 (1H), 8.83 (1H), 9.46 (1H), 12.09 (1H) ppm.

Example 213

3-{3-[(cyclopentyl{4-[5-(trifluoromethyl)pyridin-3-yl]phenyl}acetyl)amino]-2-methoxyphenyl}propanoic acid

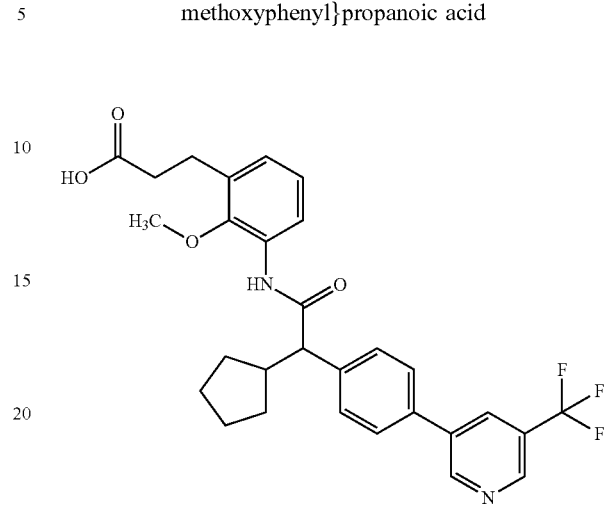

90 mg (145 µmol) tert-butyl 3-(3-{[(4-bromophenyl)(cyclopentyl)acetyl]amino}-2-methoxyphenyl)propanoate which was prepared according to intermediate 60 were reacted with 3-(4,4,5,5-tetramethyl-1,3,2-dioxaborolan-2-yl)-5-(trifluoromethyl)pyridine in analogy to example 1 to give after tBu ester deprotection with 1100 µL TFA in 1300 µL DCM and subsequent working up and purification 35 mg (49%) of the title compound.

$^1$H-NMR (DMSO-d6): δ=0.91-1.05 (1H), 1.28-1.42 (2H), 1.44-1.59 (3H), 1.65 (1H), 1.74-1.87 (1H), 2.63 (2H), 2.77 (2H), 3.30-3.54 (3H), 3.80 (1H), 6.89-6.98 (2H), 7.43-7.67 (3H), 7.78 (2H), 8.40 (1H), 8.91 (1H), 9.17 (1H), 9.48 (1H), 12.09 (1H) ppm.

Example 214

3-[3-({(2R)-2-[4-(5-chloropyridin-3-yl)phenyl]-2-cyclopentylacetyl}amino)-2-(trifluoromethyl)phenyl]propanoic acid

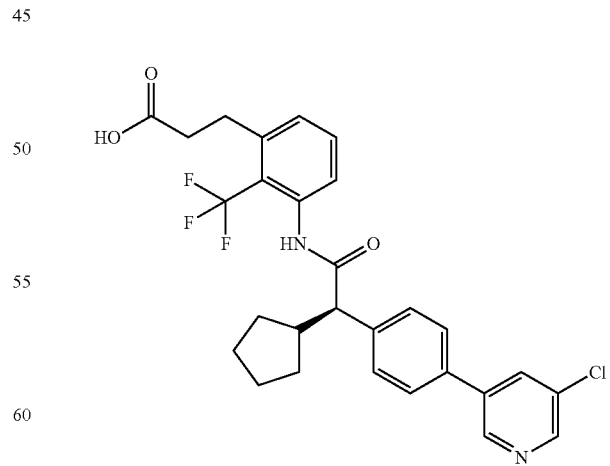

111 mg (200 µmol) tert-butyl 3-[3-{[(2R)-2-(4-bromophenyl)-2-cyclopentylacetyl]amino}-2-(trifluoromethyl)phenyl]propanoate which was prepared according to intermediate 62 were reacted with (5-chloropyridin-3-yl)boronic acid in analogy to example 1 to give after tBu ester deprotection with 6000 μL TFA in 10000 μL DCM and subsequent working up and purification 35 mg (32%) of the title compound.

$^1$H-NMR (DMSO-d6): δ=0.95-1.06 (1H), 1.27-1.43 (2H), 1.46 (1H), 1.51-1.63 (2H), 1.67 (1H), 1.84 (1H), 2.56-2.79 (2H), 2.97 (2H), 3.53 (2H), 7.05 (1H), 7.33 (1H), 7.44-7.55 (4H), 7.76 (2H), 8.25 (1H), 8.60 (1H), 8.88 (1H), 9.85 (1H) ppm.

Optical rotation: −41.4° (9.5 mg/2 ml in DMSO, temperature: 20° C., wave length: 589 nM).

Example 215

3-[3-{[(2R)-2-cyclopentyl-2-{4-[5-(trifluoromethyl)pyridin-3-yl]phenyl}acetyl]amino}-2-(trifluoromethyl)phenyl]propanoic acid

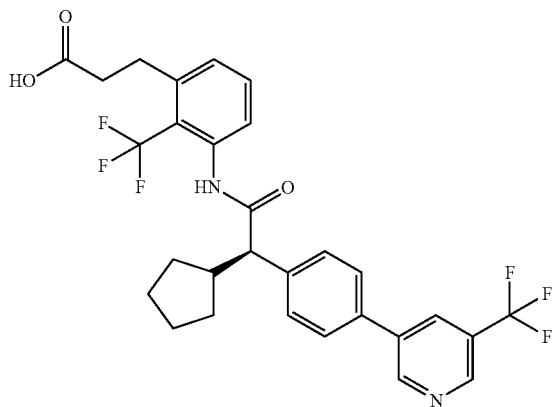 [SMILES: O=C(O)CCc1cccc(NC(=O)[C@@H](c2ccc(-c3cncc(C(F)(F)F)c3)cc2)C2CCCC2)c1C(F)(F)F]

111 mg (200 μmol) tert-butyl 3-[3-{[(2R)-2-(4-bromophenyl)-2-cyclopentylacetyl]amino}-2-(trifluoromethyl)phenyl]propanoate which was prepared according to intermediate 62 were reacted with [5-(trifluoromethyl)pyridin-3-yl]boronic acid in analogy to example 1 to give after tBu ester deprotection with 1000 μL TFA in 5000 μL DCM and subsequent working up and purification 38 mg (32%) of the title compound.

$^1$H-NMR (DMSO-d6): δ=1.01 (1H), 1.27-1.51 (3H), 1.52-1.64 (2H), 1.67 (1H), 1.78-1.90 (1H), 2.51 (1H), 2.56-2.68 (1H), 2.97 (2H), 3.55 (2H), 7.06 (1H), 7.31-7.36 (1H), 7.47-7.57 (4H), 7.83 (2H), 8.46 (1H), 8.94 (1H), 9.22 (1H), 9.86 (1H) ppm.

Optical rotation: −39.0° (9.8 mg/ml in DMSO, temperature: 20° C., wave length: 589 nM).

Pharmaceutical Compositions of the Compounds of the Invention

This invention also relates to pharmaceutical compositions containing one or more compounds of the present invention. These compositions can be utilised to achieve the desired pharmacological effect by administration to a patient in need thereof. A patient, for the purpose of this invention, is a mammal, including a human, in need of treatment for the particular condition or disease. Therefore, the present invention includes pharmaceutical compositions that are comprised of a pharmaceutically acceptable carrier and a pharmaceutically effective amount of a compound, or salt thereof, of the present invention. A pharmaceutically acceptable carrier is preferably a carrier that is relatively non-toxic and innocuous to a patient at concentrations consistent with effective activity of the active ingredient so that any side effects ascribable to the carrier do not vitiate the beneficial effects of the active ingredient. A pharmaceutically effective amount of compound is preferably that amount which produces a result or exerts an influence on the particular condition being treated. The compounds of the present invention can be administered with pharmaceutically-acceptable carriers well known in the art using any effective conventional dosage unit forms, including immediate, slow and timed release preparations, orally, parenterally, topically, nasally, ophthalmically, optically, sublingually, rectally, vaginally, and the like.

For oral administration, the compounds can be formulated into solid or liquid preparations such as capsules, pills, tablets, troches, lozenges, melts, powders, solutions, suspensions, or emulsions, and may be prepared according to methods known to the art for the manufacture of pharmaceutical compositions. The solid unit dosage forms can be a capsule that can be of the ordinary hard- or soft-shelled gelatine type containing, for example, surfactants, lubricants, and inert fillers such as lactose, sucrose, calcium phosphate, and corn starch.

In another embodiment, the compounds of this invention may be tableted with conventional tablet bases such as lactose, sucrose and cornstarch in combination with binders such as acacia, corn starch or gelatine, disintegrating agents intended to assist the break-up and dissolution of the tablet following administration such as potato starch, alginic acid, corn starch, and guar gum, gum tragacanth, acacia, lubricants intended to improve the flow of tablet granulation and to prevent the adhesion of tablet material to the surfaces of the tablet dies and punches, for example talc, stearic acid, or magnesium, calcium or zinc stearate, dyes, colouring agents, and flavouring agents such as peppermint, oil of wintergreen, or cherry flavouring, intended to enhance the aesthetic qualities of the tablets and make them more acceptable to the patient. Suitable excipients for use in oral liquid dosage forms include dicalcium phosphate and diluents such as water and alcohols, for example, ethanol, benzyl alcohol, and polyethylene alcohols, either with or without the addition of a pharmaceutically acceptable surfactant, suspending agent or emulsifying agent. Various other materials may be present as coatings or to otherwise modify the physical form of the dosage unit. For instance tablets, pills or capsules may be coated with shellac, sugar or both.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example those sweetening, flavouring and colouring agents described above, may also be present.

The pharmaceutical compositions of this invention may also be in the form of oil-in-water emulsions. The oily phase may be a vegetable oil such as liquid paraffin or a mixture of vegetable oils. Suitable emulsifying agents may be (1) naturally occurring gums such as gum acacia and gum tragacanth, (2) naturally occurring phosphatides such as soy bean and lecithin, (3) esters or partial esters derived form fatty acids and hexitol anhydrides, for example, sorbitan monooleate, (4) condensation products of said partial esters with ethylene oxide, for example, polyoxyethylene sorbitan monooleate. The emulsions may also contain sweetening and flavouring agents.

Oily suspensions may be formulated by suspending the active ingredient in a vegetable oil such as, for example, arachis oil, olive oil, sesame oil or coconut oil, or in a mineral oil such as liquid paraffin. The oily suspensions may contain a thickening agent such as, for example, beeswax, hard paraffin, or cetyl alcohol. The suspensions may also contain one or more preservatives, for example, ethyl or n-propyl p-hydroxybenzoate; one or more colouring agents; one or more flavouring agents; and one or more sweetening agents such as sucrose or saccharin.

Syrups and elixirs may be formulated with sweetening agents such as, for example, glycerol, propylene glycol, sorbitol or sucrose. Such formulations may also contain a demulcent, and preservative, such as methyl and propyl parabens and flavouring and colouring agents.

The compounds of this invention may also be administered parenterally, that is, subcutaneously, intravenously, intraocularly, intrasynovially, intramuscularly, or interperitoneally, as injectable dosages of the compound in preferably a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,1-dioxolane-4-methanol, ethers such as poly(ethylene glycol) 400, an oil, a fatty acid, a fatty acid ester or, a fatty acid glyceride, or an acetylated fatty acid glyceride, with or without the addition of a pharmaceutically acceptable surfactant such as a soap or a detergent, suspending agent such as pectin, carbomers, methylcellulose, hydroxypropylmethylcellulose, or carboxymethylcellulose, or emulsifying agent and other pharmaceutical adjuvants.

Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum and mineral oil. Suitable fatty acids include oleic acid, stearic acid, isostearic acid and myristic acid. Suitable fatty acid esters are, for example, ethyl oleate and isopropyl myristate. Suitable soaps include fatty acid alkali metal, ammonium, and triethanolamine salts and suitable detergents include cationic detergents, for example dimethyl dialkyl ammonium halides, alkyl pyridinium halides, and alkylamine acetates; anionic detergents, for example, alkyl, aryl, and olefin sulfonates, alkyl, olefin, ether, and monoglyceride sulfates, and sulfosuccinates; non-ionic detergents, for example, fatty amine oxides, fatty acid alkanolamides, and poly(oxyethylene-oxypropylene)s or ethylene oxide or propylene oxide copolymers; and amphoteric detergents, for example, alkyl-beta-aminopropionates, and 2-alkylimidazoline quarternary ammonium salts, as well as mixtures.

The parenteral compositions of this invention will typically contain from about 0.5% to about 25% by weight of the active ingredient in solution. Preservatives and buffers may also be used advantageously. In order to minimise or eliminate irritation at the site of injection, such compositions may contain a non-ionic surfactant having a hydrophile-lipophile balance (HLB) preferably of from about 12 to about 17. The quantity of surfactant in such formulation preferably ranges from about 5% to about 15% by weight. The surfactant can be a single component having the above HLB or can be a mixture of two or more components having the desired HLB.

Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The pharmaceutical compositions may be in the form of sterile injectable aqueous suspensions. Such suspensions may be formulated according to known methods using suitable dispersing or wetting agents and suspending agents such as, for example, sodium carboxymethylcellulose, methylcellulose, hydroxypropylmethyl-cellulose, sodium alginate, polyvinylpyrrolidone, gum tragacanth and gum acacia; dispersing or wetting agents which may be a naturally occurring phosphatide such as lecithin, a condensation product of an alkylene oxide with a fatty acid, for example, polyoxyethylene stearate, a condensation product of ethylene oxide with a long chain aliphatic alcohol, for example, heptadeca-ethyleneoxycetanol, a condensation product of ethylene oxide with a partial ester derived form a fatty acid and a hexitol such as polyoxyethylene sorbitol monooleate, or a condensation product of an ethylene oxide with a partial ester derived from a fatty acid and a hexitol anhydride, for example polyoxyethylene sorbitan monooleate.

The sterile injectable preparation may also be a sterile injectable solution or suspension in a non-toxic parenterally acceptable diluent or solvent. Diluents and solvents that may be employed are, for example, water, Ringer's solution, isotonic sodium chloride solutions and isotonic glucose solutions. In addition, sterile fixed oils are conventionally employed as solvents or suspending media. For this purpose, any bland, fixed oil may be employed including synthetic mono- or diglycerides. In addition, fatty acids such as oleic acid can be used in the preparation of injectables.

A composition of the invention may also be administered in the form of suppositories for rectal administration of the drug. These compositions can be prepared by mixing the drug with a suitable non-irritation excipient which is solid at ordinary temperatures but liquid at the rectal temperature and will therefore melt in the rectum to release the drug. Such materials are, for example, cocoa butter and polyethylene glycol.

Another formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art (see, e.g., U.S. Pat. No. 5,023,252, issued Jun. 11, 1991, incorporated herein by reference). Such patches may be constructed for continuous, pulsatile, or on demand delivery of pharmaceutical agents.

Controlled release formulations for parenteral administration include liposomal, polymeric microsphere and polymeric gel formulations that are known in the art.

It may be desirable or necessary to introduce the pharmaceutical composition to the patient via a mechanical delivery device. The construction and use of mechanical delivery devices for the delivery of pharmaceutical agents is well known in the art. Direct techniques for, for example, administering a drug directly to the brain usually involve placement of a drug delivery catheter into the patient's ventricular system to bypass the blood-brain barrier. One such implantable delivery system, used for the transport of agents to specific anatomical regions of the body, is described in U.S. Pat. No. 5,011,472, issued Apr. 30, 1991.

The compositions of the invention can also contain other conventional pharmaceutically acceptable compounding ingredients, generally referred to as carriers or diluents, as necessary or desired. Conventional procedures for preparing such compositions in appropriate dosage forms can be utilized.

Such ingredients and procedures include those described in the following references, each of which is incorporated herein by reference: Powell, M. F. et al., "Compendium of Excipients for Parenteral Formulations" PDA Journal of Pharmaceutical Science & Technology 1998, 52(5), 238-311; Strickley, R. G "Parenteral Formulations of Small Molecule Therapeutics Marketed in the United States (1999)-Part-1" PDA Journal of Pharmaceutical Science & Technology 1999, 53(6), 324-349; and Nema, S. et al., "Excipients and Their Use in Injectable Products" PDA Journal of Pharmaceutical Science & Technology 1997, 51(4), 166-171.

Commonly used pharmaceutical ingredients that can be used as appropriate to formulate the composition for its intended route of administration include:

acidifying agents (examples include but are not limited to acetic acid, citric acid, fumaric acid, hydrochloric acid, nitric acid);

alkalinizing agents (examples include but are not limited to ammonia solution, ammonium carbonate, diethanolamine, monoethanolamine, potassium hydroxide, sodium borate, sodium carbonate, sodium hydroxide, triethanolamine, trolamine);

adsorbents (examples include but are not limited to powdered cellulose and activated charcoal);

aerosol propellants (examples include but are not limited to carbon dioxide, $CCl_2F_2$, $F_2ClC$—$CClF_2$ and $CClF_3$)

air displacement agents (examples include but are not limited to nitrogen and argon);

antifungal preservatives (examples include but are not limited to benzoic acid, butylparaben, ethylparaben, methylparaben, propylparaben, sodium benzoate);

antimicrobial preservatives (examples include but are not limited to benzalkonium chloride, benzethonium chloride, benzyl alcohol, cetylpyridinium chloride, chlorobutanol, phenol, phenylethyl alcohol, phenylmercuric nitrate and thimerosal);

antioxidants (examples include but are not limited to ascorbic acid, ascorbyl palmitate, butylated hydroxyanisole, butylated hydroxytoluene, hypophosphorus acid, monothioglycerol, propyl gallate, sodium ascorbate, sodium bisulfite, sodium formaldehyde sulfoxylate, sodium metabisulfite);

binding materials (examples include but are not limited to block polymers, natural and synthetic rubber, polyacrylates, polyurethanes, silicones, polysiloxanes and styrene-butadiene copolymers);

buffering agents (examples include but are not limited to potassium metaphosphate, dipotassium phosphate, sodium acetate, sodium citrate anhydrous and sodium citrate dihydrate)

carrying agents (examples include but are not limited to acacia syrup, aromatic syrup, aromatic elixir, cherry syrup, cocoa syrup, orange syrup, syrup, corn oil, mineral oil, peanut oil, sesame oil, bacteriostatic sodium chloride injection and bacteriostatic water for injection)

chelating agents (examples include but are not limited to edetate disodium and edetic acid)

colourants (examples include but are not limited to FD&C Red No. 3, FD&C Red No. 20, FD&C Yellow No. 6, FD&C Blue No. 2, D&C Green No. 5, D&C Orange No. 5, D&C Red No. 8, caramel and ferric oxide red);

clarifying agents (examples include but are not limited to bentonite);

emulsifying agents (examples include but are not limited to acacia, cetomacrogol, cetyl alcohol, glyceryl monostearate, lecithin, sorbitan monooleate, polyoxyethylene 50 monostearate);

encapsulating agents (examples include but are not limited to gelatin and cellulose acetate phthalate)

flavourants (examples include but are not limited to anise oil, cinnamon oil, cocoa, menthol, orange oil, peppermint oil and vanillin);

humectants (examples include but are not limited to glycerol, propylene glycol and sorbitol);

levigating agents (examples include but are not limited to mineral oil and glycerin);

oils (examples include but are not limited to arachis oil, mineral oil, olive oil, peanut oil, sesame oil and vegetable oil);

ointment bases (examples include but are not limited to lanolin, hydrophilic ointment, polyethylene glycol ointment, petrolatum, hydrophilic petrolatum, white ointment, yellow ointment, and rose water ointment);

penetration enhancers (transdermal delivery) (examples include but are not limited to monohydroxy or polyhydroxy alcohols, mono- or polyvalent alcohols, saturated or unsaturated fatty alcohols, saturated or unsaturated fatty esters, saturated or unsaturated dicarboxylic acids, essential oils, phosphatidyl derivatives, cephalin, terpenes, amides, ethers, ketones and ureas)

plasticizers (examples include but are not limited to diethyl phthalate and glycerol);

solvents (examples include but are not limited to ethanol, corn oil, cottonseed oil, glycerol, isopropanol, mineral oil, oleic acid, peanut oil, purified water, water for injection, sterile water for injection and sterile water for irrigation);

stiffening agents (examples include but are not limited to cetyl alcohol, cetyl esters wax, microcrystalline wax, paraffin, stearyl alcohol, white wax and yellow wax);

suppository bases (examples include but are not limited to cocoa butter and polyethylene glycols (mixtures));

surfactants (examples include but are not limited to benzalkonium chloride, nonoxynol 10, oxtoxynol 9, polysorbate 80, sodium lauryl sulfate and sorbitan mono-palmitate);

suspending agents (examples include but are not limited to agar, bentonite, carbomers, carboxymethylcellulose sodium, hydroxyethyl cellulose, hydroxypropyl cellulose, hydroxypropyl methylcellulose, kaolin, methylcellulose, tragacanth and veegum);

sweetening agents (examples include but are not limited to aspartame, dextrose, glycerol, mannitol, propylene glycol, saccharin sodium, sorbitol and sucrose);

tablet anti-adherents (examples include but are not limited to magnesium stearate and talc);

tablet binders (examples include but are not limited to acacia, alginic acid, carboxymethylcellulose sodium, compressible sugar, ethylcellulose, gelatin, liquid glucose, methylcellulose, non-crosslinked polyvinyl pyrrolidone, and pregelatinized starch);

tablet and capsule diluents (examples include but are not limited to dibasic calcium phosphate, kaolin, lactose, mannitol, microcrystalline cellulose, powdered cellulose, precipitated calcium carbonate, sodium carbonate, sodium phosphate, sorbitol and starch);

tablet coating agents (examples include but are not limited to liquid glucose, hydroxyethyl cellulose, hydroxypropyl cellulose, hydroxypropyl methylcellulose, methylcellulose, ethylcellulose, cellulose acetate phthalate and shellac);

tablet direct compression excipients (examples include but are not limited to dibasic calcium phosphate);

tablet disintegrants (examples include but are not limited to alginic acid, carboxymethylcellulose calcium, microcrystalline cellulose, polacrillin potassium, cross-linked polyvinylpyrrolidone, sodium alginate, sodium starch glycollate and starch);

tablet glidants (examples include but are not limited to colloidal silica, corn starch and talc);

tablet lubricants (examples include but are not limited to calcium stearate, magnesium stearate, mineral oil, stearic acid and zinc stearate);

tablet/capsule opaquants (examples include but are not limited to titanium dioxide);

tablet polishing agents (examples include but are not limited to carnuba wax and white wax);

thickening agents (examples include but are not limited to beeswax, cetyl alcohol and paraffin);

tonicity agents (examples include but are not limited to dextrose and sodium chloride);

viscosity increasing agents (examples include but are not limited to alginic acid, bentonite, carbomers, carboxymethylcellulose sodium, methylcellulose, polyvinyl pyrrolidone, sodium alginate and tragacanth); and wetting agents (examples include but are not limited to heptadecaethylene oxycetanol, lecithins, sorbitol monooleate, polyoxyethylene sorbitol monooleate, and polyoxyethylene stearate).

Combination Therapies

The term "combination" in the present invention is used as known to persons skilled in the art and may be present as a fixed combination, a non-fixed combination or kit of parts.

A "fixed combination" in the present invention is used as known to persons skilled in the art and is defined as a combination wherein the said first active ingredient and the said second active ingredient are present together in one unit dosage or in a single entity. One example of a "fixed combination" is a pharmaceutical composition wherein the said first active ingredient and the said second active ingredient are present in admixture for simultaneous administration, such as in a formulation. Another example of a "fixed combination" is a pharmaceutical combination wherein the said first active ingredient and the said second active ingredient are present in one unit without being in admixture.

A non-fixed combination or "kit of parts" in the present invention is used as known to persons skilled in the art and is defined as a combination wherein the said first active ingredient and the said second active ingredient are present in more than one unit. One example of a non-fixed combination or kit of parts is a combination wherein the said first active ingredient and the said second active ingredient are present separately. The components of the non-fixed combination or kit of parts may be administered separately, sequentially, simultaneously, concurrently or chronologically staggered.

The compounds of the present invention can be administered as the sole pharmaceutical agent or in combination with one or more other pharmaceutical agents where the combination causes no unacceptable adverse effects. The present invention relates also to such combinations.

For example, the compounds of the present invention can be combined with known hormonal therapeutic agents.

In particular, the compounds of the present invention can be administered in combination or as co-medication with hormonal contraceptives. Hormonal contraceptives can be administered via oral, subcutaneous, transdermal, intrauterine or intravaginal route, for example as Combined Oral Contraceptives (COCs) or Progestin-Only-Pills (POPs) or hormone-containing devices like implants, patches or intravaginal rings.

COCs include but are not limited to birth control pills or a birth control method that includes a combination of an estrogen (estradiol) and a progestogen (progestin). The estrogenic part is in most of the COCs ethinyl estradiol. Some COCs contain estradiol or estradiol valerate.

Said COCs contain the progestins norethynodrel, norethindrone, norethindrone acetate, ethynodiol acetate, norgestrel, levonorgestrel, norgestimate, desogestrel, gestodene, drospirenone, dienogest, or nomegestrol acetate.

Birth control pills include for example but are not limited to Yasmin, Yaz, both containing ethinyl estradiol and drospirenone; Microgynon or Miranova containing levonorgestrel and ethinyl estradiol; Marvelon containing ethinyl estradiol and desogestrel; Valette containing ethinyl estradiol and dienogest; Belara and Enriqa containing ethinyl estradiol and chlormadinonacetate; Qlaira containing estradiol valerate and dienogest as active ingredients; and Zoely containing estradiol and normegestrol.

POPs are contraceptive pills that contain only synthetic progestogens (progestins) and do not contain estrogen. They are colloquially known as mini pills.

POPs include but are not limited to Cerazette containing desogestrel; Microlut containing levonorgestrel and Micronor containing norethindrone.

Other Progeston-Only forms are intrauterine devices (IUDs), for example Mirena containing levonorgestrel, or injectables, for example Depo-Provera containing medroxyprogesterone acetate, or implants, for example Implanon containing etonogestrel.

Other hormone-containing devices with contraceptive effect which are suitable for a combination with the compounds of the present invention are vaginal rings like Nuvaring containing ethinyl estradiol and etonogestrel, or transdermal systems like contraceptive patches, for example Ortho-Evra containing ethinyl estradiol and norelgestromin or Apleek (Lisvy) containing ethinyl estradiol and gestodene.

A preferred embodiment of the present invention is the administration of a compound of general formula (I) in combination with a COC or a POP or other Progestin-Only forms as well as vaginal rings or contraceptive patches as mentioned above.

Furthermore, the compounds of the present invention can be combined with therapeutic agents or active ingredients, that are already approved or that are still under development for the treatment and/or prophylaxis of diseases which are related to or mediated by PTGES.

For the treatment and/or prophylaxis of urinary tract diseases, the compounds of the present invention can be administered in combination or as co-medication with any substance that can be applied as therapeutic agent in the following indications:

Urinary tract disease states associated with the bladder outlet obstruction; urinary incontinence conditions such as reduced bladder capacity, increased frequency of micturition, urge incontinence, stress incontinence, or bladder hyperreactivity; benign prostatic hypertrophy; prostatic hyperplasia; prostatitis; detrusor hyperreflexia; overactive bladder and symptoms related to overactive bladder wherein said symptoms are in particular increased urinary frequency, nocturia, urinary urgency or urge incontinence; pelvic hypersensitivity; urethritis; prostatitis; prostatodynia; cystitis, in particular interstitial cystitis; idiopathic bladder hypersensitivity.

For the treatment and/or prophylaxis of overactive bladder and symptoms related to overactive bladder, the compounds of the present invention can be administered in combination or as co-medication in addition to behavioral therapy like diet, lifestyle or bladder training with anticholinergics like oxybutynin, tolterodine, propiverine, solifenacin, darifenacin, trospium, fesoterdine; β-3 agonists like mirabegron; neurotoxins like onabutolinumtoxin A; or antidepressants like imipramine, duloxetine.

For the treatment and/or prophylaxis of interstitial cystitis, the compounds of the present invention can be administered in combination or as co-medication in addition to behavioral therapy like diet, lifestyle or bladder training with pentosans like elmiron; antidepressants like amitriptyline, imipramine; or antihistamines like loratadine.

For the treatment and/or prophylaxis of gynaecological diseases, the compounds of the present invention can be administered in combination or as co-medication with any substance that can be applied as therapeutic agent in the following indications:

dysmenorrhea, including primary and secondary; dyspareunia; endometriosis; endometriosis-associated pain; endometriosis-associated symptoms, wherein said symptoms are in particular dysmenorrhea, dyspareunia, dysuria, or dyschezia.

For the treatment and/or prophylaxis of dysmenorrhea, including primary and secondary; dyspareunia; endometriosis and endometriosis-associated pain, the compounds of the present invention can be administered in combination with ovulation inhibiting treatment, in particular COCs as mentioned above or contraceptive patches like Ortho-Evra or Apleek (Lisvy); or with progestogenes like dienogest (Visanne); or with GnRH analogous, in particular GnRH agonists and antagonists, for example leuprorelin, nafarelin, goserelin, cetrorelix, abarelix, ganirelix, degarelix; or with androgens: danazol.

For the treatment and/or prophylaxis of diseases, which are associated with pain, or pain syndromes, the compounds of the present invention can be administered in combination or as co-medication with any substance that can be applied as therapeutic agent in the following indications:

pain-associated diseases or disorders like hyperalgesia, allodynia, functional bowel disorders (such as irritable bowel syndrome) and arthritis (such as osteoarthritis, rheumatoid arthritis and ankylosing spondylitis), burning mouth syndrome, burns, migraine or cluster headache, nerve injury, traumatic nerve injury, post-traumatic injuries (including fractures and sport injuries), neuritis, neuralgia, poisoning, ischemic injury, interstitial cystitis, viral, trigeminal neuralgia, small fiber neuropathy, diabetic neuropathy, chronic arthritis and related neuralgias, HIV and HIV treatment-induced neuropathy.

The compounds of the present invention can be combined with other pharmacological agents and compounds that are intended to treat inflammatory diseases, inflammatory pain or general pain conditions.

In addition to well-known medicaments which are already approved and on the market, the compounds of the present invention can be administered in combination with inhibitors of the P2X purinoceptor family (P2X3, P2X4), with inhibitors of IRAK4 and with antagonists of the prostanoid EP4 receptor.

In particular, the compounds of the present invention can be administered in combination with pharmacological endometriosis agents, intended to treat inflammatory diseases, inflammatory pain or general pain conditions and/or interfering with endometriotic proliferation and endometriosis associated symptoms, namely with inhibitors of Aldo-keto-reductase1C3 (AKR1C3) and with functional blocking antibodies of the prolactin receptor.

The compounds of the present invention can be combined with other pharmacological agents and compounds that are intended for the treatment, prevention or management of cancer.

In particular, the compounds of the present invention can be administered in combination with 131I-chTNT, abarelix, abiraterone, aclarubicin, ado-trastuzumab emtansine, afatinib, aflibercept, aldesleukin, alemtuzumab, Alendronic acid, alitretinoin, altretamine, amifostine, aminoglutethimide, Hexyl aminolevulinate, amrubicin, amsacrine, anastrozole, ancestim, anethole dithiolethione, angiotensin II, antithrombin III, aprepitant, arcitumomab, arglabin, arsenic trioxide, asparaginase, axitinib, azacitidine, basiliximab, belotecan, bendamustine, belinostat, bevacizumab, bexarotene, bicalutamide, bisantrene, bleomycin, bortezomib, buserelin, bosutinib, brentuximab vedotin, busulfan, cabazitaxel, cabozantinib, calcium folinate, calcium levofolinate, capecitabine, capromab, carboplatin, carfilzomib, carmofur, carmustine, catumaxomab, celecoxib, celmoleukin, ceritinib, cetuximab, chlorambucil, chlormadinone, chlormethine, cidofovir, cinacalcet, cisplatin, cladribine, clodronic acid, clofarabine, copanlisib, crisantaspase, cyclophosphamide, cyproterone, cytarabine, dacarbazine, dactinomycin, darbepoetin alfa, dabrafenib, dasatinib, daunorubicin, decitabine, degarelix, denileukin diftitox, denosumab, depreotide, deslorelin, dexrazoxane, dibrospidium chloride, dianhydrogalactitol, diclofenac, docetaxel, dolasetron, doxifluridine, doxorubicin, doxorubicin+estrone, dronabinol, eculizumab, edrecolomab, elliptinium acetate, eltrombopag, endostatin, enocitabine, enzalutamide, epirubicin, epitiostanol, epoetin alfa, epoetin beta, epoetin zeta, eptaplatin, eribulin, erlotinib, esomeprazole, estradiol, estramustine, etoposide, everolimus, exemestane, fadrozole, fentanyl, filgrastim, fluoxymesterone, floxuridine, fludarabine, fluorouracil, flutamide, folinic acid, formestane, fosaprepitant, fotemustine, fulvestrant, gadobutrol, gadoteridol, gadoteric acid meglumine, gadoversetamide, gadoxetic acid, gallium nitrate, ganirelix, gefitinib, gemcitabine, gemtuzumab, Glucarpidase, glutoxim, GM-CSF, goserelin, granisetron, granulocyte colony stimulating factor, histamine dihydrochloride, histrelin, hydroxycarbamide, I-125 seeds, lansoprazole, ibandronic acid, ibritumomab tiuxetan, ibrutinib, idarubicin, ifosfamide, imatinib, imiquimod, improsulfan, indisetron, incadronic acid, ingenol mebutate, interferon alfa, interferon beta, interferon gamma, iobitridol, iobenguane (123I), iomeprol, ipilimumab, irinotecan, Itraconazole, ixabepilone, lanreotide, lapatinib, lasocholine, lenalidomide, lenograstim, lentinan, letrozole, leuprorelin, levamisole, levonorgestrel, levothyroxine sodium, lisuride, lobaplatin, lomustine, lonidamine, masoprocol, medroxyprogesterone, megestrol, melarsoprol, melphalan, mepitiostane, mercaptopurine, mesna, methadone, methotrexate, methoxsalen, methylaminolevulinate, methylprednisolone, methyltestosterone, metirosine, mifamurtide, miltefosine, miriplatin, mitobronitol, mitoguazone, mitolactol, mitomycin, mitotane, mitoxantrone, mogamulizumab, molgramostim, mopidamol, morphine hydrochloride, morphine sulfate, nabilone, nabiximols, nafarelin, naloxone+pentazocine, naltrexone, nartograstim, nedaplatin, nelarabine, neridronic acid, nivolumabpentetreotide, nilotinib, nilutamide, nimorazole, nimotuzumab, nimustine, nitracrine, nivolumab, obinutuzumab, octreotide, ofatumumab, omacetaxine mepesuccinate, omeprazole, ondansetron, oprelvekin, orgotein, orilotimod, oxaliplatin, oxycodone, oxymetholone, ozogamicine, p53 gene therapy, paclitaxel, palifermin, palladium-103 seed, palonosetron, pamidronic acid, panitumumab, pantoprazole, pazopanib, pegaspargase, PEG-epoetin beta (methoxy PEG-epoetin beta), pembrolizumab, pegfilgrastim, peginterferon alfa-2b, pemetrexed, pentazocine, pentostatin, peplomycin, Perflubutane, perfosfamide, Pertuzumab, picibanil, pilocarpine, pirarubicin, pixantrone, plerixafor, plicamycin, poliglusam, polyestradiol phosphate, polyvinylpyrrolidone+sodium hyaluronate, polysaccharide-K, pomalidomide, ponatinib, porfimer sodium, pralatrexate, prednimustine, prednisone, procarbazine, procodazole, propranolol, quinagolide, rabeprazole, racotumomab, radium-223 chloride, radotinib, raloxifene, raltitrexed, ramosetron, ramucirumab, ranimustine, rasburicase, razoxane, refametinib, regorafenib, risedronic acid, rhenium-186 etidronate, rituximab, romidepsin, romiplostim, romurtide, roniciclib, samarium (153Sm) lexidronam, sargramostim, satumomab, secretin, sipuleucel-T, sizofiran, sobuzoxane, sodium glycididazole, sorafenib, stanozolol, streptozocin, sunitinib, talaporfin, tamibarotene, tamoxifen, tapentadol, tasonermin, teceleukin, technetium (99mTc) nofetumomab merpentan, 99mTc-HYNIC-[Tyr3]-octreotide, tegafur, tegafur+gimeracil+oteracil, temoporfin, temozolomide, temsirolimus, teniposide, testosterone, tetrofosmin, thalidomide, thiotepa, thymalfasin, thyrotropin alfa, tioguanine, tocilizumab, topotecan, toremifene, tositumomab, trabectedin, tramadol, trastuzumab, trastuzumab emtansine, treosulfan, tretinoin, trifluridine+tipiracil, trilostane, triptorelin, trametinib, trofosfamide, thrombopoietin, tryptophan, ubenimex, valatinib, valrubicin, vandetanib, vapreotide, vemurafenib, vinblastine, vincristine, vindesine, vinflunine, vinorelbine, vismodegib, vorinostat, vorozole, yttrium-90 glass microspheres, zinostatin, zinostatin stimalamer, zoledronic acid, zorubicin.

Furthermore, the compounds of the present invention can be combined with active ingredients, which are well known for the treatment of cancer-related pain and chronic pain. Such combinations include, but are not limited to step II opioids like codeine phosphate, dextropropoxyphene, dihydro-codeine, Tramadol), step III opioids like morphine, fentanyl, buprenorphine, oxymorphone, oxycodone and hydromorphone; and other medications used for the treatment of cancer pain like steroids as Dexamethasone and methylprednisolone; bisphosphonates like Etidronate, Clodronate, Alendronate, Risedronate, and Zoledronate; tricyclic antidepressants like Amitriptyline, Clomipramine, Desipramine, Imipramine and Doxepin; class I antiarrhythmics like mexiletine and lidocaine; anticonvulsants like carbamazepine, Gabapentin, oxcarbazepine, phenytoin, pregabalin, topiramate, alprazolam, diazepam, flurazepam, pentobarbital and phenobarbital.

Methods of Treating

The present invention relates to a method for using the compounds of the present invention and compositions thereof, to selectively inhibit the human PTGES enzyme leading to reduced PGE2 formation.

The present invention relates to a method for using the compounds of the present invention and compositions thereof, to treat mammalian and human disorders and diseases, which include but are not limited to:

genitourinary, gastrointestinal, respiratory, proliferative and pain-related diseases, conditions and disorders;

gynecological diseases including primary and secondary dysmenorrhea, dyspareunia, endometriosis, and adenomyosis; endometriosis-associated pain; endometriosis-associated symptoms, wherein said symptoms are in particular dysmenorrhea, dyspareunia, dysuria, or dyschezia; endometriosis-associated proliferation; pelvic hypersensitivity;

urinary tract disease states associated with the bladder outlet obstruction; urinary incontinence conditions such as reduced bladder capacity, increased frequency of micturition, urge incontinence, stress incontinence, or bladder hyperreactivity; benign prostatic hypertrophy; prostatic hyperplasia; prostatitis; detrusor hyperreflexia; overactive urinary bladder and symptoms related to overactive urinary bladder wherein said symptoms are in particular increased urinary frequency, nocturia, urinary urgency or urge incontinence; pelvic hypersensitivity; urethritis; prostatitis; prostatodynia; cystitis, in particular Interstitial cystitis; idiopathic bladder hypersensitivity; kidney disease as hyperprostaglandin E syndrome, classic Bartter syndrome;

cancer, cancer-related pain and cancer cachexia;

Epilepsy, partial and generalized seizures;

respiratory disorders including asthma, chronic obstructive pulmonary disease, pulmonary fibrosis, bronchospasm;

gastrointestinal disorders including irritable bowel syndrome (IBS), inflammatory bowel disease (IBD), biliary colic and other biliary disorders, renal colic, diarrhea-dominant IBS; gastroesophageal reflux, gastrointestinal distension, Crohn's disease and the like;

fatty liver disorders, in particular NASH (Non-Alcoholic Steato-Hepatitis); fibrotic diseases including lung fibrosis, heart fibrosis, kidney fibrosis and fibrosis of other organs; metabolic syndrome including, for example, insulin resistance, hypertension, refractory hypertension, dyslipoproteinaemia and obesity, diabetes mellitus, in particular Diabetes type II, myocardial infarction; atherosclerosis; lipid disorders;

neurodegenerative disorders such as Alzheimer's disease, Multiple Sclerosis, Parkinson's disease, Brain ischemia and traumatic brain injury;

pruritus.

The present invention relates to a method for using the compounds of the present invention and compositions thereof, to treat pain-associated mammalian disorders and diseases, which include but not limited to pain-associated diseases or disorders selected from the group consisting of hyperalgesia, allodynia, functional bowel disorders (such as irritable bowel syndrome), gout, arthritis (such as osteoarthritis, rheumatoid arthritis and ankylosing spondylitis), burning mouth syndrome, burns, migraine or cluster headaches, nerve injury, traumatic nerve injury, post-traumatic injuries (including fractures and sport injuries), neuritis, neuralgias, poisoning, ischemic injury, interstitial cystitis, cancer, trigeminal neuralgia, small fiber neuropathy, diabetic neuropathy, chronic arthritis and related neuralgias, HIV and HIV treatment-induced neuropathy, pruritus; impaired wound healing and disease of the skeleton like degeneration of the joints.

The present invention relates to a method for using the compounds of the present invention and compositions thereof, to treat mammalian and human disorders and diseases, which are associated with pain or pain syndromes that are in particular:

pain syndromes (including acute, chronic, inflammatory and neuropathic pain), preferably inflammatory pain, low back pain surgical pain, visceral pain, dental pain, periodontitis, premenstrual pain, endometriosis-associated pain, pain associated with fibrotic diseases, central pain, pain due to burning mouth syndrome, pain due to burns, pain due to migraine, cluster headaches, pain due to nerve injury, pain due to neuritis, neuralgias, pain due to poisoning, pain due to ischemic injury, pain due to interstitial cystitis, cancer pain, pain due to viral, parasitic or bacterial infections, pain due to traumatic nerve-injury, pain due to post-traumatic injuries (including fractures and sport injuries), pain due to trigeminal neuralgia, pain associated with small fiber neuropathy, pain associated with diabetic neuropathy, postherpetic neuralgia, chronic lower back pain, neck pain phantom limb pain, pelvic pain syndrome, chronic pelvic pain, neuroma pain, complex regional pain syndrome, pain associated with gastrointestinal distension, chronic arthritic pain and related neuralgias, and pain associated with cancer, Morphine-resistant pain, pain associated with chemotherapy, HIV and HIV treatment-induced neuropathy; and pain associated with diseases or disorders selected from the group consisting of hyperalgesia, allodynia, functional bowel disorders (such as irritable bowel syndrome) and arthritis (such as osteoarthritis, rheumatoid arthritis and ankylosing spondylitis).

Compounds of the invention are thus expected to be useful in the treatment of inflammation. The term "inflammation" is also understood to include any inflammatory disease, disorder or condition per se, any condition that has an inflammatory component associated with it, and/or any condition characterized by inflammation as a symptom, including, inter alia, acute, chronic, ulcerative, specific, allergic, infection by pathogens, immune reactions due to hypersensitivity, entering foreign bodies, physical injury, and necrotic inflammation, and other forms of inflammation known to those skilled in the art. The term thus also includes, for the purposes of this invention, inflammatory pain, pain generally and/or fever. The compounds of the present invention may also be useful in the treatment of fibromyalgia, myofascial disorders, viral infections (e.g. influenza, common cold, herpes zoster, hepatitis C and AIDS), bacterial infections, fungal infections, surgical or dental procedures, malignancies (e.g. breast cancer, colon cancer, and prostate cancer), arthritis, osteoarthritis, juvenile arthritis, rheumatoid arthritis, juvenile onset rheumatoid arthritis, rheumatic fever, ankylosing spondylitis, Hodgkin's disease, systemic lupus erythematosus, vasculitis, pancreatitis, nephritis, bursitis, conjunctivitis, iritis, scleritis, uveitis, wound healing, dermatitis, eczema, stroke, diabetes mellitus, autoimmune diseases, allergic disorders, rhinitis, ulcers, mild to moderately active ulcerative colitis, familial adenomatous polyposis, coronary heart disease, sarcoidosis and any other disease with an inflammatory component. Compounds of the invention may also have effects that are not linked to inflammatory mechanisms, such as in the reduction of bone loss in a subject. Conditions that may be mentioned in this regard include osteoporosis, osteoarthritis, Paget's disease and/or periodontal diseases.

Based on the PTGES inhibitory activity of compounds of the present invention, the compounds are useful for the relief of pain, fever and inflammation of a variety of conditions including rheumatic fever, symptoms associated with influenza or other viral infections, common cold, low back and neck pain, dysmenorrhea, headache, migraine (acute and prophylactic treatment), toothache, sprains and strains, myositis, neuralgia, synovitis, arthritis, including rheumatoid arthritis, juvenile rheumatoid arthritis, degenerative joint diseases (osteoarthritis), acute gout and ankylosing spondylitis, acute, subacute and chronic musculoskeletal pain syndromes such as bursitis, burns, injuries, and pain following surgical (post-operative pain) and dental procedures as well as the preemptive treatment of surgical pain. The pain may be mild pain, moderate pain, severe pain, musculoskeletal pain, complex regional pain syndrome, neuropathic pain, back pain such as acute visceral pain, neuropathies, acute trauma, chemotherapy-induced mononeuropathy pain states, polyneuropathy pain states (such as diabetic peripheral neuropathy and/or chemotherapy induced neuropathy), autonomic neuropathy pain states, pheriphaeral nervous system (PNS) lesion or central nervous system (CNS) lesion or disease related pain states, polyradiculopathies of cervical, lumbar or sciatica type, cauda equina syndrome, piriformis syndrome, paraplegia, quadriplegia, pain states related to various Polyneuritis conditions underlying various infections, chemical injuries, radiation exposure, underlying disease or deficiency conditions (such as beriberi, vitamin deficiencies, hypothyroidism, porphyria, cancer, HIV, autoimmune disease such as multiple sclerosis and spinal-cord injury, fibromyalgia, nerve injury, ischaemia, neurodegeneration, stroke, post stroke pain, inflammatory disorders, oesophagitis, gastroeosophagal reflux disorder (GERD), irritable bowel syndrome, inflammatory bowel disease, overactive bladder, pelvic hypersensitivity, urinary incontinence, cystitis, stomach, duodenal ulcer, muscle pain, pain due to colicky and referred pain. Compounds of the present invention may also be useful for the treatment or prevention of hemophilic arthropathy and Parkinson's disease.

The present invention relates to a method for using the compounds of the present invention and compositions thereof, to treat conditions treatable by inhibition of prostanoid-induced smooth muscle contraction by preventing the synthesis of contractile prostanoids and hence may be of relevance to use in treatment of dysmenorrhea premature labor and asthma.

The present invention relates to a method for using the compounds of the present invention and compositions thereof, to treat cancer and hyperproliferative disorders. Hyperproliferative disorders include, but are not limited to, for example: psoriasis, keloids, and other hyperplasias affecting the skin, benign prostate hyperplasia (BPH), solid tumours, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukaemias.

Examples of breast cancers include, but are not limited to, invasive ductal carcinoma, invasive lobular carcinoma, and ductal carcinoma in situ, and lobular carcinoma in situ.

Examples of cancers of the respiratory tract include, but are not limited to, small-cell and non-small-cell lung carcinoma, as well as bronchial adenoma and pleuropulmonary blastoma.

Examples of brain cancers include, but are not limited to, brain stem and hypophtalmic glioma, cerebellar and cerebral astrocytoma, medulloblastoma, ependymoma, as well as neuroectodermal and pineal tumour.

Tumours of the male reproductive organs include, but are not limited to, prostate and testicular cancer.

Tumours of the female reproductive organs include, but are not limited to, endometrial, cervical, ovarian, vaginal, and vulvar cancer, as well as sarcoma of the uterus.

Tumours of the digestive tract include, but are not limited to, anal, colon, colorectal, oesophageal, gallbladder, gastric, pancreatic, rectal, small-intestine, and salivary gland cancers.

Tumours of the urinary tract include, but are not limited to, bladder, penile, kidney, and renal pelvis, ureter, urethral and human papillary renal cancers.

Eye cancers include, but are not limited to, intraocular melanoma and retinoblastoma.

Examples of liver cancers include, but are not limited to, hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to, squamous cell carcinoma, Kaposi's sarcoma, malignant melanoma, Merkel cell skin cancer, and non-melanoma skin cancer.

Head-and-neck cancers include, but are not limited to, laryngeal, hypopharyngeal, nasopharyngeal, oropharyngeal cancer, lip and oral cavity cancer and squamous cell.

Lymphomas include, but are not limited to, AIDS-related lymphoma, non-Hodgkin's lymphoma, cutaneous T-cell lymphoma, Burkitt lymphoma, Hodgkin's disease, and lymphoma of the central nervous system.

Sarcomas include, but are not limited to, sarcoma of the soft tissue, osteosarcoma, malignant fibrous histiocytoma, lymphosarcoma, and rhabdomyosarcoma.

Leukemias include, but are not limited to, acute myeloid leukemia, acute lymphoblastic leukemia, chronic lymphocytic leukemia, chronic myelogenous leukemia, and hairy cell leukemia.

A preferred embodiment of the present invention relates to a method for using the compounds of the present invention and compositions thereof, to treat a gynaecological disease, preferably dysmenorrhea, dyspareunia or endometriosis, endometriosis-associated pain, or other endometriosis-associated symptoms, wherein said symptoms are in particular dysmenorrhea, dyspareunia, dysuria, or dyschezia.

Another preferred embodiment of the present invention relates to a method for using the compounds of the present invention and compositions thereof, to treat a urinary tract disease, in particular overactive bladder or cystitis, preferably interstitial cystitis.

Another preferred embodiment of the present invention relates to a method for using the compounds of the present invention and compositions thereof, to treat a respiratory disorder, preferably cough, in particular chronic cough.

Another preferred embodiment of the present invention relates to a method for using the compounds of the present invention and compositions thereof, to treat arthritis, in particular rheumatoid arthritis and ankylosing spondylitis.

These disorders have been well characterized in humans, but also exist with a similar etiology in other mammals, and can be treated by administering pharmaceutical compositions of the present invention.

The term "treating" or "treatment" as stated throughout this document is used conventionally, e.g., the management or care of a subject for the purpose of combating, alleviating, reducing, relieving, improving the condition of, etc., of a disease or disorder, such as a gynaecological disease or a disease associated with undesired proliferation like endometriosis or cancer.

Dose and Administration

Based upon standard laboratory techniques known to evaluate compounds useful for the treatment of disorders and/or disease, which are influenced by PTGES, by standard toxicity tests and by standard pharmacological assays for the determination of treatment of the conditions identified above in mammals, and by comparison of these results with the results of known medicaments that are used to treat these conditions. The effective dosage of the compounds of this invention can readily be determined for treatment of each desired indication. The amount of the active ingredient to be administered in the treatment of one of these conditions can vary widely according to such considerations as the particular compound and dosage unit employed the mode of administration, the period of treatment, the age and sex of the patient treated, and the nature and extent of the condition treated.

The total amount of the active ingredient to be administered will generally range from about 0.001 mg/kg to about 200 mg/kg body weight per day. Clinically useful dosing schedules will range from one to three times a day dosing to once every four weeks dosing. In addition, "drug holidays" in which a patient is not dosed with a drug for a certain period of time, may be beneficial to the overall balance between pharmacological effect and tolerability. A unit dosage may contain from about 0.5 mg to about 1500 mg of active ingredient, and can be administered one or more times per day or less than once a day. A preferred oral unit dosage for a administration of the compounds of the present invention includes but is not limited to 0.1 mg/kg to about 10 mg/kg body weight one to three times a day to once a week. The average daily dosage for administration by injection, including intravenous, intramuscular, subcutaneous and parenteral injections, and use of infusion techniques will preferably be from 0.01 to 200 mg/kg of total body weight. The average daily rectal dosage regimen will preferably be from 0.01 to 200 mg/kg of total body weight. The average daily vaginal dosage regimen will preferably be from 0.01 to 200 mg/kg of total body weight. The average daily topical dosage regimen will preferably be from 0.1 to 200 mg administered between one to four times daily. The transdermal concentration will preferably be that required to maintain a daily dose of from 0.01 to 200 mg/kg. The average daily inhalation dosage regimen will preferably be from 0.01 to 100 mg/kg of total body weight.

Of course the specific initial and continuing dosage regimen for each patient will vary according to the nature and severity of the condition as determined by the attending diagnostician, the activity of the specific compound employed, the age and general condition of the patient, time of administration, route of administration, rate of excretion of the drug, drug combinations, and the like. The desired mode of treatment and number of doses of a compound of the present invention or a pharmaceutically acceptable salt or ester or composition thereof can be ascertained by those skilled in the art using conventional treatment tests.

Preferably, the diseases treated with said method are gynaecological disorders, more preferably dysmenorrhea, dyspareunia or endometriosis, endometriosis-associated pain, or other endometriosis-associated symptoms, wherein said symptoms are in particular dysmenorrhea, dyspareunia, dysuria, or dyschezia. Further diseases, which can be treated with said method, are osteoarthritis, diabetic neuropathy, burning mouth syndrome, gastroesophageal reflux, migraine disorders, chronic cough, asthma, pruritus, irritable bowel disease, overactive urinary bladder, prostatic hyperplasia, interstitial cystitis.

Preferably, the method of treating the diseases mentioned above is not limited to the treatment of said disease but also includes the treatment of pain related to or associated with said diseases.

The compounds of the present invention can be used in particular in therapy and prevention, i.e. prophylaxis, of genitourinary, gastrointestinal, respiratory or pain-related disease, condition or disorder.

Methods of testing for a particular pharmacological or pharmaceutical property are well known to persons skilled in the art.

The example testing experiments described herein serve to illustrate the present invention and the invention is not limited to the examples given.

Biological Assays

Examples were tested in selected biological assays one or more times. When tested more than once, data are reported as either average values or as median values, wherein the average value, also referred to as the arithmetic mean value, represents the sum of the values obtained divided by the number of times tested, and the median value represents the middle number of the group of values when ranked in ascending or descending order. If the number of values in the data set is odd, the median is the middle value. If the number of values in the data set is even, the median is the arithmetic mean of the two middle values.

Examples were synthesized one or more times. When synthesized more than once, data from biological assays represent average values or median values calculated utilizing data sets obtained from testing of one or more synthetic batch.

Human PTGES Biochemical Enzyme Inhibition Assay:

PTGES (Microsomal prostaglandin E synthase 1) is an enzyme that converts prostaglandin H2 (PGH2) to prostaglandin E2 (PGE2) in the presence of reduced glutathione (GSH).

Recombinant proteins (human isoforms) of PTGES containing a FLAG tag, expressed in baculovirus infected insect cells (Hi-5) and purified by affinity chromatography was used as enzyme in the assay. Substrate was prostaglandin H2 (Cayman Chemicals).

For the assay, 50 nl of a 100-fold concentrated solution of the test compound in DMSO was pipetted into a black microtiter plate (384 or 1536, Greiner Bio-One, Frickenhausen, Germany). 4 ul of a solution of human PTGES in assay buffer [100 mM sodium phosphate pH 7.2, 2.5 mM Glutathion reduced, 1 mM EDTA, 0.01% BSA, 0.4 mM DTT, 0.15 mM n-dodecylmaltoside] was added to the well containing test compound and incubated for 15-20 minutes to allow binding of the compound to the enzyme prior to the enzymatic reaction. The reaction was started by addition of 1 ul of an ice cold solution containing PGH2 (40 nM in assay buffer resulting in a final concentration of 8 nM PGH2 in the assay). Reaction time of the mix was 60 seconds at room temperature (PGH2 in aqueous solution quickly converts nonenyzmatically to PGE2 with a short half-life). The concentration of each isoform of PTGES was adapted to the activity of the respective enzyme preparation to maintain linear reaction properties within the reaction time. Typical concentration was around 0.75 nM. The reaction was stopped by addition of 1 ul of a solution containing 15 mM SnCl2 and 400 mM KF in water. SnCl2 converts the remaining unstable PGH2 to stable PGF2alpha. Then, 3 ul of the a first detection solution containing PGE2-D2 (Cisbio Bioassays, TR-FRET reagent, diluted according to the manufacturer's recommendation, typically 1:20 in reconstitution buffer) was added. Finally, 3 μl of the second detection solution containing Lanthanide-kryptate labelled anti-PGE2 antibody (Cisbio Bioassays, diluted according to the manufacturer's recommendation, typically 1:20 in reconstitution buffer) was added to the mix. The resulting mix was incubated overnight at 4° C. to allow the formation of a complex of PGE2 and the detection reagents. The amount of PGE2 that had been produced by PTGES from PGH2 was then determined by testing resonance energy transfer of the Lanthanide-kryptate labelled anti-PGE2 antibody to PGE2-D2. Hereby the fluorescent emissions at 620 nm and 665 nm were measured after excitation at 337-350 nm in a TR-FRE compatible microplate reader (typically BMG Pherastar or Perkin-Elmer ViewLux). The ratio of the emissions at 665 nm and 620 nm was used to determine the amount of PGE2 that was catalyzed by the enzyme. Data were normalized (enzyme reaction without inhibitor=0% inhibition, assay setup without enzyme=100% inhibition). Compounds were tested in duplicates at up to 10 concentrations (for example 20 μM, 5.7 μM, 1.6 μM, 0.47 μM, 0.13 μM, 38 nM, 11 nM, 3.1 nM, 0.89 nM, 0.25 nM and 0.073 nM). Dilution series were made prior to the assay in a 100 fold concentrated form by serial dilution. IC50 values were calculated by 4-Parameter fitting.

TABLE 1

Enzymatic conversion of PGH2 to PGE2

| Patent Example | Human PTGES IC50 [mol/l] |
|---|---|
| 1 | 1.45E−8 |
| 2 | 2.04E−8 |
| 3 | 1.98E−7 |
| 4 | 1.32E−6 |
| 5 | 7.95E−7 |
| 6 | 1.62E−7 |
| 7 | 3.16E−6 |
| 8 | 1.60E−7 |
| 9 | 3.56E−6 |
| 10 | 4.70E−7 |
| 11 | 3.41E−7 |
| 12 | 5.79E−7 |
| 13 | 7.82E−8 |
| 14 | 1.15E−7 |
| 15 | 1.14E−7 |
| 16 | 5.96E−8 |
| 17 | 3.52E−8 |
| 18 | 2.36E−7 |
| 19 | 5.52E−7 |
| 20 | 2.55E−6 |
| 21 | 1.61E−7 |
| 22 | 2.99E−7 |
| 23 | 5.26E−6 |
| 24 | 2.20E−8 |
| 25 | 2.25E−6 |
| 26 | 1.56E−8 |
| 27 | 9.03E−8 |
| 28 | 3.80E−7 |
| 29 | 7.82E−8 |
| 30 | 1.88E−7 |
| 31 | 4.43E−7 |
| 32 | 4.70E−7 |
| 33 | 1.43E−8 |
| 34 | 9.85E−9 |
| 35 | 3.73E−6 |
| 36 | 3.22E−8 |
| 37 | 1.40E−8 |
| 38 | 4.62E−8 |
| 39 | 1.43E−8 |
| 40 | 2.82E−8 |
| 41 | 1.92E−8 |
| 42 | 4.60E−8 |
| 43 | 3.01E−8 |
| 44 | 1.76E−8 |
| 45 | 1.68E−6 |
| 46 | 5.53E−8 |
| 47 | 1.59E−8 |
| 48 | 1.42E−8 |
| 49 | 5.30E−7 |
| 50 | 4.29E−8 |
| 51 | 6.91E−8 |
| 52 | 2.73E−7 |
| 53 | 5.33E−8 |
| 54 | 2.73E−8 |

TABLE 1-continued

Enzymatic conversion of PGH2 to PGE2

| Patent Example | Human PTGES IC50 [mol/l] |
|---|---|
| 55 | 3.54E-8 |
| 56 | 7.52E-6 |
| 57 | 7.21E-8 |
| 58 | 2.10E-7 |
| 59 | 1.93E-7 |
| 60 | 4.78E-7 |
| 61 | 3.22E-8 |
| 62 | 1.48E-7 |
| 63 | 1.03E-7 |
| 64 | 3.44E-7 |
| 65 | 1.96E-7 |
| 66 | 5.39E-8 |
| 67 | 3.28E-7 |
| 68 | 4.65E-8 |
| 69 | 8.74E-6 |
| 70 | 5.29E-8 |
| 71 | 1.59E-5 |
| 72 | 7.10E-8 |
| 73 | 2.45E-7 |
| 74 | 1.88E-5 |
| | >2.00E-5 |
| 75 | 7.14E-8 |
| 76 | 1.62E-5 |
| 77 | 1.27E-7 |
| 78 | 1.18E-7 |
| 79 | 4.33E-7 |
| 80 | 8.85E-8 |
| 81 | 1.72E-7 |
| 82 | 9.06E-8 |
| 83 | 1.17E-5 |
| 84 | 4.11E-8 |
| 85 | 2.92E-8 |
| 86 | 2.08E-7 |
| 87 | 9.67E-9 |
| 88 | 9.61E-7 |
| 89 | 2.22E-8 |
| 90 | 1.08E-7 |
| 91 | 2.03E-8 |
| 92 | 2.20E-8 |
| 93 | 3.56E-8 |
| 94 | 3.23E-8 |
| 95 | 4.17E-8 |
| 96 | 3.69E-8 |
| 97 | 1.30E-8 |
| 98 | 3.38E-8 |
| 99 | 3.73E-8 |
| 100 | 1.12E-8 |
| 101 | 1.66E-7 |
| 102 | >2.00E-5 |
| 103 | 2.78E-7 |
| 104 | 9.51E-8 |
| 105 | 1.29E-8 |
| 106 | 1.56E-7 |
| 107 | 1.06E-7 |
| 108 | 3.19E-8 |
| 109 | 2.49E-8 |
| 110 | 5.44E-8 |
| 111 | 5.39E-8 |
| 112 | 5.19E-8 |
| 113 | 1.40E-7 |
| 114 | 2.95E-8 |
| 115 | 1.85E-8 |
| 116 | 3.49E-9 |
| 117 | 1.56E-8 |
| 118 | 3.83E-7 |
| 119 | 1.06E-6 |
| 120 | 1.59E-8 |
| 121 | 3.82E-7 |
| 122 | 2.28E-8 |
| 123 | 6.46E-7 |
| 124 | 5.06E-9 |
| 125 | 2.29E-8 |
| 126 | 6.46E-7 |
| 127 | 3.15E-8 |
| 128 | 1.73E-6 |
| 129 | 5.60E-9 |
| 130 | 7.23E-8 |
| 131 | 1.02E-6 |
| 132 | 3.86E-8 |
| 133 | 1.77E-6 |
| 134 | 7.59E-9 |
| 135 | 8.62E-8 |
| 136 | 1.27E-8 |
| 137 | 2.90E-6 |
| 138 | 2.04E-6 |
| 139 | 1.07E-7 |
| 140 | 3.58E-8 |
| 141 | 3.43E-6 |
| 142 | 1.35E-8 |
| 143 | 3.49E-7 |
| 144 | 4.76E-8 |
| 145 | 5.04E-8 |
| 146 | 1.26E-8 |
| 147 | 1.31E-6 |
| 148 | 2.42E-8 |
| 149 | 5.21E-8 |
| 150 | 2.62E-6 |
| 151 | 4.65E-8 |
| 152 | 9.14E-7 |
| 153 | 1.17E-8 |
| 154 | 4.28E-8 |
| 155 | 1.58E-7 |
| 156 | 3.29E-8 |
| 157 | 2.95E-8 |
| 161 | 2.78E-7 |
| 167 | 2.95E-7 |
| 168 | 1.19E-6 |
| 169 | 2.54E-7 |
| 170 | 5.73E-7 |
| 171 | 3.19E-7 |
| 172 | 1.86E-6 |
| 173 | 1.24E-6 |
| 174 | 4.44E-7 |
| 175 | 3.46E-8 |
| 176 | 1.98E-7 |
| 177 | 7.01E-8 |
| 178 | 2.69E-7 |
| 179 | 8.52E-8 |
| 180 | 6.64E-8 |
| 181 | 2.30E-6 |
| 182 | 7.41E-7 |
| 183 | 1.00E-6 |
| 184 | 2.37E-8 |
| 185 | 6.90E-8 |
| 186 | 4.37E-8 |
| 187 | 2.39E-8 |
| 188 | 2.42E-8 |
| 189 | 1.50E-8 |
| 190 | 3.61E-8 |
| 191 | 6.01E-8 |
| 192 | 1.35E-8 |
| 193 | 2.32E-7 |
| 194 | 6.82E-9 |
| 195 | 1.05E-8 |
| 196 | 7.47E-8 |
| 197 | 1.93E-8 |
| 198 | 2.00E-8 |
| 199 | 3.02E-8 |
| 200 | 1.77E-8 |
| 201 | 6.57E-9 |
| 202 | 1.04E-8 |
| 203 | 1.67E-8 |
| 204 | 2.08E-8 |
| 205 | 6.64E-8 |
| 206 | 1.01E-8 |
| 207 | 1.41E-8 |
| 208 | 2.81E-8 |
| 209 | 3.93E-8 |
| 210 | 3.50E-8 |
| 211 | 1.90E-7 |

TABLE 1-continued

Enzymatic conversion of PGH2 to PGE2

| Patent Example | Human PTGES IC50 [mol/l] |
|---|---|
| 212 | 5.69E−7 |
| 213 | 3.28E−7 |
| 214 | 3.81E−7 |
| 215 | 2.58E−7 |

The results of the biochemical enzyme inhibition assay demonstrate that the examples are potent human PTGES inhibitors.

Endometriosis Disease Model (Dyspareunia Model)

Female SD rats underwent endometriosis surgery in the estrus phase. 4 uterine fragments were sewn onto the mesenteric artery arc (closed to small intestine) and few other fragments (>2) were sewn onto the distal colonic wall. In parallel electrodes for later Electromyography (EMG) recordings were implanted in the abdominal wall to allow recording of the visceral motor response. After training viscero-motor response (VMR)/vaginal distension (VD) testing was performed 5 and 6 weeks post-surgery in the proestrus phase. For vaginal distension session, the uninflated balloon was lubricated and inserted into the mid-vaginal canal, located so, that it would not touch the cervix even when inflated. Inflating the balloon with different volumes of water using a computer-controlled pump distended the vaginal canal. In parallel, EMG recordings were collected to measure the VMR related to the distension. At 6 weeks, post-surgery endometriotic lesions and endometrium were excised to perform lesion analysis. RNA expression analysis was performed of lesions and endometrium. RNA of lesions and endometrium was isolated after homogenization of tissues in guanidinium thiocyanate using the RNeasy mini Kit (Qiagen) with DNase digestion. One microgram of RNA was reversely transcribed with random hexamers using the SuperScript III First-Strand Synthesis System (Invitrogen). Real-time Taqman PCR analysis was performed using the 7900HT Real Time PCR-System (Applied Biosystems). Prevalidated probes and primers for Mki67 (antigen identified by monoclonal antibody Ki-67; catalog No. Rn01451446_m1) and the endogenous control TBP* (see FIG. 1A; TATA box binding protein; catalog No. Rn01455646_m1) were purchased from Applied Biosystems. Relative mRNA levels were calculated using the comparative □CT method using the RQ-Manager software (Applied Biosystems).

Example 17 (0.75 mg/kg, bid, p.o.) was administered twice daily starting end of week 2 post surgery until week 5 post surgery.

Repeated oral dosing of Example 17 (0.75 mg/kg, bid.; n=18/group; vehicle) significantly decreased vaginal hyperalgesia versus vehicle-treated animals. The effect was maintained in the treatment free period of week 6. Treatment with Example 17 also significantly reduced proliferation in lesions compared to vehicle treated animals, as measured by decreased gene expression of the proliferation marker Ki67 vs. housekeeping control in Taqman in week 6. Thus, the data in dyspareunia model indicate that Example 17 is anti-proliferative in vivo and reduces vaginal hyperalgesia. Anti-proliferative data indicate a disease-modifying component beyond analgesic effects following sustained PTGES inhibition (see FIG. 1).

As it can be seen in FIG. 1, example 17 induced sustained pain reduction in endometriosis dyspareunia model in rats. Example 17 also significantly reduced the proliferation in endometriotic lesions compared to vehicle treated animals.

PGE2 Measurements in CFA Inflammation Model Using Humanized KI Mice

Figure 2:
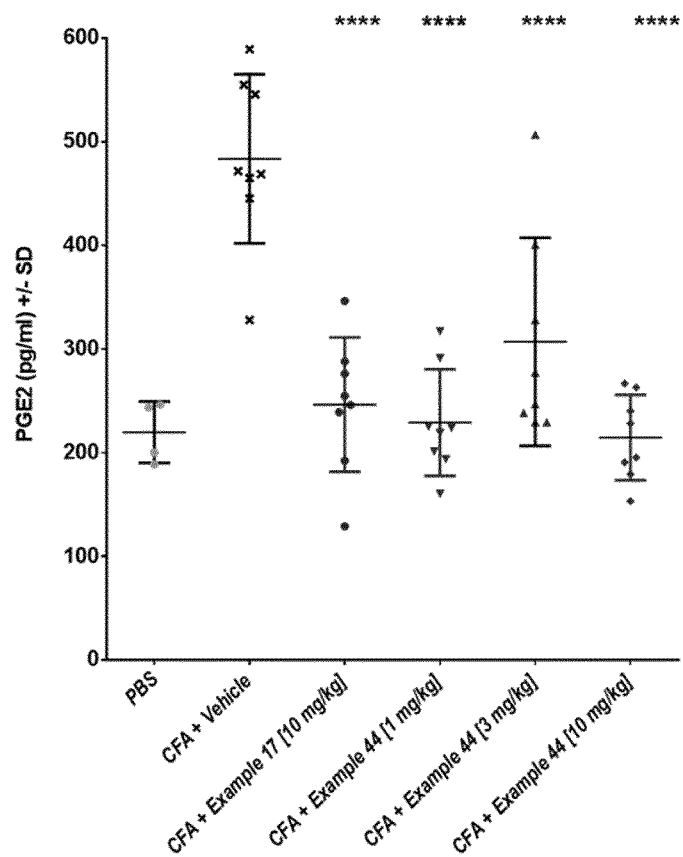

Female transgenic mice expressing the human PTGES enzyme (Taconic, Xu et al. 2008) received intraplantar injection of complete Freund's adjuvant (CFA) (30 μl, 1 mg/ml, Sigma) into the left hind paw under isoflurane anesthesia. Animals received single oral dosing of example 2, 17, 44, 48, 55, 87. At termination of the experiments (48 h after CFA, 1 h after dose), hind paw tissue is collected for analysis of PGE2 levels (ELISA, Cayman Chemical item no. 514531). The data demonstrate that all compounds tested significantly inhibited CFA-induced PGE2 formation in the ipsilateral inflamed hind paw (see table 2). FIG. 2 demonstrates strong efficacy of example 17 and example 44 on the inhibition of PGE2 release in paws of hu KI mice after CFA injection into paws, in addition PGE2 release is not completely blocked in example 17 and example 44 treated animals. PGE2 levels after treatment with example 17 and example 44 are still in the range of PGE2 levels of PBS treated animals, indicating that residual PGE2 levels are maintained after PTGES inhibition. Statistical analysis is performed with one-way analysis of variance, followed by Bonferroni's multiple comparison test vs. vehicle controls using the GraphPad PRISM software, *p<0.05, **p<0.01.

TABLE 2

Inhibition of CFA induced PGE2 release in the ipsilateral inflamed hind paw of human KI mice (expressing human PTGES)

| Compound | hu IC$_{50}$ biochem. | Doses mg/kg, p.o. | % inhibition of PGE2 in vivo vs vehicle | Plasma concentration Cplasma-unbound |
|---|---|---|---|---|
| Example 17 | 35 nM | 10 | 88 | 380 nM |
| Example 44 | 18 nM | 1 | 95 | 15 nM |
|  |  | 3 | 65 | 47 nM |
|  |  | 10 | 100 | 173 nM |
| Example 55 | 27 nM | 1 | 84 | 34 nM |
|  |  | 3 | 93 | 103 nM |
|  |  | 10 | 96 | 322 nM |
| Example 87 | 8 nM | 1 | 43 | 25 nM |
|  |  | 3 | 65 | 75 nM |
|  |  | 10 | 67 | 172 nM |
| Example 48 | 3 nM | 1 | 38 | 11 nM |
|  |  | 3 | 74 | 32 nM |
|  |  | 10 | 78 | 88 nM |
| Example 2 | 21 nM | 1 | 37 | 21 nM |
|  |  | 3 | 75 | 62 nM |
|  |  | 10 | 94 | 190 nM |

Efficacy in CFA Inflammation Model with Pain Read Out

Wild type (WT) female c57bl/6 mice (Taconic) received intraplantar injection of complete Freund's adjuvant (CFA) (30 μl, 1 mg/ml, Sigma) into the left hind paw under isoflurane anesthesia. Animals were administered single oral dosing of example 17 (30, 100 mg/kg, n=10/group) and example 44 (30, 75 mg/kg, n=10/group) on day 2 post-CFA injection. Spontaneous pain-related behavior in freely moving animals was assessed using the automated dynamic weight bearing device (DWB, Bioseb, France) according to published and validated protocols: Robinson I, Sargent B, Hatcher J P, Neurosci Lett. 2012 Aug. 30; 524(2):107-10. Use of dynamic weight bearing as a novel end-point for the assessment of Freund's Complete Adjuvant induced hypersensitivity in mice; Tétreault P, Dansereau M A, Doré-Savard L, Beaudet N, Sarret P. Physiol Behav. 2011 Sep. 1; 104(3):495-502 Weight bearing evaluation in inflammatory, neuropathic and cancer chronic pain in freely moving rats; Gruen M, Laux-Biehlmann A, Zollner T M, Nagel J. J Neurosci Methods. 2014 Jul. 30; 232:118-24. Use of dynamic weight bearing as a novel end-point for the assessment of abdominal pain in the LPS-induced peritonitis model in the rat. For behavioral testing, the animal was placed inside a Plexiglas chamber and allowed to move freely within the apparatus for a 5 min period, subsequently pain behavior is recorded for a test period of another 5 min. Both example 17 and example 44 significantly and dose-dependently reduced pain behavior as assessed by DWB after CFA-induced inflammation (see FIG. 3).

Statistical analysis is performed with one-way analysis of variance, followed by Bonferroni's multiple comparison test vs. vehicle controls using the GraphPad PRISM software, *p<0.05, **p<0.01.

Figure 3:
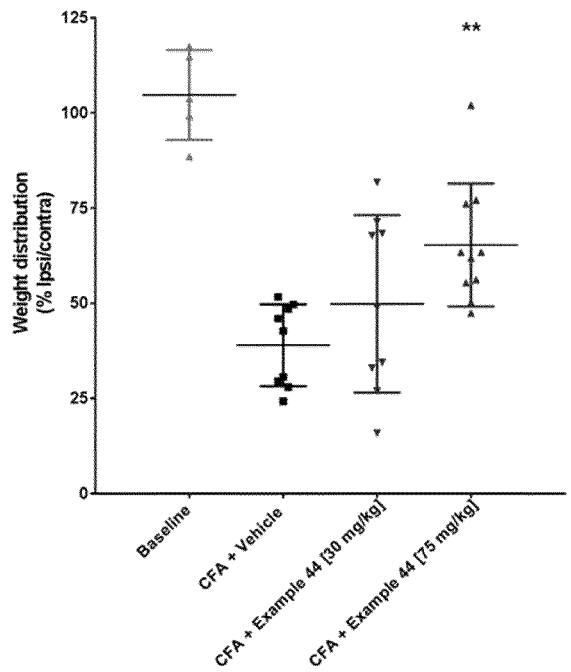
Figure 3:
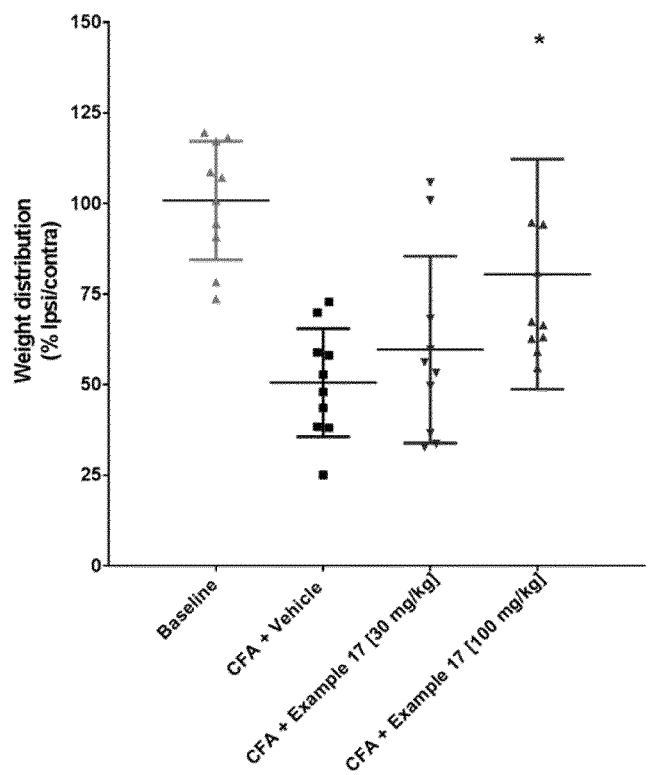

In conclusion, example 17 and example 44 dose-dependently reduced spontaneous pain behaviour in WT mice after CFA-induced inflammation as it can be seen from FIG. 3.

In Vivo NASH Mouse Model

To experimentally induce NASH, 200 µg streptozotocin (STZ; Sigma-Aldrich, USA) is each injected subcutaneously in 45 male 2-day-old C57BL/6 mice. Starting at 4 weeks of age, these animals are fed ad libitum with a high-fat diet (HFD; 57 kcal % fat, #HFD32 from CLEA, Japan). At an age of 6 weeks, the animals are randomized into 3 groups (15 animals per group). While one of the groups does not receive any treatment, the other 2 groups are daily orally treated either with vehicle or the test substance over 4 weeks. After the 4-week treatment, all animals are sacrificed painlessly under anaesthesia, and the livers are removed and fixed for the histological study in Bouin's solution (H. Denk, "Fixierung histologischer Präparate" [Fixing of Histological Preparations], in: P. Böck (ed.): "Romeis Mikroskopische Technik" [Romei's Microscopy Techniques], Urban & Schwarzenberg, Munich-Vienna-Baltimore 1989, 17th edition, page 97, ISBN 3-541-11227-1). Thereafter, the liver samples are embedded in paraffin and 5 µm-thick paraffin sections are produced. Histological sections of each liver are stained a) for the determination of the NAFLD activity score (NAS) with haematoxylin-eosin (HC), and b) for the determination of liver fibrosis with Picro-Sirius red (Waldeck, Germany). The NAFLD activity score is determined in the haematoxylin-eosin sections on the basis of the criteria recommended by D. E. Kleiner et al., Hepatology 41 (2005), 1313-1321 (Table 1). For the histological quantification of fibrotic areas, 5 digital photos (DFC280; Leica, Germany) are taken for each section under 200-fold microscope enlargement and the percentage of fibrosis is determined using the ImageJ Software (National Institute of Health, USA).

In Vivo Db/Db Mouse Model 30 male 8-week-old db/db mice are used. This model is a well-accepted model for obesity, insulin resistance and type 2 diabetes (Aileen J F King; The use of animal models in diabetes research; British Journal of Pharmacology 166 (2012), 877-894). During the experiment, the animals receive a standard diet (RM1(E) 801492, SDS) and tap water ad libitum. The animals are randomized into 3 groups (10 animals per group) and treated orally with the test substance over 6 weeks. During the study period, blood is taken from the animals at different time points (before start of treatment, 3 weeks after start of treatment and 2 days before the end of treatment) to determine insulin sensitivity parameters (e.g. HbA1c, glucose content, insulin content). In addition, an OGTT (oral glucose tolerance test) as a parameter for determination of insulin sensitivity is conducted 1 day before start of treatment and 2 days after the end of treatment. In addition, the HOMA-IR index (fasting insulin level (mU/l)*fasting glucose level (mmol/l)/22.5) is calculated.

In Vivo Adjuvant-Induced Arthritis Model

To determine the anti-inflammatory activity of the test compounds, they are examined for their in vivo efficacy in an arthritis model. For this purpose, male Lewis rats are each administered 100 µl of a complete Freund's adjuvant (CFA) solution (*M. tuberculosis* H37Ra [Difo Lab, Cat. No. −231141] dissolved in Incomplete Freund's adjuvant [Difco Lab, Cat. No. −263910]) into the tailhead subcutaneously on day 0. Both, a healthy control group and a disease control group are included in the study. Each control group is given p.o. treatment only with the vehicle of the test substance. The treatment with different dosages of the test substance is conducted in a preventative manner, i.e. starting from day 0, by oral administration. On day 0, the starting condition of the animals is additionally determined in terms of the disease activity scores (rating of the severity of arthritis based on a points system). Here, points are awarded according to the extent of joint inflammation from 0 to 4 for the presence of an erythema including joint swelling (0=none; 1=slight; 2=moderate; 3=distinct; 4=severe) for both hind paws and added up. To determine the anti-inflammatory efficacy of the test compounds, the disease activity of the animals is scored by means of disease activity scoring starting from day 8, when the animals first exhibit signs of arthritis, and subsequently 3 times per week, until the end (day 20). Statistical analysis is performed using single-factor variance analysis (ANOVA) and by comparison with the control group by means of multiple comparative analysis (Dunnett's test).

The s.c. administration of CFA in rats leads to acute arthritis with distinct joint inflammation in rats.

In Vivo Collagen Antibody-Induced Arthritis Model in Mice

The anti-inflammatory effect of the test compounds is examined in a further murine arthritis model. For this purpose, female Balb/c mice are each injected intravenously on day 0 with 200 µl of a collagen antibody cocktail (10 mg/ml; ArthritoMab, MD Bioproducts) into the tail vein (except for the healthy control group included in the study). On day 6, these mice each receive a further intraperitoneal injection of 200 µl of LPS. Both, a healthy control group and a disease control group are included in the study. Each control group is given p.o. treatment only with the vehicle of the test substance. The treatment with different dosages of the test substance is conducted in a preventative manner, i.e. starting from day 0, by oral administration. Over the course of the experiment, the extent of disease is scored based on a point award system for the disease activity score on all four paws. In this awarding of points, no points are awarded for a healthy paw, whereas points from 1 [mild inflammation, for example, of the toe(s)] to 4 [severe inflammation extending over the entire paw] are awarded in each case for the particular extent of joint inflammation that has arisen from the toes through the metatarsal joint to the ankle joint, as explained as follows:

0=normal
   1=erythema and mild swelling limited to the tarsal or ankle or toes
   2=erythema and mild swelling extending from the ankle to the metatarsus (2 segments)
   3=erythema and moderate swelling extending from the ankle as far as the metatarsal joints
   4=erythema and severe swelling encompassing the metatarsus, foot and toes For this parameter, the starting condition is determined beforehand one day before the start of the experiment (day −1) and this disease activity score is subsequently scored three times per week from day 8 onwards. Statistical analysis is performed using single-factor variance analysis (ANOVA) and by comparison with the control group by means of multiple comparative analysis (Dunnett's test).

The i.v. administration of a collagen antibody cocktail including the subsequent i.p. administration of LPS in mice leads to acute arthritis with distinct joint inflammation.

Cancer Cachexia Disease Model (C26 Tumor Model)

The aim of this study is to show efficacy of the test compound(s) on a mouse model of cancer cachexia. Mice are housed under standard laboratory conditions. The C26 tumor model is induced by unilateral subcutaneous inoculation of C26 cells (Cell Line Service, CLS, Eppelheim, Germany) dissolved in phosphate buffered saline (PBS) in susceptible BALB/c mice (C26 mice). Sham control mice receive a unilateral subcutaneous injection of PBS, instead (Sham mice).

Preventive setting: Starting on the day of C26 inoculation or Sham induction, C26 mice and Sham mice are treated with the test compound [dosages: 0/1/3/10/30/75/100/150 mg/kg dissolved in Ethanol/Solutol/Water (10/40/50 v/v/v)] once daily p.o. Therapeutic setting: Starting up to 7 days after C26 inoculation or Sham induction, C26 mice and Sham mice are treated with the test compound(s) [dosages: 0/1/3/10/30/75/100/150 mg/kg dissolved in Ethanol/Solutol/Water (10/40/50 v/v/v)] once daily p.o. In both experimental settings, the experiments continue up to day 21 post tumor inoculation.

During the experiment, body weight, tumor growth, food and water intake are monitored and body composition with regard to total body fat and lean body mass is determined before C26 inoculation or Sham induction and at the end of the experiment using either a quantitative echo magnetic resonance imaging method or dual-energy X-ray absorptiometry. Physical activity is assessed by rotarod test, grip test, open field test and total activity monitored in the home cages. At the end of the experiment, animals are weighed, killed, tumors are extirpated and the tumor-free carcasses are weighed again. Blood is collected and inner organs such as liver, heart, epididymal fat pads and peripheral muscles are freshly extirpated and weighed. Half of all collected tissues are snap frozen in liquid nitrogen and half of it proceeds to allow histological analysis. The degree of muscle atrophy is analysed by measuring the muscle fiber cross sectional area (Zeiss Observer Z1 mikroskope, zen software). RT-PCR and Western Blot technique is used to evaluate apoptosis (e.g. Caspase 3, BAX, BCL-XL) and protein degradation through the Ubiquitin-Proteolyse Pathway (e.g. MuRF1, MAFbx) in peripheral muscles. Metabolic symptoms are evaluated by measuring the content of glucose, triglycerides, albumin, and total protein in plasma, which is prepared from whole blood (cobas c111, Roche, Switzerland). Inflammatory cytokines, such as levels of interleukin (IL)-1, IL-6, IL-10, IL-12, interferon-gamma (IFN-γ), tumor necrosis factor-α (TNF-α) are analysed using Mesoscale and MSD®96-Well MULTI-ARRAY® and MULTI-SPOT®. The concentration of PGE metabolites and PGE2 in blood and muscles is determined with a Prostaglandin E Metabolite EIA Kit or a Luminex® xMAP® Prostaglandin E2 kit (Cayman Chemical, Ann Arbor, Mich.), respectively. Statistics is calculated using GraphPad Prism 6 program. Groups are compared using a one-way or two-way ANOVA. Bonferroni's post hoc test is used to determine significant differences between individual groups.

Cyclophosphamide-Induced Overactive Bladder (Rats)/Cyclophosphamide-Induced Cystitis (Rats)

The aim of this study is to test the efficacy on P2X3 receptor antagonists on overactive bladder as well as on cystitis in cyclophosphamide-treated rats.

The experimental setup is adapted to a previous descripted protocol (Lecci A et at, Br J Pharmacol 130: 331-38, 2000).

Briefly, female Sprague Daley rats (~200 g) are housed under normal conditions for laboratory rats in a 12:12-h light:dark cycle. The test compound is administrated by oral gavage (30 mg/kg) one hour before application of cyclophosphamide (100 mg/kg) by i.v. injection. Additional 1.5 hours after cyclophosphamide administration each rat is transferred to metabolic cage and voiding frequency is recorded for the next 15 hours. The micturition/per hour is recorded and the AUC during the plateau phase of the micturition (4-10 hours after transfer to metabolic cages) is calculated for each animal with GraphPad Prism 6 programme.

FIG. 1: Effect of example 17 on proliferation in lesions and endometrium (A) and vaginal hyperalgesia (B) in dyspareunia rat model)

FIG. 2: Effect of example 17 and example 44 on PGE2 levels in hu KI mice after CFA FIG. 3: Effect of example 17 and example 44 on CFA-induced pain (DWB) in WT mice

The invention claimed is:

1. A compound of formula (I):

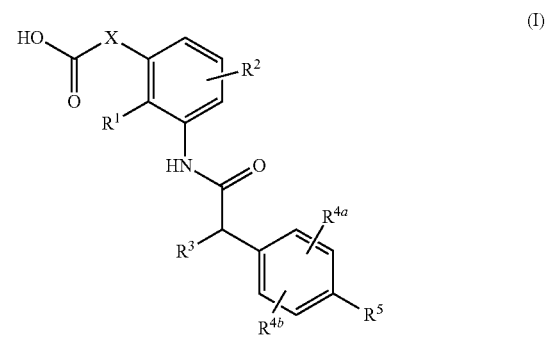

in which:
$R^1$ represents halogen, $C_1$-$C_4$-alkyl, or O—($C_1$-$C_4$-alkyl), wherein $C_1$-$C_4$-alkyl and O—($C_1$-$C_4$-alkyl) are optionally substituted with 1-5 halogen atoms which are the same or different;

$R^2$ represents hydrogen, halogen, $C_1$-$C_4$-alkyl, or O—($C_1$-$C_4$-alkyl), wherein $C_1$-$C_4$-alkyl and O—($C_1$-$C_4$-alkyl) are optionally substituted with 1-5 halogen atoms which are the same or different;

X is —$C_2H_4$—, —$CH_2$—Y—, —$CH_2$—$CR^6R^7$—, —$CR^6R^7$—$CH_2$—, or 1,2-cyclopropylidene;

$R^3$ is $C_3$-$C_6$-cycloalkyl, which is optionally substituted with one or more substituents which are the same or different and either halogen or $C_1$-$C_4$-alkyl;

$R^{4a}$ and $R^{4b}$ represent hydrogen, halogen, $C_1$-$C_4$-alkyl, —O—($C_1$-$C_4$-alkyl), $(CH_2)_n$—OH, wherein $C_1$-$C_4$-alkyl is optionally substituted with one or more substituents which are the same or different and either halogen or $C_1$-$C_4$-alkyl;

$R^5$ is pyridine, which is substituted with one or two substituents which are the same or different and selected from the group consisting of halogen, $C_1$-$C_4$-

239 alkyl, —O—(C₁-C₄-alkyl), OH, CN, —CH₂—OH, —CH₂—O—(C₁-C₄-alkyl), C₃-C₆-cycloalkyl, —O—(C₃-C₆-cycloalkyl), 3- to 7-membered-heterocycloalkyl-, and —O—(3- to 7-membered-heterocycloalkyl),
wherein said C₁-C₄-alkyl and —O—(C₁-C₄-alkyl) are optionally substituted with 1-5 halogen atoms which are the same or different;
R⁶ and R⁷ are different and selected from the group consisting of hydrogen, halogen, C₁-C₄-alkyl, and C₃-C₆-cycloalkyl;
R⁸ represents hydrogen or C₁-C₄-alkyl;
Y represents O or NR⁸;
n is 0, 1 or 2;
or a tautomer, an isomer, enantiomer, diastereomer, racemate, an N-oxide, or a salt thereof, or a mixture of same.

2. A compound according to claim 1, wherein R⁴ᵃ is in ortho position in relation to R⁵.

3. A compound according to claim 1, wherein R¹ represents an optionally substituted C₁-C₄-alkyl.

4. A compound according to claim 1, wherein R² represents hydrogen or halogen.

5. A compound according to claim 1, wherein R³ represents unsubstituted C₃-C₆-cycloalkyl.

6. A compound according to claim 1, wherein n is 1.

7. A compound according to claim 1, wherein R⁴ᵃ and R⁴ᵇ represent hydrogen, halogen, or C₁-C₄-alkyl.

8. A compound according to claim 1, wherein R⁴ᵇ is in meta position in relation to R⁵.

9. A compound according to claim 1, wherein R⁵ represents pyridine-3-yl, which is substituted with one or two substituents which are the same or different and selected from the group consisting of halogen, C₁-C₄-alkyl, —O—(C₁-C₄-alkyl), C₃-C₆-cycloalkyl, and —O—(C₃-C₆-cycloalkyl).

10. A compound according to claim 1, wherein R⁵ represents pyridine-3-yl, which is substituted with a halogen.

11. A compound according to claim 10, wherein R⁵ is additionally substituted with C₁-C₄-alkyl.

12. A compound according to claim 1, wherein R¹ represents unsubstituted C₁-C₄-alkyl; and R² represents hydrogen.

13. A compound according to claim 1, wherein R¹ represents unsubstituted C₁-C₄-alkyl; R² represents hydrogen; and R³ represents unsubstitued C₃-C₆-cycloalkyl.

14. A compound according to claim 1, wherein R¹ represents unsubstituted C₁-C₄-alkyl; R² represents hydrogen; R³ represents unsubstitued C₃-C₆-cycloalkyl; and R⁴ᵃ and R⁴ᵇ both represent hydrogen.

15. A compound according to claim 1, wherein R¹ represents unsubstituted C₁-C₄-alkyl; R² represents hydrogen; R³ represents unsubstitued C₃-C₆-cycloalkyl; R⁴ᵃ and R⁴ᵇ both represent hydrogen; and R⁵ represents pyridine-3-yl, which is substituted with one halogen.

16. A compound according to claim 1, which is selected from the group consisting of:
1) (R/S) 3-{3-[(Cyclopentyl{4-[5-(trifluormethyl)pyridin-3-yl]phenyl}-acetyl)amino]-2-methylphenyl}propanoic acid (Example 1);

240

2) (−) 3-{3-[(Cyclopentyl{4-[5-(trifluormethyl)pyridin-3-yl]phenyl}-acetyl)amino]-2-methylphenyl}propanoic acid (Example 2);
3) (+) 3-{3-[(Cyclopentyl{4-[5-(trifluormethyl)pyridin-3-yl]phenyl}-acetyl)amino]-2-methylphenyl}propanoic acid (Example 3);
4) (R/S) 3-{3-[(Cyclopentyl{4-[6-(trifluormethyl)pyridin-3-yl]phenyl}-acetyl)amino]-2-methylphenyl}propanoic acid (Example 4);
5) (−) 3-{3-[(Cyclopentyl{4-[6-(trifluormethyl)pyridin-3-yl]phenyl}-acetyl)amino]-2-methylphenyl}propanoic acid (Example 5);
6) (R/S) 3-[3-({Cyclopentyl[4-(5-fluorpyridin-3-yl)phenyl]acetyl}amino)-2methylphenyl]propanoic acid (Example 6);
7) (R/S) 3-[3-({[4-(6-Cyanpyridin-3-yl)phenyl](cyclopentyl)acetyl}-amino)-2-methylphenyl]propanoic acid (Example 7);
8) (R/S) 3-[3-({Cyclopentyl[4-(5-ethoxypyridin-3-yl)phenyl]acetyl}-amino)-2-methylphenyl]propanoic acid (Example 8);
9) (R/S) 3-{3-[(Cyclopentyl{4-[5-(2-hydroxypropan-2-yl)pyridin-3-yl]-phenyl}acetyl)amino]-2-methylphenyl}propanoic acid (Example 9);
10) (R/S) 3-{3-[(Cyclopentyl{4-[5-(methoxymethyl)pyridin-3-yl]phenyl}-acetyl)amino]-2-methylphenyl}propanoic acid (Example 10);
11) (R/S) 3-[3-({Cyclopentyl[4-(5-methoxypyridin-3-yl)phenyl]acetyl}-amino)-2-methylphenyl]propanoic acid (Example 11);
12) (R/S) 3-[3-({Cyclopentyl[4-(4-methylpyridin-3-yl)phenyl]acetyl}-amino)-2-methylphenyl]propanoic acid (Example 12);
13) (R/S) 3-[3-({Cyclopentyl[4-(5-ethylpyridin-3-yl)phenyl]acetyl}amino)-2-methylphenyl]propanoic acid (Example 13);
14) 3-[3-({Cyclopentyl[4-(5-cyclopropylpyridin-3-yl)phenyl]acetyl}amino)-2-methylphenyl]propanoic acid (Example 14);
15) (R/S) 3-{3-[(Cyclopentyl{4-[5-(tetrahydro-2H-pyran-4-yloxy)pyridin-3-yl]phenyl}acetyl)amino]-2-methylphenyl}propanoic acid (Example 15);
16) (R/S) 3-[3-({[4-(5-Chlorpyridin-3-yl)phenyl](cyclopentyl)acetyl}-amino)-2-methylphenyl]propanoic acid (Example 16);
17) (−) (R) 3-[3-({[4-(5-Chloropyridin-3-yl)phenyl](cyclopentyl)acetyl}-amino)-2-methylphenyl]propanoic acid (Example 17);
18) (R/S) 3-[3-({Cyclopentyl[4-(6-methoxypyridin-3-yl)phenyl]acetyl}-amino)-2-methylphenyl]propanoic acid (Example 18);
19) (R/S) 3-[3-({Cyclopentyl[4-(6-fluoropyridin-3-yl)-phenyl]acetyl}-amino)-2-methylphenyl]propanoic acid (Example 19);
20) (R/S) 3-[3-({Cyclopentyl[4-(2-methoxypyridin-3-yl)-phenyl]acetyl}-amino)-2-methylphenyl]propanoic acid (Example 20);
21) (R/S) 3-[3-({Cyclopentyl[4-(5-methylpyridin-3-yl)phenyl]acetyl}-amino)-2-methylphenyl]propanoic acid (Example 21);
22) (R/S) 3-[3-({Cyclopentyl[4-(6-methylpyridin-3-yl)phenyl]acetyl}-amino)-2-methylphenyl]propanoic acid (Example 22);
23) (R/S) 3-[3-acyclopentyl[4-(2-fluoropyridin-3-yl)phenyl]acetyl}-amino)-2-methyl-phenyl]propanoic acid (Example 23);

24) (R/S) 3-[3-({[4-(5-Chloro-6-methylpyridin-3-yl)phenyl](cyclopentyl)-acetyl}amino)-2-methylphenyl]propanoic acid (Example 24);
25) (+) (S) 3-[3-({[4-(5-Chloro-6-methylpyridin-3-yl)phenyl](cyclo-pentyl)-acetyl}amino)-2-methylphenyl]propanoic acid (Example 25);
26) (−) (R) 3-[3-({[4-(5-Chloro-6-methylpyridin-3-yl)phenyl](cyclopentyl)-acetyl}amino)-2-methylphenyl]propanoic acid (Example 26);
27) (R/S) 3-[3-({Cyclopentyl[4-(5,6-dimethylpyridin-3-yl)phenyl]acetyl}-amino)-2-methylphenyl]propanoic acid (Example 27);
28) (R/S) 3-{3-[(Cyclopentyl{4-[5-(difluoromethoxy)pyridin-3-yl]phenyl}-acetyl)amino]-2-methylphenyl}propanoic acid (Example 28);
29) (R/S) 3-{3-[(Cyclopentyl{4-[5-(difluoromethyl)pyridin-3-yl]phenyl}-acetyl)amino]-2-methylphenyl}propanoic acid (Example 29);
30) (R/S) 3-{3-[(Cyclopentyl{4-[5-(fluoromethyl)pyridin-3-yl]phenyl}-acetyl)amino]-2-methylphenyl}propanoic acid (Example 30);
31) (R/S) 3-[3-({[4-(5-Chlorpyridin-3-yl)phenyl](cyclopropyl)acetyl}-amino)-2-methylphenyl]propanoic acid (Example 31);
32) 3-{3-[(Cyclopropyl{4-[5-(trifluormethyl)pyridin-3-yl]phenyl}acetyl)-amino]-2-methylphenyl}propanoic acid (Example 32);
33) (R/S) {3-[(cyclopentyl{4-[5-(trifluoromethyl)pyridin-3-yl]phenyl}-acetyl)amino]-2-methylphenoxy}acetic acid (Example 33);
34) (−) {3-[(cyclopentyl{4-[5-(trifluoromethyl)pyridin-3-yl]phenyl}-acetyl)amino]-2-methylphenoxy}acetic acid (Example 34);
35) (+) {3-[(cyclopentyl{4-[5-(trifluoromethyl)pyridin-3-yl]phenyl}-acetyl)amino]-2-methylphenoxy}acetic acid (Example 35);
36) (R/S) [3-({[4-(5-chloropyridin-3-yl)phenyl](cyclopentyl)acetyl}-amino)-2-methylphenoxy]acetic acid (Example 36);
37) (−)[3-({[4-(5-chloropyridin-3-yl)phenyl](cyclopentyl)acetyl}amino)-2-methylphenoxy]acetic acid (Example 37);
38) (R/S) 3-[3-({[4-(5-Chloropyridin-3-yl)phenyl](cyclopentyl)acetyl}-amino)-6-methoxy-2-methylphenyl]propanoic acid (Example 38);
39) (−) 3-[3-({[4-(5-Chloropyridin-3-yl)phenyl](cyclopentyl)acetyl}-amino)-6-methoxy-2-methylphenyl]propanoic acid (Example 39);
40) (R/S) 3-{3-[(Cyclopentyl{4-[5-( trifluoromethyl)pyridin-3-yl]phenyl}-acetyl)amino]-6-methoxy-2-methylphenyl}propanoic acid (Example 40);
41) (R/S) 3-{3-[(Cyclopentyl{3-methyl-4-[5-(trifluoromethyl)pyridin-3-yl]phenyl}acetyl)amino]-2-methylphenyl}propanoic acid (Example 41);
42) (R/S) 3-[3-({[4-(5-Chloropyridin-3-yl)-3methylphenyl](cyclopentyl)acetyl}amino)-2-methylphenyl]propanoic acid (Example 42);
43) (R/S) 3-[3-({[4-(5-Chloropyridin-3-yl)-3-fluorophenyl](cyclopentyl)-acetyl}amino)-2-methylphenyl]propanoic acid (Example 43);
44) (−) 3-[3-({[4-(5-Chloropyridin-3-yl)-3-fluorophenyl](cyclopentyl)-acetyl}amino)-2-methylphenyl]propanoic acid (Example 44);
45) (+) 3-[3-({[4-(5-Chloropyridin-3-yl)-3-fluorophenyl](cyclopentyl)-acetyl}amino)-2-methylphenyl]propanoic acid (Example 45);
46) (R/S) 3-[3-({Cyclopentyl[4-(5-ethoxypyridin-3-yl)-3-fluorophenyl]-acetyl}amino)-2-methylphenyl]propanoic acid (Example 46);
47) (R/S) 3-{3-[(Cyclopentyl{3-fluoro-4-[5-(trifluoromethyl)pyridin-3-yl]-phenyl}acetyl)amino]-2-methylphenyl}propanoic acid (Example 47);
48) (−) 3-{3-[(Cyclopentyl{3-fluoro-4-[5-(trifluoromethyl)pyridin-3-yl]-phenyl}acetyl)amino]-2-methylphenyl}propanoic acid (Example 48);
49) (+) 3-{3-[(Cyclopentyl{3-fluoro-4-[5-(trifluoromethyl)pyridin-3-yl]-phenyl}acetyl)amino]-2-methylphenyl}propanoic acid (Example 49);
50) (R/S) 3-{3-[(cyclopentyl{4-[5-(difluoromethyl)pyridin-3-yl]-3-fluoro-phenyl}acetyl)amino]-2-methylphenyl}propanoic acid (Example 50);
51) (R/S) 3-[3-({[4-(5-Chloropyridin-3-yl)-2-fluorophenyl](cyclopentyl)-acetyl}amino)-2-methylphenyl]propanoic acid (Example 51);
52) (R/S) 3-[3-({Cyclopentyl[4-(5-ethoxypyridin-3-yl)-2-fluorophenyl]-acetyl}amino)-2-methylphenyl]propanoic acid (Example 52);
53) (R/S) 3-{3-[(Cyclopentyl{2-fluoro-4-[5-(trifluoromethyl)pyridin-3-yl]-phenyl}acetyl)amino]-2-methylphenyl}propanoic acid (Example 53);
54) (R/S) 3-{3-[(Cyclobutyl{4-[5-(trifluoromethyl)pyridin-3-yl]phenyl}-acetyl)amino]-2-methylphenyl}propanoic acid (Example 54);
55) (−) 3-{3-[(Cyclobutyl{4-[5-(trifluoromethyl)pyridin-3-yl]phenyl}-acetyl)amino]-2-methylphenyl}propanoic acid (Example 55);
56) (+) 3-{3-[(Cyclobutyl{4-[5-(trifluoromethyl)pyridin-3-yl]phenyl}-acetyl)amino]-2-methylphenyl}propanoic acid (Example 56);
57) (R/S) 3-[3-({[4-(5-Chloropyridin-3-yl)phenyl](cyclobutyl)acetyl}-amino)-2-methylphenyl]propanoic acid (Example 57);
58) (R/S) 3-[3-({Cyclobutyl[4-(5-ethoxypyridin-3-yl)phenyl]acetyl}-amino)-2-methylphenyl]propanoic acid (Example 58);
59) (R/S) 3-[3-({Cyclobutyl[4-(5, 6-dimethylpyridin-3-yl)phenyl]acetyl}-amino)-2-methylphenyl]propanoic acid (Example 59);
60) (R/S) 3-[3-({Cyclobutyl[4-(5-fluoropyridin-3-yl)phenyl]acetyl}amino)-2-methylphenyl]propanoic acid (Example 60);
61) (R/S) 3-[3-({[4-(5-chloro-6-methylpyridin-3-yl)phenyl](cyclobutyl)-acetyl}amino)-2-methylphenyl]propanoic acid (Example 61);
62) (R/S) 3-[3-({[4-(5-Fluoro-6-methylpyridin-3-yl)phenyl](cyclobutyl)-acetyl}amino)-2-methylphenyl]propanoic acid (Example 62);
63) (R/S) 3-{3-[(Cyclobutyl{4-[5-(difluoromethoxy)pyridin-3-yl]phenyl}-acetyl)amino]-2-methylphenyl}propanoic acid (Example 63);
64) (R/S) 3-[3-({Cyclobutyl[4-(5-methylpyridin-3-yl)phenyl]acetyl}-amino)-2-methylphenyl]propanoic acid (Example 64);
65) (R/S) 3-[3-({[4-(5-Chloropyridin-3-yl)phenyl](cyclohexyl)acetyl}-amino)-2-methylphenyl]propanoic acid (Example 65);
66) (R/S) 3-{3-[(Cyclohexyl{4-[5-(trifluoromethyl)pyridin-3-yl]phenyl}-acetyl)amino]-2-methylphenyl}propanoic acid (Example 66);
67) (R/S) 3-[3-({Cyclohexyl[4-(5-ethoxypyridin-3-yl)phenyl]acetyl}-amino)-2-methylphenyl]propanoic acid (Example 67);

68) (2R/S)-3-(3-{[(2R/S)-2-Cyclopentyl-2-{4-[5-(trifluoromethyl)pyridin-3-yl]phenyl}acetyl]amino}-2-methylphenyl)-2-methypropanoic acid (Example 68);
69) (2R)-3-(3-{[(2R)-2-cyclopentyl-2-{4-[5-(trifluoroethyl)pyridin-3-yl]phenyl}acetyl]annino}-2-methylphenyl)-2-methylpropanoic acid (Example 69);
70) (2S)-3-(3-{[(2S)-2-cyclopentyl-2-{4-[5-(trifluoroethyl)pyridin-3-yl]phenyl}acetyl]annino}-2-methylphenyl)-2-methylpropanoic acid (Example 70);
71) (2R)-3-(3-{[(2S)-2-cyclopentyl-2-{4-[5-(trifluoroethyl)pyridin-3-yl]phenyl}acetyl]annino}-2-methylphenyl)-2-methylpropanoic acid (Example 71);
72) (2S)-3-(3-{[(2R)-2-cyclopentyl-2-{4-[5-(trifluoroethyl)pyridin-3-yl]phenyl}acetyl]annino}-2-methylphenyl)-2-methylpropanoic acid (Example 72);
73) (2R/S)-3-[3-({(2R/S)-2-[4-(5-Chloropyridin-3-yl)phenyl]-2-cyclo-pentylacetyl}amino)-2-methylphenyl]-2-methylpropanoic acid (Example 73);
74) (2R)-3-[3-({(2R)-2-[4-(5-chloropyridin-3-yl)phenyl]-2-cyclopentyl-acetyl}amino)-2-methylphenyl]-2-methylpropanoic acid (Example 74);
75) (2S)-3-[3-({(2S)-2-[4-(5-chloropyridin-3-yl)phenyl]-2-cyclopentyl-acetyl}amino)-2-methylphenyl]-2-methylpropanoic acid (Example 75);
76) (2R)-3-[3-({(2S)-2-[4-(5-chloropyridin-3-yl)phenyl]-2-cyclopentyl-acetyl}amino)-2-methylphenyl]-2-methylpropanoic acid (Example 76);
77) (2S)-3-[3-({(2R)-2-[4-(5-chloropyridin-3-yl)phenyl]-2-cyclopentyl-acetyl}amino)-2-methylphenyl]-2-methylpropanoic acid (Example 77);
78) (2R/2S)-3-[3-({(2R/2S)-2-Cyclopentyl-2-[4-(5, 6-dimethylpyridin-3-yl)-phenyl]acetyl}amino)-2-methylphenyl]-2-methylpropanoic acid (Example 78);
79) (2R/2S)-3-[3-({(2R/2S)-2-Cyclopentyl-2-[4-(6-methylpyridin-3-yl)-phenyl]acetyl}amino)-2-methylphenyl]-2-methylpropanoic acid (Example 79);
80) (2R/2S)-3-(3-{[(2R/2S)-2-Cyclopentyl-2-{4-[5-(difluoromethoxy)-pyridin-3-yl]phenyl}acetyl]annino}-2-methylphenyl)-2-methyl-propanoic acid (Example 80);
81) (2R/2S)-3-[3-({(2R/2S)-2-Cyclopentyl-2-[4-(5-methylpyridin-3-yl)-phenyl]acetyl}amino)-2-methylphenyl]-2-methylpropanoic acid (Example 81);
82) (2R/2S)-3-[3-({(2R/2S)-2-Cyclopentyl-2-[4-(5-fluoro-6-methyl-pyridin-3-yl)phenyl]acetyl}amino)-2-methylphenyl]-2-methylpropanoic acid (Example 82);
83) (2R)-3-[3-({(2R)-2-[4-(5-chloro-6-methylpyridin-3-yl)phenyl]-2-cyclopentylacetyl}amino)-2-methylphenyl]-2-methylpropanoic acid (Example 83);
84) (2S)-3-[3-({(2R)-2-[4-(5-chloro-6-methylpyridin-3-yl)phenyl]-2-cyclopentylacetyl}amino)-2-methylphenyl]-2-methylpropanoic acid (Example 84);
85) (3R/S)-3-[3-({(2R/S)-2-[4-(5-Chloropyridin-3-yl)phenyl]-2-cyclo-pentyl-acetyl}amino)-2-methylphenyl]butanoic acid (Example 85);
86) (3R)-3-[3-({(2R)-2-[4-(5-chloropyridin-3-yl)phenyl]-2-cyclopentylacetyl}amino)-2-methylphenyl]butanoic acid (Example 86);
87) (3S)-3-[3-({(2S)-2-[4-(5-chloropyridin-3-yl)phenyl]-2-cyclopentyl-acetyl}amino)-2-methylphenyl]butanoic acid (Example 87);
88) (3R)-3-[3-({(2S)-2-[4-(5-chloropyridin-3-yl)phenyl]-2-cyclopentyl-acetyl}amino)-2-methylphenyl]butanoic acid (Example 88);
89) (3S)-3-[3-({(2R)-2-[4-(5-chloropyridin-3-yl)phenyl]-2-cyclopentyl-acetyl}amino)-2-methylphenyl]butanoic acid (Example 89);
90) (3R/S)-3-[3-({(2R/S)-2-Cyclopentyl-2-[4-(5-ethoxypyridin-3-yl)-phenyl]-acetyl}amino)-2-methylphenyl]butanoic acid (Example 90);
91) (3R/S)-3-(3-{[(2R/S)-2-Cyclopentyl-2-{4-[5-(trifluoromethyl)pyridin-3-yl]phenyl}acetyl]annino}-2-methylphenyl)butanoic acid (Example 91);
92) (3R/S)-3-[3-({(2R/S)-2-Cyclopentyl-2-[4-(5-ethylpyridin-3-yl)phenyl]-acetyl}amino)-2-methylphenyl]butanoic acid (Example 92);
93) (3R/S)-3-[3-({(2R/S)-2-Cyclopentyl-2-[4-(5, 6-dimethylpyridin-3-yl)-phenyl]acetyl}amino)-2-methylphenyl]butanoic acid (Example 93);
94) (3R/S)-3-[3-({(2R/S)-2-Cyclopentyl-2-[4-(5-methylpyridin-3-yl)phenyl]-acetyl}amino)-2-methylphenyl]butanoic acid (Example 94);
95) (3R/S)-3-[3-({(2R/S)-2-Cyclopentyl-2-[4-(5-fluoropyridin-3-yl)phenyl]-acetyl}amino)-2-methylphenyl]butanoic acid (Example 95);
96) (3R/S)-3-[3-({(2R/S)-2-[4-(5-Fluoro-6-methylpyridin-3-yl)phenyl]-2-cyclopentylacetyl}amino)-2-methylphenyl]butanoic acid (Example 96);
97) (3R/S)-3-[3-({(2R/S)-2-[4-(5-Chloro-6-methylpyridin-3-yl)phenyl]-2-cyclopentylacetyl}amino)-2-methylphenyl]butanoic acid (Example 97);
98) (3R/S)-3-(3-{[(2R/S)-2-Cyclopentyl-2-{4-[5-(difluoromethyl)pyridin-3-yl]phenyl}acetyl]annino}-2-methylphenyl)butanoic acid (Example 98);
99) (3R/S)-3-[3-({(2R/S)-2-[4-(5-Chloropyridin-3-yl)phenyl]-2-cyclo-pentylacetyl}amino)-2-methylphenyl]pentanoic acid (Example 99);
100) (3R)-3-[3-({(2R)-2-[4-(5-chloropyridin-3-yl)phenyl]-2-cyclopentyl-acetyl}amino)-2-methylphenyl]pentanoic acid (Example 100);
101) (3S)-3-[3-({(2S)-2-[4-(5-chloropyridin-3-yl)phenyl]-2-cyclopentyl-acetyl}amino)-2-methylphenyl]pentanoic acid (Example 101);
102) (3R)-3-[3-({(2S)-2-[4-(5-chloropyridin-3-yl)phenyl]-2-cyclopentyl-acetyl}amino)-2-methylphenyl]pentanoic acid (Example 102);
103) (3S)-3-[3-({(2R)-2-[4-(5-chloropyridin-3-yl)phenyl]-2-cyclopentyl-acetyl}amino)-2-methylphenyl]pentanoic acid (Example 103);
104) (3R/S)-3-[3-({(2RS)-2-Cyclopentyl-2-[4-(5-methylpyridin-3-yl)-phenyl]-acetyl}amino)-2-methylphenyl]pentanoic acid (Example 104);
105) (3R/S)-3-[3-({(2R/S)-2-Cyclopentyl-2-[4-(5-ethylpyridin-3-yl)phenyl]-acetyl}amino)-2-methylphenyl]pentanoic acid (Example 105);
106) 3-[3-({[4-(5-Fluoropyridin-3-yl)phenyl](cyclopentyl)acetyl}amino)-2-methylphenyl]pentanoic acid (Example 106);
107) (3R/S)-3-[3-({(2R/S)-2-Cyclopentyl-2-[4-(5-ethoxypyridin-3-yl)-phenyl]-acetyl}amino)-2-methylphenyl]pentanoic acid (Example 107);
108) (3R/S)-3-[3-({(2R/S)-2-[4-(5-chloro-6-methylpyridin-3-yl)phenyl]-2-cyclopentylacetyl}amino)-2-methylphenyl]-3-cyclopropylpropanoic acid (Example 108);
109) (3R/S)-3-(3-{[(2R/S)-2-cyclopentyl-2-{4-[5-(trifluoromethyl)pyridin-3-yl]phenyl}acetyl]amino}-2-methylphenyl)-3-cyclopropylpropanoic acid (Example 109);
110) (3R/S)-3-[3-({(2R/S)-2-[4-(5-chloropyridin-3-yl)phenyl]-2-cyclo-pentylacetyl}amino)-2-methylphenyl]-3-cyclopropylpropanoic acid (Example 110);

111) (3R/S)-3-[3-({(2R/S)-2-cyclopentyl-2-[4-(5-ethoxy-pyridin-3-yl)-phenyl]acetyl}amino)-2-methylphenyl]-3-cyclopropylpropanoic acid (Example 111);

112) (3R/S)-3-[3-({(2R/S)-2-cyclopentyl-2-[4-(5-fluoro-pyridin-3-yl)-phenyl]acetyl}amino)-2-methylphenyl]-3-cyclopropylpropanoic acid (Example 112);

113) (3R/S)-3-[3-({(2R/S)-2-cyclopentyl-2-[4-(5-methyl-pyridin-3-yl)-phenyl]acetyl}amino)-2-methylphenyl]-3-cyclopropylpropanoic acid (Example 113);

114) (3R/S)-3-[3-({(2R/S)-2-cyclopentyl-2-[4-(5-ethyl-pyridin-3-yl)phenyl]-acetyl}amino)-2-methylphenyl]-3-cyclopropylpropanoic acid (Example 114);

115) (3R/S)-3-(3-{[(2R/S)-2-Cyclopentyl-2-{3-fluoro-4-[5-(trifluoro-methyl)-pyridin-3-yl]phenyl}acetyl]annino}-2-methylphenyl)butanoic acid (Example 115);

116) (3R)-3-(3-{[(2R)-2-cyclopentyl-2-{3-fluoro-4-[5-(trifluoromethyl)-pyridin-3-yl]phenyl}acetyl]annino}-2-methylphenyl)butanoic acid (Example 116);

117) (3S)-3-(3-{[(2S)-2-cyclopentyl-2-{3-fluoro-4-[5-(trifluoromethyl)-pyridin-3-yl]phenyl}acetyl]annino}-2-methylphenyl)butanoic acid (Example 117);

118) (3R)-3-(3-{[(2S)-2-cyclopentyl-2-{3-fluoro-4-[5-(trifluoromethyl)-pyridin-3-yl]phenyl}acetyl)amino}-2-methylphenyl)butanoic acid (Example 118);

119) (3S)-3-(3-{[(2R)-2-cyclopentyl-2-{3-fluoro-4-[5-(trifluoromethyl)-pyridin-3-yl]phenyl}acetyl]annino}-2-methylphenyl)butanoic acid (Example 119);

120) (3R/S)-3-[3-({(2R/S)-2-[4-(5-Chloro-6-methylpyridin-3-yl)-3-fluoro-phenyl]-2-cyclopentylacetyl}amino)-2-methylphenyl]butanoic acid (Example 120);

121) (3R)-3-[3-({(2R)-2-[4-(5-chloro-6-methylpyridin-3-yl)-3-fluoro-phenyl]-2-cyclopentylacetyl}amino)-2-methylphenyl]butanoic acid (Example 121);

122) (3S)-3-[3-({(2S)-2-[4-(5-chloro-6-methylpyridin-3-yl)-3-fluoro-phenyl]-2-cyclopentylacetyl}amino)-2-methylphenyl]butanoic acid (Example 122);

123) (3R)-3-[3-({(2S)-2-[4-(5-chloro-6-methylpyridin-3-yl)-3-fluoro-phenyl]-2-cyclopentylacetyl}amino)-2-methylphenyl]butanoic acid (Example 123);

124) (3S)-3-[3-({(2R)-2-[4-(5-chloro-6-methylpyridin-3-yl)-3-fluoro-phenyl]-2-cyclopentylacetyl}amino)-2-methylphenyl]butanoic acid (Example 124);

125) (3R/S)-3-[3-({(2R/S)-2-[4-(5-Chloropyridin-3-yl)-3-fluorophenyl]-2-cyclopentylacetyl}amino)-2-methylphenyl]butanoic acid (Example 125);

126) (3R)-3-[3-({(2R)-2-[4-(5-chloropyridin-3-yl)-3-fluorophenyl]-2-cyclopentylacetyl}amino)-2-methylphenyl]butanoic acid (Example 126);

127) (3S)-3-[3-({(2S)-2-[4-(5-chloropyridin-3-yl)-3-fluorophenyl]-2-cyclopentylacetyl}amino)-2-methylphenyl]butanoic acid (Example 127);

128) (3R)-3-[3-({(2S)-2-[4-(5-chloropyridin-3-yl)-3-fluorophenyl]-2-cyclopentylacetyl}amino)-2-methylphenyl]butanoic acid (Example 128);

129) (3S)-3-[3-({(2R)-2-[4-(5-chloropyridin-3-yl)-3-fluorophenyl]-2-cyclopentylacetyl}amino)-2-methylphenyl]butanoic acid (Example 129);

130) (3R/S)-3-(3-{[(2R/S)-2-Cyclobutyl-2-{4-[5-(trifluoromethyl)pyridin-3-yl]phenyl}acetyl]annino}-2-methylphenyl)butanoic acid (Example 130);

131) (3R)-3-(3-{[(2R)-2-cyclobutyl-2-{4-[5-(trifluoromethyl)pyridin-3-yl]phenyl}acetyl]annino}-2-methylphenyl)butanoic acid (Example 131);

132) (3S)-3-(3-{[(2S)-2-cyclobutyl-2-{4-[5-(trifluoromethyl)pyridin-3-yl]phenyl}acetyl]annino}-2-methylphenyl)butanoic acid (Example 132);

133) (3R)-3-(3-{[(2S)-2-cyclobutyl-2-{4-[5-(trifluoromethyl)pyridin-3-yl]phenyl}acetyl]annino}-2-methylphenyl)butanoic acid (Example 133);

134) (3S)-3-(3-{[(2R)-2-cyclobutyl-2-{4-[5-(trifluoromethyl)pyridin-3-yl]phenyl}acetyl]annino}-2-methylphenyl)butanoic acid (Example 134);

135) (3R/S)-3-[3-({(2R/S)-2-[4-(5-Chloropyridin-3-yl)phenyl]-2-cyclobutyl-acetyl}amino)-2-methylphenyl]butanoic acid (Example 135);

136) (3R)-3-[3-({(2R)-2-[4-(5-chloropyridin-3-yl)phenyl]-2-cyclobutyl-acetyl}amino)-2-methylphenyl]butanoic acid (Example 136);

137) (3S)-3-[3-({(2S)-2-[4-(5-chloropyridin-3-yl)phenyl]-2-cyclobutyl-acetyl}amino)-2-methylphenyl]butanoic acid (Example 137);

138) (3R)-3-[3-({(2S)-2-[4-(5-chloropyridin-3-yl)phenyl]-2-cyclobutyl-acetyl}amino)-2-methylphenyl]butanoic acid (Example 138);

139) (3S)-3-[3-({(2R)-2-[4-(5-chloropyridin-3-yl)phenyl]-2-cyclobutyl-acetyl}amino)-2-methylphenyl]butanoic acid (Example 139);

140) (3R/S)-3-[3-({(2R/S)-2-[4-(5-Chloro-6-methylpyridin-3-yl)phenyl]-2-cyclobutylacetyl}amino)-2-methylphenyl]butanoic acid (Example 140);

141) (3R)-3-[3-({(2R)-2-[4-(5-chloro-6-methylpyridin-3-yl)phenyl]-2-cyclobutylacetyl}amino)-2-methylphenyl]butanoic acid (Example 141);

142) (3S)-3-[3-({(2S)-2-[4-(5-chloro-6-methylpyridin-3-yl)phenyl]-2-cyclobutylacetyl}amino)-2-methylphenyl]butanoic acid (Example 142);

143) (3R)-3-[3-({(2S)-2-[4-(5-chloro-6-methylpyridin-3-yl)phenyl]-2-cyclobutylacetyl}amino)-2-methylphenyl]butanoic acid (Example 143);

144) (3S)-3-[3-({(2R)-2-[4-(5-chloro-6-methylpyridin-3-yl)phenyl]-2-cyclobutylacetyl}amino)-2-methylphenyl]butanoic acid (Example 144);

145) (3R/S)-3-(3-{[(2R/S)-2-Cyclobutyl-2-{3-fluoro-4-[5-(trifluoromethyl)-pyridin-3-yl]phenyl}acetyl]annino}-2-methylphenyl)butanoic acid (Example 145);

146) 3-{3-[(Cyclobutyl{3-fluoro-4-[5-(trifluoromethyl)pyridin-3-yl]phenyl}-acetyl)amino]-2methylphenyl}butanoic acid (Example 146);

147) (3R)-3-(3-{[(2R)-2-cyclobutyl-2-{3-fluoro-4-[5-(trifluoromethyl)-pyridin-3-yl]phenyl}acetyl]amino}-2-methylphenyl)butanoic acid (Example 147);

148) (3S)-3-(3-{[(2R)-2-cyclobutyl-2-{3-fluoro-4-[5-(trifluoromethyl)-pyridin-3-yl]phenyl}acetyl]amino}-2-methylphenyl)butanoic acid (Example 148);

149) a3R/S)-3-[3-({(2R/S)-2-[4-(5-Chloropyridin-3-yl)-3-fluorophenyl]-2-cyclobutylacetyl}amino)-2-methylphenyl]butanoic acid (Example 149);

150) (3R)-3-[3-({(2R)-2-[4-(5-chloropyridin-3-yl)-3-fluorophenyl]-2-cyclo-butylacetyl}amino)-2-methylphenyl]butanoic acid (Example 150);

151) (3S)-3-[3-({(2S)-2-[4-(5-chloropyridin-3-yl)-3-fluorophenyl]-2-cyclo-butylacetyl}amino)-2-methylphenyl]butanoic acid (Example 151);

152) (3R)-3-[3-({(2S)-2-[4-(5-chloropyridin-3-yl)-3-fluorophenyl]-2-cyclo-butylacetyl}amino)-2-methylphenyl]butanoic acid (Example 152);

153) (3S)-3-[3-({(2R)-2-[4-(5-chloropyridin-3-yl)-3-fluorophenyl]-2-cyclo-butylacetyl}amino)-2-methylphenyl]butanoic acid (Example 153);

154) 2-[3-({2-[4-(5-chloro-6-methylpyridin-3-yl)phenyl]-2-cyclopentyl-acetyl}amino)-2-methylphenyl]cyclopropanecarboxylic acid (Example 154);

155) 2-[3-({2-cyclopentyl-2-[4-(5-ethoxypyridin-3-yl)phenyl]acetyl}-amino)-2-methylphenyl]cyclopropanecarboxylic acid (Example 155);

156) 2-(3-{[2-cyclopentyl-2-{4-[5-(trifluoromethyl)pyridin-3-yl]phenyl}-acetyl]amino}-2-methylphenyl)cyclopropanecarboxylic acid (Example 156);

157) 2-(3-{[2-cyclopentyl-2-{4-[5-chloropyridin-3-yl]phenyl}acetyl]-amino}-2-methylphenyl)cyclopropanecarboxylic acid (Example 157);

158) (R/S) 3-(3-{[{2-chloro-4-[5-(trifluoromethyl)pyridin-3-yl]phenyl}-(cyclopentyl)acetyl]annino}-2-methylphenyl)propanoic acid (Example 161);

159) (R/S) 3-{3-[(cyclopentyl{4-[5-(trifluoromethyl)pyridin-3-yl]phenyl}-acetyl)amino]-5-fluoro-2-methylphenyl}propanoic acid (Example 167)

160) (R/S) 3-[3-({[4-(5-chloropyridin-3-yl)phenyl](cyclopentyl)acetyl}-amino)-5-fluoro-2-methylphenyl]propanoic acid (Example 168);

161) (R/S) 3-[3-({[4-(5-chloro-6-methylpyridin-3-yl)phenyl](cyclopentyl)-acetyl}amino)-5-fluoro-2-methylphenyl]propanoic acid (Example 169)

162) (R/S) 3-[3-({[4-(5-ethoxypyridin-3-yl)phenyl](cyclopentyl)acetyl}-amino)-5-fluoro-2-methylphenyl]propanoic acid (Example 170);

163) (R/S) N-{3-[(cyclopentyl{4-[5-(trifluoromethyl)pyridin-3-yl]phenyl}-acetyl)amino]-2-methylphenyl}glycine (Example 171);

164) (R/S) 3-[3-({[2-chloro-4-(5-chloropyridin-3-yl)-5methylphenyl]-(cyclopentyl)acetyl}amino)-2-methylphenyl]propanoic acid (Example 172);

165) (R/S) 3-(3-{[{2-chloro-5-methyl-4-[5-(trifluoromethyl)pyridin-3-yl]-phenyl}(cyclopentyl)acetyl]annino}-2-methylphenyl)propanoic acid (Example 173);

166) (R/S) 3-[3-({[2-chloro-4-(5-chloro-6-methylpyridin-3-yl)-5-methyl-phenyl](cyclopentyl)acetyl}amino)-2-methylphenyl]propanoic acid (Example 174);

167) (R/S) 3-(3-{[(2R)-2-{3-chloro-4-[5-(trifluoromethyl)pyridin-3-yl]-phenyl}-2-cyclopentylacetyl]annino}-2-methylphenyl)propanoic acid (Example 175);

168) (R/S) 3-[3-({[3-chloro-4-(5-chloro-6-methylpyridin-3-yl)phenyl]-(cyclopentyl)acetyl}amino)-2-methylphenyl]propanoic acid (Example 176);

169) (R/S) 3-[3-({[3-chloro-4-(5-chloropyridin-3-yl)phenyl](cyclopentyl)-acetyl}amino)-2-methylphenyl]propanoic acid (Example 177);

170) (R/S) 3-[3-({[4-(5-chloropyridin-3-yl)-2,5-difluorophenyl](cyclo-pentyl)-acetyl}amino)-2-methylphenyl]propanoic acid (Example 178);

171) (R/S) 3-{3-[(cyclopentyl{2,5-difluoro-4-[5-(trifluoromethyl)pyridin-3-yl]phenyl}acetyl)amino]-2-methylphenyl}propanoic acid (Example 179);

172) (R/S) 3-[3-({[4-(5-chloro-6-methylpyridin-3-yl)-2,5-difluorophenyl]-(cyclopentyl)acetyl}amino)-2-methylphenyl]propanoic acid (Example 180);

173) (R/S) 3-[3-({[4-(5-chloropyridin-3-yl)-2-fluoro-5methylphenyl]-(cyclopentyl)acetyl}amino)-2-methylphenyl]propanoic acid (Example 181);

174) (R/S) 3-[3-({[4-(5-chloro-6-methylpyridin-3-yl)-2-fluoro-5-methyl-phenyl](cyclopentyl)acetyl}amino)-2-methylphenyl]propanoic acid (Example 182);

175) (R/S) 3-{3-[(cyclopentyl{2-fluoro-5-methyl-4-[5-(trifluoromethyl)-pyridin-3-yl]phenyl}acetyl)amino]-2-methylphenyl}propanoic acid (Example 183);

176) 3-[3-({(2R)-2-[4-(5-chloro-6-methylpyridin-3-yl)phenyl]-2-cyclo-pentyl-acetyl}amino)-6-fluoro-2-methylphenyl]propanoic acid (Example 184);

177) 3-[3-({(2R)-2-[4-(5-chloropyridin-3-yl)phenyl]-2-cyclopentylacetyl}-amino)-6-fluoro-2-methylphenyl]propanoic acid (Example 185);

178) N-[3-({(2R)-2-[4-(5-chloropyridin-3-yl)phenyl]-2-cyclopentylacetyl}-amino)-2-methylphenyl]-N-methylglycine (Example 186);

179) N-[3-({(2R)-2-[4-(5-chloro-6-methylpyridin-3-yl)phenyl]-2-cyclo-pentylacetyl}amino)-2-methylphenyl]-N-methylglycine (Example 187);

180) N-(3-{[(2R)-2-cyclopentyl-2-{3-fluoro-4-[5-(trifluoromethyl)pyridin-3-yl]phenyl}acetyl]amino}-2-methylphenyl)-N-methylglycine (Example 188);

181) 3-(3-{[(2R)-2-cyclopentyl-2-{4-[5-(2-methylpropyl)pyridin-3-yl]-phenyl}-acetyl]amino}-2-methylphenyl)propanoic acid (Example 189);

182) 3-(3-{[(2R)-2-cyclopentyl-2-{4-[5-(propan-2-yloxy)pyridin-3-yl]-phenyl}-acetyl]amino}-2-methylphenyl)propanoic acid (Example 190);

183) 3-(3-{[(2R)-2-cyclopentyl-2-{4-[5-(2,2,2-trifluoroethyl)pyridin-3-yl]-phenyl}acetyl]amino}-2-methylphenyl)propanoic acid (Example 191);

184) 3-(3-{[(2R)-2-cyclopentyl-2-{4-[6-methyl-5-(trifluoromethyl)pyridin-3-yl]phenyl}acetyl]amino}-2-methylphenyl)propanoic acid (Example 192);

185) 3-[3-({(2R)-2-[4-(5-chloropyridin-3-yl)phenyl]-2-cyclopentylacetyl}-amino)-2-methylphenyl]-3-hydroxypropanoic acid (Example 193);

186) 3-[3-acyclopentyl[3-fluoro-4-(5-isobutylpyridin-3-yl)phenyl]acetyl}-amino)-2-methylphenyl]pentanoic acid (Example 194);

187) 3-[3-acyclopentyl[4-(5-ethylpyridin-3-yl)-3-fluorophenyl]acetyl}-amino)-2-methylphenyl]pentanoic acid (Example 195);

188) (−) 3-{3-[(cyclopentyl{3-fluoro-4-[5-(2,2,2-trifluoroethyl)pyridin-3-yl]-phenyl}acetyl)amino]-2-methylphenyl}propanoic acid (Example 196);

189) (−) 3-{3-[(cyclopentyl{3-fluoro-4-[6-methyl-5-(trifluoromethyl)-pyridin-3-yl]phenyl}acetyl)amino]-2-methylphenyl}propanoic acid (Example 197);

190) (−) 3-[3-acyclopentyl[3-fluoro-4-(5-isobutyl-6-methylpyridin-3-yl)-phenyl]acetyl}amino)-2-methylphenyl]propanoic acid (Example 198);

191) (−) 3-[3-acyclopentyl[3-fluoro-4-(5-isopropoxypyridin-3-yl)phenyl]-acetyl}amino)-2-methylphenyl]propanoic acid (Example 199);

192) 3-(3-{[(2R)-2-cyclopentyl-2-{4-[5-(2,2,2-trifluoroethyl)pyridin-3-yl]-phenyl}acetyl]amino}-2-methylphenyl)pentanoic acid (Example 200);

193) 3-(3-{[(2R)-2-cyclopentyl-2-{4-[6-methyl-5-(trifluoromethyl)pyridin-3-yl]phenyl}acetyl]amino}-2-methylphenyl)pentanoic acid (Example 201);

194) 3-[3-({(2R)-2-cyclopentyl-2-[4-(5-isobutylpyridin-3-yl)phenyl]acetyl}-amino)-2-methylphenyl]pentanoic acid (Example 202);

195) 3-[3-({(2R)-2-cyclopentyl-2-[4-(5-isopropoxypyridin-3-yl)phenyl]-acetyl}amino)-2-methylphenyl]pentanoic acid (Example 203);

196) 3-[3-({(2R)-2-cyclopentyl-2-[4-(5-ethylpyridin-3-yl)phenyl]acetyl}-amino)-2-methylphenyl]pentanoic acid (Example 204);

197) 3-{3-[(cyclobutyl{3-fluoro-4-[5-(2,2,2-trifluoroethyl)pyridin-3-yl]-phenyl}acetyl)amino]-2-methylphenyl}propanoic acid (Example 205);

198) (−) 3-{3-[(cyclobutyl{3-fluoro-4-[6-methyl-5-(trifluoromethyl)pyridin-3-yl]phenyl}acetyl)amino]-2-methylphenyl}propanoic acid (Example 206);

199) 3-[3-acyclobutyl[3-fluoro-4-(5-isobutylpyridin-3-yl)phenyl]acetyl}-amino)-2-methylphenyl]propanoic acid (Example 207);
200) (−) 3-{3-[(cyclobutyl{3-fluoro-4-[5-(trifluoromethyl)pyridin-3-yl]phenyl}acetyl)amino]-2-methylphenyl}propanoic acid (Example 208);
201) (−) 3-[3-acyclobutyl[3-fluoro-4-(5-isopropoxypyridin-3-yl)phenyl]-acetyl}amino)-2-methylphenyl]propanoic acid (Example 209);
202) (−) 3-[3-acyclobutyl[4-(5-ethylpyridin-3-yl)-3-fluorophenyl]acetyl}-amino)-2-methylphenyl]propanoic acid (Example 210);
203) (R/S) 3-[3-acyclopentyl[4-(5-fluoro-6-methylpyridin-3-yl)phenyl]-acetyl}amino)-2-methylphenyl]propanoic acid (Example 211);
204) 3-[3-({[4-(5-chloropyridin-3-yl)phenyl](cyclopentyl)acetyl}amino)-2-methoxyphenyl]propanoic acid (Example 212);
205) 3-{3-[(cyclopentyl{4-[5-(trifluoromethyl)pyridin-3-yl]phenyl}acetyl)-amino]-2-methoxyphenyl}propanoic acid (Example 213);
206) 3-[3-({(2R)-2-[4-(5-chloropyridin-3-yl)phenyl]-2-cyclopentylacetyl}-amino)-2-(trifluoromethyl)phenyl]propanoic acid (Example 214); and
207) 3-[3-{[(2R)-2-cyclopentyl-2-{4-[5-(trifluoromethyl)pyridin-3-yl]-phenylyacetyl]annino}-2-(trifluoromethyl)phenyl]propanoic acid (Example 215).

17. A pharmaceutical composition comprising a compound according to claim 1, or an isomer, enantiomer, diastereomer, racemate, or a pharmaceutically acceptable salt thereof, or a mixture of same; and a pharmaceutically acceptable diluent or carrier.

18. A compound according to claim 12, wherein $R^1$ represents methyl.

19. A compound according to claim 15, wherein $R^1$ represents methyl.

20. A compound according to claim 15, wherein $R^3$ represents cyclopentyl.

21. A compound according to claim 15, wherein $R^5$ represents chlorine.

\* \* \* \* \*